United States Patent
Heyes et al.

(10) Patent No.: US 12,043,833 B2
(45) Date of Patent: *Jul. 23, 2024

(54) TARGETED COMPOSITIONS

(71) Applicant: ARBUTUS BIOPHARMA CORPORATION, Warminster, PA (US)

(72) Inventors: James Heyes, Vancouver (CA); Richard J. Holland, Vancouver (CA); Adam Judge, Bainbridge Island, WA (US); Amy C. H. Lee, Burnaby (CA); Alan D. Martin, Vancouver (CA); Nicholas Michael Snead, San Francisco, CA (US); Emily P. Thi, Coquitlam (CA); Mark Wood, Port Moody (CA); Xin Ye, Richmond (CA)

(73) Assignee: ARBUTUS BIOPHARMA CORPORATION, Burnaby (CA)

(*) Notice: Subject to any disclaimer, the term of this patent is extended or adjusted under 35 U.S.C. 154(b) by 0 days.

This patent is subject to a terminal disclaimer.

(21) Appl. No.: 17/854,575

(22) Filed: Jun. 30, 2022

(65) Prior Publication Data

US 2023/0110295 A1    Apr. 13, 2023

Related U.S. Application Data

(63) Continuation of application No. 16/603,771, filed as application No. PCT/US2018/026918 on Apr. 10, 2018, now Pat. No. 11,427,823.

(60) Provisional application No. 62/525,071, filed on Jun. 26, 2017, provisional application No. 62/484,247, filed on Apr. 11, 2017.

(51) Int. Cl.
C12N 15/113    (2010.01)

(52) U.S. Cl.
CPC ...... *C12N 15/1131* (2013.01); *C12N 2310/14* (2013.01); *C12N 2310/344* (2013.01); *C12N 2310/346* (2013.01); *C12N 2310/3515* (2013.01)

(58) Field of Classification Search
CPC ............ C12N 15/1131; C12N 2310/14; C12N 2310/344; C12N 2310/346; C12N 2310/3515
See application file for complete search history.

(56) References Cited

U.S. PATENT DOCUMENTS

| | | | |
|---|---|---|---|
| 7,833,992 B2 | 11/2010 | Vargeese et al. | |
| 8,258,288 B2 | 9/2012 | McSwiggen et al. | |
| 8,313,772 B2 | 11/2012 | Rozema et al. | |
| 8,541,388 B2 | 9/2013 | Monia et al. | |
| 8,828,956 B2 | 9/2014 | Manoharan et al. | |
| 8,956,825 B2 | 2/2015 | Weisbart | |
| 9,181,549 B2 | 11/2015 | Prakash et al. | |
| 9,249,179 B2 | 2/2016 | Hadwiger et al. | |
| 9,345,775 B2 | 5/2016 | Lewis et al. | |
| 9,399,775 B2 | 7/2016 | Rajeev et al. | |
| 9,796,974 B2 | 10/2017 | Rajeev et al. | |
| 9,879,265 B2 | 1/2018 | Albæk et al. | |
| 10,000,754 B2 | 6/2018 | Beigelman et al. | |
| 10,294,477 B2 | 5/2019 | Swayze | |
| 11,427,823 B2 | 8/2022 | Heyes et al. | |
| 2019/0160176 A1 | 5/2019 | Heyes et al. | |
| 2022/0168430 A1 | 6/2022 | Ardzinski et al. | |

FOREIGN PATENT DOCUMENTS

| | | |
|---|---|---|
| CN | 101603042 A | 12/2009 |
| CN | 114340663 A | 4/2022 |
| JP | 2016501195 A | 1/2016 |
| WO | 2003070918 A2 | 8/2003 |
| WO | 2005021751 A1 | 3/2005 |
| WO | 2005026165 A1 | 3/2005 |
| WO | 2009073809 A2 | 6/2009 |
| WO | 2009082606 A2 | 7/2009 |
| WO | 2009082607 A2 | 7/2009 |
| WO | 2011056883 A1 | 5/2011 |
| WO | 2011104169 A1 | 9/2011 |
| WO | 2012083046 A2 | 6/2012 |
| WO | 2013033230 A1 | 3/2013 |
| WO | 2014076195 A1 | 5/2014 |
| WO | 2014179626 A2 | 11/2014 |
| WO | 2014179627 A2 | 11/2014 |
| WO | 2014205451 A2 | 12/2014 |
| WO | 2014207232 A1 | 12/2014 |
| WO | 2015042564 A1 | 3/2015 |
| WO | 2015168532 A2 | 11/2015 |
| WO | 2016055601 A1 | 4/2016 |
| WO | 2016057893 A1 | 4/2016 |
| WO | 2016077321 A1 | 5/2016 |

(Continued)

OTHER PUBLICATIONS

Boese, Q , et al., "Mechanical Insights Aid Computational Short Interfering RNA Design", Methods in Enzymology 392, 73-96 (2005).

(Continued)

*Primary Examiner* — J. E. Angell

(74) *Attorney, Agent, or Firm* — Viksnins Harris Padys Malen LLP

(57) ABSTRACT

The invention provides certain nucleic acids (e.g., double stranded siRNA molecules), as well as conjugates that comprise a targeting moiety, a double stranded siRNA, and optional linking groups. Certain embodiments also provide synthetic methods useful for preparing the conjugates. The conjugates are useful to target therapeutic double stranded siRNA to the liver and to treat liver diseases including hepatitis (e.g. hepatitis B and hepatitis D).

18 Claims, 3 Drawing Sheets

Specification includes a Sequence Listing.

(56) References Cited

FOREIGN PATENT DOCUMENTS

| WO | 2016077349 A1 | 5/2016 |
|----|---------------|--------|
| WO | 2016179342 A2 | 11/2016 |
| WO | 2017177326 A1 | 10/2017 |
| WO | 2018195165 A1 | 10/2018 |

OTHER PUBLICATIONS

Das, et al., "A Peptide Nucleic Acid-Aminosugar Conjugate Targeting Transactivation Response Element of HIV-1 RNA Genome Shows a High Bioavailability in Human Cells and Strongly Inhibits Tat-mediated Transactivation of HIV-1 Transcription", J Med Chem 55(13), 6021-6032 (2012).
Database, "Hepatitis B virus mRNA-targeted antisense oligonucleotide, SEQ 1309", EBI assession No. GSN: BEP71596, Database accession No. BEP71596 sequence, (Mar. 30, 2017).
Database, "Hepatitis B virus X ORF targeted siRNA sense strand, SEQ ID 1793", EBI accession No. GSN: BDA34147, Databse accession No. BDA34147, Jun. 30, 2016.
Holen, et al., "Positional effects of short interfering RNAs targeting the human coagulation trigger Tissue Factor", Nucleic Acids Res, 30(8), pp. 1757-6617, 2002.
Huang, Y, "Preclinical and Clinical Advances of GalNAc-Decorated Nucleic Acid Therapeutics", Molecular Therapy—Nucleic Acids 6, 116-132 (2017).
Kinberger, G, et al., "Conjugation of mono and di-GalNAc sugars enhances the potency of antisense oligonucleotides via ASGR mediated delivery to hepatocytes", Bioorganic & Medicinal Chemistry Letters 26(15), 3690-3693 (2016).
Nair, J, et al., "Multivalent N-acetylgalactosamine-conjugated siRNA localizes in hepatocytes and elicits robust RNAi-mediated gene silencing", J Am Chem Soc 136(49), 16958-16961 (2014).
National Center, for Biotechnology Information, "SCHEMBL4352939", PubChem Compound Database, Dec. 4, 2011, vol. CID=54474605, retrieved on Jul. 18, 2017.
Patent Cooperation Treaty, International Searching Authority, Search Report and Written Opinion for PCT/US2018/026918, 21 pages, dated Oct. 8, 2018.
Prakash, T, et al., "Targeted delivery of antisense oligonucleotides to hepatocytes using triantennary N-acetyl galactosamine improves potency 10-fold in mice", Nucleic Acids Research 42(13), 8796-8807 (2014).
Reynolds, A, et al., "Rational siRNA design for RNA interference", Nat Biotechnol 22(3), 326-330 (2004).
Winkler, J, "Oligonucleotide conjugates for therapeutic applications", Ther Deliv 4(7), 791-809 (2013).
Zimmermann, T, et al., "Clinical Proof of Concept for a Novel Hepatocyte-Targeting GalNAc-siRNA Conjugate", Molecular Therapy: The Journal of the American Society of Gene Therapy 25(1), 71-78 (2017).
Zhang, X, et al., "Research progress in chemical modification and in vivo transmission of siRNA in the field of anti HBV infection", Drug evaluation, pp. 9-13 and 41 (2013). [English Abstract].
Holland, R, et al., "Ligand conjugate SAR and enhanced delivery in NHP", Molecular Therapy 29 (10), 2910-2919 (2021).

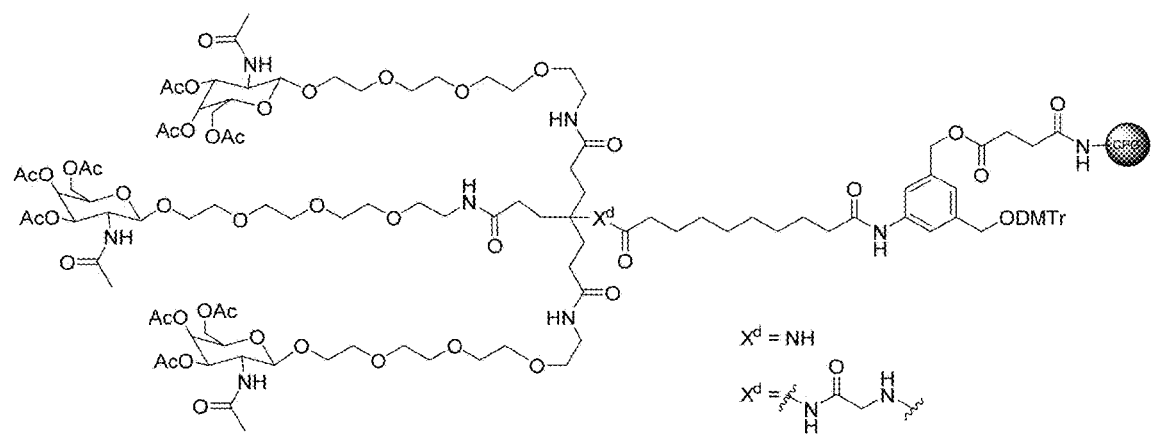
Figure 1: Intermediate compound of formula Ie, wherein a targeting ligand/linker is bound to a solid phase support, and wherein $Pg^1$ is the protecting group DMTr.

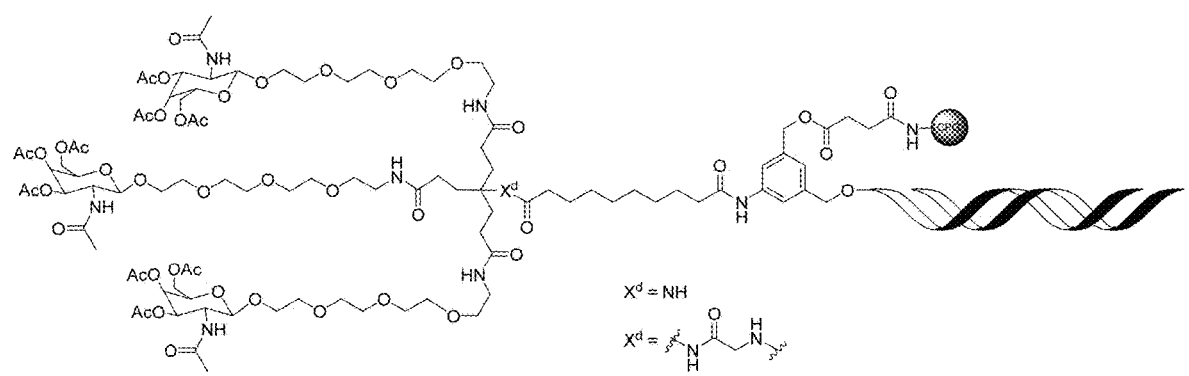
Figure 2: Representative compound of formula Id wherein a targeting ligand is bound to a solid phase support, with an oligonucleotide covalently bound.

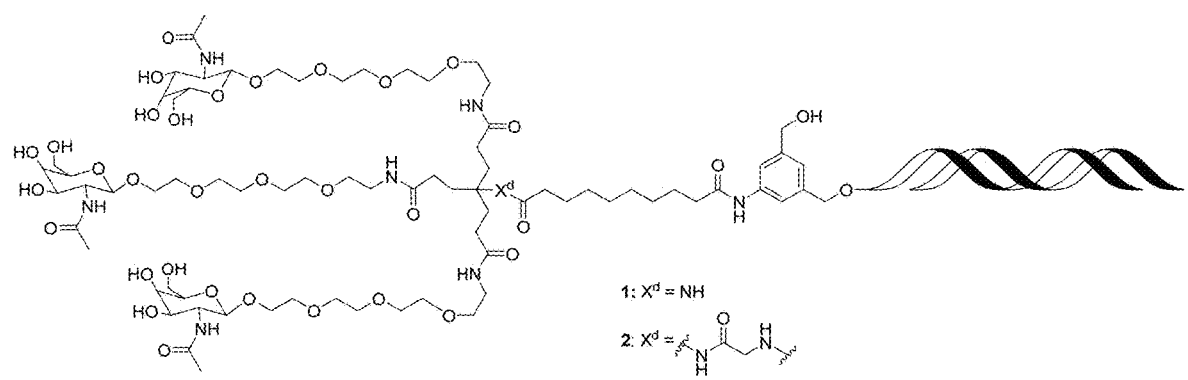
Figure 3: Representative compound of formula Id, wherein a targeting ligand-oligo nucleotide conjugate has been cleaved from a solid phase support and deprotected.

SEQUENCE LISTING

<160> NUMBER OF SEQ ID NOS: 76

<210> SEQ ID NO 1
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-O-Methyl nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-O-Methyl nucleotide
<220> FEATURE:

```
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-O-Methyl nucleotide
<220> FEATURE:
<221> NAME/KEY: modified_base
<222> LOCATION: (6)..(6)
<223> OTHER INFORMATION: 2'-O-Methyl nucleotide
<220> FEATURE:
<221> NAME/KEY: modified_base
<222> LOCATION: (7)..(7)
<223> OTHER INFORMATION: 2'-Fluoro nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-Fluoro nucleotide
<220> FEATURE:
<221> NAME/KEY: modified_base
<222> LOCATION: (10)..(10)
<223> OTHER INFORMATION: 2'-Fluoro nucleotide
<220> FEATURE:
<221> NAME/KEY: modified_base
<222> LOCATION: (11)..(11)
<223> OTHER INFORMATION: 2'-Fluoro nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-O-Methyl nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-O-Methyl nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-O-Methyl nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-O-Methyl nucleotide
<220> FEATURE:
<221> NAME/KEY: modified_base
<222> LOCATION: (21)..(21)
<223> OTHER INFORMATION: 2'-O-Methyl nucleotide

<400> SEQUENCE: 1
cgugugcacu ucgcuucacc u                                            21

<210> SEQ ID NO 2
<211> LENGTH: 25
```

```
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-Fluoro nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-O-Methyl nucleotide
<220> FEATURE:
<221> NAME/KEY: modified_base
<222> LOCATION: (6)..(6)
<223> OTHER INFORMATION: 2'-Fluoro nucleotide
<220> FEATURE:
<221> NAME/KEY: modified_base
<222> LOCATION: (7)..(7)
<223> OTHER INFORMATION: 2'-O-Methyl nucleotide
<220> FEATURE:
<221> NAME/KEY: modified_base
<222> LOCATION: (8)..(8)
<223> OTHER INFORMATION: 2'-Fluoro nucleotide
<220> FEATURE:
<221> NAME/KEY: modified_base
<222> LOCATION: (9)..(9)
<223> OTHER INFORMATION: 2'-Fluoro nucleotide
<220> FEATURE:
<221> NAME/KEY: modified_base
<222> LOCATION: (10)..(10)
<223> OTHER INFORMATION: 2'-O-Methyl nucleotide
<220> FEATURE:
<221> NAME/KEY: modified_base
<222> LOCATION: (11)..(11)
<223> OTHER INFORMATION: 2'-O-Methyl nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-Fluoro nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-Fluoro nucleotide
<220> FEATURE:
<221> NAME/KEY: modified_base
```

```
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-O-Methyl nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-O-Methyl nucleotide
<220> FEATURE:
<221> NAME/KEY: modified_base
<222> LOCATION: (21)..(21)
<223> OTHER INFORMATION: 2'-O-Methyl nucleotide
<220> FEATURE:
<221> NAME/KEY: misc_feature
<222> LOCATION: (21)..(22)
<223> OTHER INFORMATION: Phosphorothioate linker
<220> FEATURE:
<221> NAME/KEY: modified_base
<222> LOCATION: (22)..(22)
<223> OTHER INFORMATION: 2'-O-Methyl nucleotide
<220> FEATURE:
<221> NAME/KEY: misc_feature
<222> LOCATION: (22)..(23)
<223> OTHER INFORMATION: Phosphorothioate linker
<220> FEATURE:
<221> NAME/KEY: modified_base
<222> LOCATION: (23)..(23)
<223> OTHER INFORMATION: 2'-O-Methyl nucleotide

<400> SEQUENCE: 2
aggugaagcg aagugcacac gguuu                                             25

<210> SEQ ID NO 3
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-O-Methyl nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-Fluoro nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-Fluoro nucleotide
<220> FEATURE:
<221> NAME/KEY: modified_base
<222> LOCATION: (6)..(6)
<223> OTHER INFORMATION: 2'-Fluoro nucleotide
```

```
<220> FEATURE:
<221> NAME/KEY: modified_base
<222> LOCATION: (7)..(7)
<223> OTHER INFORMATION: 2'-Fluoro nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-O-Methyl nucleotide
<220> FEATURE:
<221> NAME/KEY: modified_base
<222> LOCATION: (10)..(10)
<223> OTHER INFORMATION: 2'-O-Methyl nucleotide
<220> FEATURE:
<221> NAME/KEY: modified_base
<222> LOCATION: (11)..(11)
<223> OTHER INFORMATION: 2'-O-Methyl nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-O-Methyl nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-O-Methyl nucleotide
<220> FEATURE:
<221> NAME/KEY: modified_base
<222> LOCATION: (17)..(17)
<223> OTHER INFORMATION: 2'-O-Methyl nucleotide

<400> SEQUENCE: 3
ugcacuucgc uucaccu                                                17

<210> SEQ ID NO 4
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-Fluoro nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
```

```
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-O-Methyl nucleotide
<220> FEATURE:
<221> NAME/KEY: modified_base
<222> LOCATION: (6)..(6)
<223> OTHER INFORMATION: 2'-Fluoro nucleotide
<220> FEATURE:
<221> NAME/KEY: modified_base
<222> LOCATION: (7)..(7)
<223> OTHER INFORMATION: 2'-O-Methyl nucleotide
<220> FEATURE:
<221> NAME/KEY: modified_base
<222> LOCATION: (8)..(8)
<223> OTHER INFORMATION: 2'-Fluoro nucleotide
<220> FEATURE:
<221> NAME/KEY: modified_base
<222> LOCATION: (9)..(9)
<223> OTHER INFORMATION: 2'-Fluoro nucleotide
<220> FEATURE:
<221> NAME/KEY: modified_base
<222> LOCATION: (10)..(10)
<223> OTHER INFORMATION: 2'-O-Methyl nucleotide
<220> FEATURE:
<221> NAME/KEY: modified_base
<222> LOCATION: (11)..(11)
<223> OTHER INFORMATION: 2'-O-Methyl nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-Fluoro nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-Fluoro nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-O-Methyl nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: misc_feature
<222> LOCATION: (19)..(20)
<223> OTHER INFORMATION: Phosphorothioate linker
<220> FEATURE:
<221> NAME/KEY: modified_base
<222> LOCATION: (20)..(20)
<223> OTHER INFORMATION: 2'-O-Methyl nucleotide
<220> FEATURE:
<221> NAME/KEY: misc_feature
<222> LOCATION: (20)..(21)
<223> OTHER INFORMATION: Phosphorothioate linker
<220> FEATURE:
<221> NAME/KEY: modified_base
<222> LOCATION: (21)..(21)
<223> OTHER INFORMATION: 2'-O-Methyl nucleotide
```

-continued

<400> SEQUENCE: 4
aggugaagcg aagugcacac gu                                              22

<210> SEQ ID NO 5
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-O-Methyl nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-Fluoro nucleotide
<220> FEATURE:
<221> NAME/KEY: modified_base
<222> LOCATION: (6)..(6)
<223> OTHER INFORMATION: 2'-Fluoro nucleotide
<220> FEATURE:
<221> NAME/KEY: modified_base
<222> LOCATION: (7)..(7)
<223> OTHER INFORMATION: 2'-Fluoro nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-O-Methyl nucleotide
<220> FEATURE:
<221> NAME/KEY: modified_base
<222> LOCATION: (10)..(10)
<223> OTHER INFORMATION: 2'-O-Methyl nucleotide
<220> FEATURE:
<221> NAME/KEY: modified_base
<222> LOCATION: (11)..(11)
<223> OTHER INFORMATION: 2'-O-Methyl nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-O-Methyl nucleotide
<220> FEATURE:
<221> NAME/KEY: modified_base
<222> LOCATION: (15)..(15)

```
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-O-Methyl nucleotide
<220> FEATURE:
<221> NAME/KEY: modified_base
<222> LOCATION: (17)..(17)
<223> OTHER INFORMATION: 2'-O-Methyl nucleotide

<400> SEQUENCE: 5
ugcacuucgc uucaccu                                                    17

<210> SEQ ID NO 6
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-Fluoro nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-O-Methyl nucleotide
<220> FEATURE:
<221> NAME/KEY: modified_base
<222> LOCATION: (6)..(6)
<223> OTHER INFORMATION: 2'-O-Methyl nucleotide
<220> FEATURE:
<221> NAME/KEY: modified_base
<222> LOCATION: (7)..(7)
<223> OTHER INFORMATION: 2'-O-Methyl nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-O-Methyl nucleotide
<220> FEATURE:
<221> NAME/KEY: modified_base
<222> LOCATION: (10)..(10)
<223> OTHER INFORMATION: 2'-O-Methyl nucleotide
<220> FEATURE:
<221> NAME/KEY: modified_base
<222> LOCATION: (11)..(11)
<223> OTHER INFORMATION: 2'-O-Methyl nucleotide
<220> FEATURE:
<221> NAME/KEY: modified_base
<222> LOCATION: (12)..(12)
<223> OTHER INFORMATION: 2'-O-Methyl nucleotide
<220> FEATURE:
```

<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-Fluoro nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-Fluoro nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-O-Methyl nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: misc_feature
<222> LOCATION: (19)..(20)
<223> OTHER INFORMATION: Phosphorothioate linker
<220> FEATURE:
<221> NAME/KEY: modified_base
<222> LOCATION: (20)..(20)
<223> OTHER INFORMATION: 2'-O-Methyl nucleotide
<220> FEATURE:
<221> NAME/KEY: misc_feature
<222> LOCATION: (20)..(21)
<223> OTHER INFORMATION: Phosphorothioate linker
<220> FEATURE:
<221> NAME/KEY: modified_base
<222> LOCATION: (21)..(21)
<223> OTHER INFORMATION: 2'-O-Methyl nucleotide

<400> SEQUENCE: 6
aggugaagcg aagugcacac gu                                          22

<210> SEQ ID NO 7
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-O-Methyl nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (4)..(4)

<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-Fluoro nucleotide
<220> FEATURE:
<221> NAME/KEY: modified_base
<222> LOCATION: (6)..(6)
<223> OTHER INFORMATION: 2'-Fluoro nucleotide
<220> FEATURE:
<221> NAME/KEY: modified_base
<222> LOCATION: (7)..(7)
<223> OTHER INFORMATION: 2'-Fluoro nucleotide
<220> FEATURE:
<221> NAME/KEY: modified_base
<222> LOCATION: (8)..(8)
<223> OTHER INFORMATION: 2'-Fluoro nucleotide
<220> FEATURE:
<221> NAME/KEY: modified_base
<222> LOCATION: (9)..(9)
<223> OTHER INFORMATION: 2'-O-Methyl nucleotide
<220> FEATURE:
<221> NAME/KEY: modified_base
<222> LOCATION: (10)..(10)
<223> OTHER INFORMATION: 2'-O-Methyl nucleotide
<220> FEATURE:
<221> NAME/KEY: modified_base
<222> LOCATION: (11)..(11)
<223> OTHER INFORMATION: 2'-O-Methyl nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-O-Methyl nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-O-Methyl nucleotide
<220> FEATURE:
<221> NAME/KEY: modified_base
<222> LOCATION: (17)..(17)
<223> OTHER INFORMATION: 2'-O-Methyl nucleotide

<400> SEQUENCE: 7
ugcacuucgc uucaccu                                                  17

<210> SEQ ID NO 8
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-Fluoro nucleotide
<220> FEATURE:

```
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-O-Methyl nucleotide
<220> FEATURE:
<221> NAME/KEY: modified_base
<222> LOCATION: (6)..(6)
<223> OTHER INFORMATION: 2'-Fluoro nucleotide
<220> FEATURE:
<221> NAME/KEY: modified_base
<222> LOCATION: (7)..(7)
<223> OTHER INFORMATION: 2'-O-Methyl nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-O-Methyl nucleotide
<220> FEATURE:
<221> NAME/KEY: modified_base
<222> LOCATION: (10)..(10)
<223> OTHER INFORMATION: 2'-O-Methyl nucleotide
<220> FEATURE:
<221> NAME/KEY: modified_base
<222> LOCATION: (11)..(11)
<223> OTHER INFORMATION: 2'-O-Methyl nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-Fluoro nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-Fluoro nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-O-Methyl nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: misc_feature
<222> LOCATION: (19)..(20)
<223> OTHER INFORMATION: Phosphorothioate linker
<220> FEATURE:
<221> NAME/KEY: modified_base
<222> LOCATION: (20)..(20)
<223> OTHER INFORMATION: 2'-O-Methyl nucleotide
```

```
<220> FEATURE:
<221> NAME/KEY: misc_feature
<222> LOCATION: (20)..(21)
<223> OTHER INFORMATION: Phosphorothioate linker
<220> FEATURE:
<221> NAME/KEY: modified_base
<222> LOCATION: (21)..(21)
<223> OTHER INFORMATION: 2'-O-Methyl nucleotide

<400> SEQUENCE: 8
aggugaagcg aagugcacac gu                                              22

<210> SEQ ID NO 9
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-Fluoro nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-O-Methyl nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-Fluoro nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-Fluoro nucleotide
<220> FEATURE:
<221> NAME/KEY: modified_base
<222> LOCATION: (6)..(6)
<223> OTHER INFORMATION: 2'-O-Methyl nucleotide
<220> FEATURE:
<221> NAME/KEY: modified_base
<222> LOCATION: (7)..(7)
<223> OTHER INFORMATION: 2'-Fluoro nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-Fluoro nucleotide
<220> FEATURE:
<221> NAME/KEY: modified_base
<222> LOCATION: (10)..(10)
<223> OTHER INFORMATION: 2'-Fluoro nucleotide
<220> FEATURE:
<221> NAME/KEY: modified_base
<222> LOCATION: (11)..(11)
<223> OTHER INFORMATION: 2'-Fluoro nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
```

```
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-Fluoro nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-O-Methyl nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-Fluoro nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-O-Methyl nucleotide
<220> FEATURE:
<221> NAME/KEY: modified_base
<222> LOCATION: (21)..(21)
<223> OTHER INFORMATION: 2'-O-Methyl nucleotide

<400> SEQUENCE: 9
ccgugugcac uucgcuucac c                                                   21

<210> SEQ ID NO 10
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-Fluoro nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-Fluoro nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-Fluoro nucleotide
<220> FEATURE:
<221> NAME/KEY: modified_base
<222> LOCATION: (6)..(6)
<223> OTHER INFORMATION: 2'-O-Methyl nucleotide
```

```
<220> FEATURE:
<221> NAME/KEY: modified_base
<222> LOCATION: (7)..(7)
<223> OTHER INFORMATION: 2'-Fluoro nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-O-Methyl nucleotide
<220> FEATURE:
<221> NAME/KEY: modified_base
<222> LOCATION: (10)..(10)
<223> OTHER INFORMATION: 2'-Fluoro nucleotide
<220> FEATURE:
<221> NAME/KEY: modified_base
<222> LOCATION: (11)..(11)
<223> OTHER INFORMATION: 2'-O-Methyl nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-Fluoro nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-Fluoro nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-Fluoro nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-Fluoro nucleotide
<220> FEATURE:
<221> NAME/KEY: modified_base
<222> LOCATION: (21)..(21)
<223> OTHER INFORMATION: 2'-O-Methyl nucleotide
<220> FEATURE:
<221> NAME/KEY: misc_feature
<222> LOCATION: (21)..(22)
<223> OTHER INFORMATION: Phosphorothioate linker
<220> FEATURE:
<221> NAME/KEY: modified_base
<222> LOCATION: (22)..(22)
<223> OTHER INFORMATION: 2'-O-Methyl nucleotide
<220> FEATURE:
<221> NAME/KEY: misc_feature
<222> LOCATION: (22)..(23)
<223> OTHER INFORMATION: Phosphorothioate linker
<220> FEATURE:
<221> NAME/KEY: modified_base
<222> LOCATION: (23)..(23)
<223> OTHER INFORMATION: 2'-O-Methyl nucleotide

<400> SEQUENCE: 10
```
ggugaagcga agugcacacg guc                                                  23

<210> SEQ ID NO 11
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-O-Methyl nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-O-Methyl nucleotide
<220> FEATURE:
<221> NAME/KEY: modified_base
<222> LOCATION: (6)..(6)
<223> OTHER INFORMATION: 2'-O-Methyl nucleotide
<220> FEATURE:
<221> NAME/KEY: modified_base
<222> LOCATION: (7)..(7)
<223> OTHER INFORMATION: 2'-Fluoro nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-Fluoro nucleotide
<220> FEATURE:
<221> NAME/KEY: modified_base
<222> LOCATION: (10)..(10)
<223> OTHER INFORMATION: 2'-Fluoro nucleotide
<220> FEATURE:
<221> NAME/KEY: modified_base
<222> LOCATION: (11)..(11)
<223> OTHER INFORMATION: 2'-Fluoro nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-O-Methyl nucleotide
<220> FEATURE:
<221> NAME/KEY: modified_base
<222> LOCATION: (15)..(15)
<223> OTHER INFORMATION: 2'-O-Methyl nucleotide
<220> FEATURE:

```
<221> NAME/KEY: modified_base
<222> LOCATION: (16)..(16)
<223> OTHER INFORMATION: 2'-O-Methyl nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-O-Methyl nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-O-Methyl nucleotide
<220> FEATURE:
<221> NAME/KEY: modified_base
<222> LOCATION: (21)..(21)
<223> OTHER INFORMATION: 2'-O-Methyl nucleotide

<400> SEQUENCE: 11
ccgugugcac uucgcuucac c                                              21

<210> SEQ ID NO 12
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-Fluoro nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-O-Methyl nucleotide
<220> FEATURE:
<221> NAME/KEY: modified_base
<222> LOCATION: (6)..(6)
<223> OTHER INFORMATION: 2'-Fluoro nucleotide
<220> FEATURE:
<221> NAME/KEY: modified_base
<222> LOCATION: (7)..(7)
<223> OTHER INFORMATION: 2'-O-Methyl nucleotide
<220> FEATURE:
<221> NAME/KEY: modified_base
<222> LOCATION: (8)..(8)
<223> OTHER INFORMATION: 2'-Fluoro nucleotide
<220> FEATURE:
<221> NAME/KEY: modified_base
<222> LOCATION: (9)..(9)
```

```
<223> OTHER INFORMATION: 2'-Fluoro nucleotide
<220> FEATURE:
<221> NAME/KEY: modified_base
<222> LOCATION: (10)..(10)
<223> OTHER INFORMATION: 2'-O-Methyl nucleotide
<220> FEATURE:
<221> NAME/KEY: modified_base
<222> LOCATION: (11)..(11)
<223> OTHER INFORMATION: 2'-O-Methyl nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-Fluoro nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-Fluoro nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-O-Methyl nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-O-Methyl nucleotide
<220> FEATURE:
<221> NAME/KEY: modified_base
<222> LOCATION: (21)..(21)
<223> OTHER INFORMATION: 2'-O-Methyl nucleotide
<220> FEATURE:
<221> NAME/KEY: misc_feature
<222> LOCATION: (21)..(22)
<223> OTHER INFORMATION: Phosphorothioate linker
<220> FEATURE:
<221> NAME/KEY: modified_base
<222> LOCATION: (22)..(22)
<223> OTHER INFORMATION: 2'-O-Methyl nucleotide
<220> FEATURE:
<221> NAME/KEY: misc_feature
<222> LOCATION: (22)..(23)
<223> OTHER INFORMATION: Phosphorothioate linker
<220> FEATURE:
<221> NAME/KEY: modified_base
<222> LOCATION: (23)..(23)
<223> OTHER INFORMATION: 2'-O-Methyl nucleotide

<400> SEQUENCE: 12
ggugaagcga agugcacacg guc                                            23

<210> SEQ ID NO 13
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
```

```
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-O-Methyl nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-Fluoro nucleotide
<220> FEATURE:
<221> NAME/KEY: modified_base
<222> LOCATION: (6)..(6)
<223> OTHER INFORMATION: 2'-O-Methyl nucleotide
<220> FEATURE:
<221> NAME/KEY: modified_base
<222> LOCATION: (7)..(7)
<223> OTHER INFORMATION: 2'-Fluoro nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-Fluoro nucleotide
<220> FEATURE:
<221> NAME/KEY: modified_base
<222> LOCATION: (10)..(10)
<223> OTHER INFORMATION: 2'-O-Methyl nucleotide
<220> FEATURE:
<221> NAME/KEY: modified_base
<222> LOCATION: (11)..(11)
<223> OTHER INFORMATION: 2'-Fluoro nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-O-Methyl nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-O-Methyl nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-O-Methyl nucleotide
```

```
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-O-Methyl nucleotide
<220> FEATURE:
<221> NAME/KEY: modified_base
<222> LOCATION: (21)..(21)
<223> OTHER INFORMATION: 2'-O-Methyl nucleotide

<400> SEQUENCE: 13
ccgugugcac uucgcuucac c                                              21

<210> SEQ ID NO 14
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-Fluoro nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-O-Methyl nucleotide
<220> FEATURE:
<221> NAME/KEY: modified_base
<222> LOCATION: (6)..(6)
<223> OTHER INFORMATION: 2'-Fluoro nucleotide
<220> FEATURE:
<221> NAME/KEY: modified_base
<222> LOCATION: (7)..(7)
<223> OTHER INFORMATION: 2'-O-Methyl nucleotide
<220> FEATURE:
<221> NAME/KEY: modified_base
<222> LOCATION: (8)..(8)
<223> OTHER INFORMATION: 2'-Fluoro nucleotide
<220> FEATURE:
<221> NAME/KEY: modified_base
<222> LOCATION: (9)..(9)
<223> OTHER INFORMATION: 2'-Fluoro nucleotide
<220> FEATURE:
<221> NAME/KEY: modified_base
<222> LOCATION: (10)..(10)
<223> OTHER INFORMATION: 2'-O-Methyl nucleotide
<220> FEATURE:
<221> NAME/KEY: modified_base
<222> LOCATION: (11)..(11)
<223> OTHER INFORMATION: 2'-O-Methyl nucleotide
<220> FEATURE:
<221> NAME/KEY: modified_base
```

<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-Fluoro nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-Fluoro nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-O-Methyl nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-O-Methyl nucleotide
<220> FEATURE:
<221> NAME/KEY: modified_base
<222> LOCATION: (21)..(21)
<223> OTHER INFORMATION: 2'-O-Methyl nucleotide
<220> FEATURE:
<221> NAME/KEY: misc_feature
<222> LOCATION: (21)..(22)
<223> OTHER INFORMATION: Phosphorothioate linker
<220> FEATURE:
<221> NAME/KEY: modified_base
<222> LOCATION: (22)..(22)
<223> OTHER INFORMATION: 2'-O-Methyl nucleotide
<220> FEATURE:
<221> NAME/KEY: misc_feature
<222> LOCATION: (22)..(23)
<223> OTHER INFORMATION: Phosphorothioate linker
<220> FEATURE:
<221> NAME/KEY: modified_base
<222> LOCATION: (23)..(23)
<223> OTHER INFORMATION: 2'-O-Methyl nucleotide

<400> SEQUENCE: 14
ggugaagcga agugcacacg guc                                              23

<210> SEQ ID NO 15
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-O-Methyl nucleotide

```
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-O-Methyl nucleotide
<220> FEATURE:
<221> NAME/KEY: modified_base
<222> LOCATION: (6)..(6)
<223> OTHER INFORMATION: 2'-O-Methyl nucleotide
<220> FEATURE:
<221> NAME/KEY: modified_base
<222> LOCATION: (7)..(7)
<223> OTHER INFORMATION: 2'-Fluoro nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-Fluoro nucleotide
<220> FEATURE:
<221> NAME/KEY: modified_base
<222> LOCATION: (10)..(10)
<223> OTHER INFORMATION: 2'-Fluoro nucleotide
<220> FEATURE:
<221> NAME/KEY: modified_base
<222> LOCATION: (11)..(11)
<223> OTHER INFORMATION: 2'-Fluoro nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-O-Methyl nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-O-Methyl nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-Fluoro nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-O-Methyl nucleotide
<220> FEATURE:
<221> NAME/KEY: modified_base
<222> LOCATION: (21)..(21)
```

<223> OTHER INFORMATION: 2'-O-Methyl nucleotide

<400> SEQUENCE: 15
ccgugugcac uucgcuucac c                                              21

<210> SEQ ID NO 16
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-Fluoro nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-O-Methyl nucleotide
<220> FEATURE:
<221> NAME/KEY: modified_base
<222> LOCATION: (6)..(6)
<223> OTHER INFORMATION: 2'-Fluoro nucleotide
<220> FEATURE:
<221> NAME/KEY: modified_base
<222> LOCATION: (7)..(7)
<223> OTHER INFORMATION: 2'-O-Methyl nucleotide
<220> FEATURE:
<221> NAME/KEY: modified_base
<222> LOCATION: (8)..(8)
<223> OTHER INFORMATION: 2'-Fluoro nucleotide
<220> FEATURE:
<221> NAME/KEY: modified_base
<222> LOCATION: (9)..(9)
<223> OTHER INFORMATION: 2'-O-Methyl nucleotide
<220> FEATURE:
<221> NAME/KEY: modified_base
<222> LOCATION: (10)..(10)
<223> OTHER INFORMATION: 2'-O-Methyl nucleotide
<220> FEATURE:
<221> NAME/KEY: modified_base
<222> LOCATION: (11)..(11)
<223> OTHER INFORMATION: 2'-O-Methyl nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-Fluoro nucleotide
<220> FEATURE:

```
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-Fluoro nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-O-Methyl nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-Fluoro nucleotide
<220> FEATURE:
<221> NAME/KEY: modified_base
<222> LOCATION: (21)..(21)
<223> OTHER INFORMATION: 2'-O-Methyl nucleotide
<220> FEATURE:
<221> NAME/KEY: misc_feature
<222> LOCATION: (21)..(22)
<223> OTHER INFORMATION: Phosphorothioate linker
<220> FEATURE:
<221> NAME/KEY: modified_base
<222> LOCATION: (22)..(22)
<223> OTHER INFORMATION: 2'-O-Methyl nucleotide
<220> FEATURE:
<221> NAME/KEY: misc_feature
<222> LOCATION: (22)..(23)
<223> OTHER INFORMATION: Phosphorothioate linker
<220> FEATURE:
<221> NAME/KEY: modified_base
<222> LOCATION: (23)..(23)
<223> OTHER INFORMATION: 2'-O-Methyl nucleotide

<400> SEQUENCE: 16
ggugaagcga agugcacacg guc                                           23

<210> SEQ ID NO 17
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-O-Methyl nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (4)..(4)
```

```
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-O-Methyl nucleotide
<220> FEATURE:
<221> NAME/KEY: modified_base
<222> LOCATION: (6)..(6)
<223> OTHER INFORMATION: 2'-O-Methyl nucleotide
<220> FEATURE:
<221> NAME/KEY: modified_base
<222> LOCATION: (7)..(7)
<223> OTHER INFORMATION: 2'-O-Methyl nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-Fluoro nucleotide
<220> FEATURE:
<221> NAME/KEY: modified_base
<222> LOCATION: (10)..(10)
<223> OTHER INFORMATION: 2'-Fluoro nucleotide
<220> FEATURE:
<221> NAME/KEY: modified_base
<222> LOCATION: (11)..(11)
<223> OTHER INFORMATION: 2'-Fluoro nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-O-Methyl nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-O-Methyl nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-O-Methyl nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-O-Methyl nucleotide
<220> FEATURE:
<221> NAME/KEY: modified_base
<222> LOCATION: (21)..(21)
<223> OTHER INFORMATION: 2'-O-Methyl nucleotide

<400> SEQUENCE: 17
ccgugugcac uucgcuucac c                                              21

<210> SEQ ID NO 18
<211> LENGTH: 23
<212> TYPE: RNA
<213> ORGANISM: Artificial Sequence
```

-continued

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-Fluoro nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-O-Methyl nucleotide
<220> FEATURE:
<221> NAME/KEY: modified_base
<222> LOCATION: (6)..(6)
<223> OTHER INFORMATION: 2'-O-Methyl nucleotide
<220> FEATURE:
<221> NAME/KEY: modified_base
<222> LOCATION: (7)..(7)
<223> OTHER INFORMATION: 2'-O-Methyl nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-O-Methyl nucleotide
<220> FEATURE:
<221> NAME/KEY: modified_base
<222> LOCATION: (10)..(10)
<223> OTHER INFORMATION: 2'-O-Methyl nucleotide
<220> FEATURE:
<221> NAME/KEY: modified_base
<222> LOCATION: (11)..(11)
<223> OTHER INFORMATION: 2'-O-Methyl nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-Fluoro nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-Fluoro nucleotide
<220> FEATURE:
<221> NAME/KEY: modified_base
<222> LOCATION: (17)..(17)
<223> OTHER INFORMATION: 2'-O-Methyl nucleotide
```

```
<220> FEATURE:
<221> NAME/KEY: modified_base
<222> LOCATION: (18)..(18)
<223> OTHER INFORMATION: 2'-O-Methyl nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-O-Methyl nucleotide
<220> FEATURE:
<221> NAME/KEY: modified_base
<222> LOCATION: (21)..(21)
<223> OTHER INFORMATION: 2'-O-Methyl nucleotide
<220> FEATURE:
<221> NAME/KEY: misc_feature
<222> LOCATION: (21)..(22)
<223> OTHER INFORMATION: Phosphorothioate linker
<220> FEATURE:
<221> NAME/KEY: modified_base
<222> LOCATION: (22)..(22)
<223> OTHER INFORMATION: 2'-O-Methyl nucleotide
<220> FEATURE:
<221> NAME/KEY: misc_feature
<222> LOCATION: (22)..(23)
<223> OTHER INFORMATION: Phosphorothioate linker
<220> FEATURE:
<221> NAME/KEY: modified_base
<222> LOCATION: (23)..(23)
<223> OTHER INFORMATION: 2'-O-Methyl nucleotide

<400> SEQUENCE: 18
ggugaagcga agugcacacg guc                                           23

<210> SEQ ID NO 19
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-O-Methyl nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-O-Methyl nucleotide
<220> FEATURE:
<221> NAME/KEY: modified_base
<222> LOCATION: (6)..(6)
<223> OTHER INFORMATION: 2'-O-Methyl nucleotide
<220> FEATURE:
<221> NAME/KEY: modified_base
```

```
<222> LOCATION: (7)..(7)
<223> OTHER INFORMATION: 2'-Fluoro nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-O-Methyl nucleotide
<220> FEATURE:
<221> NAME/KEY: modified_base
<222> LOCATION: (10)..(10)
<223> OTHER INFORMATION: 2'-O-Methyl nucleotide
<220> FEATURE:
<221> NAME/KEY: modified_base
<222> LOCATION: (11)..(11)
<223> OTHER INFORMATION: 2'-O-Methyl nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-O-Methyl nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-O-Methyl nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-O-Methyl nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-O-Methyl nucleotide
<220> FEATURE:
<221> NAME/KEY: modified_base
<222> LOCATION: (21)..(21)
<223> OTHER INFORMATION: 2'-O-Methyl nucleotide

<400> SEQUENCE: 19
ccgugugcac uucgcuucac c                                              21

<210> SEQ ID NO 20
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
```

-continued

```
<220> FEATURE:
<221> NAME/KEY: modified_base
<222> LOCATION: (2)..(2)
<223> OTHER INFORMATION: 2'-O-Methyl nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-O-Methyl nucleotide
<220> FEATURE:
<221> NAME/KEY: modified_base
<222> LOCATION: (6)..(6)
<223> OTHER INFORMATION: 2'-Fluoro nucleotide
<220> FEATURE:
<221> NAME/KEY: modified_base
<222> LOCATION: (7)..(7)
<223> OTHER INFORMATION: 2'-O-Methyl nucleotide
<220> FEATURE:
<221> NAME/KEY: modified_base
<222> LOCATION: (8)..(8)
<223> OTHER INFORMATION: 2'-Fluoro nucleotide
<220> FEATURE:
<221> NAME/KEY: modified_base
<222> LOCATION: (9)..(9)
<223> OTHER INFORMATION: 2'-Fluoro nucleotide
<220> FEATURE:
<221> NAME/KEY: modified_base
<222> LOCATION: (10)..(10)
<223> OTHER INFORMATION: 2'-O-Methyl nucleotide
<220> FEATURE:
<221> NAME/KEY: modified_base
<222> LOCATION: (11)..(11)
<223> OTHER INFORMATION: 2'-O-Methyl nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-O-Methyl nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-O-Methyl nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-O-Methyl nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: modified_base
<222> LOCATION: (20)..(20)
```

```
<223> OTHER INFORMATION: 2'-O-Methyl nucleotide
<220> FEATURE:
<221> NAME/KEY: modified_base
<222> LOCATION: (21)..(21)
<223> OTHER INFORMATION: 2'-O-Methyl nucleotide
<220> FEATURE:
<221> NAME/KEY: misc_feature
<222> LOCATION: (21)..(22)
<223> OTHER INFORMATION: Phosphorothioate linker
<220> FEATURE:
<221> NAME/KEY: modified_base
<222> LOCATION: (22)..(22)
<223> OTHER INFORMATION: 2'-O-Methyl nucleotide
<220> FEATURE:
<221> NAME/KEY: misc_feature
<222> LOCATION: (22)..(23)
<223> OTHER INFORMATION: Phosphorothioate linker
<220> FEATURE:
<221> NAME/KEY: modified_base
<222> LOCATION: (23)..(23)
<223> OTHER INFORMATION: 2'-O-Methyl nucleotide

<400> SEQUENCE: 20
ggugaagcga agugcacacg guc                                            23

<210> SEQ ID NO 21
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-Fluoro nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-O-Methyl nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-Fluoro nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-Fluoro nucleotide
<220> FEATURE:
<221> NAME/KEY: modified_base
<222> LOCATION: (6)..(6)
<223> OTHER INFORMATION: 2'-O-Methyl nucleotide
<220> FEATURE:
<221> NAME/KEY: modified_base
<222> LOCATION: (7)..(7)
<223> OTHER INFORMATION: 2'-Fluoro nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-Fluoro nucleotide
<220> FEATURE:
```

```
<221> NAME/KEY: modified_base
<222> LOCATION: (10)..(10)
<223> OTHER INFORMATION: 2'-Fluoro nucleotide
<220> FEATURE:
<221> NAME/KEY: modified_base
<222> LOCATION: (11)..(11)
<223> OTHER INFORMATION: 2'-Fluoro nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-Fluoro nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-O-Methyl nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-Fluoro nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-O-Methyl nucleotide
<220> FEATURE:
<221> NAME/KEY: modified_base
<222> LOCATION: (21)..(21)
<223> OTHER INFORMATION: 2'-O-Methyl nucleotide

<400> SEQUENCE: 21
ccgugugcac uucgcuucac c                                             21

<210> SEQ ID NO 22
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-Fluoro nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
```

```
<223> OTHER INFORMATION: 2'-Fluoro nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-Fluoro nucleotide
<220> FEATURE:
<221> NAME/KEY: modified_base
<222> LOCATION: (6)..(6)
<223> OTHER INFORMATION: 2'-O-Methyl nucleotide
<220> FEATURE:
<221> NAME/KEY: modified_base
<222> LOCATION: (7)..(7)
<223> OTHER INFORMATION: 2'-Fluoro nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-O-Methyl nucleotide
<220> FEATURE:
<221> NAME/KEY: modified_base
<222> LOCATION: (10)..(10)
<223> OTHER INFORMATION: 2'-Fluoro nucleotide
<220> FEATURE:
<221> NAME/KEY: modified_base
<222> LOCATION: (11)..(11)
<223> OTHER INFORMATION: 2'-O-Methyl nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-Fluoro nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-Fluoro nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-Fluoro nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-Fluoro nucleotide
<220> FEATURE:
<221> NAME/KEY: modified_base
<222> LOCATION: (21)..(21)
<223> OTHER INFORMATION: 2'-O-Methyl nucleotide
<220> FEATURE:
<221> NAME/KEY: misc_feature
<222> LOCATION: (21)..(22)
<223> OTHER INFORMATION: Phosphorothioate linker
<220> FEATURE:
<221> NAME/KEY: modified_base
```

```
<222> LOCATION: (22)..(22)
<223> OTHER INFORMATION: 2'-O-Methyl nucleotide
<220> FEATURE:
<221> NAME/KEY: misc_feature
<222> LOCATION: (22)..(23)
<223> OTHER INFORMATION: Phosphorothioate linker
<220> FEATURE:
<221> NAME/KEY: modified_base
<222> LOCATION: (23)..(23)
<223> OTHER INFORMATION: 2'-O-Methyl nucleotide

<400> SEQUENCE: 22
ggugaagcga agugcacacg gucuu                                          25

<210> SEQ ID NO 23
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-O-Methyl nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-O-Methyl nucleotide
<220> FEATURE:
<221> NAME/KEY: modified_base
<222> LOCATION: (6)..(6)
<223> OTHER INFORMATION: 2'-O-Methyl nucleotide
<220> FEATURE:
<221> NAME/KEY: modified_base
<222> LOCATION: (7)..(7)
<223> OTHER INFORMATION: 2'-Fluoro nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-Fluoro nucleotide
<220> FEATURE:
<221> NAME/KEY: modified_base
<222> LOCATION: (10)..(10)
<223> OTHER INFORMATION: 2'-Fluoro nucleotide
<220> FEATURE:
<221> NAME/KEY: modified_base
<222> LOCATION: (11)..(11)
<223> OTHER INFORMATION: 2'-Fluoro nucleotide
<220> FEATURE:
<221> NAME/KEY: modified_base
<222> LOCATION: (12)..(12)
<223> OTHER INFORMATION: 2'-O-Methyl nucleotide
```

```
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-O-Methyl nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-O-Methyl nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-O-Methyl nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-O-Methyl nucleotide
<220> FEATURE:
<221> NAME/KEY: modified_base
<222> LOCATION: (21)..(21)
<223> OTHER INFORMATION: 2'-O-Methyl nucleotide

<400> SEQUENCE: 23
ccgugugcac uucgcuucac c                                              21

<210> SEQ ID NO 24
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-Fluoro nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-O-Methyl nucleotide
<220> FEATURE:
<221> NAME/KEY: modified_base
```

```
<222> LOCATION: (6)..(6)
<223> OTHER INFORMATION: 2'-Fluoro nucleotide
<220> FEATURE:
<221> NAME/KEY: modified_base
<222> LOCATION: (7)..(7)
<223> OTHER INFORMATION: 2'-O-Methyl nucleotide
<220> FEATURE:
<221> NAME/KEY: modified_base
<222> LOCATION: (8)..(8)
<223> OTHER INFORMATION: 2'-Fluoro nucleotide
<220> FEATURE:
<221> NAME/KEY: modified_base
<222> LOCATION: (9)..(9)
<223> OTHER INFORMATION: 2'-Fluoro nucleotide
<220> FEATURE:
<221> NAME/KEY: modified_base
<222> LOCATION: (10)..(10)
<223> OTHER INFORMATION: 2'-O-Methyl nucleotide
<220> FEATURE:
<221> NAME/KEY: modified_base
<222> LOCATION: (11)..(11)
<223> OTHER INFORMATION: 2'-O-Methyl nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-Fluoro nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-Fluoro nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-O-Methyl nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-O-Methyl nucleotide
<220> FEATURE:
<221> NAME/KEY: modified_base
<222> LOCATION: (21)..(21)
<223> OTHER INFORMATION: 2'-O-Methyl nucleotide
<220> FEATURE:
<221> NAME/KEY: misc_feature
<222> LOCATION: (21)..(22)
<223> OTHER INFORMATION: Phosphorothioate linker
<220> FEATURE:
<221> NAME/KEY: modified_base
<222> LOCATION: (22)..(22)
<223> OTHER INFORMATION: 2'-O-Methyl nucleotide
<220> FEATURE:
<221> NAME/KEY: misc_feature
<222> LOCATION: (22)..(23)
<223> OTHER INFORMATION: Phosphorothioate linker
<220> FEATURE:
<221> NAME/KEY: modified_base
<222> LOCATION: (23)..(23)
<223> OTHER INFORMATION: 2'-O-Methyl nucleotide
```

<400> SEQUENCE: 24
ggugaagcga agugcacacg gucuu     25

<210> SEQ ID NO 25
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-O-Methyl nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-Fluoro nucleotide
<220> FEATURE:
<221> NAME/KEY: modified_base
<222> LOCATION: (6)..(6)
<223> OTHER INFORMATION: 2'-O-Methyl nucleotide
<220> FEATURE:
<221> NAME/KEY: modified_base
<222> LOCATION: (7)..(7)
<223> OTHER INFORMATION: 2'-Fluoro nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-Fluoro nucleotide
<220> FEATURE:
<221> NAME/KEY: modified_base
<222> LOCATION: (10)..(10)
<223> OTHER INFORMATION: 2'-O-Methyl nucleotide
<220> FEATURE:
<221> NAME/KEY: modified_base
<222> LOCATION: (11)..(11)
<223> OTHER INFORMATION: 2'-Fluoro nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-O-Methyl nucleotide
<220> FEATURE:
<221> NAME/KEY: modified_base
<222> LOCATION: (15)..(15)

```
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-O-Methyl nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-O-Methyl nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-O-Methyl nucleotide
<220> FEATURE:
<221> NAME/KEY: modified_base
<222> LOCATION: (21)..(21)
<223> OTHER INFORMATION: 2'-O-Methyl nucleotide

<400> SEQUENCE: 25
ccgugugcac uucgcuucac c                                              21

<210> SEQ ID NO 26
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-Fluoro nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-O-Methyl nucleotide
<220> FEATURE:
<221> NAME/KEY: modified_base
<222> LOCATION: (6)..(6)
<223> OTHER INFORMATION: 2'-Fluoro nucleotide
<220> FEATURE:
<221> NAME/KEY: modified_base
<222> LOCATION: (7)..(7)
<223> OTHER INFORMATION: 2'-O-Methyl nucleotide
<220> FEATURE:
<221> NAME/KEY: modified_base
<222> LOCATION: (8)..(8)
<223> OTHER INFORMATION: 2'-Fluoro nucleotide
<220> FEATURE:
```

```
<221> NAME/KEY: modified_base
<222> LOCATION: (9)..(9)
<223> OTHER INFORMATION: 2'-Fluoro nucleotide
<220> FEATURE:
<221> NAME/KEY: modified_base
<222> LOCATION: (10)..(10)
<223> OTHER INFORMATION: 2'-O-Methyl nucleotide
<220> FEATURE:
<221> NAME/KEY: modified_base
<222> LOCATION: (11)..(11)
<223> OTHER INFORMATION: 2'-O-Methyl nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-Fluoro nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-Fluoro nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-O-Methyl nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-O-Methyl nucleotide
<220> FEATURE:
<221> NAME/KEY: modified_base
<222> LOCATION: (21)..(21)
<223> OTHER INFORMATION: 2'-O-Methyl nucleotide
<220> FEATURE:
<221> NAME/KEY: misc_feature
<222> LOCATION: (21)..(22)
<223> OTHER INFORMATION: Phosphorothioate linker
<220> FEATURE:
<221> NAME/KEY: modified_base
<222> LOCATION: (22)..(22)
<223> OTHER INFORMATION: 2'-O-Methyl nucleotide
<220> FEATURE:
<221> NAME/KEY: misc_feature
<222> LOCATION: (22)..(23)
<223> OTHER INFORMATION: Phosphorothioate linker
<220> FEATURE:
<221> NAME/KEY: modified_base
<222> LOCATION: (23)..(23)
<223> OTHER INFORMATION: 2'-O-Methyl nucleotide

<400> SEQUENCE: 26
ggugaagcga agugcacacg gucuu                                                25

<210> SEQ ID NO 27
<211> LENGTH: 21
<212> TYPE: RNA
<213> ORGANISM: Artificial Sequence
<220> FEATURE:
<223> OTHER INFORMATION: Description of Artificial Sequence: Synthetic
```

```
         oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-O-Methyl nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-O-Methyl nucleotide
<220> FEATURE:
<221> NAME/KEY: modified_base
<222> LOCATION: (6)..(6)
<223> OTHER INFORMATION: 2'-O-Methyl nucleotide
<220> FEATURE:
<221> NAME/KEY: modified_base
<222> LOCATION: (7)..(7)
<223> OTHER INFORMATION: 2'-Fluoro nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-Fluoro nucleotide
<220> FEATURE:
<221> NAME/KEY: modified_base
<222> LOCATION: (10)..(10)
<223> OTHER INFORMATION: 2'-Fluoro nucleotide
<220> FEATURE:
<221> NAME/KEY: modified_base
<222> LOCATION: (11)..(11)
<223> OTHER INFORMATION: 2'-Fluoro nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-O-Methyl nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-O-Methyl nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
```

```
<222> LOCATION: (18)..(18)
<223> OTHER INFORMATION: 2'-Fluoro nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-O-Methyl nucleotide
<220> FEATURE:
<221> NAME/KEY: modified_base
<222> LOCATION: (21)..(21)
<223> OTHER INFORMATION: 2'-O-Methyl nucleotide

<400> SEQUENCE: 27
ccgugugcac uucgcuucac c                                          21

<210> SEQ ID NO 28
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-Fluoro nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-O-Methyl nucleotide
<220> FEATURE:
<221> NAME/KEY: modified_base
<222> LOCATION: (6)..(6)
<223> OTHER INFORMATION: 2'-Fluoro nucleotide
<220> FEATURE:
<221> NAME/KEY: modified_base
<222> LOCATION: (7)..(7)
<223> OTHER INFORMATION: 2'-O-Methyl nucleotide
<220> FEATURE:
<221> NAME/KEY: modified_base
<222> LOCATION: (8)..(8)
<223> OTHER INFORMATION: 2'-Fluoro nucleotide
<220> FEATURE:
<221> NAME/KEY: modified_base
<222> LOCATION: (9)..(9)
<223> OTHER INFORMATION: 2'-O-Methyl nucleotide
<220> FEATURE:
<221> NAME/KEY: modified_base
<222> LOCATION: (10)..(10)
<223> OTHER INFORMATION: 2'-O-Methyl nucleotide
<220> FEATURE:
<221> NAME/KEY: modified_base
<222> LOCATION: (11)..(11)
<223> OTHER INFORMATION: 2'-O-Methyl nucleotide
```

```
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-Fluoro nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-Fluoro nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-O-Methyl nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-Fluoro nucleotide
<220> FEATURE:
<221> NAME/KEY: modified_base
<222> LOCATION: (21)..(21)
<223> OTHER INFORMATION: 2'-O-Methyl nucleotide
<220> FEATURE:
<221> NAME/KEY: misc_feature
<222> LOCATION: (21)..(22)
<223> OTHER INFORMATION: Phosphorothioate linker
<220> FEATURE:
<221> NAME/KEY: modified_base
<222> LOCATION: (22)..(22)
<223> OTHER INFORMATION: 2'-O-Methyl nucleotide
<220> FEATURE:
<221> NAME/KEY: misc_feature
<222> LOCATION: (22)..(23)
<223> OTHER INFORMATION: Phosphorothioate linker
<220> FEATURE:
<221> NAME/KEY: modified_base
<222> LOCATION: (23)..(23)
<223> OTHER INFORMATION: 2'-O-Methyl nucleotide

<400> SEQUENCE: 28
ggugaagcga agugcacacg gucuu                                              25

<210> SEQ ID NO 29
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-Fluoro nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
```

```
<222> LOCATION: (2)..(2)
<223> OTHER INFORMATION: 2'-O-Methyl nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-Fluoro nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-Fluoro nucleotide
<220> FEATURE:
<221> NAME/KEY: modified_base
<222> LOCATION: (6)..(6)
<223> OTHER INFORMATION: 2'-Fluoro nucleotide
<220> FEATURE:
<221> NAME/KEY: modified_base
<222> LOCATION: (7)..(7)
<223> OTHER INFORMATION: 2'-Fluoro nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-O-Methyl nucleotide
<220> FEATURE:
<221> NAME/KEY: modified_base
<222> LOCATION: (10)..(10)
<223> OTHER INFORMATION: 2'-Fluoro nucleotide
<220> FEATURE:
<221> NAME/KEY: modified_base
<222> LOCATION: (11)..(11)
<223> OTHER INFORMATION: 2'-O-Methyl nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-Fluoro nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-O-Methyl nucleotide
<220> FEATURE:
<221> NAME/KEY: modified_base
<222> LOCATION: (17)..(17)
<223> OTHER INFORMATION: 2'-O-Methyl nucleotide

<400> SEQUENCE: 29
gugcacuucg cuucacc                                              17

<210> SEQ ID NO 30
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
```

-continued

```
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-Fluoro nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-Fluoro nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-Fluoro nucleotide
<220> FEATURE:
<221> NAME/KEY: modified_base
<222> LOCATION: (6)..(6)
<223> OTHER INFORMATION: 2'-O-Methyl nucleotide
<220> FEATURE:
<221> NAME/KEY: modified_base
<222> LOCATION: (7)..(7)
<223> OTHER INFORMATION: 2'-Fluoro nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-O-Methyl nucleotide
<220> FEATURE:
<221> NAME/KEY: modified_base
<222> LOCATION: (10)..(10)
<223> OTHER INFORMATION: 2'-Fluoro nucleotide
<220> FEATURE:
<221> NAME/KEY: modified_base
<222> LOCATION: (11)..(11)
<223> OTHER INFORMATION: 2'-O-Methyl nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-Fluoro nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-Fluoro nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
```

```
<223> OTHER INFORMATION: 2'-Fluoro nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: misc_feature
<222> LOCATION: (19)..(20)
<223> OTHER INFORMATION: Phosphorothioate linker
<220> FEATURE:
<221> NAME/KEY: modified_base
<222> LOCATION: (20)..(20)
<223> OTHER INFORMATION: 2'-Fluoro nucleotide
<220> FEATURE:
<221> NAME/KEY: misc_feature
<222> LOCATION: (20)..(21)
<223> OTHER INFORMATION: Phosphorothioate linker
<220> FEATURE:
<221> NAME/KEY: modified_base
<222> LOCATION: (21)..(21)
<223> OTHER INFORMATION: 2'-O-Methyl nucleotide

<400> SEQUENCE: 30
ggugaagcga agugcacacg gu                                               22

<210> SEQ ID NO 31
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-Fluoro nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-O-Methyl nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-Fluoro nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-Fluoro nucleotide
<220> FEATURE:
<221> NAME/KEY: modified_base
<222> LOCATION: (6)..(6)
<223> OTHER INFORMATION: 2'-Fluoro nucleotide
<220> FEATURE:
<221> NAME/KEY: modified_base
<222> LOCATION: (7)..(7)
<223> OTHER INFORMATION: 2'-Fluoro nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-O-Methyl nucleotide
<220> FEATURE:
```

```
<221> NAME/KEY: modified_base
<222> LOCATION: (10)..(10)
<223> OTHER INFORMATION: 2'-Fluoro nucleotide
<220> FEATURE:
<221> NAME/KEY: modified_base
<222> LOCATION: (11)..(11)
<223> OTHER INFORMATION: 2'-O-Methyl nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-Fluoro nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-O-Methyl nucleotide
<220> FEATURE:
<221> NAME/KEY: modified_base
<222> LOCATION: (17)..(17)
<223> OTHER INFORMATION: 2'-O-Methyl nucleotide

<400> SEQUENCE: 31
gugcacuucg cuucacc                                                    17

<210> SEQ ID NO 32
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-Fluoro nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-Fluoro nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-Fluoro nucleotide
<220> FEATURE:
<221> NAME/KEY: modified_base
<222> LOCATION: (6)..(6)
<223> OTHER INFORMATION: 2'-O-Methyl nucleotide
<220> FEATURE:
<221> NAME/KEY: modified_base
<222> LOCATION: (7)..(7)
```

```
<223> OTHER INFORMATION: 2'-Fluoro nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-O-Methyl nucleotide
<220> FEATURE:
<221> NAME/KEY: modified_base
<222> LOCATION: (10)..(10)
<223> OTHER INFORMATION: 2'-Fluoro nucleotide
<220> FEATURE:
<221> NAME/KEY: modified_base
<222> LOCATION: (11)..(11)
<223> OTHER INFORMATION: 2'-O-Methyl nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-Fluoro nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-Fluoro nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-Fluoro nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: misc_feature
<222> LOCATION: (19)..(20)
<223> OTHER INFORMATION: Phosphorothioate linker
<220> FEATURE:
<221> NAME/KEY: modified_base
<222> LOCATION: (20)..(20)
<223> OTHER INFORMATION: 2'-Fluoro nucleotide
<220> FEATURE:
<221> NAME/KEY: misc_feature
<222> LOCATION: (20)..(21)
<223> OTHER INFORMATION: Phosphorothioate linker
<220> FEATURE:
<221> NAME/KEY: modified_base
<222> LOCATION: (21)..(21)
<223> OTHER INFORMATION: 2'-O-Methyl nucleotide

<400> SEQUENCE: 32
ggugaagcga agugcacacg g                                              21

<210> SEQ ID NO 33
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
```

```
<221> NAME/KEY: modified_base
<222> LOCATION: (1)..(1)
<223> OTHER INFORMATION: 2'-Fluoro nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-O-Methyl nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-Fluoro nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-Fluoro nucleotide
<220> FEATURE:
<221> NAME/KEY: modified_base
<222> LOCATION: (6)..(6)
<223> OTHER INFORMATION: 2'-Fluoro nucleotide
<220> FEATURE:
<221> NAME/KEY: modified_base
<222> LOCATION: (7)..(7)
<223> OTHER INFORMATION: 2'-Fluoro nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-O-Methyl nucleotide
<220> FEATURE:
<221> NAME/KEY: modified_base
<222> LOCATION: (10)..(10)
<223> OTHER INFORMATION: 2'-Fluoro nucleotide
<220> FEATURE:
<221> NAME/KEY: modified_base
<222> LOCATION: (11)..(11)
<223> OTHER INFORMATION: 2'-O-Methyl nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-Fluoro nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-O-Methyl nucleotide
<220> FEATURE:
<221> NAME/KEY: modified_base
<222> LOCATION: (17)..(17)
<223> OTHER INFORMATION: 2'-O-Methyl nucleotide

<400> SEQUENCE: 33
gugcacuucg cuucacc                                                   17
```

```
<210> SEQ ID NO 34
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-Fluoro nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-Fluoro nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-Fluoro nucleotide
<220> FEATURE:
<221> NAME/KEY: modified_base
<222> LOCATION: (6)..(6)
<223> OTHER INFORMATION: 2'-O-Methyl nucleotide
<220> FEATURE:
<221> NAME/KEY: modified_base
<222> LOCATION: (7)..(7)
<223> OTHER INFORMATION: 2'-Fluoro nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-O-Methyl nucleotide
<220> FEATURE:
<221> NAME/KEY: modified_base
<222> LOCATION: (10)..(10)
<223> OTHER INFORMATION: 2'-Fluoro nucleotide
<220> FEATURE:
<221> NAME/KEY: modified_base
<222> LOCATION: (11)..(11)
<223> OTHER INFORMATION: 2'-O-Methyl nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-Fluoro nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
```

<222> LOCATION: (16)..(16)
<223> OTHER INFORMATION: 2'-Fluoro nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: misc_feature
<222> LOCATION: (17)..(18)
<223> OTHER INFORMATION: Phosphorothioate linker
<220> FEATURE:
<221> NAME/KEY: modified_base
<222> LOCATION: (18)..(18)
<223> OTHER INFORMATION: 2'-Fluoro nucleotide
<220> FEATURE:
<221> NAME/KEY: misc_feature
<222> LOCATION: (18)..(19)
<223> OTHER INFORMATION: Phosphorothioate linker
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: misc_feature
<222> LOCATION: (19)..(20)
<223> OTHER INFORMATION: Phosphorothioate linker
<220> FEATURE:
<221> NAME/KEY: modified_base
<222> LOCATION: (20)..(20)
<223> OTHER INFORMATION: 2'-Fluoro nucleotide
<220> FEATURE:
<221> NAME/KEY: misc_feature
<222> LOCATION: (20)..(21)
<223> OTHER INFORMATION: Phosphorothioate linker
<220> FEATURE:
<221> NAME/KEY: modified_base
<222> LOCATION: (21)..(21)
<223> OTHER INFORMATION: 2'-O-Methyl nucleotide

<400> SEQUENCE: 34
ggugaagcga agugcacacg g                                              21

<210> SEQ ID NO 35
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-Fluoro nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-O-Methyl nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-Fluoro nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-Fluoro nucleotide

```
<220> FEATURE:
<221> NAME/KEY: modified_base
<222> LOCATION: (6)..(6)
<223> OTHER INFORMATION: 2'-O-Methyl nucleotide
<220> FEATURE:
<221> NAME/KEY: modified_base
<222> LOCATION: (7)..(7)
<223> OTHER INFORMATION: 2'-Fluoro nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-Fluoro nucleotide
<220> FEATURE:
<221> NAME/KEY: modified_base
<222> LOCATION: (10)..(10)
<223> OTHER INFORMATION: 2'-Fluoro nucleotide
<220> FEATURE:
<221> NAME/KEY: modified_base
<222> LOCATION: (11)..(11)
<223> OTHER INFORMATION: 2'-Fluoro nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-Fluoro nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-O-Methyl nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-Fluoro nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-O-Methyl nucleotide
<220> FEATURE:
<221> NAME/KEY: modified_base
<222> LOCATION: (21)..(21)
<223> OTHER INFORMATION: 2'-O-Methyl nucleotide

<400> SEQUENCE: 35
ccgugugcac uucgcuucac a                                              21

<210> SEQ ID NO 36
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
```

-continued

```
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-Fluoro nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-Fluoro nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-Fluoro nucleotide
<220> FEATURE:
<221> NAME/KEY: modified_base
<222> LOCATION: (6)..(6)
<223> OTHER INFORMATION: 2'-O-Methyl nucleotide
<220> FEATURE:
<221> NAME/KEY: modified_base
<222> LOCATION: (7)..(7)
<223> OTHER INFORMATION: 2'-Fluoro nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-O-Methyl nucleotide
<220> FEATURE:
<221> NAME/KEY: modified_base
<222> LOCATION: (10)..(10)
<223> OTHER INFORMATION: 2'-Fluoro nucleotide
<220> FEATURE:
<221> NAME/KEY: modified_base
<222> LOCATION: (11)..(11)
<223> OTHER INFORMATION: 2'-O-Methyl nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-Fluoro nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-Fluoro nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-Fluoro nucleotide
<220> FEATURE:
```

```
<221> NAME/KEY: modified_base
<222> LOCATION: (19)..(19)
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-Fluoro nucleotide
<220> FEATURE:
<221> NAME/KEY: modified_base
<222> LOCATION: (21)..(21)
<223> OTHER INFORMATION: 2'-O-Methyl nucleotide
<220> FEATURE:
<221> NAME/KEY: misc_feature
<222> LOCATION: (21)..(22)
<223> OTHER INFORMATION: Phosphorothioate linker
<220> FEATURE:
<221> NAME/KEY: modified_base
<222> LOCATION: (22)..(22)
<223> OTHER INFORMATION: 2'-O-Methyl nucleotide
<220> FEATURE:
<221> NAME/KEY: misc_feature
<222> LOCATION: (22)..(23)
<223> OTHER INFORMATION: Phosphorothioate linker
<220> FEATURE:
<221> NAME/KEY: modified_base
<222> LOCATION: (23)..(23)
<223> OTHER INFORMATION: 2'-O-Methyl nucleotide

<400> SEQUENCE: 36
ugugaagcga agugcacacg guc                                              23

<210> SEQ ID NO 37
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-Fluoro nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-O-Methyl nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-Fluoro nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-Fluoro nucleotide
<220> FEATURE:
<221> NAME/KEY: modified_base
<222> LOCATION: (6)..(6)
<223> OTHER INFORMATION: 2'-O-Methyl nucleotide
<220> FEATURE:
<221> NAME/KEY: modified_base
<222> LOCATION: (7)..(7)
<223> OTHER INFORMATION: 2'-Fluoro nucleotide
<220> FEATURE:
<221> NAME/KEY: modified_base
<222> LOCATION: (8)..(8)
```

```
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-Fluoro nucleotide
<220> FEATURE:
<221> NAME/KEY: modified_base
<222> LOCATION: (10)..(10)
<223> OTHER INFORMATION: 2'-Fluoro nucleotide
<220> FEATURE:
<221> NAME/KEY: modified_base
<222> LOCATION: (11)..(11)
<223> OTHER INFORMATION: 2'-Fluoro nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-Fluoro nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-O-Methyl nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-Fluoro nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-O-Methyl nucleotide
<220> FEATURE:
<221> NAME/KEY: modified_base
<222> LOCATION: (21)..(21)
<223> OTHER INFORMATION: 2'-O-Methyl nucleotide

<400> SEQUENCE: 37
ccgugugcac uucgcuucac a                                             21

<210> SEQ ID NO 38
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-Fluoro nucleotide
<220> FEATURE:
```

```
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-Fluoro nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-Fluoro nucleotide
<220> FEATURE:
<221> NAME/KEY: modified_base
<222> LOCATION: (6)..(6)
<223> OTHER INFORMATION: 2'-O-Methyl nucleotide
<220> FEATURE:
<221> NAME/KEY: modified_base
<222> LOCATION: (7)..(7)
<223> OTHER INFORMATION: 2'-Fluoro nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-O-Methyl nucleotide
<220> FEATURE:
<221> NAME/KEY: modified_base
<222> LOCATION: (10)..(10)
<223> OTHER INFORMATION: 2'-Fluoro nucleotide
<220> FEATURE:
<221> NAME/KEY: modified_base
<222> LOCATION: (11)..(11)
<223> OTHER INFORMATION: 2'-O-Methyl nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-Fluoro nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-Fluoro nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-Fluoro nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-Fluoro nucleotide
<220> FEATURE:
<221> NAME/KEY: modified_base
<222> LOCATION: (21)..(21)
<223> OTHER INFORMATION: 2'-O-Methyl nucleotide
```

```
<220> FEATURE:
<221> NAME/KEY: misc_feature
<222> LOCATION: (21)..(22)
<223> OTHER INFORMATION: Phosphorothioate linker
<220> FEATURE:
<221> NAME/KEY: modified_base
<222> LOCATION: (22)..(22)
<223> OTHER INFORMATION: 2'-O-Methyl nucleotide
<220> FEATURE:
<221> NAME/KEY: misc_feature
<222> LOCATION: (22)..(23)
<223> OTHER INFORMATION: Phosphorothioate linker
<220> FEATURE:
<221> NAME/KEY: modified_base
<222> LOCATION: (23)..(23)
<223> OTHER INFORMATION: 2'-O-Methyl nucleotide

<400> SEQUENCE: 38
ugugaagcga agugcacacg gucuu                                             25

<210> SEQ ID NO 39
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-O-Methyl nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-O-Methyl nucleotide
<220> FEATURE:
<221> NAME/KEY: modified_base
<222> LOCATION: (6)..(6)
<223> OTHER INFORMATION: 2'-O-Methyl nucleotide
<220> FEATURE:
<221> NAME/KEY: modified_base
<222> LOCATION: (7)..(7)
<223> OTHER INFORMATION: 2'-Fluoro nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-Fluoro nucleotide
<220> FEATURE:
<221> NAME/KEY: modified_base
<222> LOCATION: (10)..(10)
<223> OTHER INFORMATION: 2'-Fluoro nucleotide
<220> FEATURE:
<221> NAME/KEY: modified_base
```

```
<222> LOCATION: (11)..(11)
<223> OTHER INFORMATION: 2'-Fluoro nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-O-Methyl nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-O-Methyl nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-O-Methyl nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-O-Methyl nucleotide
<220> FEATURE:
<221> NAME/KEY: modified_base
<222> LOCATION: (21)..(21)
<223> OTHER INFORMATION: 2'-O-Methyl nucleotide

<400> SEQUENCE: 39
ccgugugcac uucgcuucac a                                              21

<210> SEQ ID NO 40
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-Fluoro nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (4)..(4)
<223> OTHER INFORMATION: 2'-O-Methyl nucleotide
```

-continued

```
<220> FEATURE:
<221> NAME/KEY: modified_base
<222> LOCATION: (5)..(5)
<223> OTHER INFORMATION: 2'-O-Methyl nucleotide
<220> FEATURE:
<221> NAME/KEY: modified_base
<222> LOCATION: (6)..(6)
<223> OTHER INFORMATION: 2'-Fluoro nucleotide
<220> FEATURE:
<221> NAME/KEY: modified_base
<222> LOCATION: (7)..(7)
<223> OTHER INFORMATION: 2'-O-Methyl nucleotide
<220> FEATURE:
<221> NAME/KEY: modified_base
<222> LOCATION: (8)..(8)
<223> OTHER INFORMATION: 2'-Fluoro nucleotide
<220> FEATURE:
<221> NAME/KEY: modified_base
<222> LOCATION: (9)..(9)
<223> OTHER INFORMATION: 2'-Fluoro nucleotide
<220> FEATURE:
<221> NAME/KEY: modified_base
<222> LOCATION: (10)..(10)
<223> OTHER INFORMATION: 2'-O-Methyl nucleotide
<220> FEATURE:
<221> NAME/KEY: modified_base
<222> LOCATION: (11)..(11)
<223> OTHER INFORMATION: 2'-O-Methyl nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-Fluoro nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-Fluoro nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-O-Methyl nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-O-Methyl nucleotide
<220> FEATURE:
<221> NAME/KEY: modified_base
<222> LOCATION: (21)..(21)
<223> OTHER INFORMATION: 2'-O-Methyl nucleotide
<220> FEATURE:
<221> NAME/KEY: misc_feature
<222> LOCATION: (21)..(22)
<223> OTHER INFORMATION: Phosphorothioate linker
<220> FEATURE:
<221> NAME/KEY: modified_base
<222> LOCATION: (22)..(22)
<223> OTHER INFORMATION: 2'-O-Methyl nucleotide
<220> FEATURE:
<221> NAME/KEY: misc_feature
<222> LOCATION: (22)..(23)
```

```
<223> OTHER INFORMATION: Phosphorothioate linker
<220> FEATURE:
<221> NAME/KEY: modified_base
<222> LOCATION: (23)..(23)
<223> OTHER INFORMATION: 2'-O-Methyl nucleotide

<400> SEQUENCE: 40
ugugaagcga agugcacacg gucuu                                              25

<210> SEQ ID NO 41
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-O-Methyl nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-Fluoro nucleotide
<220> FEATURE:
<221> NAME/KEY: modified_base
<222> LOCATION: (6)..(6)
<223> OTHER INFORMATION: 2'-O-Methyl nucleotide
<220> FEATURE:
<221> NAME/KEY: modified_base
<222> LOCATION: (7)..(7)
<223> OTHER INFORMATION: 2'-Fluoro nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-Fluoro nucleotide
<220> FEATURE:
<221> NAME/KEY: modified_base
<222> LOCATION: (10)..(10)
<223> OTHER INFORMATION: 2'-O-Methyl nucleotide
<220> FEATURE:
<221> NAME/KEY: modified_base
<222> LOCATION: (11)..(11)
<223> OTHER INFORMATION: 2'-Fluoro nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
```

```
<221> NAME/KEY: modified_base
<222> LOCATION: (14)..(14)
<223> OTHER INFORMATION: 2'-O-Methyl nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-O-Methyl nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-O-Methyl nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-O-Methyl nucleotide
<220> FEATURE:
<221> NAME/KEY: modified_base
<222> LOCATION: (21)..(21)
<223> OTHER INFORMATION: 2'-O-Methyl nucleotide

<400> SEQUENCE: 41
ccgugugcac uucgcuucac a                                              21

<210> SEQ ID NO 42
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-Fluoro nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-O-Methyl nucleotide
<220> FEATURE:
<221> NAME/KEY: modified_base
<222> LOCATION: (6)..(6)
<223> OTHER INFORMATION: 2'-Fluoro nucleotide
<220> FEATURE:
<221> NAME/KEY: modified_base
<222> LOCATION: (7)..(7)
```

```
<223> OTHER INFORMATION: 2'-O-Methyl nucleotide
<220> FEATURE:
<221> NAME/KEY: modified_base
<222> LOCATION: (8)..(8)
<223> OTHER INFORMATION: 2'-Fluoro nucleotide
<220> FEATURE:
<221> NAME/KEY: modified_base
<222> LOCATION: (9)..(9)
<223> OTHER INFORMATION: 2'-Fluoro nucleotide
<220> FEATURE:
<221> NAME/KEY: modified_base
<222> LOCATION: (10)..(10)
<223> OTHER INFORMATION: 2'-O-Methyl nucleotide
<220> FEATURE:
<221> NAME/KEY: modified_base
<222> LOCATION: (11)..(11)
<223> OTHER INFORMATION: 2'-O-Methyl nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-Fluoro nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-Fluoro nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-O-Methyl nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-O-Methyl nucleotide
<220> FEATURE:
<221> NAME/KEY: modified_base
<222> LOCATION: (21)..(21)
<223> OTHER INFORMATION: 2'-O-Methyl nucleotide
<220> FEATURE:
<221> NAME/KEY: misc_feature
<222> LOCATION: (21)..(22)
<223> OTHER INFORMATION: Phosphorothioate linker
<220> FEATURE:
<221> NAME/KEY: modified_base
<222> LOCATION: (22)..(22)
<223> OTHER INFORMATION: 2'-O-Methyl nucleotide
<220> FEATURE:
<221> NAME/KEY: misc_feature
<222> LOCATION: (22)..(23)
<223> OTHER INFORMATION: Phosphorothioate linker
<220> FEATURE:
<221> NAME/KEY: modified_base
<222> LOCATION: (23)..(23)
<223> OTHER INFORMATION: 2'-O-Methyl nucleotide

<400> SEQUENCE: 42
ugugaagcga agugcacacg gucuu                                       25
```

-continued

```
<210> SEQ ID NO 43
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-O-Methyl nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-O-Methyl nucleotide
<220> FEATURE:
<221> NAME/KEY: modified_base
<222> LOCATION: (6)..(6)
<223> OTHER INFORMATION: 2'-O-Methyl nucleotide
<220> FEATURE:
<221> NAME/KEY: modified_base
<222> LOCATION: (7)..(7)
<223> OTHER INFORMATION: 2'-Fluoro nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-Fluoro nucleotide
<220> FEATURE:
<221> NAME/KEY: modified_base
<222> LOCATION: (10)..(10)
<223> OTHER INFORMATION: 2'-Fluoro nucleotide
<220> FEATURE:
<221> NAME/KEY: modified_base
<222> LOCATION: (11)..(11)
<223> OTHER INFORMATION: 2'-Fluoro nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-O-Methyl nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-O-Methyl nucleotide
```

-continued

```
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-Fluoro nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-O-Methyl nucleotide
<220> FEATURE:
<221> NAME/KEY: modified_base
<222> LOCATION: (21)..(21)
<223> OTHER INFORMATION: 2'-O-Methyl nucleotide

<400> SEQUENCE: 43
ccgugugcac uucgcuucac a                                              21

<210> SEQ ID NO 44
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-Fluoro nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-O-Methyl nucleotide
<220> FEATURE:
<221> NAME/KEY: modified_base
<222> LOCATION: (6)..(6)
<223> OTHER INFORMATION: 2'-Fluoro nucleotide
<220> FEATURE:
<221> NAME/KEY: modified_base
<222> LOCATION: (7)..(7)
<223> OTHER INFORMATION: 2'-O-Methyl nucleotide
<220> FEATURE:
<221> NAME/KEY: modified_base
<222> LOCATION: (8)..(8)
<223> OTHER INFORMATION: 2'-Fluoro nucleotide
<220> FEATURE:
<221> NAME/KEY: modified_base
<222> LOCATION: (9)..(9)
<223> OTHER INFORMATION: 2'-O-Methyl nucleotide
<220> FEATURE:
<221> NAME/KEY: modified_base
```

```
<222> LOCATION: (10)..(10)
<223> OTHER INFORMATION: 2'-O-Methyl nucleotide
<220> FEATURE:
<221> NAME/KEY: modified_base
<222> LOCATION: (11)..(11)
<223> OTHER INFORMATION: 2'-O-Methyl nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-Fluoro nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-Fluoro nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-O-Methyl nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-Fluoro nucleotide
<220> FEATURE:
<221> NAME/KEY: modified_base
<222> LOCATION: (21)..(21)
<223> OTHER INFORMATION: 2'-O-Methyl nucleotide
<220> FEATURE:
<221> NAME/KEY: misc_feature
<222> LOCATION: (21)..(22)
<223> OTHER INFORMATION: Phosphorothioate linker
<220> FEATURE:
<221> NAME/KEY: modified_base
<222> LOCATION: (22)..(22)
<223> OTHER INFORMATION: 2'-O-Methyl nucleotide
<220> FEATURE:
<221> NAME/KEY: misc_feature
<222> LOCATION: (22)..(23)
<223> OTHER INFORMATION: Phosphorothioate linker
<220> FEATURE:
<221> NAME/KEY: modified_base
<222> LOCATION: (23)..(23)
<223> OTHER INFORMATION: 2'-O-Methyl nucleotide

<400> SEQUENCE: 44
ugugaagcga agugcacacg gucuu                                     25

<210> SEQ ID NO 45
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
```

```
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-O-Methyl nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-O-Methyl nucleotide
<220> FEATURE:
<221> NAME/KEY: modified_base
<222> LOCATION: (6)..(6)
<223> OTHER INFORMATION: 2'-O-Methyl nucleotide
<220> FEATURE:
<221> NAME/KEY: modified_base
<222> LOCATION: (7)..(7)
<223> OTHER INFORMATION: 2'-O-Methyl nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-Fluoro nucleotide
<220> FEATURE:
<221> NAME/KEY: modified_base
<222> LOCATION: (10)..(10)
<223> OTHER INFORMATION: 2'-Fluoro nucleotide
<220> FEATURE:
<221> NAME/KEY: modified_base
<222> LOCATION: (11)..(11)
<223> OTHER INFORMATION: 2'-Fluoro nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-O-Methyl nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-O-Methyl nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-O-Methyl nucleotide
<220> FEATURE:
<221> NAME/KEY: modified_base
<222> LOCATION: (19)..(19)
```

```
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-O-Methyl nucleotide
<220> FEATURE:
<221> NAME/KEY: modified_base
<222> LOCATION: (21)..(21)
<223> OTHER INFORMATION: 2'-O-Methyl nucleotide

<400> SEQUENCE: 45
ccgugugcac uucgcuucac a                                             21

<210> SEQ ID NO 46
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-Fluoro nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-O-Methyl nucleotide
<220> FEATURE:
<221> NAME/KEY: modified_base
<222> LOCATION: (6)..(6)
<223> OTHER INFORMATION: 2'-O-Methyl nucleotide
<220> FEATURE:
<221> NAME/KEY: modified_base
<222> LOCATION: (7)..(7)
<223> OTHER INFORMATION: 2'-O-Methyl nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-O-Methyl nucleotide
<220> FEATURE:
<221> NAME/KEY: modified_base
<222> LOCATION: (10)..(10)
<223> OTHER INFORMATION: 2'-O-Methyl nucleotide
<220> FEATURE:
<221> NAME/KEY: modified_base
<222> LOCATION: (11)..(11)
<223> OTHER INFORMATION: 2'-O-Methyl nucleotide
<220> FEATURE:
<221> NAME/KEY: modified_base
<222> LOCATION: (12)..(12)
<223> OTHER INFORMATION: 2'-O-Methyl nucleotide
<220> FEATURE:
```

```
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-Fluoro nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-Fluoro nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-O-Methyl nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-O-Methyl nucleotide
<220> FEATURE:
<221> NAME/KEY: modified_base
<222> LOCATION: (21)..(21)
<223> OTHER INFORMATION: 2'-O-Methyl nucleotide
<220> FEATURE:
<221> NAME/KEY: misc_feature
<222> LOCATION: (21)..(22)
<223> OTHER INFORMATION: Phosphorothioate linker
<220> FEATURE:
<221> NAME/KEY: modified_base
<222> LOCATION: (22)..(22)
<223> OTHER INFORMATION: 2'-O-Methyl nucleotide
<220> FEATURE:
<221> NAME/KEY: misc_feature
<222> LOCATION: (22)..(23)
<223> OTHER INFORMATION: Phosphorothioate linker
<220> FEATURE:
<221> NAME/KEY: modified_base
<222> LOCATION: (23)..(23)
<223> OTHER INFORMATION: 2'-O-Methyl nucleotide

<400> SEQUENCE: 46
ugugaagcga agugcacacg gucuu                                         25

<210> SEQ ID NO 47
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-O-Methyl nucleotide
<220> FEATURE:
<221> NAME/KEY: misc_feature
<222> LOCATION: (2)..(3)
```

```
<223> OTHER INFORMATION: Phosphorothioate linker
<220> FEATURE:
<221> NAME/KEY: modified_base
<222> LOCATION: (3)..(3)
<223> OTHER INFORMATION: 2'-Fluoro nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-Fluoro nucleotide
<220> FEATURE:
<221> NAME/KEY: modified_base
<222> LOCATION: (6)..(6)
<223> OTHER INFORMATION: 2'-Fluoro nucleotide
<220> FEATURE:
<221> NAME/KEY: modified_base
<222> LOCATION: (7)..(7)
<223> OTHER INFORMATION: 2'-Fluoro nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-O-Methyl nucleotide
<220> FEATURE:
<221> NAME/KEY: modified_base
<222> LOCATION: (10)..(10)
<223> OTHER INFORMATION: 2'-O-Methyl nucleotide
<220> FEATURE:
<221> NAME/KEY: modified_base
<222> LOCATION: (11)..(11)
<223> OTHER INFORMATION: 2'-O-Methyl nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-O-Methyl nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-O-Methyl nucleotide
<220> FEATURE:
<221> NAME/KEY: modified_base
<222> LOCATION: (17)..(17)
<223> OTHER INFORMATION: 2'-O-Methyl nucleotide

<400> SEQUENCE: 47
gugcacuucg cuucaca                                                17

<210> SEQ ID NO 48
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
```

```
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-Fluoro nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-O-Methyl nucleotide
<220> FEATURE:
<221> NAME/KEY: modified_base
<222> LOCATION: (6)..(6)
<223> OTHER INFORMATION: 2'-Fluoro nucleotide
<220> FEATURE:
<221> NAME/KEY: modified_base
<222> LOCATION: (7)..(7)
<223> OTHER INFORMATION: 2'-O-Methyl nucleotide
<220> FEATURE:
<221> NAME/KEY: modified_base
<222> LOCATION: (8)..(8)
<223> OTHER INFORMATION: 2'-Fluoro nucleotide
<220> FEATURE:
<221> NAME/KEY: modified_base
<222> LOCATION: (9)..(9)
<223> OTHER INFORMATION: 2'-Fluoro nucleotide
<220> FEATURE:
<221> NAME/KEY: modified_base
<222> LOCATION: (10)..(10)
<223> OTHER INFORMATION: 2'-O-Methyl nucleotide
<220> FEATURE:
<221> NAME/KEY: modified_base
<222> LOCATION: (11)..(11)
<223> OTHER INFORMATION: 2'-O-Methyl nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-Fluoro nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-Fluoro nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-O-Methyl nucleotide
<220> FEATURE:
<221> NAME/KEY: modified_base
<222> LOCATION: (19)..(19)
<223> OTHER INFORMATION: 2'-O-Methyl nucleotide
```

```
<220> FEATURE:
<221> NAME/KEY: misc_feature
<222> LOCATION: (19)..(20)
<223> OTHER INFORMATION: Phosphorothioate linker
<220> FEATURE:
<221> NAME/KEY: modified_base
<222> LOCATION: (20)..(20)
<223> OTHER INFORMATION: 2'-O-Methyl nucleotide
<220> FEATURE:
<221> NAME/KEY: misc_feature
<222> LOCATION: (20)..(21)
<223> OTHER INFORMATION: Phosphorothioate linker
<220> FEATURE:
<221> NAME/KEY: modified_base
<222> LOCATION: (21)..(21)
<223> OTHER INFORMATION: 2'-O-Methyl nucleotide

<400> SEQUENCE: 48
ugugaagcga agugcacacg gu                                                  22

<210> SEQ ID NO 49
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-O-Methyl nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-Fluoro nucleotide
<220> FEATURE:
<221> NAME/KEY: modified_base
<222> LOCATION: (6)..(6)
<223> OTHER INFORMATION: 2'-Fluoro nucleotide
<220> FEATURE:
<221> NAME/KEY: modified_base
<222> LOCATION: (7)..(7)
<223> OTHER INFORMATION: 2'-Fluoro nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-O-Methyl nucleotide
<220> FEATURE:
<221> NAME/KEY: modified_base
<222> LOCATION: (10)..(10)
<223> OTHER INFORMATION: 2'-O-Methyl nucleotide
<220> FEATURE:
<221> NAME/KEY: modified_base
```

```
<222> LOCATION: (11)..(11)
<223> OTHER INFORMATION: 2'-O-Methyl nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-O-Methyl nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-O-Methyl nucleotide
<220> FEATURE:
<221> NAME/KEY: modified_base
<222> LOCATION: (17)..(17)
<223> OTHER INFORMATION: 2'-O-Methyl nucleotide

<400> SEQUENCE: 49
gugcacuucg cuucaca                                                17

<210> SEQ ID NO 50
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-Fluoro nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-O-Methyl nucleotide
<220> FEATURE:
<221> NAME/KEY: modified_base
<222> LOCATION: (6)..(6)
<223> OTHER INFORMATION: 2'-O-Methyl nucleotide
<220> FEATURE:
<221> NAME/KEY: modified_base
<222> LOCATION: (7)..(7)
<223> OTHER INFORMATION: 2'-O-Methyl nucleotide
<220> FEATURE:
<221> NAME/KEY: modified_base
<222> LOCATION: (8)..(8)
<223> OTHER INFORMATION: 2'-O-Methyl nucleotide
```

```
<220> FEATURE:
<221> NAME/KEY: modified_base
<222> LOCATION: (9)..(9)
<223> OTHER INFORMATION: 2'-O-Methyl nucleotide
<220> FEATURE:
<221> NAME/KEY: modified_base
<222> LOCATION: (10)..(10)
<223> OTHER INFORMATION: 2'-O-Methyl nucleotide
<220> FEATURE:
<221> NAME/KEY: modified_base
<222> LOCATION: (11)..(11)
<223> OTHER INFORMATION: 2'-O-Methyl nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-Fluoro nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-Fluoro nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-O-Methyl nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: misc_feature
<222> LOCATION: (19)..(20)
<223> OTHER INFORMATION: Phosphorothioate linker
<220> FEATURE:
<221> NAME/KEY: modified_base
<222> LOCATION: (20)..(20)
<223> OTHER INFORMATION: 2'-O-Methyl nucleotide
<220> FEATURE:
<221> NAME/KEY: misc_feature
<222> LOCATION: (20)..(21)
<223> OTHER INFORMATION: Phosphorothioate linker
<220> FEATURE:
<221> NAME/KEY: modified_base
<222> LOCATION: (21)..(21)
<223> OTHER INFORMATION: 2'-O-Methyl nucleotide

<400> SEQUENCE: 50
ugugaagcga agugcacacg gu                                           22

<210> SEQ ID NO 51
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
```

```
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-O-Methyl nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-Fluoro nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-O-Methyl nucleotide
<220> FEATURE:
<221> NAME/KEY: modified_base
<222> LOCATION: (6)..(6)
<223> OTHER INFORMATION: 2'-Fluoro nucleotide
<220> FEATURE:
<221> NAME/KEY: modified_base
<222> LOCATION: (7)..(7)
<223> OTHER INFORMATION: 2'-Fluoro nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-O-Methyl nucleotide
<220> FEATURE:
<221> NAME/KEY: modified_base
<222> LOCATION: (10)..(10)
<223> OTHER INFORMATION: 2'-O-Methyl nucleotide
<220> FEATURE:
<221> NAME/KEY: modified_base
<222> LOCATION: (11)..(11)
<223> OTHER INFORMATION: 2'-O-Methyl nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-O-Methyl nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-O-Methyl nucleotide
<220> FEATURE:
<221> NAME/KEY: modified_base
<222> LOCATION: (17)..(17)
<223> OTHER INFORMATION: 2'-O-Methyl nucleotide

<400> SEQUENCE: 51
gugcacuucg cuucaca                                                  17

<210> SEQ ID NO 52
<211> LENGTH: 22
<212> TYPE: RNA
```

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-Fluoro nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-O-Methyl nucleotide
<220> FEATURE:
<221> NAME/KEY: modified_base
<222> LOCATION: (6)..(6)
<223> OTHER INFORMATION: 2'-O-Methyl nucleotide
<220> FEATURE:
<221> NAME/KEY: modified_base
<222> LOCATION: (7)..(7)
<223> OTHER INFORMATION: 2'-O-Methyl nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-O-Methyl nucleotide
<220> FEATURE:
<221> NAME/KEY: modified_base
<222> LOCATION: (10)..(10)
<223> OTHER INFORMATION: 2'-O-Methyl nucleotide
<220> FEATURE:
<221> NAME/KEY: modified_base
<222> LOCATION: (11)..(11)
<223> OTHER INFORMATION: 2'-O-Methyl nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-Fluoro nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-Fluoro nucleotide
<220> FEATURE:
<221> NAME/KEY: modified_base
<222> LOCATION: (17)..(17)
```

```
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-O-Methyl nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: misc_feature
<222> LOCATION: (19)..(20)
<223> OTHER INFORMATION: Phosphorothioate linker
<220> FEATURE:
<221> NAME/KEY: modified_base
<222> LOCATION: (20)..(20)
<223> OTHER INFORMATION: 2'-O-Methyl nucleotide
<220> FEATURE:
<221> NAME/KEY: misc_feature
<222> LOCATION: (20)..(21)
<223> OTHER INFORMATION: Phosphorothioate linker
<220> FEATURE:
<221> NAME/KEY: modified_base
<222> LOCATION: (21)..(21)
<223> OTHER INFORMATION: 2'-O-Methyl nucleotide

<400> SEQUENCE: 52
ugugaagcga agugcacacg gu                                              22

<210> SEQ ID NO 53
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-Fluoro nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-O-Methyl nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-Fluoro nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-Fluoro nucleotide
<220> FEATURE:
<221> NAME/KEY: modified_base
<222> LOCATION: (6)..(6)
<223> OTHER INFORMATION: 2'-Fluoro nucleotide
<220> FEATURE:
<221> NAME/KEY: modified_base
<222> LOCATION: (7)..(7)
<223> OTHER INFORMATION: 2'-Fluoro nucleotide
<220> FEATURE:
<221> NAME/KEY: modified_base
<222> LOCATION: (8)..(8)
<223> OTHER INFORMATION: 2'-O-Methyl nucleotide
<220> FEATURE:
```

```
<221> NAME/KEY: modified_base
<222> LOCATION: (9)..(9)
<223> OTHER INFORMATION: 2'-O-Methyl nucleotide
<220> FEATURE:
<221> NAME/KEY: modified_base
<222> LOCATION: (10)..(10)
<223> OTHER INFORMATION: 2'-Fluoro nucleotide
<220> FEATURE:
<221> NAME/KEY: modified_base
<222> LOCATION: (11)..(11)
<223> OTHER INFORMATION: 2'-O-Methyl nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-Fluoro nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-O-Methyl nucleotide
<220> FEATURE:
<221> NAME/KEY: modified_base
<222> LOCATION: (17)..(17)
<223> OTHER INFORMATION: 2'-O-Methyl nucleotide

<400> SEQUENCE: 53
gugcacuucg cuucaca                                                  17

<210> SEQ ID NO 54
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-Fluoro nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-Fluoro nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-Fluoro nucleotide
<220> FEATURE:
<221> NAME/KEY: modified_base
<222> LOCATION: (6)..(6)
```

```
<223> OTHER INFORMATION: 2'-O-Methyl nucleotide
<220> FEATURE:
<221> NAME/KEY: modified_base
<222> LOCATION: (7)..(7)
<223> OTHER INFORMATION: 2'-Fluoro nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-O-Methyl nucleotide
<220> FEATURE:
<221> NAME/KEY: modified_base
<222> LOCATION: (10)..(10)
<223> OTHER INFORMATION: 2'-Fluoro nucleotide
<220> FEATURE:
<221> NAME/KEY: modified_base
<222> LOCATION: (11)..(11)
<223> OTHER INFORMATION: 2'-O-Methyl nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-Fluoro nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-Fluoro nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-Fluoro nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: misc_feature
<222> LOCATION: (19)..(20)
<223> OTHER INFORMATION: Phosphorothioate linker
<220> FEATURE:
<221> NAME/KEY: modified_base
<222> LOCATION: (20)..(20)
<223> OTHER INFORMATION: 2'-Fluoro nucleotide
<220> FEATURE:
<221> NAME/KEY: misc_feature
<222> LOCATION: (20)..(21)
<223> OTHER INFORMATION: Phosphorothioate linker
<220> FEATURE:
<221> NAME/KEY: modified_base
<222> LOCATION: (21)..(21)
<223> OTHER INFORMATION: 2'-O-Methyl nucleotide

<400> SEQUENCE: 54
ugugaagcga agugcacacg g                                              21

<210> SEQ ID NO 55
<211> LENGTH: 21
<212> TYPE: RNA
<213> ORGANISM: Artificial Sequence
```

-continued

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-O-Methyl nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-O-Methyl nucleotide
<220> FEATURE:
<221> NAME/KEY: modified_base
<222> LOCATION: (6)..(6)
<223> OTHER INFORMATION: 2'-O-Methyl nucleotide
<220> FEATURE:
<221> NAME/KEY: modified_base
<222> LOCATION: (7)..(7)
<223> OTHER INFORMATION: 2'-Fluoro nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-Fluoro nucleotide
<220> FEATURE:
<221> NAME/KEY: modified_base
<222> LOCATION: (10)..(10)
<223> OTHER INFORMATION: 2'-Fluoro nucleotide
<220> FEATURE:
<221> NAME/KEY: modified_base
<222> LOCATION: (11)..(11)
<223> OTHER INFORMATION: 2'-Fluoro nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-O-Methyl nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-O-Methyl nucleotide
<220> FEATURE:
<221> NAME/KEY: modified_base
<222> LOCATION: (17)..(17)
<223> OTHER INFORMATION: 2'-O-Methyl nucleotide
```

```
<220> FEATURE:
<221> NAME/KEY: modified_base
<222> LOCATION: (18)..(18)
<223> OTHER INFORMATION: 2'-O-Methyl nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-O-Methyl nucleotide
<220> FEATURE:
<221> NAME/KEY: modified_base
<222> LOCATION: (21)..(21)
<223> OTHER INFORMATION: 2'-O-Methyl nucleotide

<400> SEQUENCE: 55
ucgcuucacc ucugcacguc g                                              21

<210> SEQ ID NO 56
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-Fluoro nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-O-Methyl nucleotide
<220> FEATURE:
<221> NAME/KEY: modified_base
<222> LOCATION: (6)..(6)
<223> OTHER INFORMATION: 2'-Fluoro nucleotide
<220> FEATURE:
<221> NAME/KEY: modified_base
<222> LOCATION: (7)..(7)
<223> OTHER INFORMATION: 2'-O-Methyl nucleotide
<220> FEATURE:
<221> NAME/KEY: modified_base
<222> LOCATION: (8)..(8)
<223> OTHER INFORMATION: 2'-Fluoro nucleotide
<220> FEATURE:
<221> NAME/KEY: modified_base
<222> LOCATION: (9)..(9)
<223> OTHER INFORMATION: 2'-Fluoro nucleotide
<220> FEATURE:
<221> NAME/KEY: modified_base
<222> LOCATION: (10)..(10)
<223> OTHER INFORMATION: 2'-O-Methyl nucleotide
<220> FEATURE:
<221> NAME/KEY: modified_base
```

```
<222> LOCATION: (11)..(11)
<223> OTHER INFORMATION: 2'-O-Methyl nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-Fluoro nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-Fluoro nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-O-Methyl nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-O-Methyl nucleotide
<220> FEATURE:
<221> NAME/KEY: modified_base
<222> LOCATION: (21)..(21)
<223> OTHER INFORMATION: 2'-O-Methyl nucleotide
<220> FEATURE:
<221> NAME/KEY: misc_feature
<222> LOCATION: (21)..(22)
<223> OTHER INFORMATION: Phosphorothioate linker
<220> FEATURE:
<221> NAME/KEY: modified_base
<222> LOCATION: (22)..(22)
<223> OTHER INFORMATION: 2'-O-Methyl nucleotide
<220> FEATURE:
<221> NAME/KEY: misc_feature
<222> LOCATION: (22)..(23)
<223> OTHER INFORMATION: Phosphorothioate linker
<220> FEATURE:
<221> NAME/KEY: modified_base
<222> LOCATION: (23)..(23)
<223> OTHER INFORMATION: 2'-O-Methyl nucleotide

<400> SEQUENCE: 56
cgacgugcag aggugaagcg aaguu                                         25

<210> SEQ ID NO 57
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
```

-continued

```
<220> FEATURE:
<221> NAME/KEY: modified_base
<222> LOCATION: (2)..(2)
<223> OTHER INFORMATION: 2'-O-Methyl nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-O-Methyl nucleotide
<220> FEATURE:
<221> NAME/KEY: modified_base
<222> LOCATION: (6)..(6)
<223> OTHER INFORMATION: 2'-O-Methyl nucleotide
<220> FEATURE:
<221> NAME/KEY: modified_base
<222> LOCATION: (7)..(7)
<223> OTHER INFORMATION: 2'-Fluoro nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-Fluoro nucleotide
<220> FEATURE:
<221> NAME/KEY: modified_base
<222> LOCATION: (10)..(10)
<223> OTHER INFORMATION: 2'-Fluoro nucleotide
<220> FEATURE:
<221> NAME/KEY: modified_base
<222> LOCATION: (11)..(11)
<223> OTHER INFORMATION: 2'-Fluoro nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-O-Methyl nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-O-Methyl nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-O-Methyl nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: modified_base
<222> LOCATION: (20)..(20)
```

```
<223> OTHER INFORMATION: 2'-O-Methyl nucleotide
<220> FEATURE:
<221> NAME/KEY: modified_base
<222> LOCATION: (21)..(21)
<223> OTHER INFORMATION: 2'-O-Methyl nucleotide

<400> SEQUENCE: 57
ucgcuucacc ucugcacguc a                                            21

<210> SEQ ID NO 58
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-Fluoro nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-O-Methyl nucleotide
<220> FEATURE:
<221> NAME/KEY: modified_base
<222> LOCATION: (6)..(6)
<223> OTHER INFORMATION: 2'-Fluoro nucleotide
<220> FEATURE:
<221> NAME/KEY: modified_base
<222> LOCATION: (7)..(7)
<223> OTHER INFORMATION: 2'-O-Methyl nucleotide
<220> FEATURE:
<221> NAME/KEY: modified_base
<222> LOCATION: (8)..(8)
<223> OTHER INFORMATION: 2'-Fluoro nucleotide
<220> FEATURE:
<221> NAME/KEY: modified_base
<222> LOCATION: (9)..(9)
<223> OTHER INFORMATION: 2'-Fluoro nucleotide
<220> FEATURE:
<221> NAME/KEY: modified_base
<222> LOCATION: (10)..(10)
<223> OTHER INFORMATION: 2'-O-Methyl nucleotide
<220> FEATURE:
<221> NAME/KEY: modified_base
<222> LOCATION: (11)..(11)
<223> OTHER INFORMATION: 2'-O-Methyl nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
```

```
<221> NAME/KEY: modified_base
<222> LOCATION: (14)..(14)
<223> OTHER INFORMATION: 2'-Fluoro nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-Fluoro nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-O-Methyl nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-O-Methyl nucleotide
<220> FEATURE:
<221> NAME/KEY: modified_base
<222> LOCATION: (21)..(21)
<223> OTHER INFORMATION: 2'-O-Methyl nucleotide
<220> FEATURE:
<221> NAME/KEY: misc_feature
<222> LOCATION: (21)..(22)
<223> OTHER INFORMATION: Phosphorothioate linker
<220> FEATURE:
<221> NAME/KEY: modified_base
<222> LOCATION: (22)..(22)
<223> OTHER INFORMATION: 2'-O-Methyl nucleotide
<220> FEATURE:
<221> NAME/KEY: misc_feature
<222> LOCATION: (22)..(23)
<223> OTHER INFORMATION: Phosphorothioate linker
<220> FEATURE:
<221> NAME/KEY: modified_base
<222> LOCATION: (23)..(23)
<223> OTHER INFORMATION: 2'-O-Methyl nucleotide

<400> SEQUENCE: 58
ugacgugcag aggugaagcg aaguu                                    25

<210> SEQ ID NO 59
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-O-Methyl nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
```

```
<223> OTHER INFORMATION: 2'-O-Methyl nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-Fluoro nucleotide
<220> FEATURE:
<221> NAME/KEY: modified_base
<222> LOCATION: (6)..(6)
<223> OTHER INFORMATION: 2'-O-Methyl nucleotide
<220> FEATURE:
<221> NAME/KEY: modified_base
<222> LOCATION: (7)..(7)
<223> OTHER INFORMATION: 2'-Fluoro nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-Fluoro nucleotide
<220> FEATURE:
<221> NAME/KEY: modified_base
<222> LOCATION: (10)..(10)
<223> OTHER INFORMATION: 2'-O-Methyl nucleotide
<220> FEATURE:
<221> NAME/KEY: modified_base
<222> LOCATION: (11)..(11)
<223> OTHER INFORMATION: 2'-Fluoro nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-O-Methyl nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-O-Methyl nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-O-Methyl nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-O-Methyl nucleotide
<220> FEATURE:
<221> NAME/KEY: modified_base
<222> LOCATION: (21)..(21)
<223> OTHER INFORMATION: 2'-O-Methyl nucleotide

<400> SEQUENCE: 59
ucgcuucacc ucugcacguc a                                              21
```

```
<210> SEQ ID NO 60
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-Fluoro nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-O-Methyl nucleotide
<220> FEATURE:
<221> NAME/KEY: modified_base
<222> LOCATION: (6)..(6)
<223> OTHER INFORMATION: 2'-Fluoro nucleotide
<220> FEATURE:
<221> NAME/KEY: modified_base
<222> LOCATION: (7)..(7)
<223> OTHER INFORMATION: 2'-O-Methyl nucleotide
<220> FEATURE:
<221> NAME/KEY: modified_base
<222> LOCATION: (8)..(8)
<223> OTHER INFORMATION: 2'-Fluoro nucleotide
<220> FEATURE:
<221> NAME/KEY: modified_base
<222> LOCATION: (9)..(9)
<223> OTHER INFORMATION: 2'-Fluoro nucleotide
<220> FEATURE:
<221> NAME/KEY: modified_base
<222> LOCATION: (10)..(10)
<223> OTHER INFORMATION: 2'-O-Methyl nucleotide
<220> FEATURE:
<221> NAME/KEY: modified_base
<222> LOCATION: (11)..(11)
<223> OTHER INFORMATION: 2'-O-Methyl nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-Fluoro nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-Fluoro nucleotide
```

```
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-O-Methyl nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-O-Methyl nucleotide
<220> FEATURE:
<221> NAME/KEY: modified_base
<222> LOCATION: (21)..(21)
<223> OTHER INFORMATION: 2'-O-Methyl nucleotide
<220> FEATURE:
<221> NAME/KEY: misc_feature
<222> LOCATION: (21)..(22)
<223> OTHER INFORMATION: Phosphorothioate linker
<220> FEATURE:
<221> NAME/KEY: modified_base
<222> LOCATION: (22)..(22)
<223> OTHER INFORMATION: 2'-O-Methyl nucleotide
<220> FEATURE:
<221> NAME/KEY: misc_feature
<222> LOCATION: (22)..(23)
<223> OTHER INFORMATION: Phosphorothioate linker
<220> FEATURE:
<221> NAME/KEY: modified_base
<222> LOCATION: (23)..(23)
<223> OTHER INFORMATION: 2'-O-Methyl nucleotide

<400> SEQUENCE: 60
ugacgugcag aggugaagcg aaguu                                  25

<210> SEQ ID NO 61
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-O-Methyl nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-Fluoro nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-Fluoro nucleotide
<220> FEATURE:
<221> NAME/KEY: modified_base
```

```
<222> LOCATION: (6)..(6)
<223> OTHER INFORMATION: 2'-Fluoro nucleotide
<220> FEATURE:
<221> NAME/KEY: modified_base
<222> LOCATION: (7)..(7)
<223> OTHER INFORMATION: 2'-Fluoro nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-O-Methyl nucleotide
<220> FEATURE:
<221> NAME/KEY: modified_base
<222> LOCATION: (10)..(10)
<223> OTHER INFORMATION: 2'-O-Methyl nucleotide
<220> FEATURE:
<221> NAME/KEY: modified_base
<222> LOCATION: (11)..(11)
<223> OTHER INFORMATION: 2'-O-Methyl nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-O-Methyl nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-O-Methyl nucleotide
<220> FEATURE:
<221> NAME/KEY: modified_base
<222> LOCATION: (17)..(17)
<223> OTHER INFORMATION: 2'-O-Methyl nucleotide

<400> SEQUENCE: 61
uucaccucug cacguca                                                17

<210> SEQ ID NO 62
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-Fluoro nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-O-Methyl nucleotide
```

-continued

```
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-O-Methyl nucleotide
<220> FEATURE:
<221> NAME/KEY: modified_base
<222> LOCATION: (6)..(6)
<223> OTHER INFORMATION: 2'-Fluoro nucleotide
<220> FEATURE:
<221> NAME/KEY: modified_base
<222> LOCATION: (7)..(7)
<223> OTHER INFORMATION: 2'-O-Methyl nucleotide
<220> FEATURE:
<221> NAME/KEY: modified_base
<222> LOCATION: (8)..(8)
<223> OTHER INFORMATION: 2'-Fluoro nucleotide
<220> FEATURE:
<221> NAME/KEY: modified_base
<222> LOCATION: (9)..(9)
<223> OTHER INFORMATION: 2'-Fluoro nucleotide
<220> FEATURE:
<221> NAME/KEY: modified_base
<222> LOCATION: (10)..(10)
<223> OTHER INFORMATION: 2'-O-Methyl nucleotide
<220> FEATURE:
<221> NAME/KEY: modified_base
<222> LOCATION: (11)..(11)
<223> OTHER INFORMATION: 2'-O-Methyl nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-Fluoro nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-Fluoro nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-O-Methyl nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: misc_feature
<222> LOCATION: (19)..(20)
<223> OTHER INFORMATION: Phosphorothioate linker
<220> FEATURE:
<221> NAME/KEY: modified_base
<222> LOCATION: (20)..(20)
<223> OTHER INFORMATION: 2'-O-Methyl nucleotide
<220> FEATURE:
<221> NAME/KEY: misc_feature
<222> LOCATION: (20)..(21)
<223> OTHER INFORMATION: Phosphorothioate linker
<220> FEATURE:
<221> NAME/KEY: modified_base
<222> LOCATION: (21)..(21)
```

-continued

<223> OTHER INFORMATION: 2'-O-Methyl nucleotide

<400> SEQUENCE: 62
ugacgugcag aggugaagcg au                                              22

<210> SEQ ID NO 63
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-O-Methyl nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-Fluoro nucleotide
<220> FEATURE:
<221> NAME/KEY: modified_base
<222> LOCATION: (6)..(6)
<223> OTHER INFORMATION: 2'-Fluoro nucleotide
<220> FEATURE:
<221> NAME/KEY: modified_base
<222> LOCATION: (7)..(7)
<223> OTHER INFORMATION: 2'-Fluoro nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-O-Methyl nucleotide
<220> FEATURE:
<221> NAME/KEY: modified_base
<222> LOCATION: (10)..(10)
<223> OTHER INFORMATION: 2'-O-Methyl nucleotide
<220> FEATURE:
<221> NAME/KEY: modified_base
<222> LOCATION: (11)..(11)
<223> OTHER INFORMATION: 2'-O-Methyl nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-O-Methyl nucleotide
<220> FEATURE:

```
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-O-Methyl nucleotide
<220> FEATURE:
<221> NAME/KEY: modified_base
<222> LOCATION: (17)..(17)
<223> OTHER INFORMATION: 2'-O-Methyl nucleotide

<400> SEQUENCE: 63
uucaccucug cacguca                                                          17

<210> SEQ ID NO 64
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-Fluoro nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-O-Methyl nucleotide
<220> FEATURE:
<221> NAME/KEY: modified_base
<222> LOCATION: (6)..(6)
<223> OTHER INFORMATION: 2'-O-Methyl nucleotide
<220> FEATURE:
<221> NAME/KEY: modified_base
<222> LOCATION: (7)..(7)
<223> OTHER INFORMATION: 2'-O-Methyl nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-O-Methyl nucleotide
<220> FEATURE:
<221> NAME/KEY: modified_base
<222> LOCATION: (10)..(10)
<223> OTHER INFORMATION: 2'-O-Methyl nucleotide
<220> FEATURE:
<221> NAME/KEY: modified_base
<222> LOCATION: (11)..(11)
<223> OTHER INFORMATION: 2'-O-Methyl nucleotide
<220> FEATURE:
<221> NAME/KEY: modified_base
<222> LOCATION: (12)..(12)
```

```
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-Fluoro nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-Fluoro nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-O-Methyl nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: misc_feature
<222> LOCATION: (19)..(20)
<223> OTHER INFORMATION: Phosphorothioate linker
<220> FEATURE:
<221> NAME/KEY: modified_base
<222> LOCATION: (20)..(20)
<223> OTHER INFORMATION: 2'-O-Methyl nucleotide
<220> FEATURE:
<221> NAME/KEY: misc_feature
<222> LOCATION: (20)..(21)
<223> OTHER INFORMATION: Phosphorothioate linker
<220> FEATURE:
<221> NAME/KEY: modified_base
<222> LOCATION: (21)..(21)
<223> OTHER INFORMATION: 2'-O-Methyl nucleotide

<400> SEQUENCE: 64
ugacgugcag aggugaagcg au                                              22

<210> SEQ ID NO 65
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-O-Methyl nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-Fluoro nucleotide
<220> FEATURE:
```

<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-Fluoro nucleotide
<220> FEATURE:
<221> NAME/KEY: modified_base
<222> LOCATION: (6)..(6)
<223> OTHER INFORMATION: 2'-Fluoro nucleotide
<220> FEATURE:
<221> NAME/KEY: modified_base
<222> LOCATION: (7)..(7)
<223> OTHER INFORMATION: 2'-Fluoro nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-O-Methyl nucleotide
<220> FEATURE:
<221> NAME/KEY: modified_base
<222> LOCATION: (10)..(10)
<223> OTHER INFORMATION: 2'-O-Methyl nucleotide
<220> FEATURE:
<221> NAME/KEY: modified_base
<222> LOCATION: (11)..(11)
<223> OTHER INFORMATION: 2'-O-Methyl nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-O-Methyl nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-O-Methyl nucleotide
<220> FEATURE:
<221> NAME/KEY: modified_base
<222> LOCATION: (17)..(17)
<223> OTHER INFORMATION: 2'-O-Methyl nucleotide

<400> SEQUENCE: 65
uucaccucug cacguca                                                17

<210> SEQ ID NO 66
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)

```
<223> OTHER INFORMATION: 2'-Fluoro nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-O-Methyl nucleotide
<220> FEATURE:
<221> NAME/KEY: modified_base
<222> LOCATION: (6)..(6)
<223> OTHER INFORMATION: 2'-Fluoro nucleotide
<220> FEATURE:
<221> NAME/KEY: modified_base
<222> LOCATION: (7)..(7)
<223> OTHER INFORMATION: 2'-O-Methyl nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-O-Methyl nucleotide
<220> FEATURE:
<221> NAME/KEY: modified_base
<222> LOCATION: (10)..(10)
<223> OTHER INFORMATION: 2'-O-Methyl nucleotide
<220> FEATURE:
<221> NAME/KEY: modified_base
<222> LOCATION: (11)..(11)
<223> OTHER INFORMATION: 2'-O-Methyl nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-Fluoro nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-Fluoro nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-O-Methyl nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: misc_feature
<222> LOCATION: (19)..(20)
<223> OTHER INFORMATION: Phosphorothioate linker
<220> FEATURE:
<221> NAME/KEY: modified_base
```

```
<222> LOCATION: (20)..(20)
<223> OTHER INFORMATION: 2'-O-Methyl nucleotide
<220> FEATURE:
<221> NAME/KEY: misc_feature
<222> LOCATION: (20)..(21)
<223> OTHER INFORMATION: Phosphorothioate linker
<220> FEATURE:
<221> NAME/KEY: modified_base
<222> LOCATION: (21)..(21)
<223> OTHER INFORMATION: 2'-O-Methyl nucleotide

<400> SEQUENCE: 66
ugacgugcag aggugaagcg au                                              22

<210> SEQ ID NO 67
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-O-Methyl nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-Fluoro nucleotide
<220> FEATURE:
<221> NAME/KEY: modified_base
<222> LOCATION: (6)..(6)
<223> OTHER INFORMATION: 2'-O-Methyl nucleotide
<220> FEATURE:
<221> NAME/KEY: modified_base
<222> LOCATION: (7)..(7)
<223> OTHER INFORMATION: 2'-Fluoro nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-Fluoro nucleotide
<220> FEATURE:
<221> NAME/KEY: modified_base
<222> LOCATION: (10)..(10)
<223> OTHER INFORMATION: 2'-Fluoro nucleotide
<220> FEATURE:
<221> NAME/KEY: modified_base
<222> LOCATION: (11)..(11)
<223> OTHER INFORMATION: 2'-Fluoro nucleotide
<220> FEATURE:
<221> NAME/KEY: modified_base
<222> LOCATION: (12)..(12)
<223> OTHER INFORMATION: 2'-O-Methyl nucleotide
```

-continued

```
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-Fluoro nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-O-Methyl nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-O-Methyl nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-O-Methyl nucleotide
<220> FEATURE:
<221> NAME/KEY: modified_base
<222> LOCATION: (21)..(21)
<223> OTHER INFORMATION: 2'-O-Methyl nucleotide

<400> SEQUENCE: 67
uuuacuagug ccauuuguuc a                                              21

<210> SEQ ID NO 68
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-Fluoro nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-Fluoro nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-Fluoro nucleotide
<220> FEATURE:
<221> NAME/KEY: modified_base
```

```
<222> LOCATION: (6)..(6)
<223> OTHER INFORMATION: 2'-O-Methyl nucleotide
<220> FEATURE:
<221> NAME/KEY: modified_base
<222> LOCATION: (7)..(7)
<223> OTHER INFORMATION: 2'-Fluoro nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-O-Methyl nucleotide
<220> FEATURE:
<221> NAME/KEY: modified_base
<222> LOCATION: (10)..(10)
<223> OTHER INFORMATION: 2'-Fluoro nucleotide
<220> FEATURE:
<221> NAME/KEY: modified_base
<222> LOCATION: (11)..(11)
<223> OTHER INFORMATION: 2'-O-Methyl nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-Fluoro nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-Fluoro nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-Fluoro nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-Fluoro nucleotide
<220> FEATURE:
<221> NAME/KEY: modified_base
<222> LOCATION: (21)..(21)
<223> OTHER INFORMATION: 2'-O-Methyl nucleotide
<220> FEATURE:
<221> NAME/KEY: misc_feature
<222> LOCATION: (21)..(22)
<223> OTHER INFORMATION: Phosphorothioate linker
<220> FEATURE:
<221> NAME/KEY: modified_base
<222> LOCATION: (22)..(22)
<223> OTHER INFORMATION: 2'-O-Methyl nucleotide
<220> FEATURE:
<221> NAME/KEY: misc_feature
<222> LOCATION: (22)..(23)
<223> OTHER INFORMATION: Phosphorothioate linker
<220> FEATURE:
<221> NAME/KEY: modified_base
<222> LOCATION: (23)..(23)
<223> OTHER INFORMATION: 2'-O-Methyl nucleotide
```

<400> SEQUENCE: 68
ugaacaaaug gcacuaguaa acu                                           23

<210> SEQ ID NO 69
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-O-Methyl nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-Fluoro nucleotide
<220> FEATURE:
<221> NAME/KEY: modified_base
<222> LOCATION: (6)..(6)
<223> OTHER INFORMATION: 2'-O-Methyl nucleotide
<220> FEATURE:
<221> NAME/KEY: modified_base
<222> LOCATION: (7)..(7)
<223> OTHER INFORMATION: 2'-Fluoro nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-Fluoro nucleotide
<220> FEATURE:
<221> NAME/KEY: modified_base
<222> LOCATION: (10)..(10)
<223> OTHER INFORMATION: 2'-Fluoro nucleotide
<220> FEATURE:
<221> NAME/KEY: modified_base
<222> LOCATION: (11)..(11)
<223> OTHER INFORMATION: 2'-Fluoro nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-Fluoro nucleotide
<220> FEATURE:
<221> NAME/KEY: modified_base
<222> LOCATION: (15)..(15)

```
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-O-Methyl nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-O-Methyl nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-O-Methyl nucleotide
<220> FEATURE:
<221> NAME/KEY: modified_base
<222> LOCATION: (21)..(21)
<223> OTHER INFORMATION: 2'-O-Methyl nucleotide

<400> SEQUENCE: 69
uuuacuagug ccauuuguuc a                                              21

<210> SEQ ID NO 70
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-Fluoro nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-Fluoro nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-Fluoro nucleotide
<220> FEATURE:
<221> NAME/KEY: modified_base
<222> LOCATION: (6)..(6)
<223> OTHER INFORMATION: 2'-O-Methyl nucleotide
<220> FEATURE:
<221> NAME/KEY: modified_base
<222> LOCATION: (7)..(7)
<223> OTHER INFORMATION: 2'-Fluoro nucleotide
<220> FEATURE:
<221> NAME/KEY: modified_base
<222> LOCATION: (8)..(8)
<223> OTHER INFORMATION: 2'-O-Methyl nucleotide
<220> FEATURE:
```

```
<221> NAME/KEY: modified_base
<222> LOCATION: (9)..(9)
<223> OTHER INFORMATION: 2'-O-Methyl nucleotide
<220> FEATURE:
<221> NAME/KEY: modified_base
<222> LOCATION: (10)..(10)
<223> OTHER INFORMATION: 2'-Fluoro nucleotide
<220> FEATURE:
<221> NAME/KEY: modified_base
<222> LOCATION: (11)..(11)
<223> OTHER INFORMATION: 2'-O-Methyl nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-Fluoro nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-Fluoro nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-Fluoro nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-Fluoro nucleotide
<220> FEATURE:
<221> NAME/KEY: modified_base
<222> LOCATION: (21)..(21)
<223> OTHER INFORMATION: 2'-O-Methyl nucleotide
<220> FEATURE:
<221> NAME/KEY: misc_feature
<222> LOCATION: (21)..(22)
<223> OTHER INFORMATION: Phosphorothioate linker
<220> FEATURE:
<221> NAME/KEY: modified_base
<222> LOCATION: (22)..(22)
<223> OTHER INFORMATION: 2'-O-Methyl nucleotide
<220> FEATURE:
<221> NAME/KEY: misc_feature
<222> LOCATION: (22)..(23)
<223> OTHER INFORMATION: Phosphorothioate linker
<220> FEATURE:
<221> NAME/KEY: modified_base
<222> LOCATION: (23)..(23)
<223> OTHER INFORMATION: 2'-O-Methyl nucleotide

<400> SEQUENCE: 70
ugaacaaaug gcacuaguaa acuuu                                          25

<210> SEQ ID NO 71
<211> LENGTH: 21
<212> TYPE: RNA
<213> ORGANISM: Artificial Sequence
<220> FEATURE:
<223> OTHER INFORMATION: Description of Artificial Sequence: Synthetic
```

```
            oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-O-Methyl nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-O-Methyl nucleotide
<220> FEATURE:
<221> NAME/KEY: modified_base
<222> LOCATION: (6)..(6)
<223> OTHER INFORMATION: 2'-O-Methyl nucleotide
<220> FEATURE:
<221> NAME/KEY: modified_base
<222> LOCATION: (7)..(7)
<223> OTHER INFORMATION: 2'-Fluoro nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-Fluoro nucleotide
<220> FEATURE:
<221> NAME/KEY: modified_base
<222> LOCATION: (10)..(10)
<223> OTHER INFORMATION: 2'-Fluoro nucleotide
<220> FEATURE:
<221> NAME/KEY: modified_base
<222> LOCATION: (11)..(11)
<223> OTHER INFORMATION: 2'-Fluoro nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-O-Methyl nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-O-Methyl nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
```

```
<222> LOCATION: (18)..(18)
<223> OTHER INFORMATION: 2'-O-Methyl nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-O-Methyl nucleotide
<220> FEATURE:
<221> NAME/KEY: modified_base
<222> LOCATION: (21)..(21)
<223> OTHER INFORMATION: 2'-O-Methyl nucleotide

<400> SEQUENCE: 71
uuuacuagug ccauuuguuc a                                     21

<210> SEQ ID NO 72
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-Fluoro nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-O-Methyl nucleotide
<220> FEATURE:
<221> NAME/KEY: modified_base
<222> LOCATION: (6)..(6)
<223> OTHER INFORMATION: 2'-Fluoro nucleotide
<220> FEATURE:
<221> NAME/KEY: modified_base
<222> LOCATION: (7)..(7)
<223> OTHER INFORMATION: 2'-O-Methyl nucleotide
<220> FEATURE:
<221> NAME/KEY: modified_base
<222> LOCATION: (8)..(8)
<223> OTHER INFORMATION: 2'-Fluoro nucleotide
<220> FEATURE:
<221> NAME/KEY: modified_base
<222> LOCATION: (9)..(9)
<223> OTHER INFORMATION: 2'-Fluoro nucleotide
<220> FEATURE:
<221> NAME/KEY: modified_base
<222> LOCATION: (10)..(10)
<223> OTHER INFORMATION: 2'-O-Methyl nucleotide
<220> FEATURE:
<221> NAME/KEY: modified_base
<222> LOCATION: (11)..(11)
<223> OTHER INFORMATION: 2'-O-Methyl nucleotide
```

```
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-Fluoro nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-Fluoro nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-O-Methyl nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-O-Methyl nucleotide
<220> FEATURE:
<221> NAME/KEY: modified_base
<222> LOCATION: (21)..(21)
<223> OTHER INFORMATION: 2'-O-Methyl nucleotide
<220> FEATURE:
<221> NAME/KEY: misc_feature
<222> LOCATION: (21)..(22)
<223> OTHER INFORMATION: Phosphorothioate linker
<220> FEATURE:
<221> NAME/KEY: modified_base
<222> LOCATION: (22)..(22)
<223> OTHER INFORMATION: 2'-O-Methyl nucleotide
<220> FEATURE:
<221> NAME/KEY: misc_feature
<222> LOCATION: (22)..(23)
<223> OTHER INFORMATION: Phosphorothioate linker
<220> FEATURE:
<221> NAME/KEY: modified_base
<222> LOCATION: (23)..(23)
<223> OTHER INFORMATION: 2'-O-Methyl nucleotide

<400> SEQUENCE: 72
ugaacaaaug gcacuaguaa acuuu                                         25

<210> SEQ ID NO 73
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
```

```
<222> LOCATION: (2)..(2)
<223> OTHER INFORMATION: 2'-O-Methyl nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-Fluoro nucleotide
<220> FEATURE:
<221> NAME/KEY: modified_base
<222> LOCATION: (6)..(6)
<223> OTHER INFORMATION: 2'-O-Methyl nucleotide
<220> FEATURE:
<221> NAME/KEY: modified_base
<222> LOCATION: (7)..(7)
<223> OTHER INFORMATION: 2'-Fluoro nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-Fluoro nucleotide
<220> FEATURE:
<221> NAME/KEY: modified_base
<222> LOCATION: (10)..(10)
<223> OTHER INFORMATION: 2'-O-Methyl nucleotide
<220> FEATURE:
<221> NAME/KEY: modified_base
<222> LOCATION: (11)..(11)
<223> OTHER INFORMATION: 2'-Fluoro nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-O-Methyl nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-O-Methyl nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-O-Methyl nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-O-Methyl nucleotide
<220> FEATURE:
```

<221> NAME/KEY: modified_base
<222> LOCATION: (21)..(21)
<223> OTHER INFORMATION: 2'-O-Methyl nucleotide

<400> SEQUENCE: 73
uuuacuagug ccauuuguuc a                                              21

<210> SEQ ID NO 74
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-Fluoro nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-O-Methyl nucleotide
<220> FEATURE:
<221> NAME/KEY: modified_base
<222> LOCATION: (6)..(6)
<223> OTHER INFORMATION: 2'-Fluoro nucleotide
<220> FEATURE:
<221> NAME/KEY: modified_base
<222> LOCATION: (7)..(7)
<223> OTHER INFORMATION: 2'-O-Methyl nucleotide
<220> FEATURE:
<221> NAME/KEY: modified_base
<222> LOCATION: (8)..(8)
<223> OTHER INFORMATION: 2'-Fluoro nucleotide
<220> FEATURE:
<221> NAME/KEY: modified_base
<222> LOCATION: (9)..(9)
<223> OTHER INFORMATION: 2'-Fluoro nucleotide
<220> FEATURE:
<221> NAME/KEY: modified_base
<222> LOCATION: (10)..(10)
<223> OTHER INFORMATION: 2'-O-Methyl nucleotide
<220> FEATURE:
<221> NAME/KEY: modified_base
<222> LOCATION: (11)..(11)
<223> OTHER INFORMATION: 2'-O-Methyl nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)

```
<223> OTHER INFORMATION: 2'-Fluoro nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-Fluoro nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-O-Methyl nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-O-Methyl nucleotide
<220> FEATURE:
<221> NAME/KEY: modified_base
<222> LOCATION: (21)..(21)
<223> OTHER INFORMATION: 2'-O-Methyl nucleotide
<220> FEATURE:
<221> NAME/KEY: misc_feature
<222> LOCATION: (21)..(22)
<223> OTHER INFORMATION: Phosphorothioate linker
<220> FEATURE:
<221> NAME/KEY: modified_base
<222> LOCATION: (22)..(22)
<223> OTHER INFORMATION: 2'-O-Methyl nucleotide
<220> FEATURE:
<221> NAME/KEY: misc_feature
<222> LOCATION: (22)..(23)
<223> OTHER INFORMATION: Phosphorothioate linker
<220> FEATURE:
<221> NAME/KEY: modified_base
<222> LOCATION: (23)..(23)
<223> OTHER INFORMATION: 2'-O-Methyl nucleotide

<400> SEQUENCE: 74
ugaacaaaug gcacuaguaa acuuu                                              25

<210> SEQ ID NO 75
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-Fluoro nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-O-Methyl nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-Fluoro nucleotide
<220> FEATURE:
```

```
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-Fluoro nucleotide
<220> FEATURE:
<221> NAME/KEY: modified_base
<222> LOCATION: (6)..(6)
<223> OTHER INFORMATION: 2'-O-Methyl nucleotide
<220> FEATURE:
<221> NAME/KEY: modified_base
<222> LOCATION: (7)..(7)
<223> OTHER INFORMATION: 2'-Fluoro nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (9)..(9)
<223> OTHER INFORMATION: 2'-Fluoro nucleotide
<220> FEATURE:
<221> NAME/KEY: modified_base
<222> LOCATION: (10)..(10)
<223> OTHER INFORMATION: 2'-Fluoro nucleotide
<220> FEATURE:
<221> NAME/KEY: modified_base
<222> LOCATION: (11)..(11)
<223> OTHER INFORMATION: 2'-Fluoro nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-Fluoro nucleotide
<220> FEATURE:
<221> NAME/KEY: modified_base
<222> LOCATION: (14)..(14)
<223> OTHER INFORMATION: 2'-O-Methyl nucleotide
<220> FEATURE:
<221> NAME/KEY: modified_base
<222> LOCATION: (15)..(15)
<223> OTHER INFORMATION: 2'-Fluoro nucleotide
<220> FEATURE:
<221> NAME/KEY: modified_base
<222> LOCATION: (16)..(16)
<223> OTHER INFORMATION: 2'-O-Methyl nucleotide
<220> FEATURE:
<221> NAME/KEY: modified_base
<222> LOCATION: (17)..(17)
<223> OTHER INFORMATION: 2'-Fluoro nucleotide
<220> FEATURE:
<221> NAME/KEY: modified_base
<222> LOCATION: (18)..(18)
<223> OTHER INFORMATION: 2'-O-Methyl nucleotide
<220> FEATURE:
<221> NAME/KEY: modified_base
<222> LOCATION: (19)..(19)
<223> OTHER INFORMATION: 2'-Fluoro nucleotide
<220> FEATURE:
<221> NAME/KEY: modified_base
<222> LOCATION: (20)..(20)
<223> OTHER INFORMATION: 2'-O-Methyl nucleotide
<220> FEATURE:
<221> NAME/KEY: modified_base
<222> LOCATION: (21)..(21)
<223> OTHER INFORMATION: 2'-Fluoro nucleotide

<400> SEQUENCE: 75
aacaguguuc uugcucuaua a                                            21

<210> SEQ ID NO 76
<211> LENGTH: 23
```

```
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: misc_feature
<222> LOCATION: (1)..(2)
<223> OTHER INFORMATION: Phosphorothioate linker
<220> FEATURE:
<221> NAME/KEY: modified_base
<222> LOCATION: (2)..(2)
<223> OTHER INFORMATION: 2'-Fluoro nucleotide
<220> FEATURE:
<221> NAME/KEY: misc_feature
<222> LOCATION: (2)..(3)
<223> OTHER INFORMATION: Phosphorothioate linker
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (4)..(4)
<223> OTHER INFORMATION: 2'-Fluoro nucleotide
<220> FEATURE:
<221> NAME/KEY: modified_base
<222> LOCATION: (5)..(5)
<223> OTHER INFORMATION: 2'-O-Methyl nucleotide
<220> FEATURE:
<221> NAME/KEY: modified_base
<222> LOCATION: (6)..(6)
<223> OTHER INFORMATION: 2'-Fluoro nucleotide
<220> FEATURE:
<221> NAME/KEY: modified_base
<222> LOCATION: (7)..(7)
<223> OTHER INFORMATION: 2'-O-Methyl nucleotide
<220> FEATURE:
<221> NAME/KEY: modified_base
<222> LOCATION: (8)..(8)
<223> OTHER INFORMATION: 2'-Fluoro nucleotide
<220> FEATURE:
<221> NAME/KEY: modified_base
<222> LOCATION: (9)..(9)
<223> OTHER INFORMATION: 2'-O-Methyl nucleotide
<220> FEATURE:
<221> NAME/KEY: modified_base
<222> LOCATION: (10)..(10)
<223> OTHER INFORMATION: 2'-Fluoro nucleotide
<220> FEATURE:
<221> NAME/KEY: modified_base
<222> LOCATION: (11)..(11)
<223> OTHER INFORMATION: 2'-O-Methyl nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-Fluoro nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-Fluoro nucleotide
<220> FEATURE:
<221> NAME/KEY: modified_base
```

```
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-Fluoro nucleotide
<220> FEATURE:
<221> NAME/KEY: modified_base
<222> LOCATION: (19)..(19)
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-Fluoro nucleotide
<220> FEATURE:
<221> NAME/KEY: modified_base
<222> LOCATION: (21)..(21)
<223> OTHER INFORMATION: 2'-O-Methyl nucleotide
<220> FEATURE:
<221> NAME/KEY: misc_feature
<222> LOCATION: (21)..(22)
<223> OTHER INFORMATION: Phosphorothioate linker
<220> FEATURE:
<221> NAME/KEY: modified_base
<222> LOCATION: (22)..(22)
<223> OTHER INFORMATION: 2'-O-Methyl nucleotide
<220> FEATURE:
<221> NAME/KEY: misc_feature
<222> LOCATION: (22)..(23)
<223> OTHER INFORMATION: Phosphorothioate linker
<220> FEATURE:
<221> NAME/KEY: modified_base
<222> LOCATION: (23)..(23)
<223> OTHER INFORMATION: 2'-O-Methyl nucleotide

<400> SEQUENCE: 76
uuauagagca agaacacugu uuu                           23
```

TARGETED COMPOSITIONS

CROSS-REFERENCE TO RELATED APPLICATIONS

This application is a continuation of U.S. patent application Ser. No. 16/603,771, filed Oct. 8, 2019, which is a 35 U.S.C. § 371 application of International Application Serial No. PCT/US2018/026918, filed Apr. 10, 2018, and claims the benefit of priority of U.S. Provisional Application Ser. No. 62/525,071, filed Jun. 26, 2017, and U.S. Provisional Application Ser. No. 62/484,247, filed Apr. 11, 2017, which applications are all herein incorporated by reference.

SEQUENCE LISTING

The instant application contains a Sequence Listing which has been filed electronically in ASCII format and is hereby incorporated by reference in its entirety. Said ASCII copy, created on May 4, 2020, is named 08155_067US1_SL.txt and is 159,911 bytes in size.

BACKGROUND

A number of diseases are specific to the liver, for example Hepatitis B and nonalcoholic steatohepatitis (NASH). Accordingly, it would be beneficial to have therapeutic compositions that can be targeted primarily to the liver, kidney, heart, pancreas or other organs in living subjects.

Nucleic acids, including siRNA are useful as therapeutic agents.

Currently there is a need for compositions and methods that can be used to deliver (e.g. target) therapeutic nucleic acids, such as double stranded siRNA, in living subjects.

BRIEF SUMMARY

The invention provides nucleic acid molecules (e.g., therapeutic double stranded siRNA molecules), as well as compounds, compositions and methods that can be used to target such nucleic acids (e.g. to the liver).

Accordingly, in one aspect this invention provides a double stranded siRNA molecule selected from the group consisting of siRNA 1 (SEQ ID NO:1 and 2), 2 (SEQ ID NO:3 and 4), 3 (SEQ ID NO:5 and 6), 4 (SEQ ID NO:7 and 8), 5 (SEQ ID NO:9 and 10), 6 (SEQ ID NO:11 and 12), 7 (SEQ ID NO:13 and 14), 8 (SEQ ID NO:15 and 16), 9 (SEQ ID NO:17 and 18), 10 (SEQ ID NO:19 and 20), 11 (SEQ ID NO:21 and 22), 12 (SEQ ID NO:23 and 24), 13 (SEQ ID NO:25 and 26), 14 (SEQ ID NO:27 and 28), 15 (SEQ ID NO:29 and 30), 16 (SEQ ID NO:31 and 32), 17 (SEQ ID NO:33 and 34), 18 (SEQ ID NO:35 and 36), 19 (SEQ ID NO:37 and 38), 20 (SEQ ID NO:39 and 40), 21 (SEQ ID NO:41 and 42), 22 (SEQ ID NO:43 and 44), 23 (SEQ ID NO:45 and 46), 24 (SEQ ID NO:47 and 48), 25 (SEQ ID NO:49 and 50), 26 (SEQ ID NO:51 and 52), 27 (SEQ ID NO:53 and 54), 28 (SEQ ID NO:55 and 56), 29 (SEQ ID NO:57 and 58), 30 (SEQ ID NO:59 and 60), 31 (SEQ ID NO:61 and 62), 32 (SEQ ID NO:63 and 64), 33 (SEQ ID NO:65 and 66), 34 (SEQ ID NO:67 and 68), 35 (SEQ ID NO:69 and 70), 36 (SEQ ID NO:71 and 72) and 37 (SEQ ID NO:73 and 74).

Another aspect this invention provides a compound of formula I

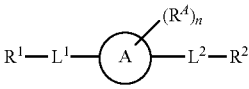

wherein:
$R^1$ a is targeting ligand;
$L^1$ is absent or a linking group;
$L^2$ is absent or a linking group;
$R^2$ is a double stranded siRNA molecule selected from the double stranded siRNA of Table 1;
the ring A is absent, a 3-20 membered cycloalkyl, a 5-20 membered aryl, a 5-20 membered heteroaryl, or a 3-20 membered heterocycloalkyl;
each $R^A$ is independently selected from the group consisting of hydrogen, hydroxy, CN, F, Cl, Br, I, —$C_{1-2}$ alkyl-$OR^B$, $C_{1-10}$ alkyl $C_{2-10}$ alkenyl, and $C_{2-10}$ alkynyl; wherein the $C_{1-10}$ alkyl $C_{2-10}$ alkenyl, and $C_{2-10}$ alkynyl are optionally substituted with one or more groups independently selected from halo, hydroxy, and $C_{1-3}$ alkoxy;
$R^B$ is hydrogen, a protecting group, a covalent bond to a solid support, or a bond to a linking group that is bound to a solid support; and
n is 0, 1, 2, 3, 4, 5, 6, 7, 8, 9, or 10;
or a salt thereof.

Another aspect of the invention provides GalNAc conjugates that comprise one of the siRNAs described herein, which conjugates are not limited to conjugates that comprise the ligand-linkers disclosed herein. For example, an aspect of the invention provides a GalNAc conjugate of Formula X:

$$A-B-C \qquad (X)$$

wherein A is a targeting ligand;
B is an optional linker; and
C is an siRNA molecule described herein.

The therapeutic double stranded siRNA described herein, as well as, compounds and compositions comprising such siRNA, may be used to treat Hepatitis B virus and Hepatitis B virus/Hepatitis D virus.

The invention also provides synthetic intermediates and methods disclosed herein that are useful to prepare compounds of formula I.

Other objects, features, and advantages of the present invention will be apparent to one of skill in the art from the following detailed description and figures.

BRIEF DESCRIPTION OF THE FIGURES

FIG. 1: Illustrates an intermediate compound of formula Ie, wherein a targeting ligand/linker is bound to a solid phase support, and wherein $Pg^1$ is the protecting group DMTr.

FIG. 2: Illustrates a representative compound of formula Id wherein a targeting ligand is bound to a solid phase support, with a nucleic acid covalently bound.

FIG. 3: Illustrates a representative compound of formula Id, wherein a targeting ligand-nucleic acid conjugate has been cleaved from a solid phase support and deprotected to provide the compound of formula I.

In the application, including Figures, Examples and Schemes, it is to be understood that an oligonucleotide can be a double stranded siRNA molecule as described in Table 1.

DETAILED DESCRIPTION

As used herein, the following terms have the meanings ascribed to them unless specified otherwise.

The term "conjugate" as used herein includes compounds of formula (I) that comprise an oligonucleotide (e.g., an siRNA molecule) linked to a targeting ligand. Thus, the terms compound and conjugate may be used herein interchangeably.

The term "small-interfering RNA" or "siRNA" as used herein refers to double stranded RNA (i.e., duplex RNA) that is capable of reducing or inhibiting the expression of a target gene or sequence (e.g., by mediating the degradation or inhibiting the translation of mRNAs which are complementary to the siRNA sequence) when the siRNA is in the same cell as the target gene or sequence. The siRNA may have substantial or complete identity to the target gene or sequence, or may comprise a region of mismatch (i.e., a mismatch motif). In certain embodiments, the siRNAs may be about 19-25 (duplex) nucleotides in length, and is preferably about 20-24, 21-22, or 21-23 (duplex) nucleotides in length. siRNA duplexes may comprise 3' overhangs of about 1 to about 4 nucleotides or about 2 to about 3 nucleotides and 5' phosphate termini. Examples of siRNA include, without limitation, a double-stranded polynucleotide molecule assembled from two separate stranded molecules, wherein one strand is the sense strand and the other is the complementary antisense strand.

In certain embodiments, the 5' and/or 3' overhang on one or both strands of the siRNA comprises 1-4 (e.g., 1, 2, 3, or 4) modified and/or unmodified deoxythymidine (t or dT) nucleotides, 1-4 (e.g., 1, 2, 3, or 4) modified (e.g., 2'OMe) and/or unmodified uridine (U) ribonucleotides, and/or 1-4 (e.g., 1, 2, 3, or 4) modified (e.g., 2'OMe) and/or unmodified ribonucleotides or deoxyribonucleotides having complementarity to the target sequence (e.g., 3'overhang in the antisense strand) or the complementary strand thereof (e.g., 3' overhang in the sense strand).

Preferably, siRNA are chemically synthesized. siRNA can also be generated by cleavage of longer dsRNA (e.g., dsRNA greater than about 25 nucleotides in length) with the *E. coli* RNase III or Dicer. These enzymes process the dsRNA into biologically active siRNA (see, e.g., Yang et al., *Proc. Natl. Acad. Sci. USA*, 99:9942-9947 (2002); Calegari et al., *Proc. Natl. Acad. Sci. USA*, 99:14236 (2002); Byrom et al., *Ambion TechNotes*, 10(1):4-6 (2003); Kawasaki et al., *Nucleic Acids Res.*, 31:981-987 (2003); Knight et al., *Science*, 293:2269-2271 (2001); and Robertson et al., *J. Biol. Chem.*, 243:82 (1968)). Preferably, dsRNA are at least 50 nucleotides to about 100, 200, 300, 400, or 500 nucleotides in length. A dsRNA may be as long as 1000, 1500, 2000, 5000 nucleotides in length, or longer. The dsRNA can encode for an entire gene transcript or a partial gene transcript. In certain instances, siRNA may be encoded by a plasmid (e.g., transcribed as sequences that automatically fold into duplexes with hairpin loops).

The phrase "inhibiting expression of a target gene" refers to the ability of a siRNA of the invention to silence, reduce, or inhibit expression of a target gene. To examine the extent of gene silencing, a test sample (e.g., a biological sample from an organism of interest expressing the target gene or a sample of cells in culture expressing the target gene) is contacted with a siRNA that silences, reduces, or inhibits expression of the target gene. Expression of the target gene in the test sample is compared to expression of the target gene in a control sample (e.g., a biological sample from an organism of interest expressing the target gene or a sample of cells in culture expressing the target gene) that is not contacted with the siRNA. Control samples (e.g., samples expressing the target gene) may be assigned a value of 100%. In particular embodiments, silencing, inhibition, or reduction of expression of a target gene is achieved when the value of the test sample relative to the control sample (e.g., buffer only, an siRNA sequence that targets a different gene, a scrambled siRNA sequence, etc.) is about 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 70%, 65%, 60%, 55%, 50%, 45%, 40%, 35%, 30%, 25%, 20%, 15%, 10%, 5%, or 0%. Suitable assays include, without limitation, examination of protein or mRNA levels using techniques known to those of skill in the art, such as, e.g., dot blots, Northern blots, in situ hybridization, ELISA, immunoprecipitation, enzyme function, as well as phenotypic assays known to those of skill in the art.

The term "synthetic activating group" refers to a group that can be attached to an atom to activate that atom to allow it to form a covalent bond with another reactive group. It is understood that the nature of the synthetic activating group may depend on the atom that it is activating. For example, when the synthetic activating group is attached to an oxygen atom, the synthetic activating group is a group that will activate that oxygen atom to form a bond (e.g. an ester, carbamate, or ether bond) with another reactive group. Such synthetic activating groups are known. Examples of synthetic activating groups that can be attached to an oxygen atom include, but are not limited to, acetate, succinate, triflate, and mesylate. When the synthetic activating group is attached to an oxygen atom of a carboxylic acid, the synthetic activating group can be a group that is derivable from a known coupling reagent (e.g. a known amide coupling reagent). Such coupling reagents are known. Examples of such coupling reagents include, but are not limited to, N,N'-Dicyclohexylcarbodimide (DCC), hydroxybenzotriazole (HOBt), N-(3-Dimethylaminopropyl)-N'-ethylcarbonate (EDC), (Benzotriazol-1-yloxy)tris(dimethylamino)phosphonium hexafluorophosphate (BOP), benzotriazol-1-yl-oxytripyrrolidinophosphonium hexafluorophosphate (PyBOP) or O-benzotriazol-1-yl-N,N,N',N'-tetramethyluronium hexafluorophosphate (HBTU).

An "effective amount" or "therapeutically effective amount" of a therapeutic nucleic acid such as siRNA is an amount sufficient to produce the desired effect, e.g., an inhibition of expression of a target sequence in comparison to the normal expression level detected in the absence of a siRNA. In particular embodiments, inhibition of expression of a target gene or target sequence is achieved when the value obtained with a siRNA relative to the control (e.g., buffer only, an siRNA sequence that targets a different gene, a scrambled siRNA sequence, etc.) is about 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 70%, 65%, 60%, 55%, 50%, 45%, 40%, 35%, 30%, 25%, 20%, 15%, 10%, 5%, or 0%. Suitable assays for measuring the expression of a target gene or target sequence include, but are not limited to, examination of protein or mRNA levels using techniques known to those of skill in the art, such as, e.g., dot blots, Northern blots, in situ hybridization, ELISA, immunoprecipitation, enzyme function, as well as phenotypic assays known to those of skill in the art.

The term "nucleic acid" as used herein refers to a polymer containing at least two nucleotides (i.e., deoxyribonucleotides or ribonucleotides) in either single- or double-stranded form and includes DNA and RNA. "Nucleotides"

contain a sugar deoxyribose (DNA) or ribose (RNA), a base, and a phosphate group. Nucleotides are linked together through the phosphate groups. "Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylates, and alkyl-halides. Nucleic acids include nucleic acids containing known nucleotide analogs or modified backbone residues or linkages, which are synthetic, naturally occurring, and non-naturally occurring, and which have similar binding properties as the reference nucleic acid. Examples of such analogs and/or modified residues include, without limitation, phosphorothioates, phosphoramidates, methyl phosphonates, chiral-methyl phosphonates, 2'-O-methyl ribonucleotides, and peptide-nucleic acids (PNAs). Additionally, nucleic acids can include one or more UNA moieties.

The term "nucleic acid" includes any oligonucleotide or polynucleotide, with fragments containing up to 60 nucleotides generally termed oligonucleotides, and longer fragments termed polynucleotides. A deoxyribooligonucleotide consists of a 5-carbon sugar called deoxyribose joined covalently to phosphate at the 5' and 3' carbons of this sugar to form an alternating, unbranched polymer. DNA may be in the form of, e.g., antisense molecules, plasmid DNA, pre-condensed DNA, a PCR product, vectors, expression cassettes, chimeric sequences, chromosomal DNA, or derivatives and combinations of these groups. A ribooligonucleotide consists of a similar repeating structure where the 5-carbon sugar is ribose.

RNA may be in the form, for example, of small interfering RNA (siRNA), Dicer-substrate dsRNA, small hairpin RNA (shRNA), asymmetrical interfering RNA (aiRNA), microRNA (miRNA), mRNA, tRNA, rRNA, tRNA, viral RNA (vRNA), and combinations thereof.

Accordingly, in the context of this invention, the terms "polynucleotide" and "oligonucleotide" refer to a polymer or oligomer of nucleotide or nucleoside monomers consisting of naturally-occurring bases, sugars and intersugar (backbone) linkages. The terms "polynucleotide" and "oligonucleotide" also include polymers or oligomers comprising non-naturally occurring monomers, or portions thereof, which function similarly. Such modified or substituted oligonucleotides are often preferred over native forms because of properties such as, for example, enhanced cellular uptake, reduced immunogenicity, and increased stability in the presence of nucleases.

Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.*, 19:5081 (1991); Ohtsuka et al., *J. Biol. Chem.*, 260: 2605-2608 (1985); Rossolini et al., *Mol. Cell. Probes*, 8:91-98 (1994)).

The term "gene" refers to a nucleic acid (e.g., DNA or RNA) sequence that comprises partial length or entire length coding sequences necessary for the production of a polypeptide or precursor polypeptide.

"Gene product," as used herein, refers to a product of a gene such as an RNA transcript or a polypeptide.

As used herein, the term "alkyl", by itself or as part of another substituent, means, unless otherwise stated, a straight or branched chain hydrocarbon radical, having the number of carbon atoms designated (i.e., $C_{1-8}$ means one to eight carbons). Examples of alkyl groups include methyl, ethyl, n-propyl, iso-propyl, n-butyl, t-butyl, iso-butyl, sec-butyl, n-pentyl, n-hexyl, n-heptyl, n-octyl, and the like. The term "alkenyl" refers to an unsaturated alkyl radical having one or more double bonds. Similarly, the term "alkynyl" refers to an unsaturated alkyl radical having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkane (including straight and branched alkanes), as exemplified by —$CH_2CH_2CH_2CH_2$— and —$CH(CH_3)CH_2CH_2$—.

The term "cycloalkyl," "carbocyclic," or "carbocycle" refers to hydrocarbon ring system having 3 to 20 overall number of ring atoms (e.g., 3-20 membered cycloalkyl is a cycloalkyl with 3 to 20 ring atoms, or $C_{3-20}$ cycloalkyl is a cycloalkyl with 3-20 carbon ring atoms) and for a 3-5 membered cycloalkyl being fully saturated or having no more than one double bond between ring vertices and for a 6 membered cycloalkyl or larger being fully saturated or having no more than two double bonds between ring vertices. As used herein, "cycloalkyl," "carbocyclic," or "carbocycle" is also meant to refer to bicyclic, polycyclic and spirocyclic hydrocarbon ring system, such as, for example, bicyclo[2.2.1]heptane, pinane, bicyclo[2.2.2]octane, adamantane, norborene, spirocyclic $C_{5-12}$ alkane, etc. As used herein, the terms, "alkenyl," "alkynyl," "cycloalkyl,", "carbocycle," and "carbocyclic," are meant to include mono and polyhalogenated variants thereof.

The term "heterocycloalkyl," "heterocyclic," or "heterocycle" refers to a saturated or partially unsaturated ring system radical having the overall having from 3-20 ring atoms (e.g., 3-20 membered heterocycloalkyl is a heterocycloalkyl radical with 3-20 ring atoms, a $C_{2-19}$ heterocycloalkyl is a heterocycloalkyl having 3-10 ring atoms with between 2-19 ring atoms being carbon) that contain from one to ten heteroatoms selected from N, O, and S, wherein the nitrogen and sulfur atoms are optionally oxidized, nitrogen atom(s) are optionally quaternized, as ring atoms. Unless otherwise stated, a "heterocycloalkyl," "heterocyclic," or "heterocycle" ring can be a monocyclic, a bicyclic, spirocyclic or a polycylic ring system. Non limiting examples of "heterocycloalkyl," "heterocyclic," or "heterocycle" rings include pyrrolidine, piperidine, N-methylpiperidine, imidazolidine, pyrazolidine, butyrolactam, valerolactam, imidazolidinone, hydantoin, dioxolane, phthalimide, piperidine, pyrimidine-2,4(1H,3H)-dione, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrhydrothiophene, quinuclidine, tropane, 2-azaspiro[3.3]heptane, (1R,5S)-3-azabicyclo[3.2.1]octane, (1s,4s)-2-azabicyclo[2.2.2]octane, (1R,4R)-2-oxa-5-azabicyclo[2.2.2]octane and the like A "heterocycloalkyl," "heterocyclic," or "heterocycle" group can be attached to the remainder of the molecule through one or more ring carbons or heteroatoms. A "heterocycloalkyl," "heterocyclic," or "heterocycle" can include mono- and poly-halogenated variants thereof.

The terms "alkoxy," and "alkylthio", are used in their conventional sense, and refer to those alkyl groups attached to the remainder of the molecule via an oxygen atom ("oxy") or thio group, and further include mono- and poly-halogenated variants thereof.

The terms "halo" or "halogen," by themselves or as part of another substituent, mean, unless otherwise stated, a fluorine, chlorine, bromine, or iodine atom. The term "(halo) alkyl" is meant to include both a "alkyl" and "haloalkyl" substituent. Additionally, the term "haloalkyl," is meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, difluoromethyl, and the like.

The term "aryl" means a carbocyclic aromatic group having 6-14 carbon atoms, whether or not fused to one or more groups. Examples of aryl groups include phenyl, naphthyl, biphenyl and the like unless otherwise stated.

The term "heteroaryl" refers to aryl ring(s) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Examples of heteroaryl groups include pyridyl, pyridazinyl, pyrazinyl, pyrimidinyl, triazinyl, quinolinyl, quinoxalinyl, quinazolinyl, cinnolinyl, phthalaziniyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like.

The term saccharide includes monosaccharides, disaccharides and trisaccharides. The term includes glucose, sucrose fructose, galactose and ribose, as well as deoxy sugars such as deoxyribose and amino sugar such as galactosamine. Saccharide derivatives can conveniently be prepared as described in International Patent Applications Publication Numbers WO 96/34005 and 97/03995. A saccharide can conveniently be linked to the remainder of a compound of formula I through an ether bond, a thioether bond (e.g. an S-glycoside), an amine nitrogen (e.g., an N-glycoside), or a carbon-carbon bond (e.g. a C-glycoside). In one embodiment the saccharide can conveniently be linked to the remainder of a compound of formula I through an ether bond. In one embodiment the term saccharide includes a group of the formula:

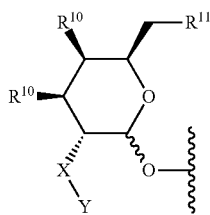

wherein:
X is $NR^3$, and Y is selected from —(C=O)$R^4$, —SO$_2$$R^5$, and —(C=O)N$R^6$$R^7$; or X is —(C=O)— and Y is N$R^8$$R^9$;
$R^3$ is hydrogen or ($C_1$-$C_4$)alkyl;
$R^4$, $R^5$, $R^6$, $R^7$, $R^8$ and $R^9$ are each independently selected from the group consisting of hydrogen, ($C_1$-$C_8$)alkyl, ($C_1$-$C_8$)haloalkyl, ($C_1$-$C_8$)alkoxy and ($C_3$-$C_6$)cycloalkyl that is optionally substituted with one or more groups independently selected from the group consisting of halo, ($C_1$-$C_4$) alkyl, ($C_1$-$C_4$)haloalkyl, ($C_1$-$C_4$)alkoxy and ($C_1$-$C_4$)haloalkoxy;

$R^{10}$ is —OH, —N$R^8$$R^9$ or —F; and
$R^{11}$ is —OH, —N$R^8$$R^9$, —F or 5 membered heterocycle that is optionally substituted with one or more groups independently selected from the group consisting of halo, hydroxyl, carboxyl, amino, ($C_1$-$C_4$)alkyl, ($C_1$-$C_4$)haloalkyl, ($C_1$-$C_4$)alkoxy and ($C_1$-$C_4$)haloalkoxy. In another embodiment the saccharide can be selected from the group consisting of:

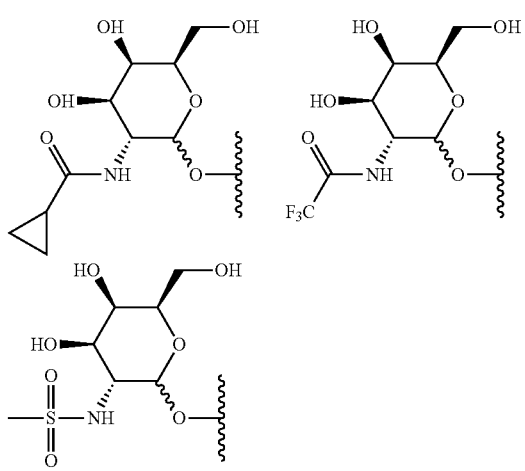

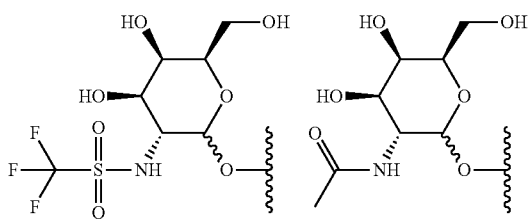

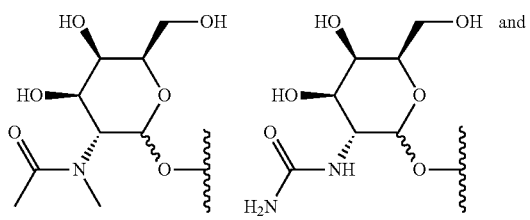 and

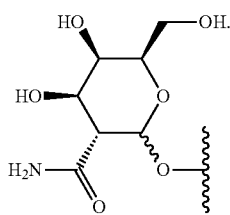

In another embodiment the saccharide can be:

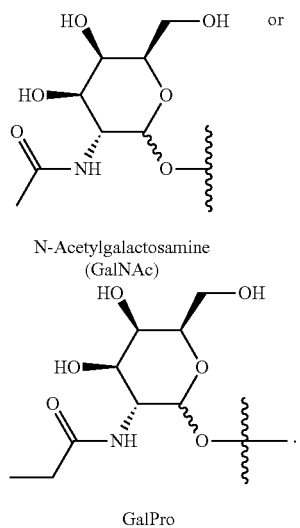

N-Acetylgalactosamine
(GalNAc)

GalPro

The term "animal" includes mammalian species, such as a human, mouse, rat, dog, cat, hamster, guinea pig, rabbit, livestock, and the like.

The term "lipid" refers to a group of organic compounds that include, but are not limited to, esters of fatty acids and are characterized by being insoluble in water, but soluble in many organic solvents. They are usually divided into at least three classes: (1) "simple lipids," which include fats and oils as well as waxes; (2) "compound lipids," which include phospholipids and glycolipids; and (3) "derived lipids" such as steroids.

The term "lipid particle" includes a lipid formulation that can be used to deliver a therapeutic nucleic acid (e.g., siRNA) to a target site of interest (e.g., cell, tissue, organ, and the like). In preferred embodiments, the lipid particle of the invention is a nucleic acid-lipid particle, which is typically formed from a cationic lipid, a non-cationic lipid (e.g., a phospholipid), a conjugated lipid that prevents aggregation of the particle (e.g., a PEG-lipid), and optionally cholesterol. Typically, the therapeutic nucleic acid (e.g., siRNA) may be encapsulated in the lipid portion of the particle, thereby protecting it from enzymatic degradation.

The term "electron dense core", when used to describe a lipid particle of the present invention, refers to the dark appearance of the interior portion of a lipid particle when visualized using cryo transmission electron microscopy ("cryoTEM"). Some lipid particles of the present invention have an electron dense core and lack a lipid bilayer structure. Some lipid particles of the present invention have an electron dense core, lack a lipid bilayer structure, and have an inverse Hexagonal or Cubic phase structure. While not wishing to be bound by theory, it is thought that the non-bilayer lipid packing provides a 3-dimensional network of lipid cylinders with water and nucleic on the inside, i.e., essentially, a lipid droplet interpenetrated with aqueous channels containing the nucleic acid.

As used herein, the term "SNALP" refers to a stable nucleic acid-lipid particle. A SNALP is a particle made from lipids (e.g., a cationic lipid, a non-cationic lipid, and a conjugated lipid that prevents aggregation of the particle), wherein the nucleic acid (e.g., siRNA) is fully encapsulated within the lipid. In certain instances, SNALP are extremely useful for systemic applications, as they can exhibit extended circulation lifetimes following intravenous (i.v.) injection, they can accumulate at distal sites (e.g., sites physically separated from the administration site), and they can mediate siRNA expression at these distal sites. The nucleic acid may be complexed with a condensing agent and encapsulated within a SNALP as set forth in PCT Publication No. WO 00/03683, the disclosure of which is herein incorporated by reference in its entirety for all purposes.

The lipid particles of the invention (e.g., SNALP) typically have a mean diameter of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm, and are substantially non-toxic. In addition, nucleic acids, when present in the lipid particles of the present invention, are resistant to degradation in aqueous solution with a nuclease. Nucleic acid-lipid particles and their method of preparation are disclosed in, e.g., U.S. Patent Publication Nos. 20040142025 and 20070042031, the disclosures of which are herein incorporated by reference in their entirety for all purposes.

As used herein, "lipid encapsulated" can refer to a lipid particle that provides a therapeutic nucleic acid such as an siRNA with full encapsulation, partial encapsulation, or both. In a preferred embodiment, the nucleic acid (e.g., siRNA) is fully encapsulated in the lipid particle (e.g., to form a SNALP or other nucleic acid-lipid particle).

The term "lipid conjugate" refers to a conjugated lipid that inhibits aggregation of lipid particles. Such lipid conjugates include, but are not limited to, PEG-lipid conjugates such as, e.g., PEG coupled to dialkyloxypropyls (e.g., PEG-DAA conjugates), PEG coupled to diacylglycerols (e.g., PEG-DAG conjugates), PEG coupled to cholesterol, PEG coupled to phosphatidylethanolamines, and PEG conjugated to ceramides (see, e.g., U.S. Pat. No. 5,885,613), cationic PEG lipids, polyoxazoline (POZ)-lipid conjugates, polyamide oligomers (e.g., ATTA-lipid conjugates), and mixtures thereof. Additional examples of POZ-lipid conjugates are described in PCT Publication No. WO 2010/006282. PEG or POZ can be conjugated directly to the lipid or may be linked to the lipid via a linker moiety. Any linker moiety suitable for coupling the PEG or the POZ to a lipid can be used including, e.g., non-ester containing linker moieties and ester-containing linker moieties. In certain preferred embodiments, non-ester containing linker moieties, such as amides or carbamates, are used. The disclosures of each of the above patent documents are herein incorporated by reference in their entirety for all purposes.

The term "amphipathic lipid" refers, in part, to any suitable material wherein the hydrophobic portion of the lipid material orients into a hydrophobic phase, while the hydrophilic portion orients toward the aqueous phase. Hydrophilic characteristics derive from the presence of polar or charged groups such as carbohydrates, phosphate, carboxylic, sulfato, amino, sulfhydryl, nitro, hydroxyl, and other like groups. Hydrophobicity can be conferred by the inclusion of apolar groups that include, but are not limited to, long-chain saturated and unsaturated aliphatic hydrocarbon groups and such groups substituted by one or more aromatic, cycloaliphatic, or heterocyclic group(s). Examples of amphipathic compounds include, but are not limited to, phospholipids, aminolipids, and sphingolipids.

Representative examples of phospholipids include, but are not limited to, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine, and dilinoleoylphosphatidylcholine. Other compounds lacking in phosphorus, such as sphingolipid, glycosphingolipid families, diacylglycerols, and β-acyloxyacids, are also within the group designated as amphipathic lipids. Additionally, the amphipathic lipids described above can be mixed with other lipids including triglycerides and sterols.

The term "neutral lipid" refers to any of a number of lipid species that exist either in an uncharged or neutral zwitterionic form at a selected pH. At physiological pH, such lipids include, for example, diacylphosphatidylcholine, diacylphosphatidylethanolamine, ceramide, sphingomyelin, cephalin, cholesterol, cerebrosides, and diacylglycerols.

The term "non-cationic lipid" refers to any amphipathic lipid as well as any other neutral lipid or anionic lipid.

The term "anionic lipid" refers to any lipid that is negatively charged at physiological pH. These lipids include, but are not limited to, phosphatidylglycerols, cardiolipins, diacylphosphatidylserines, diacylphosphatidic acids, N-dodecanoyl phosphatidylethanolamines, N-succinyl phosphatidylethanolamines, N-glutarylphosphatidylethanolamines, lysylphosphatidylglycerols, palmitoyloleoylphosphatidylglycerol (POPG), and other anionic modifying groups joined to neutral lipids.

The term "hydrophobic lipid" refers to compounds having apolar groups that include, but are not limited to, long-chain saturated and unsaturated aliphatic hydrocarbon groups and such groups optionally substituted by one or more aromatic, cycloaliphatic, or heterocyclic group(s). Suitable examples include, but are not limited to, diacylglycerol, dialkylglycerol, N—N-dialkylamino, 1,2-diacyloxy-3-aminopropane, and 1,2-dialkyl-3-aminopropane.

The terms "cationic lipid" and "amino lipid" are used interchangeably herein to include those lipids and salts thereof having one, two, three, or more fatty acid or fatty alkyl chains and a pH-titratable amino head group (e.g., an alkylamino or dialkylamino head group). The cationic lipid is typically protonated (i.e., positively charged) at a pH below the pKa of the cationic lipid and is substantially neutral at a pH above the pKa. The cationic lipids of the invention may also be termed titratable cationic lipids. In some embodiments, the cationic lipids comprise: a protonatable tertiary amine (e.g., pH-titratable) head group; $C_{18}$ alkyl chains, wherein each alkyl chain independently has 0 to 3 (e.g., 0, 1, 2, or 3) double bonds; and ether, ester, or ketal linkages between the head group and alkyl chains. Such cationic lipids include, but are not limited to, DSDMA, DODMA, DLinDMA, DLenDMA, γ-DLenDMA, DLin-K-DMA, DLin-K-C2-DMA (also known as DLin-C2K-DMA, XTC2, and C2K), DLin-K-C3-DMA, DLin-K-C4-DMA, DLen-C2K-DMA, γ-DLen-C2K-DMA, DLin-M-C2-DMA (also known as MC2), DLin-M-C3-DMA (also known as MC3) and (DLin-MP-DMA)(also known as 1-B11).

The term "alkylamino" includes a group of formula —N(H)R, wherein R is an alkyl as defined herein.

The term "dialkylamino" includes a group of formula —NR$_2$, wherein each R is independently an alkyl as defined herein.

The term "salts" includes any anionic and cationic complex, such as the complex formed between a cationic lipid and one or more anions. Non-limiting examples of anions include inorganic and organic anions, e.g., hydride, fluoride, chloride, bromide, iodide, oxalate (e.g., hemioxalate), phosphate, phosphonate, hydrogen phosphate, dihydrogen phosphate, oxide, carbonate, bicarbonate, nitrate, nitrite, nitride, bisulfite, sulfide, sulfite, bisulfate, sulfate, thiosulfate, hydrogen sulfate, borate, formate, acetate, benzoate, citrate, tartrate, lactate, acrylate, polyacrylate, fumarate, maleate, itaconate, glycolate, gluconate, malate, mandelate, tiglate, ascorbate, salicylate, polymethacrylate, perchlorate, chlorate, chlorite, hypochlorite, bromate, hypobromite, iodate, an alkylsulfonate, an arylsulfonate, arsenate, arsenite, chromate, dichromate, cyanide, cyanate, thiocyanate, hydroxide, peroxide, permanganate, and mixtures thereof. In particular embodiments, the salts of the cationic lipids disclosed herein are crystalline salts.

The term "acyl" includes any alkyl, alkenyl, or alkynyl wherein the carbon at the point of attachment is substituted with an oxo group, as defined below. The following are non-limiting examples of acyl groups: —C(=O)alkyl, —C(=O)alkenyl, and —C(=O)alkynyl.

The term "fusogenic" refers to the ability of a lipid particle, such as a SNALP, to fuse with the membranes of a cell. The membranes can be either the plasma membrane or membranes surrounding organelles, e.g., endosome, nucleus, etc.

As used herein, the term "aqueous solution" refers to a composition comprising in whole, or in part, water.

As used herein, the term "organic lipid solution" refers to a composition comprising in whole, or in part, an organic solvent having a lipid.

"Distal site," as used herein, refers to a physically separated site, which is not limited to an adjacent capillary bed, but includes sites broadly distributed throughout an organism.

"Serum-stable" in relation to nucleic acid-lipid particles such as SNALP means that the particle is not significantly degraded after exposure to a serum or nuclease assay that would significantly degrade free DNA or RNA. Suitable assays include, for example, a standard serum assay, a DNAse assay, or an RNAse assay.

"Systemic delivery," as used herein, refers to delivery of lipid particles that leads to a broad biodistribution of an active agent such as an siRNA within an organism. Some techniques of administration can lead to the systemic delivery of certain agents, but not others.

Systemic delivery means that a useful, preferably therapeutic, amount of an agent is exposed to most parts of the body. To obtain broad biodistribution generally requires a blood lifetime such that the agent is not rapidly degraded or cleared (such as by first pass organs (liver, lung, etc.) or by rapid, nonspecific cell binding) before reaching a disease site distal to the site of administration. Systemic delivery of lipid particles can be by any means known in the art including, for example, intravenous, subcutaneous, and intraperitoneal. In a preferred embodiment, systemic delivery of lipid particles is by intravenous delivery.

"Local delivery," as used herein, refers to delivery of an active agent such as an siRNA directly to a target site within an organism. For example, an agent can be locally delivered by direct injection into a disease site, other target site, or a target organ such as the liver, heart, pancreas, kidney, and the like.

When used herein to describe the ratio of lipid:siRNA, the term "lipid" refers to the total lipid in the particle.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. Unless otherwise specifically noted, when a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

Unless stated otherwise herein, the term "about", when used in connection with a value or range of values, means plus or minus 5% of the stated value or range of values.

Generating siRNA Molecules siRNA can be provided in several forms including, e.g., as one or more isolated small-interfering RNA (siRNA) duplexes, as longer double-stranded RNA (dsRNA), or as siRNA or dsRNA transcribed from a transcriptional cassette in a DNA plasmid. In some embodiments, siRNA may be produced enzymatically or by partial/total organic synthesis, and modified ribonucleotides can be introduced by in vitro enzymatic or organic synthesis. In certain instances, each strand is prepared chemically. Methods of synthesizing RNA molecules are known in the art, e.g., the chemical synthesis methods as described in Verma and Eckstein (1998) or as described herein.

Methods for isolating RNA, synthesizing RNA, hybridizing nucleic acids, making and screening cDNA libraries, and performing PCR are well known in the art (see, e.g., Gubler and Hoffman, Gene, 25:263-269 (1983); Sambrook et al., supra; Ausubel et al., supra), as are PCR methods (see, U.S. Pat. Nos. 4,683,195 and 4,683,202; *PCR Protocols: A Guide to Methods and Applications* (Innis et al., eds, 1990)). Expression libraries are also well known to those of skill in the art. Additional basic texts disclosing the general methods of use in this invention include Sambrook et al., *Molecular Cloning, A Laboratory Manual* (2nd ed. 1989); Kriegler, Gene *Transfer and Expression: A Laboratory Manual* (1990); and *Current Protocols in Molecular Biology* (Ausubel et al., eds., 1994). The disclosures of these references are herein incorporated by reference in their entirety for all purposes.

Typically, siRNA are chemically synthesized. The oligonucleotides that comprise the siRNA molecules of the invention can be synthesized using any of a variety of techniques known in the art, such as those described in Usman et al., *J. Am. Chem. Soc.*, 109:7845 (1987); Scaringe et al., *Nucl. Acids Res.*, 18:5433 (1990); Wincott et al., *Nucl. Acids Res.*, 23:2677-2684 (1995); and Wincott et al., *Methods Mol. Bio.*, 74:59 (1997). The synthesis of oligonucleotides makes use of common nucleic acid protecting and coupling groups, such as dimethoxytrityl at the 5'-end and phosphoramidites at the 3'-end. As a non-limiting example, small scale syntheses can be conducted on an Applied Biosystems synthesizer using a 0.2 μmol scale protocol. Alternatively, syntheses at the 0.2 μmol scale can be performed on a 96-well plate synthesizer from Protogene (Palo Alto, CA). However, a larger or smaller scale of synthesis is also within the scope of this invention. Suitable reagents for oligonucleotide synthesis, methods for RNA deprotection, and methods for RNA purification are known to those of skill in the art.

siRNA molecules can be assembled from two distinct oligonucleotides, wherein one oligonucleotide comprises the sense strand and the other comprises the antisense strand of the siRNA. For example, each strand can be synthesized separately and joined together by hybridization or ligation following synthesis and/or deprotection.

EMBODIMENTS OF THE INVENTION

Table 1 in Example 25 describes a series of chemically modified siRNA duplexes (sense and antisense strands shown) that target the Hepatitis B virus (abbreviated as "HBV").

As described herein, a compound of the invention may comprise such a siRNA (i.e., siRNA 1-37).

Accordingly, one aspect of the invention is a nucleic acid molecule selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71 and SEQ ID NO:73.

Another aspect of this invention is a nucleic acid molecule selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72 and SEQ ID NO:74.

One aspect of the invention is a composition comprising a nucleic acid molecule described herein, or a combination thereof.

One aspect of the invention provides a double stranded siRNA molecule selected from the group consisting of siRNA 1 (SEQ ID NO:1 and 2), 2 (SEQ ID NO:3 and 4), 3 (SEQ ID NO:5 and 6), 4 (SEQ ID NO:7 and 8), 5 (SEQ ID NO:9 and 10), 6 (SEQ ID NO:11 and 12), 7 (SEQ ID NO:13 and 14), 8 (SEQ ID NO:15 and 16), 9 (SEQ ID NO:17 and 18), 10 (SEQ ID NO:19 and 20), 11 (SEQ ID NO:21 and 22), 12 (SEQ ID NO:23 and 24), 13 (SEQ ID NO: 25 and 26), 14 (SEQ ID NO:27 and 28), 15 (SEQ ID NO:29 and 30), 16 (SEQ ID NO:31 and 32), 17 (SEQ ID NO:33 and 34), 18 (SEQ ID NO:35 and 36), 19 (SEQ ID NO:37 and 38), 20 (SEQ ID NO:39 and 40), 21 (SEQ ID NO:41 and 42), 22 (SEQ ID NO:43 and 44), 23 (SEQ ID NO:45 and 46), 24 (SEQ ID NO:47 and 48), 25 (SEQ ID NO:49 and 50), 26 (SEQ ID NO:51 and 52), 27 (SEQ ID NO:53 and 54), 28 (SEQ ID NO:55 and 56), 29 (SEQ ID NO:57 and 58), 30 (SEQ ID NO:59 and 60), 31 (SEQ ID NO:61 and 62), 32 (SEQ ID NO:63 and 64), 33 (SEQ ID NO:65 and 66), 34 (SEQ ID NO:67 and 68), 35 (SEQ ID NO:69 and 70), 36 (SEQ ID NO:71 and 72) and 37 (SEQ ID NO:73 and 74).

Another aspect of the invention provides a composition comprising a double stranded siRNA molecule described herein.

In one embodiment, the composition is a pharmaceutical composition that comprises a pharmaceutically acceptable carrier.

One aspect of the invention is a compound of formula I, as set forth about in the Summary of the Invention, or a salt thereof.

In one embodiment of the compound of formula I, $R^1$ a is targeting ligand;

$L^1$ is absent or a linking group;

$L^2$ is absent or a linking group;

$R^2$ is a double stranded siRNA molecule selected from the double stranded siRNA of Table 1;

the ring A is absent, a 3-20 membered cycloalkyl, a 5-20 membered aryl, a 5-20 membered heteroaryl, or a 3-20 membered heterocycloalkyl;

each $R^A$ is independently selected from the group consisting of hydrogen, hydroxy, CN, F, Cl, Br, I, —$C_{1-2}$alkyl-$OR^B$ and $C_{1-8}$ alkyl that is optionally substituted with one or more groups independently selected from halo, hydroxy, and $C_{1-3}$ alkoxy;

$R^B$ is hydrogen, a protecting group, a covalent bond to a solid support, or a bond to a linking group that is bound to a solid support; and n is 0, 1, 2, 3, 4, 5, 6, 7, 8, 9, or 10.

In one embodiment $R^1$ is —$C(H)_{(3-p)}(L^3$-saccharide$)_p$, wherein each $L^3$ is independently a linking group; p is 1, 2, or 3; and saccharide is a monosaccharide or disaccharide.

In one embodiment the saccharide is:

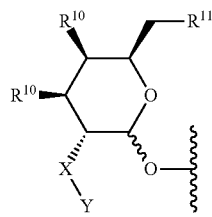

wherein:

X is $NR^3$, and Y is selected from —(C=O)$R^4$, —$SO_2R^5$, and —(C=O)$NR^6R^7$; or X is —(C=O)— and Y is $NR^8R^9$;

$R^3$ is hydrogen or (C$_1$-C$_4$)alkyl;

$R^4$, $R^5$, $R^6$, $R^7$, $R^8$ and $R^9$ are each independently selected from the group consisting of hydrogen, (C$_1$-C$_8$)alkyl, (C$_1$-C$_8$)haloalkyl, (C$_1$-C$_8$)alkoxy and (C$_3$-C$_6$)cycloalkyl that is optionally substituted with one or more groups independently selected from the group consisting of halo, (C$_1$-C$_4$)alkyl, (C$_1$-C$_4$)haloalkyl, (C$_1$-C$_4$)alkoxy and (C$_1$-C$_4$)haloalkoxy;

$R^{10}$ is —OH, —$NR^8R^9$ or —F; and $R^{11}$ is —OH, —$NR^8R^9$, —F or 5 membered heterocycle that is optionally substituted with one or more groups independently selected from the group consisting of halo, hydroxyl, carboxyl, amino, (C$_1$-C$_4$)alkyl, (C$_1$-C$_4$)haloalkyl, (C$_1$-C$_4$)alkoxy and (C$_1$-C$_4$)haloalkoxy;

or a salt thereof.

In one embodiment the saccharide is selected from the group consisting of:

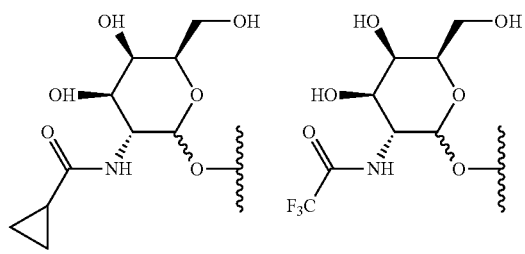

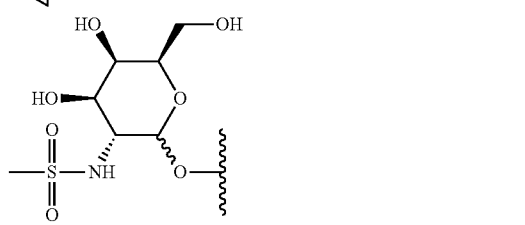

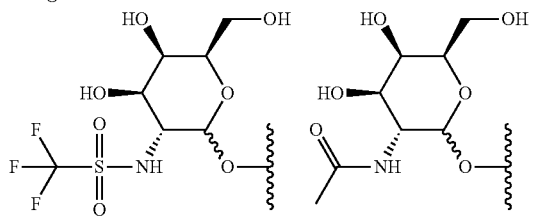

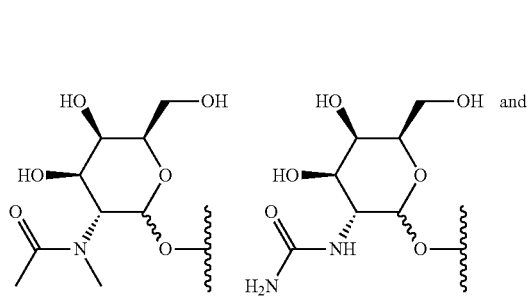

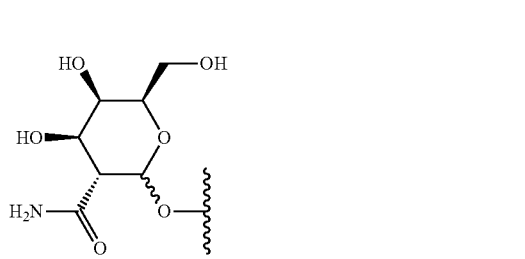

and salts thereof.

In one embodiment the saccharide is:

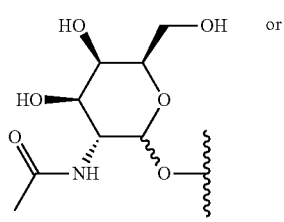

N-Acetylgalactosamine
(GalNAc)

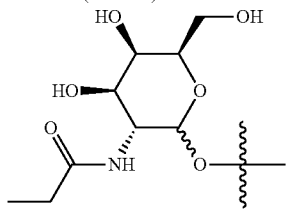

GalPro

In one embodiment each $L^3$ is independently a divalent, branched or unbranched, saturated or unsaturated, hydrocarbon chain, having from 0 to 50 carbon atoms, wherein one or more (e.g. 1, 2, 3, or 4) of the carbon atoms in the hydrocarbon chain is optionally replaced by —O—, —NR$^X$—, —NR$^X$—C(=O)—, —C(=O)—NR$^X$— or —S—, and wherein R$^X$ is hydrogen or $(C_1-C_6)$alkyl, and wherein the hydrocarbon chain, is optionally substituted with one or more (e.g. 1, 2, 3, or 4) substituents selected from $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo (=O), carboxy, aryl, aryloxy, heteroaryl, and heteroaryloxy.

In one embodiment $L^3$ is:

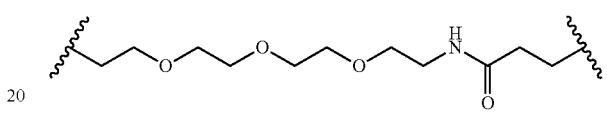

or a salt thereof.

In one embodiment $R^1$ is:

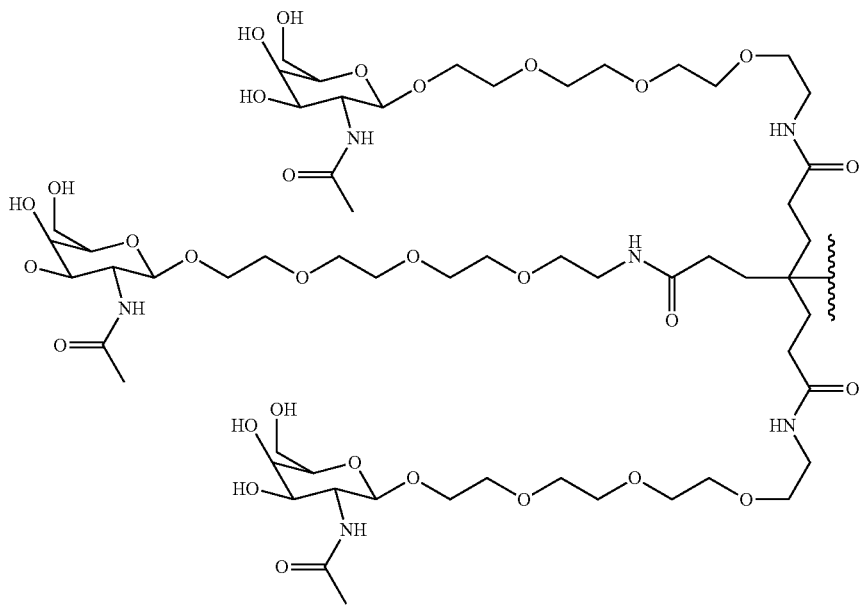 [SMILES: *C(CCC(=O)NCCOCCOCCOCCOC1OC(CO)C(O)C(O)C1NC(C)=O)(CCC(=O)NCCOCCOCCOCCOC1OC(CO)C(O)C(O)C1NC(C)=O)CCC(=O)NCCOCCOCCOCCOC1OC(CO)C(O)C(O)C1NC(C)=O]

or a salt thereof.

In one embodiment $R^1$ is:

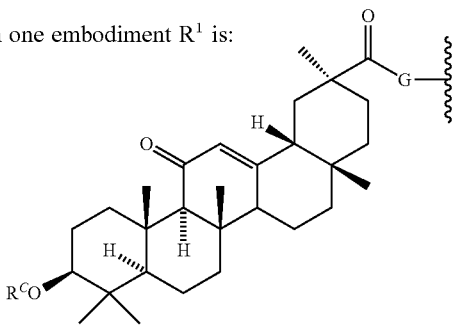

bon chain, having from 0 to 50 carbon atoms, wherein one or more (e.g. 1, 2, 3, or 4) of the carbon atoms in the hydrocarbon chain is optionally replaced by —O—, —NR$^X$—, —NR$^X$—C(=O)—, —C(=O)—NR$^X$— or —S—, and wherein R$^X$ is hydrogen or $(C_1-C_6)$alkyl, and wherein the hydrocarbon chain, is optionally substituted with one or more (e.g. 1, 2, 3, or 4) substituents selected from $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo (=O), carboxy, aryl, aryloxy, heteroaryl, and heteroaryloxy.

In one embodiment each $L^3$ is independently a divalent, branched or unbranched, saturated or unsaturated, hydrocarbon chain, having from 1 to 20 carbon atoms, wherein one or more (e.g. 1, 2, 3, or 4) of the carbon atoms in the

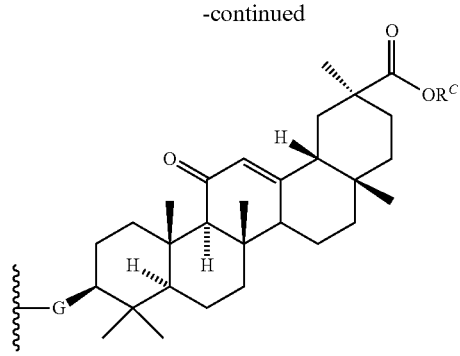

wherein G is —NH— or —O—;
$R^C$ is hydrogen, $(C_1-C_8)$alkyl, $(C_1-C_8)$haloalkyl, $(C_1-C_8)$alkoxy, $(C_1-C_6)$alkanoyl, $(C_3-C_{20})$cycloalkyl, $(C_3-C_{20})$heterocycle, aryl, heteroaryl, monosaccharide, disaccharide or trisaccharide; and wherein the cycloalkyl, heterocycle, aryl, heteroaryl and saccharide are optionally substituted with one or more groups independently selected from the group consisting of halo, carboxyl, hydroxyl, amino, $(C_1-C_4)$alkyl, $(C_1-C_4)$haloalkyl, $(C_1-C_4)$alkoxy and $(C_1-C_4)$haloalkoxy;
or a salt thereof.

In one embodiment $R^C$ is:

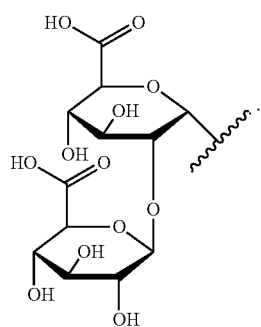

In one embodiment $R^1$ is:

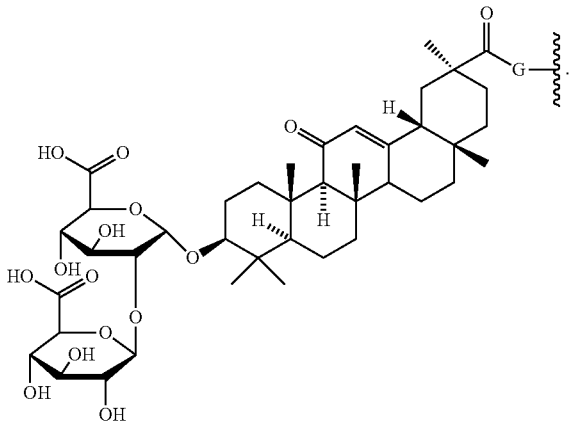

In one embodiment $R^C$ is:

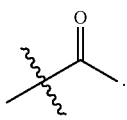 [SMILES: *C(C)=O]

In one embodiment G is —NH—.

In one embodiment $R^1$ is:

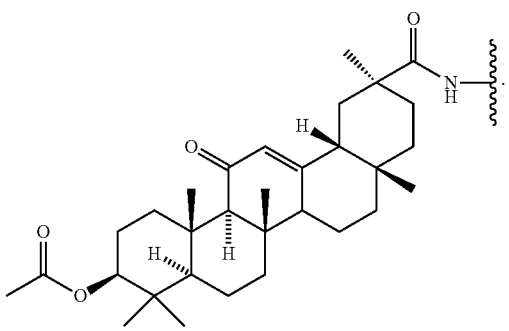

In one embodiment $R^1$ is:

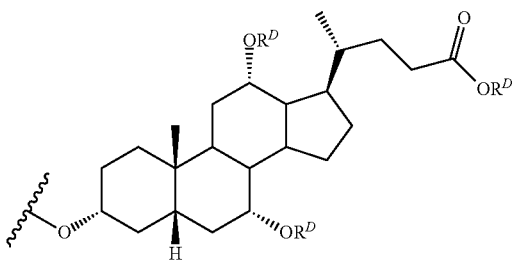

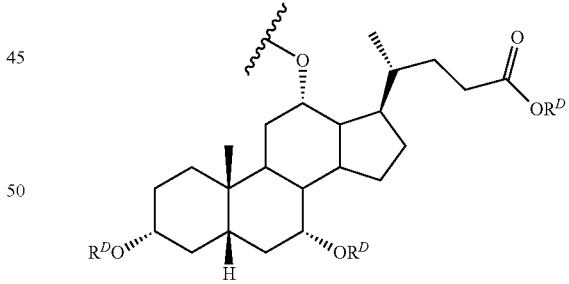

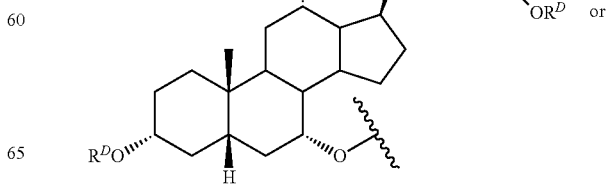

or

-continued

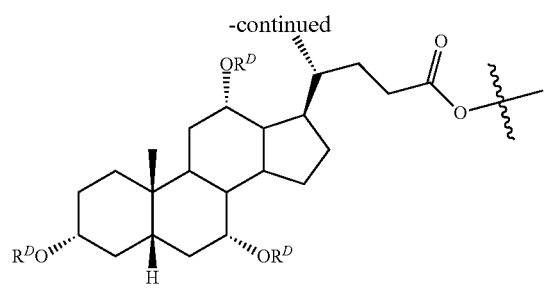

wherein each RD is independently selected from the group consisting of hydrogen, $(C_1-C_6)$alkyl, $(C_9-C_{20})$alkylsilyl, $(R^W)_3Si-$, $(C_2-C_6)$alkenyl, tetrahydropyranyl, $(C_1-C_6)$alkanoyl, benzoyl, aryl$(C_1-C_3)$alkyl, TMTr (Trimethoxytrityl), DMTr (Dimethoxytrityl), MMTr (Monomethoxytrityl), and Tr (Trityl); and each $R^W$ is independently selected from the group consisting of $(C_1-C_4)$alkyl and aryl.

In one embodiment linking groups $L^1$ and $L^2$ are independently a divalent, branched or unbranched, saturated or unsaturated, hydrocarbon chain, having from 1 to 50 carbon atoms, wherein one or more (e.g. 1, 2, 3, or 4) of the carbon atoms in the hydrocarbon chain is optionally replaced by —O—, —NR$^X$—, —NR$^X$—C(=O)—, —C(=O)—NR$^X$— or —S—, and wherein R$^X$ is hydrogen or $(C_1-C_6)$alkyl, and wherein the hydrocarbon chain, is optionally substituted with one or more (e.g. 1, 2, 3, or 4) substituents selected from $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo (=O), carboxy, aryl, aryloxy, heteroaryl, and heteroaryloxy.

In one embodiment $L^1$ and $L^2$ are independently a divalent, branched or unbranched, saturated or unsaturated, hydrocarbon chain, having from 1 to 20 carbon atoms, wherein one or more (e.g. 1, 2, 3, or 4) of the carbon atoms in the hydrocarbon chain is optionally replaced by —O—, —NR$^X$—, —NR$^X$—C(=O)—, —C(=O)—NR$^X$— or —S—, and wherein R$^X$ is hydrogen or $(C_1-C_6)$alkyl, and wherein the hydrocarbon chain, is optionally substituted with one or more (e.g. 1, 2, 3, or 4) substituents selected from $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo (=O), carboxy, aryl, aryloxy, heteroaryl, and heteroaryloxy.

In one embodiment $L^1$ and $L^2$ are independently, a divalent, branched or unbranched, saturated or unsaturated, hydrocarbon chain, having from 1 to 14 carbon atoms, wherein one or more (e.g. 1, 2, 3, or 4) of the carbon atoms in the hydrocarbon chain is optionally replaced —O—, —NR$^X$—, —NR$^X$—C(=O)—, —C(=O)—NR$^X$— or —S—, and wherein R$^X$ is hydrogen or $(C_1-C_6)$alkyl, and wherein the hydrocarbon chain, is optionally substituted with one or more (e.g. 1, 2, 3, or 4) substituents selected from $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo (=O), carboxy, aryl, aryloxy, heteroaryl, and heteroaryloxy.

In one embodiment $L^1$ is connected to $R^1$ through —NH—, —O—, —S—, —(C=O)—, —(C=O)—NH—, —NH—(C=O)—, —(C=O)—O—, —NH—(C=O)—NH—, or —NH—(SO$_2$)—.

In one embodiment $L^2$ is connected to $R^2$ through —O—.

In one embodiment $L^1$ is selected from the group consisting of:

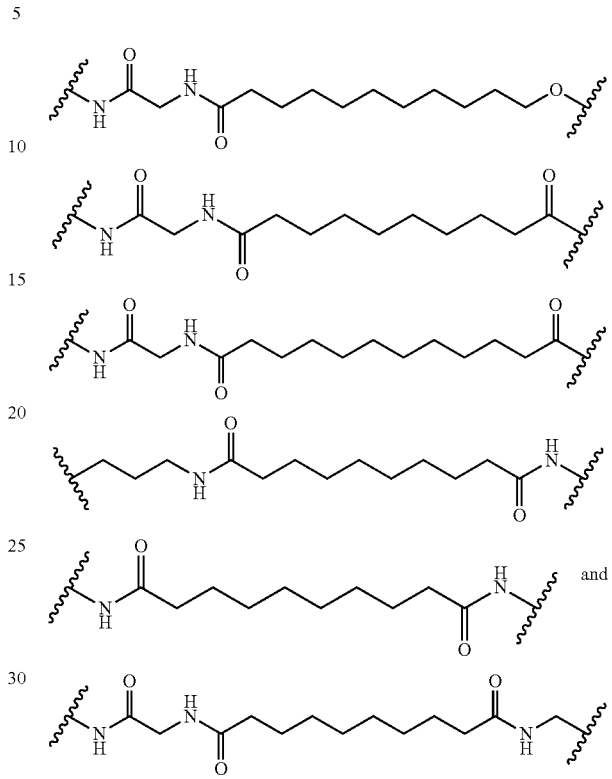

In one embodiment $L^2$ is selected from the group consisting of:

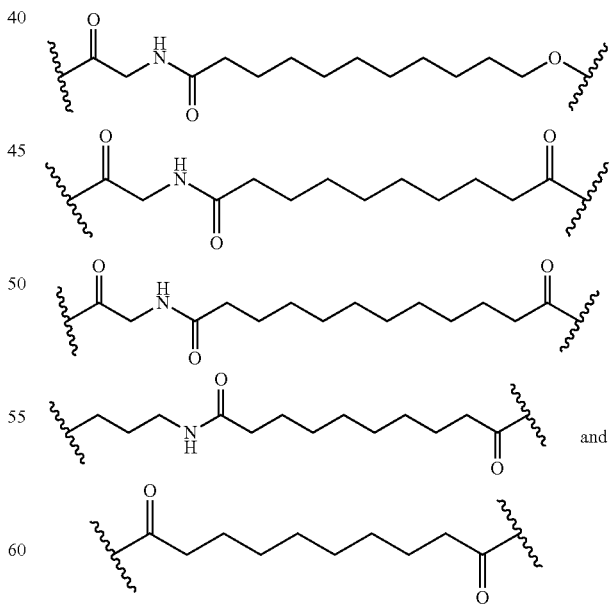

and salts thereof.

In one embodiment $L^2$ is —CH$_2$—O— or —CH$_2$—CH$_2$—O—.

In one embodiment a compound of formula I has the following formula Ia:
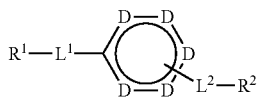
wherein:
each D is independently selected from the group consisting of
and —N≡;
or a salt thereof.
In one embodiment a compound of formula Ia is selected from the group consisting of:
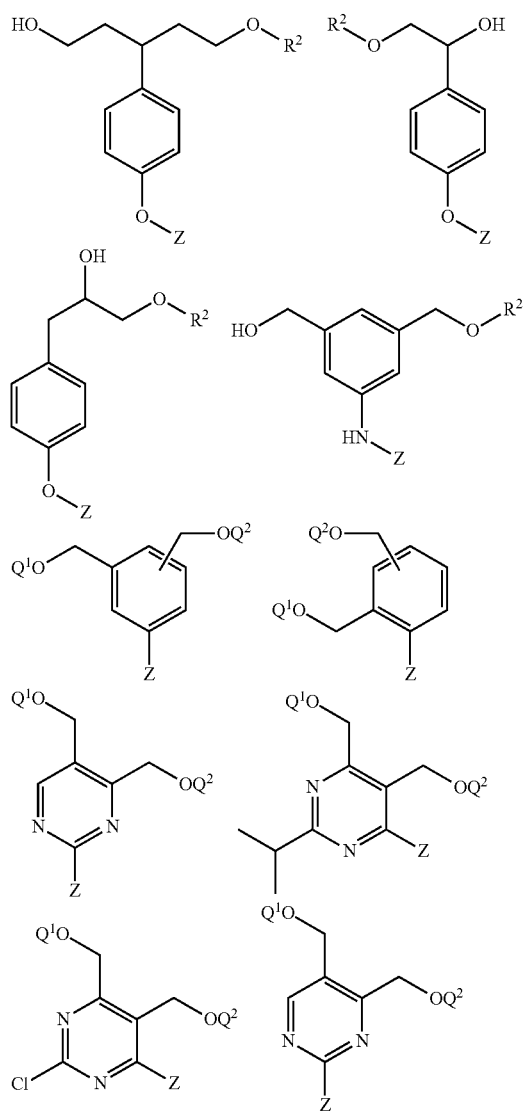
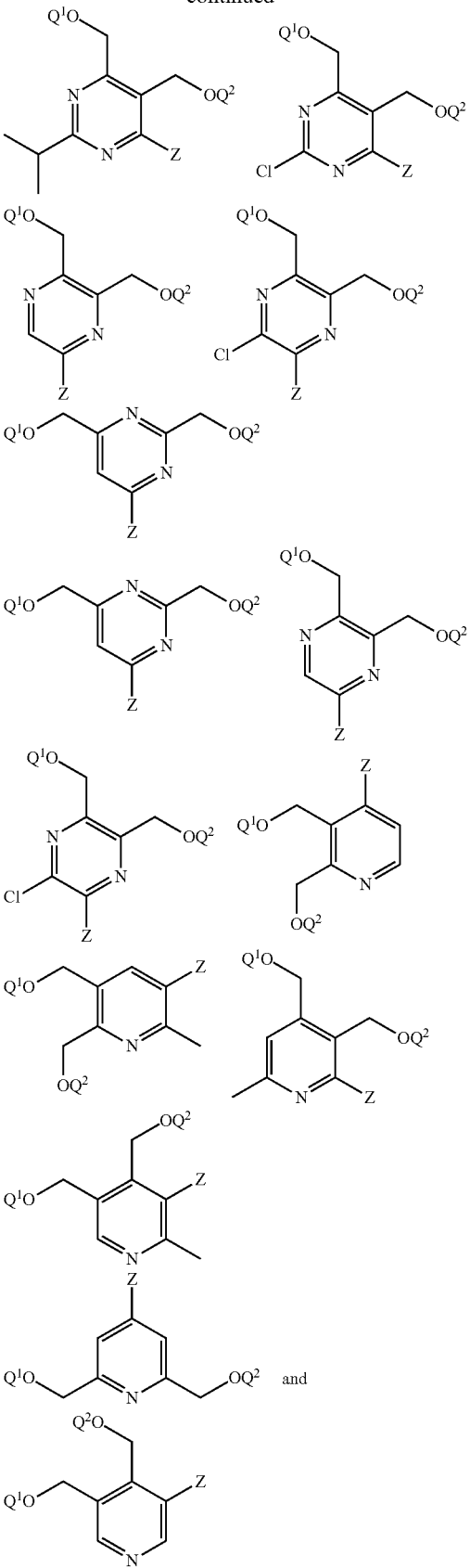

wherein:

$Q^1$ is hydrogen and $Q^2$ is $R^2$; or $Q^1$ is $R^2$ and $Q^2$ is hydrogen;

Z is -$L^1$-$R^1$;

and salts thereof.

In one embodiment a compound of formula I has the following formula Ib:

(Ib)

wherein:

each D is independently selected from the group consisting of

and —N=;

each m is independently 1 or 2; or a salt thereof.

In one embodiment a compound of formula Ib is selected from the group consisting of:

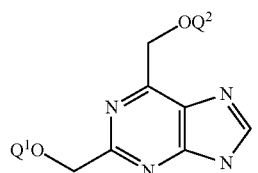

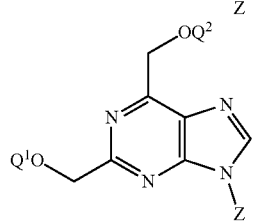

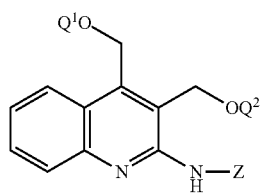

wherein:

$Q^1$ is hydrogen and $Q^2$ is $R^2$; or $Q^1$ is $R^2$ and $Q^2$ is hydrogen;

Z is -$L^1$-$R^1$;

and salts thereof.

In one embodiment a compound of formula I has the following formula (Ic):

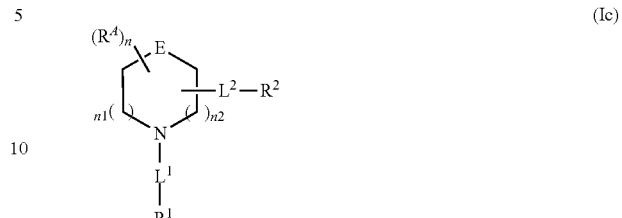

(Ic)

wherein E is —O— or —CH$_2$—;

n is selected from the group consisting of 0, 1, 2, 3, and 4; and n1 and n2 are each independently selected from the group consisting of 0, 1, 2, and 3;

or a salt thereof.

In certain embodiments a compound of formula (Ic) is selected from the group consisting of:

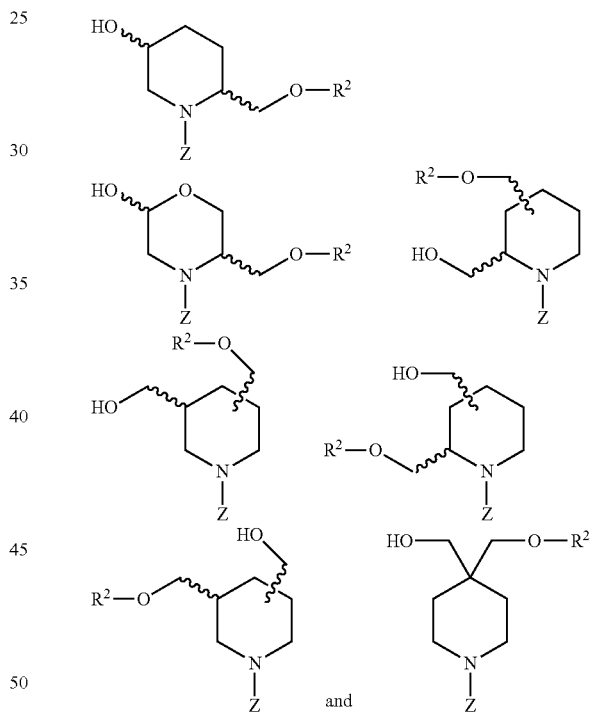

wherein Z is -$L^1$-$R^1$;

and salts thereof.

In one embodiment the -A-$L^2$-$R^2$ moiety is:

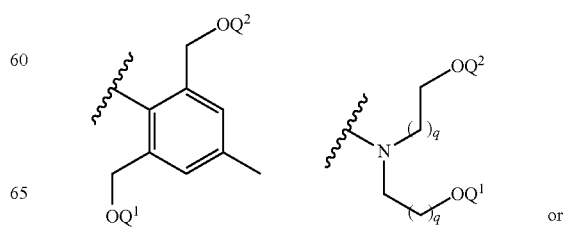

or

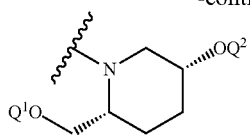
wherein:
Q$^1$ is hydrogen and Q$^2$ is R$^2$; or Q$^1$ is R$^2$ and Q$^2$ is hydrogen; and
each q is independently 0, 1, 2, 3, 4 or 5;
or a salt thereof.
In one embodiment a compound of formula (I) is selected from the group consisting of:
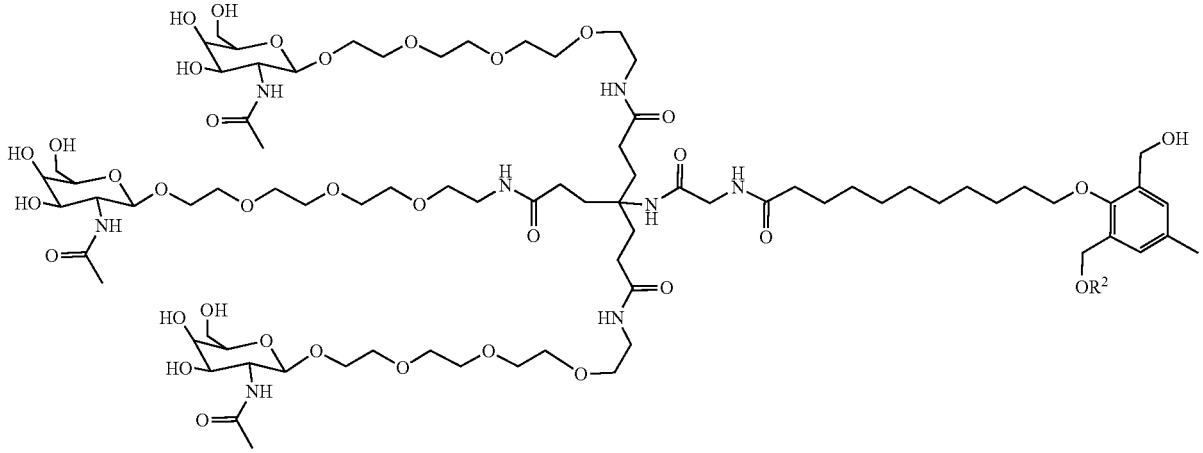
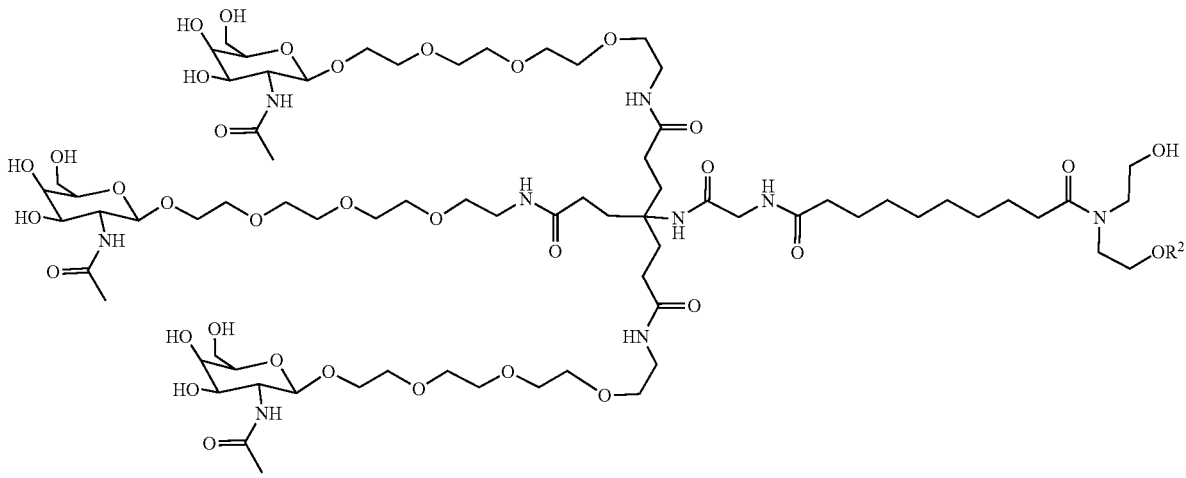
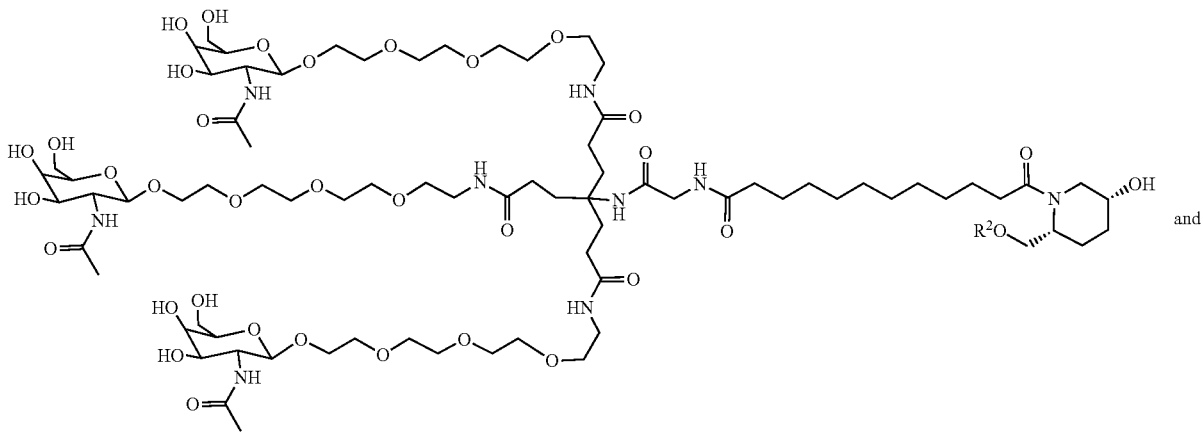
and

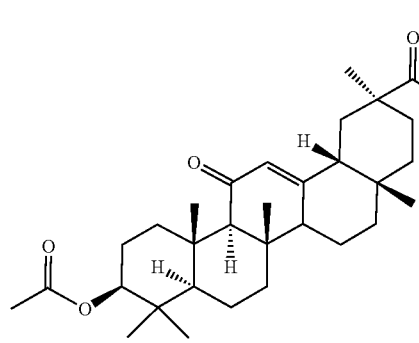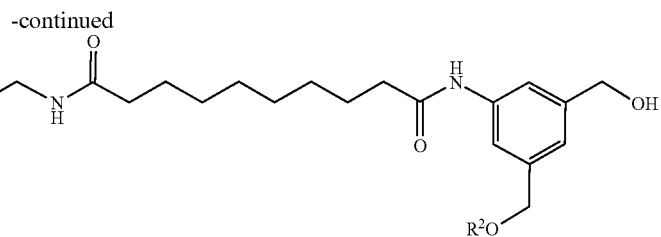
and salts thereof.
In one embodiment $R^1$ is selected from the group consisting of:
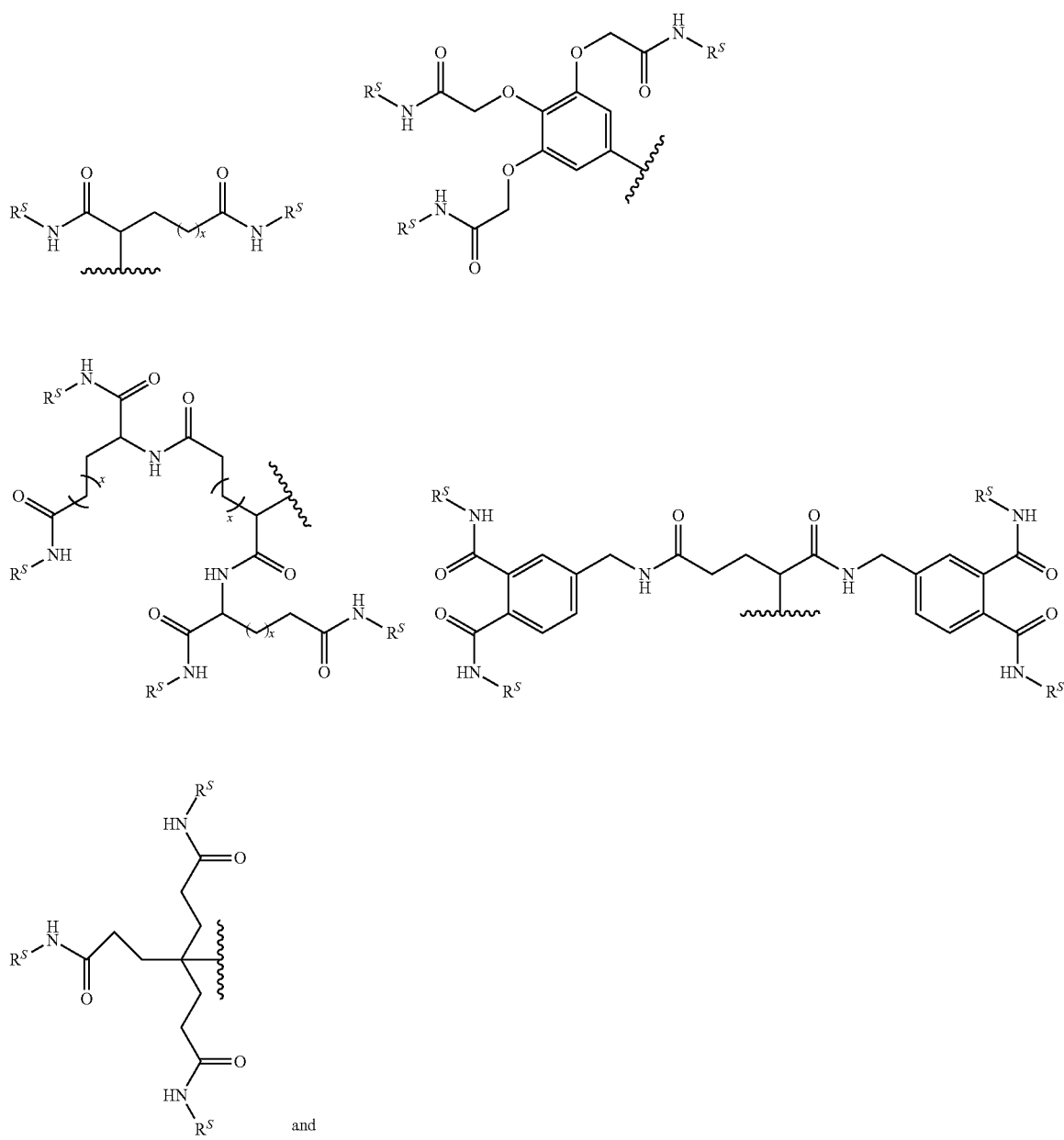
and -continued
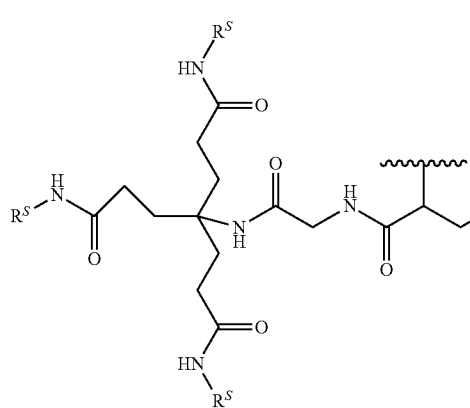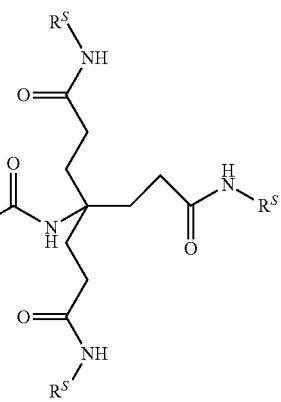
wherein $R^S$ is
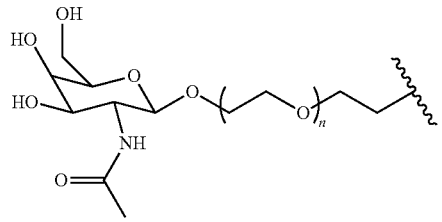
n is 2, 3, or 4;
x is 1 or 2.
In one embodiment $L^1$ is selected from the group consisting of:
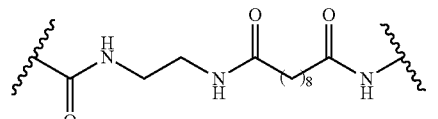
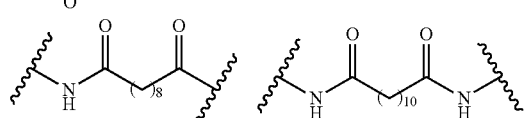
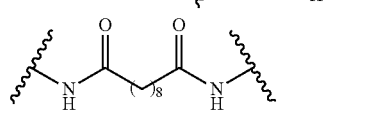
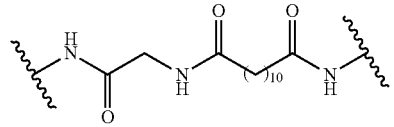
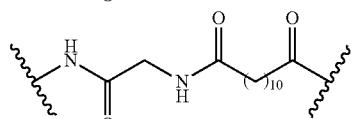
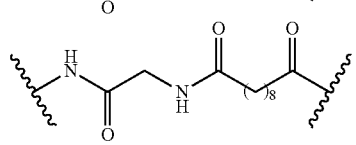
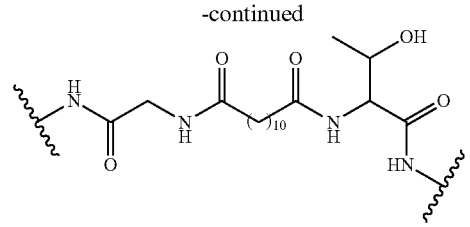
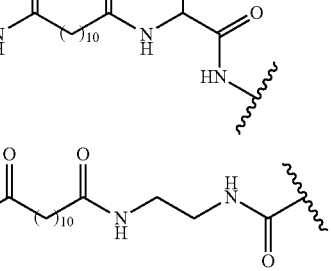
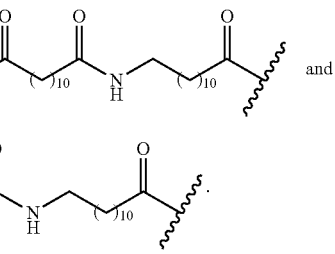 and
In one embodiment $L^1$ is selected from the group consisting of:
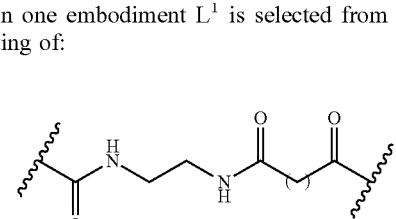
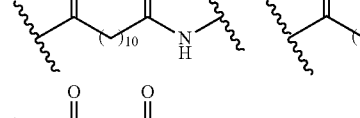
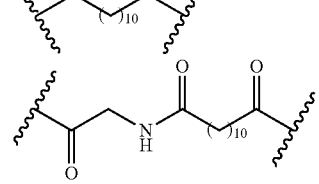

-continued

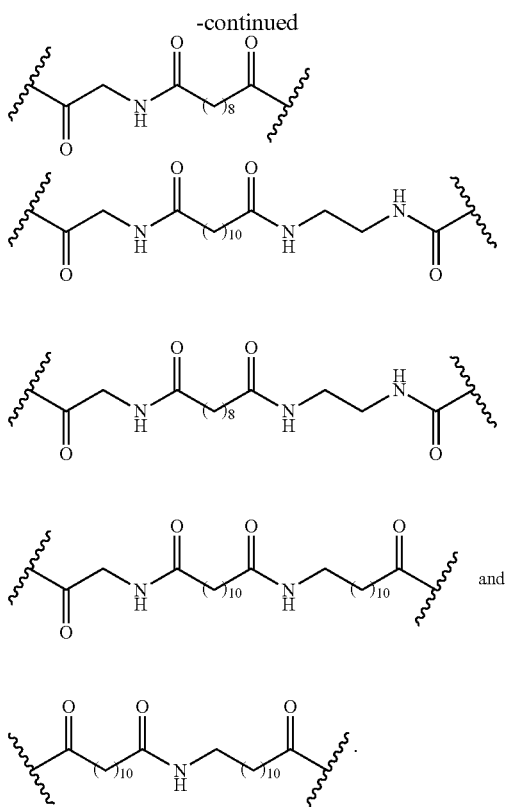

In one embodiment A is absent, phenyl, pyrrolidinyl, or cyclopentyl.

In one embodiment $L^2$ is $C_{1-4}$ alkylene-O— that is optionally substituted with hydroxy.

In one embodiment $L^2$ is —CH$_2$O—, —CH$_2$CH$_2$O—, or —CH(OH)CH$_2$O—.

In one embodiment each $R^A$ is independently hydroxy or $C_{1-8}$ alkyl that is optionally substituted with hydroxyl.

In one embodiment each $R^A$ is independently selected from the group consisting of hydroxy, methyl and —CH$_2$OH.

In one embodiment a compound of formula I has the following formula (Ig):

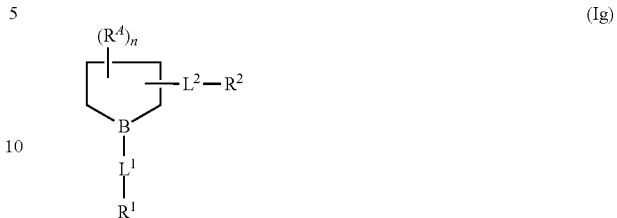

wherein B is —N— or —CH—;
$L^1$ is absent or —NH—;
$L^2$ is $C_{1-4}$ alkylene-O— that is optionally substituted with hydroxyl or halo;
n is 0, 1, or 2;
or a salt thereof.

In one embodiment a compound of formula I has the following formula (Ig):

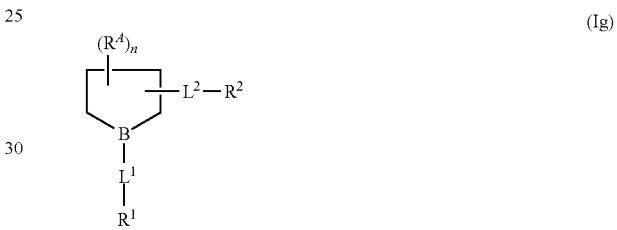

wherein B is —N— or —CH—;
$L^1$ is absent or —NH—;
$L^2$ is $C_{1-4}$ alkylene-O— that is optionally substituted with hydroxyl or halo;
n is 0, 1, 2, 3, 4, 5, 6, or 7;
or a salt thereof.

In one embodiment a compound of formula I has the following formula (Ig):

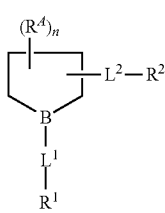

wherein B is —N— or —CH—;
$L^1$ is absent or —NH—;
$L^2$ is $C_{1-4}$ alkylene-O— that is optionally substituted with hydroxyl or halo;
n is 0, 1, 2, 3, or 4;
or a salt thereof.

In one embodiment a compound of formula Ig is selected from the group consisting of:

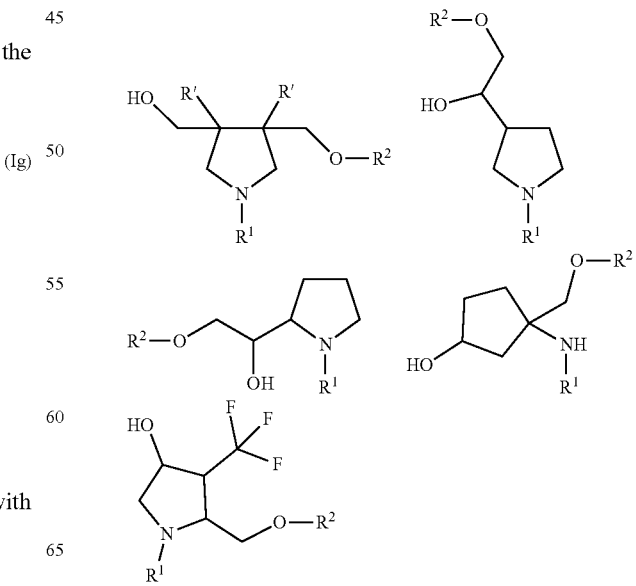

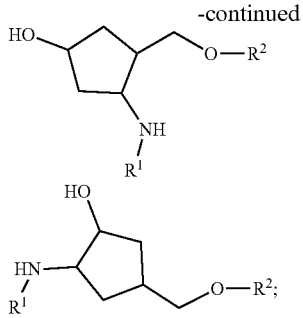

and

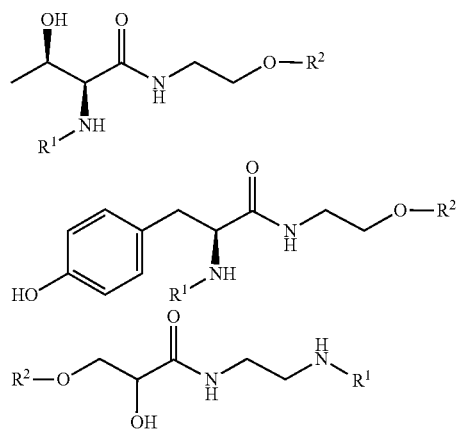

wherein R' is $C_{1-9}$ alkyl, $C_{2-9}$ alkenyl or $C_{2-9}$ alkynyl; wherein the $C_{1-9}$ alkyl, $C_{2-9}$ alkenyl or $C_{2-9}$ alkynyl are optionally substituted with halo or hydroxyl;

and salts thereof.

In one embodiment a compound of formula I is selected from the group consisting of:

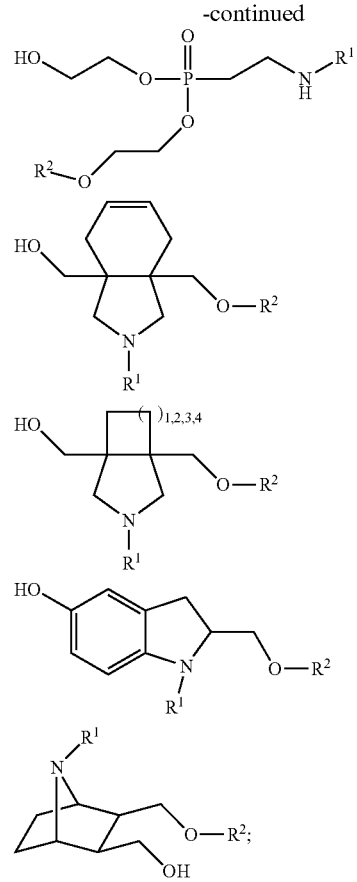

and and salts thereof.

In one embodiment the compound of formula I or the salt thereof is selected from the group consisting of:

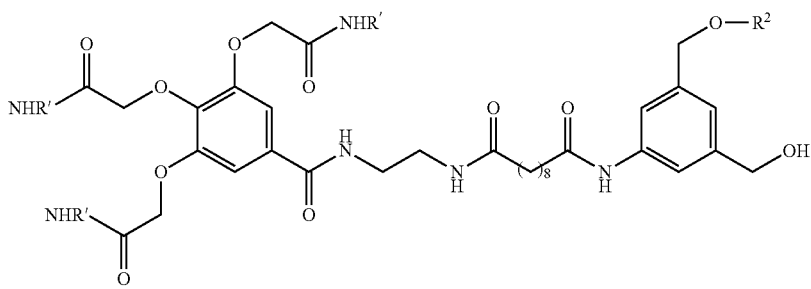

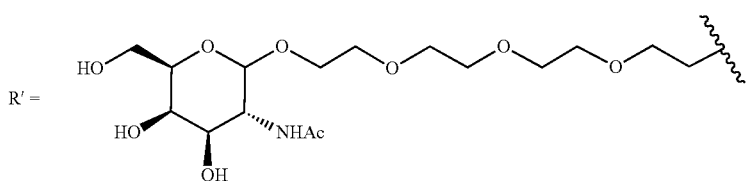

-continued
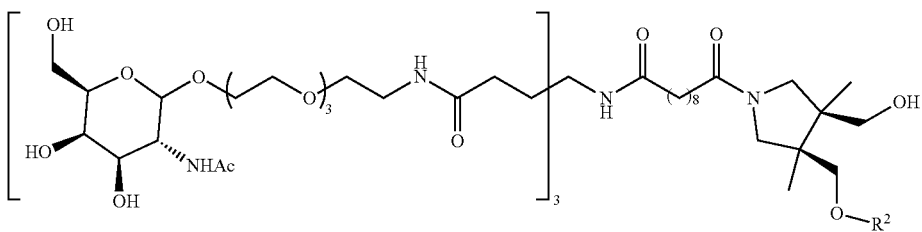
145
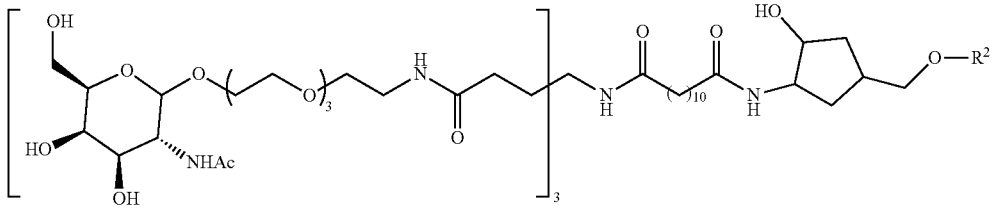
150
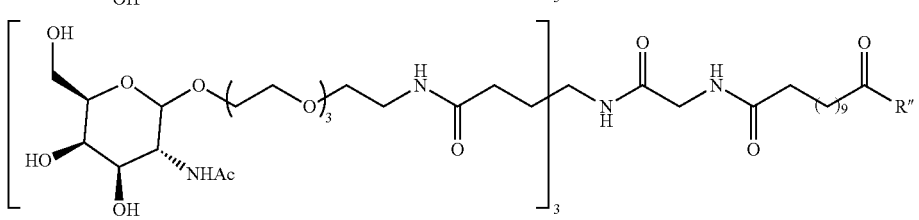
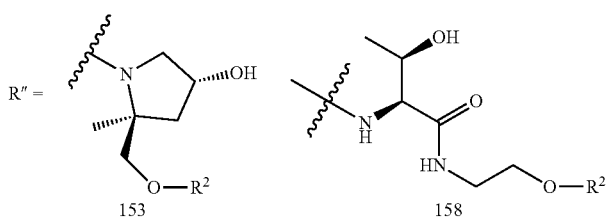
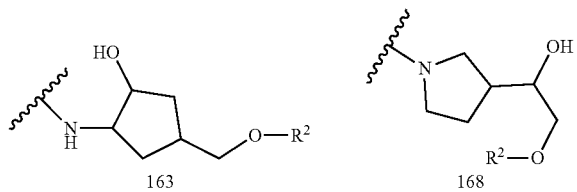
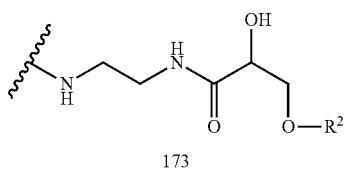
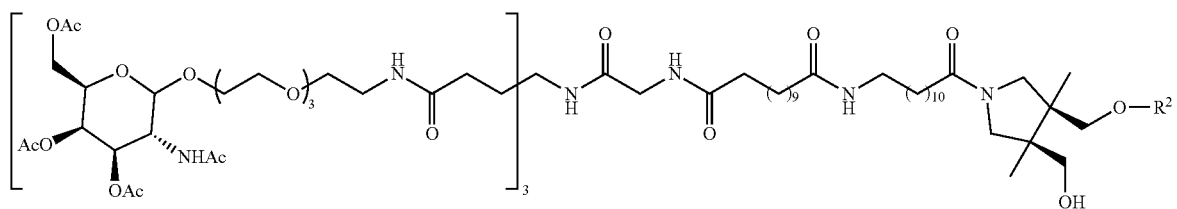
176

179
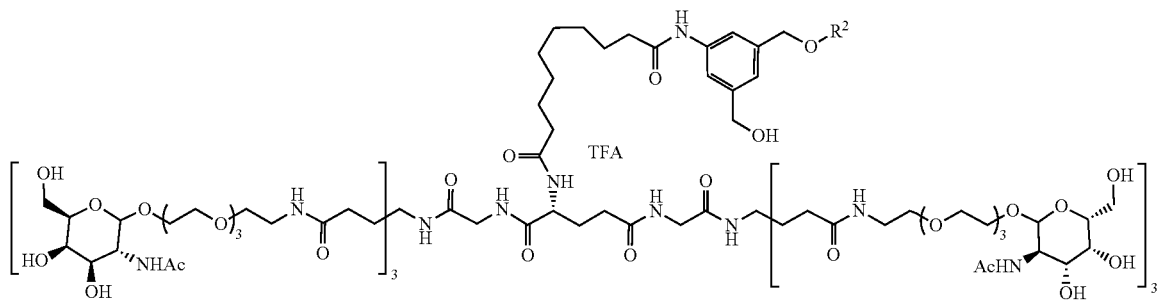
182
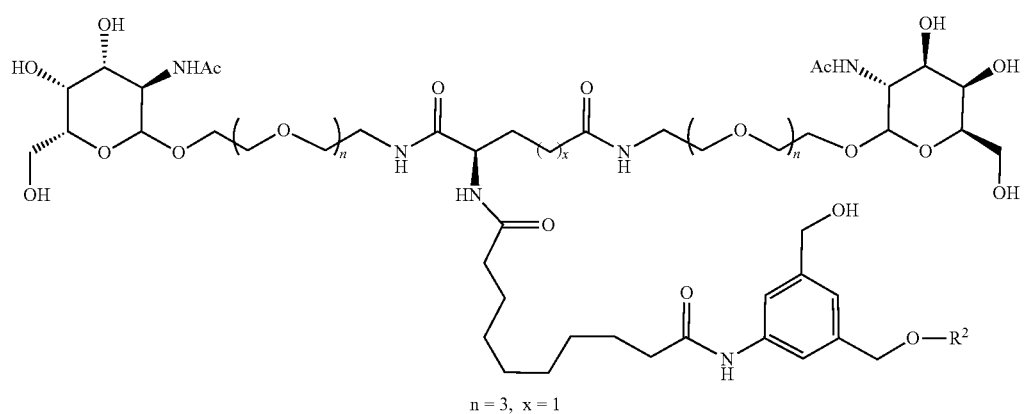
n = 3, x = 1
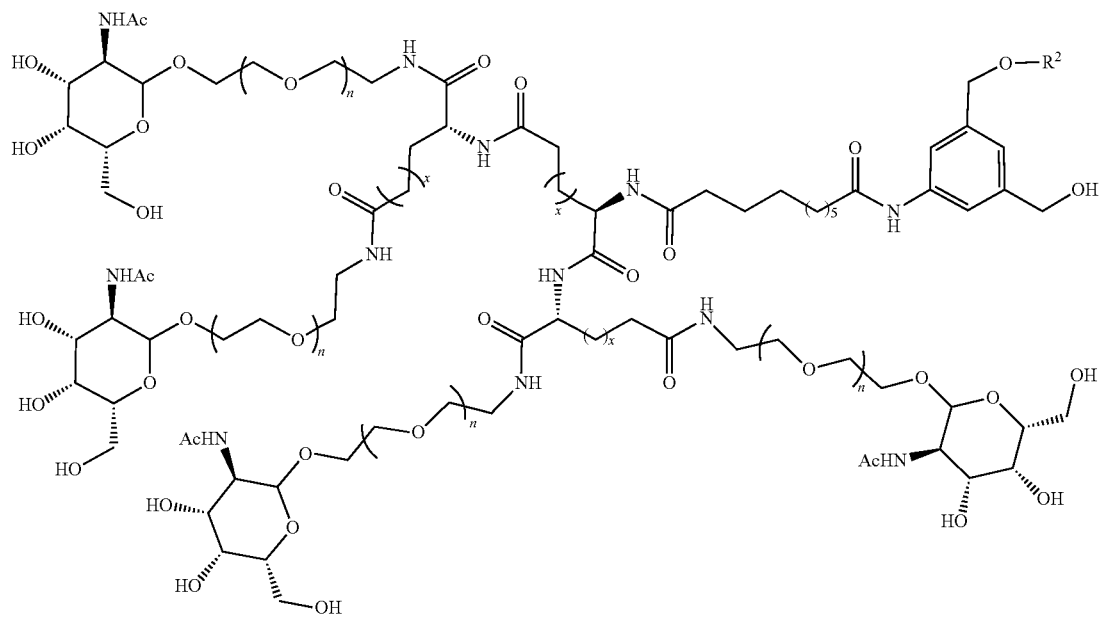
185, n = 3, x = 1
188, n = 4, x = 1

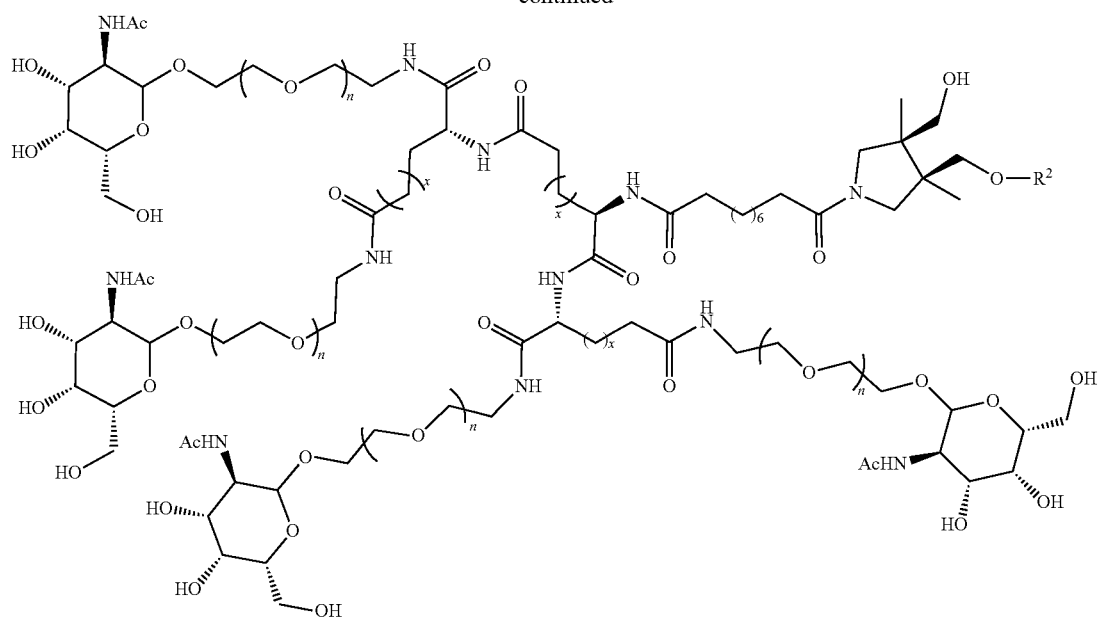
191, n = 2, x = 1
194, n = 3, x = 1
197, n = 4, x = 1
200, n = 3, x = 2
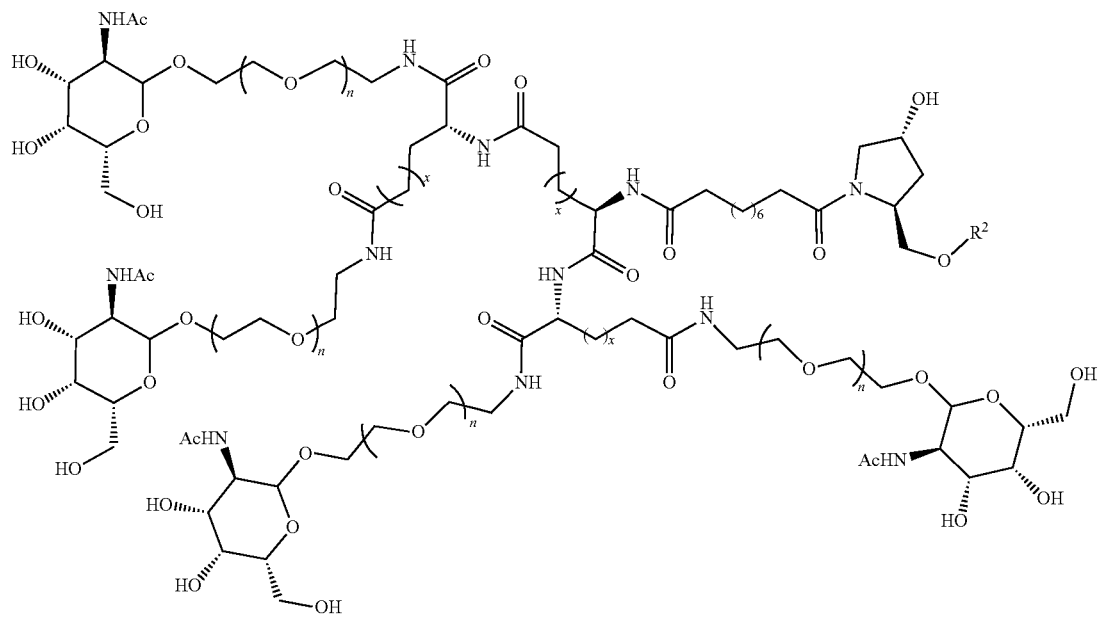
203, n = 3, x = 1
206, n = 4, x = 1

-continued
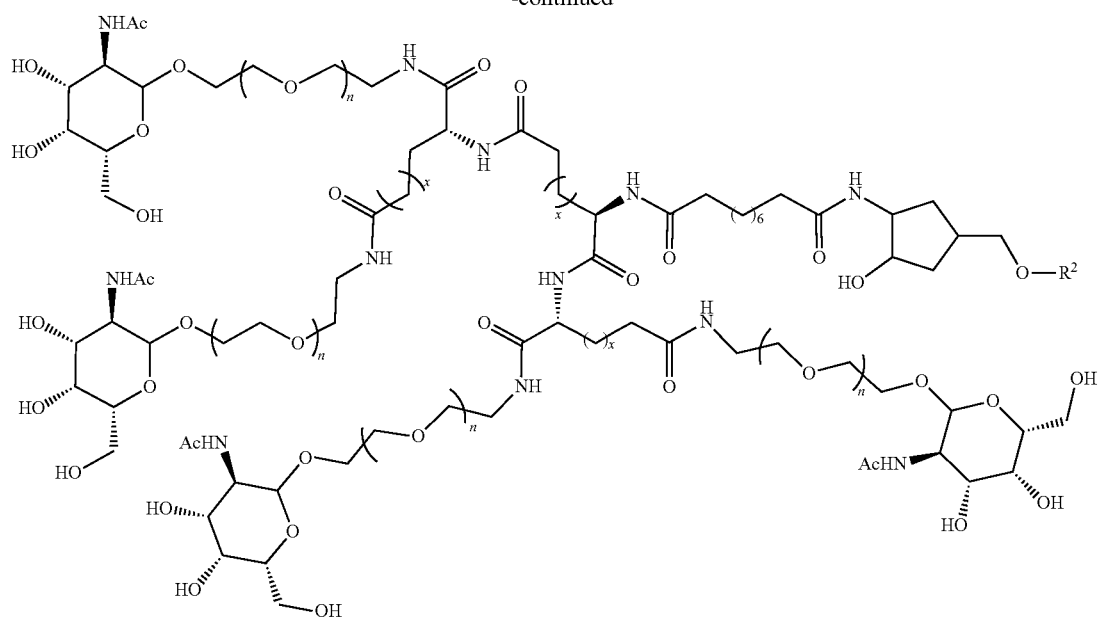
209, n = 3, x = 1
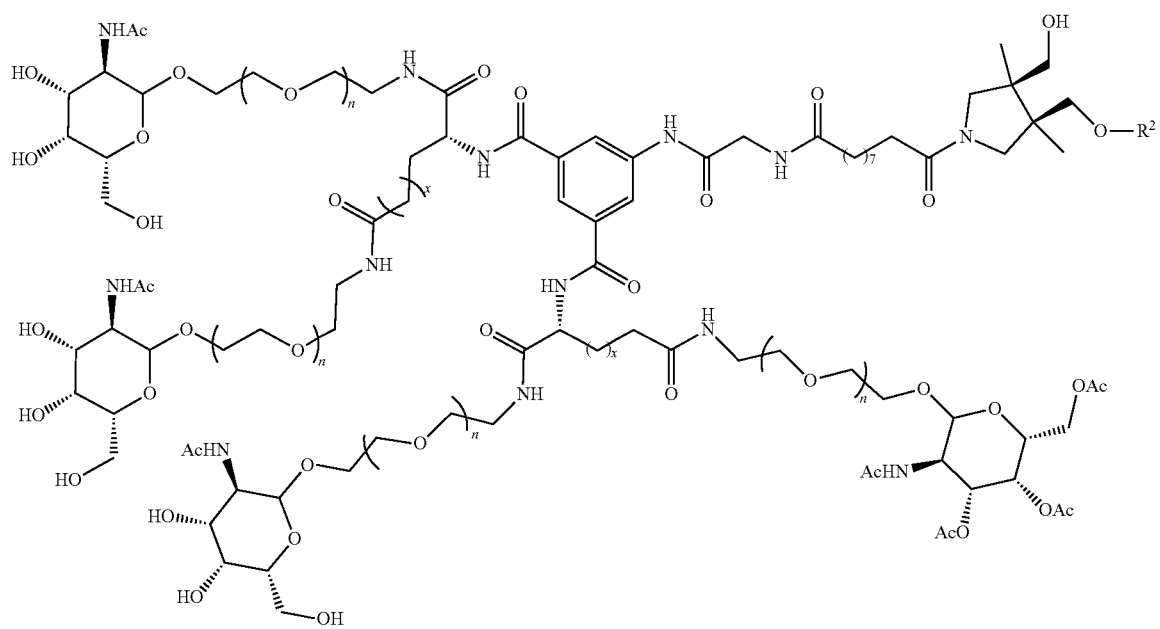
212, n = 3, x = 1
215, n = 4, x = 1

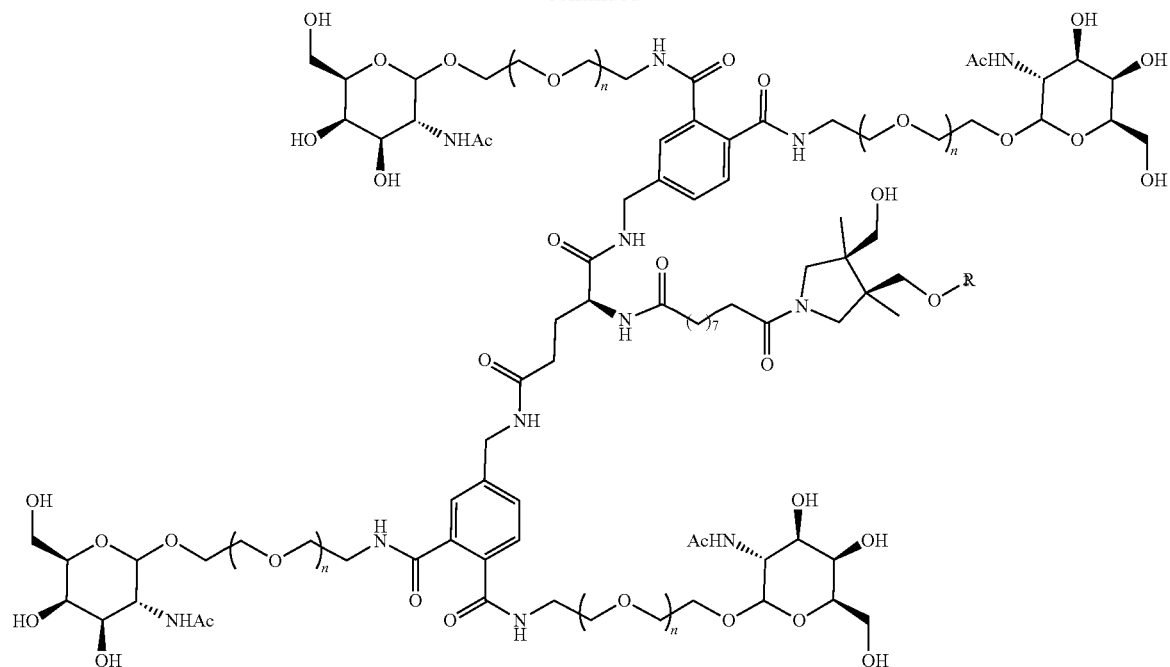
218, n = 2
221, n = 3
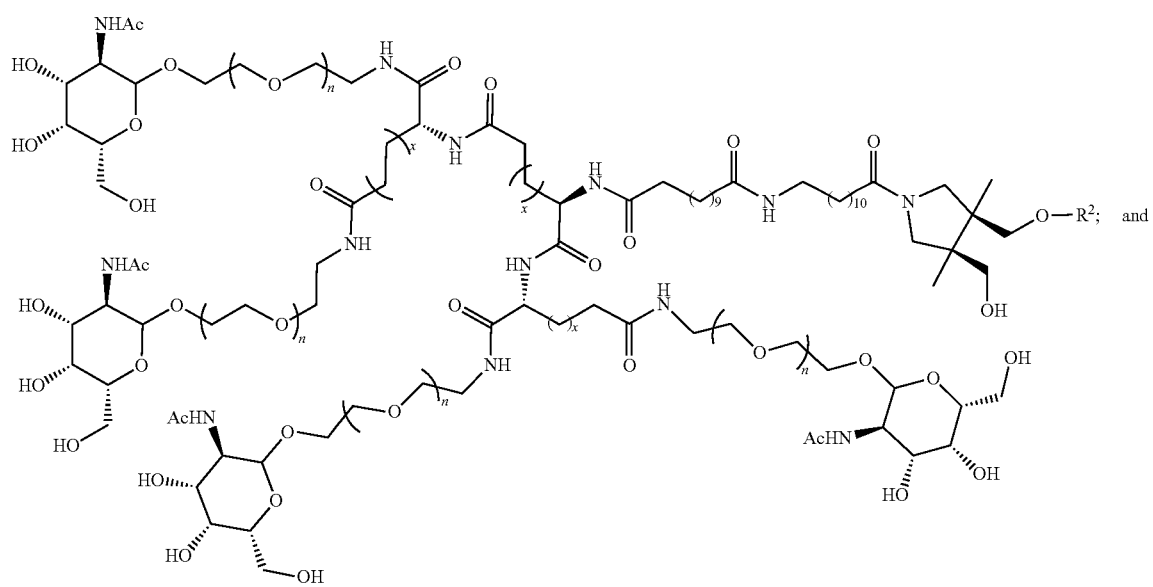
224, n = 3, x = 1

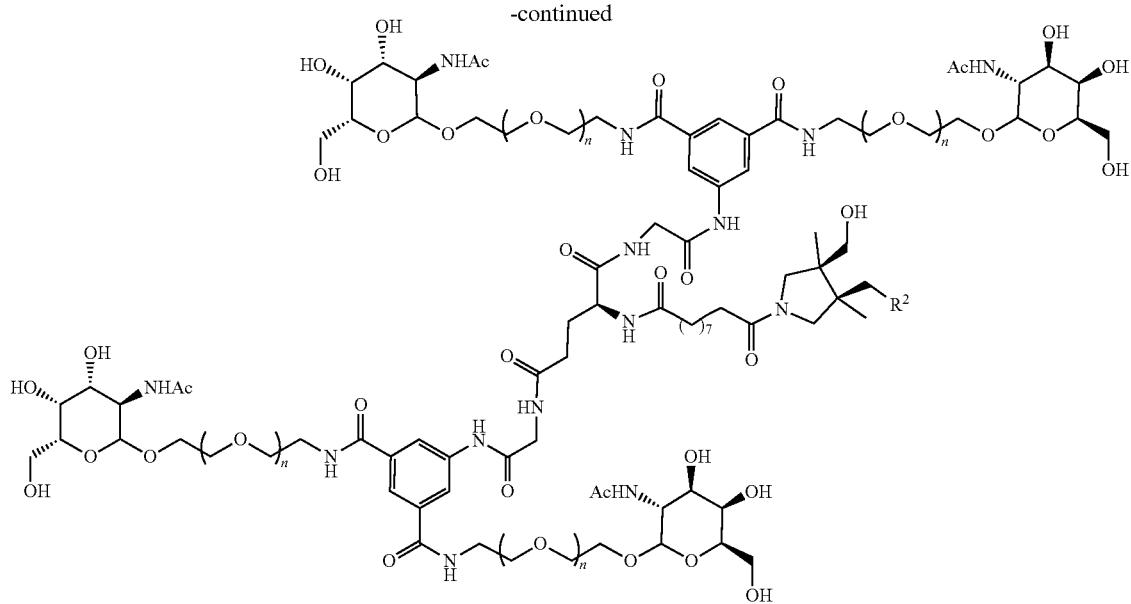
231, n = 3
In one embodiment the compound of formula I or the salt thereof is selected from the group consisting of:
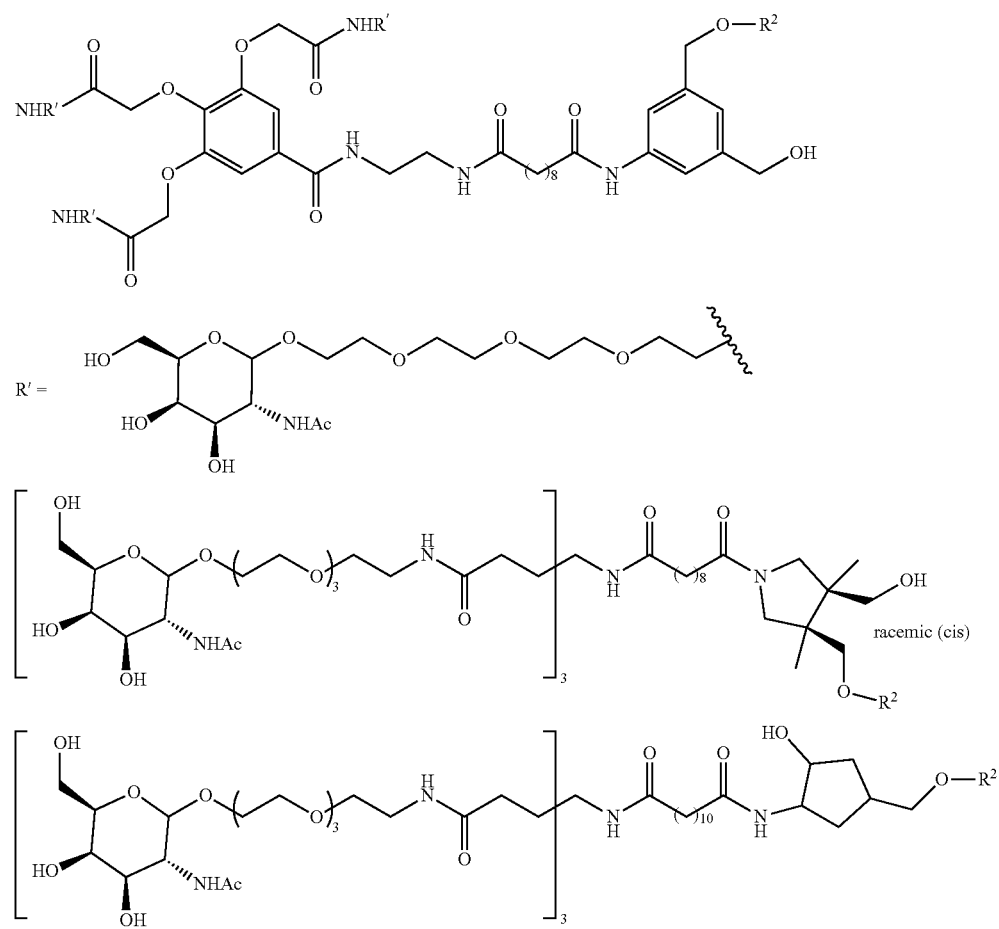

-continued
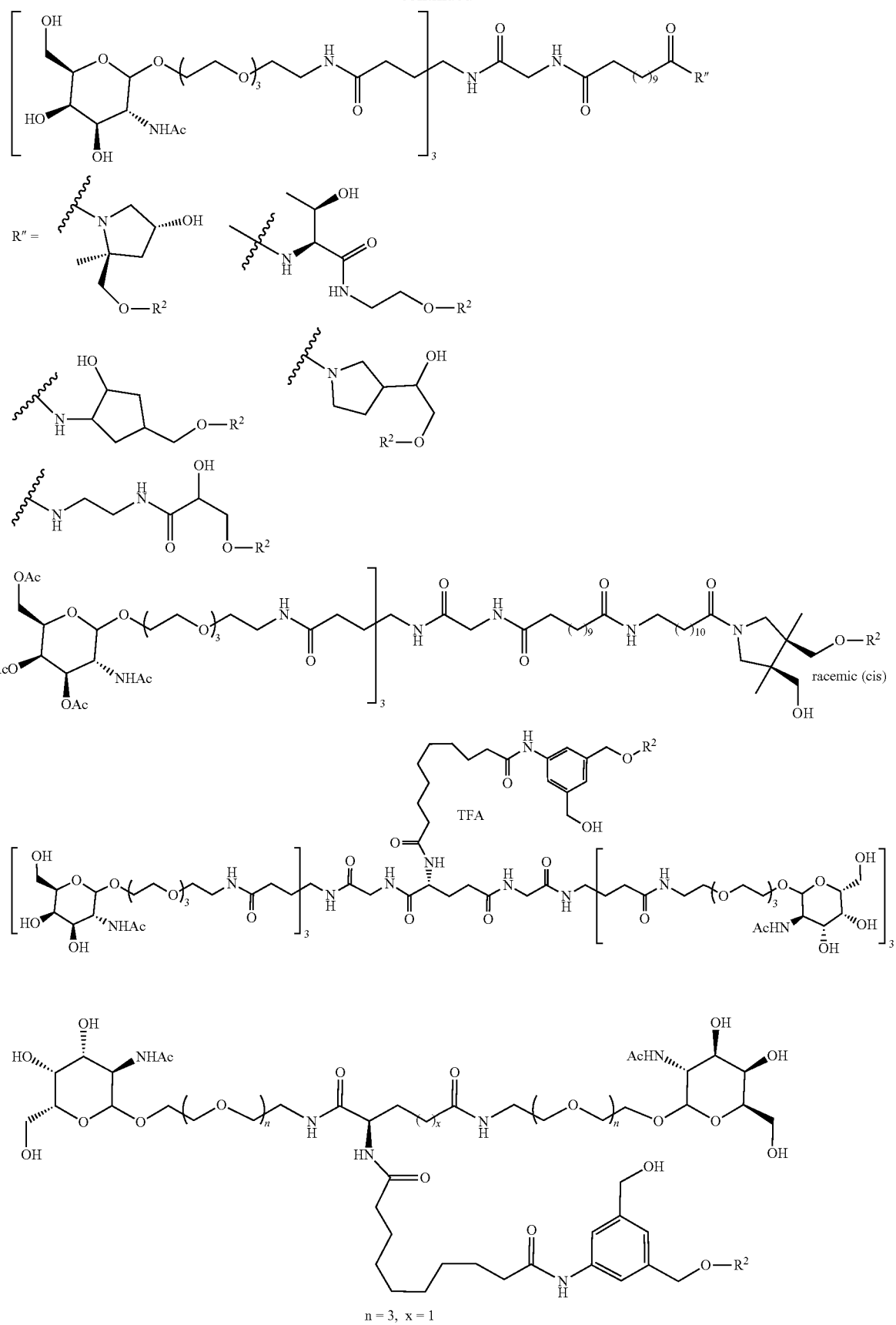

-continued
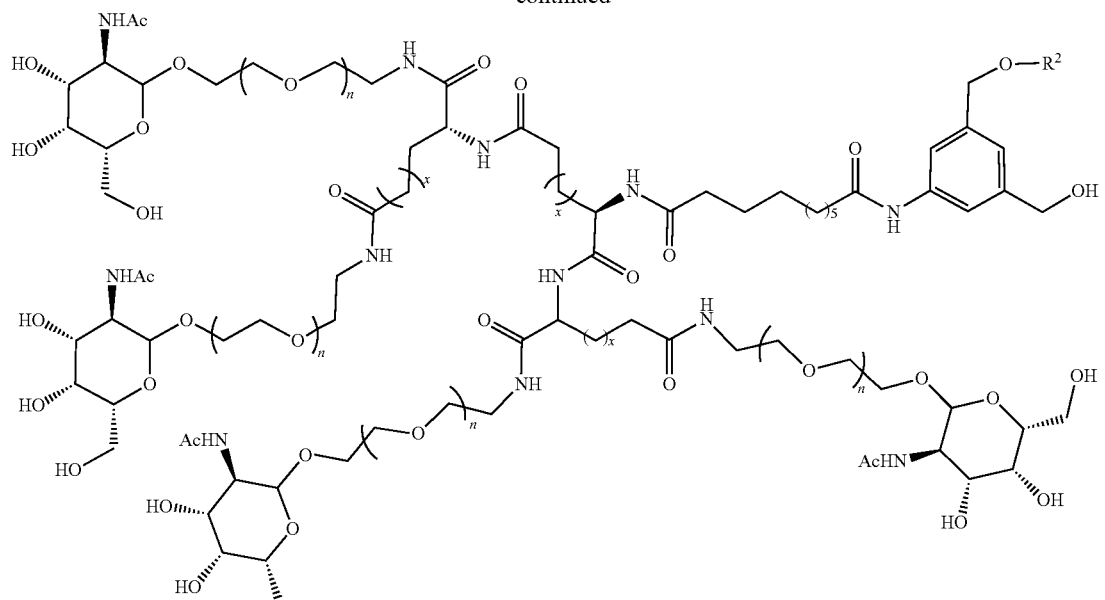
n = 3, x = 1
n = 4, x = 1
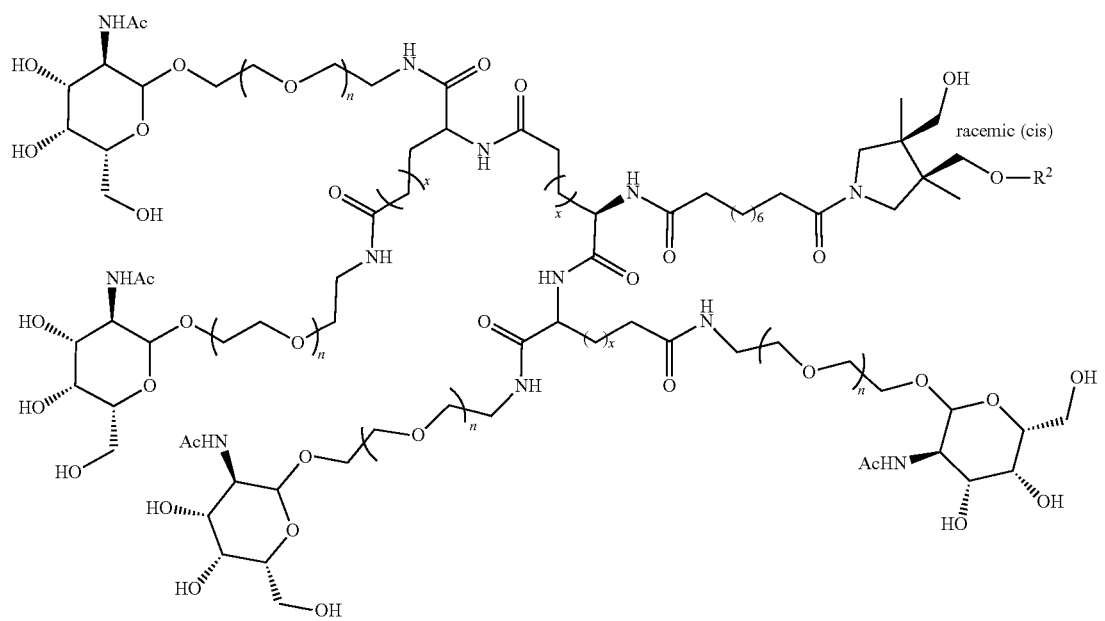
n = 2, x = 1
n = 3, x = 1
n = 4, x = 1
n = 3, x = 2

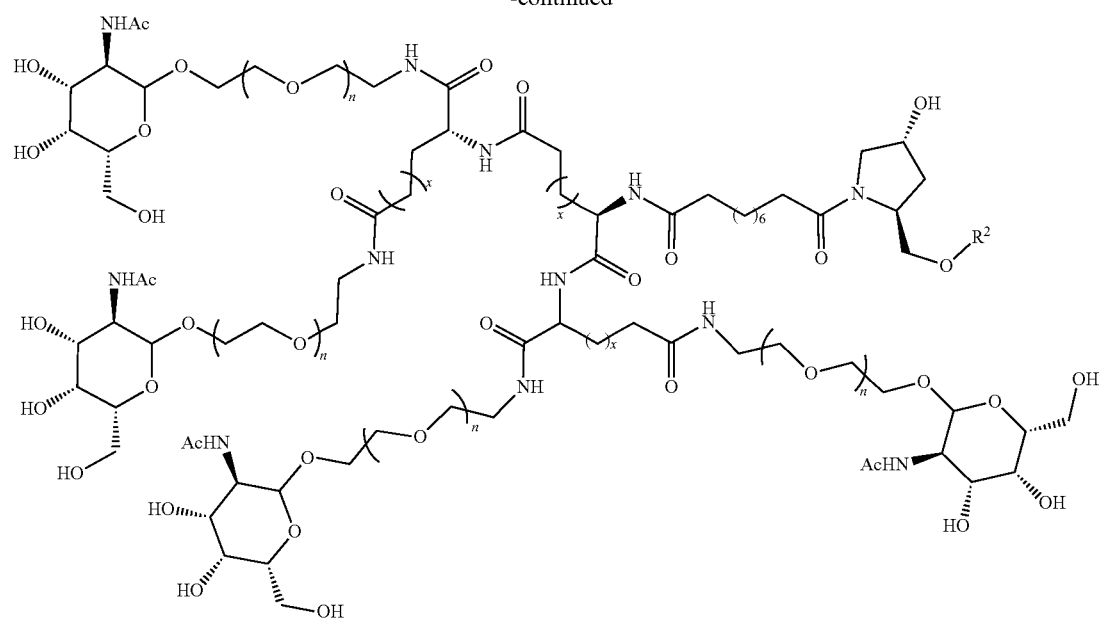
n = 3, x = 1
n = 4, x = 1
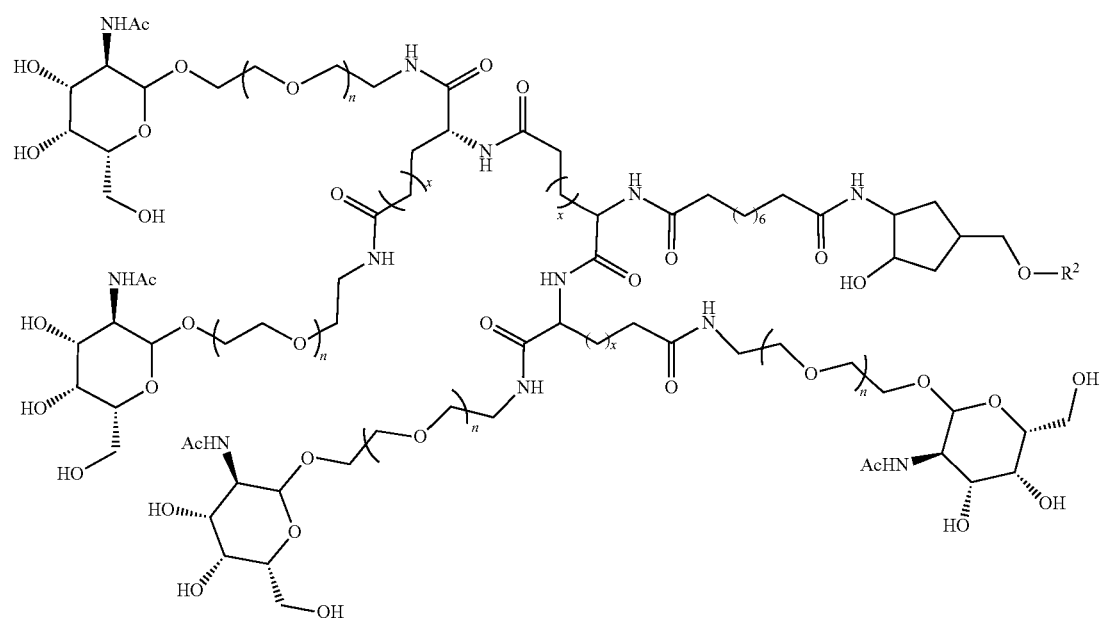
n = 3, x = 1

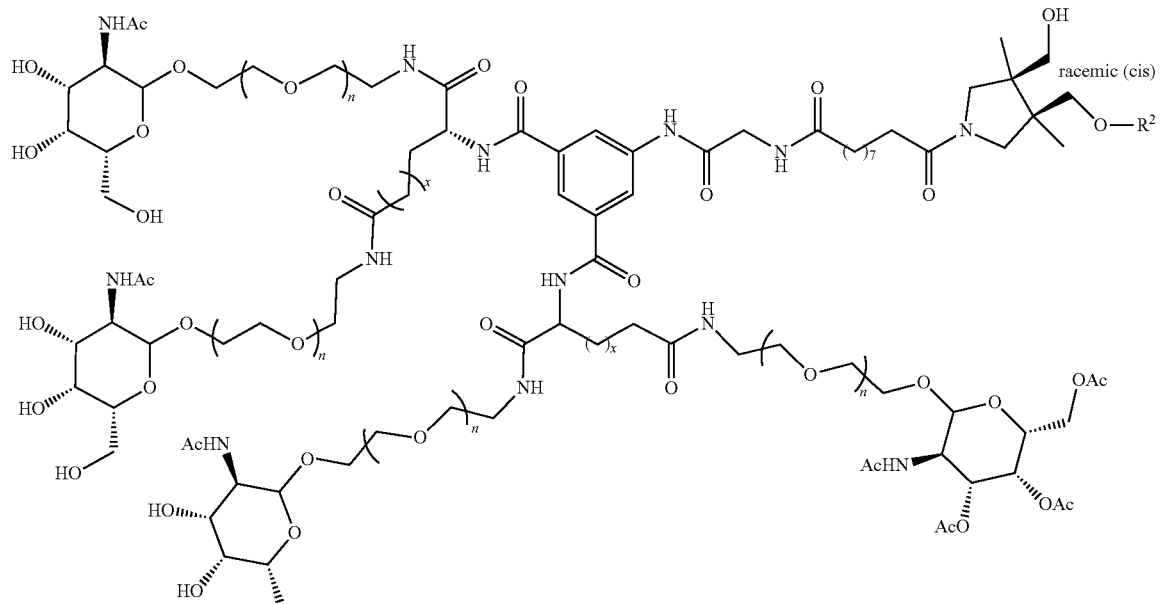
n = 3, x = 1
n = 4, x = 1
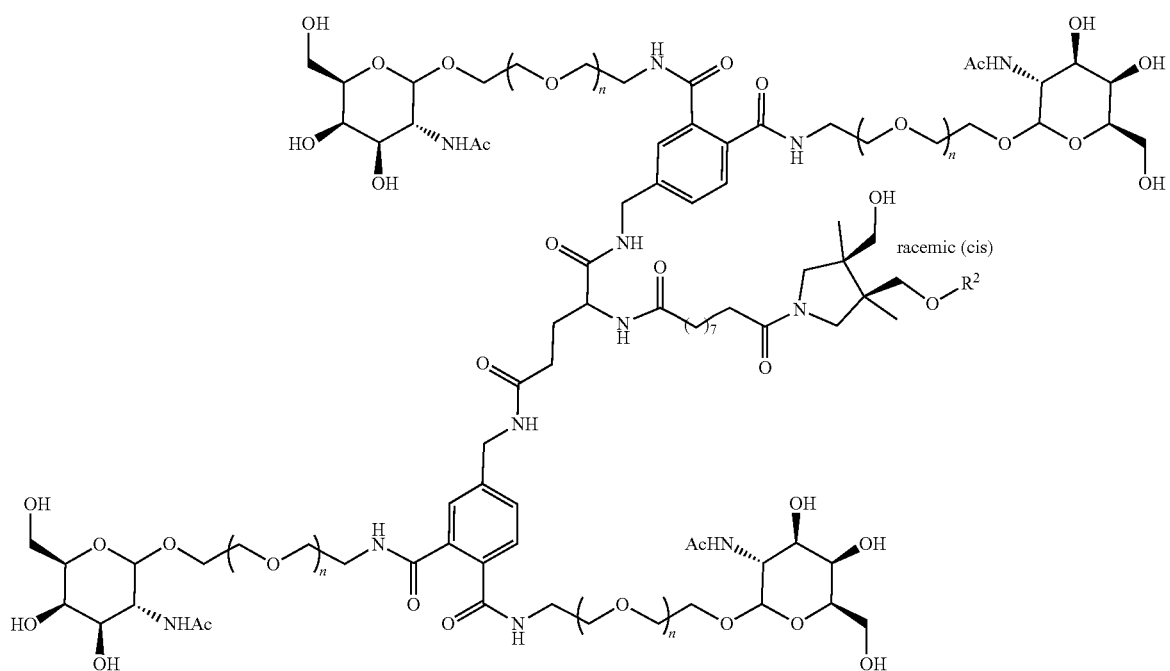
n = 2
n = 3

-continued
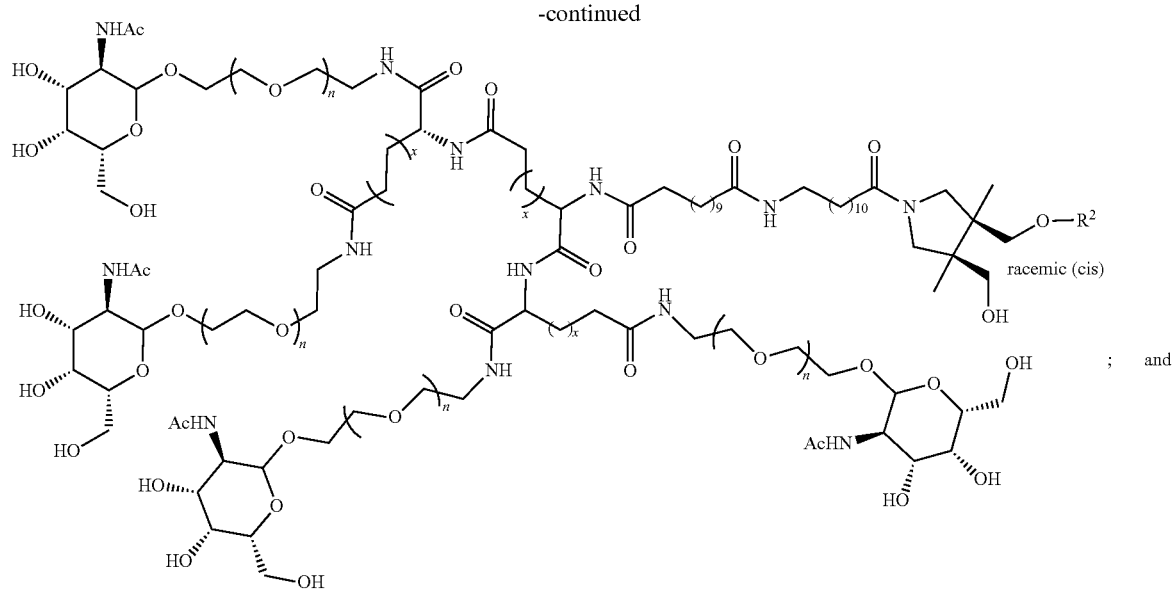
n = 3, x = 1
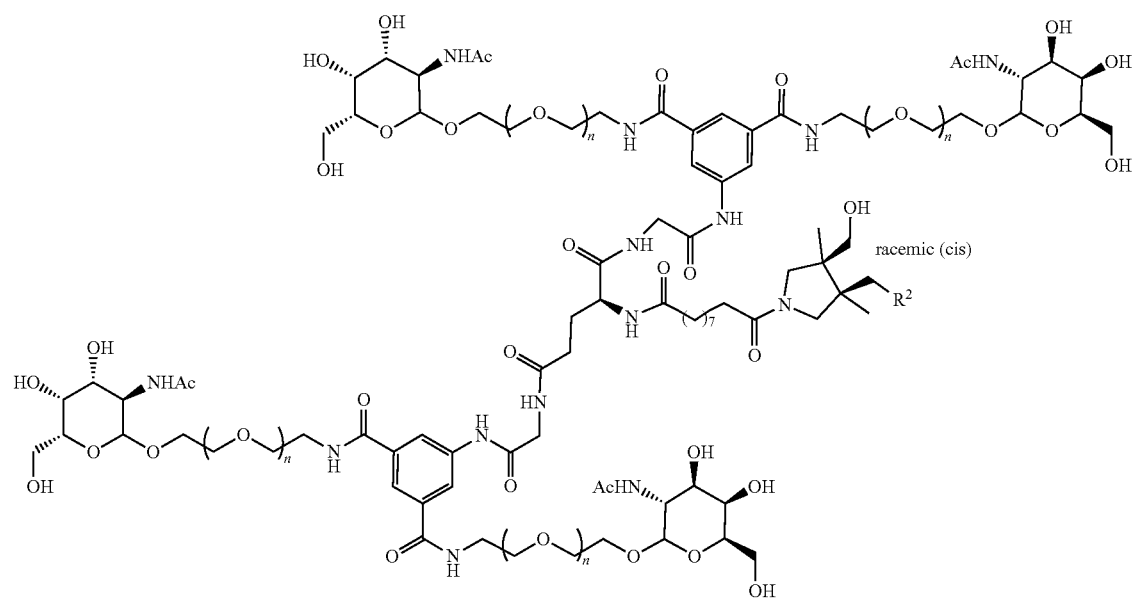
n = 3 or pharmaceutically acceptable salts thereof, wherein $R^2$ is a double stranded siRNA molecule selected from the double stranded siRNA molecules of Table 1.

In one embodiment the compound of formula I is:

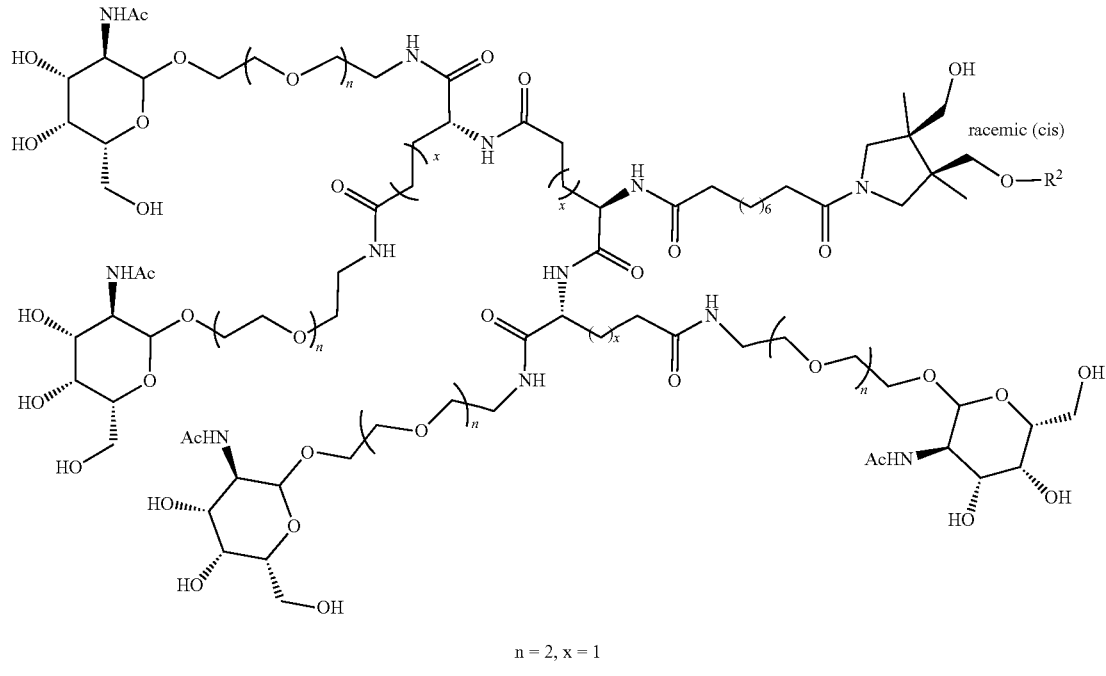

n = 2, x = 1 or a pharmaceutically acceptable salt thereof, wherein $R^2$ is a double stranded siRNA molecule (e.g. a double stranded siRNA molecule selected from the double stranded siRNA molecules of Table 1).

In one embodiment the compound of formula I is:

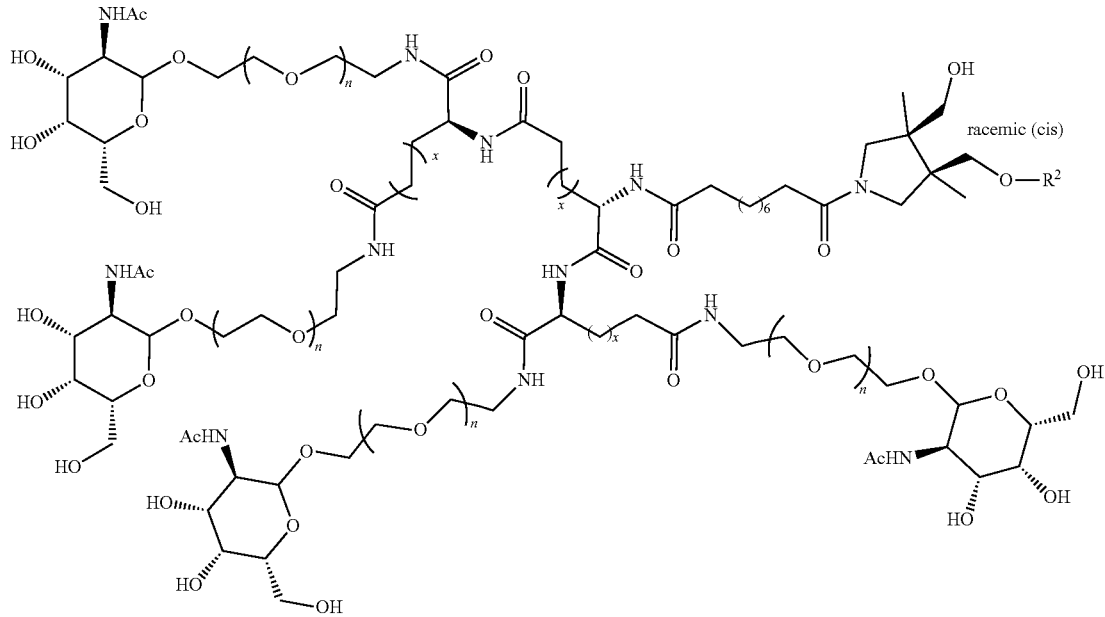

n = 2, x = 1 or a pharmaceutically acceptable salt thereof, wherein $R^2$ is a double stranded siRNA molecule (e.g. a double stranded siRNA molecule selected from the double stranded siRNA molecules of Table 1).

In one embodiment the compound of formula I is:

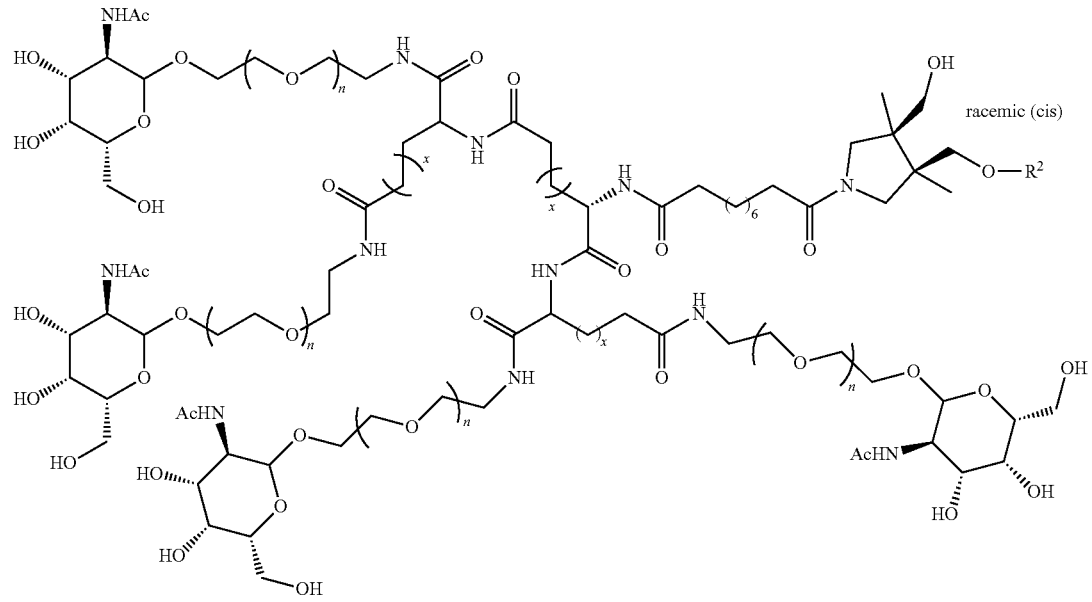

n = 2, x = 1 or a pharmaceutically acceptable salt thereof, wherein $R^2$ is a double stranded siRNA molecule (e.g. a double stranded siRNA molecule selected from the double stranded siRNA molecules of Table 1).

In one embodiment the compound of formula I is:

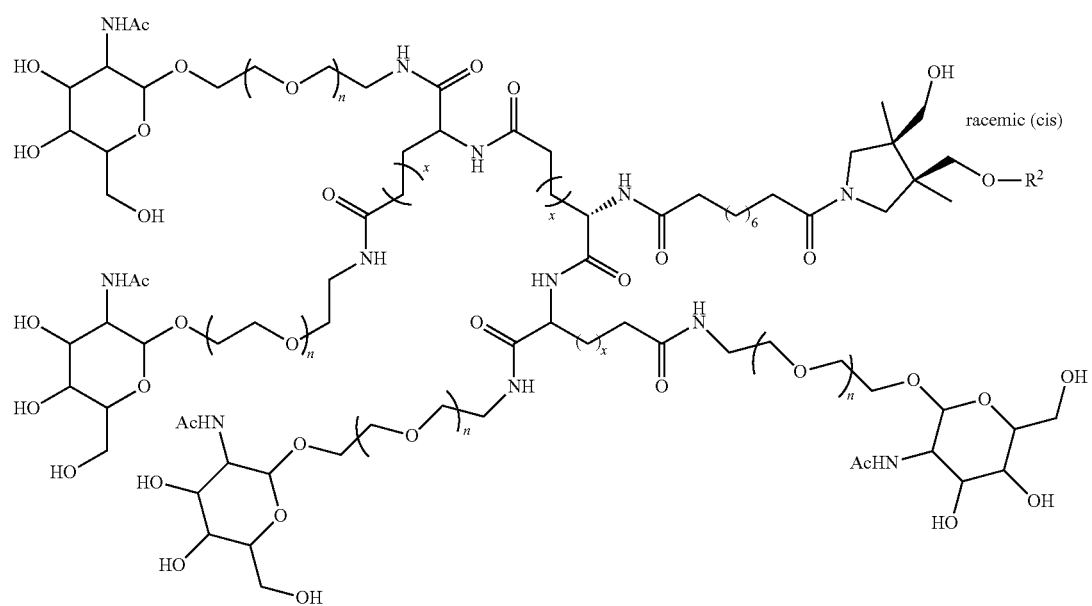

n = 2, x = 1 or a pharmaceutically acceptable salt thereof, wherein $R^2$ is a double stranded siRNA molecule (e.g. a double stranded siRNA molecule selected from the double stranded siRNA molecules of Table 1).

In one embodiment the compound of formula I is:

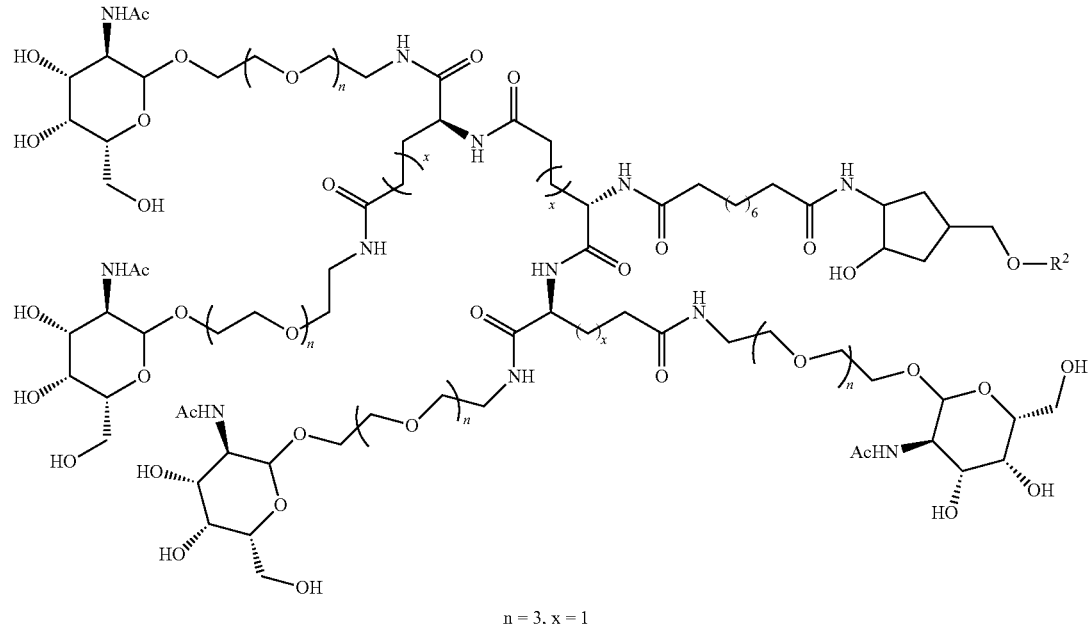

n = 3, x = 1 or a pharmaceutically acceptable salt thereof, wherein $R^2$ is a double stranded siRNA molecule (e.g. a double stranded siRNA molecule selected from the double stranded siRNA molecules of Table 1).

In one embodiment the compound of formula I is:

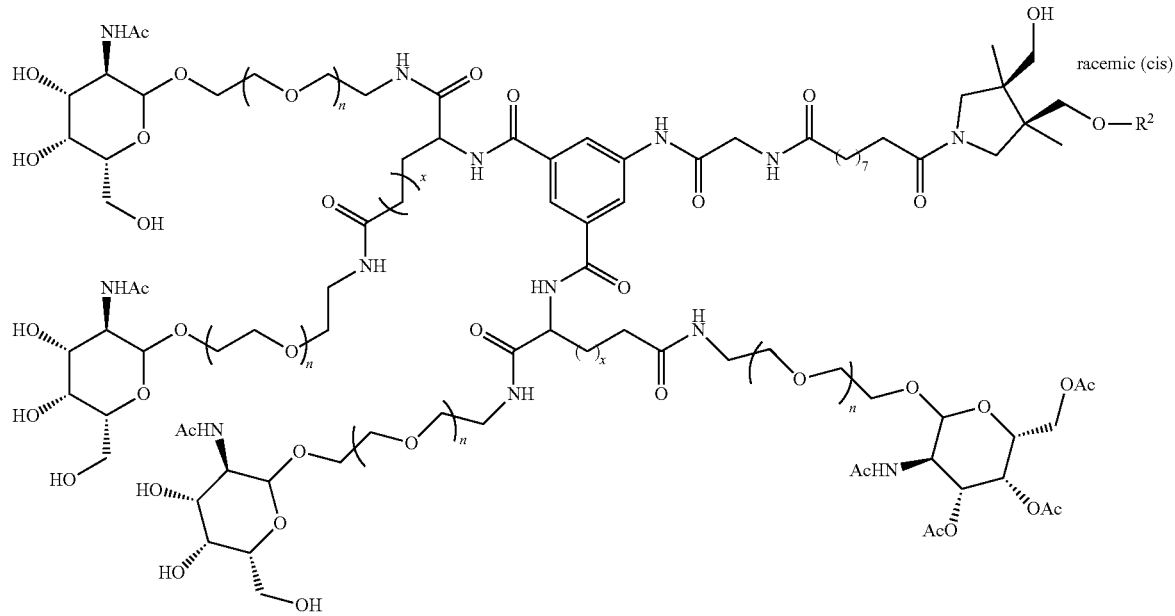

n = 3, x = 1 or a pharmaceutically acceptable salt thereof, wherein $R^2$ is a double stranded siRNA molecule (e.g. a double stranded siRNA molecule selected from the double stranded siRNA molecules of Table 1).

In one embodiment the compound of formula I is:

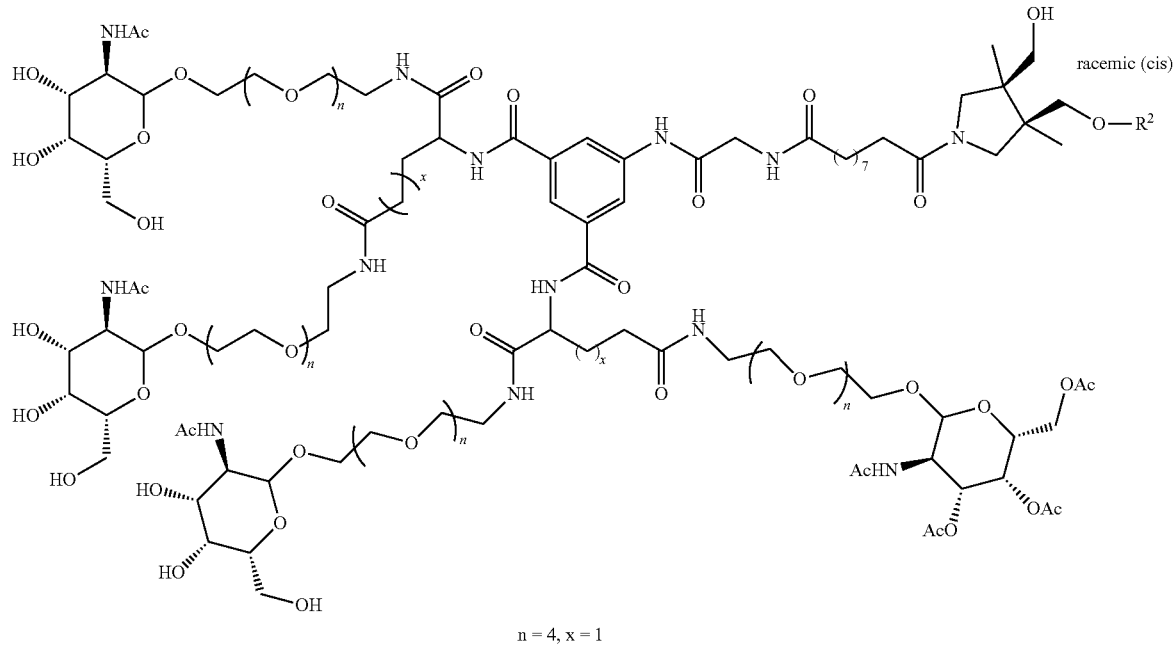

n = 4, x = 1 or a pharmaceutically acceptable salt thereof, wherein $R^2$ is a double stranded siRNA molecule (e.g. a double stranded siRNA molecule selected from the double stranded siRNA molecules of Table 1).

In one embodiment the compound of formula I is:

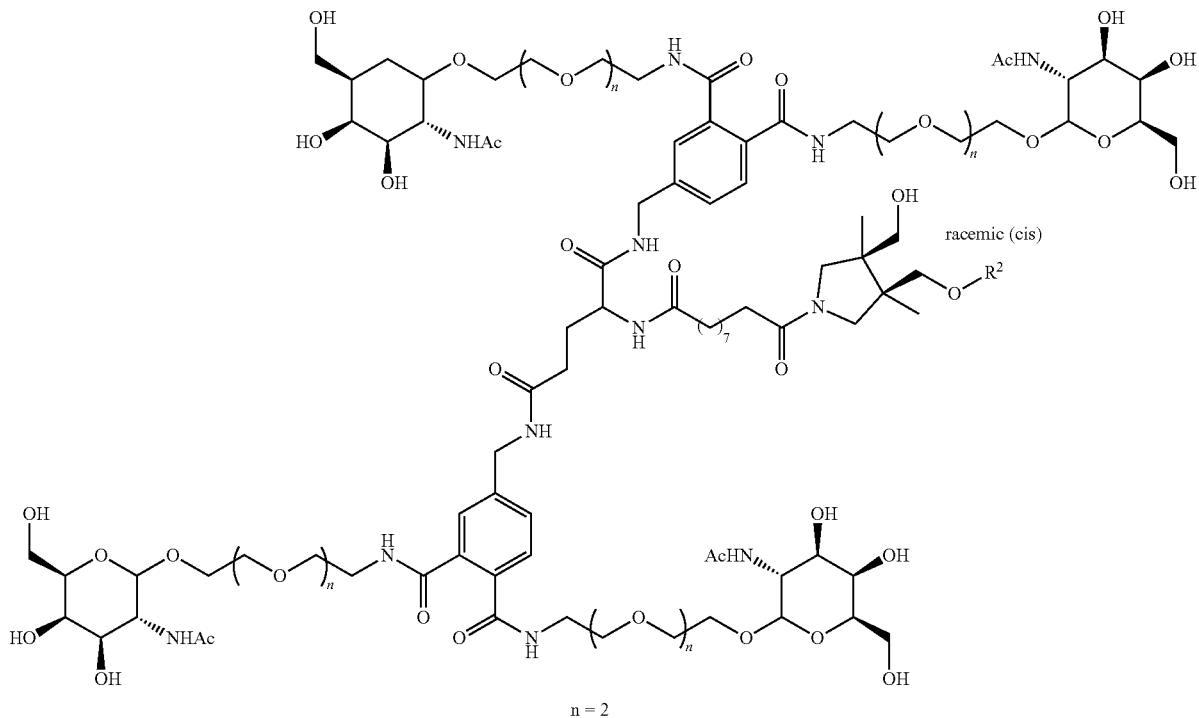

n = 2 or a pharmaceutically acceptable salt thereof, wherein $R^2$ is a double stranded siRNA molecule (e.g. a double stranded siRNA molecule selected from the double stranded siRNA molecules of Table 1).

In one embodiment the compound of formula I is:

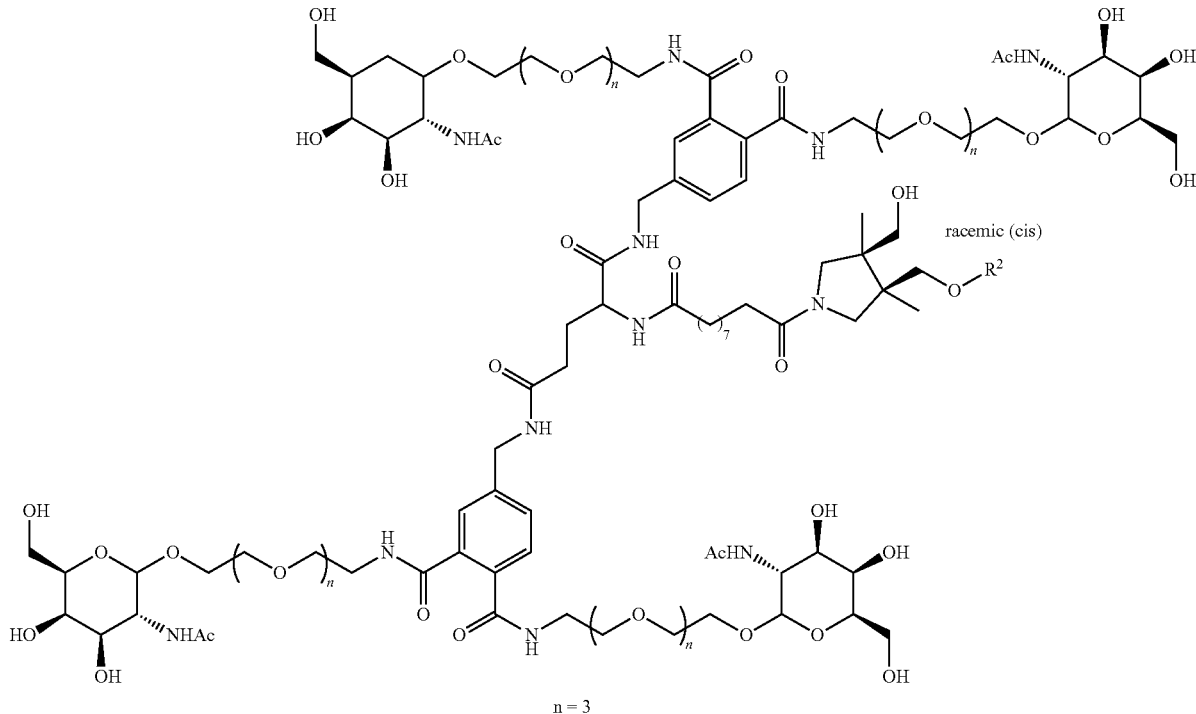

or a pharmaceutically acceptable salt thereof, wherein $R^2$ is a double stranded siRNA molecule (e.g. a double stranded siRNA molecule selected from the double stranded siRNA molecules of Table 1).

In one embodiment the compound of formula I is:

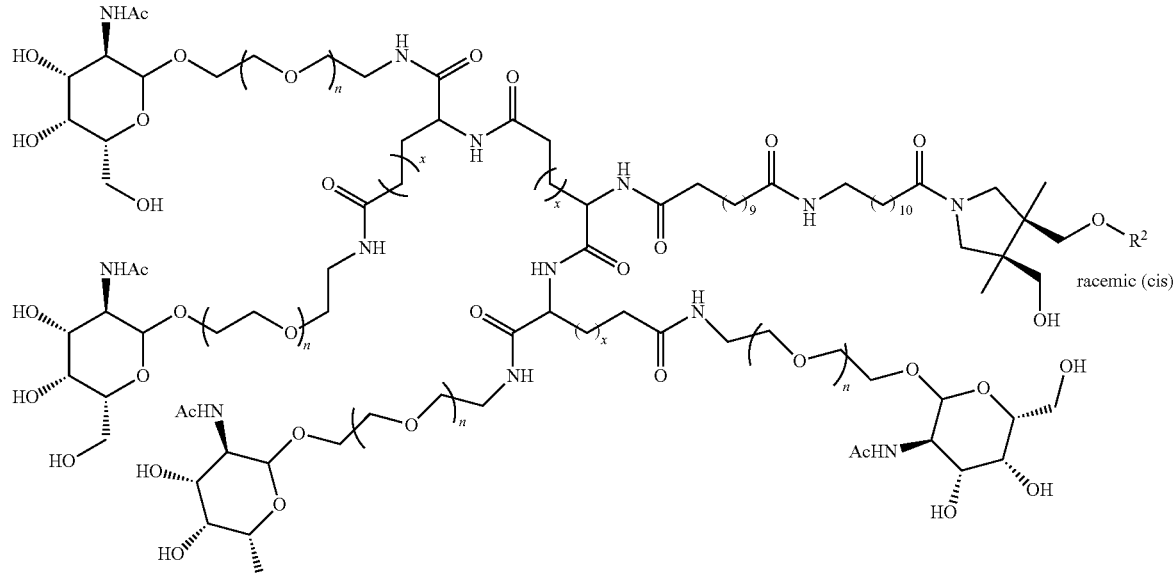

or a pharmaceutically acceptable salt thereof, wherein $R^2$ is a double stranded siRNA molecule (e.g. a double stranded siRNA molecule selected from the double stranded siRNA molecules of Table 1).

In one embodiment the compound of formula I is:

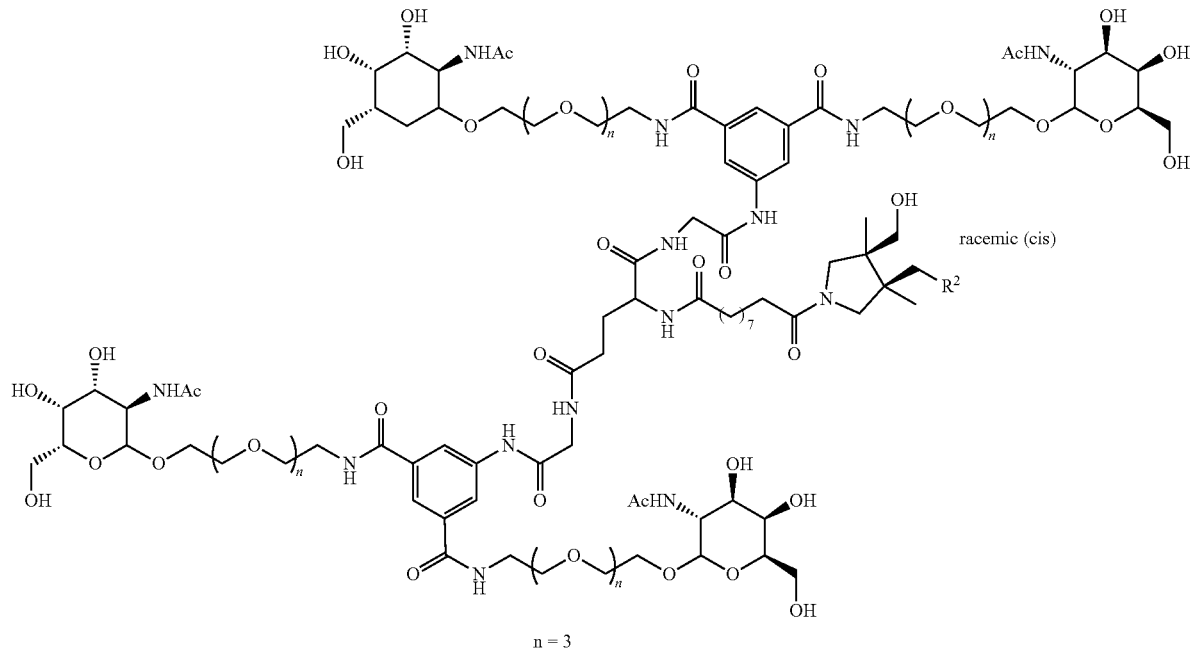

or a pharmaceutically acceptable salt thereof, wherein $R^2$ is a double stranded siRNA molecule (e.g. a double stranded siRNA molecule selected from the double stranded siRNA molecules of Table 1).

In one embodiment the compound of formula I is:

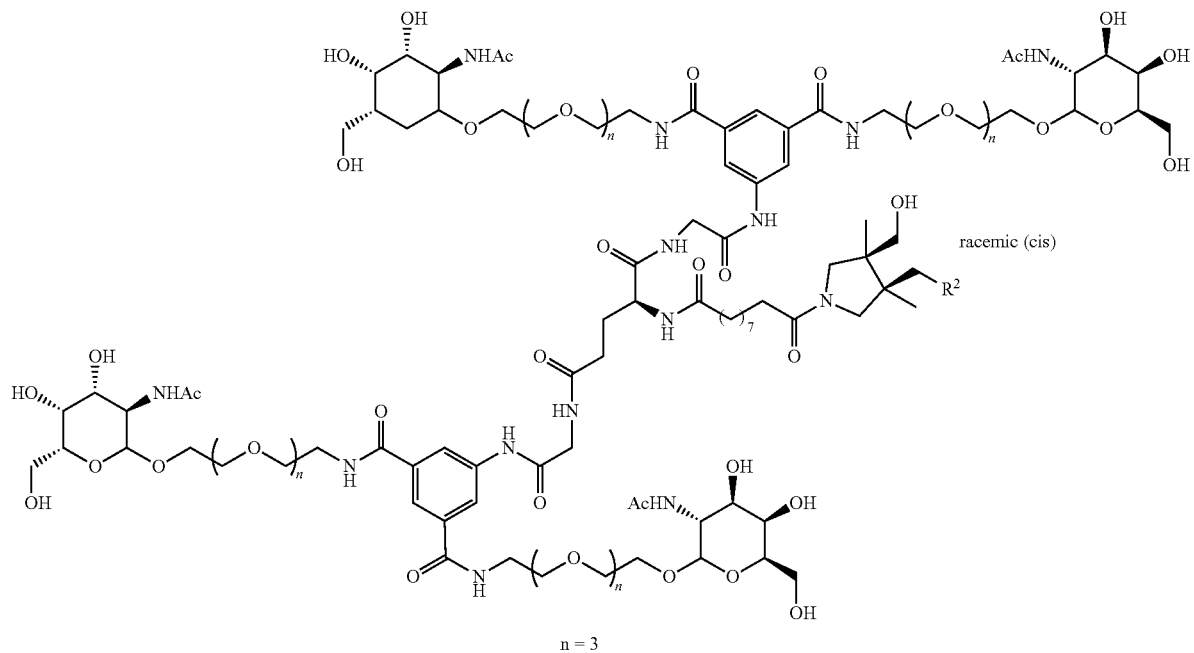

or a pharmaceutically acceptable salt thereof, wherein $R^2$ is a double stranded siRNA molecule (e.g. a double stranded siRNA molecule selected from the double stranded siRNA molecules of Table 1).

In one embodiment the compound of formula I is:

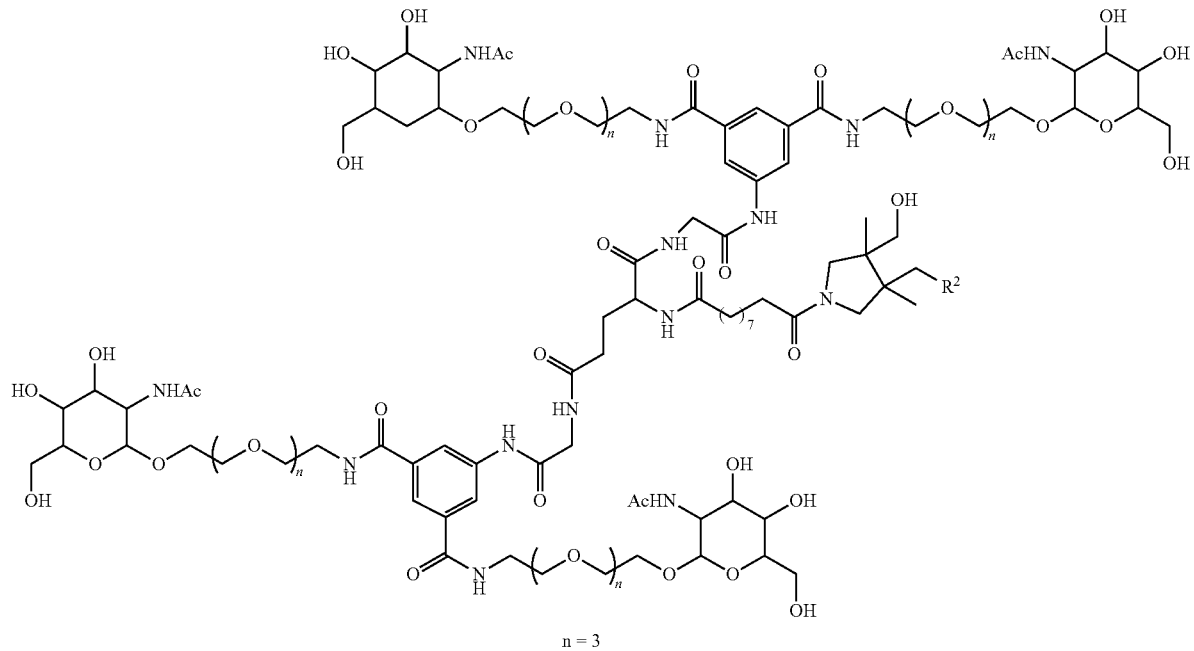

n = 3 or a pharmaceutically acceptable salt thereof, wherein $R^2$ is a double stranded siRNA molecule (e.g. a double stranded siRNA molecule selected from the double stranded siRNA molecules of Table 1).

In one embodiment the compound of formula I is:

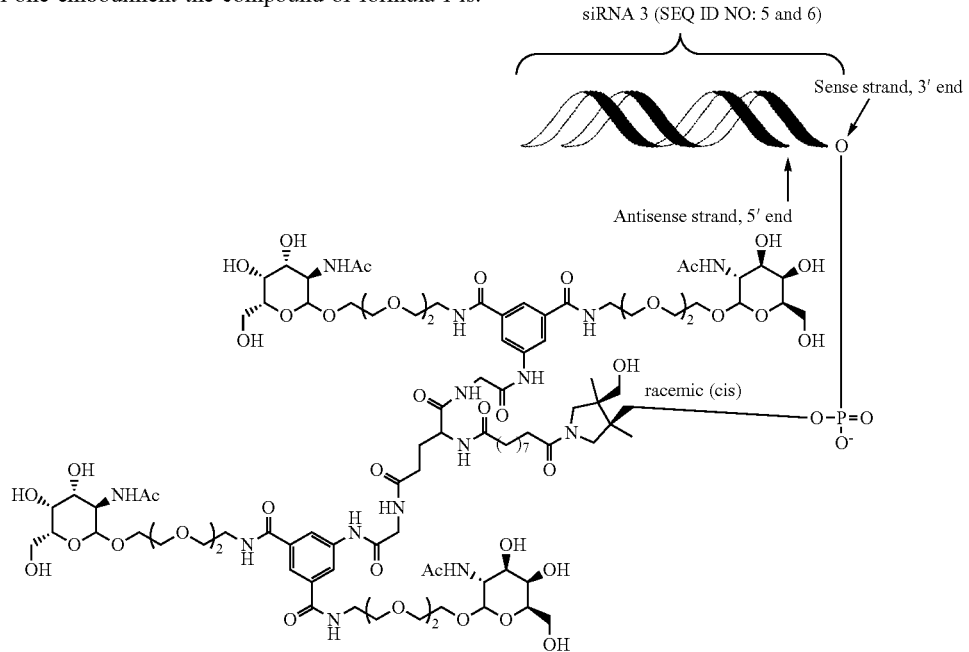

or a pharmaceutically acceptable salt thereof.

In one embodiment the compound of formula I is:
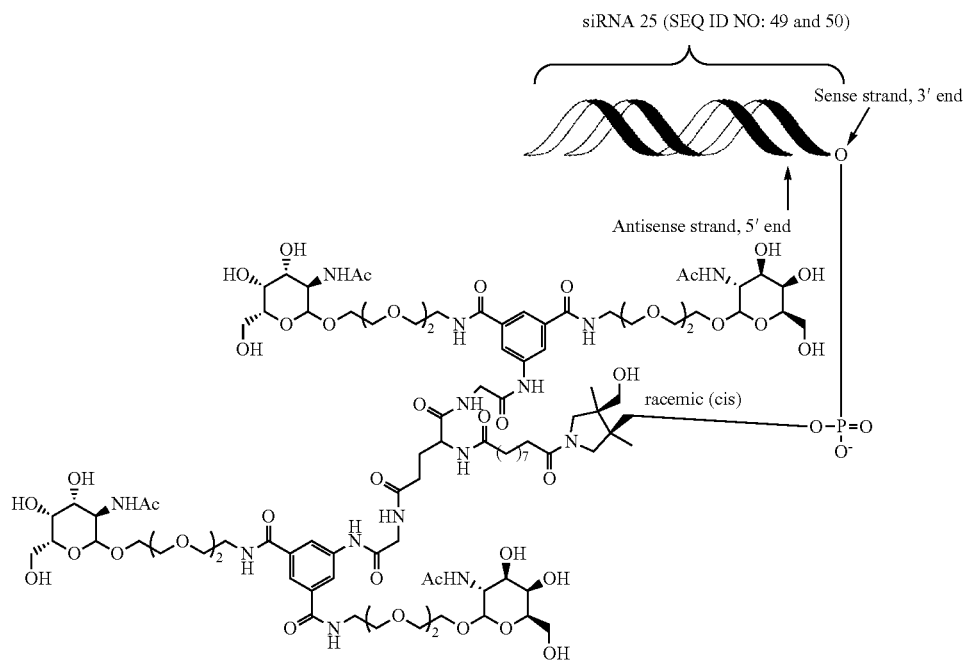
35
or a pharmaceutically acceptable salt thereof.
In one embodiment the compound of formula I is:
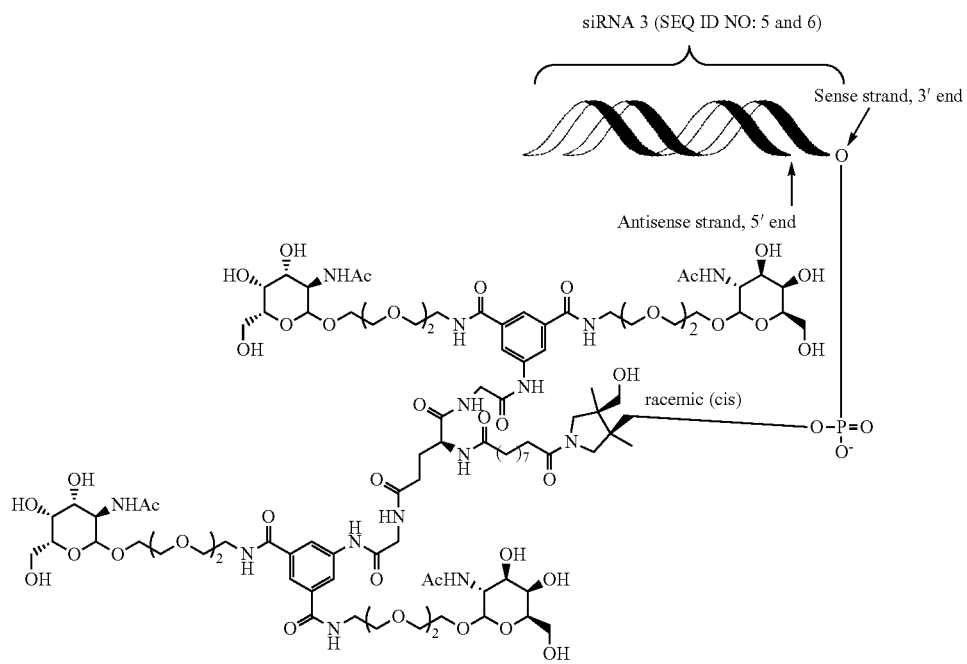
or a pharmaceutically acceptable salt thereof.

In one embodiment the compound of formula I is:
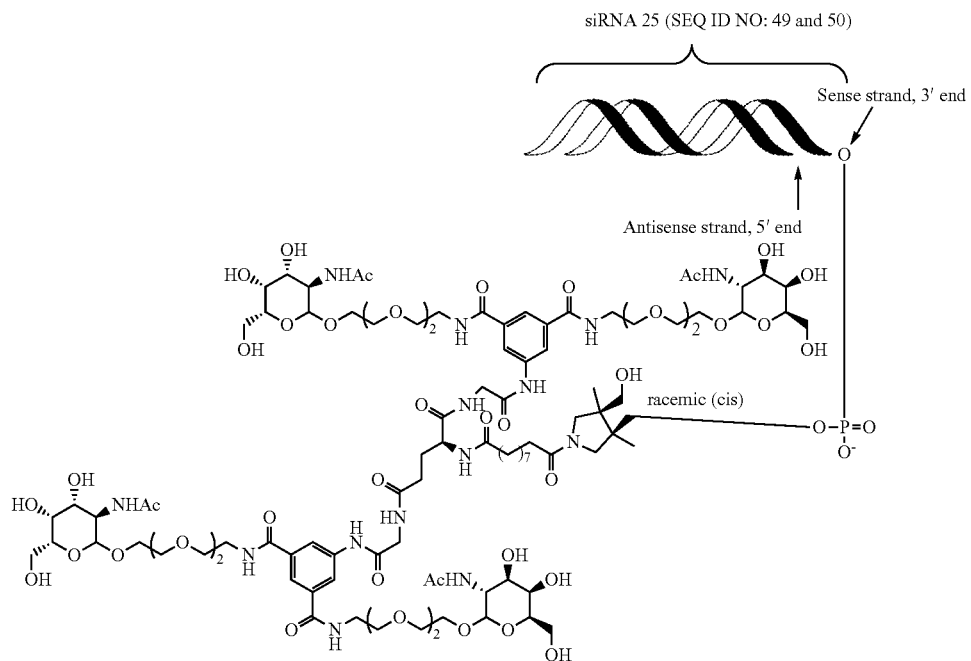
or a pharmaceutically acceptable salt thereof.
In one embodiment the compound of formula I is:
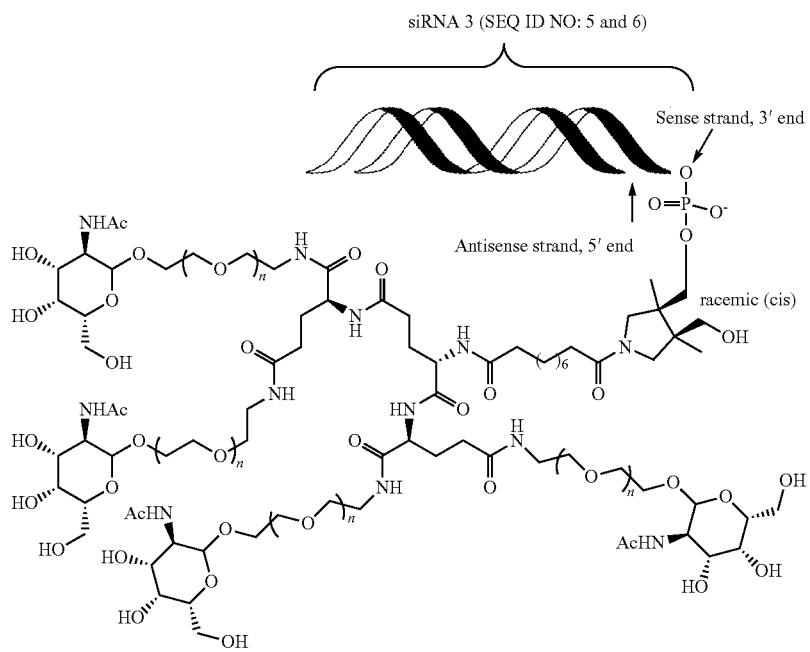
or a pharmaceutically acceptable salt thereof.

In one embodiment the compound of formula I is:
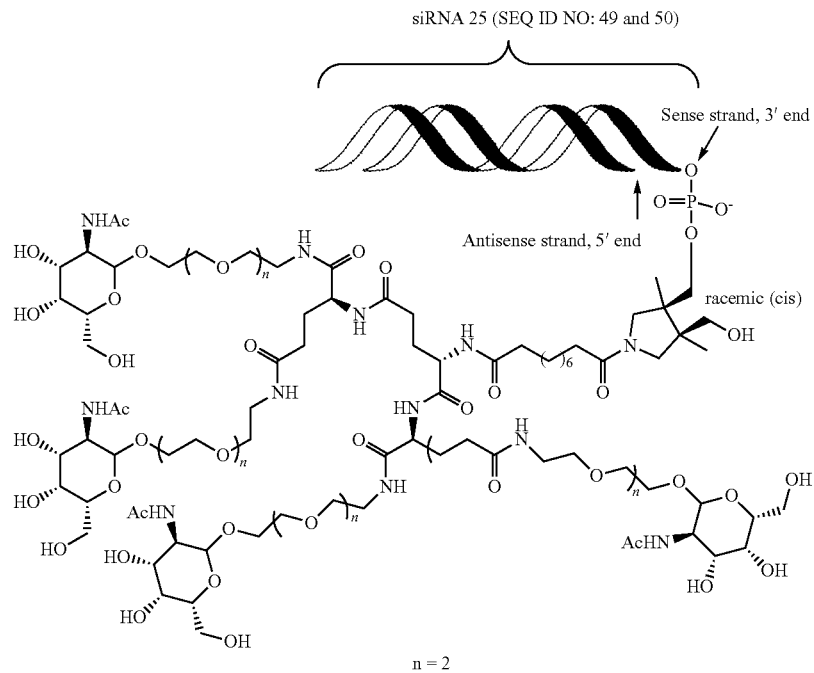
35
or a pharmaceutically acceptable salt thereof.
In one embodiment the compound of formula I is:
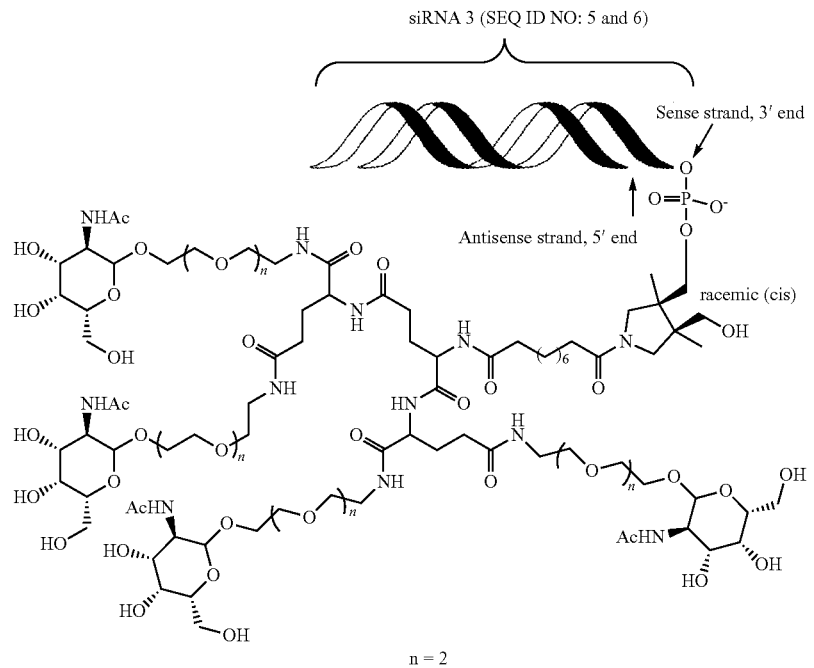
or a pharmaceutically acceptable salt thereof.

In one embodiment the compound of formula I is:
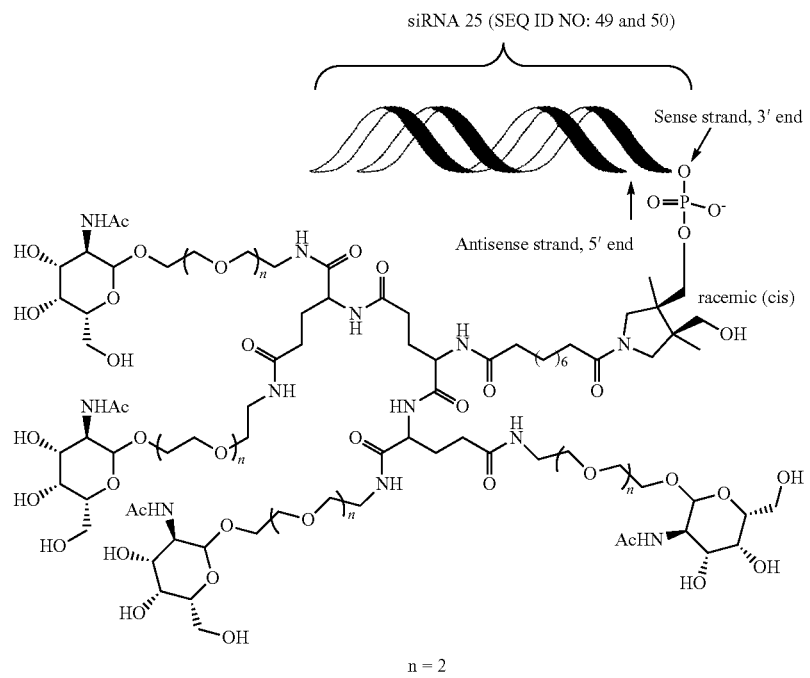
or a pharmaceutically acceptable salt thereof.
In one embodiment the invention provides a compound of formula (I):
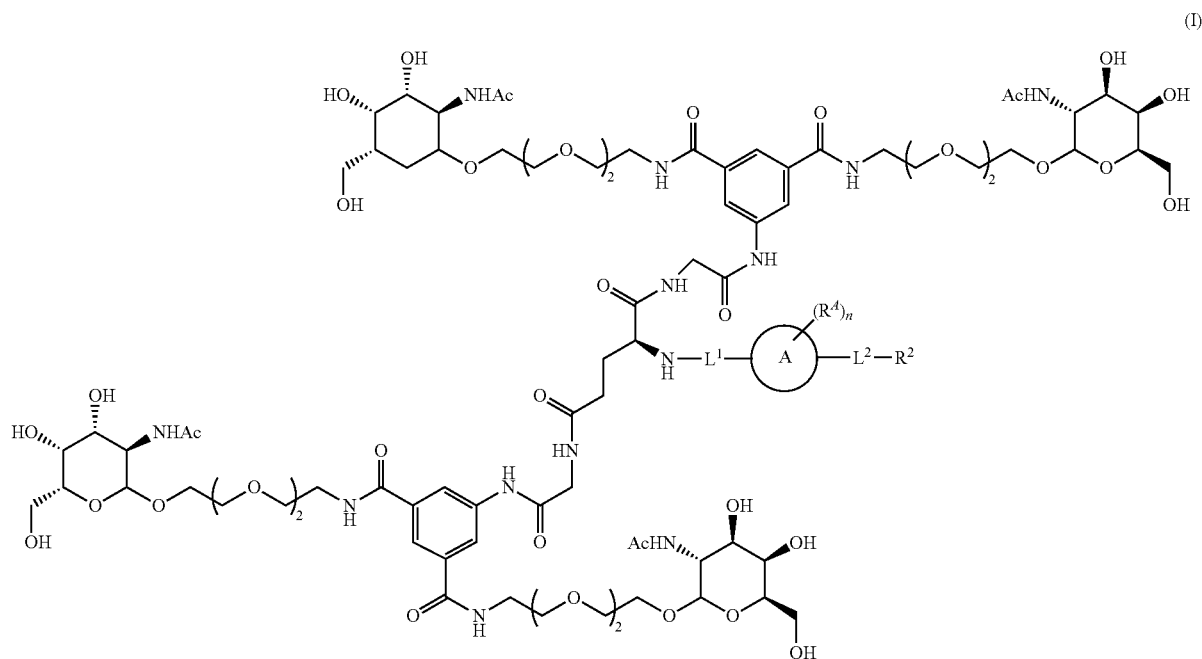

wherein:

L¹ is absent or a linking group;

L² is absent or a linking group;

R² is a nucleic acid;

the ring A is absent, a 3-20 membered cycloalkyl, a 5-20 membered aryl, a 5-20 membered heteroaryl, or a 3-20 membered heterocycloalkyl;

each $R^A$ is independently selected from the group consisting of hydrogen, hydroxy, CN, F, Cl, Br, I, —$C_{1-2}$ alkyl-$OR^B$, $C_{1-10}$ alkyl $C_{2-10}$ alkenyl, and $C_{2-10}$ alkynyl; wherein the $C_{1-10}$ alkyl $C_{2-10}$ alkenyl, and $C_{2-10}$ alkynyl are optionally substituted with one or more groups independently selected from halo, hydroxy, and $C_{1-3}$ alkoxy;

$R^B$ is hydrogen, a protecting group, a covalent bond to a solid support, or a bond to a linking group that is bound to a solid support; and n is 0, 1, 2, 3, 4, 5, 6, 7, 8, 9, or 10;

or a salt thereof.

In one embodiment the invention provides a compound of formula:

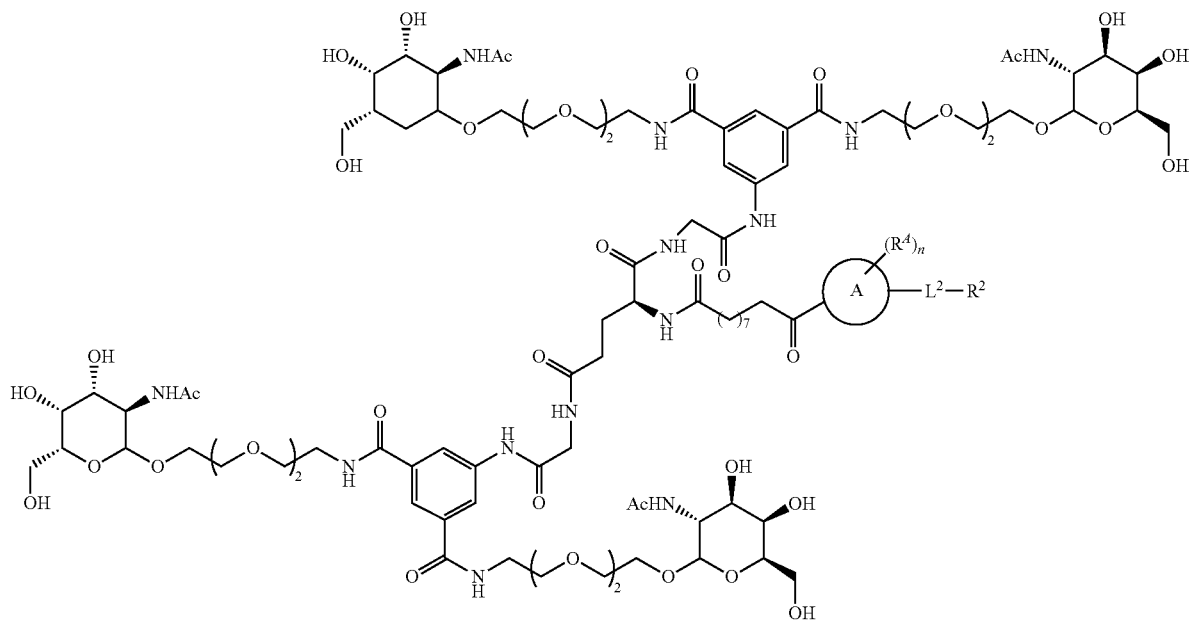

wherein:

L² is absent or a linking group;

R² is a nucleic acid;

the ring A is absent, a 3-20 membered cycloalkyl, a 5-20 membered aryl, a 5-20 membered heteroaryl, or a 3-20 membered heterocycloalkyl;

each $R^A$ is independently selected from the group consisting of hydrogen, hydroxy, CN, F, Cl, Br, I, —$C_{1-2}$ alkyl-$OR^B$, $C_{1-10}$ alkyl $C_{2-10}$ alkenyl, and $C_{2-10}$ alkynyl; wherein the $C_{1-10}$ alkyl $C_{2-10}$ alkenyl, and $C_{2-10}$ alkynyl are optionally substituted with one or more groups independently selected from halo, hydroxy, and $C_{1-3}$ alkoxy;

$R^B$ is hydrogen, a protecting group, a covalent bond to a solid support, or a bond to a linking group that is bound to a solid support; and n is 0, 1, 2, 3, 4, 5, 6, 7, 8, 9, or 10;

or a salt thereof.

In one embodiment the invention provides a compound of formula:
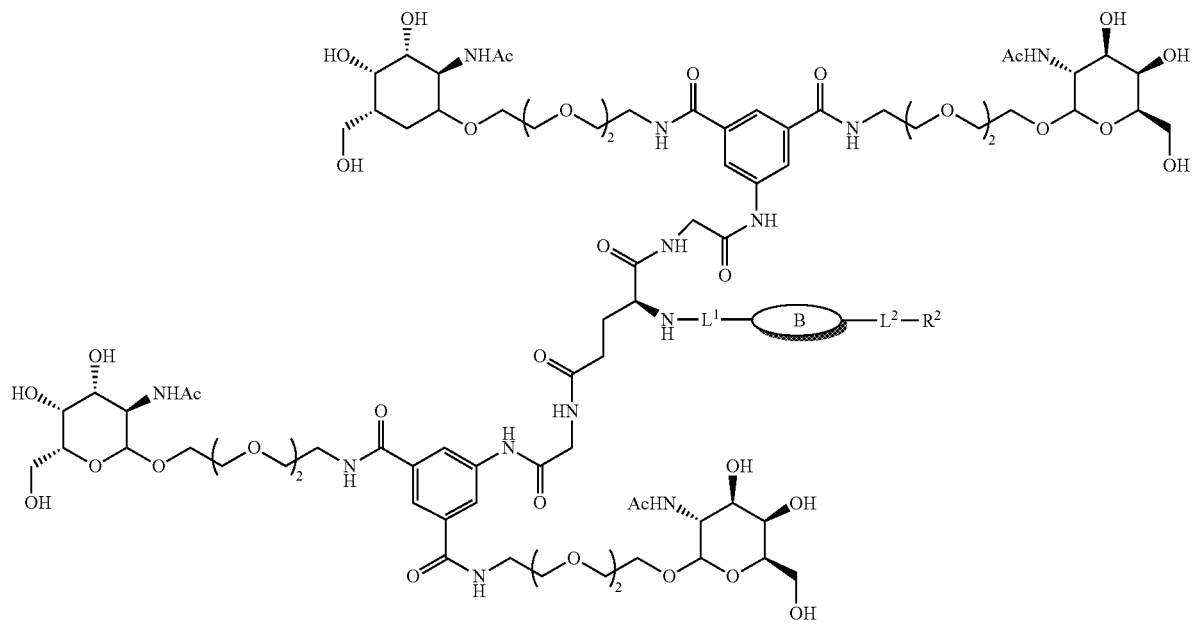
wherein:
L¹ is absent or a linking group;
L² is absent or a linking group;
R² is a nucleic acid;
B is divalent and is selected from the group consisting of:
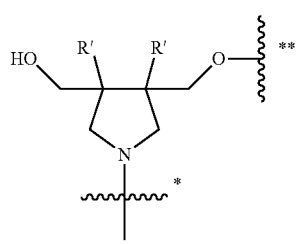
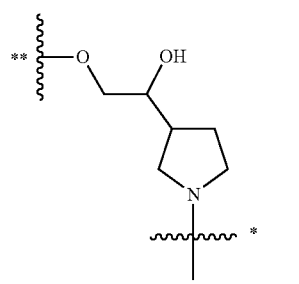
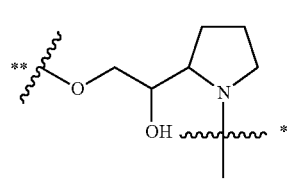
-continued
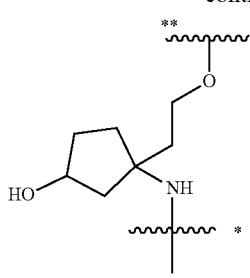
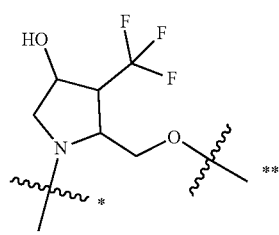
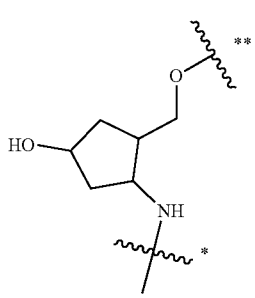

-continued

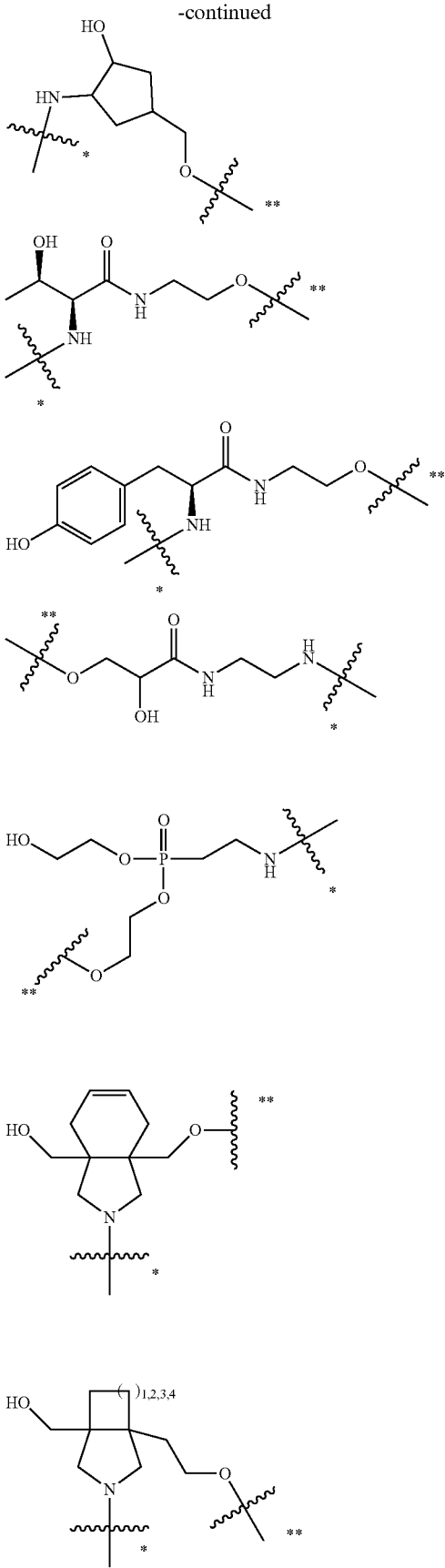

-continued

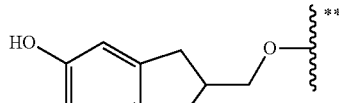

and

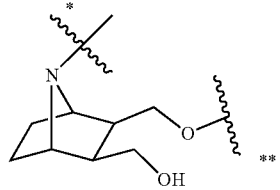

wherein:

each R' is independently $C_{1-9}$ alkyl, $C_{2-9}$ alkenyl or $C_{2-9}$ alkynyl; wherein the $C_{1-9}$ alkyl, $C_{2-9}$ alkenyl or $C_{2-9}$ alkynyl are optionally substituted with halo or hydroxyl;

the valence marked with * is attached to $L^1$ or is attached to $R^1$ if $L^1$ is absent; and the valence marked with ** is attached to $L^2$ or is attached to $R^2$ if $L^2$ is absent;

or a salt thereof.

In one embodiment $L^1$ and $L^2$ are independently a divalent, branched or unbranched, saturated or unsaturated, hydrocarbon chain, having from 1 to 50 carbon atoms, wherein one or more (e.g. 1, 2, 3, or 4) of the carbon atoms in the hydrocarbon chain is optionally replaced by —O—, —$NR^X$—, —$NR^X$—C(=O)—, —C(=O)—$NR^X$— or —S—, and wherein $R^X$ is hydrogen or ($C_1$-$C_6$)alkyl, and wherein the hydrocarbon chain, is optionally substituted with one or more substituents selected from ($C_1$-$C_6$)alkoxy, ($C_3$-$C_6$)cycloalkyl, ($C_1$-$C_6$)alkanoyl, ($C_1$-$C_6$)alkanoyloxy, ($C_1$-$C_6$)alkoxycarbonyl, ($C_1$-$C_6$)alkylthio, azido, cyano, nitro, halo, hydroxy, oxo (=O), carboxy, aryl, aryloxy, heteroaryl, and heteroaryloxy.

In one embodiment $L^1$ is selected from the group consisting of:

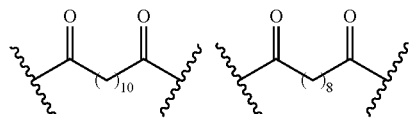

and

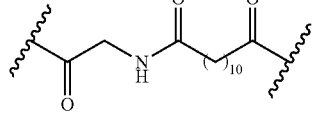

or a salt thereof.

In one embodiment $L^1$ is connected to $B^1$ through a linkage selected from the group consisting of: —O—, —S—, —(C=O)—, —(C=O)—NH—, —NH—(C=O), —(C=O)—O—, —NH—(C=O)—NH—, or —NH—($SO_2$)—.

In one embodiment $L^1$ is selected from the group consisting of:

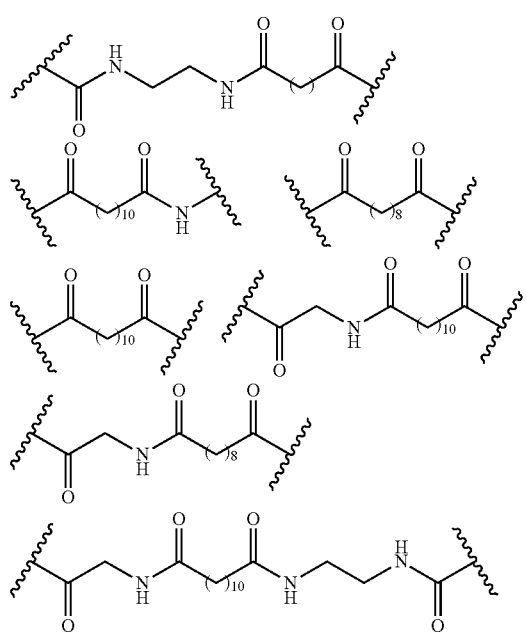
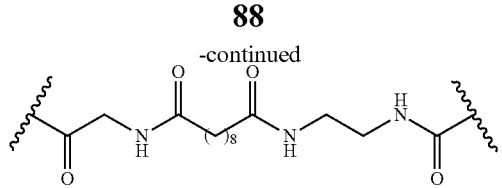
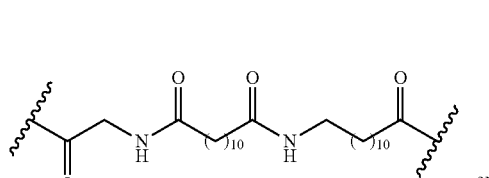
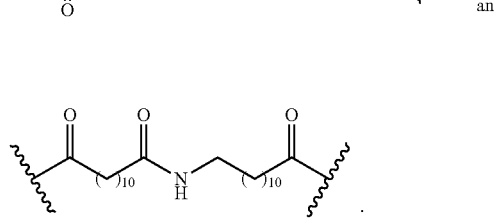

and

.

In one embodiment $L^2$ is connected to $R^2$ through —O—.

In one embodiment $L^2$ is $C_{1-4}$ alkylene-O— that is optionally substituted with hydroxy.

In one embodiment $L^2$ is absent.

In one embodiment the invention provides a compound,

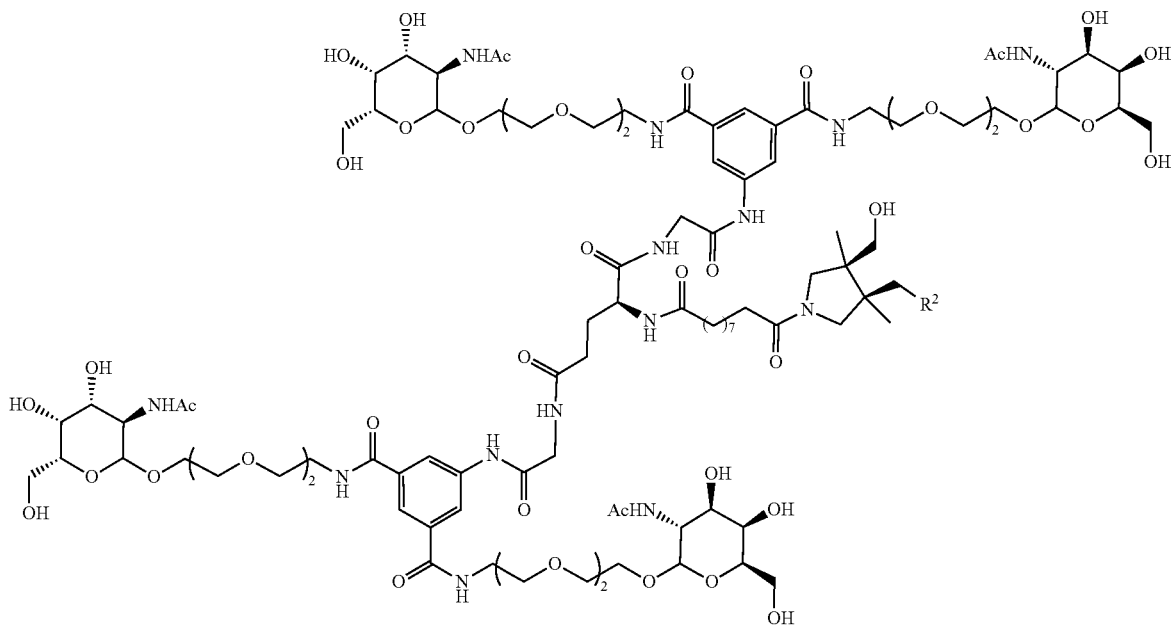

or a salt thereof wherein $R^2$ is a nucleic acid.

One aspect of this invention is pharmaceutical composition comprising a compound of formula I, and a pharmaceutically acceptable carrier.

Another aspect of this invention is a method to deliver a double stranded siRNA to the liver of an animal comprising administering a compound of formula I or a pharmaceutically acceptable salt thereof, to the animal.

Another aspect of this invention is a method to treat a disease or disorder (e.g., a liver disease or a viral infection, such as a hepatitis B viral infection) in an animal comprising administering a compound of formula I or a pharmaceutically acceptable salt thereof, to the animal.

Certain embodiments of the invention provide a compound of formula (I) or a pharmaceutically acceptable salt thereof for use in medical therapy.

Certain embodiments of the invention provide a compound of formula (I) or a pharmaceutically acceptable salt thereof for the prophylactic or therapeutic treatment of a disease or disorder (e.g., a liver disease or a viral infection, such as a hepatitis B virus infection) in an animal.

Certain embodiments of the invention provide the use of a compound of formula (I) or a pharmaceutically acceptable salt thereof to prepare a medicament for treating a disease or disorder (e.g., a liver disease or a viral infection, such as a hepatitis B virus infection) in an animal.

In certain embodiments, the animal is a mammal, such as a human (e.g., an HBV infected patient).

In one embodiment a compound of formula I has the following formula (Id):

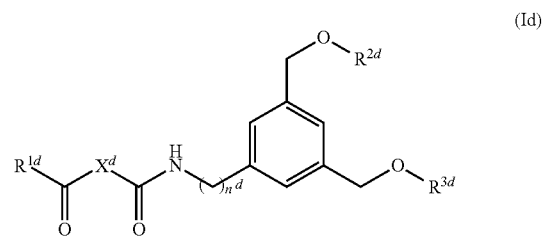

wherein:

$R^{1d}$ is selected from:

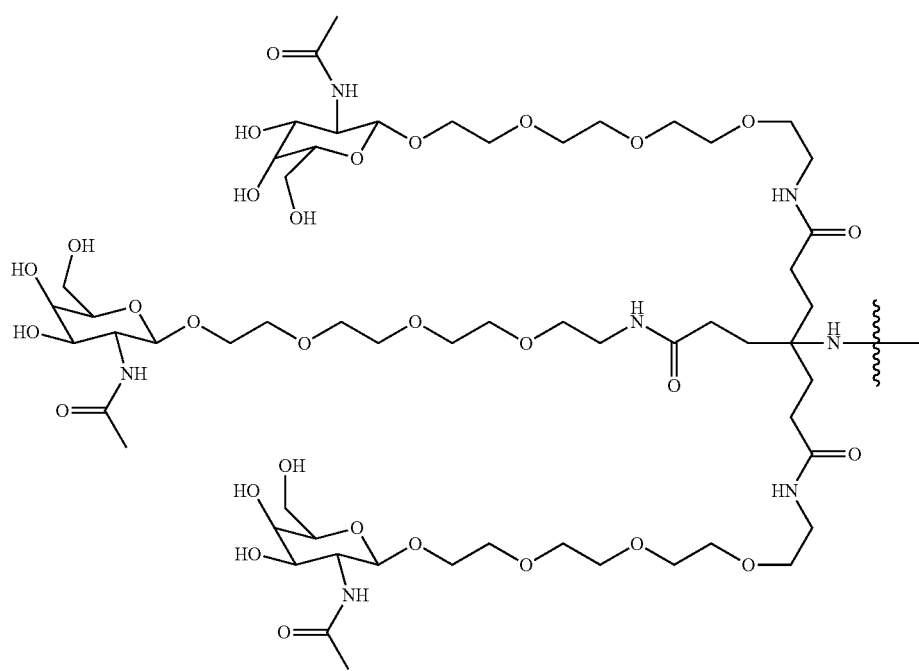

and

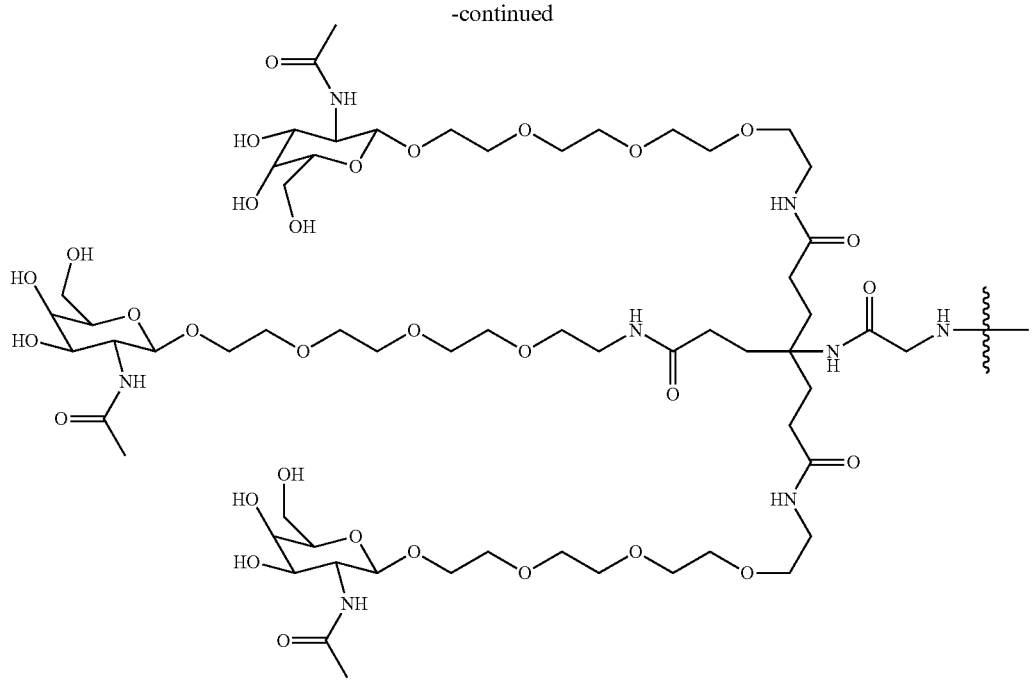

$X^d$ is $C_{2-10}$ alkylene;

$n^d$ is 0 or 1;

$R^{2d}$ is a double stranded siRNA molecule selected from the double stranded siRNA of Table 1; and $R^{3d}$ is H, a protecting group, a covalent bond to a solid support, or a bond to a linking group that is bound to a solid support.

In one embodiment $R^{3d}$ includes a linking group that joins the remainder of the compound of formula Id to a solid support. The nature of the linking group is not critical provided the compound is a suitable intermediate for preparing a compound of formula Id wherein $R^{2d}$ is a double stranded siRNA molecule selected from the double stranded siRNA of Table 1.

In one embodiment the linker in $R^{3d}$ has a molecular weight of from about 20 daltons to about 1,000 daltons.

In one embodiment the linker in $R^{3d}$ has a molecular weight of from about 20 daltons to about 500 daltons.

In one embodiment the linker in $R^{3d}$ separates the solid support from the remainder of the compound of formula I by about 5 angstroms to about 40 angstroms, inclusive, in length.

In one embodiment the linker in $R^{3d}$ is a divalent, branched or unbranched, saturated or unsaturated, hydrocarbon chain, having from 2 to 15 carbon atoms, wherein one or more (e.g. 1, 2, 3, or 4) of the carbon atoms is optionally replaced by (—O—) or (—N(H)—), and wherein the chain is optionally substituted on carbon with one or more (e.g. 1, 2, 3, or 4) substituents selected from $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo (=O), carboxy, aryl, aryloxy, heteroaryl, and heteroaryloxy.

In one embodiment the linker in $R^{3d}$ is a divalent, branched or unbranched, saturated or unsaturated, hydrocarbon chain, having from 2 to 10 carbon atoms, wherein one or more (e.g. 1, 2, 3, or 4) of the carbon atoms is optionally replaced by (—O—) or (—N(H)—), and wherein the chain is optionally substituted on carbon with one or more (e.g. 1, 2, 3, or 4) substituents selected from $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo (=O), carboxy, aryl, aryloxy, heteroaryl, and heteroaryloxy.

In one embodiment the linker in $R^{3d}$ is —C(=O)CH$_2$CH$_2$C(=O)N(H)—.

In one embodiment $R^{1d}$ is:
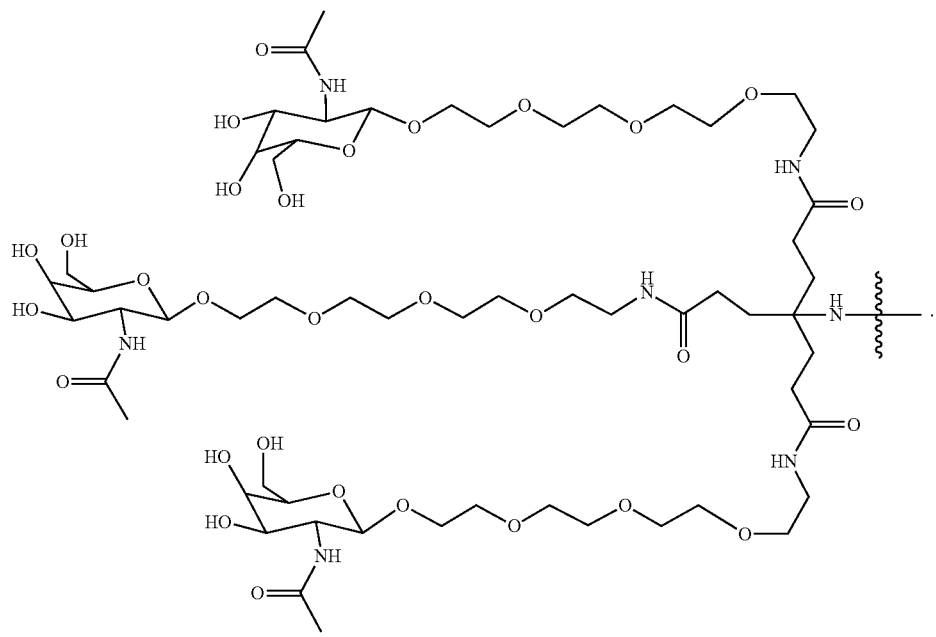 [SMILES: *NC(CCC(=O)NCCOCCOCCOCCOC1OC(CO)C(O)C(O)C1NC(C)=O)(CCC(=O)NCCOCCOCCOCCOC1OC(CO)C(O)C(O)C1NC(C)=O)CCC(=O)NCCOCCOCCOCCOC1OC(CO)C(O)C(O)C1NC(C)=O]
In one embodiment $R^{1d}$ is:
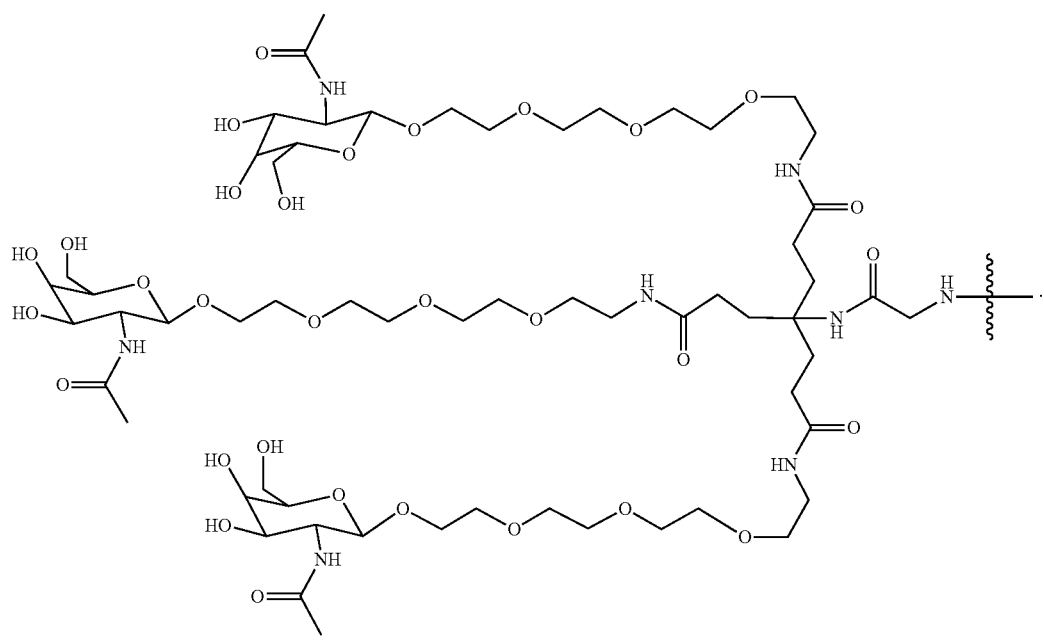 [SMILES: *NCC(=O)NC(CCC(=O)NCCOCCOCCOCCOC1OC(CO)C(O)C(O)C1NC(C)=O)(CCC(=O)NCCOCCOCCOCCOC1OC(CO)C(O)C(O)C1NC(C)=O)CCC(=O)NCCOCCOCCOCCOC1OC(CO)C(O)C(O)C1NC(C)=O]
In one embodiment $X^d$ is $C_8$alkylene.
In one embodiment $n^d$ is 0.
In one embodiment $R^{2d}$ is an siRNA.
In one embodiment $R^{3d}$ is H.

In another embodiment a compound of (Id) or the salt thereof is selected from the group consisting of:

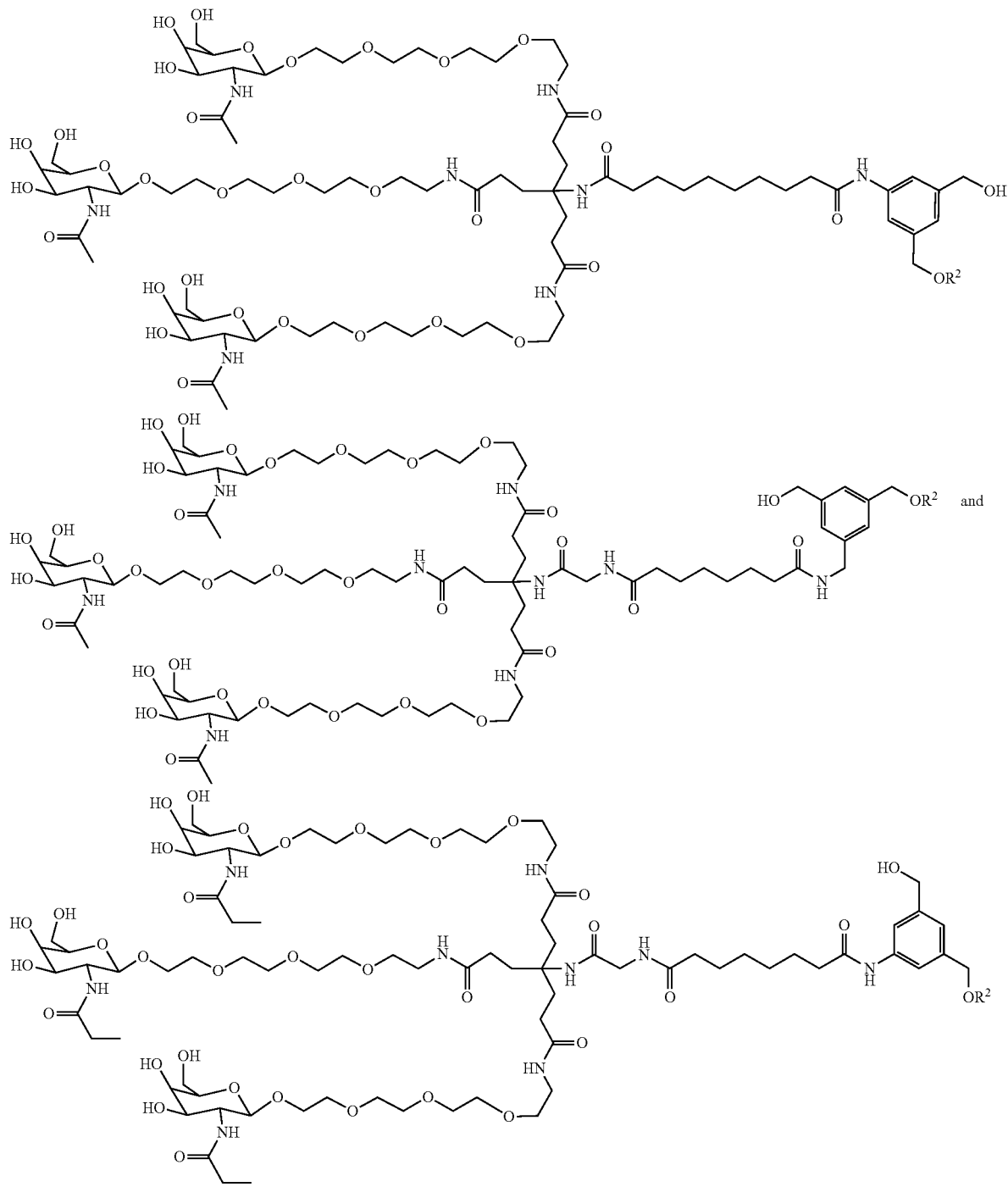

and salts thereof.

One aspect of this invention is a pharmaceutical composition comprising a compound of formula (Id), and a pharmaceutically acceptable carrier.

One aspect of this invention is a method to deliver is a double stranded siRNA to the liver of an animal comprising administering a compound of formula (Id) or a pharmaceutically acceptable salt thereof, to the animal.

Another aspect of this invention is a method to treat a disease or disorder (e.g., a viral infection, such as a hepatitis B viral infection) in an animal comprising administering a compound of formula (Id) or a pharmaceutically acceptable salt thereof, to the animal.

Certain embodiments of the invention provide a compound of formula (Id) or a pharmaceutically acceptable salt thereof for use in medical therapy.

Certain embodiments of the invention provide a compound of formula (Id) or a pharmaceutically acceptable salt thereof for the prophylactic or therapeutic treatment of a disease or disorder (e.g., a viral infection, such as a hepatitis B virus infection) in an animal.

Certain embodiments of the invention provide the use of a compound of formula (Id) or a pharmaceutically acceptable salt thereof to prepare a medicament for treating a disease or disorder (e.g., a viral infection, such as a hepatitis B virus infection) in an animal.

In certain embodiments, the animal is a mammal, such as a human (e.g., an HBV infected patient).

The invention also provides synthetic intermediates and methods disclosed herein that are useful to prepare compounds of formula (Id). For example, the invention includes an intermediate compound of formula Ie:

or a salt thereof, wherein:
$R^{1d}$ is selected from:

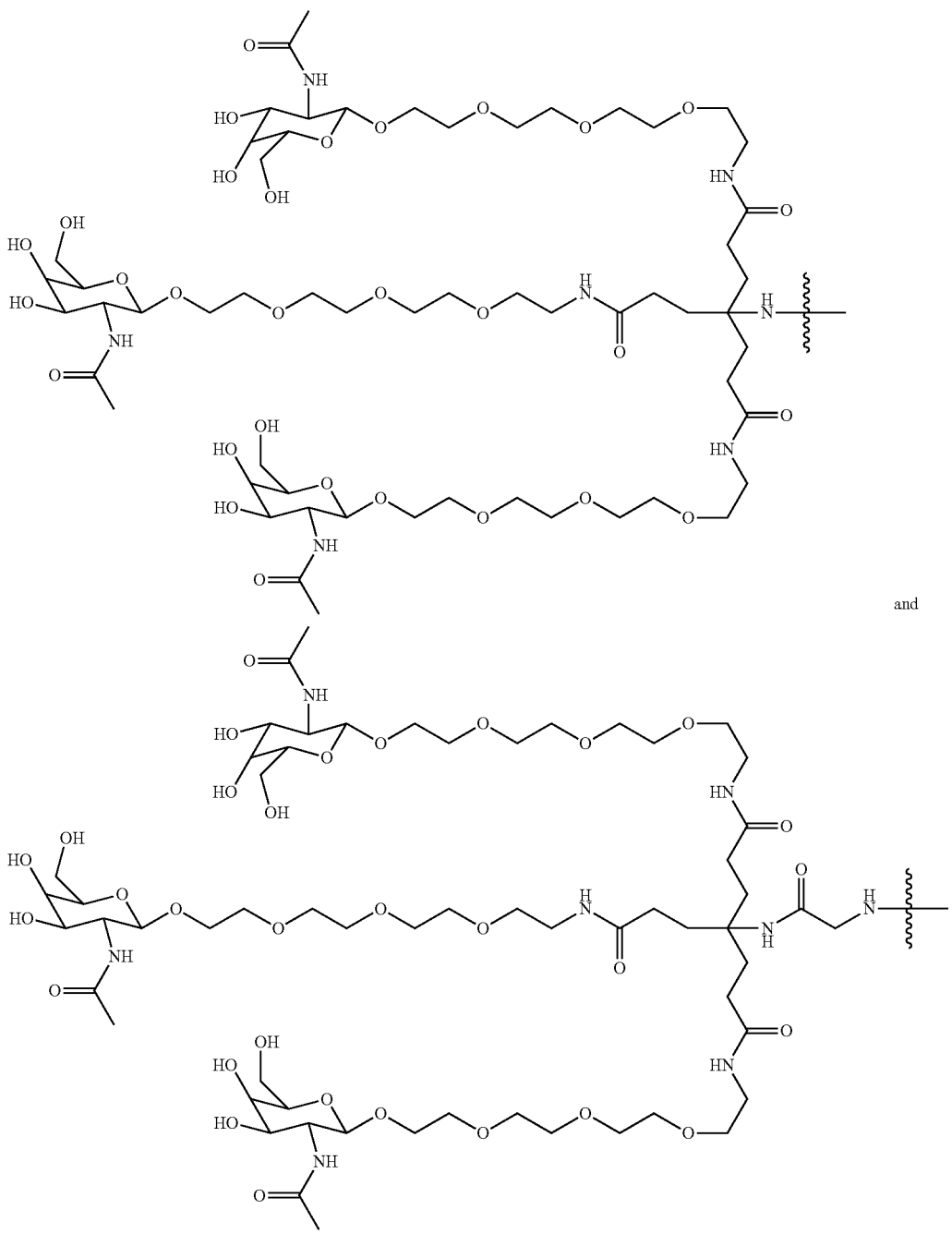

and $X^d$ is $C_{2-8}$ alkylene;

$n^d$ is 0 or 1;

$Pg^1$ is H or a suitable protecting group; and $R^{3d}$ is H, a protecting group, a covalent bond to a solid support, or a bond to a linking group that is bound to a solid support. FIG. 1 illustrates a representative intermediate compound of formula (Ie), wherein a targeting ligand/linker is bound to a solid phase support, and wherein $Pg^1$ is the protecting group DMTr.

In one embodiment $Pg^1$ is TMTr (Trimethoxytrityl), DMTr (Dimethoxytrityl), MMTr (Monomethoxytrityl), or Tr (Trityl).

The invention also provides a method to prepare a compound of formula (Id) as described herein comprising subjecting a corresponding compound of formula (Ie):

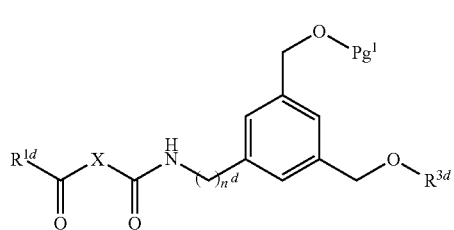
(Ie)

wherein:

$X^d$ is $C_{2-8}$ alkylene;

$n^d$ is 0 or 1;

$Pg^1$ is H; and $R^{3d}$ is a covalent bond to a solid support or a bond to a linking group that is bound to a solid support, to solid phase nucleic acid synthesis conditions to provide a corresponding compound of formula Id wherein $R^{2d}$ is a double stranded siRNA molecule selected from the double stranded siRNA molecules of Table 1.

In one embodiment the method further comprises removing the compound from the solid support to provide the corresponding compound of formula Id wherein $R^{3d}$ is H.

In one embodiment the compound is not a compound formula Id:

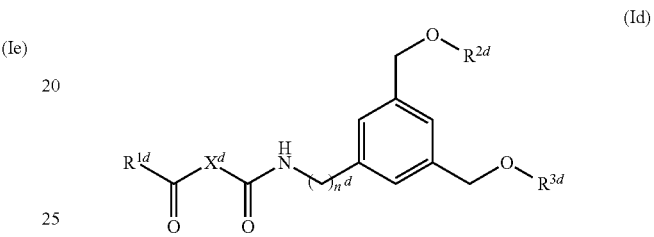
(Id)

or a salt thereof, wherein:

$R^{1d}$ is selected from:

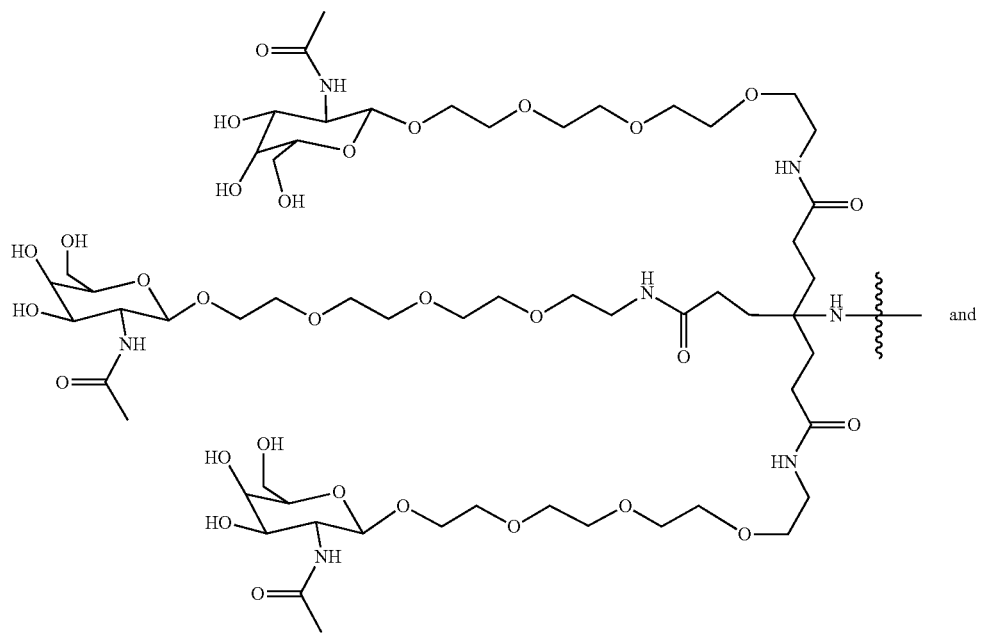
and

-continued
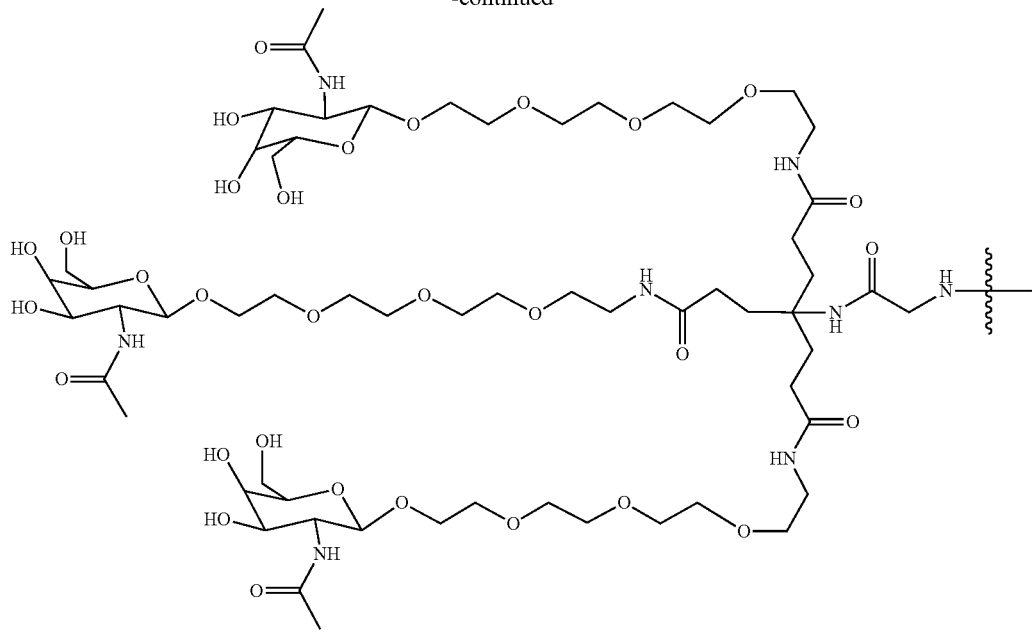
$X^d$ is $C_{2-10}$ alkylene;
$N^d$ is 0 or 1;
$R^{2d}$ is a double stranded siRNA molecule selected from the double stranded siRNA molecules of Table 1; and
$R^{3d}$ is H, a protecting group, a covalent bond to a solid support, or a bond to a linking group that is bound to a solid support.
In one embodiment the compound is not a compound formula Ie:
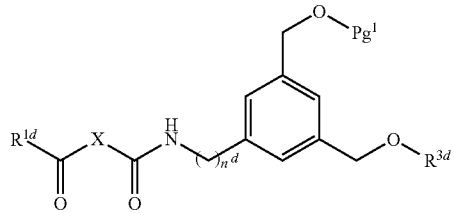

or a salt thereof, wherein:
$R^{1d}$ is selected from:

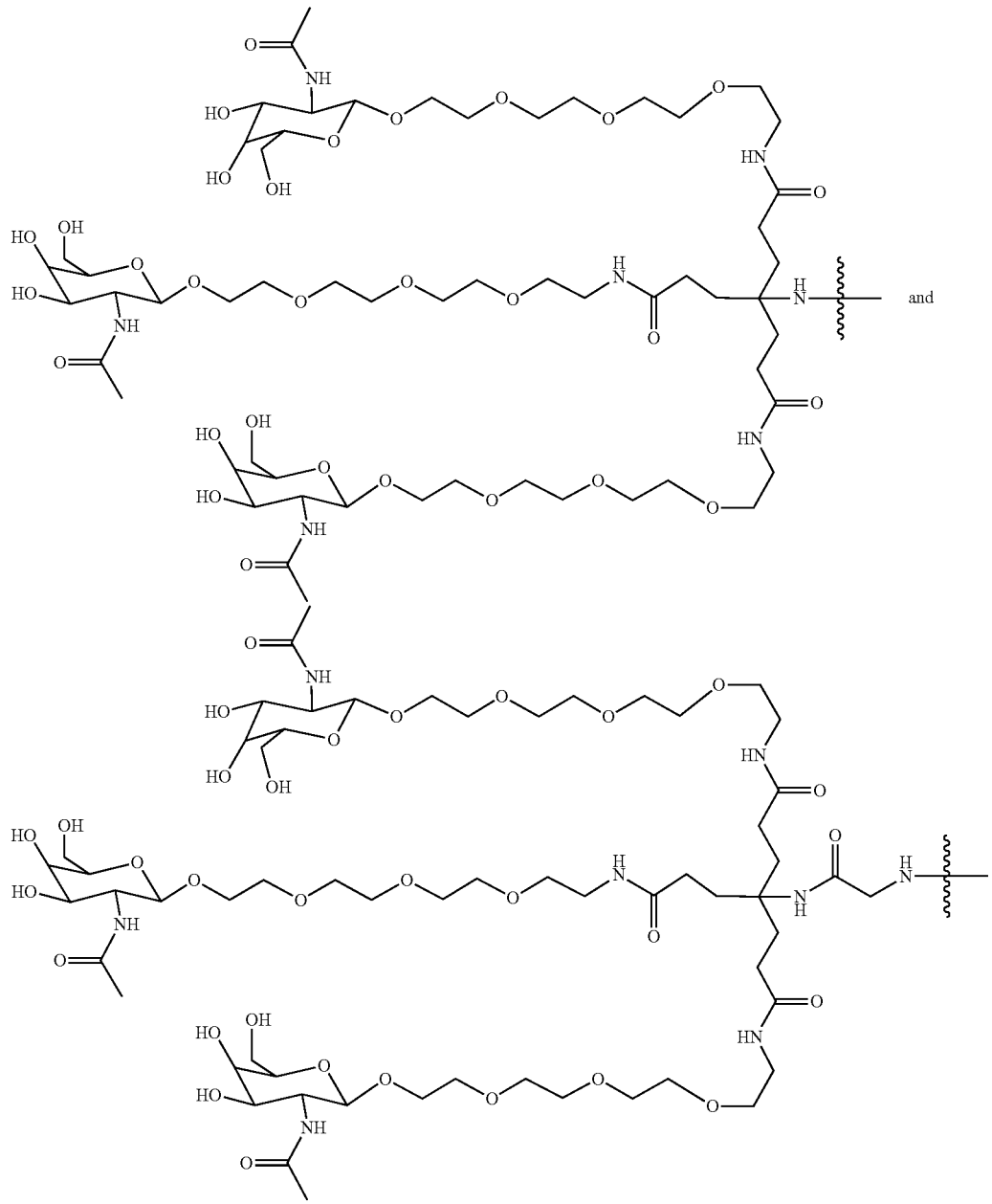

$X^d$ is $C_{2-8}$ alkylene;
$n^d$ is 0 or 1;
$Pg^1$ is H or a suitable protecting group; and
$R^{3d}$ is H, a protecting group, a covalent bond to a solid support, or a bond to a linking group that is bound to a solid support.

In one embodiment $R^{3d}$ is H.
In one embodiment $R^{3d}$ is a covalent bond to a solid support.
In one embodiment $R^{3d}$ is a bond to a linking group that is bound to a solid support, wherein the linking group is a divalent, branched or unbranched, saturated or unsaturated, hydrocarbon chain, having from 2 to 15 carbon atoms, wherein one or more (e.g. 1, 2, 3, or 4) of the carbon atoms is optionally replaced by (—O—) or (—N(H)—), and wherein the chain is optionally substituted on carbon with one or more (e.g. 1, 2, 3, or 4) substituents selected from $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo (=O), carboxy, aryl, aryloxy, heteroaryl, and heteroaryloxy.

In one embodiment $R^{3d}$ is a bond to a linking group that is bound to a solid support, wherein the linking group is a divalent, branched or unbranched, saturated or unsaturated, hydrocarbon chain, having from 2 to 10 carbon atoms, wherein one or more (e.g. 1, 2, 3, or 4) of the carbon atoms is optionally replaced by (—O—) or (—N(H)—), and wherein the chain is optionally substituted on carbon with one or more (e.g. 1, 2, 3, or 4) substituents selected from $(C_1-C_6)$alkoxy, $(C_3-C_6)$cycloalkyl, $(C_1-C_6)$alkanoyl, $(C_1-$ $C_6$)alkanoyloxy, ($C_1$-$C_6$)alkoxycarbonyl, ($C_1$-$C_6$)alkylthio, azido, cyano, nitro, halo, hydroxy, oxo (=O), carboxy, aryl, aryloxy, heteroaryl, and heteroaryloxy.

In one embodiment $R^{3d}$ is a bond to a linking group that is bound to a solid support, wherein the linking group is —C(=O)CH$_2$CH$_2$C(=O)N(H)—.

In one embodiment the invention provides a compound of formula (I):

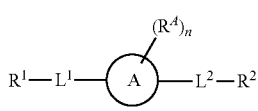

(I)

wherein:
$R^1$ is H or a synthetic activating group;
$L^1$ is absent or a linking group;
$L^2$ is absent or a linking group;
$R^2$ is a double stranded siRNA molecule selected from the double stranded siRNA molecules of Table 1;
the ring A is absent, a 3-20 membered cycloalkyl, a 5-20 membered aryl, a 5-20 membered heteroaryl, or a 3-20 membered heterocycloalkyl;
each $R^A$ is independently selected from the group consisting of hydrogen, hydroxy, CN, F, Cl, Br, I, —$C_{1-2}$ alkyl-OR$^B$, $C_{1-10}$ alkyl $C_{2-10}$ alkenyl, and $C_{2-10}$ alkynyl; wherein the $C_{1-10}$ alkyl $C_{2-10}$ alkenyl, and $C_{2-10}$ alkynyl are optionally substituted with one or more groups independently selected from halo, hydroxy, and $C_{1-3}$ alkoxy;
$R^B$ is hydrogen, a protecting group, a covalent bond to a solid support, or a bond to a linking group that is bound to a solid support; and
n is 0, 1, 2, 3, 4, 5, 6, 7, 8, 9, or 10;
or a salt thereof.

In one embodiment the invention provides a compound of formula (I):

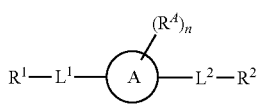

(I)

wherein:
$R^1$ a is targeting ligand;
$L^1$ is absent or a linking group;
$L^2$ is absent or a linking group;
$R^2$ is H or a synthetic activating group;
the ring A is absent, a 3-20 membered cycloalkyl, a 5-20 membered aryl, a 5-20 membered heteroaryl, or a 3-20 membered heterocycloalkyl;
each $R^A$ is independently selected from the group consisting of hydrogen, hydroxy, CN, F, Cl, Br, I, —$C_{1-2}$ alkyl-OR$^B$, $C_{1-10}$ alkyl $C_{2-10}$ alkenyl, and $C_{2-10}$ alkynyl; wherein the $C_{1-10}$ alkyl $C_{2-10}$ alkenyl, and $C_{2-10}$ alkynyl are optionally substituted with one or more groups independently selected from halo, hydroxy, and $C_{1-3}$ alkoxy;
$R^B$ is hydrogen, a protecting group, a covalent bond to a solid support, or a bond to a linking group that is bound to a solid support; and
n is 0, 1, 2, 3, 4, 5, 6, 7, 8, 9, or 10;
or a salt thereof.

In one embodiment the invention provides a compound of formula (Ig):

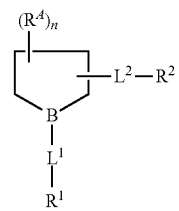

(Ig)

wherein:
B is —N— or —CH—;
$L^2$ is $C_{1-4}$ alkylene-O— that is optionally substituted with hydroxyl or halo; and
n is 0, 1, 2, 3, 4, 5, 6, or 7;
or a salt thereof.

In one embodiment the invention provides a compound selected from the group consisting of:

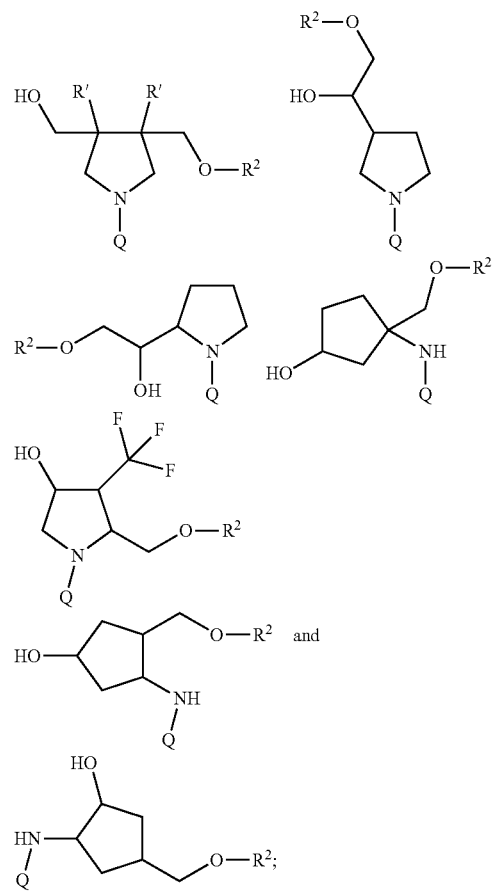

wherein:
Q is -$L^1$-$R^1$; and
R' is $C_{1-9}$ alkyl, $C_{2-9}$ alkenyl or $C_{2-9}$ alkynyl; wherein the $C_{1-9}$ alkyl, $C_{2-9}$ alkenyl or $C_{2-9}$ alkynyl are optionally substituted with halo or hydroxyl;
and salts thereof.

In one embodiment the invention provides a compound selected from the group consisting of:

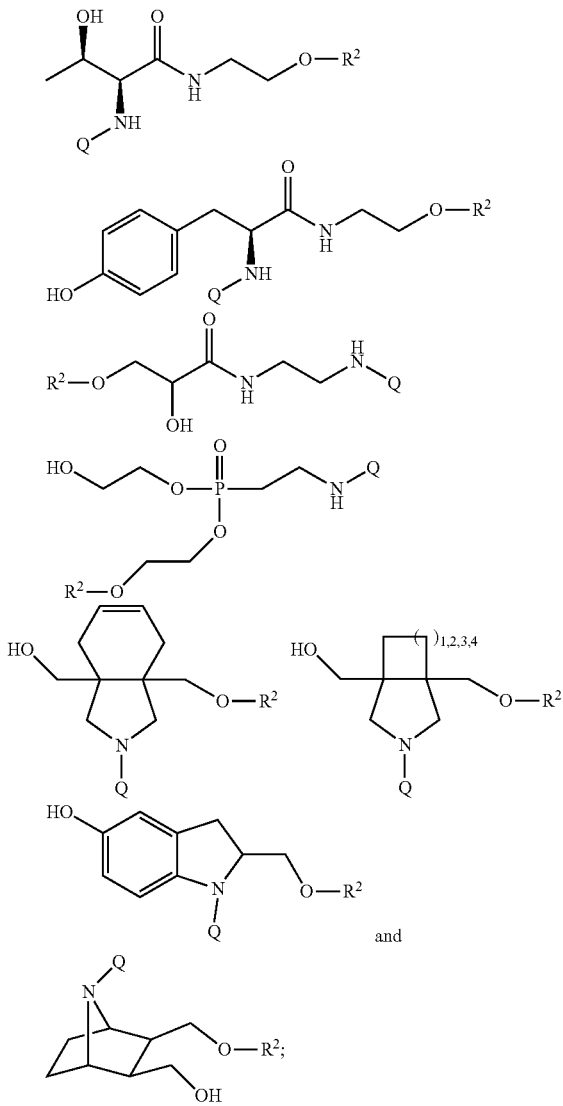

wherein: Q is -L¹-R¹; and salts thereof.

In one embodiment the invention provides a compound of formula (Ig):

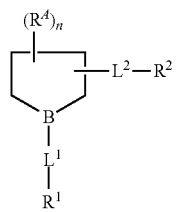

(Ig)

wherein:
B is —N— or —CH—;
L¹ is absent or a linking group;
L² is $C_{1-4}$ alkylene-O— that is optionally substituted with hydroxyl or halo;
n is 0, 1, 2, 3, 4, 5, 6, or 7;
R¹ is H or a synthetic activating group; and
R² is H or a synthetic activating group;
or a salt thereof.

In one embodiment the invention provides a compound selected from the group consisting of:

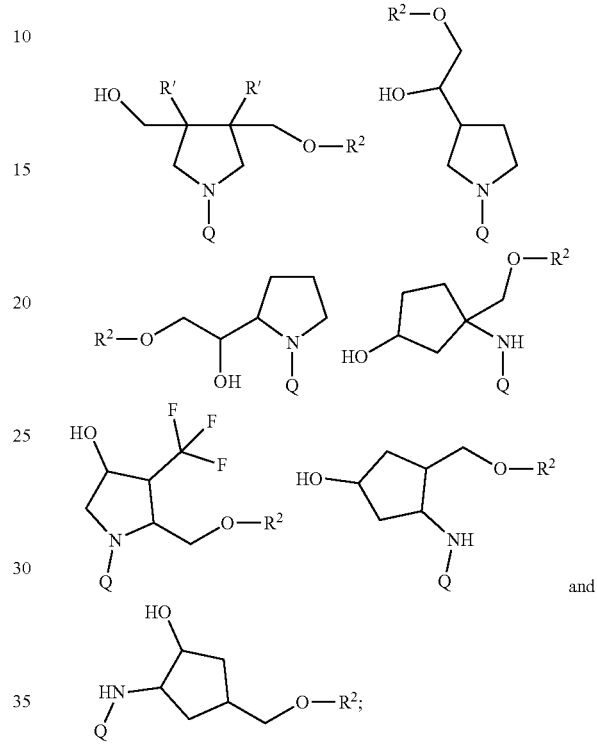

wherein Q is -L¹-R¹;
L¹ is absent or a linking group;
R' is $C_{1-9}$ alkyl, $C_{2-9}$ alkenyl or $C_{2-9}$ alkynyl; wherein the $C_{1-9}$ alkyl, $C_{2-9}$ alkenyl or $C_{2-9}$ alkynyl are optionally substituted with halo or hydroxyl;
R¹ is H or a synthetic activating group; and
R² is H or a synthetic activating group;
or a salt thereof.

In one embodiment the invention provides a compound selected from the group consisting of:

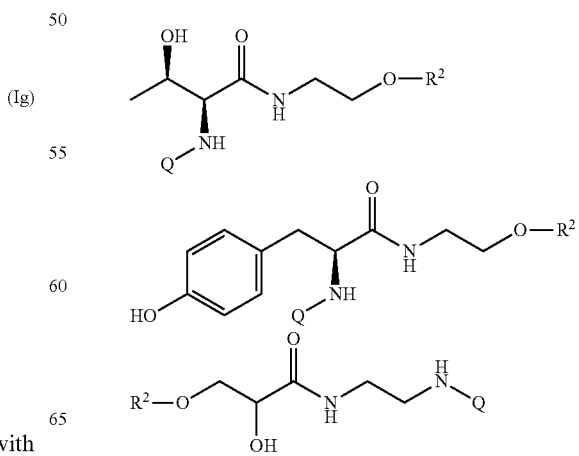

-continued

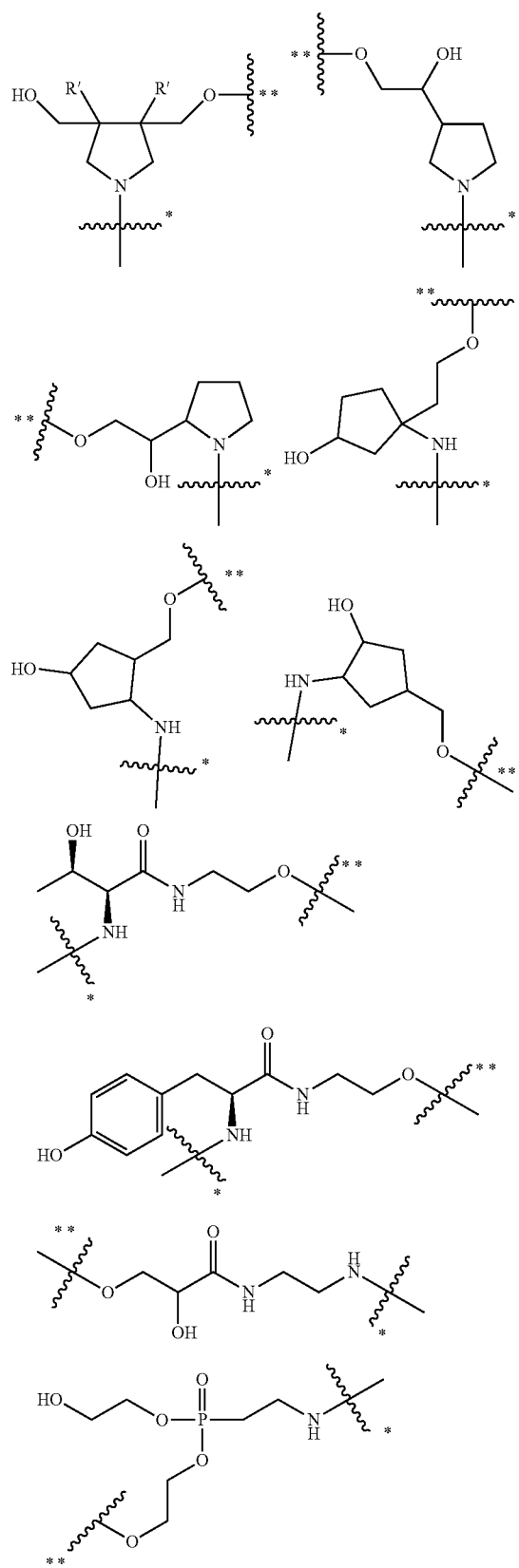

wherein:

Q is -L¹-R¹;

L¹ is absent or a linking group;

R¹ is H or a synthetic activating group; and

R² is H or a synthetic activating group;

or a salt thereof.

In one embodiment R¹ is H or a synthetic activating group derivable from DCC, HOBt, EDC, BOP, PyBOP or HBTU.

In one embodiment R² is H, acetate, triflate, mesylate or succinate.

In one embodiment R¹ is a synthetic activating group derivable from DCC, HOBt, EDC, BOP, PyBOP or HBTU.

In one embodiment R² is acetate, triflate, mesylate or succinate.

In one embodiment L¹ is a divalent, branched or unbranched, saturated or unsaturated, hydrocarbon chain, having from 5 to 20 carbon atoms, wherein one or more (e.g. 1, 2, 3, or 4) of the carbon atoms in the hydrocarbon chain is optionally replaced —O—, —NH—, —NH—C(=O)—, —C(=O)—NH— or —S—.

In one embodiment the invention provides a compound of formula (XX):

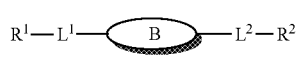

(XX)

wherein:

R¹ a is targeting ligand;

L¹ is absent or a linking group;

L² is absent or a linking group;

R² is a double stranded siRNA molecule selected from the double stranded siRNA molecules of Table 1;

B is divalent and is selected from the group consisting of:

-continued

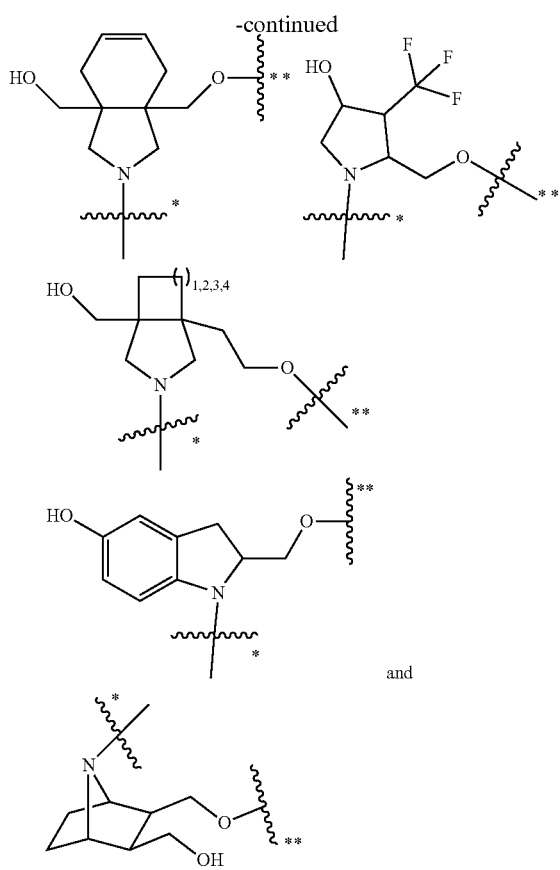

wherein:
each R' is independently $C_{1-9}$ alkyl, $C_{2-9}$ alkenyl or $C_{2-9}$ alkynyl; wherein the $C_{1-9}$ alkyl, $C_{2-9}$ alkenyl or $C_{2-9}$ alkynyl are optionally substituted with halo or hydroxyl;
the valence marked with * is attached to $L^1$ or is attached to $R^1$ if $L^1$ is absent; and
the valence marked with ** is attached to $L^2$ or is attached to $R^2$ if $L^2$ is absent;
or a salt thereof.
In one embodiment $R^1$ comprises 2-8 saccharides.
In one embodiment $R^1$ comprises 2-6 saccharides.
In one embodiment $R^1$ comprises 2-4 saccharides.
In one embodiment $R^1$ comprises 3-8 saccharides.
In one embodiment $R^1$ comprises 3-6 saccharides.
In one embodiment $R^1$ comprises 3-4 saccharides.
In one embodiment $R^1$ comprises 3 saccharides.
In one embodiment $R^1$ comprises 4 saccharides.
In one embodiment $R^1$ has the following formula:

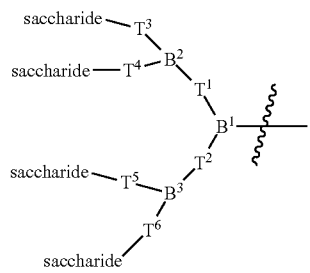

wherein:
$B^1$ is a trivalent group comprising about 1 to about 20 atoms and is covalently bonded to $L^1$, $T^1$, and $T^2$.
$B^2$ is a trivalent group comprising about 1 to about 20 atoms and is covalently bonded to $T^1$, $T^3$, and $T^4$;
$B^3$ is a trivalent group comprising about 1 to about 20 atoms and is covalently bonded to $T^2$, $T^5$, and $T^6$;
$T^1$ is absent or a linking group;
$T^2$ is absent or a linking group;
$T^3$ is absent or a linking group;
$T^4$ is absent or a linking group;
$T^5$ is absent or a linking group; and
$T^6$ is absent or a linking group
In one embodiment each saccharide is independently selected from:

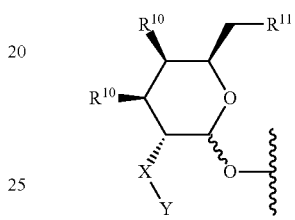

wherein:
X is $NR^3$, and Y is selected from —(C=O)$R^4$, —SO$_2R^5$, and —(C=O)$NR^6R^7$; or X is —(C=O)— and Y is $NR^8R^9$;
$R^3$ is hydrogen or $(C_1$-$C_4)$alkyl;
$R^4$, $R^5$, $R^6$, $R^7$, $R^8$ and $R^9$ are each independently selected from the group consisting of hydrogen, $(C_1$-$C_8)$alkyl, $(C_1$-$C_8)$haloalkyl, $(C_1$-$C_8)$alkoxy and $(C_3$-$C_6)$cycloalkyl that is optionally substituted with one or more groups independently selected from the group consisting of halo, $(C_1$-$C_4)$alkyl, $(C_1$-$C_4)$haloalkyl, $(C_1$-$C_4)$alkoxy and $(C_1$-$C_4)$haloalkoxy;
$R^{10}$ is —OH, —$NR^8R^9$ or —F; and
$R^{11}$ is —OH, —$NR^8R^9$, —F or 5 membered heterocycle that is optionally substituted with one or more groups independently selected from the group consisting of halo, hydroxyl, carboxyl, amino, $(C_1$-$C_4)$alkyl, $(C_1$-$C_4)$haloalkyl, $(C_1$-$C_4)$alkoxy and $(C_1$-$C_4)$haloalkoxy.
In one embodiment each saccharide is independently selected from the group consisting of:

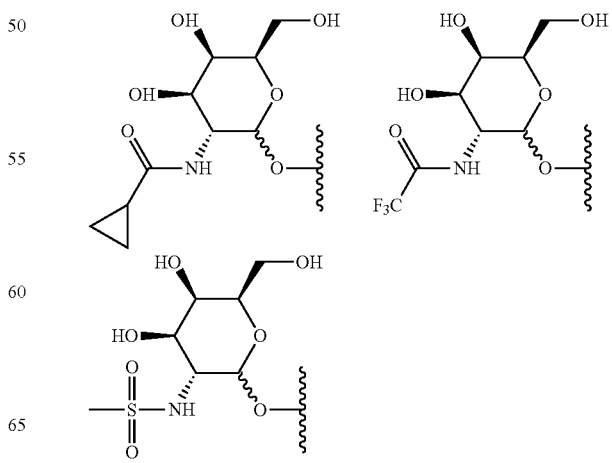

-continued

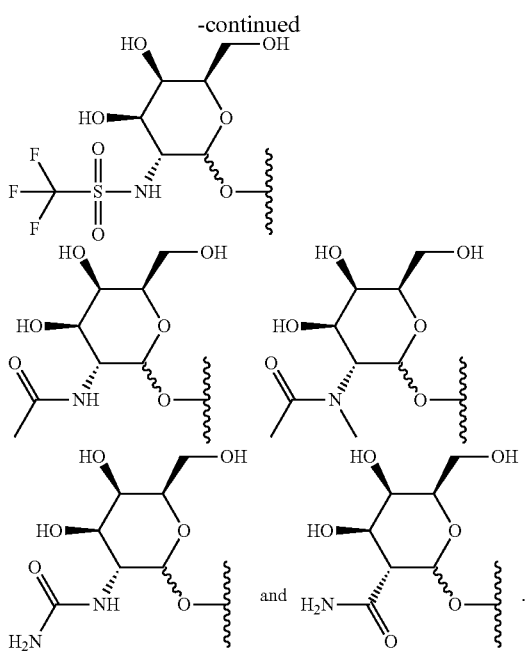

In one embodiment each saccharide is independently:

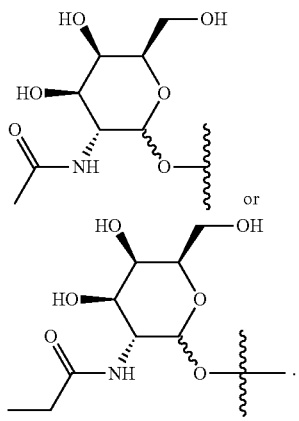

In one embodiment one of $T^1$ and $T^2$ is absent.

In one embodiment both $T^1$ and $T^2$ are absent.

In one embodiment each of $T^1$, $T^2$, $T^3$, $T^4$, $T^5$, and $T^6$ is independently absent or a branched or unbranched, saturated or unsaturated, hydrocarbon chain, having from 1 to 50 carbon atoms, wherein one or more (e.g. 1, 2, 3, or 4) of the carbon atoms in the hydrocarbon chain is optionally replaced by —O—, —NR$^X$—, —NR$^X$—C(=O)—, —C(=O)—NR$^X$— or —S—, and wherein R$^X$ is hydrogen or ($C_1$-$C_6$)alkyl, and wherein the hydrocarbon chain, is optionally substituted with one or more (e.g. 1, 2, 3, or 4) substituents selected from ($C_1$-$C_6$)alkoxy, ($C_3$-$C_6$)cycloalkyl, ($C_1$-$C_6$)alkanoyl, ($C_1$-$C_6$)alkanoyloxy, ($C_1$-$C_6$)alkoxycarbonyl, ($C_1$-$C_6$)alkylthio, azido, cyano, nitro, halo, hydroxy, oxo (=O), carboxy, aryl, aryloxy, heteroaryl, and heteroaryloxy.

In one embodiment each of $T^1$, $T^2$, $T^3$, $T^4$, $T^5$, and $T^6$ is independently absent or a branched or unbranched, saturated or unsaturated, hydrocarbon chain, having from 1 to 20 carbon atoms, wherein one or more (e.g. 1, 2, 3, or 4) of the carbon atoms in the hydrocarbon chain is optionally replaced by —O—, —NR$^X$—, —NR$^X$—C(=O)—, —C(=O)—NR$^X$— or —S—, and wherein R$^X$ is hydrogen or ($C_1$-$C_6$)alkyl, and wherein the hydrocarbon chain, is optionally substituted with one or more (e.g. 1, 2, 3, or 4) substituents selected from ($C_1$-$C_6$)alkoxy, ($C_3$-$C_6$)cycloalkyl, ($C_1$-$C_6$)alkanoyl, ($C_1$-$C_6$)alkanoyloxy, ($C_1$-$C_6$)alkoxycarbonyl, ($C_1$-$C_6$)alkylthio, azido, cyano, nitro, halo, hydroxy, oxo (=O), carboxy, aryl, aryloxy, heteroaryl, and heteroaryloxy.

In one embodiment each of $T^1$, $T^2$, $T^3$, $T^4$, $T^5$, and $T^6$ is independently absent or a branched or unbranched, saturated or unsaturated, hydrocarbon chain, having from 1 to 50 carbon atoms, or a salt thereof, wherein one or more (e.g. 1, 2, 3, or 4) of the carbon atoms in the hydrocarbon chain is optionally replaced by —O— or —NR$^X$—, and wherein R$^X$ is hydrogen or ($C_1$-$C_6$)alkyl, and wherein the hydrocarbon chain, is optionally substituted with one or more (e.g. 1, 2, 3, or 4) substituents selected from halo, hydroxy, and oxo (=O).

In one embodiment each of $T^1$, $T^2$, $T^3$, $T^4$, $T^5$, and $T^6$ is independently absent or a branched or unbranched, saturated or unsaturated, hydrocarbon chain, having from 1 to 20 carbon atoms, wherein one or more (e.g. 1, 2, 3, or 4) of the carbon atoms in the hydrocarbon chain is optionally replaced by —O— and wherein the hydrocarbon chain, is optionally substituted with one or more (e.g. 1, 2, 3, or 4) substituents selected from halo, hydroxy, and oxo (=O).

In one embodiment each of $T^1$, $T^2$, $T^3$, $T^4$, $T^5$, and $T^6$ is independently absent or a branched or unbranched, saturated or unsaturated, hydrocarbon chain, having from 1 to 20 carbon atoms, wherein one or more (e.g. 1, 2, 3, or 4) of the carbon atoms in the hydrocarbon chain is optionally replaced by —O— and wherein the hydrocarbon chain, is optionally substituted with one or more (e.g. 1, 2, 3, or 4) substituents selected from halo, hydroxy, and oxo (=O).

In one embodiment at least one of $T^3$, $T^4$, $T^5$, and $T^6$ is:

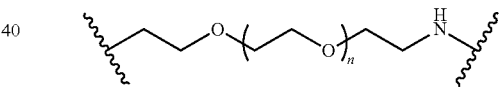

wherein:
n=1, 2, 3.

In one embodiment each of $T^3$, $T^4$, $T^5$, and $T^6$ is independently selected from the group consisting of:

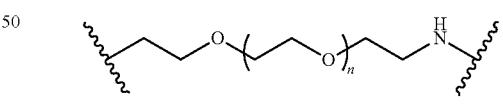

wherein:
n=1, 2, 3.

In one embodiment at least one of $T^1$ and $T^2$ is glycine

In one embodiment each of $T^1$ and $T^2$ is glycine.

In one embodiment $B^1$ is a trivalent group comprising 1 to 15 atoms and is covalently bonded to $L^1$, $T^1$, and $T^2$.

In one embodiment $B^1$ is a trivalent group comprising 1 to 10 atoms and is covalently bonded to $L^1$, $T^1$, and $T^2$.

In one embodiment $B^1$ comprises a ($C_1$-$C_6$)alkyl.

In one embodiment $B^1$ comprises a $C_{3-8}$ cycloalkyl.

In one embodiment $B^1$ comprises a silyl group.

In one embodiment $B^1$ comprises a D- or L-amino acid.

In one embodiment $B^1$ comprises a saccharide.

In one embodiment $B^1$ comprises a phosphate group.
In one embodiment $B^1$ comprises a phosphonate group.
In one embodiment $B^1$ comprises an aryl.
In one embodiment $B^1$ comprises a phenyl ring.
In one embodiment $B^1$ is a phenyl ring.
In one embodiment $B^1$ is CH.
In one embodiment $B^1$ comprises a heteroaryl.
In one embodiment $B^1$ is selected from the group consisting of:

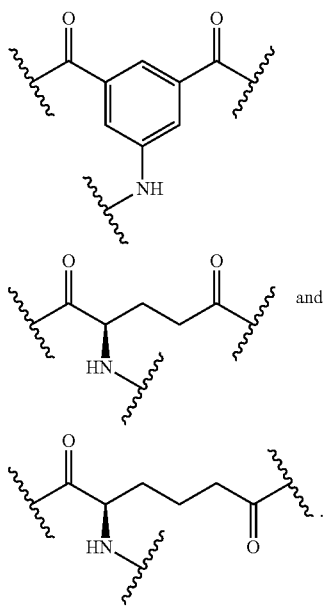

and

In one embodiment B is selected from the group consisting of:

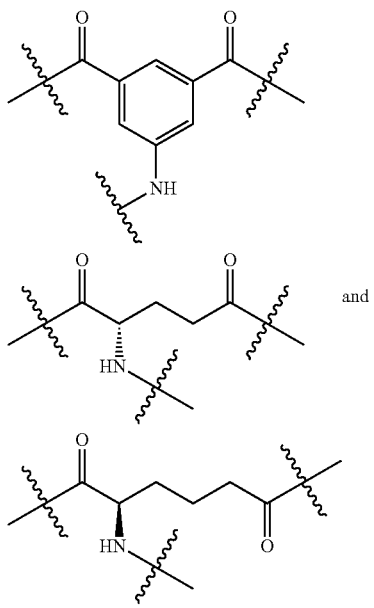

and

In one embodiment $B^2$ is a trivalent group comprising 1 to 15 atoms and is covalently bonded to $L^1$, T, and $T^2$.
In one embodiment $B^2$ is a trivalent group comprising 1 to 10 atoms and is covalently bonded to $L^1$, T, and $T^2$.

In one embodiment $B^2$ comprises a $(C_1-C_6)$alkyl
In one embodiment $B^2$ comprises a $C_{3-8}$ cycloalkyl.
In one embodiment $B^2$ comprises a silyl group.
In one embodiment $B^2$ comprises a D- or L-amino acid.
In one embodiment $B^2$ comprises a saccharide.
In one embodiment $B^2$ comprises a phosphate group.
In one embodiment $B^2$ comprises a phosphonate group.
In one embodiment $B^2$ comprises an aryl.
In one embodiment $B^2$ comprises a phenyl ring.
In one embodiment $B^2$ is a phenyl ring.
In one embodiment $B^2$ is CH.
In one embodiment $B^2$ comprises a heteroaryl.
In one embodiment $B^2$ is selected from the group consisting of:

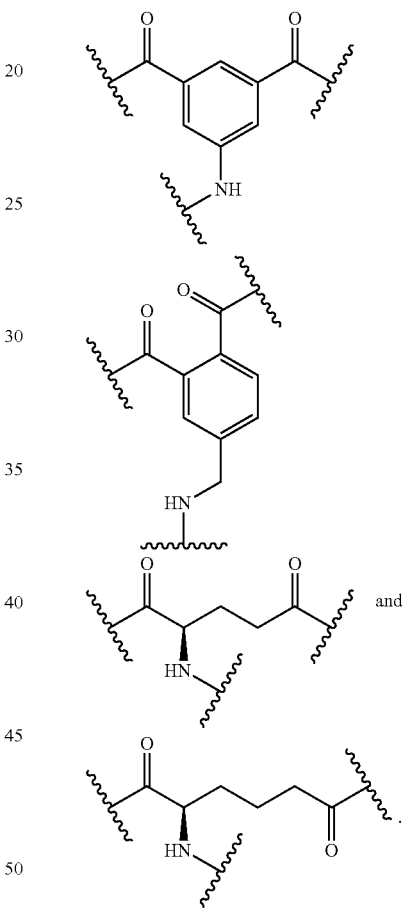

In one embodiment $B^2$ is selected from the group consisting of:

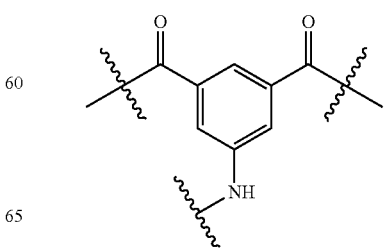

117

-continued

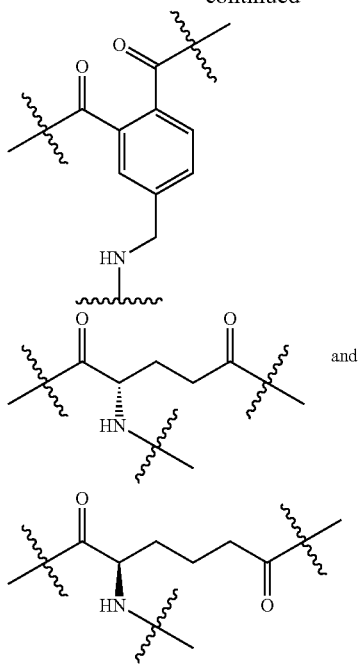

or a salt thereof.

In one embodiment B³ is a trivalent group comprising 1 to 15 atoms and is covalently bonded to L¹, T, and T².

In one embodiment B³ is a trivalent group comprising 1 to 10 atoms and is covalently bonded to L¹, T, and T².

In one embodiment B³ comprises a ($C_1$-$C_6$)alkyl.
In one embodiment B³ comprises a $C_{3-8}$ cycloalkyl.
In one embodiment B³ comprises a silyl group.
In one embodiment B³ comprises a D- or L-amino acid.
In one embodiment B³ comprises a saccharide.
In one embodiment B³ comprises a phosphate group.
In one embodiment B³ comprises a phosphonate group.
In one embodiment B³ comprises an aryl.
In one embodiment B³ comprises a phenyl ring.
In one embodiment B³ is a phenyl ring.
In one embodiment B³ is CH.
In one embodiment B³ comprises a heteroaryl.
In one embodiment B³ is selected from the group consisting of:

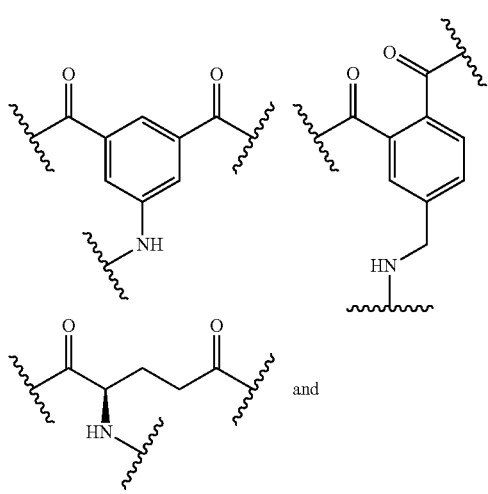

118

-continued

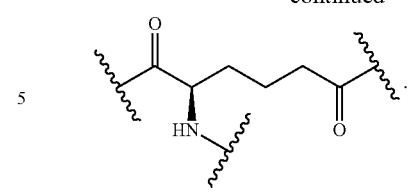

In one embodiment B³ is selected from the group consisting of:

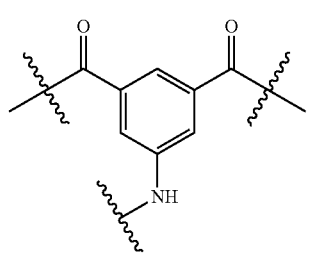

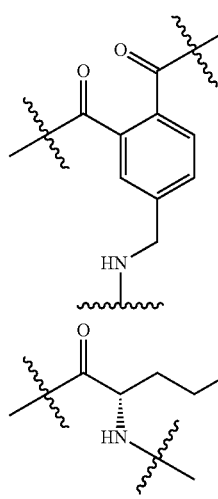
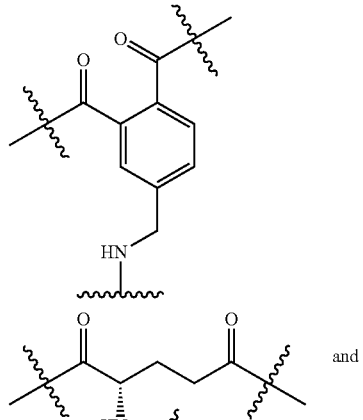

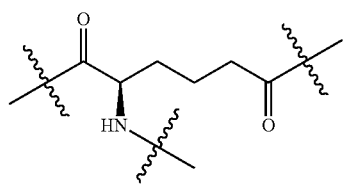

or a salt thereof.

In one embodiment L¹ and L² are independently a divalent, branched or unbranched, saturated or unsaturated, hydrocarbon chain, having from 1 to 50 carbon atoms, wherein one or more (e.g. 1, 2, 3, or 4) of the carbon atoms in the hydrocarbon chain is optionally replaced by —O—, —NR$^X$—, —NR$^X$—C(═O)—, —C(═O)—NR$^X$— or —S—, and wherein R$^X$ is hydrogen or ($C_1$-$C_6$)alkyl, and wherein the hydrocarbon chain, is optionally substituted with one or more (e.g. 1, 2, 3, or 4) substituents selected from ($C_1$-$C_6$)alkoxy, ($C_3$-$C_6$)cycloalkyl, ($C_1$-$C_6$)alkanoyl, ($C_1$-$C_6$)alkanoyloxy, ($C_1$-$C_6$)alkoxycarbonyl, ($C_1$-$C_6$)alkylthio, azido, cyano, nitro, halo, hydroxy, oxo (═O), carboxy, aryl, aryloxy, heteroaryl, and heteroaryloxy.

In one embodiment L¹ is selected from the group consisting of:

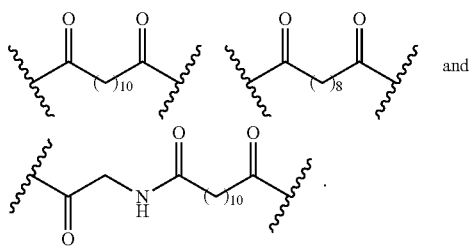

and or a salt thereof.

In one embodiment L¹ is connected to B¹ through a linkage selected from the group consisting of: —O—, —S—, —(C=O)—, —(C=O)—NH—, —NH—(C=O), —(C=O)—O—, —NH—(C=O)—NH—, or —NH—(SO₂)—.

In one embodiment L¹ is selected from the group consisting of:

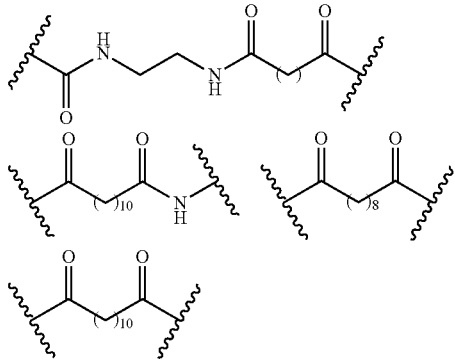

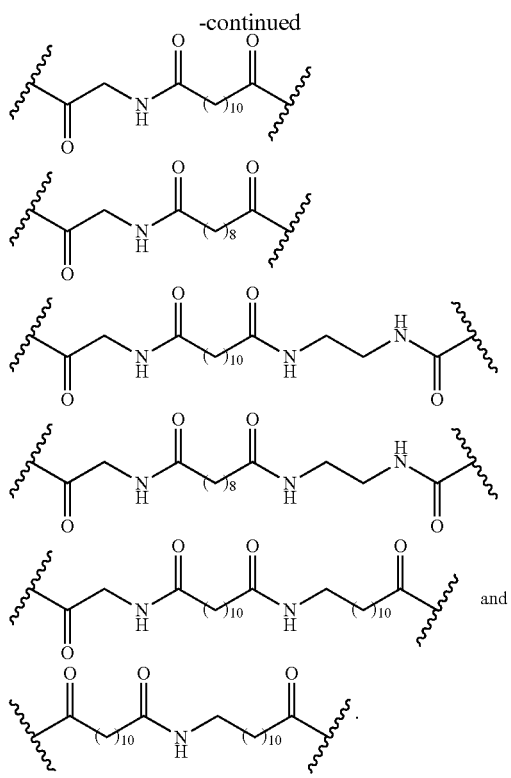

In one embodiment L² is connected to R² through —O—.

In one embodiment L² is $C_{1-4}$ alkylene-O— that is optionally substituted with hydroxy.

In one embodiment L² is connected to R² through —O—.

In one embodiment L² is absent.

In one embodiment the invention provides a compound or salt selected from the group consisting of:

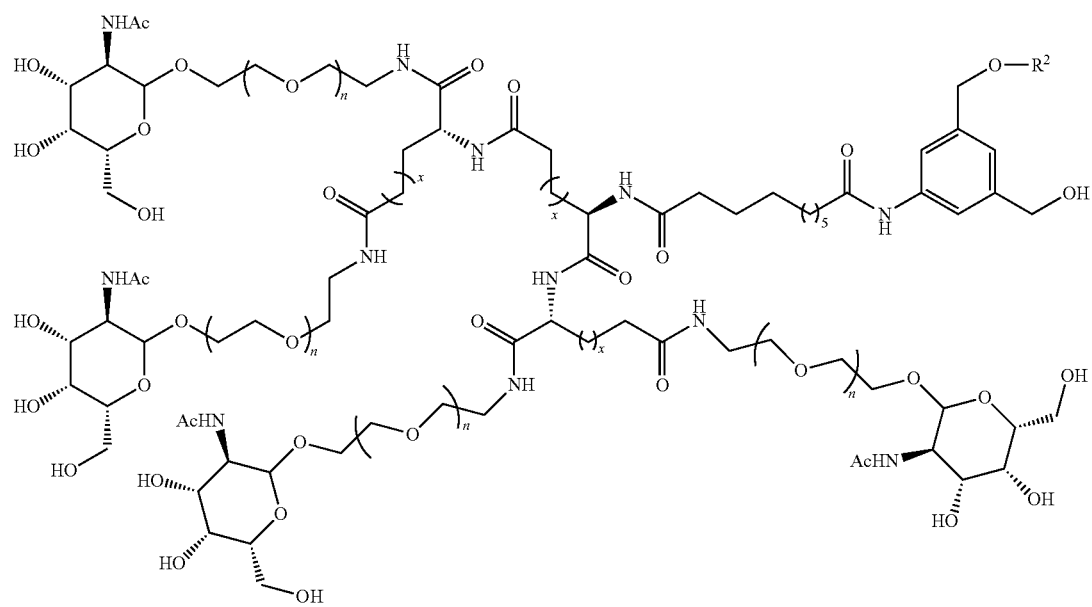

185, n = 3, x = 1
188, n = 4, x = 1

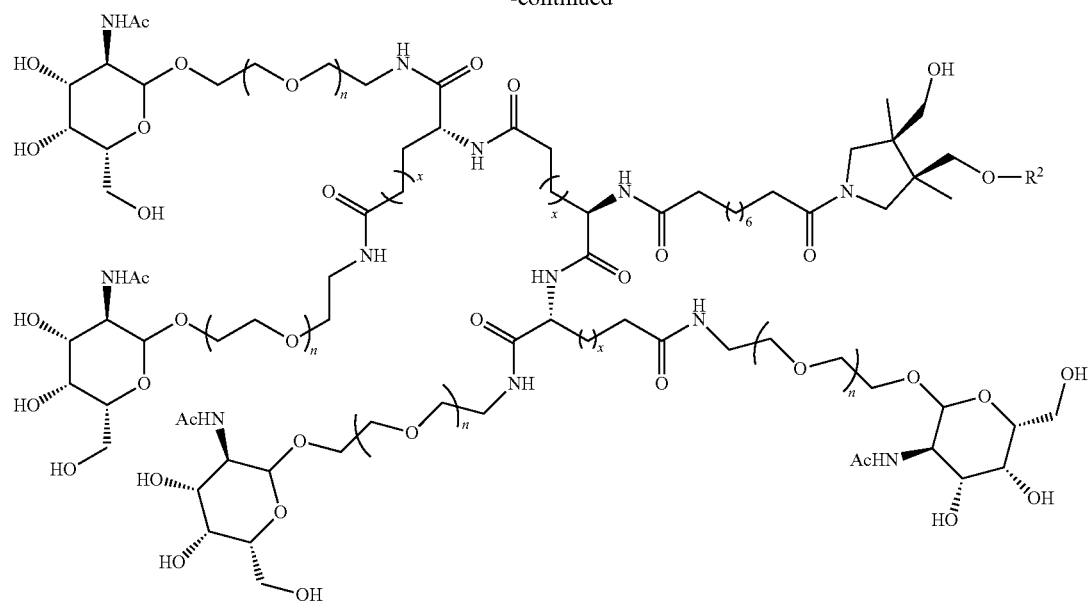
191, n = 2, x = 1
194, n = 3, x = 1
197, n = 4, x = 1
200, n = 3, x = 2
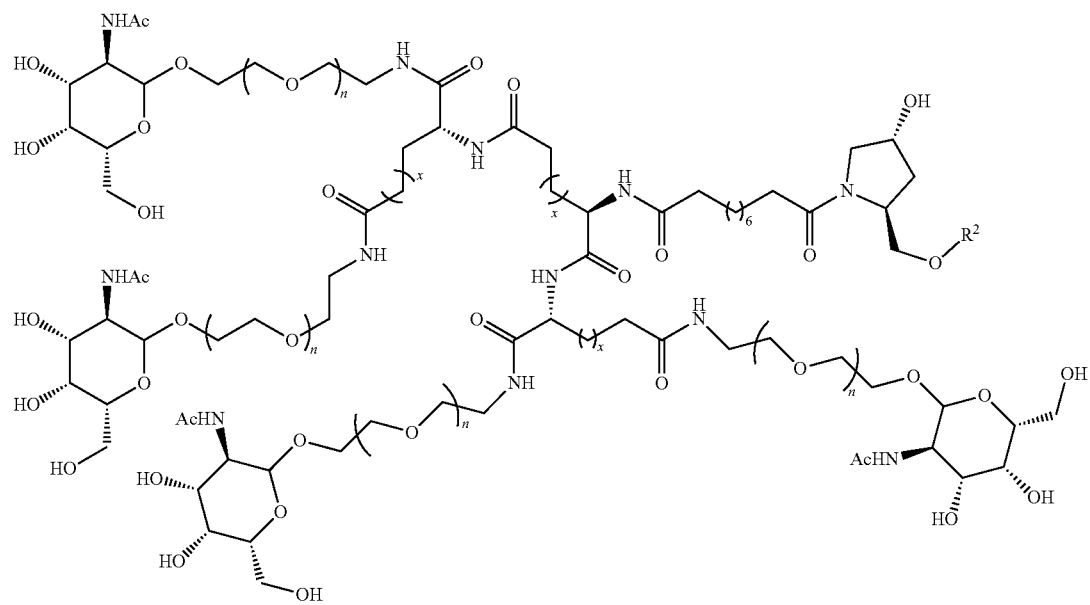
203, n = 3, x = 1
206, n = 4, x = 1

-continued
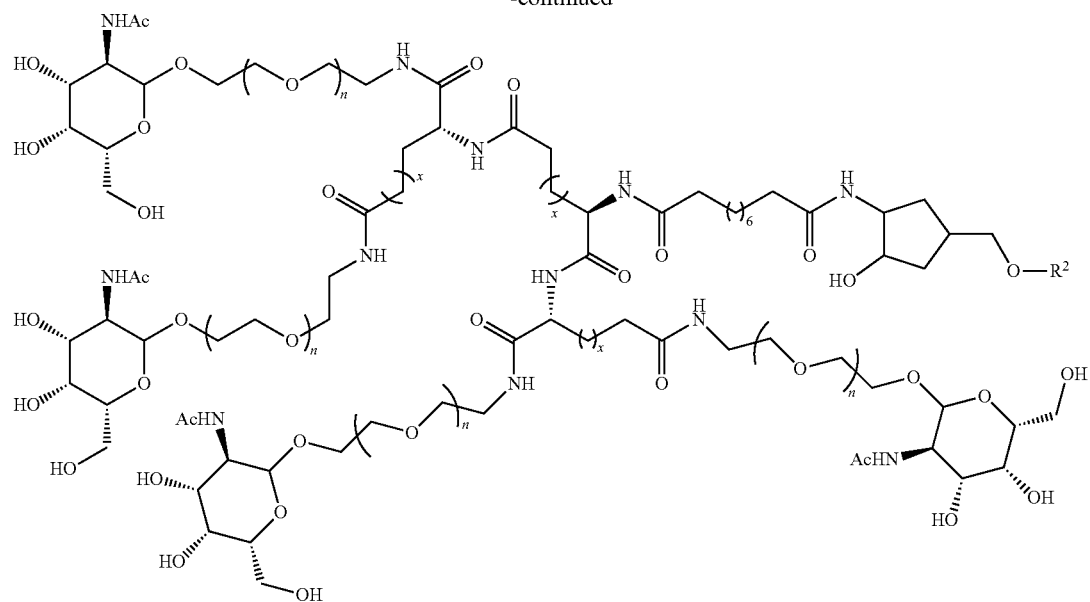
209, n = 3, x = 1
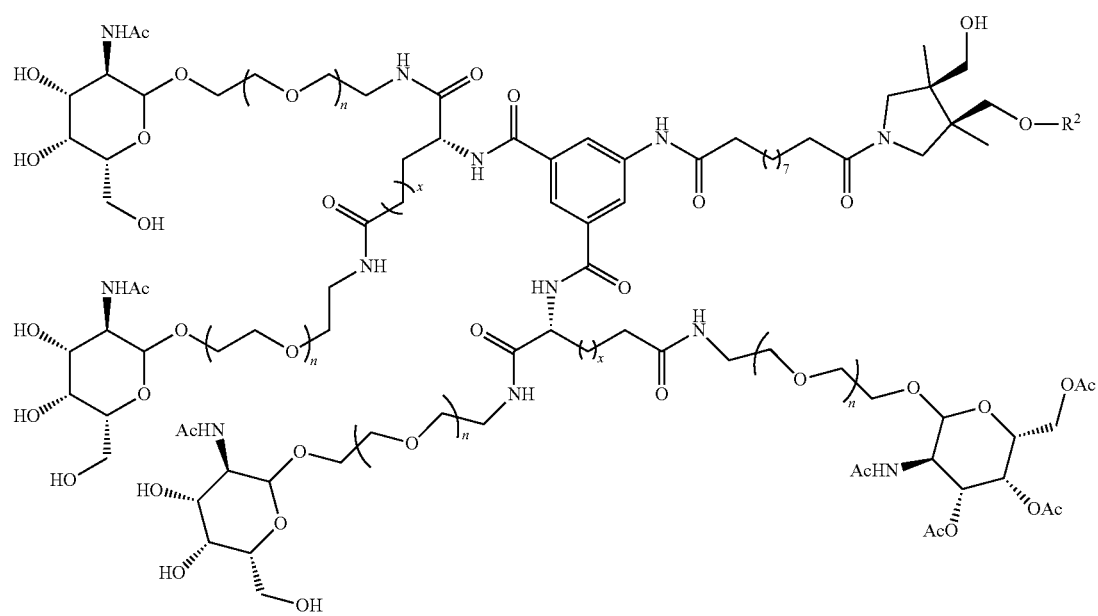
212, n = 3, x = 1
215, n = 4, x = 1

-continued
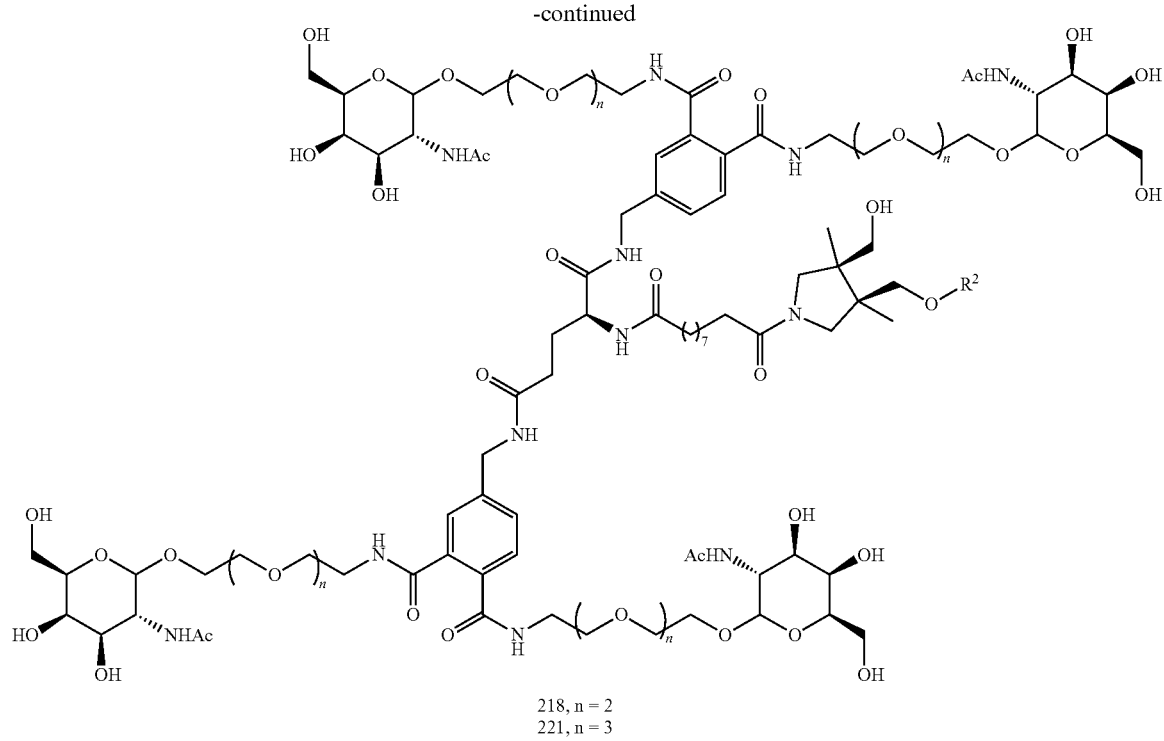
218, n = 2
221, n = 3
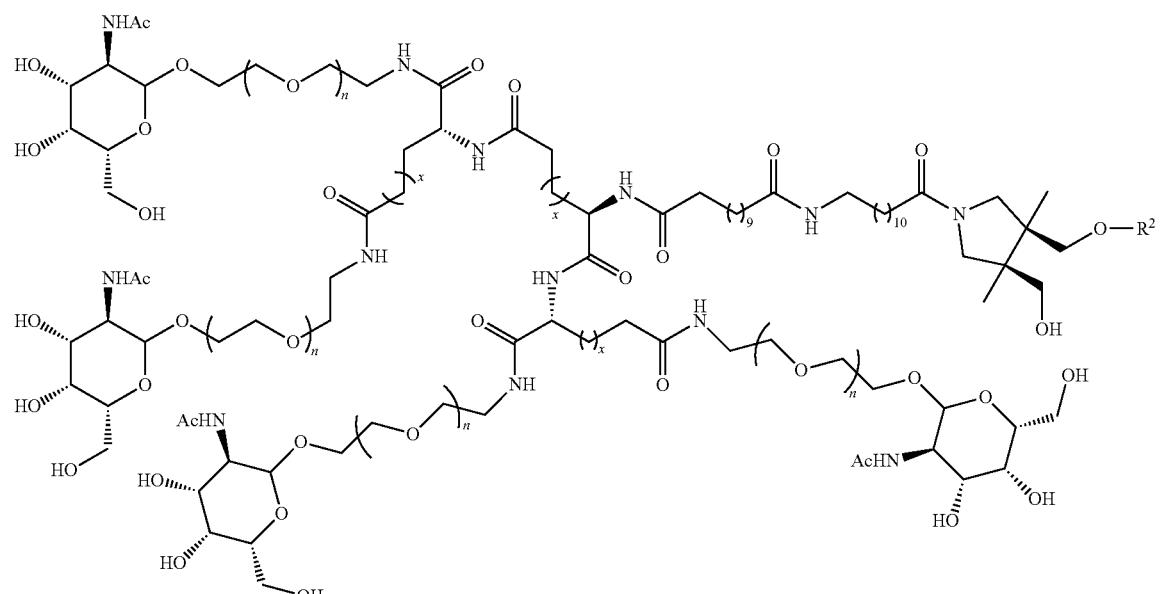
224, n = 3, x = 1
and

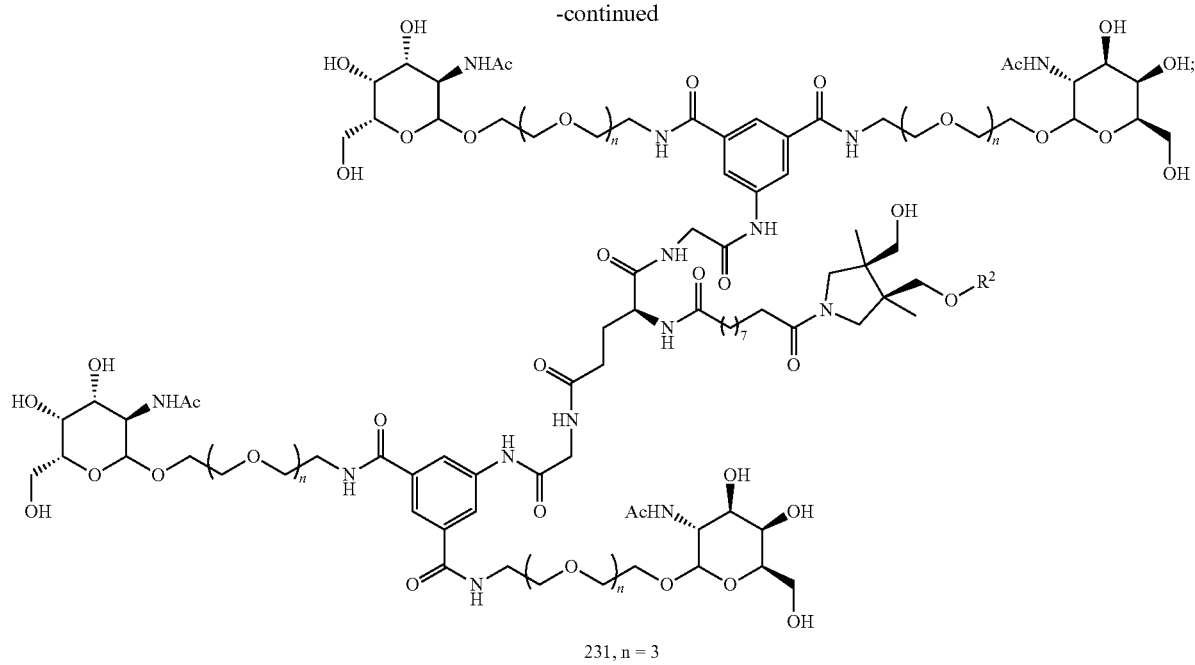
231, n = 3
and pharmaceutically acceptable salts thereof, wherein $R^2$ is a double stranded siRNA molecule selected from the double stranded siRNA molecules of Table 1.
In one embodiment the invention provides a compound of formula
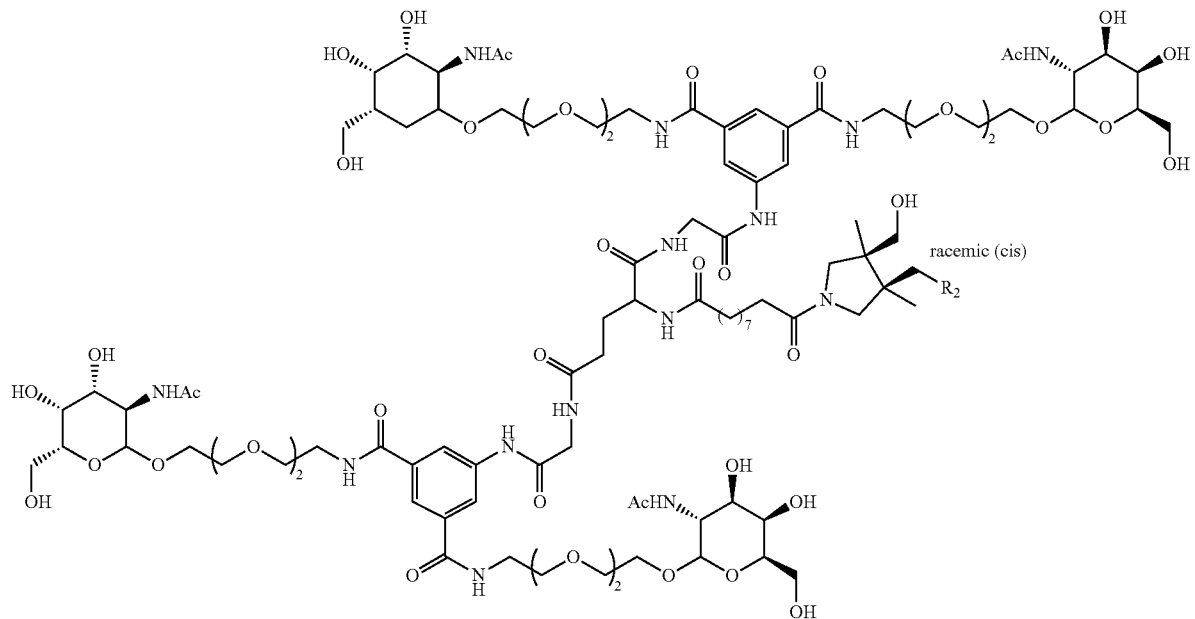
or a salt thereof wherein $R^2$ is a nucleic acid.

In one embodiment the invention provides a compound of formula:

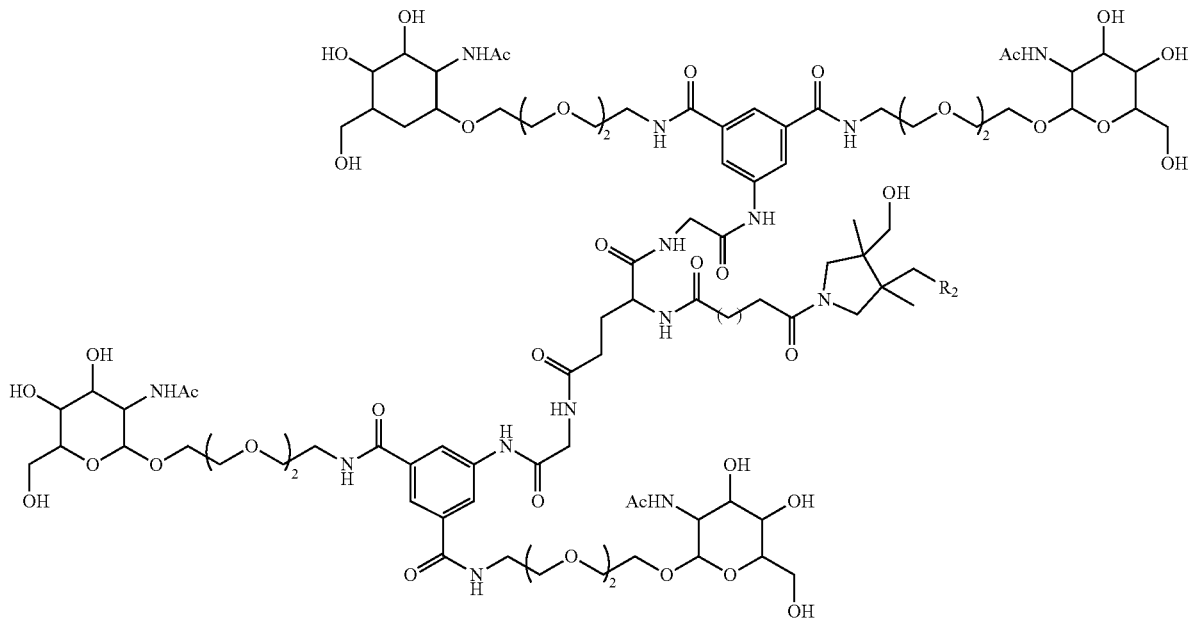

or a salt thereof wherein R is a nucleic acid.

In one embodiment, the nucleic acid molecule (e.g., siRNA) is attached to the reminder of the compound through the oxygen of a phosphate at the 3'-end of the sense strand.

In one embodiment the compound or salt is administered subcutaneously.

When a compound comprises a group of the following formula:

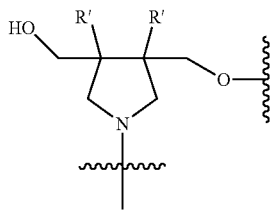

there are four stereoisomers possible on the ring, two cis and two trans. Unless otherwise noted, the compounds of the invention include all four stereoisomers about such a ring. In one embodiment, the two R' groups are in a cis conformation. In one embodiment, the two R' groups are in a trans conformation.

One aspect of the invention is a nucleic acid-lipid particle comprising:
  (a) one or more double stranded siRNA molecules selected from the double stranded siRNA molecules of Table 1;
  (b) a cationic lipid; and
  (c) a non-cationic lipid.

Examples

The present invention will be described in greater detail by way of specific examples.

The following examples are offered for illustrative purposes, and are not intended to limit the invention in any manner. Those of skill in the art will readily recognize a variety of noncritical parameters which can be changed or modified to yield essentially the same results. It is understood that in one embodiment the oligonucleotide is a double stranded siRNA molecule as described in Table 1.

Example 1. Synthesis of Conjugate 1

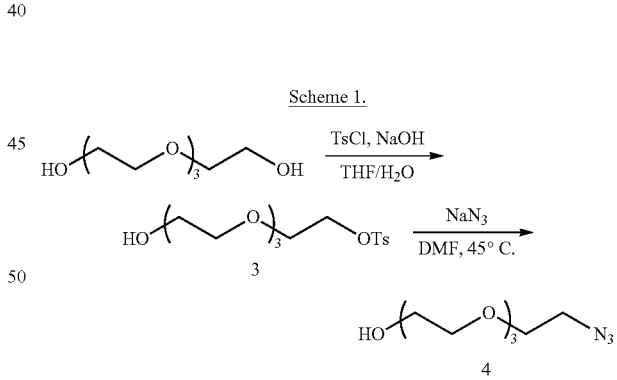

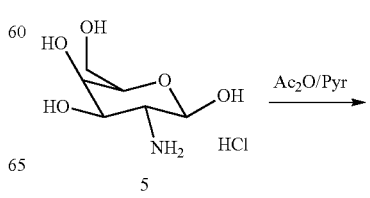

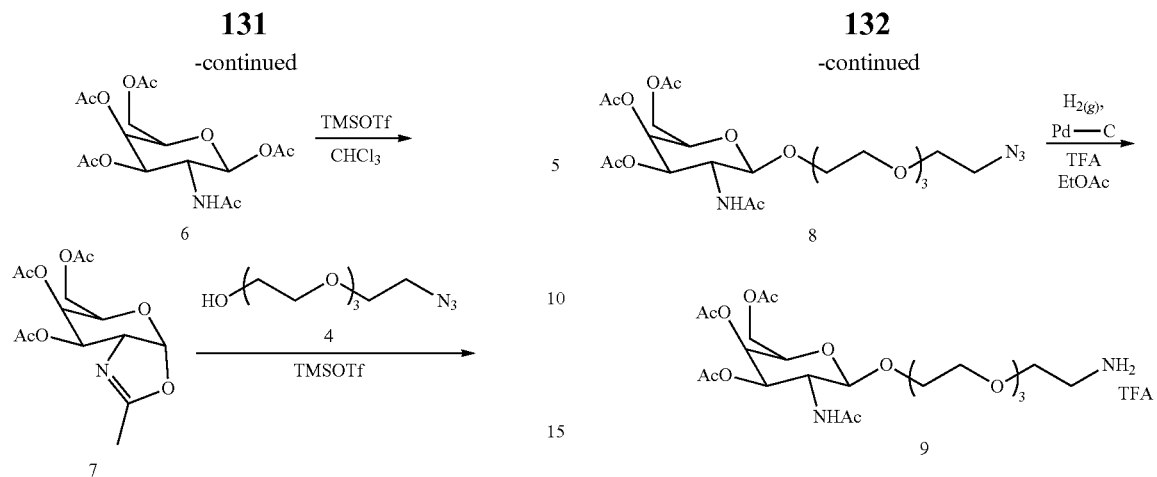
Scheme 3.
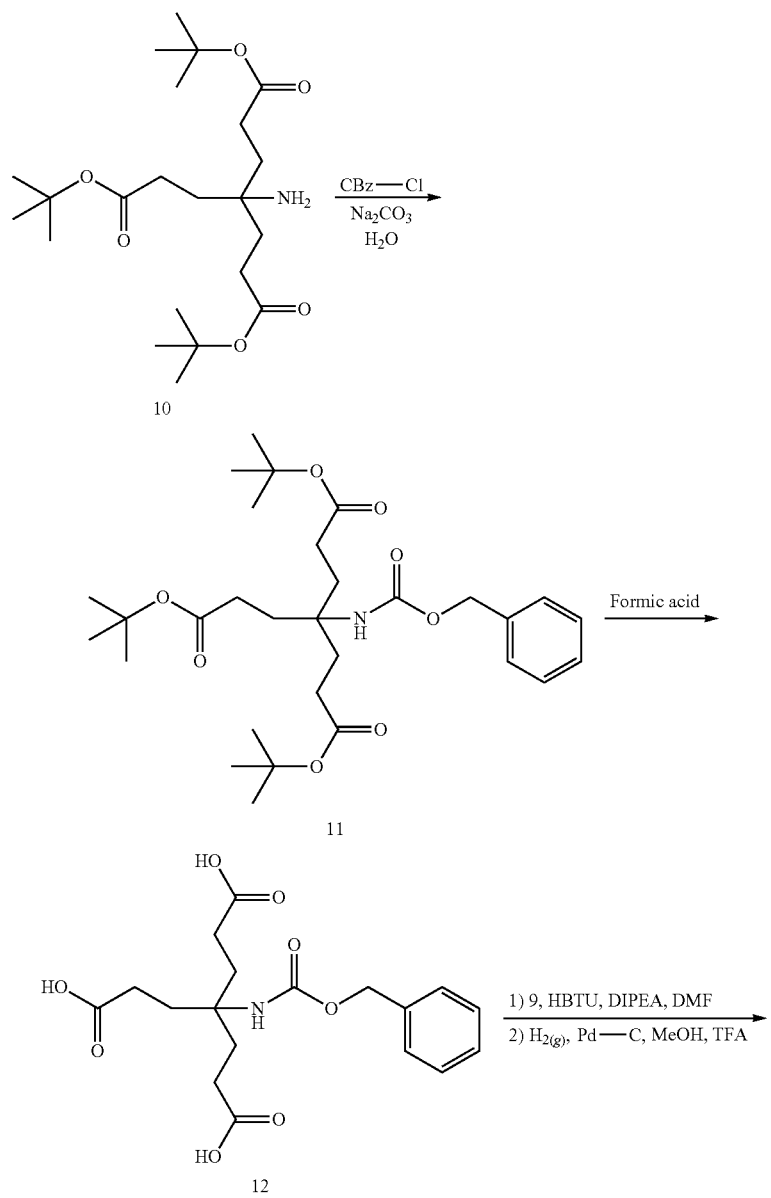

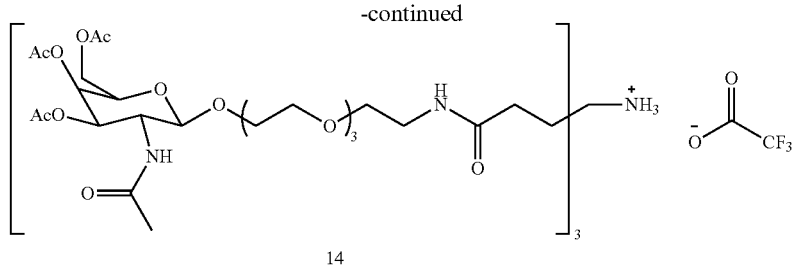
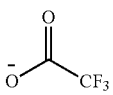
Scheme 4.
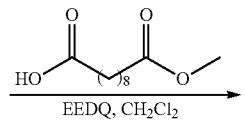
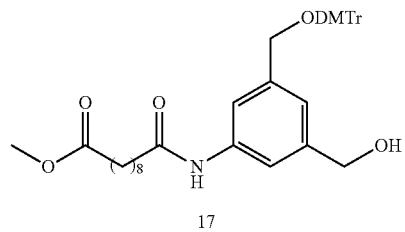
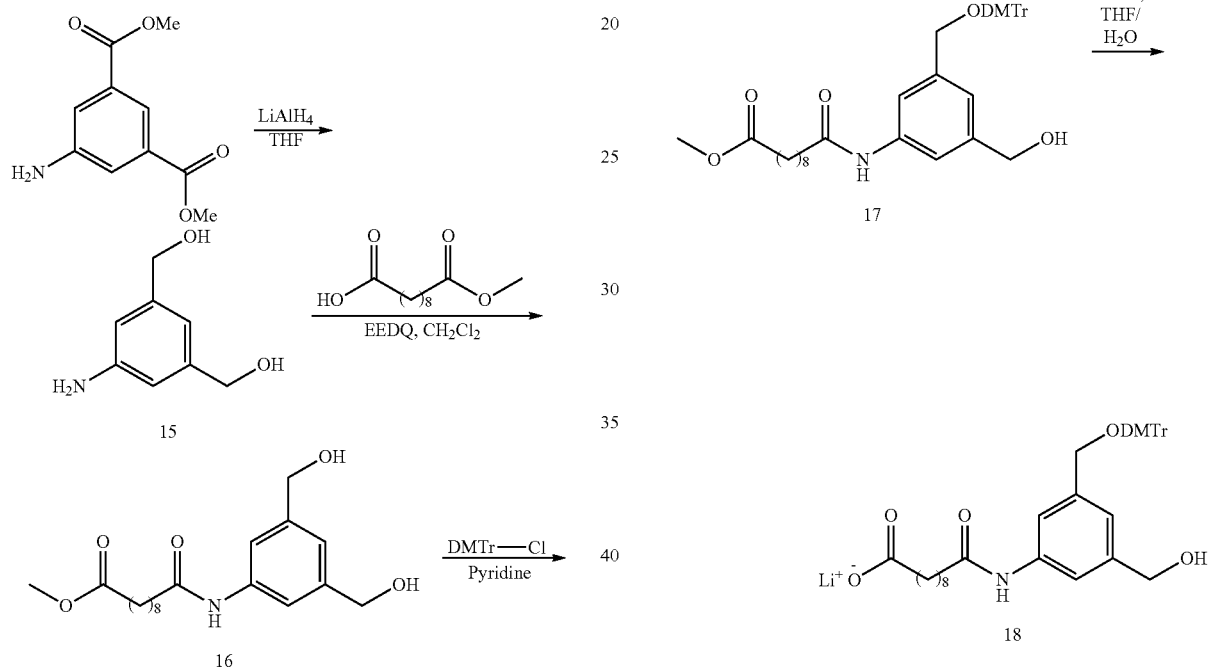
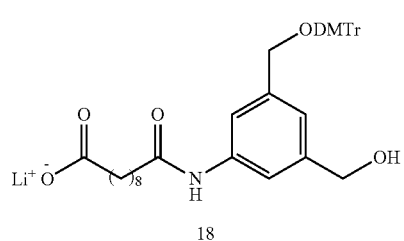
Scheme 5.
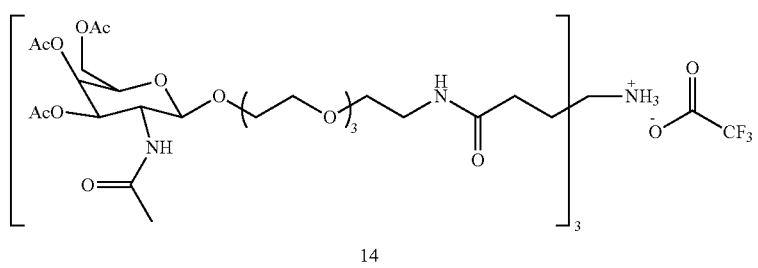

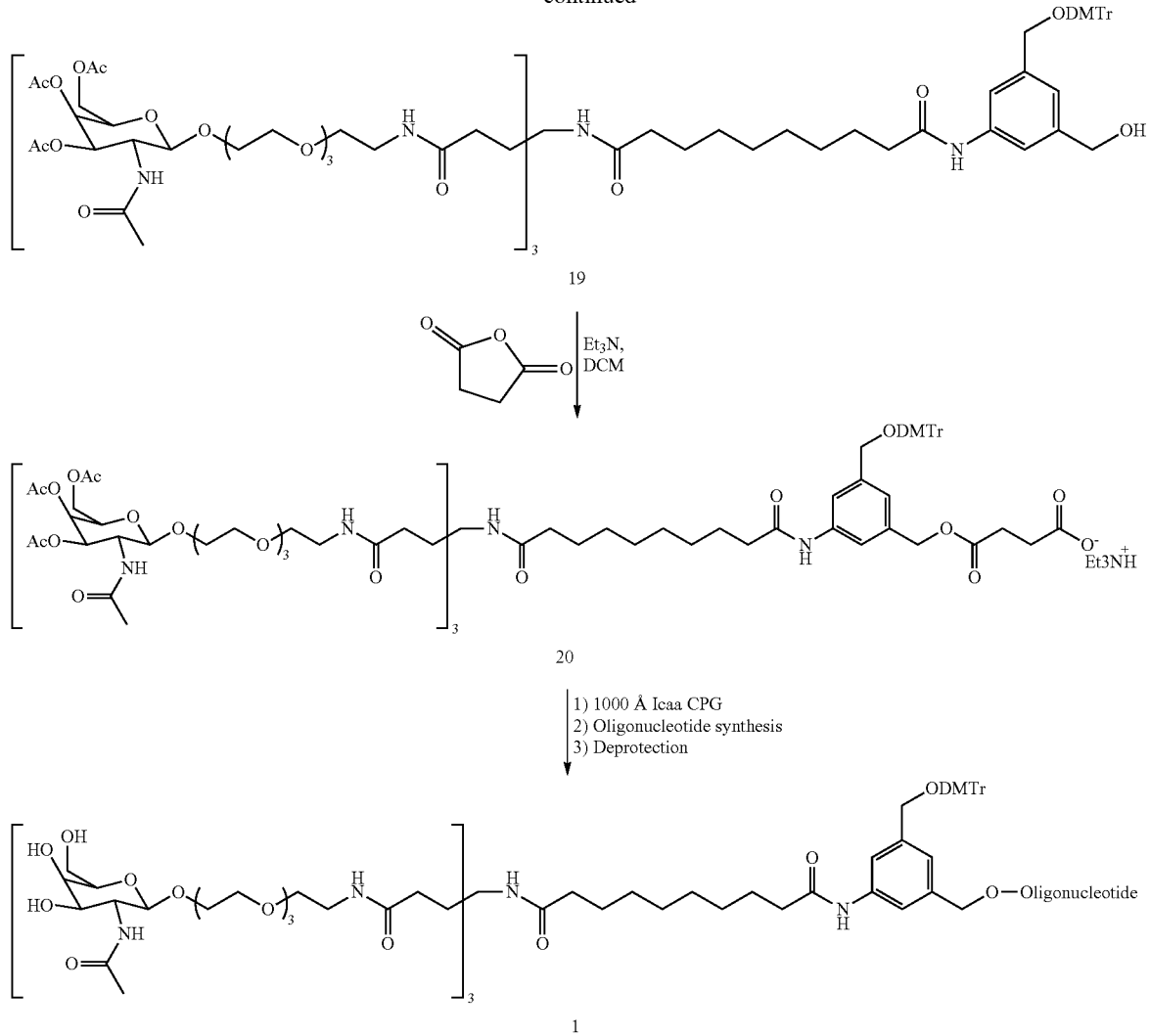

Step 1. Preparation of 2-(2-(2-(2-hydroxyethoxy)ethoxy)ethoxy)ethyl 4-methylbenzenesulfonate 3

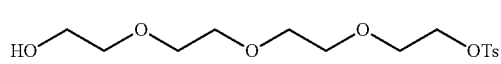 [SMILES: Cc1ccc(S(=O)(=O)OCCOCCOCCOCCO)cc1]

A solution of tetraethylene glycol (934 g, 4.8 mol) in THF (175 mL) and aqueous NaOH (5M, 145 mL) was cooled (0° C.) and treated with p-Toluensulfonyl chloride (91.4 g, 480 mmol) dissolved in THF (605 mL) and then stirred for two hours (0° C.). The reaction mixture was diluted with water (3 L) and extracted (3×500 mL) with $CH_2Cl_2$. The combined extracts were washed with water and brine then dried ($MgSO_4$), filtered and concentrated to afford 2-(2-(2-(2-hydroxyethoxy)ethoxy)ethoxy)ethyl 4-methylbenzenesulfonate 3 (140 g, 84%) as a pale yellow oil. $R_f$ (0.57, 10% MeOH—$CH_2Cl_2$).

Step 2. Preparation of 2-(2-(2-(2-azidoethoxy)ethoxy)ethoxy)ethan-1-ol 4

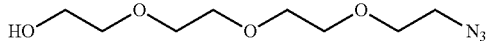

A solution of 3 (140 g, 403 mmol) in DMF (880 mL) was treated with sodium azide (131 g, 2.02 mol) and heated (45° C.) overnight. A majority of the DMF was removed under reduced pressure and the residue was dissolved in $CH_2Cl_2$ (500 mL) and washed (3×500 mL) with brine then dried ($MgSO_4$), filtered and concentrated. The residue was passed through a short bed of silica (5% MeOH—$CH_2Cl_2$) and concentrated to yield 2-(2-(2-(2-azidoethoxy)ethoxy)ethoxy)ethan-1-ol 4 (65 g, 74%) as a yellow oil. $R_f$ (0.56, 10% MeOH—$CH_2Cl_2$).

Step 3. Preparation of peracetylated galactosamine 6

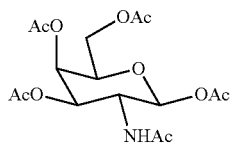 [SMILES: CC(=O)NC1C(OC(C)=O)OC(COC(C)=O)C(OC(C)=O)C1OC(C)=O]

D-Galactosamine hydrochloride 5 (250 g, 1.16 mol) in pyridine (1.5 L) was treated with acetic anhydride (1.25 L, 13.2 mol) over 45 minutes. After stirring overnight the reaction mixture was divided into three 1 L portions. Each 1 L portion was poured into 3 L of ice water and mixed for one hour. After mixing the solids were filtered off, combined, frozen over liquid nitrogen and then lyophilized for five days to yield peracetylated galactosamine 6 (369.4 g, 82%) as a white solid. Rf (0.58, 10% MeOH—CH$_2$Cl$_2$).

Step 4. Preparation of (3aR,5R,6R,7R,7aR)-5-(acetoxymethyl)-2-methyl-3a,6,7,7a-tetrahydro-5H-pyrano[3,2-d]oxazole-6,7-diyl diacetate 7

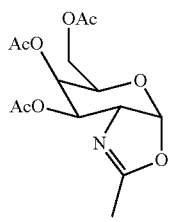 [SMILES: CC(=O)OCC1OC2OC(C)=NC2C(OC(C)=O)C1OC(C)=O]

A solution of per-acetylated galactosamine 6 (8.45 g, 21.7 mmol) in CHCl$_3$ (320 mL) was treated dropwise with TMSOTf (4.32 mL, 23.9 mmol). After stirring (1.5 hr, 40° C.) the reaction was quenched by the addition of triethylamine (5 mL) and concentrated to dryness to afford compound 7 as a pale yellow glass (7.2 g, Quant.). The product was used without further purification. Rf (0.59, 10% MeOH—CH$_2$Cl$_2$).

Step 5. Preparation of (2R,3R,4R,5R,6R)-5-acetamido-2-(acetoxymethyl)-6-(2-(2-(2-(2-azidoethoxy)ethoxy)ethoxy)tetrahydro-2H-pyran-3,4-diyl diacetate 8

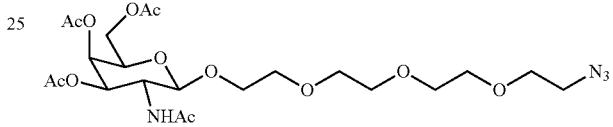

Compound 7 (7.2 g, 21.7 mmol) and 2-(2-(2-(2-azidoethoxy)ethoxy)ethoxy)ethan-1-ol 4 (2.65 g, 15.2 mmol) were azeotroped (3×) from toluene (150 mL) to remove traces of water. The dried material was dissolved in 1,2-dichloroethane (150 mL), cooled (~5° C.) and treated with TMSOTf (784 µL, 4.34 mmol). After stirring overnight the reaction was quenched by the addition of triethylamine (5 mL) and concentrated. The residue was purified by chromatography (1%→5% MeOH—CH$_2$Cl$_2$) to afford 8 (7.12 g, 85%) as a brown oil. Rf (0.3, 10% MeOH—CH$_2$Cl$_2$).

Step 6. Preparation of 2-(2-(2-(2-(((2R,3R,4R,5R,6R)-3-acetamido-4,5-diacetoxy-6-(acetoxymethyl)tetrahydro-2H-pyran-2-yl)oxy)ethoxy)ethoxy)ethoxy)ethan-1-aminium 2,2,2-trifluoroacetate 9

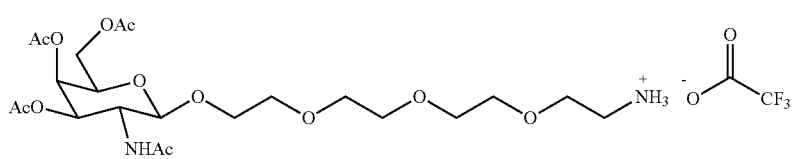

A solution of the azide 8 (7.12 g, 13 mmol) in EtOAc (150 mL) and trifluoroacetic acid (2 mL) was treated with palladium on charcoal (1.5 g, 10% w/w wet basis). The reaction mixture was then purged with hydrogen and stirred vigorously overnight. After purging with nitrogen, the mixture was filtered through Celite, rinsing with MeOH. The filtrate was concentrated and purified via chromatography (5%→10%→20% MeOH—CH$_2$Cl$_2$) to afford 9 (5.8 g, 72%) as a brown oil. Rf (0.34, 15% MeOH—CH$_2$Cl$_2$).

Step 7. Preparation of di-tert-butyl 4-(((benzyloxy)carbonyl)amino)-4-(3-(tert-butoxy)-3-oxopropyl)heptanedioate 11

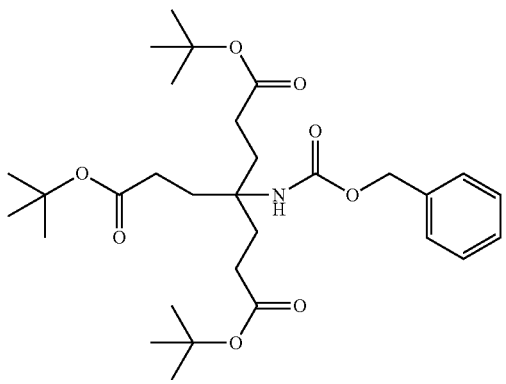 [SMILES: CC(C)(C)OC(=O)CCC(CCC(=O)OC(C)(C)C)(CCC(=O)OC(C)(C)C)NC(=O)OCc1ccccc1]

To a solution of di-tert-butyl 4-amino-4-(3-(tert-butoxy)-3-oxopropyl)heptanedioate 10 (13.5 g, 33 mmol), 25% Na$_2$CO$_3$ (aq (150 mL) and dichloromethane (300 mL) was added slowly benzyl chloroformate (14 mL, 98 mmol). The solution was stirred vigorously overnight (16 h) at room temperature. Upon completion, additional dichloromethane (100 mL) was added and the dichloromethane layer was separated. The aqueous layer was extracted with dichloromethane (2×100 mL). The combine dichloromethane extracts were dried on magnesium sulfate, filtered and concentrated to dryness. The product 11 was isolated as a colorless oil that required no further purification (15.8 g, 88%). Rf (0.7, 1:1 EtOAc-Hexane).

Step 8. Preparation of 4-(((benzyloxy)carbonyl)amino)-4-(2-carboxyethyl)heptanedioic acid 12

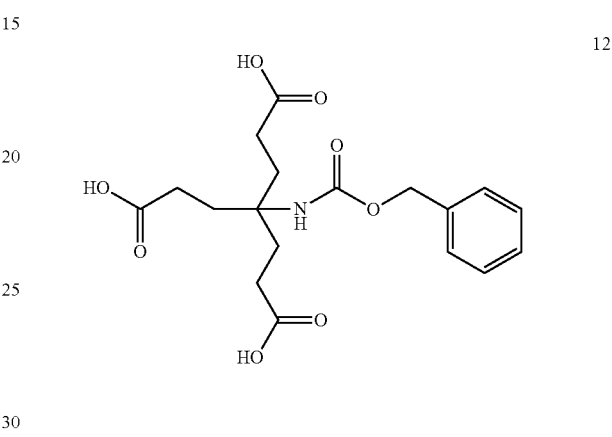

A solution of 11 (15.6 g, 28.8 mmol) in formic acid (50 mL) was stirred at room temperature for 2 hours. The solution was concentrated to dryness and dissolved in ethyl acetate (~25 mL). Upon standing, the product crystallized as a colorless solid. The solid was filtered, washed with ethyl acetate and air dried to afford 12 as a colorless solid (10.2 g, 93%). Rf (0.1, 10% MeOH—CH$_2$Cl$_2$).

Step 9. Preparation of Compound 13

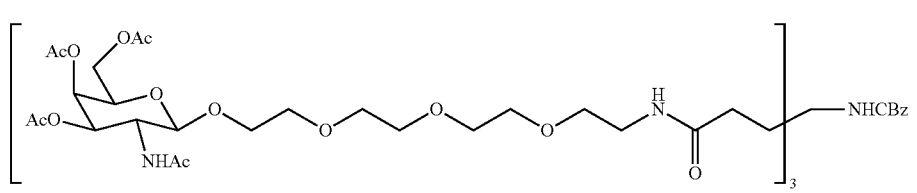

A solution of 12 (793 mg, 2.08 mmol) and 9 (5.8 g, 9.36 mmol) in DMF (50 mL) was treated with BOP (3.67 g, 8.32 mmol) then N,N-diisopropylethylamine (4.31 mL, 25 mmol).

After stirring overnight the mixture was concentrated to dryness and subjected to chromatography (1%→2%→5%→10%→15% MeOH—CH$_2$Cl$_2$) to afford 13 (5.71 g [crude], >100%-contained coupling by-products that did not affect the next step). Rf (0.45, 10% MeOH—CH$_2$Cl$_2$).

Step 10. Preparation of Compound 14

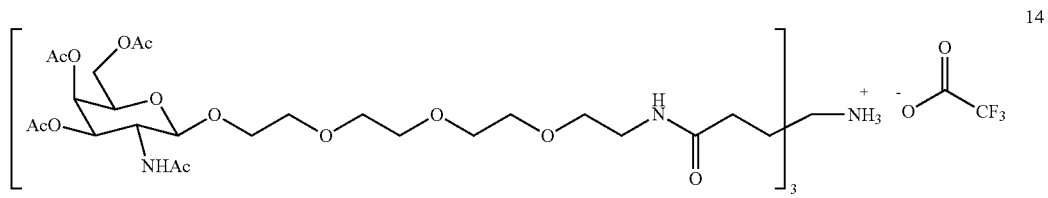

Compound 13 (5.7 g) was dissolved in MeOH (150 mL) and TFA (1.5 mL) and treated with palladium on charcoal (1 g, 10% w/w wet basis). The reaction mixture was then purged with hydrogen and stirred vigorously overnight. After purging with nitrogen, the mixture was filtered through Celite, rinsing with MeOH. The filtrate was concentrated and purified via chromatography (5%→10%→20% MeOH—CH$_2$Cl$_2$) to afford 14 as a brown oil (2.15 g, 56% over two steps). Rf (0.32, 10% MeOH—CH$_2$Cl$_2$).

Step 11. Preparation of (5-amino-1,3-phenylene)dimethanol 15

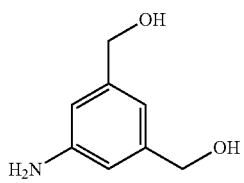

A solution of dimethyl 5-aminoisophthalate (20.0 g, 96 mmol) in THF (350 mL) was added, dropwise, to a refluxing mixture of 3.75 eq LiAlH$_4$ (13.6 g, 358 mmol) in THF (440 mL) over one hour. The mixture was stirred at reflux for a further two hours, then cooled to room temperature and quenched by the careful addition of MeOH (27 mL) then water (40 mL). After stirring the quenched mixture for two hours it was filtered and concentrated to dryness. The residue was recrystallized (2×) from EtOAc to afford 15 as brownish-yellow crystals (10.2 g, 70%).

Step 12. Preparation of methyl 10-((3,5-bis(hydroxymethyl)phenyl)amino)-10-oxodecanoate 16

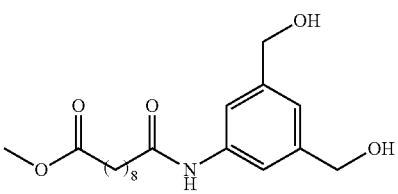

A solution of methyl sebacate (3.8 g, 17 mmol), 15 (2.5 g, 17 mmol) and EEDQ (8.1 g, 33 mmol) in 2:1 dichloromethane/methanol (200 mL) was stirred at room temperature for 2 hours. Upon completion the solution was concentrated to dryness. The solid obtained was triturated with dichloromethane (50 mL) and filtered. The solid was rinsed with cold dichloromethane and air dried to afford 16 as a colorless solid (4.3 g, 72%). Rf (0.33, EtOAc).

Step 13. Preparation of methyl 10-((3-((bis(4-methoxyphenyl)(phenyl)methoxy)methyl)-5-(hydroxymethyl)phenyl)amino)-10-oxodecanoate 17

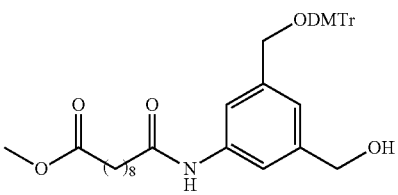

To a solution of 16 (4.3 g, 12 mmol) in pyridine (50 mL) was added 4,4'-(chloro(phenyl)methylene)bis(methoxybenzene) (4.1 g, 12 mmol). The solution was stirred under nitrogen overnight at room temperature. Upon completion the solution was concentrated to dryness and the residue was purified by column chromatography (0.5%→0.75%→1%→1.5% MeOH—CH$_2$Cl$_2$) to afford 17 as a yellow solid (2.9 g, 35%). Rf (0.6, 10% MeOH—CH$_2$Cl$_2$).

Step 14. Preparation of lithium 10-((3-((bis(4-methoxyphenyl)(phenyl)methoxy)methyl)-5-(hydroxymethyl)phenyl)amino)-10-oxodecanoate 18

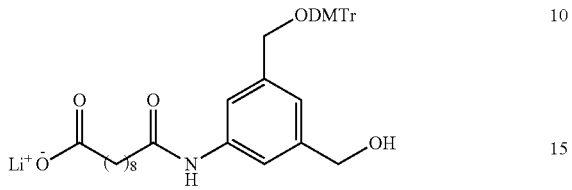

To a solution of 17 (2.9 g, 4.3 mmol) in THF (60 mL) was added water (15 mL) and lithium hydroxide (112 mg, 4.7 mmol). The solution was stirred overnight at room temperature. Upon completion the solution was concentrated to remove the THF. The remaining aqueous solution was flash frozen on liquid nitrogen and lyophilized overnight to afford a colorless solid (2.9 g, quant.). Rf (0.3, 10% MeOH—CH$_2$Cl$_2$).

Step 15. Preparation of Compound 19

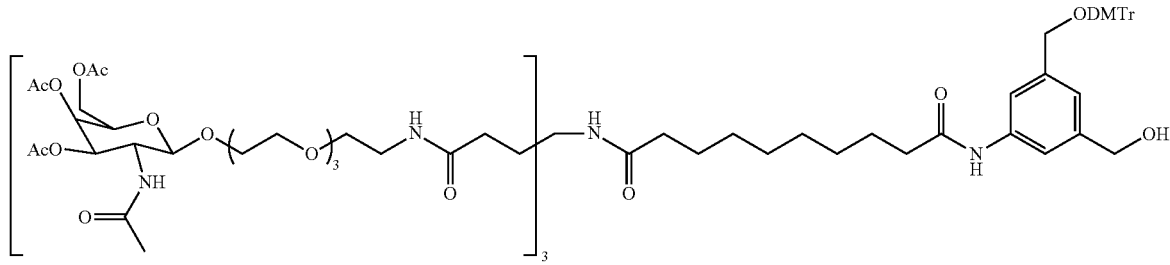

To a solution 14 (454 mg, 0.67 mmol), 18 (1.25 g, 0.67 mmol) and HBTU (381 mg, 1.0 mmol) in anhydrous DMF (25 mL) was added N,N-diisopropylethylamine (0.35 mL, 2.0 mmol). The solution was stirred overnight at room temperature. Upon completion, the solution was poured into ethyl acetate (250 mL) and washed with brine (3×200 mL). The ethyl acetate layer was dried on magnesium sulfate, filtered and concentration to dryness. Purification by column chromatography (5%→7.5%→10%→15% MeOH in CH$_2$Cl$_2$) afforded 19 as a pale orange foam (1.5 g, 94%). Rf (0.25, 10% MeOH—CH$_2$Cl$_2$).

Step 16. Preparation of Compound 20 DT

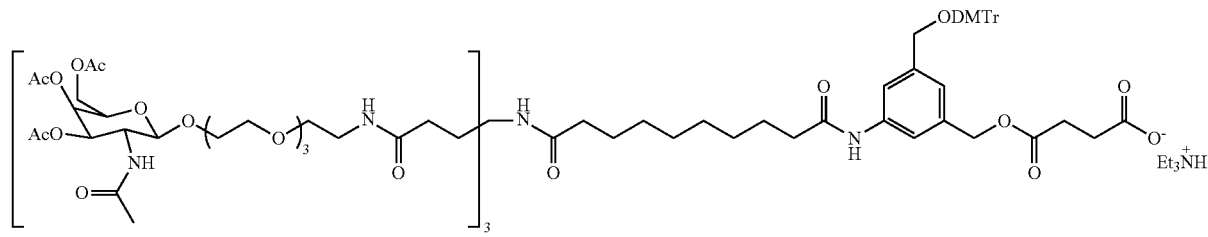

A solution of compound 19 (1.5 g, 0.6 mmol), succinic anhydride (120 mg, 1.2 mmol), DMAP (220 mg, 1.8 mmol) and trimethylamine (250 µL, 1.8 mmol) in anhydrous $CH_2Cl_2$ (50 mL) was stirred overnight at room temperature. Upon completion, the solution was concentrated to dryness and filtered through a short plug of silica (100% $CH_2Cl_2 \rightarrow 15\%$ MeOH in $CH_2Cl_2$) to afford the product 20 as a light beige foam (1.1 g, 70%). Mass m/z (ES-TOF MS) 727.7 [M+3H-DMTr]$^+$, 1091.1 [M+2H-DMTr]. $^1$H NMR (400 MHz, $CDCl_3$) δ 8.92 (br s, 1H), 7.78 (s, 1H), 7.49-7.47 (m, 3H), 7.41 (br s, 1H), 7.38-7.34 (m, 5H), 7.32-7.26 (m, 4H), 7.24-7.08 (br s, 3H), 7.08 (s, 1H), 6.90-6.80 (m, 7H), 5.31 (d, 3H, J=2.7 Hz), 5.12 (s, 2H), 5.06 (dd, 3H, J=11.2, 3.2 Hz), 4.78 (d, 3H, J=8.5 Hz), 4.24-4.08 (m, 12H), 3.95-3.88 (m, 7H), 3.85-3.76 (m, 4H), 3.78 (s, 6H), 3.68-3.56 (m, 34H), 3.54-3.44 (m, 8H), 3.41-3.33 (m, 6H), 2.70-2.60 (m, 4H), 2.52-2.30 (m, 30H), 2.24-2.16 (m, 8H), 2.14 (s, 9H), 2.04 (s, 9H), 2.02-1.96 (m, 6H), 1.98 (s, 9H), 1.96 (s, 9H), 1.74-1.52 (m, 4H), 1.36-1.24 (m, 12H).

Step 17. Preparation of Conjugate 1

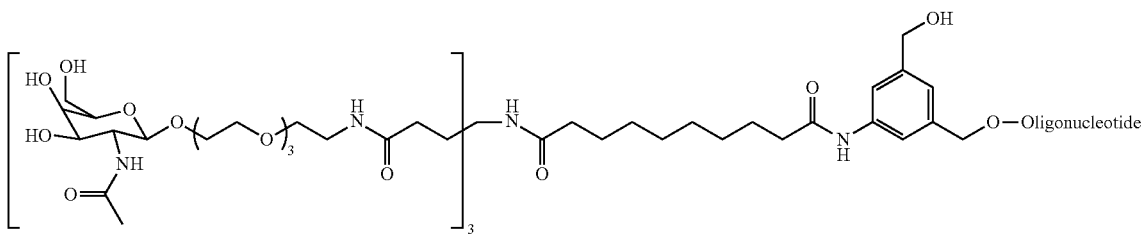

The succinate 20 was loaded onto 1000 Å LCAA (long chain aminoalkyl) CPG (control pore glass) using standard amide coupling chemistry. A solution of diisopropylcarbodiimide (52.6 µmol), N-hydroxy succinimide (0.3 mg, 2.6 µmol) and pyridine (10 µL) in anhydrous acetonitrile (0.3 mL) was added to 20 (20.6 mg, 8 µmol) in anhydrous dichloromethane (0.2 mL). This mixture was added to LCAA CPG (183 mg). The suspension was gently mixed overnight at room temperature. Upon disappearance of 20 (HPLC), the reaction mixture was filtered and the CPG was washed with 1 mL of each dichloromethane, acetonitrile, a solution of 5% acetic anhydride/5% N-methylimidazole/5% pyridine in THF, then THF, acetonitrile and dichloromethane. The CPG was then dried overnight under high vacuum. Loading was determined by standard DMTr assay by UV/Vis (504 nm) to be 25 µmol/g. The resulting GalNAc loaded CPG solid support was employed in automated oligonucleotide synthesis using standard procedures. Nucleotide deprotection followed by removal from the solid support (with concurrent galactosamine acetate deprotection) afforded the GalNAc-oligonucleotide conjugate 1 as a representative example.

Example 2: Synthesis of Conjugate 34

Scheme 6.

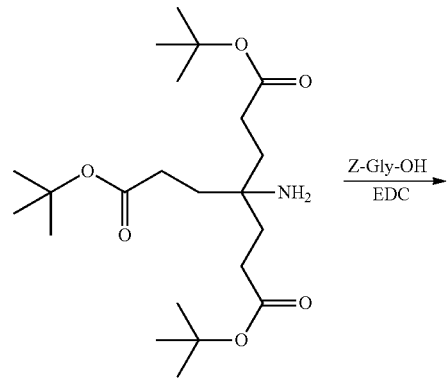

-continued
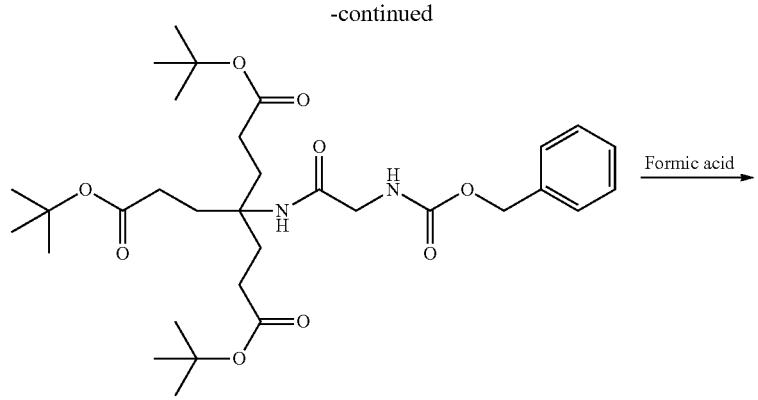
21
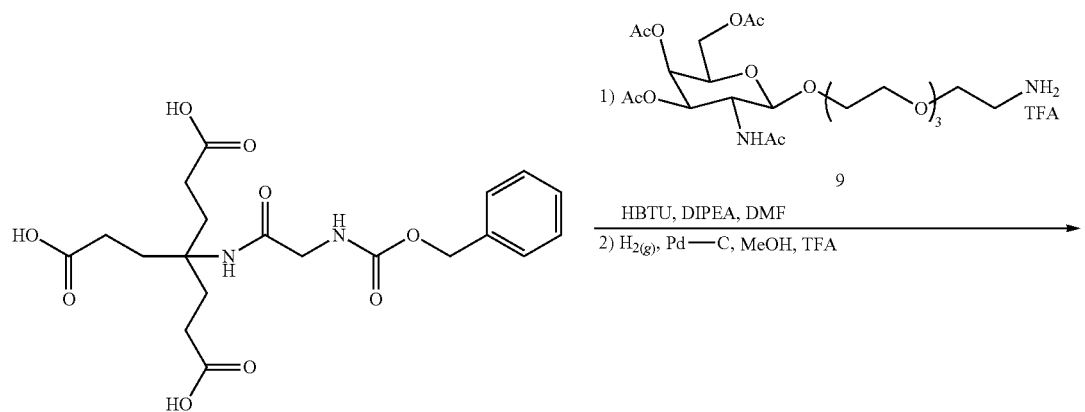
22
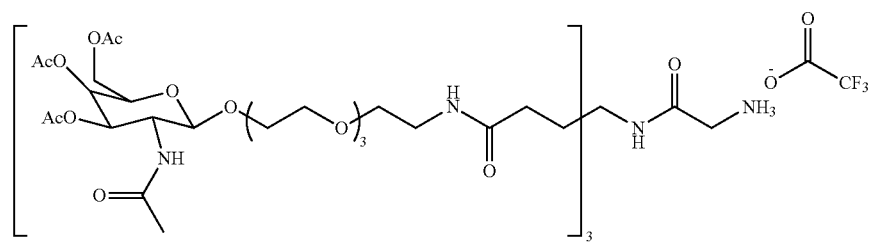
24

Scheme 7.
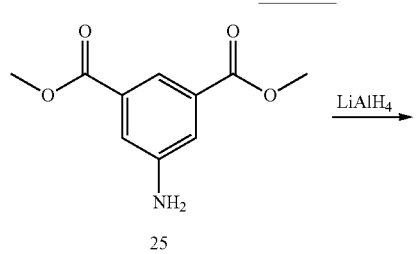
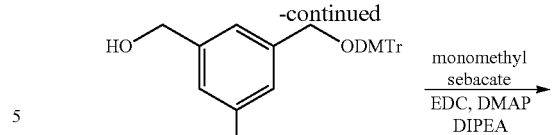
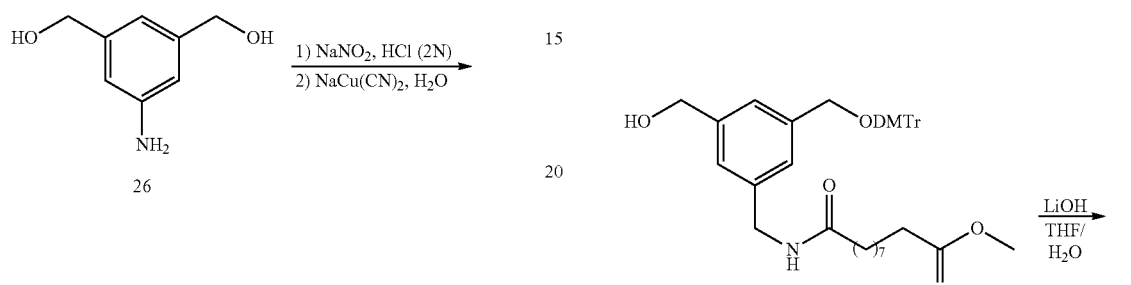
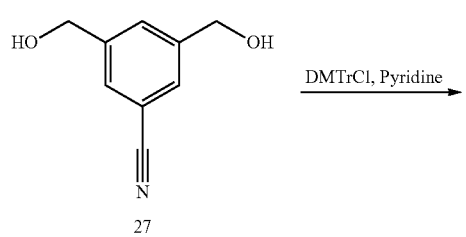
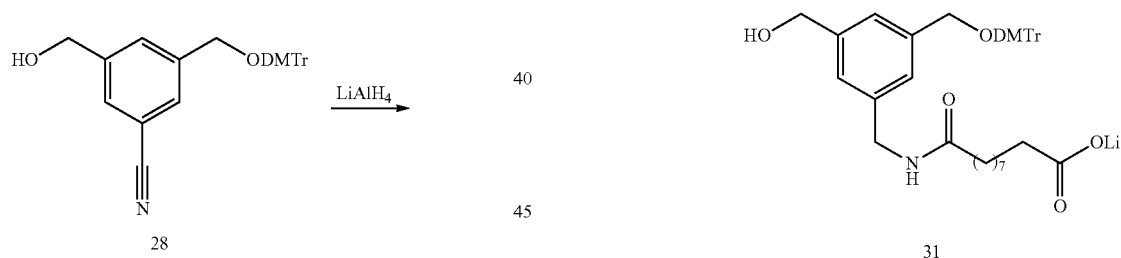
Scheme 8.
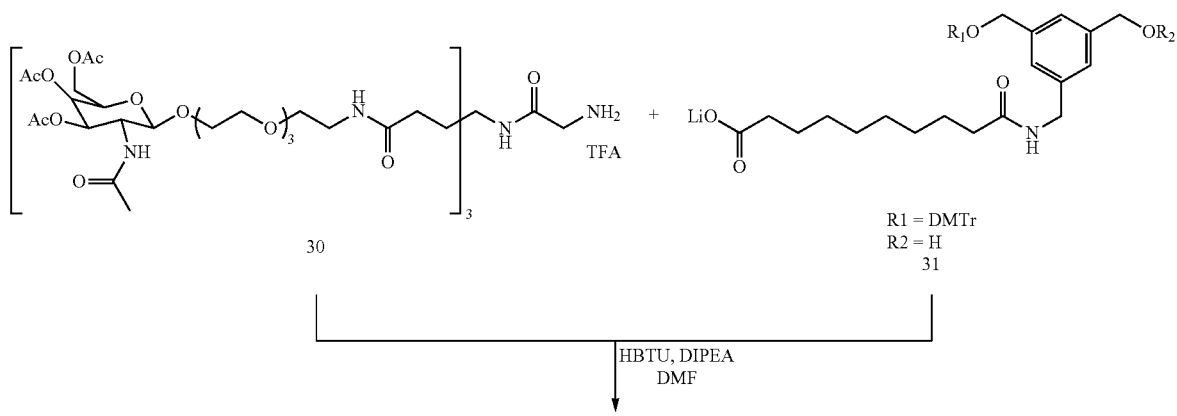

-continued

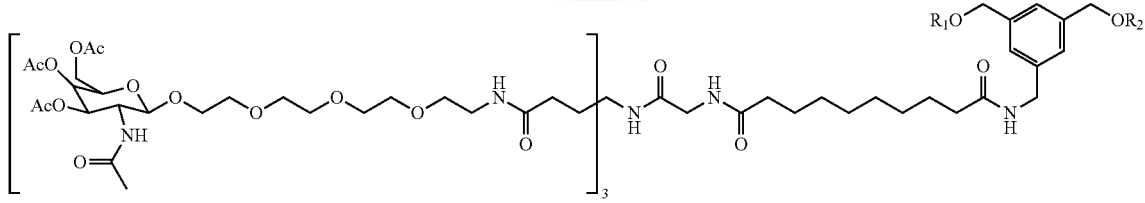

- 32, R₁ = DMTr
  R₂ = H

- 33, R₁ = DMTr
  R₂ = 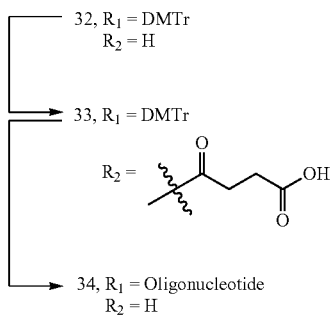

- 34, R₁ = Oligonucleotide
  R₂ = H

Step 1. Preparation of di-tert-butyl 4-(2-(((benzyloxy)carbonyl)amino)acetamido)-4-(3-(tert-butoxy)-3-oxopropyl)heptanedioate 21

A solution of di-tert-butyl 4-amino-4-(3-(tert-butoxy)-3-oxopropyl)heptanedioate (25 g, 60 mmol) and Z-glycine (18.9 g, 90.2 mmol) in CH₂Cl₂ (300 mL) was treated successively with EDC (23 g, 120 mmol), Diisopropylethylamine (32 mL, 180 mmol) and DMAP (Cat. 17 mg). After stirring (16 h) the reaction mixture was poured into NaHCO₃ (Sat. Aq.), extracted with CH₂Cl₂, washed with brine, dried (MgSO₄), filtered and concentrated to afford di-tert-butyl 4-(2-(((benzyloxy)carbonyl)amino)acetamido)-4-(3-(tert-butoxy)-3-oxopropyl)heptanedioate 21 as an amorphous solid and was used without further processing (36 g, quant.). Rf (0.85, 10% MeOH—CH₂Cl₂).

Step 2. Preparation of 4-(2-(((benzyloxy)carbonyl)amino)acetamido)-4-(2-carboxyethyl)heptanedioic acid 22

A solution of di-tert-butyl 4-(2-(((benzyloxy)carbonyl)amino)acetamido)-4-(3-(tert-butoxy)-3-oxopropyl)heptanedioate 21 (59.3 mmol, 36 g) was stirred in neat formic acid (150 mL) for 72 hours. Upon completion, the formic acid was removed under reduced pressure and the crude solid was dried overnight on high-vacuum to yield 22 as a colorless solid (15.9 g, 61%). Rf (0.15, 10% MeOH—CH₂Cl₂).

Step 3. Preparation of Compound 23

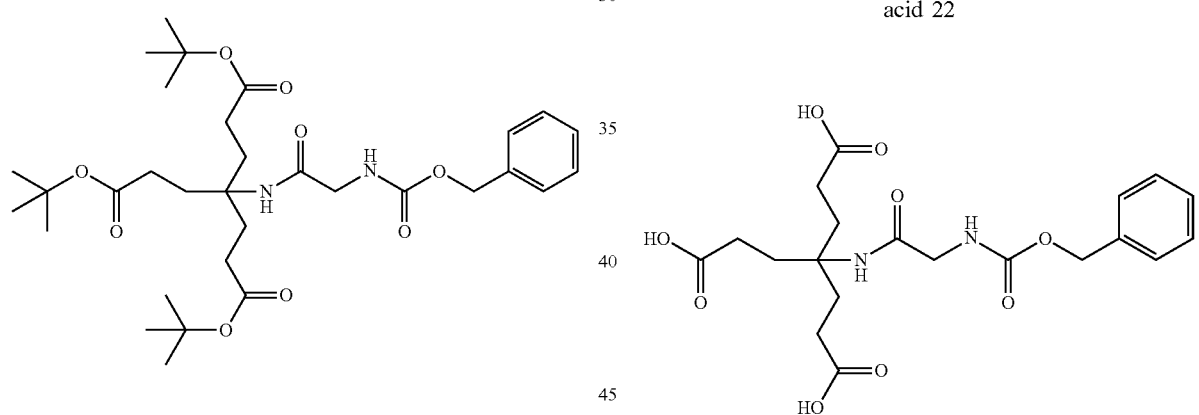

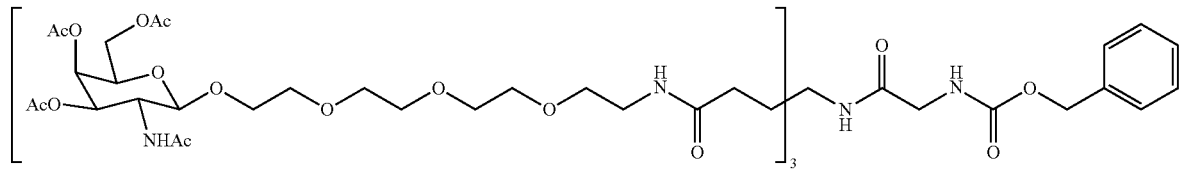

A solution of 22 (6.2 g, 14.1 mmol) and 2-(2-(2-(2-(((2R,3R,4R,5R,6R)-3-acetamido-4,5-diacetoxy-6-(acetoxymethyl)tetrahydro-2H-pyran-2-yl)oxy)ethoxy)ethoxy)ethoxy)ethan-1-aminium 2,2,2-trifluoroacetate (35 g, 56.5 mmol) in DMF (250 mL) was treated with BOP (25 g, 56.5 mmol) then N,N-diisopropylethylamine (29 mL, 170 mmol). After stirring overnight the mixture was concentrated to dryness and subjected to chromatography (100% CH₂Cl₂ to 15% MeOH—CH₂Cl₂) to afford compound 23 (24.6 g, 89%). Rf (0.55, 15% MeOH—CH₂Cl₂).

Step 4. Preparation of Compound 24

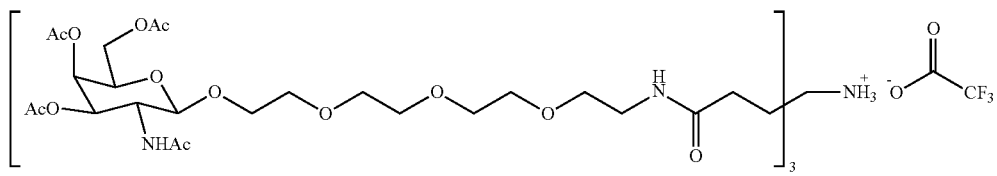

Compound 23 (24.6 g) was dissolved in MeOH (200 mL) and TFA (1.5 mL) and purged with nitrogen. Palladium on charcoal (1 g, 10% w/w wet basis) was added and then the reaction mixture was purged with hydrogen and stirred vigorously overnight. Upon completion, the reaction was purged with nitrogen, filtered through Celite and rinsed with MeOH. The filtrate was concentrated and purified by column chromatography on silica gel 60 (gradient: 5%→10%→20% MeOH—CH₂Cl₂) to afford 24 as a pale brown viscous oil (23 g).

Rf (0.32, 10% MeOH—CH₂Cl₂).

Step 5. Preparation of (5-amino-1,3-phenylene)dimethanol 26

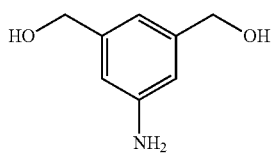

A suspension of lithium aluminum hydride (13.6 g, 358 mmol) in anhydrous tetrahydrofuran (450 mL) was brought to reflux under a nitrogen atmosphere and treated, dropwise, with a solution of dimethyl-5-aminoisophthalate 25 (20 g, 96 mmol) in anhydrous tetrahydrofuran (350 mL). After the addition was complete the mixture was heated to reflux for an additional 2 hours. Upon completion, the solution was cooled to room temperature and quenched by the slow addition of MeOH (27 mL) then water (40 mL). After stirring for 2 hours the mixture was filtered, concentrated and recrystallized from EtOAc to yield (5-amino-1,3-phenylene)dimethanol 26 as off-white crystals (10.2 g, 70%). Rf 0.5 (15% MeOH—CH₂Cl₂).

Step 6. Preparation of 3,5-bis(hydroxymethyl)benzonitrile 27

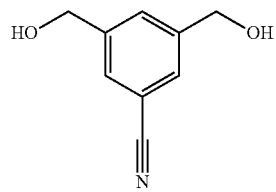 [SMILES: N#Cc1cc(CO)cc(CO)c1]

A solution of 26 (5 g, 33 mmol) in 2N hydrochloric acid (100 mL) was cooled to 0° C. and treated with a cold solution of sodium nitrite (3.53 g, 36 mmol) in water (50 mL). The reaction mixture was maintained at a temperature ≤5° C. for 30 min then treated with a solution of copper(I) cyanide (3.19 g, 35.6 mmol) and sodium cyanide (3.53 g, 72 mmol) in water (50 mL) in a single portion. After stirring overnight at room temperature the mixture was filtered, extracted with dichloromethane (3×100 mL), concentrated and used without further purification. The diol, 3,5-bis(hydroxymethyl)benzonitrile 27 was obtained as a yellow solid (2.19 g, 41%). Rf 0.75 (15% MeOH—CH₂Cl₂).

Step 7. Preparation of 3-((bis(4-methoxyphenyl)(phenyl)methoxy)methyl)-5-(hydroxymethyl)benzonitrile 28

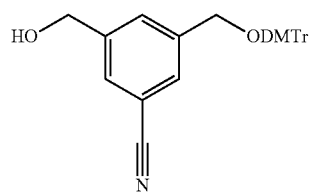

A solution of 3,5-bis(hydroxymethyl)benzonitrile 27 (538 mg, 3.3 mmol) in pyridine (14 mL) was treated with 4,4'-Dimethoxytrityl chloride (1.17 g, 3.46 mmol) and stirred overnight at room temperature. Once complete, the mixture was concentrated and dispersed in diethyl ether (25 mL), filtered and concentrated. The crude product was purified by column chromatography of silica gel 60 (gradient: 10% to 50% EtOAc-Hexane) to yield the 28 as a yellow solid (725 mg, 47%). Rf 0.5 (1:1 EtOAc-hexane).

Step 8. Preparation of (3-(aminomethyl)-5-((bis(4-methoxyphenyl)(phenyl)methoxy)methyl)phenyl) methanol 29

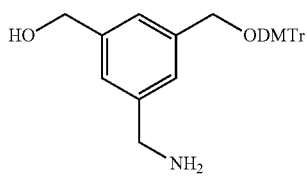

A solution of the 28 (100 mg, 0.22 mmol) in methyl tetrahydrofuran (5 mL) was cooled to 0° C. and treated slowly with lithium aluminum hydride (0.64 mmol=0.28 mL of a 2.3M solution in MeTHF). After stirring for one hour the reaction was quenched by the addition of methanol (1 mL) then water (0.3 mL) and stirred for 30 min. The mixture was filtered and concentrated, to yield (3-(aminomethyl)-5-((bis(4-methoxyphenyl)(phenyl)methoxy)methyl)phenyl) methanol 29 (78 mg, 77%). Rf 0.15 (10% MeOH—$CH_2Cl_2$).

Step 9. Preparation of methyl 10-((3-((bis(4-methoxyphenyl)(phenyl)methoxy)methyl)-5-(hydroxymethyl)benzyl)amino)-10-oxodecanoate 30

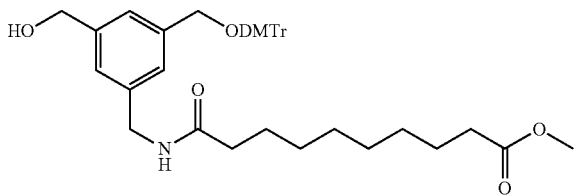

A solution of (3-(aminomethyl)-5-((bis(4-methoxyphenyl)(phenyl)methoxy)-methyl)phenyl)methanol 29 (78 mg, 0.17 mmol) and monomethyl sebacate (38 mg, 0.17 mmol) in dichloromethane (5 mL) were treated successively with EDC (48 mg, 0.25 mmol), DMAP (cat., 5 mg) and diisopropylethylamine (57 µL, 0.33 mmol). After stirring (3.5 hr) the reaction mixture was poured into saturated sodium bicarbonate solution (50 mL). The sodium bicarbonate solution was extracted with dichloromethane (3×50 mL), washed with brine (50 mL), dried on magnesium sulfate, filtered and concentrated to dryness. The crude material was purified by column chromatography on silica gel 60 (gradient: 2% to 5% MeOH—$CH_2Cl_2$) to afford methyl 10-((3-((bis(4-methoxyphenyl)(phenyl)methoxy)methyl)-5-(hydroxymethyl)benzyl)amino)-10-oxodecanoate 30 as a yellow oil (57 mg, 53%). Rf 0.45 (10% MeOH—$CH_2Cl_2$).

Step 10. Preparation of lithium 10-((3-((bis(4-methoxyphenyl)(phenyl)methoxy)methyl)-5-(hydroxymethyl)benzyl)amino)-10-oxodecanoate 31

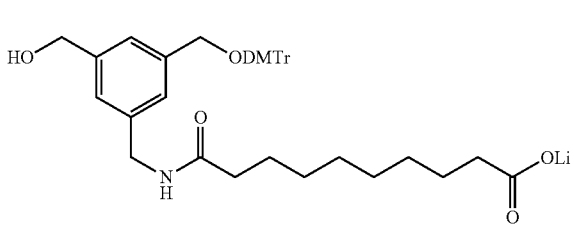

Compound 30 (188 mg, 0.28 mmol) was dissolved in tetrahydrofuran (5 mL) and treated with a solution of LiOH (7 mg, 0.30 mmol) in water (1 mL). Upon completion, the tetrahydrofuran was removed in vacuo and the remaining aqueous mixture was frozen and lyophilized to afford lithium 10-((3-((bis(4-methoxyphenyl)(phenyl)methoxy)methyl)-5-(hydroxymethyl)benzyl)amino)-10-oxodecanoate 31 as a colorless solid (180 mg, 99%). Rf 0.45 (10% MeOH—$CH_2Cl_2$).

Step 11. Preparation of Compounds 32, 33, and 34

Compounds 32, 33 and 34 were prepared according to same procedure used to synthesize compounds 19, 20, and 1 respectfully.

Example 3. Synthesis of Conjugate 36

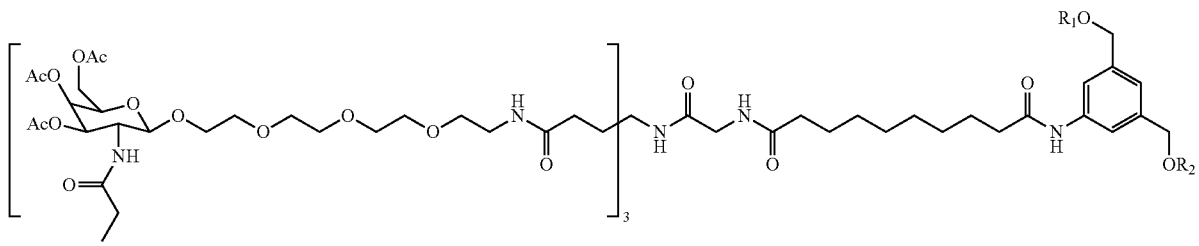

36, $R_1$ = Oligonucleotide
$R_2$ = H

Step 1. Preparation of Conjugate 36
Conjugate 36 was prepared using identical procedures as used to synthesize compound 34 and all corresponding intermediates. The only exception being the synthesis of compound 6 where propanoic anhydride was used in place of acetic anhydride.
Example 4. Synthesis of Conjugate 42
Scheme 9.
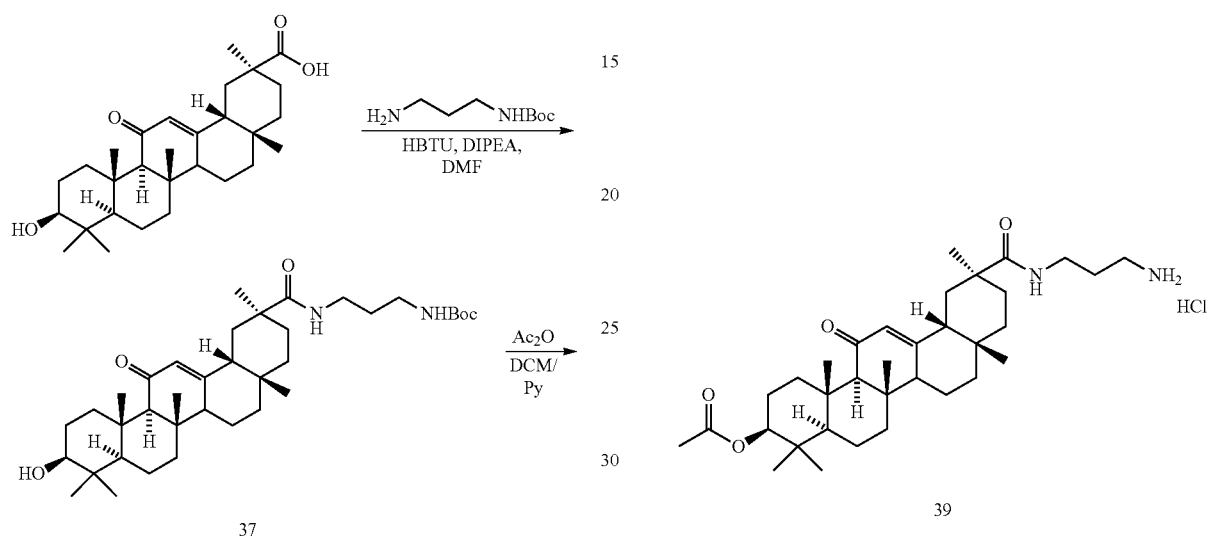
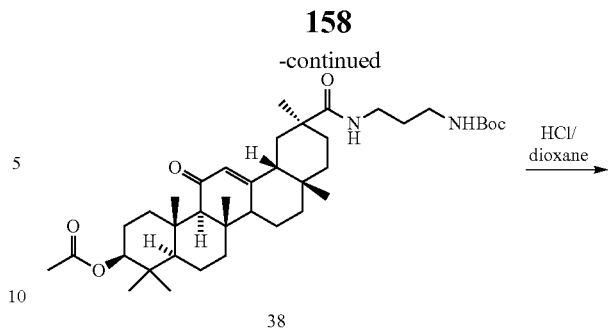
Scheme 10.
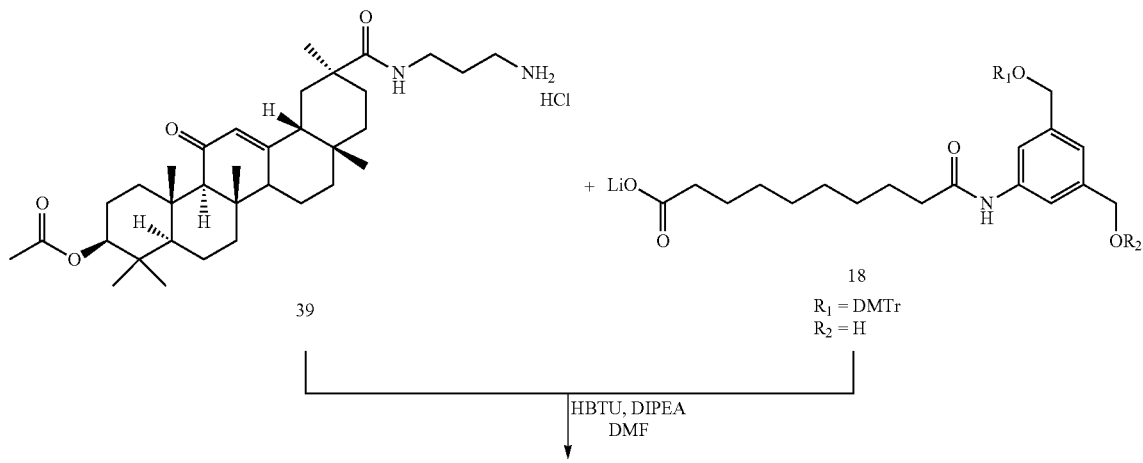

-continued

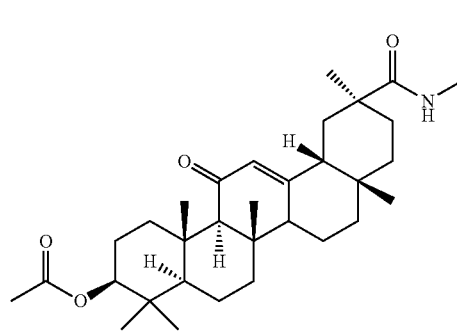

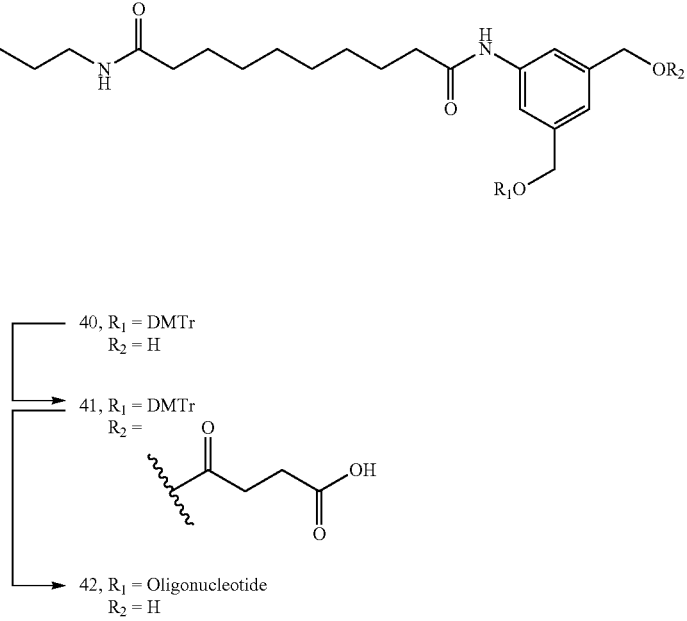

40, R₁ = DMTr
R₂ = H

41, R₁ = DMTr
R₂ =

42, R₁ = Oligonucleotide
R₂ = H

Step 1. Preparation of Compound 37

Step 2. Preparation of Compound 38

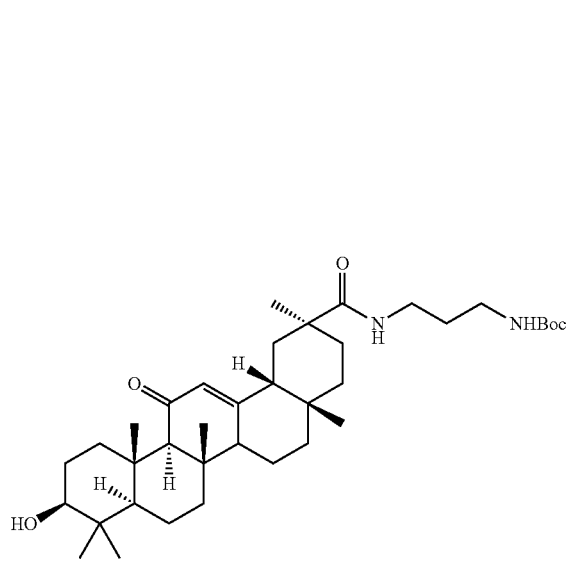

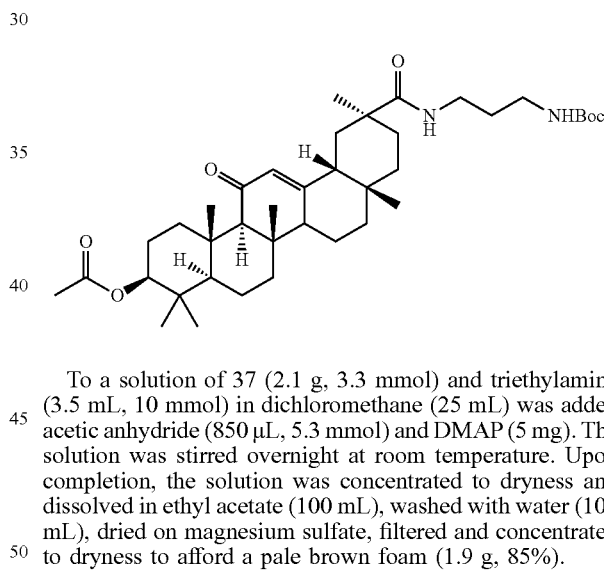

To a solution of 37 (2.1 g, 3.3 mmol) and triethylamine (3.5 mL, 10 mmol) in dichloromethane (25 mL) was added acetic anhydride (850 µL, 5.3 mmol) and DMAP (5 mg). The solution was stirred overnight at room temperature. Upon completion, the solution was concentrated to dryness and dissolved in ethyl acetate (100 mL), washed with water (100 mL), dried on magnesium sulfate, filtered and concentrated to dryness to afford a pale brown foam (1.9 g, 85%).

Step 3. Preparation of Compound 39

A solution of 18β-glycyrrhetinic acid (2.5 g, 5.3 mmol), tert-butyl (3-aminopropyl)carbamate (1.1 g, 6.4 mmol) and HBTU (3.0 g, 8.0 mmol) in N,N-dimethylformamide (20 mL) was added diisopropylethylamine (2.75 mL, 15.9 mmol). The solution was stirred overnight at room temperature. Upon completion, the solution was concentrated in vacuo to dryness. The residue was purified by column chromatography on silica gel 60 (gradient: 2% to 5% MeOH/CH₂Cl₂) to afford the product as a colorless solid (2.1 g, 63%).

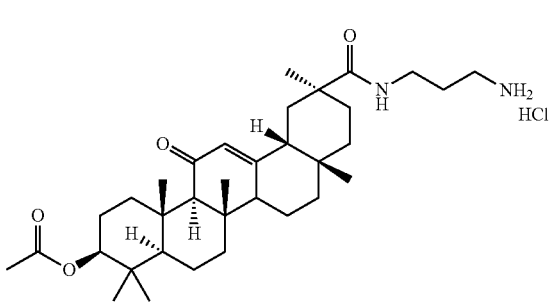

To a solution of 38 (1.5 g, 2.3 mmol) in anhydrous dioxane (25 mL) was added 2M Hydrogen chloride in dioxane (25 mL). The solution was stirred overnight at room temperature then concentrated in vacuo to dryness to afford a light brown solid (1.3 g, 96%).

Step 4. Preparation of Compounds 40, 41 and 42

Compounds 40, 41 and 42 were prepared according to the same procedure used to synthesize compounds 19, 20, and 1 respectfully.

Example 5. Synthesis of Conjugate 43

Scheme 11.

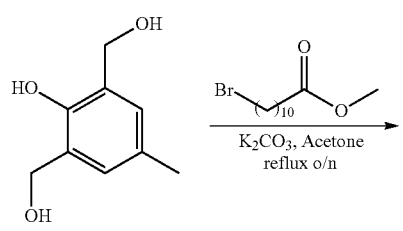

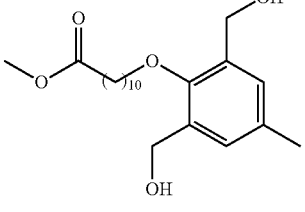

44

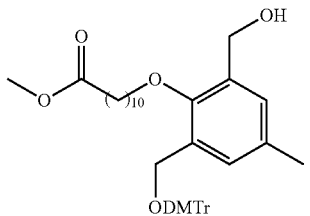

45

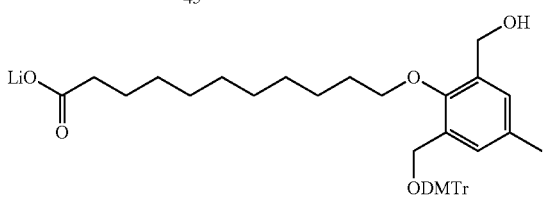

46

Scheme 12.

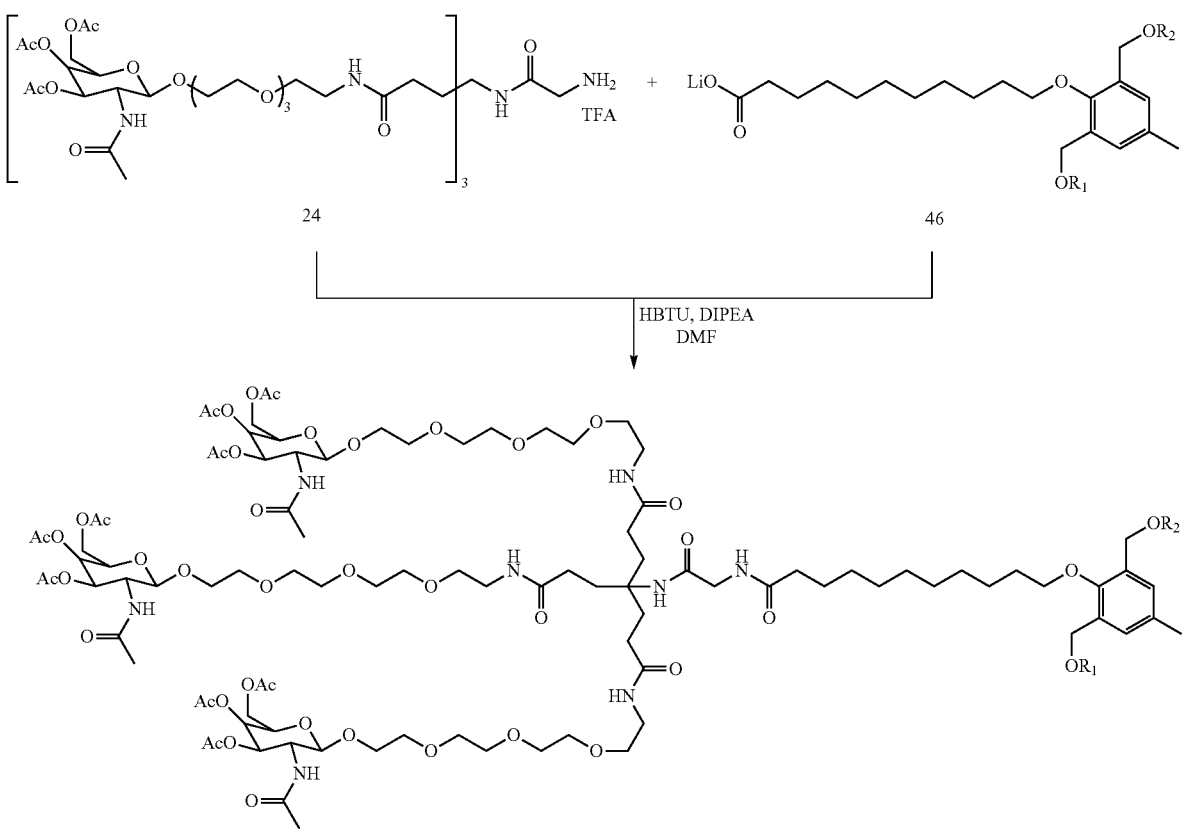

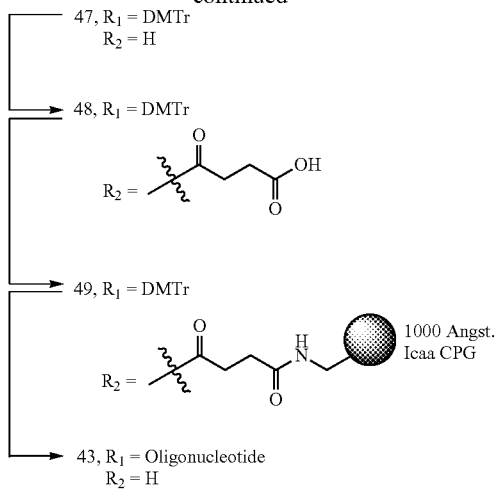

43, R₁ = Oligonucleotide
R₂ = H

Step 1. Preparation of methyl 11-(2,6-bis(hydroxymethyl)-4-methylphenoxy)undecanoate 44

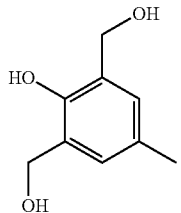

To a solution of 2,6-bis(hydroxymethyl)-p-cresol (2.7 g, 16.3 mmol), methyl 11-bromoundecanoate (5.0 g, 17.9 mmol) and potassium carbonate (4.5 g, 32.6 mmol) in acetone (100 mL) was refluxed for 16 hours. Upon completion the solution was concentrated in vacuo to dryness, suspended in ethyl acetate (150 mL) and washed with water (2×100 mL) and brine (100 mL). The ethyl acetate layer was dried on magnesium sulfate, filtered and concentrated in vacuo to dryness. The residue was purified by column chromatography on silica gel 60 (gradient 100% Hex→50% EtOAc/Hex) to afford methyl 11-(2,6-bis(hydroxymethyl)-4-methylphenoxy)undecanoate 44 as a colorless oil (1.6 g, 27%).

Step 2. Preparation of methyl 11-(2-((bis(4-methoxyphenyl)(phenyl)methoxy)methyl)-6-(hydroxymethyl)-4-methylphenoxy)undecanoate 45

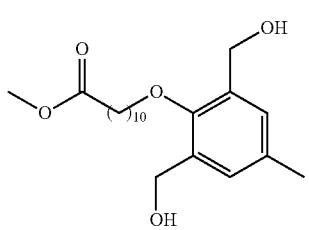

To a solution of methyl 11-(2,6-bis(hydroxymethyl)-4-methylphenoxy)undecanoate 44 (1.5 g, 4.1 mmol) in anhydrous pyridine (20 mL) was added 4,4'-Dimethoxytrityl chloride (1.4 g, 4.1 mmol). The solution was stirred overnight at room temperature. Upon completion the solution was concentrated in vacuo to dryness and purified by column chromatography on silica gel 60 (0.5 to 1% MeOH in CH₂Cl₂) to afford Methyl 11-(2-((bis(4-methoxyphenyl)(phenyl)methoxy)methyl)-6-(hydroxymethyl)-4-methylphenoxy)undecanoate 45 as a pale yellow solid (1.1 g, 40%).

Step 3. Preparation of lithium 11-(2-((bis(4-methoxyphenyl)(phenyl)methoxy)methyl)-6-(hydroxymethyl)-4-methylphenoxy)undecanoate 46

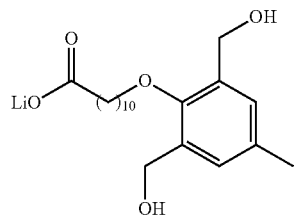

To a solution of Methyl 11-(2-((bis(4-methoxyphenyl)(phenyl)methoxy)methyl)-6-(hydroxymethyl)-4-methylphenoxy)undecanoate 45 (1.1 g, 1.7 mmol) in anhydrous tetrahydrofuran (40 mL) and water (10 mL) was added lithium hydroxide (44 mg, 1.8 mmol). The solution was concentrated in vacuo to remove all tetrahydrofuran. The remaining aqueous solution was flash frozen on liquid nitrogen then lyophilized overnight to afford lithium 11-(2-((bis(4-methoxyphenyl)(phenyl)methoxy)methyl)-6-(hydroxymethyl)-4-methylphenoxy)undecanoate 46 as a pale pink solid (1.1 g, 94%).

Step 4. Preparation of Compound 47

A solution of 10 (1.33 g, 0.66 mmol), 46 (0.5 g, 0.73 mmol), HBTU (400 mg, 1 mmol) in N,N-dimethylformamide (25 mL) was added diisopropylethylamine (0.35 mL, 2 mmol). The solution was stirred overnight (18 hours) at room temperature. Upon completion, the solvent was remove in vacuo and the residue was purified by column chromatography on silica gel (gradient: 100% $CH_2Cl_2$-5%-10%-15% MeOH in $CH_2Cl_2$) to afford 47 as a colorless solid (710 mg, 41%).

Step 5. Preparation of Compound 48

To a solution of 47 (0.71 g, 0.3 mmol), triethylamine (0.4 mL, 3.0 mmol) and polystyrene-DMAP (3 mmol/g loading, 200 mg, 0.6 mmol) in dichloromethane (15 mL) was added succinic anhydride (60 mg, 0.6 mmol). The solution was stirred overnight at room temperature and upon completion filtered and concentrated in vacuo to dryness. The residue was purified by column chromatography on silica gel 60 (gradient 5% to 20% MeOH in $CH_2Cl_2$) to afford the 48 as a pale yellow solid (570 mg, 70%). $^1$H NMR (DMSO-$d_6$, 400 MHz) δ 7.91 (m, 1H), 7.86-7.76 (m, 6H), 7.45-7.40 (m, 2H), 7.36-7.14 (m, 10H), 7.10 (s, 1H), 6.91 (d, J=8.9 Hz, 4H), 5.21 (d, J=3.3 Hz, 3H), 5.01 (s, 2H), 4.97 (dd, J=11.2, 3.4 Hz, 3H), 4.56 (d, J=8.5 Hz, 3H), 4.06-3.98 (m, 11H), 3.93-3.84 (m, 3H), 3.81-3.72 (m, 3H), 3.74 (s, 6H), 3.65-3.46 (m, 38H), 3.40-3.35 (m, 6H), 3.20-3.16 (m, 6H), 2.56-2.44 (m, 4H), 2.33 (s, 3H), 2.15-2.08 (m, 2H), 2.10 (s, 9H), 2.04-1.96 (m, 6H), 1.89 (s, 9H), 1.82-1.76 (m, 4H), 1.77 (s, 9H), 1.54-1.34 (m, 4H), 1.28-1.10 (m, 12H),

Step 6. Preparation of Compound 49

To a solution of 48 (100 mg, 40 µmol), N-Hydroxysuccinimide (30 mg/mL soln in acetonitrile, 50 µL, 13 µmol), N,N-Diisopropylcarbodiimide (40 µL, 264 µmol) and pyridine (50 µL) in dichloromethane (2 mL) and acetonitrile (3 mL) was added 1000 Alcaa CPG (prime synthesis, 920 mg). The solution was stirred overnight at room temperature on an orbital shaker. TLC analysis of the reaction solution showed only partial consumption of the activated N-Hydroxysuccinic ester so additional CPG (500 mg) was added. The solution was stirred again overnight. Upon completion, the CPG was filtered and washed with dichloromethane (25 mL), acetonitrile (25 mL) and tetrahydrofuran (25 mL). The unreacted amine residues on the CPG were acetylated (capped) by adding a 1:1 solution of acetic anhydride in acetonitrile (3 mL) and 10% N-methylimidazole/10% pyridine in tetrahydrofuran (3 mL). The suspension was left for 2 hours then filtered and rinsed with equal parts tetrahydrofuran (25 mL), acetonitrile (25 mL) and dichloromethane (25 mL). The loaded CPG 49 was dried under high vacuum overnight. The ligand loading efficiency was determined to be 22 µmole/g using a standard DMT loading assay (3% trichloroacetic acid in $CH_2Cl_2$, UV-VIS, $A_{504}$).

Step 7. Preparation of Conjugate 43

The resulting GalNAc loaded CPG solid support 49 was employed in automated oligonucleotide synthesis using standard procedures. Nucleotide deprotection followed by removal from the solid support (with concurrent galactosamine acetate deprotection) afforded a GalNAc-oligonucleotide conjugate 43.

Example 6. Synthesis of Conjugate 50

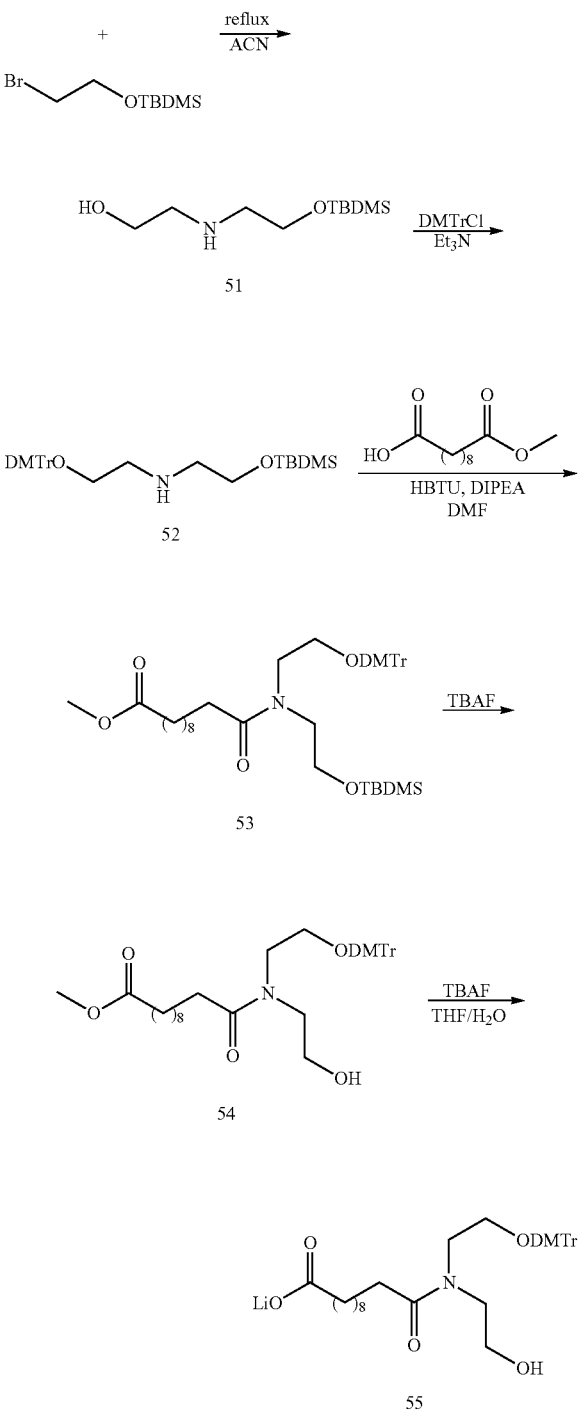

Scheme 13.

Scheme 14.

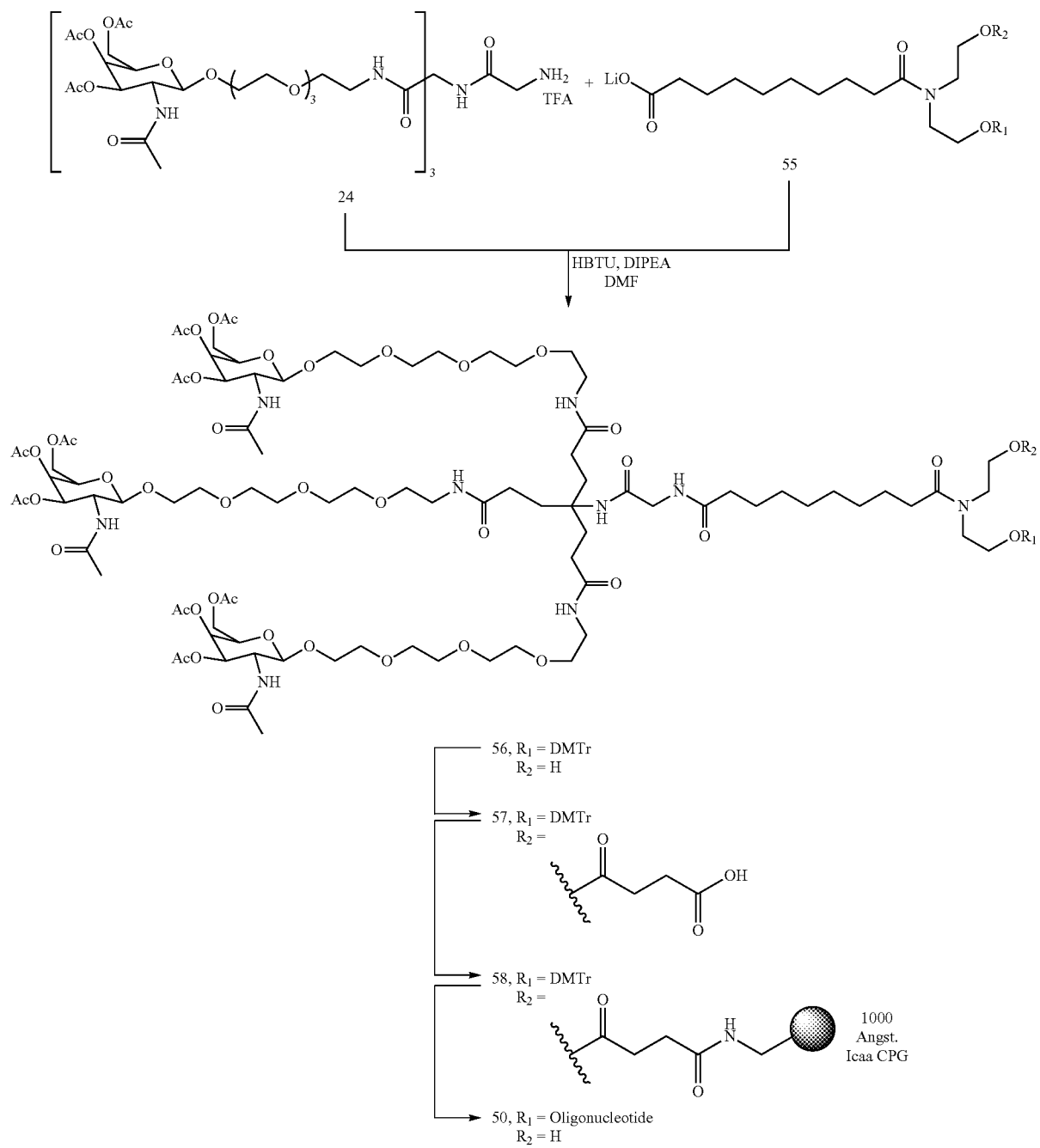

Step 1. Preparation of 2-((2-((tert-butyldimethylsi-lyl)oxy)ethyl)amino)ethan-1-ol 51

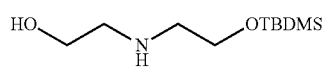

A solution of ethanolamine (77 mL, 1.25 mol) and (2-bromoethoxy)-tert-butyl dimethylsilane (15 g, 62.7 mmol) in anhydrous acetonitrile (200 mL) was refluxed for 3 hours. Upon completion the reaction was cooled to room temperature, diluted with water (400 mL) and extracted with ethyl acetate (3×150 mL). The combined ethyl acetate extracts were dried on magnesium sulfate, filtered and concentrated in vacuo to dryness. The residue was purified by filtration through a pad of silica first with 50% ethyl acetate/hexanes then 50% MeOH/EtOAc to afford 51 as a pale yellow oil (14 g, 100%).

Step 2. Preparation of 2-(bis(4-methoxyphenyl)(phenyl)methoxy)-N-(2-((tert-butyldimethylsilyl)oxy)ethyl)ethan-1-amine 52

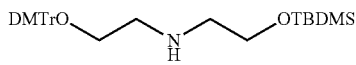

To a solution of 2-((2-((tert-butyldimethylsilyl)oxy)ethyl)amino)ethan-1-ol 51 (14 g, 64 mmol) and triethylamine (17.5 mL, 128 mmol) in anhydrous dichloromethane (250 mL) was added 4,4'-Dimethoxytrityl chloride (24 g, 70 mmol). The solution was stirred overnight at room temperature then concentrated in vacuo to dryness. The residue was dissolved in ethyl acetate (300 mL) and washed with water (250 mL) and brine (250 mL). The ethyl acetate was dried on magnesium sulfate, filtered and concentrated in vacuo to dryness. Purification by column chromatography on silica gel 60 (1% to 5% MeOH in $CH_2Cl_2$) afforded 52 as a pale yellow viscous oil (13 g, 39%).

Step 3. Preparation of methyl 10-((2-(bis(4-methoxyphenyl)(phenyl)methoxy)ethyl)(2-((tert-butyldimethylsilyl)oxy)ethyl)amino)-10-oxodecanoate 53

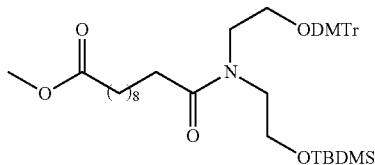

A solution of 2-(bis(4-methoxyphenyl)(phenyl)methoxy)-N-(2-((tert-butyldimethylsilyl)oxy)ethyl)ethan-1-amine 52 (5.4 g, 10.3 mmol), monomethyl sebacate (2.2 g, 10.3 g), HBTU (4.9 g, 12.9 mmol), DIPEA (5.3 mL, 30.9 mmol) in N,N-dimethylformamide (100 mL) was stirred for 3 hours at room temperature. Upon completion, the solution was poured into water (400 mL) and extracted with ethyl acetate (1×500 mL). The ethyl acetate extract was washed with brine (2×250 mL), dried on magnesium sulfate, filtered and concentrated in vacuo to dryness. Purification by column chromatography on silica gel 60 (10% to 25% ethyl acetate in hexanes) afforded 53 as a viscous yellow oil (6.5 g, 87%).

Step 4. Preparation of methyl 10-((2-(bis(4-methoxyphenyl)(phenyl)methoxy)ethyl)(2-hydroxyethyl)amino)-10-oxodecanoate 54

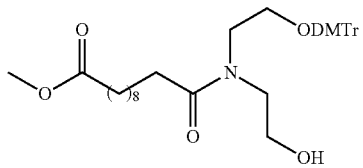

To a solution of methyl 10-((2-(bis(4-methoxyphenyl)(phenyl)methoxy)ethyl)(2-((tert-butyldimethylsilyl)oxy)ethyl)amino)-10-oxodecanoate 53 (2.0 g, 2.8 mmol) and triethylamine (1 mL) in anhydrous tetrahydrofuran (20 mL) was added TBAF (1M in THF, 3.4 mL, 3.3 mmol). The solution was stirred for 6 h, but only partial conversion observed by TLC (5% MeOH in $CH_2Cl_2$). Additional 1.7 mL TBAF added and the solution was stirred overnight at room temperature. Upon completion, the solution was concentrated in vacuo and purified by column chromatography on silica gel 60 (10% to 50% EtOAc in hexanes then 100% EtOAc) to afford 54 as a viscous colorless oil (0.5 g, 29%).

Step 5. Preparation of lithium 10-((2-(bis(4-methoxyphenyl)(phenyl)methoxy)ethyl)(2-hydroxyethyl)amino)-10-oxodecanoate 55

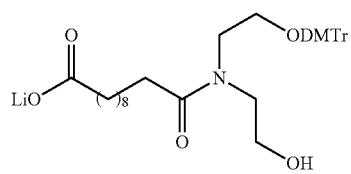

To a solution of methyl 10-((2-(bis(4-methoxyphenyl)(phenyl)methoxy)ethyl)(2-hydroxyethyl)amino)-10-oxodecanoate 54 (0.5 g, 0.83 mmol) in THF (40 mL) was added water (10 mL) and lithium hydroxide (24 mg, 1.0 mmol). The solution was stirred overnight at room temperature then concentrated in vacuo to remove the THF. The remaining aqueous solution was flash frozen on liquid nitrogen and lyophilized to afford 55 as a colorless solid (485 mg, 95%).

Step 6. Preparation of Compounds 56, 57, 58 and 50

Compounds 56, 57, 58 and 50 were prepared using the identical procedures to those used to synthesize compounds 47, 48, 49 and 43 respectfully.

Example 7. Synthesis of Conjugate 59

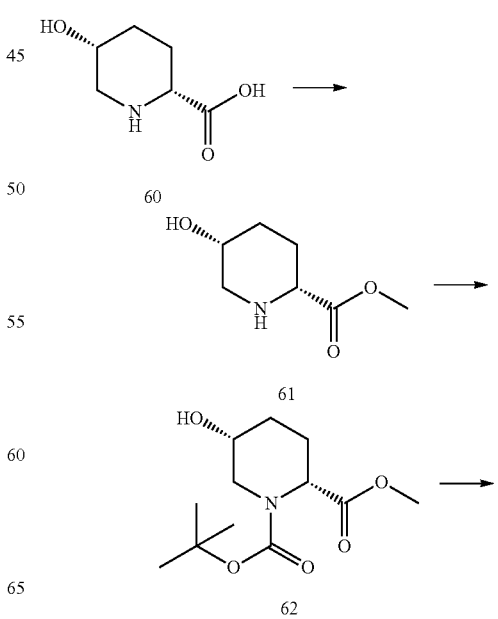

Scheme 15.

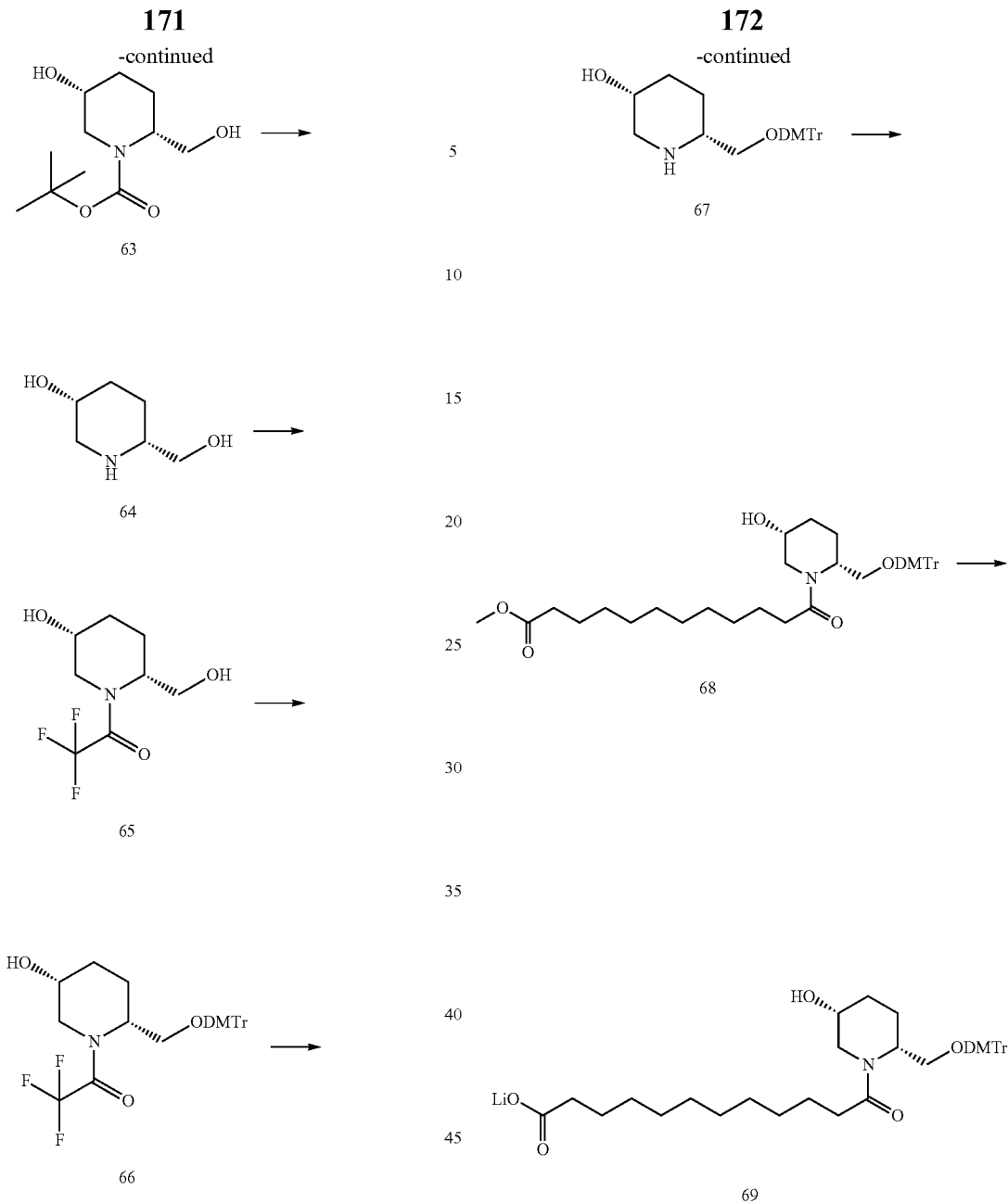
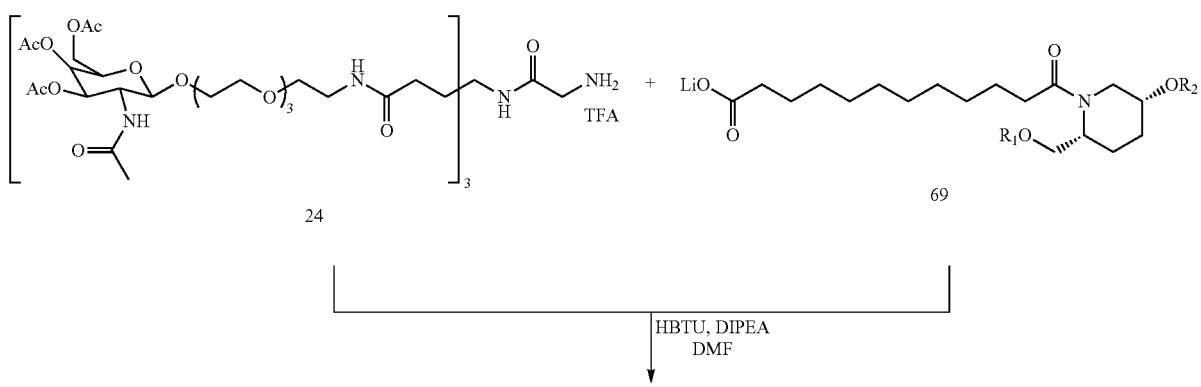
Scheme 16.

-continued

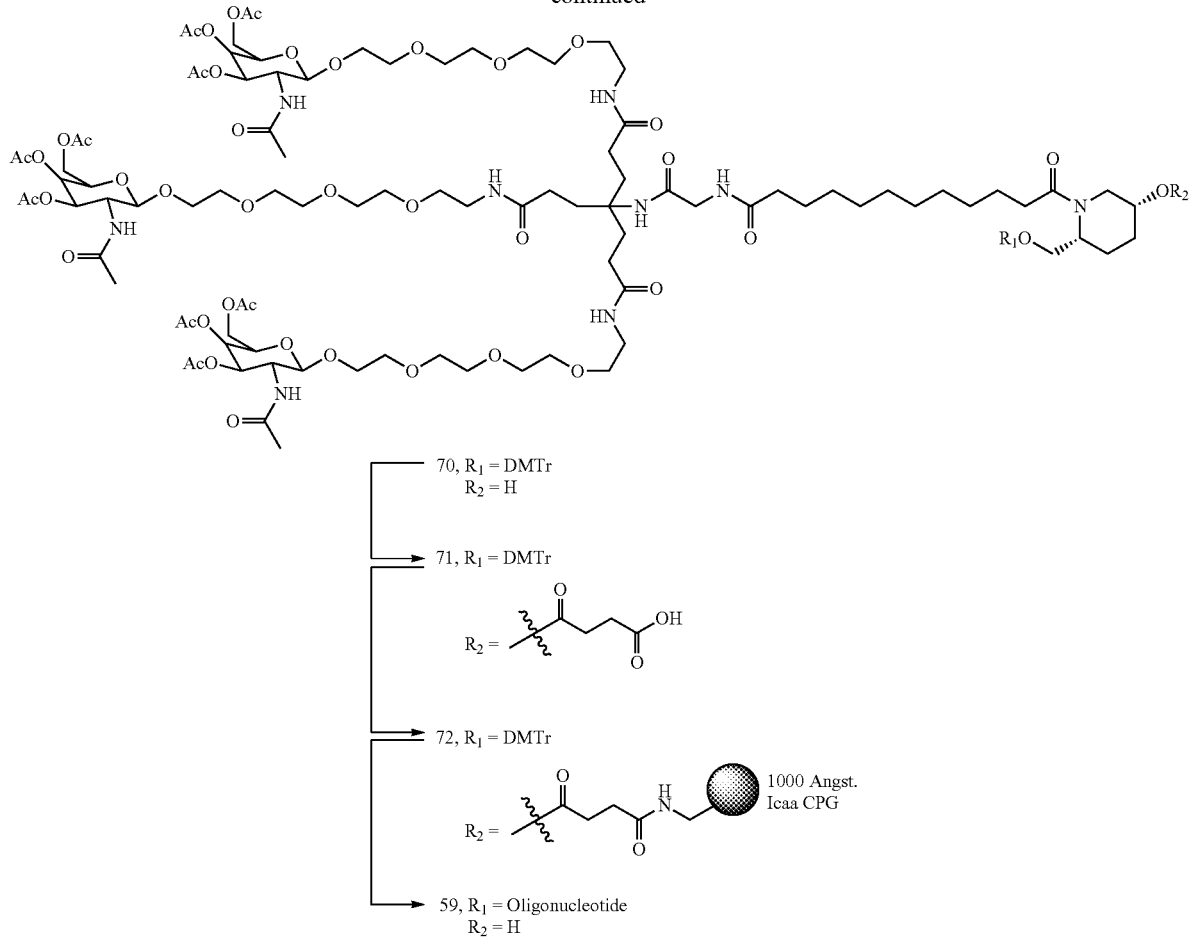

Step 1. Preparation of methyl (2R,5R)-5-hydroxypiperidine-2-carboxylate 61

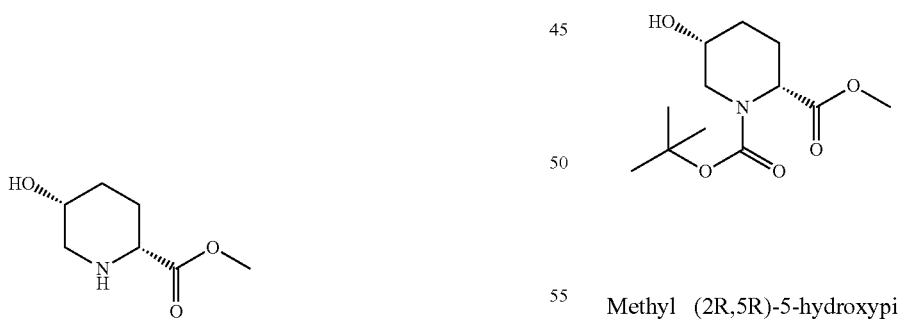

(2R,5R)-5-hydroxypiperidine-2-carboxylic acid 60 (3.5 g, 24.1 mmol) was stirred in MeOH (50 mL). HCl (g) was bubbled through the solution for 2 mins and the reaction stirred at reflux for 1.5 h. The reaction was concentrated in-vacuo to give methyl (2R,5R)-5-hydroxypiperidine-2-carboxylate 61 in quantitative yield which was used without further purification.

Step 2. Preparation of 1-(tert-butyl) 2-methyl (2R, 5R)-5-hydroxypiperidine-1,2-dicarboxylate 62

Methyl (2R,5R)-5-hydroxypiperidine-2-carboxylate 61 (24.1 mmol) and TEA (7.2 mL, 53.02 mmol) were stirred in DCM (100 mL) at RT. Di-tert-butyl-di-carbonate (5.7 g, 26.5 mmol) was added in portions and the reaction stirred for 2 h. The reaction was diluted with DCM (100 mL) and washed sequentially with 1 M HCl (2×75 mL), saturated NaHCO$_3$ (2×75 mL), H$_2$O (2×75 mL) and saturated NaCl solution (2×75 mL). The organics were separated, dried (Na$_2$SO$_4$) and concentrated in-vacuo to give 1-(tert-butyl) 2-methyl (2R,5R)-5-hydroxypiperidine-1,2-dicarboxylate 62 (5.53 g, 88%) which was used without further purification.

Step 3. Preparation of tert-butyl (2R,5R)-5-hydroxy-2-(hydroxymethyl)piperidine-1-carboxylate 63

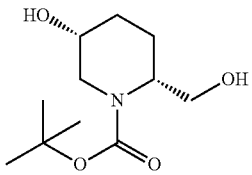 [SMILES: CC(C)(C)OC(=O)N1C[C@H](O)CC[C@@H]1CO]

(2R,5R)-1-(tert-Butoxycarbonyl)-5-hydroxypiperidine-2-carboxylic acid 62 (5.53 g, 21.4 mmol) was stirred in THF at 0° C. LiBH$_4$ (3.0 M solution in THF)(8.9 mL, 27.7 mmol) was added dropwise over 1 hr. The reaction was allowed to warm to RT and stirring continued for 16 h. Reaction was quenched with 1M NaOH, THF removed in-vacuo and the aqueous exhaustively extracted with EtOAc (10×100 mL). The combined organics were washed with H$_2$O (50 mL), saturated NaCl solution (2×50 mL), dried (Na$_2$SO$_4$) and concentrated in-vacuo to give tert-butyl (2R,5R)-5-hydroxy-2-(hydroxymethyl)piperidine-1-carboxylate 63 (2.4 g, 49.0%) which was used without further purification.

Step 4. Preparation of (3R,6R)-6-(hydroxymethyl)piperidin-3-ol 64

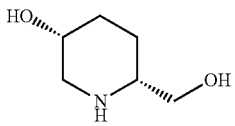

tert-Butyl (2R,5R)-5-hydroxy-2-(hydroxymethyl)piperidine-1-carboxylate 63 (2.4 g, 10.4 mmol) was stirred in Et$_2$O at RT. HCl (g) was bubbled through for 45 secs and the reaction stirred at RT for 45 mins. The reaction was concentrated in-vacuo and dried under hi-vac to afford (3R,6R)-6-(hydroxymethyl)piperidin-3-ol 64. The product was used without further purification.

Step 5. Preparation of 2,2,2-trifluoro-1-((2R,5R)-5-hydroxy-2-(hydroxymethyl)piperidin-1-yl)ethan-1-one 65

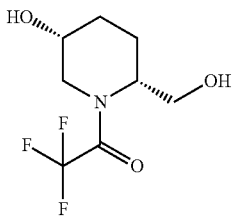 [SMILES: O=C(N1C[C@H](O)CC[C@@H]1CO)C(F)(F)F]

Crude (3R,6R)-6-(hydroxymethyl)piperidin-3-ol 64 from the previous reaction was stirred in MeCN (50 mL) with TEA (3.5 mL, 25.2 mmol) at RT. Ethyl trifluoroacetate (3 mL, 25.2 mmol) was added and the reaction stirred at RT for 16 hr, then concentrated in-vacuo to give 2,2,2-trifluoro-1-((2R,5R)-5-hydroxy-2-(hydroxymethyl)piperidin-1-yl)ethan-1-one 65. The product was used without further purification.

Step 6. Preparation of 1-((2R,5R)-2-((bis(4-methoxyphenyl)(phenyl)methoxy)methyl)-5-hydroxypiperidin-1-yl)-2,2,2-trifluoroethan-1-one 66

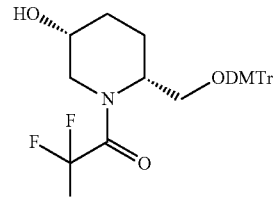

Crude 2,2,2-trifluoro-1-((2R,5R)-5-hydroxy-2-(hydroxymethyl)piperidin-1-yl)ethan-1-one 65 from the previous reaction was stirred in DCM with TEA (50 mL) at RT. 4,4'-Dimethoxytrityl chloride (DMTrCl) (3.87 g, 11.44 mmol) was added in one portion and the reaction stirred at RT for 3 hours. The reaction was diluted with DCM (50 mL) and washed sequentially with saturated NaHCO$_3$ (2×75 mL), H$_2$O (2×75 mL) and saturated NaCl solution (2×75 mL). The organics were separated, dried (Na$_2$SO$_4$), concentrated in-vacuo and purified by column chromatography (100% hexanes-60% EtOAc/Hexanes) (0.1% TEA) to give 1-((2R,5R)-2-((bis(4-methoxyphenyl)(phenyl)methoxy)methyl)-5-hydroxypiperidin-1-yl)-2,2,2-trifluoroethan-1-one 66 (3.14 g, 57%)

Step 7. Preparation of (3R,6R)-6-((bis(4-methoxyphenyl)(phenyl)methoxy)methyl)-piperidin-3-ol 67

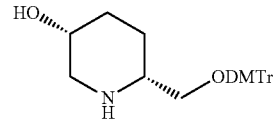

1-((2R,5R)-2-((bis(4-methoxyphenyl)(phenyl)methoxy)methyl)-5-hydroxypiperidin-1-yl)-2,2,2-trifluoroethan-1-one 66 (3.14 g, 6.0 mmol) was stirred in MeOH (50 mL) at RT. KOH (672 mg, 12 mmol) was added and the reaction stirred at RT for 16 hours. Additional KOH (300 mg, 6 mmol) was added and stirring continued for an additional 24 h. The reaction was concentrated in-vacuo, taken up in DCM (150 mL), washed with H$_2$O (4×50 mL), dried (Na$_2$SO$_4$) and concentrated in-vacuo to give (3R,6R)-6-((bis(4-methoxyphenyl)(phenyl)methoxy)methyl)piperidin-3-ol 67 (2.34 g, 90%) which was used without further purification.

Step 8. Preparation of methyl 12-((2R,5R)-2-((bis (4-methoxyphenyl)(phenyl)-methoxy)methyl)-5-hydroxypiperidin-1-yl)-12-oxododecanoate 68

Example 8. Synthesis of Conjugate 142

Scheme 17.

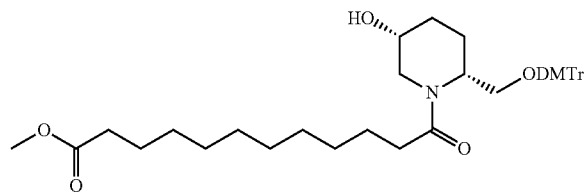

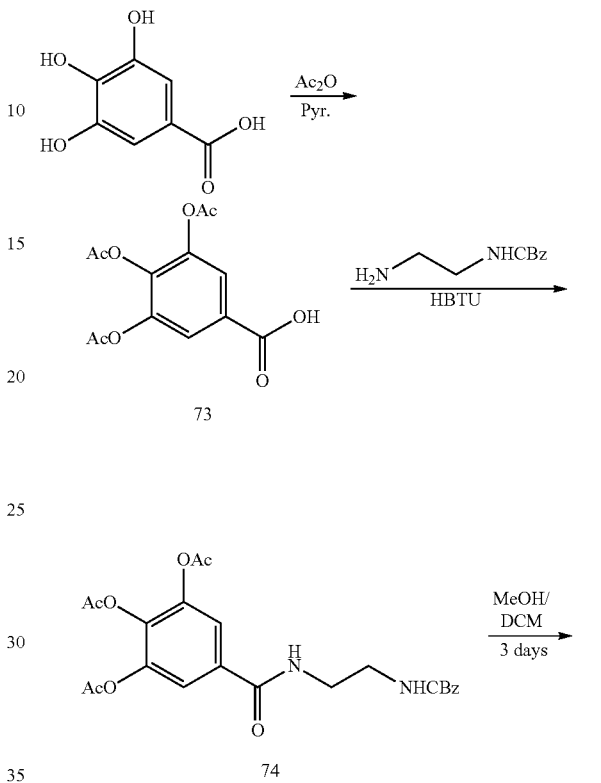

(3R,6R)-6-((Bis(4-methoxyphenyl)(phenyl)methoxy) methyl)piperidin-3-ol 67 (2.34 g, 5.34 mmol) was stirred in DCM (75 mL) at RT. Triethylamine (2.2 mL, 16.2 mmol), HATU (3.5 g, 9.2 mmol) and 12-methoxy-12-oxododecanoic acid (1.32 g, 5.4 mmol) were added and the reaction stirred at RT for 3 h. The resultant solid precipitate was removed by filtration, the filtrate concentrated in-vacuo and the residue purified by column chromatography (2.5% MeOH/DCM, 0.1% TEA) to give methyl 12-((2R,5R)-2-((bis(4-methoxyphenyl)(phenyl)methoxy)methyl)-5-hydroxypiperidin-1-yl)-12-oxododecanoate 68 in quantitative yield.

Step 9. Preparation of lithium 12-((2R,5R)-2-((bis (4-methoxyphenyl)(phenyl)methoxy)-methyl)-5-hydroxypiperidin-1-yl)-12-oxododecanoate 69

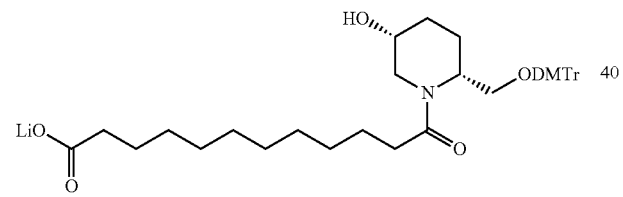

Methyl 12-((2R,5R)-2-((bis(4-methoxyphenyl)(phenyl) methoxy)methyl)-5-hydroxypiperidin-1-yl)-12-oxododecanoate 68 (5.4 mmol) and LiOH (140 mg, 5.94 mmol) were stirred in THF:H$_2$O (1:1, 100 mL) at RT for 48 h. The THF was removed in-vacuo, the aqueous frozen and lyophilized to give lithium 12-((2R,5R)-2-((bis(4-methoxyphenyl)(phenyl)methoxy)methyl)-5-hydroxypiperidin-1-yl)-12-oxododecanoate 69 (3.2 g, 91%). Which was used in subsequent reactions without additional purification.

Step 10. Preparation of Compounds 70, 71, 72, and 59

Compounds 70, 71, 72 and 59 were prepared using the identical procedures to those used to synthesize compounds 47, 48, 49 and 43 respectfully.

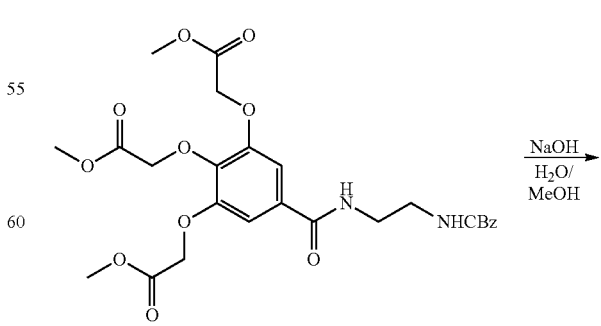

179
-continued
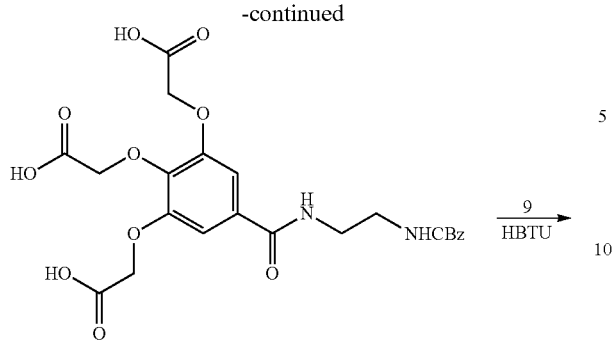
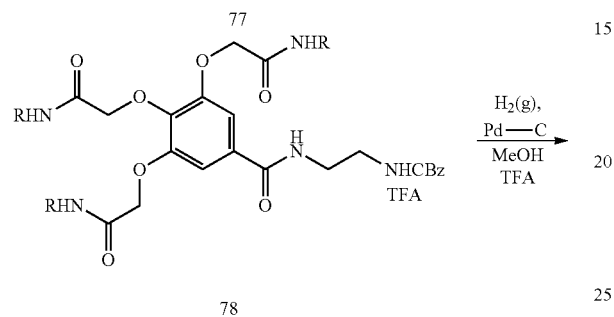
180
-continued
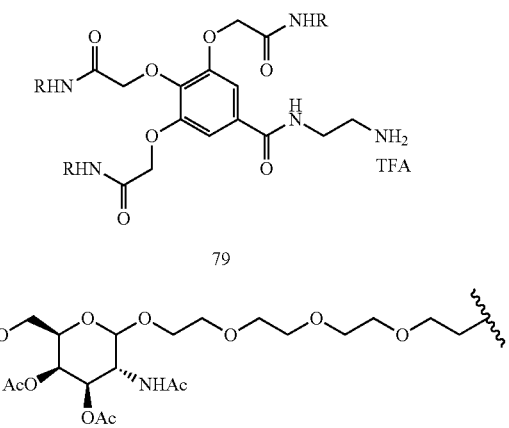
Scheme 18.
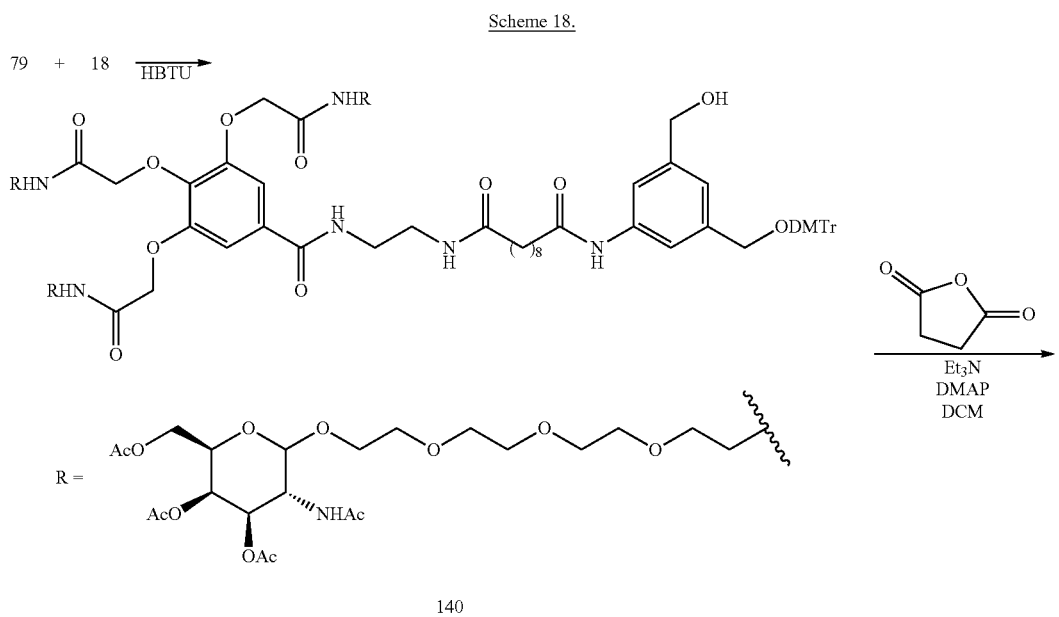
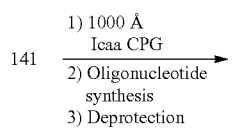

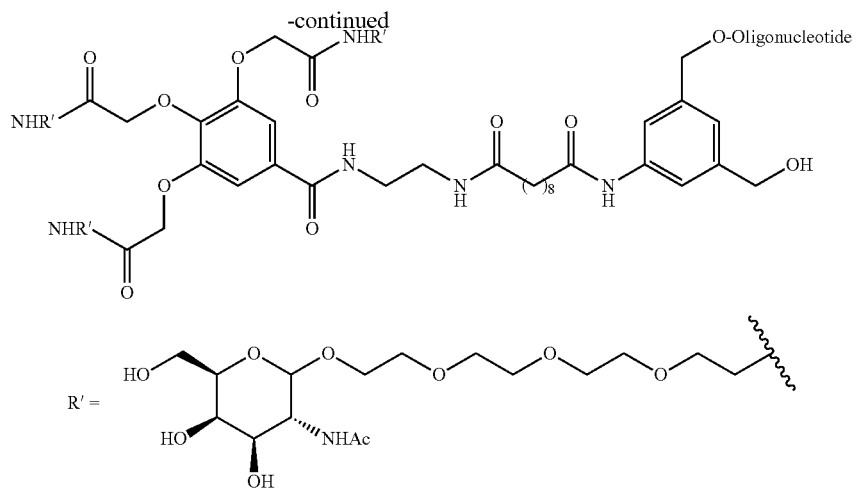

Step 1. Preparation of 3,4,5-Triacetoxybenzoic acid 73

To a solution of Gallic acid (20 g) in pyridine (50 mL) and acetic anhydride (50 mL). The solution was stirred overnight at room temperature then poured into ice water (1 L). The solution was made acidic with concentrated hydrochloric acid where upon a colorless solid precipitated. The solid was collected via filtration and washed with water (5×100 mL). The wet solid was frozen on liquid nitrogen and freeze dried to afford 3,4,5-triacetoxybenzoic acid (26 g, 75%).

Step 2. Preparation of 5-((2-((2-Oxo-2-phenyl-1λ²-ethyl)amino)ethyl)carbamoyl)benzene-1,2,3-triyl triacetate 74

To a solution of 3,4,5-triacetoxybenzoic acid (10 g, 33.8 mmol), N-carbobenzoxy-1,2-diaminoethane hydrochloride (5.3 g, 33.8 mmol) and HBTU (13.5 g, 35.5 mmol) in DMF (200 mL) was added DIPEA (17.5 mL, 101 mmol). The solution was stirred for 16 hours then diluted with ethyl acetate (250 mL), washed with brine (3×200 mL), dried on magnesium sulfate, filtered and concentrated in vacuo to dryness. The crude product was purified by column chromatography on silica gel (Gradient 1% to 5% MeOH in DCM) to afford 5-((2-((2-Oxo-2-phenyl-1λ²-ethyl)amino)ethyl)carbamoyl)benzene-1,2,3-triyl triacetate as an off white solid (5.5 g).

Step 3. Preparation of 3,4,5-Trihydroxy-N-(2-((2-oxo-2-phenyl-1λ²-ethyl)amino)ethyl)benzamide 75

A solution of 5-((2-((2-Oxo-2-phenyl-1λ²-ethyl)amino)ethyl)carbamoyl)benzene-1,2,3-triyl triacetate (5 g, 1.1 mmol) in 1:1 MeOH/CH₂Cl₂ (100 mL) was stirred for 3 days at room temperature. Upon completion the solvent was removed to afford 3,4,5-Trihydroxy-N-(2-((2-oxo-2-phenyl-1λ²-ethyl)amino)ethyl)benzamide as a colorless solid (4 g, quantitative).

Step 4. Preparation of Trimethyl 2,2',2"-((5-((2-((2-oxo-2-phenyl-1)₂-ethyl)amino)ethyl)carbamoyl)benzene-1,2,3-triyl)tris(oxy))triacetate 76

A solution of 3,4,5-Trihydroxy-N-(2-((2-oxo-2-phenyl-1λ²-ethyl)amino)ethyl)benzamide (4 g, 11.6 mmol), methyl bromoacetate (7.7 g, 46.4 mmol) and potassium carbonate (9.6 g, 69.4 mmol) in DMF (100 mL) was stirred overnight at 60° C.

Upon completion the solution was cooled to room temperature, diluted with ethyl acetate (200 mL), washed with water (200 mL), brine (3×100 mL), dried on magnesium sulfate, filtered and concentrated in vacuo to dryness. The crude product was purified by column chromatography on silica gel (Gradient 2% to 10% MeOH in DCM) to afford trimethyl 2,2',2"-((5-((2-((2-oxo-2-phenyl-1λ²-ethyl)amino)ethyl)carbamoyl)benzene-1,2,3-triyl)tris(oxy))-triacetate as a beige solid (5 g, 79%)

Step 5. Preparation of 2,2',2"-((5-((2-((2-Oxo-2-phenyl-1λ²-ethyl)amino)ethyl)-carbamoyl)benzene-1,2,3-triyl)tris(oxy))triacetic acid 77

A solution of trimethyl 2,2',2"-((5-((2-((2-oxo-2-phenyl-1λ²-ethyl)amino)ethyl)-carbamoyl)benzene-1,2,3-triyl)tris(oxy))triacetate (5 g, 9.2 mmol) and 1M NaOH (30 mL) in methanol (100 mL) was stirred for 2 hours at room temperature. Upon completion the reaction was concentrated to remove the methanol and diluted with water (75 mL). The mixture was cooled to 0° C., acidified with 2M HCl and extracted with ethyl acetate (5×150 mL). The combined ethyl acetate extracts were dried on magnesium sulfate, filtered and concentrated in vacuo to dryness to afford 2,2',2"-((5-((2-((2-Oxo-2-phenyl-1λ²-ethyl)amino)ethyl)carbamoyl)benzene-1,2,3-triyl)tris(oxy))triacetic acid as a colorless solid (2.3 g, 50%).

Step 6. Preparation of Compound 78

Compound 78 was prepared from compounds 9 (2.75 g, 4.3 mmol) and 77 (0.5 g, 0.96 mmol) using an identical procedure to that used for compound 13. Yield: 600 mg.

Step 7. Preparation of Compound 79

Compound 79 was prepared from compounds 78 (0.6 g) using an identical procedure to that used for compound 14. Yield: 500 mg.

Step 8. Preparation of Compound 140

Compound 140 was prepared from compound 79 (500 mg, 0.25 mmol) and compound 18 (175 mg, 0.25 mmol) using an identical procedure to that used for compound 19. Yield: 250 mg, 44%.

Step 9. Preparation of Compound 141

Compound 141 was prepared from compound 140 (250 mg, 0.11 mmol) using an identical procedure to that used for compound 20. Yield: 200 mg.

Step 10. Preparation of Conjugate 142

Conjugate 142 was prepared from compound 141 (200 mg) and 1000A lcaa CPG (1.8 g) using an identical procedure to that used for compound 1. Yield: 1.9 g, 22 µmol/g CPG loading. The resulting GalNAc loaded CPG solid support was employed in automated oligonucleotide synthesis using standard procedures. Nucleotide deprotection followed by removal from the solid support (with concurrent galactosamine acetate deprotection) afforded the GalNAc-oligonucleotide conjugate 142.

Example 9. Synthesis of Conjugate 145

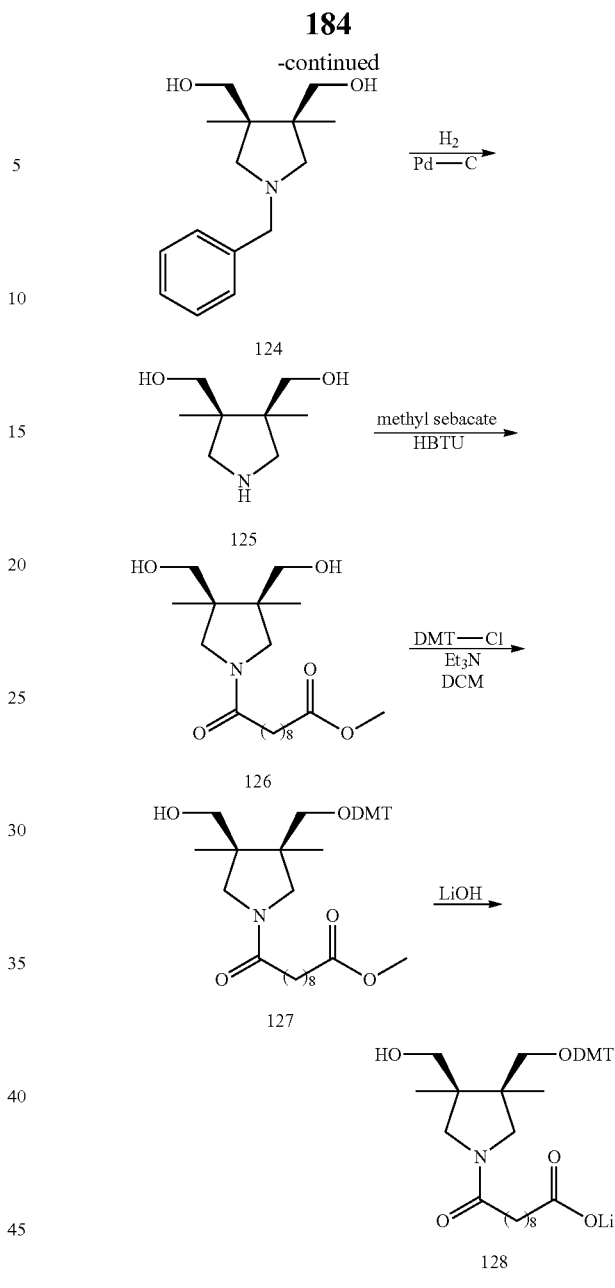

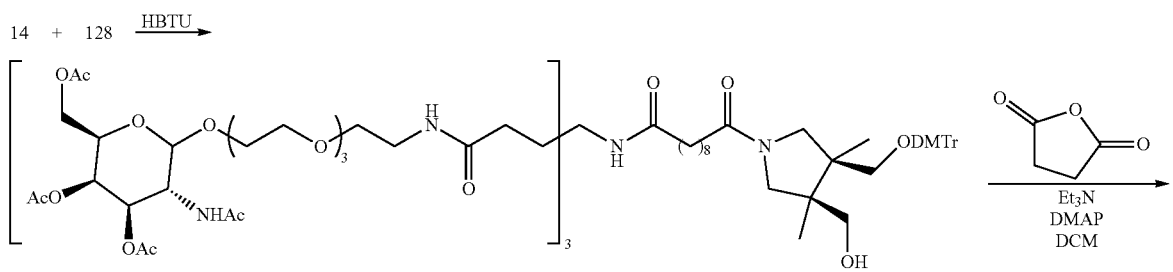

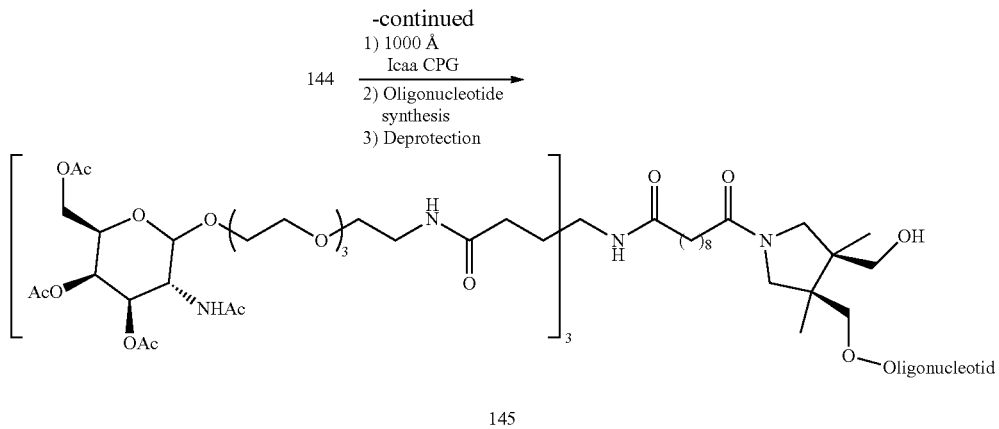

Step 1. Preparation of Racemic (cis) 5-Benzyl-3a, 6a-dimethyltetrahydro-1H-furo[3,4-c]pyrrole-1,3 (3aH)-dione 123

To a cooled solution (0° C.) of 3,4-dimethylfuran-2,5-dione (3 g, 24 mmol) and N-benzyl-1-methoxy-N-((trimethylsilyl)methyl)methanamine (7 g, 29.8 mmol) in dichloromethane (75 mL) was slowly added trifluoroacetic acid (75 µL). Stir overnight allowing the solution to slowly warm to room temperature as the ice bath melted. The reaction mixture was concentrated to dryness, dissolved in ethyl acetate (100 mL), washed with saturated sodium bicarbonate (2×100 mL), dried on magnesium sulfate, filtered and concentrated to dryness. Purification by column chromatography on silica gel (gradient: 20% ethyl acetate in hexanes to 100% ethyl acetate) afforded racemic (cis) 5-Benzyl-3a,6a-dimethyltetrahydro-1H-furo[3,4-c]pyrrole-1,3(3aH)-dione as a yellow oil (3.5 g, 56%).

Step 2. Preparation of Racemic (cis) 1-Benzyl-3,4-dimethylpyrrolidine-3,4-diyl)dimethanol 124

To a cooled (0° C.) solution of (3aR,6aS)-5-Benzyl-3a, 6a-dimethyltetrahydro-1H-furo[3,4-c]pyrrole-1,3(3aH)-dione (3.5 g, 13.4 mmol) in anhydrous diethyl ether (50 mL) was added slowly lithium aluminum hydride pellets (1.5 g, 40 mmol) over three portions. The solution was stirred overnight warming to room temperature as the ice water bath melted. Upon completion, the reaction was cooled to 0° C. and very slowly quenched with 1.5 mL of 5M NaOH followed by 1.5 mL of water. Stir for 30 minutes then add magnesium sulfate and filter. The filtrate was concentrated to afford racemic (cis) 1-Benzyl-3,4-dimethylpyrrolidine-3,4-diyl)dimethanol as a colorless oil (2.7 g).

Step 3. Preparation of Racemic (cis) 3,4-Dimethylpyrrolidine-3,4-diyl)dimethanol 125

To a solution of ((3R,4S)-1-Benzyl-3,4-dimethylpyrrolidine-3,4-diyl)dimethanol (10 g, 40 mmol) in methanol (10 mL) was added 10% palladium on activated charcoal wet (1 g). The solution was stirred vigorously under a hydrogen atmosphere for 16 hours. Upon completion the solution was filtered through Celite, and concentrated to dryness to afford racemic (cis) 3,4-Dimethylpyrrolidine-3,4-diyl)dimethanol as a colorless solid (5.5 g, 86%).

Step 4. Preparation of Racemic (cis) Methyl 10-(3, 4-bis(hydroxymethyl)-3,4-dimethylpyrrolidin-1-yl)-10-oxodecanoate 126

Compound 126 was prepared from compound 125 (1.3 g, 8.2 mmol) and monomethyl sebacate (1.8 g, 8.2 mmol) using an identical procedure to that used for compound 17. Yield: 1.8 g, 61%.

Step 5. Preparation of Racemic (cis) Methyl 10-(3-((bis(4-methoxyphenyl-)(phenyl)methoxy)-methyl)-4-(hydroxymethyl)-3,4-dimethylpyrrolidin-1-yl)-10-oxodecanoate 127

Compound 127 was prepared from compound 126 (1.8 g, 5.0 mmol) and 4,4'-Dimethoxytrityl chloride (1.7 g, 5.0 mmol) using an identical procedure to that used for compound 18. Yield: 1.4 g, 42%.

Step 6. Preparation of Racemic (cis) Lithium 10-(3-((bis(4-methoxyphenyl)-(phenyl)methoxy)-methyl)-4-(hydroxymethyl)-3,4-dimethylpyrrolidin-1-yl)-10-oxodecanoate 128

To a solution of compound 127 (3.0 g, 4.6 mmol) in THF (50 mL) and water (50 mL) was added lithium hydroxide (121 mg, 5.0 mmol). The solution was stirred for 4 hours at room temperature then concentrated to remove the THF. The remaining aqueous solution was freeze dried overnight to afford a pale pink solid (2.9 g, quantitative).

Step 7. Preparation of Compound 143

Compound 143 was prepared from compound 128 (270 mg, 0.42 mmol) and compound 14 (800 mg, 0.42 mmol) using an identical procedure to that used for compound 19. Yield: 900 mg, 87%.

Step 8. Preparation of Compound 144

Compound 144 was prepared from compound 143 (500 mg, 0.2 mmol) using an identical procedure to that used for compound 20. Yield: 200 mg.

Step 9. Preparation of Conjugate 145

Conjugate 145 was prepared from compound 144 (200 mg) and 1000A lcaa CPG (1.8 g) using an identical procedure to that used for compound 1. Yield: 1.9 g, 20 μmol/g CPG loading. The resulting GalNAc loaded CPG solid support was employed in automated oligonucleotide synthesis using standard procedures. Nucleotide deprotection followed by removal from the solid support (with concurrent galactosamine acetate deprotection) afforded the GalNAc-oligonucleotide conjugate 145.

Example 10. Synthesis of Conjugate 150

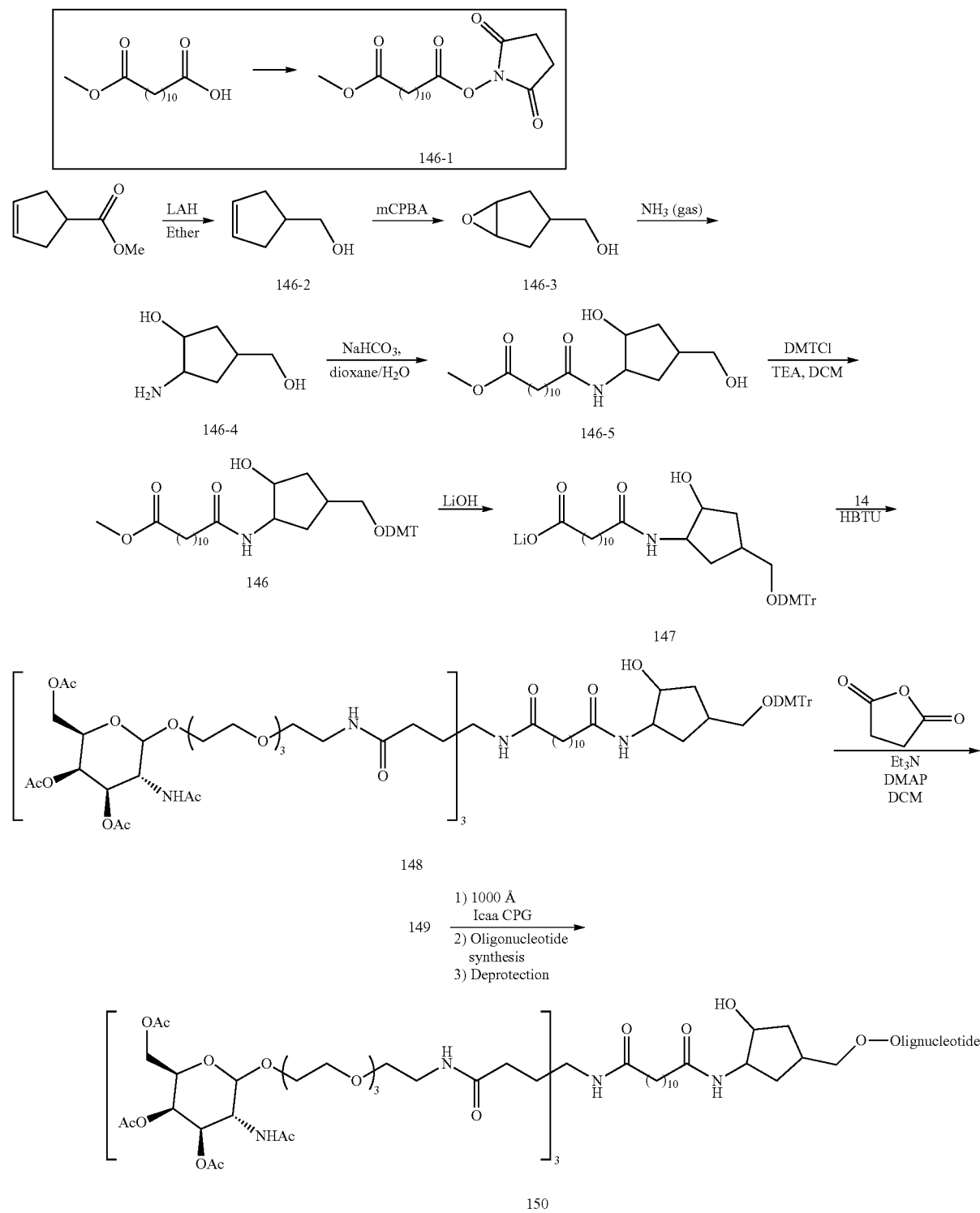

Step 1. Preparation of 146-1

To a solution of mono methyl ester of dodecanedioic acid (12.2 g, 50.0 mmol) in dichloromethane (300 mL) was added N-hydroxysuccinimide (6.10 g, 53.0 mmol) and 1-ethyl-3-(3-dimethylaminopropyl)carbodiimide hydrochloride (EDC) (10.52 g, 55.0 mmol). The cloudy mixture was stirred overnight at room temperature and the reaction became a clear solution. TLC indicated the reaction was completed. The organics were washed with saturated $NH_4Cl$ (300 mL) and brine (100 mL). The organic layer was separated, dried over $MgSO_4$ and concentrated to dryness to pure 1-(2,5-dioxopyrrolidin-1-yl) 12-methyl dodecanedioate 146-1 as a white solid (16.7 g, 97.8%).

Step 2. Preparation of cyclopent-3-en-1-ylmethanol 146-2

To a suspension of lithium aluminum hydride (15.2 g, 0.40 mol) in anhydrous ether (1 L) at 0° C. under nitrogen, was added the solution of methyl cyclopent-3-enecarboxylate (50 g, 0.40 mol) in ether (300 mL) dropwise over 5 hrs. The suspension was stirred at room temperature overnight. TLC indicated the completion of the reaction. The reaction was re-cooled to 0° C. Saturated solution of $Na_2SO_4$ (32 mL) was added dropwise to quench the reaction. After the addition was complete, the mixture was stirred for another 3 hrs and was filtered through a pad of celite. Evaporation of solvent afforded cyclopent-3-enylmethanol 146-2 (37.3 g, 95%) as a colorless liquid.

Step 3. Preparation of (6-oxabicyclo[3.1.0]hexan-3-yl)methanol 146-3

To a solution of cyclopent-3-enylmethanol 146-2 (4.0 g, 41 mmol) in dichloromethane (150 mL) at 0° C. was added 3-chloroperbenzoic acid (10 g, 45 mmol, 77% purity) by portion. The reaction was stirred overnight. Dichloromethane (150 mL) was added. The organics was washed with sodium thiosulfate (12 g in 10 mL water), followed by saturated $NaHCO_3$ (40 mL). This was repeated till all the remaining 3-chloroperbenzoic acid was washed away. The organic was dried over $MgSO_4$. Evaporation of solvent gave a mixture of cis- and trans-6-oxabicyclo[3.1.0]hexan-3-ylmethanol 146-3 (2.6 g, 57%) as a yellow oil. GC-MS: m/z 114 (5) ($M^+$), 95 (15), 88 (100), 81 (15).

Step 4. Preparation of 2-amino-4-(hydroxymethyl)cyclopentan-1-ol 146-4

To a solution of 6-oxabicyclo[3.1.0]hexan-3-ylmethanol 146-3 (2.0 g, 17.6 mmol) in methanol (20 mL) at 0° C. was purged ammonia gas for 10 min. The reaction was stirred at room temperature overnight. TLC indicated the incompletion of the reaction. Methanol was removed and $NH_3·H_2O$ (50 mL) was added and this was stirred at room temperature over a week. TLC confirmed the completion of the reaction. Water was removed by azeotropically with ethanol to afford 2-amino-4-(hydroxymethyl)cyclopentanol 146-4 (2.1 g, 91%) as a yellow oil.

Step 5. Preparation of Methyl 12-(2-hydroxy-4-(hydroxymethyl)cyclopentylamino)-12-oxododecanoate 146-5

Compound 146-5 was prepared from 2-amino-4-(hydroxymethyl)cyclopentanol 146-4 and 1-(2,5-dioxopyrrolidin-1-yl) 12-methyl dodecanedioate 146-1, using the same procedure as described in the synthesis of 12-(2-(tert-butoxycarbonylamino)ethylamino)-12-oxododecanoate (3-2). Methyl 12-(2-hydroxy-4-(hydroxymethyl)cyclopentylamino)-12-oxododecanoate 146-5 was obtained in 87.4% yield as an off-white solid.

Step 6. Preparation of Compound 147

Compound 147 was prepared quantitatively from compound 146 (1.4 g, 2.33 mmol) using an identical procedure to that used for compound 18.

Step 7. Preparation of Compound 148

Compound 148 was prepared from compound 147 (150 mg, 0.23 mmol) and compound 14 (431 mg, 0.23 mmol) using an identical procedure to that used for compound 19. Yield: 460 mg, 84%.

Step 8. Preparation of Compound 149

Compound 149 was prepared from compound 148 (460 mg, 0.19 mmol) using an identical procedure to that used for compound 20. Yield: 436 mg, 91%.

Step 9. Preparation of Conjugate 150

Compound 150 was prepared from compound 149 (436 mg) and 1000A lcaa CPG (2.62 g) using an identical procedure to that used for compound 1. Yield: 2.7 g, 21.3 μmol/g CPG loading. The resulting GalNAc loaded CPG solid support was employed in automated oligonucleotide synthesis using standard procedures. Nucleotide deprotection followed by removal from the solid support (with concurrent galactosamine acetate deprotection) afforded the GalNAc-oligonucleotide conjugate 150.

Example 11. Synthesis of Conjugates 153, 158, 163, 168 and 173

Scheme 22.

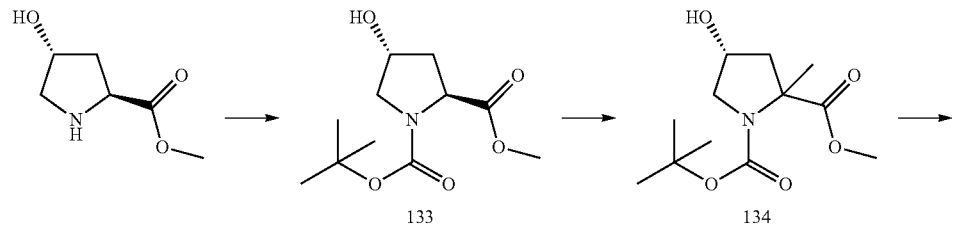

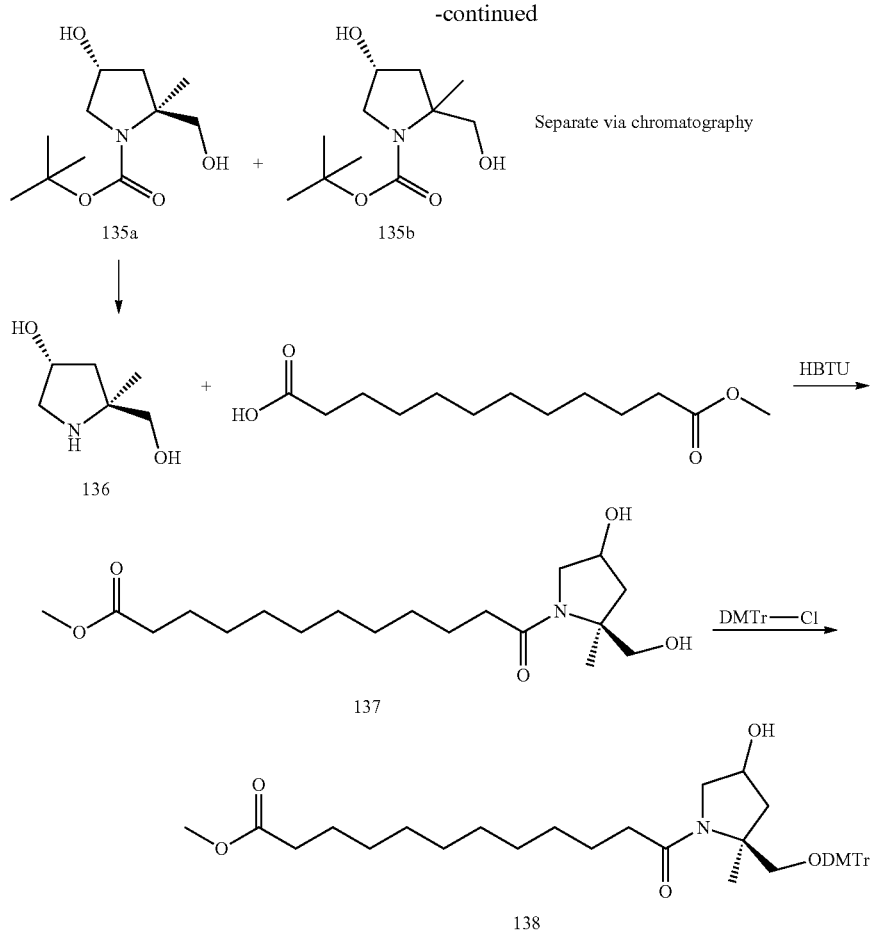

Step 1. Preparation of 1-(tert-butyl) 2-methyl (2S, 4R)-4-hydroxypyrrolidine-1,2-dicarboxylate (133)

Methyl (2S,4R)-4-hydroxypyrrolidine-2-carboxylate (25.9 g, 46 mmol), BOC anhydride (65.9 g, 302.5 mmol) and TEA (42 ml, 302.5 mmol) were stirred in DCM at RT for 16 h. The organics were washed sequentially with 1M HCl (×2), saturated NaHCO₃ (×2), H₂O and brine, dried and concentrated in-vacuo to give 1-(tert-butyl) 2-methyl (2S, 4R)-4-hydroxypyrrolidine-1,2-dicarboxylate (133) (58.1 g, 85%).

Step 2. Preparation of 1-(tert-butyl) 2-methyl (4R)-4-hydroxy-2-methylpyrrolidine-1,2-dicarboxylate (134)

1-(tert-butyl) 2-methyl (2S,4R)-4-hydroxypyrrolidine-1,2-dicarboxylate (133) (5 g, 20.4 mmol) and MeI (12 g, 84.5 mmol) were stirred in anhydrous THF at −40° C. LDA (2.0 M solution in THF) (37.5 mL, 75 mmol) was added dropwise. The reaction was allowed to warm to RT and stirred for 4 h then quenched with saturated NH₄Cl. The reaction was extracted with EtOAc, washed with H₂O and brine, dried (Na₂SO₄) and concentrated in-vacuo. The residue was purified by column chromatography 50:50 EtOAc/hexanes to give 1-(tert-butyl) 2-methyl (4R)-4-hydroxy-2-methylpyrrolidine-1,2-dicarboxylate (134) as a racemic mixture (3.6 g, 68%)

Step 3. Preparation of tert-butyl (2S,4R)-4-hydroxy-2-(hydroxymethyl)-2-methylpyrrolidine-1-carboxylate (135a)

1-(Tert-butyl) 2-methyl (4R)-4-hydroxy-2-methylpyrrolidine-1,2-dicarboxylate (134) (19 g, 73.5 mmol) was stirred in anhydrous THF under N₂. LiBH₄ solution (48 ml, 96 mmol) was added dropwise and the reaction stirred at RT for 48 h. The reaction was quenched with 1M NaOH, the THF removed in-vacuo and the residual extracted with EtOAc (4×100 ml). The organics were washed with H₂O and brine, dried (Na₂SO₄) and concentrated in-vacuo. The residue was purified by column chromatography (5% MeOH/DCM) to give tert-butyl (2S,4R)-4-hydroxy-2-(hydroxymethyl)-2-methylpyrrolidine-1-carboxylate (135a) as the major product (8 g, 47%). Structure assigned according to literature references.

Step 4. Preparation of (3R,5S)-5-(hydroxymethyl)-5-methylpyrrolidin-3-ol hydrochloride (136)

tert-Butyl (2S,4R)-4-hydroxy-2-(hydroxymethyl)-2-methylpyrrolidine-1-carboxylate (135a) (8 g, 34.6 mmol) was stirred in EtOAc at RT and gaseous HCl applied for approximately two minutes. The reaction was stirred for one hour then concentrated in-vacuo and dried under high vacuum to give (3R,5S)-5-(hydroxymethyl)-5-methylpyrrolidin-3-ol hydrochloride (136) in quantitative fashion.

Step 5. Preparation of methyl 12-((2S,4R)-4-hydroxy-2-(hydroxymethyl)-2-methylpyrrolidin-1-yl)-12-oxododecanoate (137)

(3R,5S)-5-(Hydroxymethyl)-5-methylpyrrolidin-3-ol hydrochloride (136) (7.9 g, 47.4 mmol), 12-methoxy-12-oxododecanoic acid (11.5 g, 47.4 mmol), HBTU (36 g, 76 mmol) and TEA 20 mL, 142.2 mmol) were stirred in DCM at RT for 16 h. The precipitate was removed by filtration and the organics washed with 1M HCl (×2), saturated NaHCO₃ (×2), H₂O and brine. After drying the organics were concentrated in-vacuo and purified by column chromatography (5% MeOH/DCM) to give methyl 12-((2S,4R)-4-hydroxy-2-(hydroxymethyl)-2-methylpyrrolidin-1-yl)-12-oxododecanoate (137) (3.1 g, 18.3%).

Step 6. Preparation of methyl 12-((2S,4R)-2-((bis(4-methoxyphenyl)(phenyl)methoxy)-methyl)-4-hydroxy-2-methylpyrrolidin-1-yl)-12-oxododecanoate (138)

Methyl 12-((2S,4R)-4-hydroxy-2-(hydroxymethyl)-2-methylpyrrolidin-1-yl)-12-oxododecanoate (137) (3.1 g, 9.0 mmol), DMTr-Cl (2.8 g, 8.2 mmol) and TEA (1.1 ml, 8.2 mmol) were stirred in DC< at RT for 16 h. The reaction was concentrated in-vacuo and the residue purified by column chromatography (5% MeOH/DCM, 0.1% TEA) to give methyl 12-((2S,4R)-2-((bis(4-methoxyphenyl)(phenyl)methoxy)methyl)-4-hydroxy-2-methylpyrrolidin-1-yl)-12-oxododecanoate (138) (2.7 g, 45.5 mmol).

MgSO₄, and concentrated to dryness. This was used directly for the next reaction without purification.

Step 8. Preparation of Compound 154-2

2-(2-(Bis(4-methoxyphenyl)(phenyl)methoxy)ethyl)isoindoline-1,3-dione (154-1) obtained above and hydrazine monohydrate (3.6 mL, 74 mmol) in ethanol (100 mL) was stirred overnight at room temperature. TLC indicated the completion of the reaction. The precipitate was filtered out. The filtrate was evaporated. The residue was taken up by ethyl acetate (100 mL). The organic solution was washed with 10% NaOH, water and brine, and dried over MgSO₄. Evaporation of solvent afforded 2-(bis(4-methoxyphenyl)(phenyl)methoxy)ethanamine (154-2) as a yellow liquid (8.11 g, 89.3% yield over two steps). This was used for the next reaction without further purification.

Step 9. Preparation of Compound 154-3

To a solution of L-threonine (1.19 g, 10.0 mmol) and NaHCO₃ (2.3 g, 27 mmol) in water (20 mL) and dioxane (10 mL), was added 1-(2,5-dioxopyrrolidin-1-yl) 12-methyl dodecanedioate 146-1 (3.1 g, 9.1 mmol) in dioxane (10 mL) dropwise. The reaction mixture was stirred at room temperature overnight. 4N HCl (10 mL) was added. The precipitate was collected by filtration and washed with water (3×10 mL). The solid was dried over P₂O₅ in a desiccator to afford (2S,3R)-3-hydroxy-2-(12-methoxy-12-oxododecanamido)butanoic acid 154-3 as an off-white solid (2.84 g, 82.2%). LC-MS (ESI): m/z: 346 (100), (M+H⁺).

Scheme 23

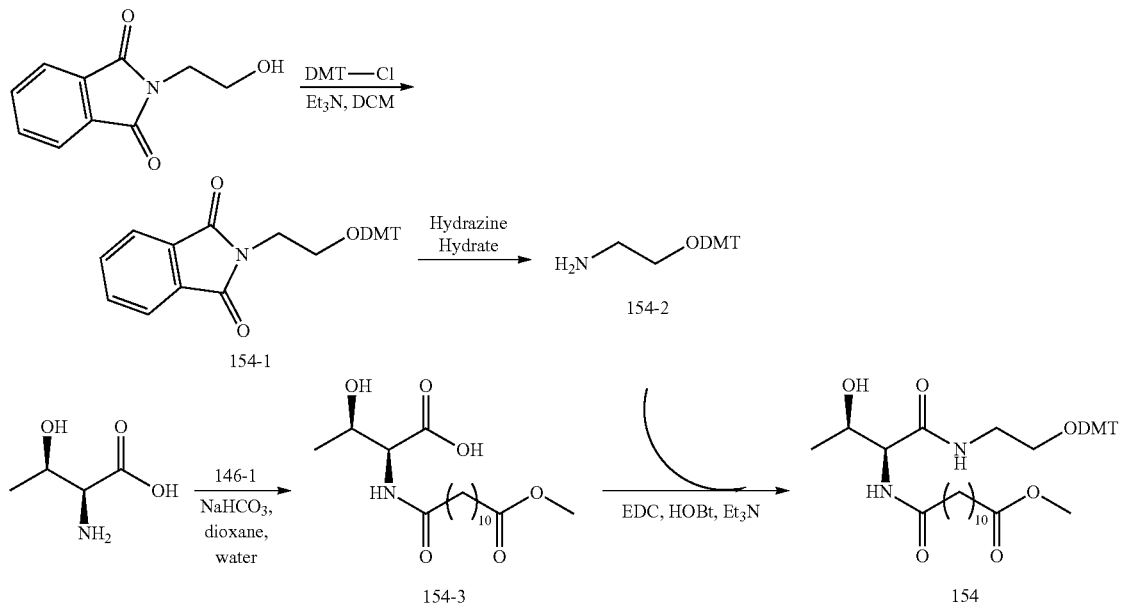

Step 7. Preparation of Compound 154-1

To a solution of N-(2-hydroxyethyl)phthalimide (4.80 g, 25.0 mmol) and 4,4'-dimethoxytrityl chloride (8.8 g, 26.0 mmol) in dichloromethane (200 mL) at 0° C. under nitrogen, was added triethylamine (10.4 mL, 74.6 mmol) dropwise. The reaction mixture was stirred at room temperature for 3 hrs. TLC indicated the completion of the reaction. The organic layer was washed with brine (100 mL), dried over

Step 10. Preparation of Compound 154

(2S,3R)-3-hydroxy-2-(12-methoxy-12-oxododecanamido)butanoic acid 154-3 (2.47 g, 7.15 mmol), 2-(bis(4-methoxyphenyl)(phenyl)methoxy)ethanamine 154-2 (2.60 g, 7.15 mmol), EDC (1.64 g, 8.58 mmol), 1-hydroxybenzotriazole (HOBt) (1.16 g, 8.58 mmol) and TEA (2.4 mL, 17.2 mmol) were stirred in dichloromethane (72 mL) at room temperature for 2 hrs. Water (30 mL) was added. The organic layer was separated and washed with brine (2×30 mL).

Evaporation of solvent followed by column chromatography (30% ethyl acetate/hexanes-50% ethyl acetate/hexanes) afforded methyl 12-((2S,3R)-1-(2-(bis(4-methoxyphenyl)(phenyl)methoxy)ethylamino)-3-hydroxy-1-oxobutan-2-ylamino)-12-oxododecanoate 154 as a waxy yellow semi-solid (2.60 g, 52.6%). $^1$HNMR (400 MHz, acetone-d6, ppm): δ 7.51 (t, J=5.5 Hz, 1H), 7.45-7.49 (m, 2H), 7.28-7.36 (m, 6H), 7.21 (tt, J=7.2, 1.2 Hz, 1H), 7.08 (d, J=8.1 Hz, 1H), 6.88 (dt, J=8.9, 2.5 Hz, 4H), 4.39 (dd, J=8.2, 3.0 Hz, 1H), 4.20-4.27 (m, 1H), 3.78 (s, 6H), 3.60 (s, 1H), 3.35-3.52 (m, 2H), 3.07-3.16 (m, 2H), 2.23-2.37 (m, 4H), 1.53-1.65 (m, 4H), 1.23-1.36 (m, 12H), 1.10 (d, J=6.4 Hz, 3H).

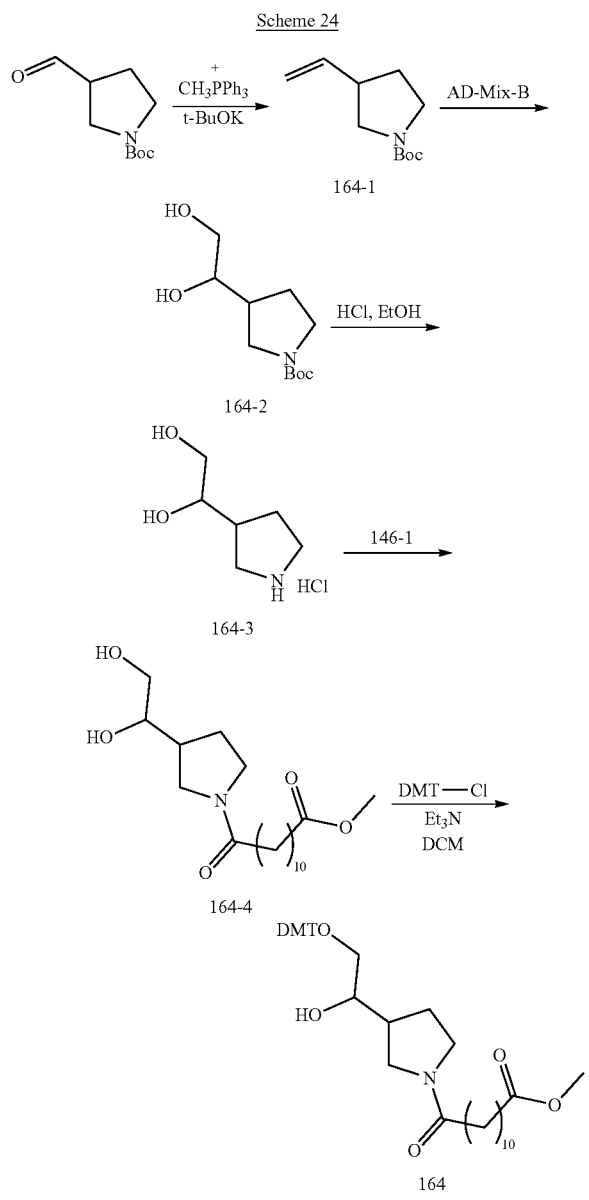

Scheme 24

Step 11. Preparation of Compound 164-1

To a suspension of potassium t-butoxide (14.6 g, 130 mol) in THF (120 mL)/ether (360 mL) was added methyltriphenylphosphonium bromide (46.6 g, 130 mmol). The mixture was refluxed for 2 hrs and then cooled to 0° C. tert-butyl 2-formylpyrrolidine-1-carboxylate (13.0 g, 65.2 mmol) in ether (50 mL) was added dropwise. The reaction mixture was stirred at 0° C. and then quenched by the addition of water (250 mL). The organic layer was separated and the aqueous was extracted with ether (250 mL). The combined extract was dried over MgSO$_4$. Evaporation of solvent, followed by column chromatography purification (5% ethyl acetate/hexanes) gave tert-butyl 3-vinylpyrrolidine-1-carboxylate 164-1 (11.5 g, 89.4%) as a colorless liquid. GC-MS: m/z: 197 (2) (M*), 141 (40), 124 (30), 57 (100).

Step 12. Preparation of Compound 164-2

To a mixture of t-BuOH (140 mL) and water (70 mL), was charged AD-mix-P (47.4 g) and methanesulfonamide (2.89 g, 30.4 mmol). The mixture was stirred at room temperature for 30 min and was then cooled to 0° C. tert-Butyl 3-vinylpyrrolidine-1-carboxylate 164-1 (6.00 g, 30.4 mmol) was added. The reaction was stirred at room temperature overnight. The reaction mixture was cooled to 0° C. Sodium thiosulfate pentahydrate (96 g, 387 mmol) was added and the temperature was allowed to warm to room temperature. Water (700 mL) was added and the mixture was extracted with ethyl acetate (500 mL). The extract was washed with water (2×50 mL) and brine (50 mL), and dried over MgSO$_4$. Evaporation of solvent, followed by column chromatography (2% methanol/dichloromethane-7% methanol/dichloromethane) gave tert-butyl 3-(1,2-dihydroxyethyl)pyrrolidine-1-carboxylate 164-2 (5.4 g, 77%) as a light brown oil.

Step 13. Preparation of Compound 164-3

To a solution of tert-butyl 3-(1,2-dihydroxyethyl)pyrrolidine-1-carboxylate 164-2 (3.1 g, 13.4 mmol) in ethanol (10 mL) was added 3N HCl (30 mL, 90 mmol). The reaction mixture was stirred at room temperature overnight. TLC indicated the completion of the reaction. Ethanol was evaporated. Toluene was added and evaporated. This was repeated three times to give 1-(pyrrolidin-3-yl)ethane-1,2-diol hydrochloride 164-3 (2.0 g, 89%) as a brown oil. LC-MS (ESI): m/z: 132 (100), (M+H$^+$, free amine).

Step 14 Preparation of Compound 164-4

To a solution of 1-(pyrrolidin-3-yl)ethane-1,2-diol hydrochloride 164-2 (2.0 g, 12 mmol) in water (30 mL) was added NaHCO$_3$ (3.7 g, 44 mmol) by portion. Dioxane (20 mL) was then added. To the above solution was added 1-(2,5-dioxopyrrolidin-1-yl) 12-methyl dodecanedioate 146-1 (3.7 g, 11 mmol) in dioxane (30 mL). The reaction mixture was stirred overnight. This was extracted with ethyl acetate (3×100 mL). The combined extract was washed with 0.5N HCl (50 mL) and brine (50 mL), and dried over MgSO$_4$.

Step 15. Preparation of Compound 164

This substance was prepared from methyl 12-(3-(1,2-dihydroxyethyl)pyrrolidin-1-yl)-12-oxododecanoate 164-4 and 4,4-dimethoxytrityl chloride (1 eq) using the same procedure as described in the synthesis of 2-(2-(bis(4-methoxyphenyl)(phenyl)methoxy)ethyl)isoindoline-1,3-dione 138. The product was purified by column chromatography (1.5% methanol/dichloromethane). Methyl 12-(3-(2-(bis(4-methoxyphenyl)(phenyl)methoxy)-1-hydroxyethyl) pyrrolidin-1-yl)-12-oxododecanoate 164 was obtained in 51% yield as a yellow oil. ¹HNMR (400 MHz, acetone-d6, ppm): δ 7.49-7.54 (m, 2H), 7.35-7.40 (m, 4H), 7.28-7.34 (m, 2H), 7.19-7.25 (m, 1H), 6.86-6.91 (m, 4H), 4.11-4.20 (m, 1H), 3.79 (s, 6H), 3.68-3.77 (m, 1H), 3.60 (s, 3H), 3.29-3.59 (m, 3H), 3.06-3.20 (m, 3H), 2.33-2.55 (m, 1H), 2.29 (t, J=7.4 Hz, 2H), 2.19 (t, J=7.6 Hz, 2H), 1.65-2.0 (m, 2H), 1.51-1.62 (m, 4H), 1.26-1.35 (m, 12H).

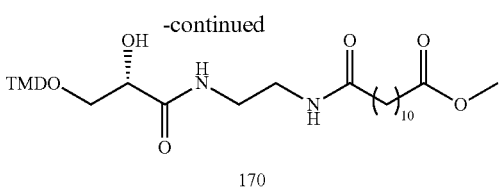

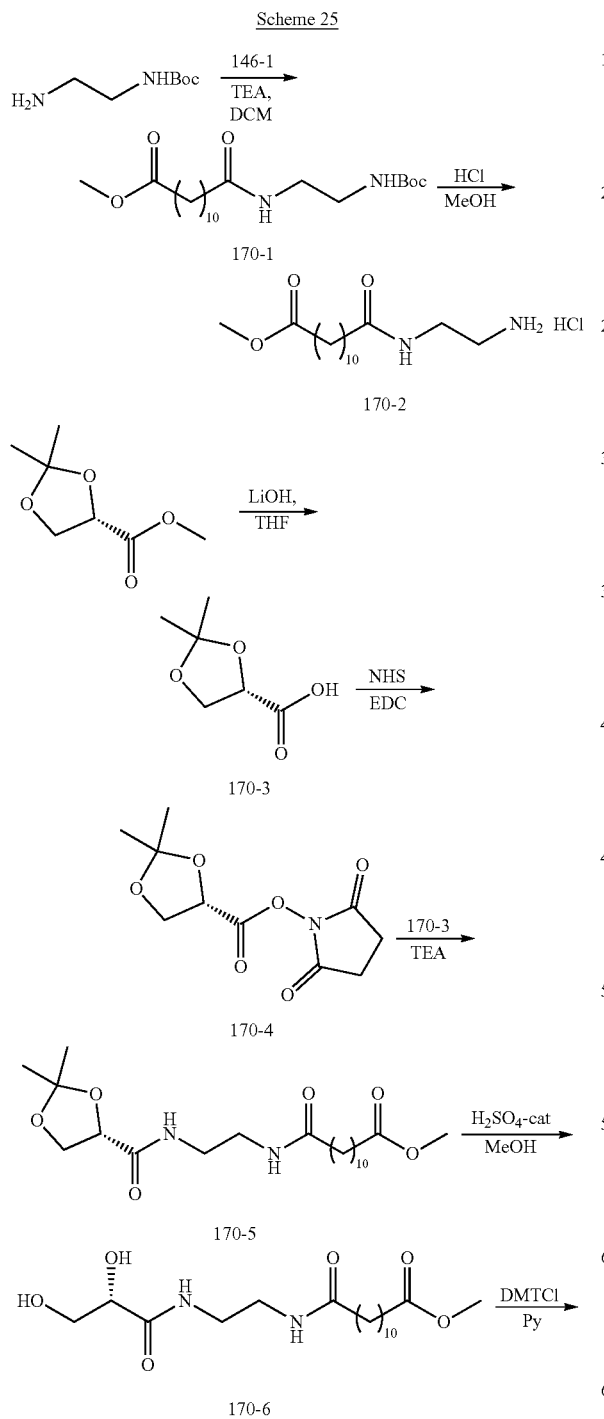

Step 16. Preparation of Compound 170-1

To a solution of tert-butyl 2-aminoethylcarbamate (2.88 g, 18.0 mmol) and triethylamine (2.98 g, 29.4 mmol) in dichloromethane (100 mL), was added 1-(2,5-dioxopyrrolidin-1-yl) 12-methyl dodecanedioate (146-1) (5.09 g, 14.9 mmol) in dichloromethane (50 mL) dropwise at room temperature. The reaction mixture was stirred overnight and TLC indicated the completion of the reaction. 100 mL brine was added and the organic layer was separated. The organic layer was washed with 0.5N HCl (150 mL), brine (2×100 mL) and dried over MgSO₄. Evaporation of solvent gave pure methyl 12-(2-(tert-butoxycarbonylamino)ethylamino)-12-oxododecanoate 170-1 (5.85 g 100%) as a white solid.

Step 17. Preparation of Compound 170-2

To a solution of 12-(2-(tert-butoxycarbonylamino)ethylamino)-12-oxododecanoate 170-1 (5.55 g, 14.4 mmol) in methanol (100 mL) at 0° C., was added thionyl chloride (3.3 mL, 45.5 mmol) dropwise. The reaction was then stirred at room temperature overnight. TLC indicated the completion of the reaction. The solvent and volatile organics were evaporated. The residue was then co-evaporated with heptanes twice to give methyl 12-(2-aminoethylamino)-12-oxododecanoate hydrochloride 170-2 quantitatively as a white solid.

LC-MS (ESI): m/z: 287 (100), (M+H⁺, free amine).

Step 18. Preparation of Compound 170-3

(−)-Methyl (S)-2,2-dimethyl-1,3-dioxolane-4-carboxylate (5.01 g, 31.2 mmol) and LiOH H₂O (2.55 g, 60.8 mmol) in THF (50 mL) and water (50 mL) was stirred overnight. TLC indicated the completion of the reaction. THF was evaporated and the aqueous was acidified with 1N HCl to pH=1. This was extracted with ethyl acetate (5×50 mL). The combined extract was dried over MgSO₄. Evaporation of solvent gave (S)-2,2-dimethyl-1,3-dioxolane-4-carboxylic acid 170-3 (2.93 g, 64.3%) as a light yellow liquid.

Step 19. Preparation of Compound 170-4

Compound 170-4 was synthesized from (S)-2,2-dimethyl-1,3-dioxolane-4-carboxylic acid 170-3 and N-hydroxysuccinimide in 86% yield, using the same procedure as described in the synthesis of 1-(2,5-dioxopyrrolidin-1-yl) 12-methyl dodecanedioate 146-1. (S)-2,5-Dioxopyrrolidin-1-yl 2,2-dimethyl-1,3-dioxolane-4-carboxylate 170-4 was obtained in 86% yield as a white solid.

Step 20. Preparation of Compound 170-5

To a suspension of methyl 12-(2-aminoethylamino)-12-oxododecanoate hydrochloride 170-2 (14.4 mmol) and (S)-2,5-dioxopyrrolidin-1-yl 2,2-dimethyl-1,3-dioxolane-4-carboxylate 170-4 (3.80 g, 15.6 mmol) in dichloromethane (100 mL) was added triethylamine (6 mL, 43.0 mmol) in dichloromethane (25 mL) over 4 hrs at 0° C. The reaction mixture was then stirred at room temperature overnight. LC-MS indicated that the starting material 170-2 was completely converted. The organic layer was washed with brine (50 mL), 1N HCl (50 mL), brine (50 mL), dried over MgSO$_4$ and concentrated to dryness to afford (S)-methyl 12-(2-(2,2-dimethyl-1,3-dioxolane-4-carboxamido)ethylamino)-12-oxododecanoate 170-5 (5.93 g, 99.3%) as a white solid.

Step 21. Preparation of Compound 170-6

To a solution of (S)-methyl 12-(2-(2,2-dimethyl-1,3-dioxolane-4-carboxamido)ethylamino)-12-oxododecanoate 170-5 (5.93 g, 14.3 mmol) was added one drop of concentrated sulfuric acid. This was refluxed for 6 hrs and then cooled to room temperature. The solid was collected through filtration and washed twice with cold methanol. The solid was dried in the air (3.32 g). The second crop (0.42 g) was obtained from the mother liquid to give (S)-methyl 12-(2-(2,3-dihydroxypropanamido)ethylamino)-12-oxododecanoate 170-6 (3.74 g in total, 69.4%) as a white crystal. LC-MS (ESI): m/z: 375 (100), (M+H$^+$). $^1$HNMR (400 MHz, DMSO-d6, ppm): δ 7.79 (br, 2H), 5.49 (d, J=5.3 Hz, 1H), 4.66 (t, J=5.8 Hz, 1H), 3.83-3.88 (m, 1H), 3.55-3.61 (m, 4H), 3.41-3.47 (m, 1H), 3.05-3.15 (m, 4H), 2.29 (t, J=7.4 Hz, 2H), 2.03 (t, J=7.6 Hz, 2H), 1.42-1.52 (m, 4H), 1.18-1.29 (m, 12H).

Step 22. Preparation of Compound 170

To a solution of (S)-methyl 12-(2-(2,3-dihydroxypropanamido)ethylamino)-12-oxododecanoate 170-6 (2.99 g, 7.99 mmol) in dry pyridine (57.5 mL) under nitrogen, was added 4,4'-dimethoxytrityl chloride (2.84 g, 8.38 mmol) in one portion. The reaction was stirred at room temperature for two days. Methanol (5 mL) was added to quench the reaction.

Pyridine was evaporated. Toluene was added and then evaporated. This was repeated three times. Water (100 mL) was added and this was extracted with ethyl acetate (5×250 mL). The extracts were combined and dried over MgSO4. Evaporation of solvent, followed by column chromatography (1% methanol/dichloromethane-3% methanol/dichloromethane) gave (S)-methyl 12-(2-(3-(bis(4-methoxyphenyl)(phenyl)methoxy)-2-hydroxypropanamido)-ethylamino)-12-oxododecanoate 170 (1.70 g, 31.4%) as a viscous oil. $^1$HNMR (400 MHz, acetone-d6, ppm): δ 7.64-7.70 (br, 1H), 7.47-7.51 (m, 2H), 7.33-7.37 (m, 4H), 7.26-7.32 (m, 2H), 7.20 (dt, J=7.3, 2.1 Hz, 1H), 7.11 (br, 1H), 6.86 (d, J=8.7 Hz, 4H), 4.84 (br, 1H), 4.21 (dd, J=5.1, 3.8 Hz, 1H), 3.78 (s, 6H), 3.60 (s, 1H), 3.25-3.42 (m, 6H), 2.28 (t, J=7.4 Hz, 2H), 1.48-1.62 (m, 4H), 1.21-1.34 (m, 12H).

Scheme 26.

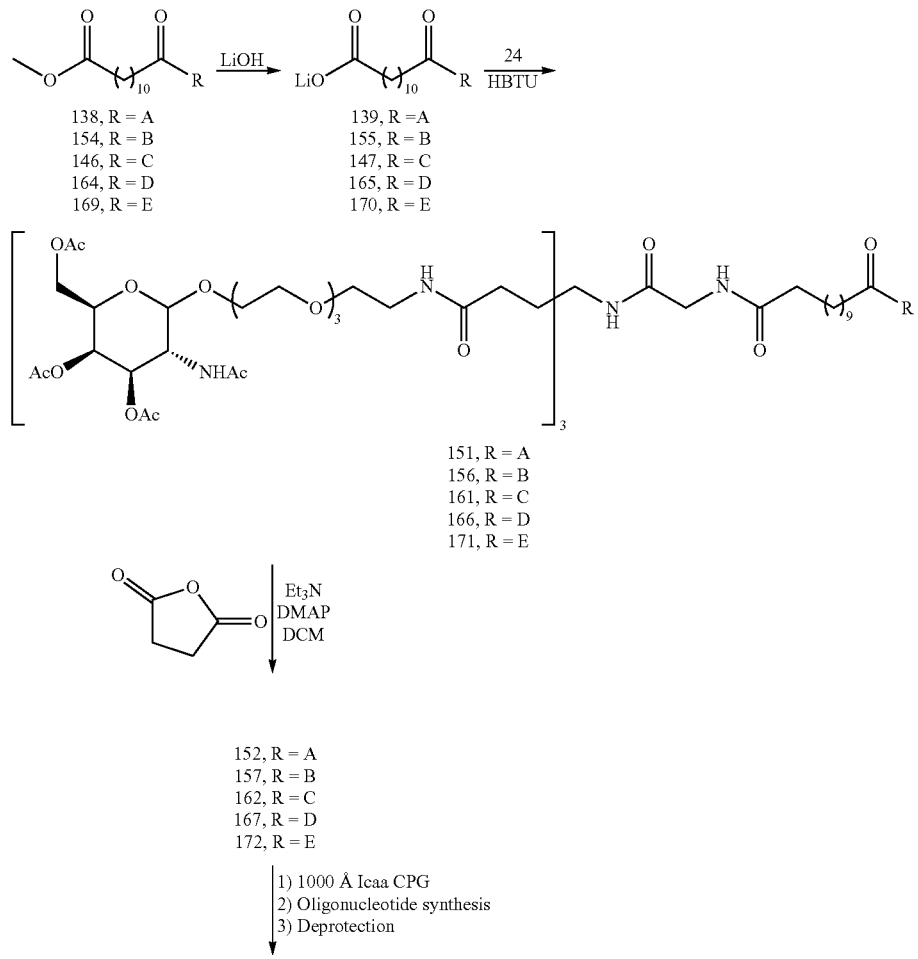

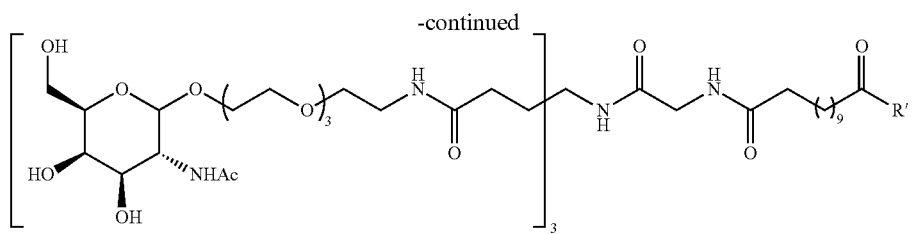
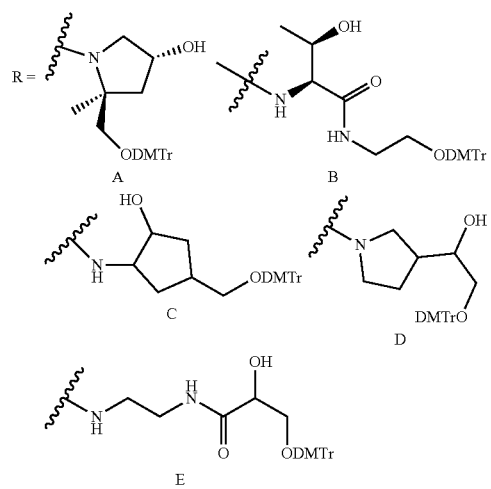
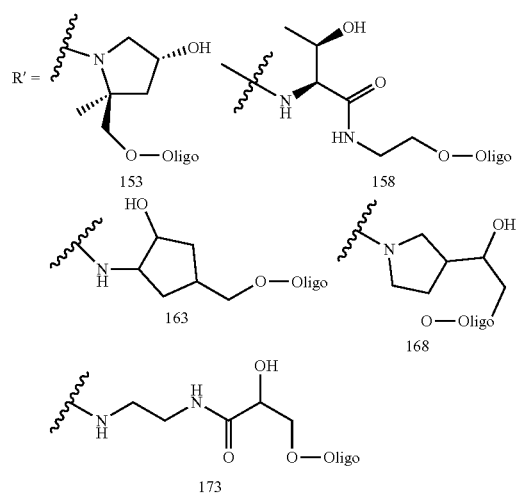
Step 23. Preparation of Compounds 139, 155, 160, 165 and 170
Compounds 139, 155, 160, 165 and 170 were prepared from compounds 138, 154, 159, 164 and 169 using an identical procedure to that used for compound 18.
Step 24. Preparation of Conjugates 153, 158, 163, 168 and 173
Conjugates 153, 158, 163, 168 and 173 were prepared from compound 139, 154, 159, 164 and 169 using an identical procedure to that used for compound 1.

Example 12. Synthesis of Conjugate 176
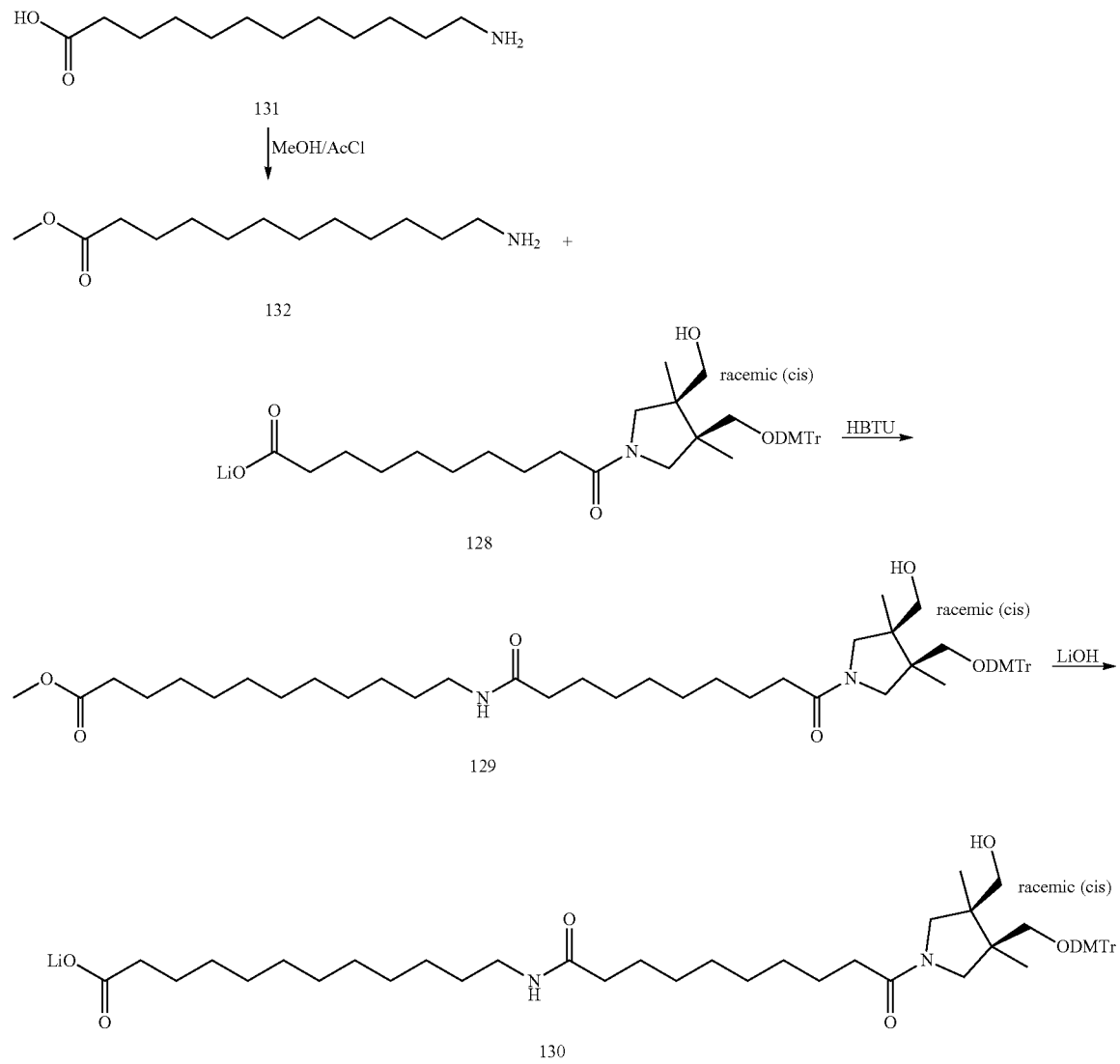
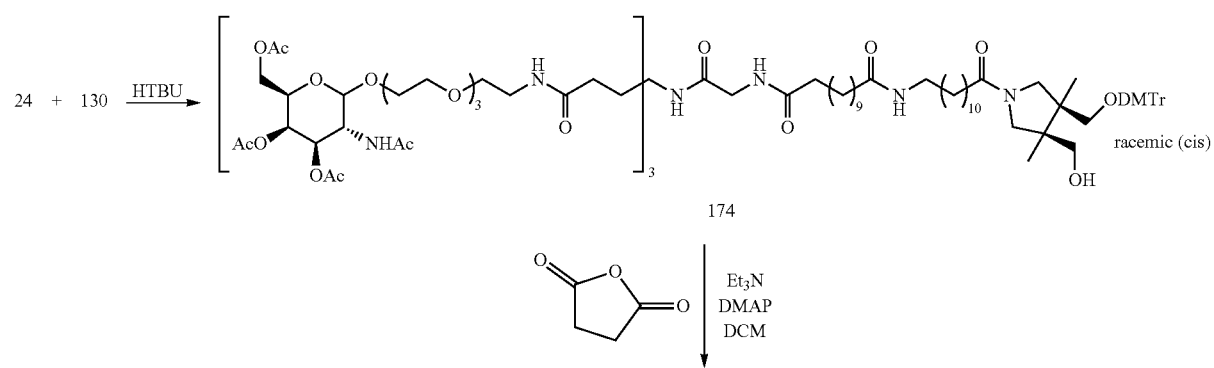

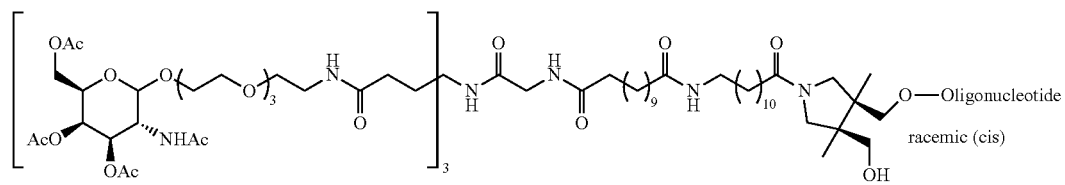

176

Step. 1. Preparation of methyl 12-aminododecanoate 132

12-aminoundecanoic acid (131) (10 g, 4.64 mmol) was stirred in MeOH at RT. Acetyl chloride (856 μL, 12 mmol) was added dropwise and the reaction stirred for 1.5 hr. The solvent was removed in-vacuo, the residue taken up in MTBE and chilled in the fridge overnight. The resultant precipitate was collected by filtration, washed with ice cold MTBE and dried under high vacuum to afford methyl 12-aminododecanoate 132.

Step 2. Preparation of Racemic (cis) Methyl 12-(12-(10-(3-((bis(4-methoxyphenyl)-(phenyl)methoxy)methyl)-4-(hydroxymethyl)-3,4-dimethylpyrrolidin-1-yl)-10-oxodecanamido)dodecanamido)dodecanoate 129

Lithium racemic (cis) 10-(3-((bis(4-methoxyphenyl)(phenyl)methoxy)methyl)-4-(hydroxymethyl)-3,4-dimethylpyrrolidin-1-yl)-10-oxodecanoate (128) (2 g, 3.1 mmol), of methyl 12-aminododecanoate (132) (778 mg, 3.1 mmol), HBTU (1.2 g, 3.1 mmol) and TEA (1.4 mL, 10 mmol) were stirred in DCM at RT O/N. The precipitate was removed by filtration, the filtrate concentrated in-vacuo and the residue purified by column chromatography (5% MeOH, DCM). TLC showed two close running spots with identical mass that were assigned as geometric isomers and pooled together to give of Methyl 12-(12-(10-((3R,4S)-3-((bis(4-methoxyphenyl)(phenyl)methoxy)methyl)-4-(hydroxymethyl)-3,4-dimethylpyrrolidin-1-yl)-10-oxodecanamido)dodecanamido)dodecanoate (129) in quantitative fashion.

Step 3. Preparation of Racemic (cis) Lithium 12-(12-(10-(~3-((bis(4-methoxyphenyl)(phenyl)methoxy)methyl)-4-(hydroxymethyl)-3,4-dimethylpyrrolidin-1-yl)-10-oxodecanamido)-dodecanamido)dodecanoate 130

Racemic (cis) methyl 12-(12-(10-(3-((bis(4-methoxyphenyl)(phenyl)methoxy)methyl)-4-(hydroxymethyl)-3,4-dimethylpyrrolidin-1-yl)-10-oxodecanamido)dodecanamido)dodecanoate (129) (3.1 mmol) was stirred in THF:H$_2$O (50:50) with LiOH (88 mg, 3.7 mmol) at RT O/N. Reaction was confirmed by TLC and the THF removed in-vacuo. The aqueous solution was frozen in liquid N$_2$ and lyophilized for 48 hours to give racemic (cis) Lithium 12-(12-(10-(3-((bis(4-methoxyphenyl)(phenyl)-methoxy)methyl)-4-(hydroxymethyl)-3,4-dimethylpyrrolidin-1-yl)-10-oxodecanamido)-dodecanamido)dodecanoate 130 quantitatively.

Step 4. Preparation of Conjugate 176

Conjugate 176 was prepared from compounds 24 and 130 using an identical procedure to that used for compound 1.

Example 13. Synthesis of Conjugate 179

Scheme 29.

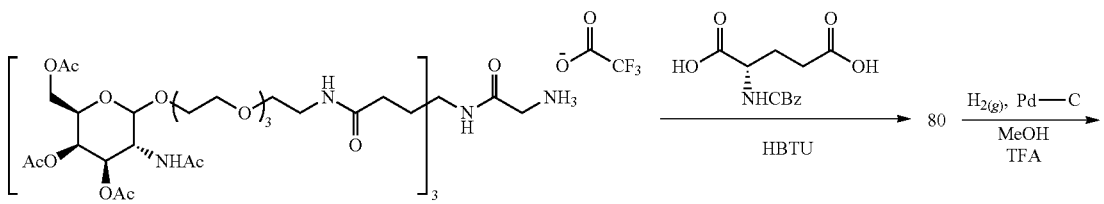

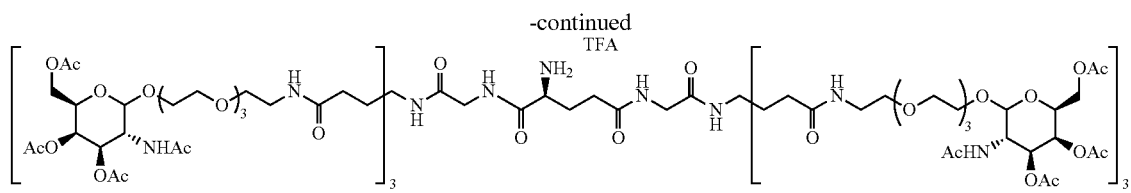

81

Scheme 30.

81 + 18

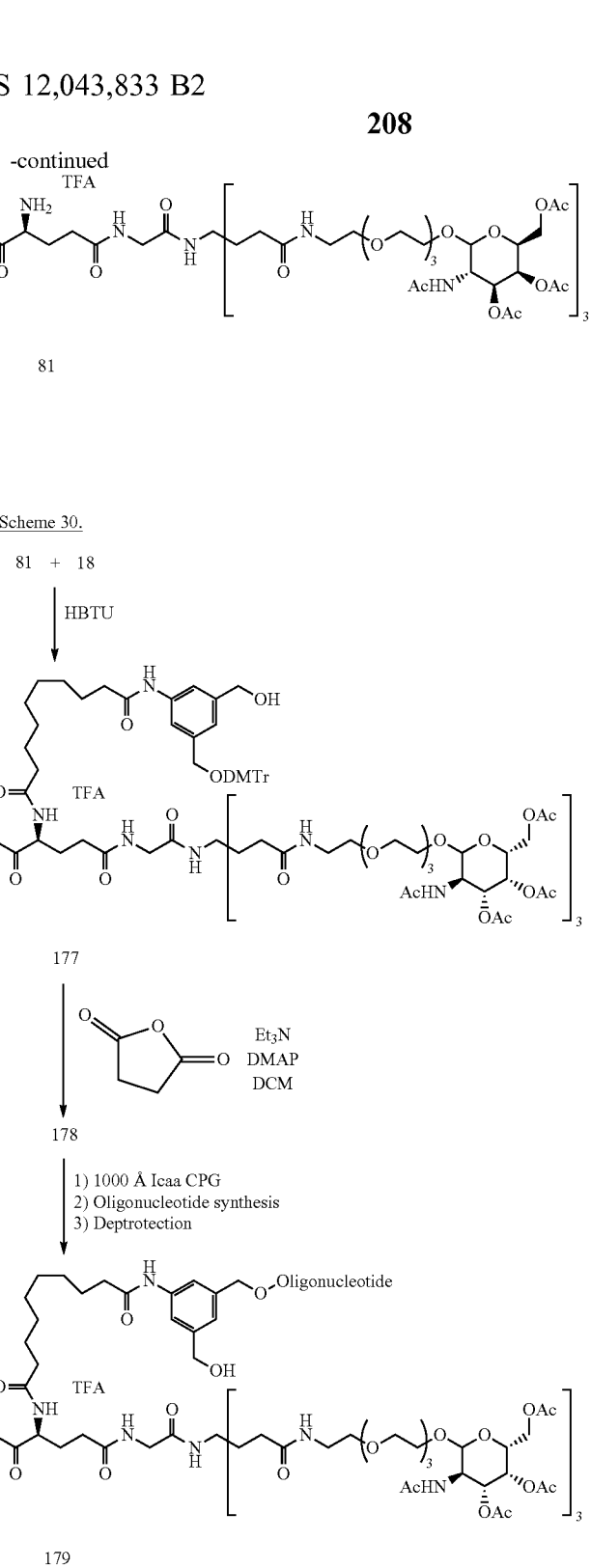

Step 1. Preparation of Compound 80

Compound 24 (2 g, 0.86 mmol), N-carbobenzoxy-L-glutamic acid (120 mg, 0.43 mmol), HBTU (326 mg, 0.86 mmol) and TEA (353 µL, 2.6 mmol) were stirred in DCM at RT O/N. The mixture was concentrated in-vacuo and purified by column chromatography to give compound 80 (2.88 g, 83%).

Step 2. Preparation of Compound 81

Compound 81 was prepared from compounds 80 (670 mg, 0.17 mmol) using an identical procedure to that used for compound 14. The compound was used crude in subsequent reactions and the yield taken as quantitative.

Step 3. Preparation of Conjugate 179
Conjugate 179 was prepared from compounds 18 and 81 using an identical procedure to that used for compound 1.
Example 14. Synthesis of Conjugate 182
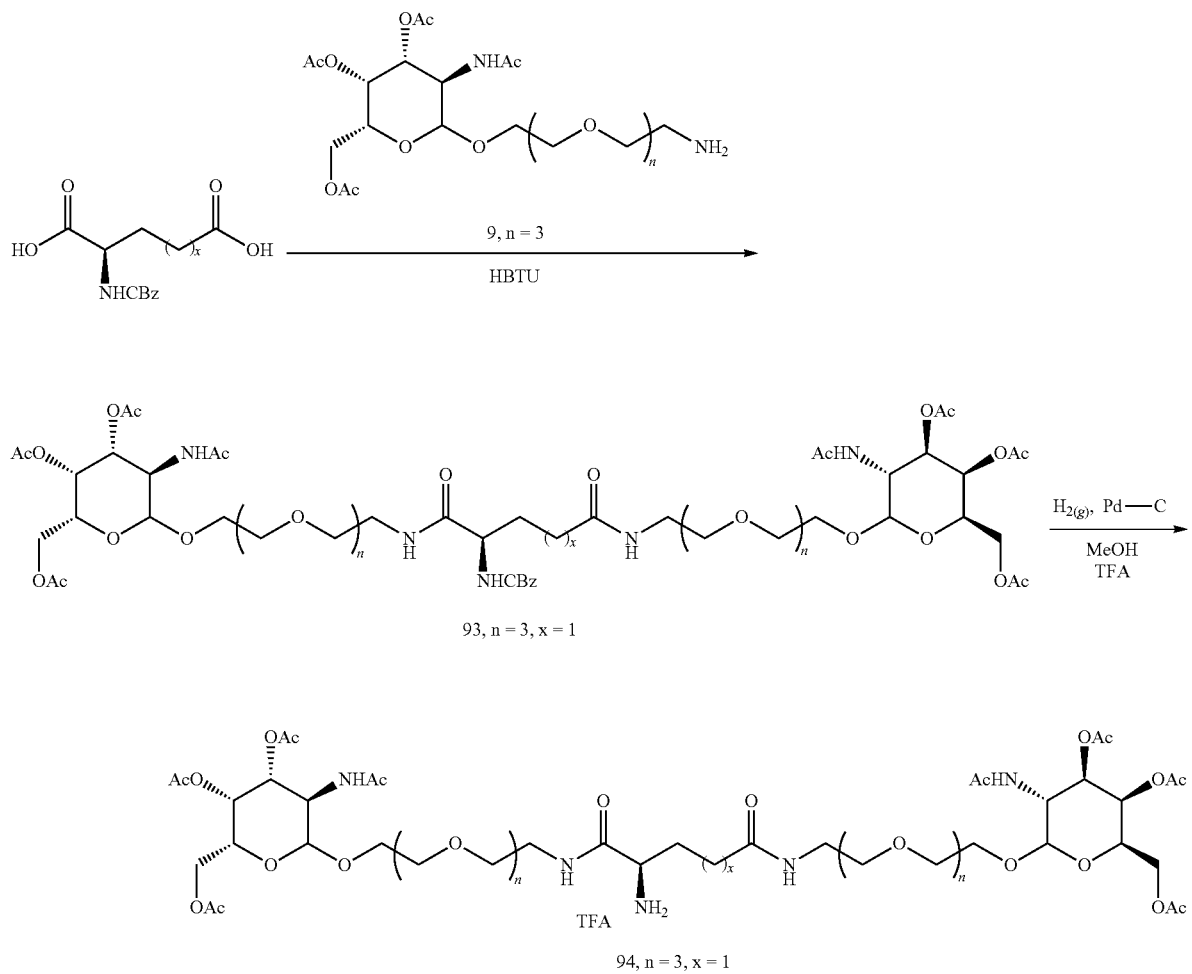
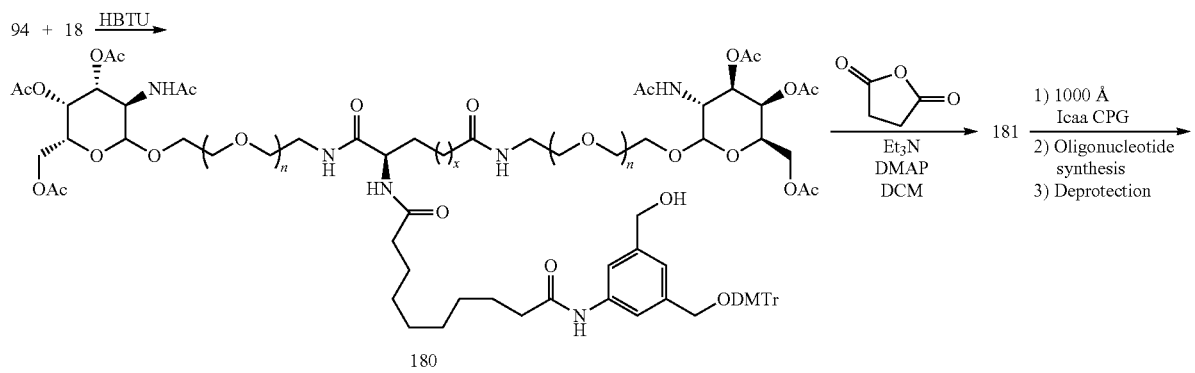

211

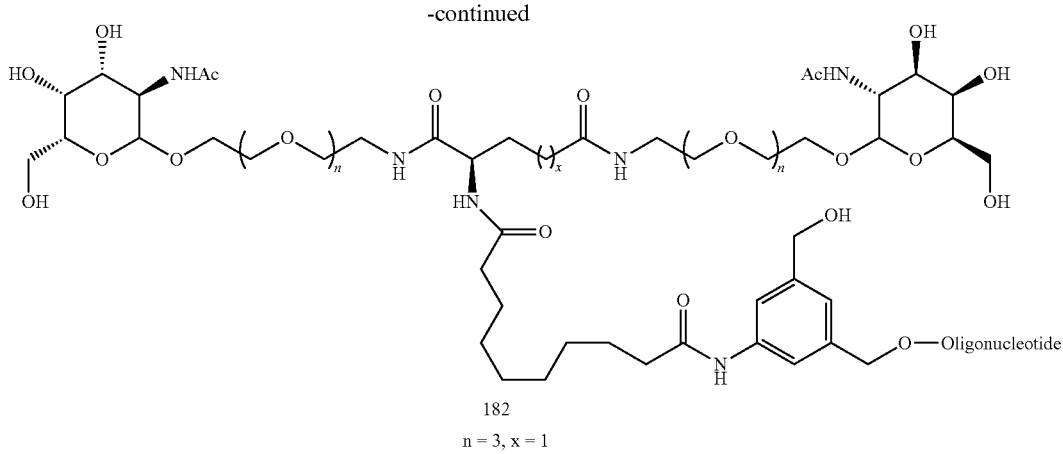

182
n = 3, x = 1

Step 1. Preparation of Compound 93

Compound 93 was prepared from (2-oxo-2-phenyl-1λ²-ethyl)-D-glutamic acid (2.25 g, 8.1 mmol) and 9 (13 g, 21 mmol) using an identical procedure to that used for compound 89.
Yield: 11.2 g.

Step 2. Preparation of Compound 94

Compound 94 was prepared from compound 93 (11.1 g) using an identical procedure to that used for compound 90.
Yield: 10.2 g.

Step 3. Preparation of Conjugate 182

Conjugate 182 was prepared from compounds 18 and 94 using an identical procedure to that used for compound 1.

Example 15. Synthesis of Conjugates 185 and 188

Scheme 33.

Scheme 34.

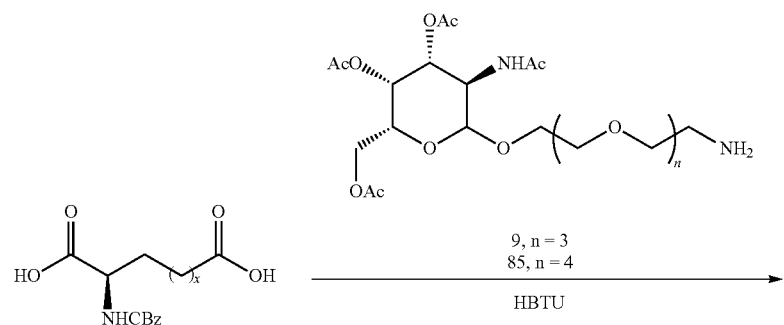

-continued
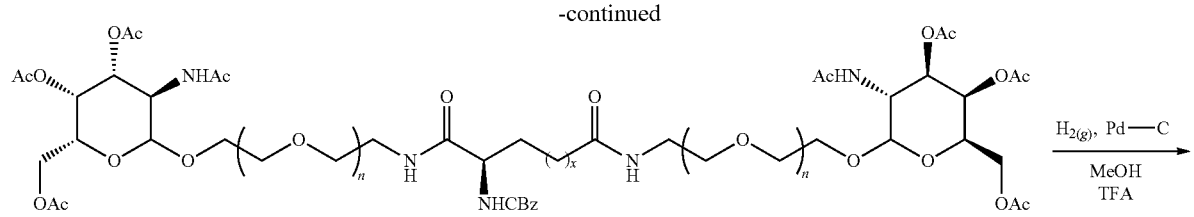
93, n = 3, x = 1
97, n = 4, x = 1
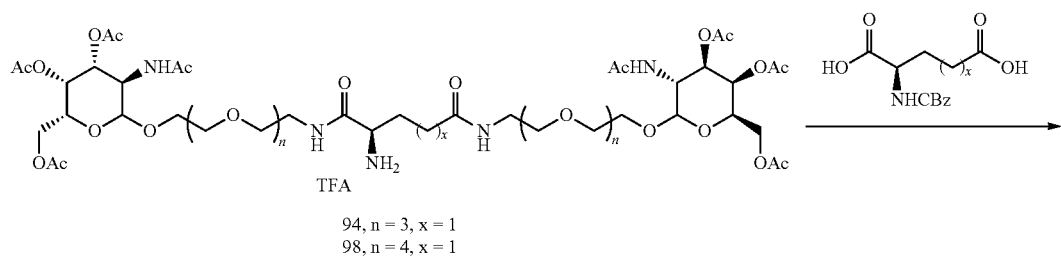
94, n = 3, x = 1
98, n = 4, x = 1
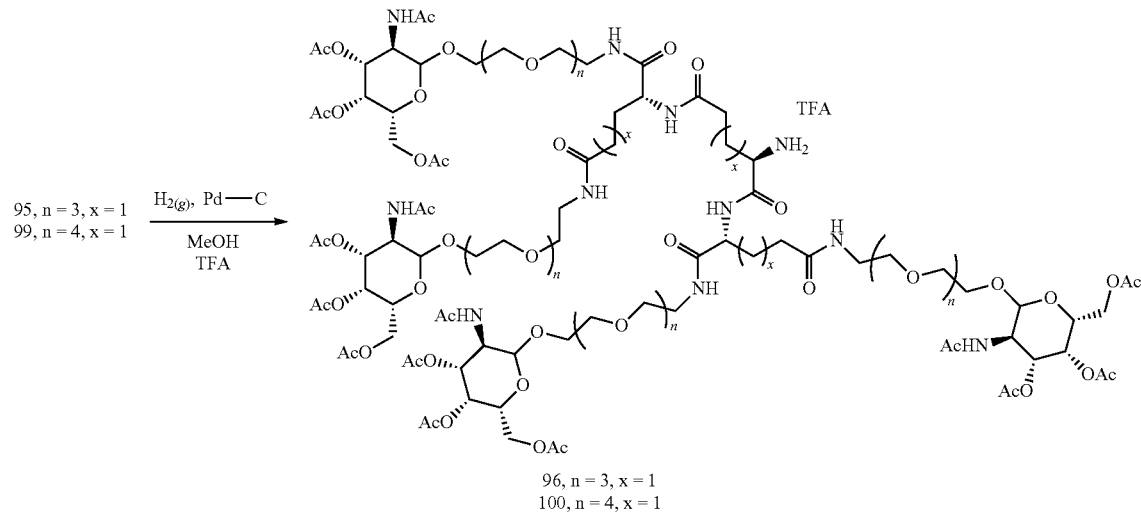
95, n = 3, x = 1
99, n = 4, x = 1
96, n = 3, x = 1
100, n = 4, x = 1

Scheme 35.

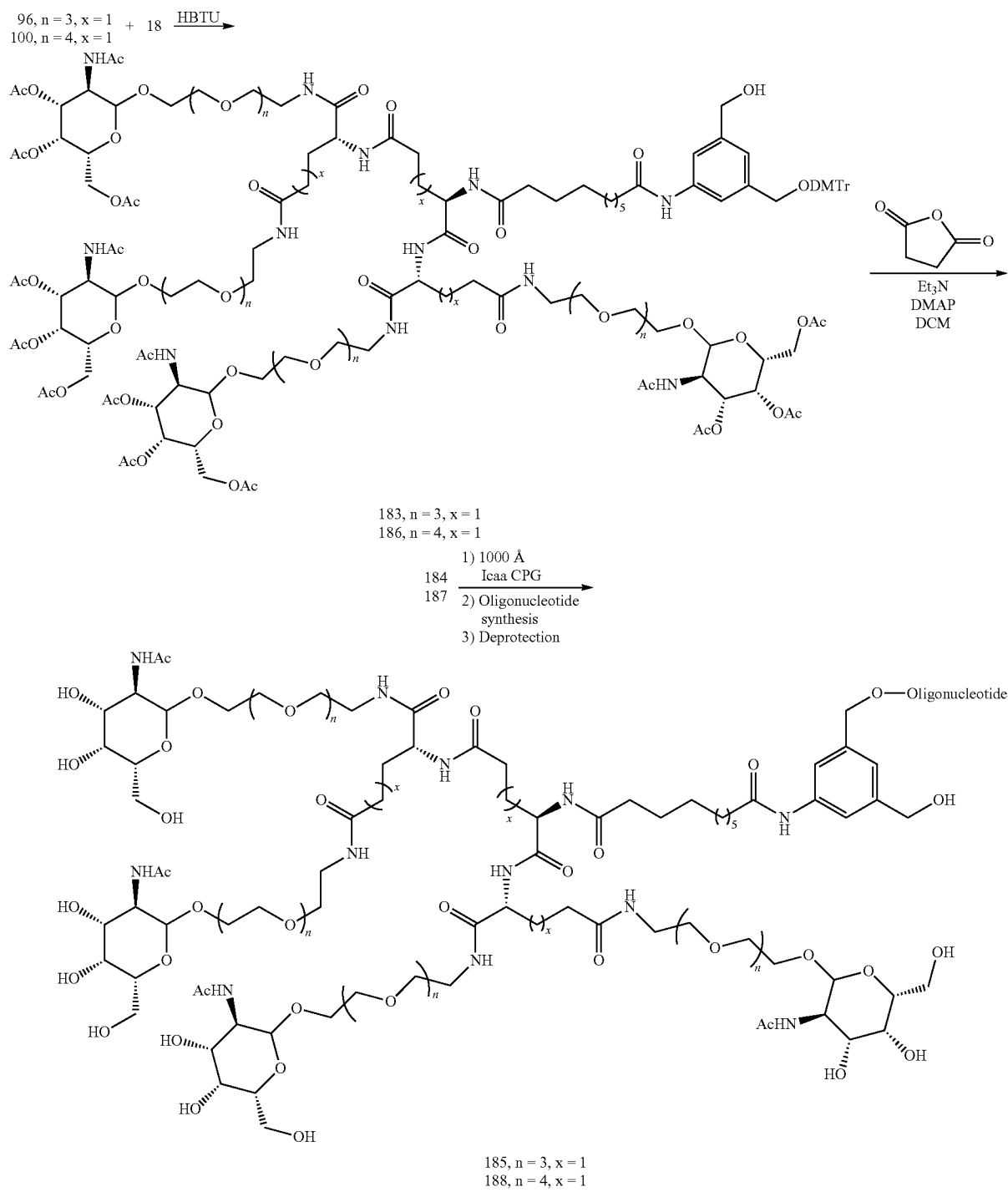

96, n = 3, x = 1
100, n = 4, x = 1

183, n = 3, x = 1
186, n = 4, x = 1

184  1) 1000 Å Icaa CPG
187  2) Oligonucleotide synthesis
     3) Deprotection 185, n = 3, x = 1
188, n = 4, x = 1

Step 1. Preparation of 14-Hydroxy-3,6,9,12-tetraoxatetradecyl 4-methylbenzenesulfonate 82

A solution of pentaethylene glycol (35 g, 147 mmol), TEA (41 mL, 294 mmol) and trimethylamine-HCl (1.4 g, 14.7 mmol) in $CH_2Cl_2$ (600 mL) was treated with tosyl chloride (29.4 g, 154 mmol). After stirring (18 h) the reaction mixture was washed with $H_2O$-brine (1:1), dried ($MgSO_4$), filtered, concentrated and subjected to chromatography to yield 82 (24.6 g, 43%) as a pale yellow oil. Rf 0.8 (10% $CH_3OH$—$CH_2Cl_2$).

Step 2. 14-azido-3,6,9,12-tetraoxatetradecan-1-ol 83

14-azido-3,6,9,12-tetraoxatetradecan-1-ol (83) was prepared from 82 (24.6 g, 62.7 mmol) and sodium azide (7.13 g, 110 mmol) using an identical procedure to that used for compound 4. Yield: 14.8 g, 90%.

Step 3. Preparation of Compound 84

A solution of GalNAc 6 (12.2 g, 31.4 mmol) and HO-PEG-N$_3$ 83 (9.2 g, 35 mmol) in 1,2-dichloroethane (150 mL) was treated with Sc(OTf)$_3$ (771 mg, 1.6 mmol). After stirring (85° C., 2 hr) the reaction was cooled (RT), quenched by the addition of TEA (40 mL) and concentrated. The crude material was subjected to chromatography to yield 84 (11.16 g, 60%) as a pale yellow foam. Rf 0.7 (10% CH$_3$OH—CH$_2$Cl$_2$).

Step 4. Preparation of Compound 85

A solution of 84 (11.16 g, 18.8 mmol) and Pd/C (1.1 g, 10%—wet support) in EtOAc (120 mL) was treated with TFA (4.32 mL, 56.5 mmol) and purged with H$_2$. After stirring vigorously (4.5 h) the reaction was purged with N$_2$, filtered through Celite and concentrated. The crude material was subjected to chromatography to yield 85 (5.77 g, 45%) as a colorless foam. Rf 0.5 (10% CH$_3$OH—CH$_2$Cl$_2$).

Step 5. Preparation of Compound 95

Compound 95 was prepared from (2-oxo-2-phenyl-1λ$^2$-ethyl)-D-glutamic acid (1.04 g, 3.7 mmol) and compound 94 (10.2 g) using an identical procedure to that used for compound 91. Yield: 7.2 g.

Step 6. Preparation of Compound 96

Compound 96 was prepared from compound 95 (11.1 g) using an identical procedure to that used for compound 92. Yield: 6.5 g.

Step 7. Preparation of Compound 97

Compound 97 was prepared from (2-oxo-2-phenyl-1λ$^2$-ethyl)-D-glutamic acid (2 g, 7.1 mmol) and 85 (12.1 g, 17.8 mmol) using an identical procedure to that used for compound 89. Yield: 10 g, quantitative.

Step 8. Preparation of Compound 98

Compound 98 was prepared from compound 97 (10 g, 7.2 mmol) using an identical procedure to that used for compound 90. Yield: 3.5 g, 36%.

Step 9. Preparation of Compound 99

Compound 99 was prepared quantitatively from (2-oxo-2-phenyl-1λ$^2$-ethyl)-D-glutamic acid (350 mg, 1.25 mmol) and compound 98 (2.86 mg, 2.5 mmol) using an identical procedure to that used for compound 91.

Step 10. Preparation of Compound 100

Compound 100 was prepared quantitatively from compound 99 (3.2 g, 1.25 mmol) using an identical procedure to that used for compound 92.

Step 11. Preparation of Conjugates 185 and 188

Conjugate 185 and 188 were prepared from compounds 18 and 96 or 18 and 100 using an identical procedure to that used for compound 1.

Example 16. Synthesis of Conjugates 191, 194, 197 and 200

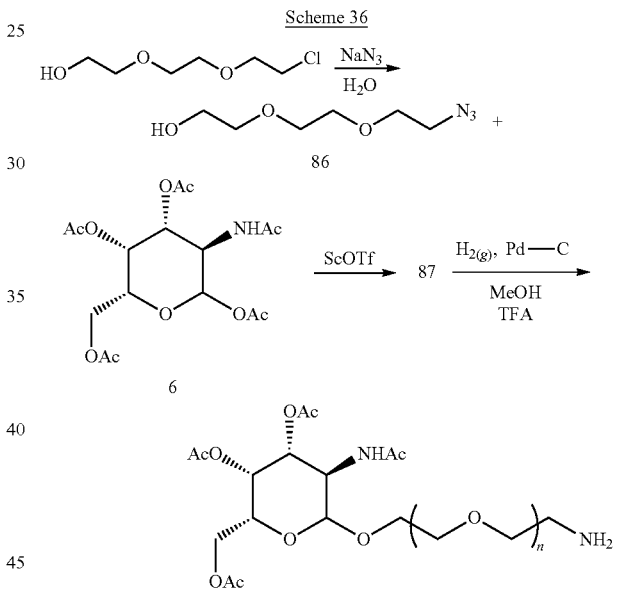

Scheme 36

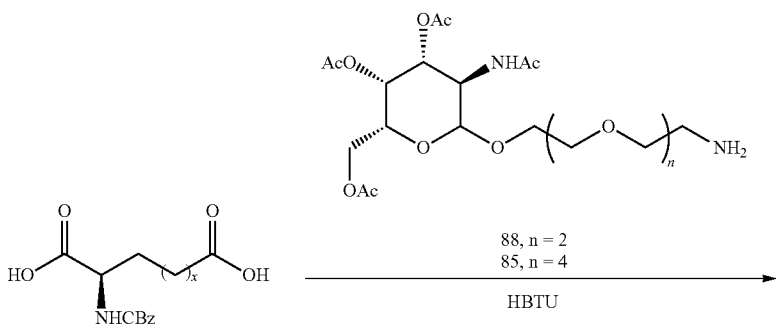

Scheme 37.

-continued
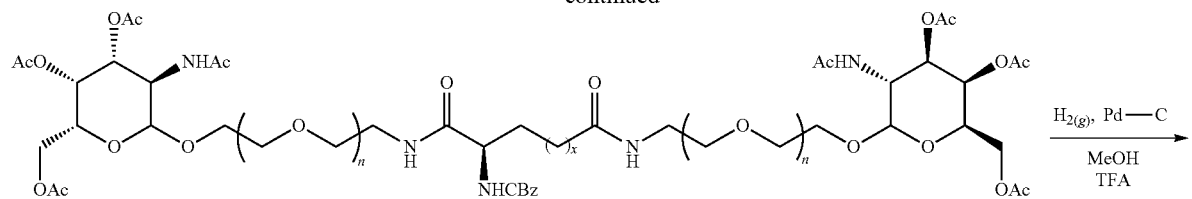
89, n = 2, x = 1
101, n = 3, x = 2
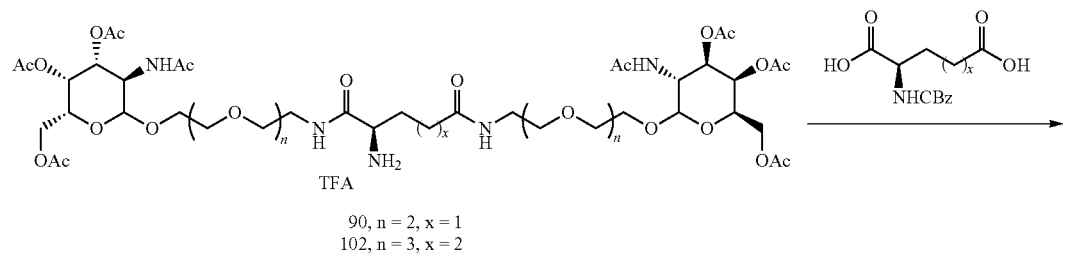
90, n = 2, x = 1
102, n = 3, x = 2
91, n = 2, x = 1
103, n = 3, x = 2
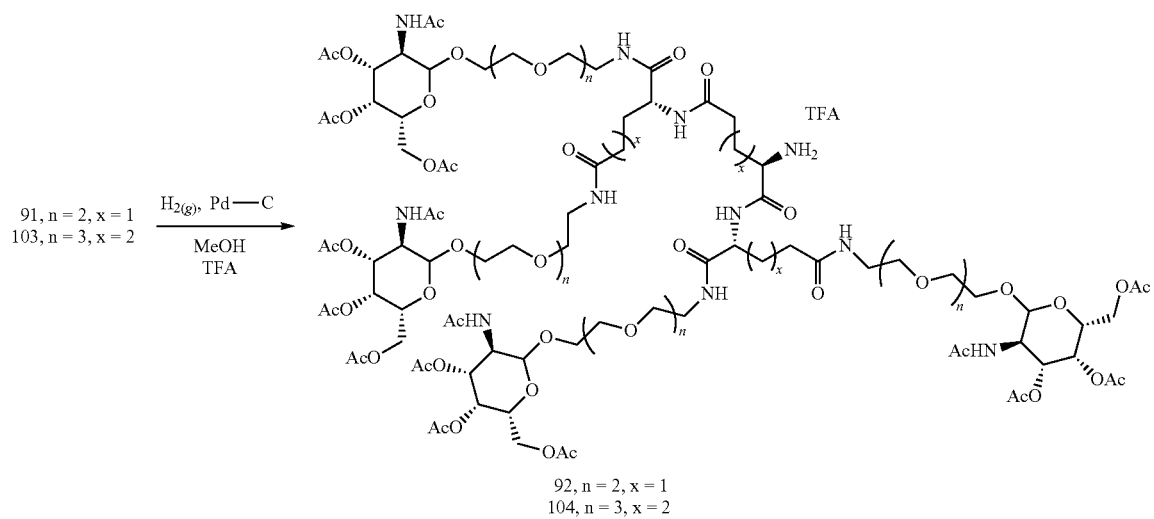
92, n = 2, x = 1
104, n = 3, x = 2

Scheme 38.

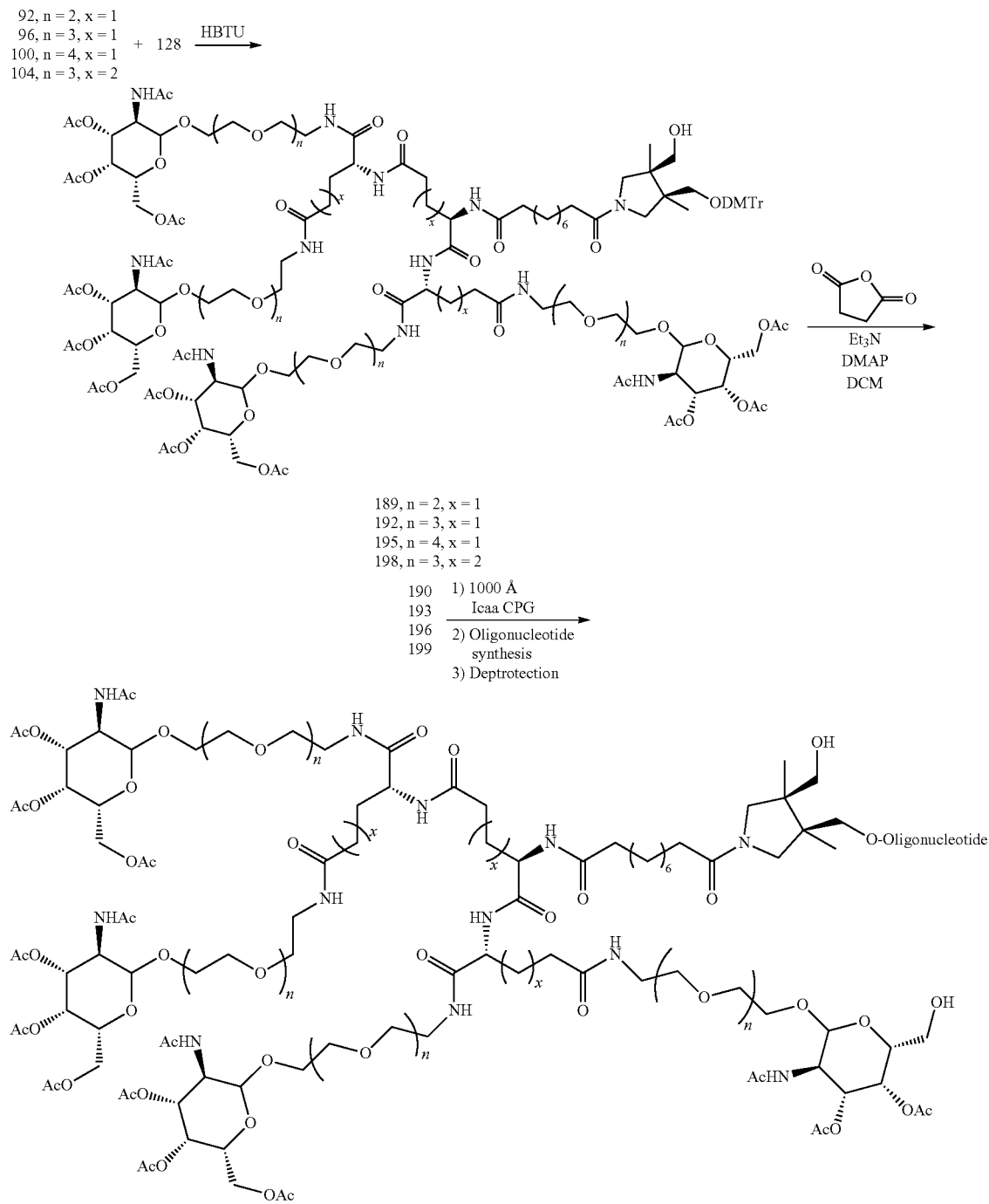

Step 1. Preparation of 2-(2-(2-azidoethoxy)ethoxy)ethan-1-ol 86

To a solution of 2-(2-(2-chloroethoxy)ethoxy)ethan-1-ol (13 g, 77 mmol) in water (200 mL) is added sodium azide (10 g, 154 mmol). The reaction was heated to 100° C. for 18 hours. The reaction is cooled to room temperature and poured into a 1 L separatory funnel and extracted with dichloromethane (3×200 mL). The combine dichloromethane extracts are dried on magnesium sulfate, filtered and concentrated to dryness to afford 2-(2-(2-azidoethoxy)ethoxy)ethan-1-ol as a colorless oil (11.7 g).

Step 2. Preparation of Compound 87

Compound 87 is prepared from 86 (4.95 g, 28.3 mmol) and 6 (10 g, 25.7 mmol) using an identical procedure to that used for compound 84. Yield: 10 g, 77%.

Step 3. Preparation of Compound 88

Compound 88 is prepared from 87 (10 g, 19.8 mmol) using an identical procedure to that used for compound 85. Yield: 7.63 g, 65%.

Step 4. Preparation of Compound 89

A solution of 88 (2 g, 3.38 mmol) and Z-glutamic acid (427 mg, 1.52 mmol) in $CH_2Cl_2$ (50 mL) is treated with HBTU (1.41 g, 3.7 mmol) and Hünig's base (1.77 mL, 10.1 mmol). After stirring (18 h) the mixture is concentrated and subjected to chromatography to yield 89 (871 mg, 48%) as a colorless foam. Rf 0.5 (10% $CH_3OH—CH_2Cl_2$).

Step 5. Preparation of Compound 90

A solution of 89 (870 mg, 0.72 mmol) and Pd/C (90 mg, 10%—wet support) in EtOAc (10 mL) is treated with TFA (84 µL, 1.1 mmol) and purged with $H_2$. After stirring vigorously (2 h) the reaction is purged with $N_2$, filtered through Celite and concentrated. The crude material is used without further processing and yielded 90 (850 mg, quantitative) as a colorless foam. Rf 0.25 (10% $CH_3OH—CH_2Cl_2$).

Step 6. Preparation of Compound 91

A solution of 90 (850 mg, 0.72 mmol) and Z-glutamic acid (91 mg, 0.32 mmol) in $CH_2Cl_2$ (10 mL) is treated with HBTU (300 mg, 0.79 mmol) and Hünig's base (502 µL, 2.9 mmol). After stirring (1.5 h) the mixture is diluted with $CH_2Cl_2$ and washed with $NaHCO_3$ (Sat. Aq.), dried ($MgSO_4$), filtered and concentrated. The crude material is subjected to chromatography to yield 91 (590 mg, 76%) as a colorless foam. Rf 0.5 (10% $CH_3OH—CH_2Cl_2$).

Step 7. Preparation of Compound 92

A solution of 91 (590 mg, 0.25 mmol) and Pd/C (100 mg, 10%—wet support) in $CH_3OH$ (30 mL) is treated with TFA (29 µL, 0.37 mmol) and purged with $H_2$. After stirring (3 h) the mixture is purged with $N_2$, then filtered through Celite and concentrated. The crude material is used without further processing and yielded 92 (600 mg, quantitative) as a colorless foam. Rf 0.1 (10% $CH_3OH—CH_2Cl_2$).

Step 8. Preparation of Compound 101

Compound 101 is prepared from (R)-2-((2-oxo-2-phenyl-112-ethyl)amino)hexanedioic acid (2.51 g, 8.6 mmol) and 9 (11 g, 17.2 mmol) using an identical procedure to that used for compound 89. Yield: 4.2 g, 37%.

Step 9. Preparation of Compound 102

Compound 102 is prepared from compound 101 (4.2 g, 3.2 mmol) using an identical procedure to that used for compound 90. Yield: 2.1 g, 47%.

Step 10. Preparation of Compound 103

Compound 103 is prepared from (R)-2-((2-oxo-2-phenyl-112-ethyl)amino)hexanedioic acid (265 mg, 0.9 mmol) and compound 102 (2.1 g, 1.8 mmol) using an identical procedure to that used for compound 91. Yield: (560 mg, 24%).

Step 11. Preparation of Compound 104

Compound 104 is prepared quantitatively from compound 103 (560 mg) using an identical procedure to that used for compound 92. The compound is used without purification.

Step 12. Preparation of Conjugates 191, 194, and 197

Conjugates 191, 194, and 197 are prepared from compound 128 and 92, 96, and 100 using an identical procedure to that used for compound 1.

Example 16a. Synthesis of Conjugates 191a

Scheme 36a

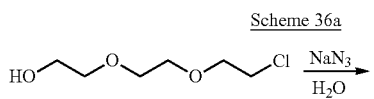

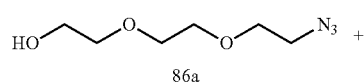

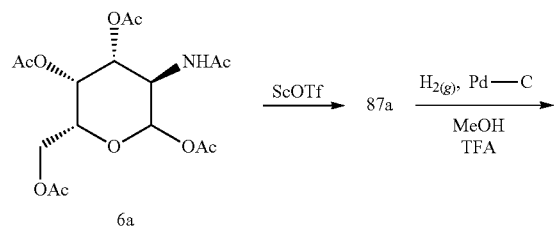

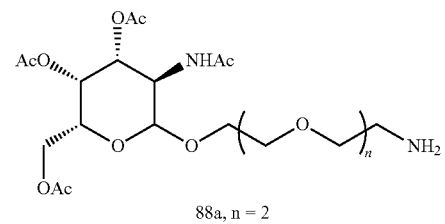

Scheme 37a.
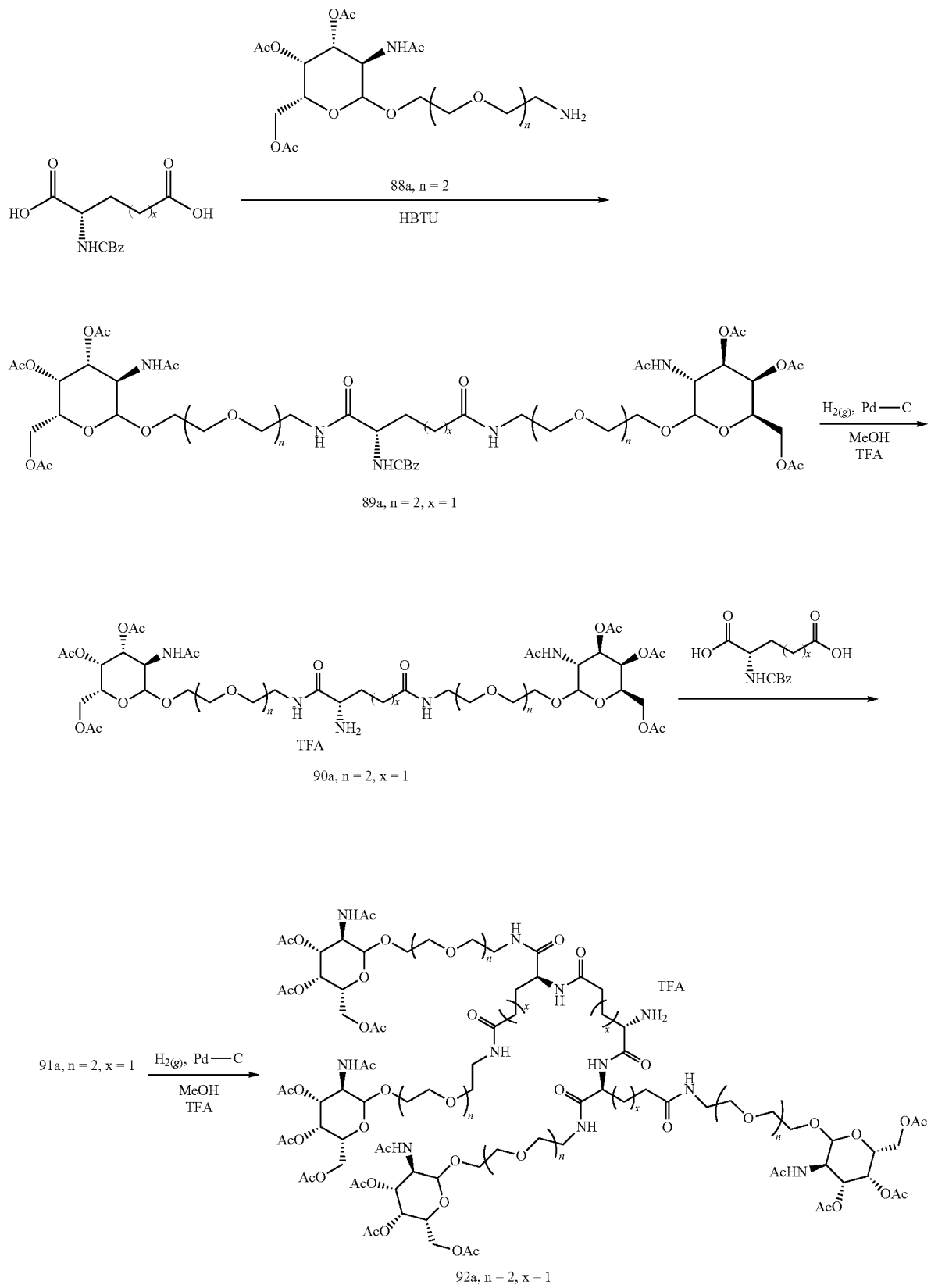

Scheme 38a.

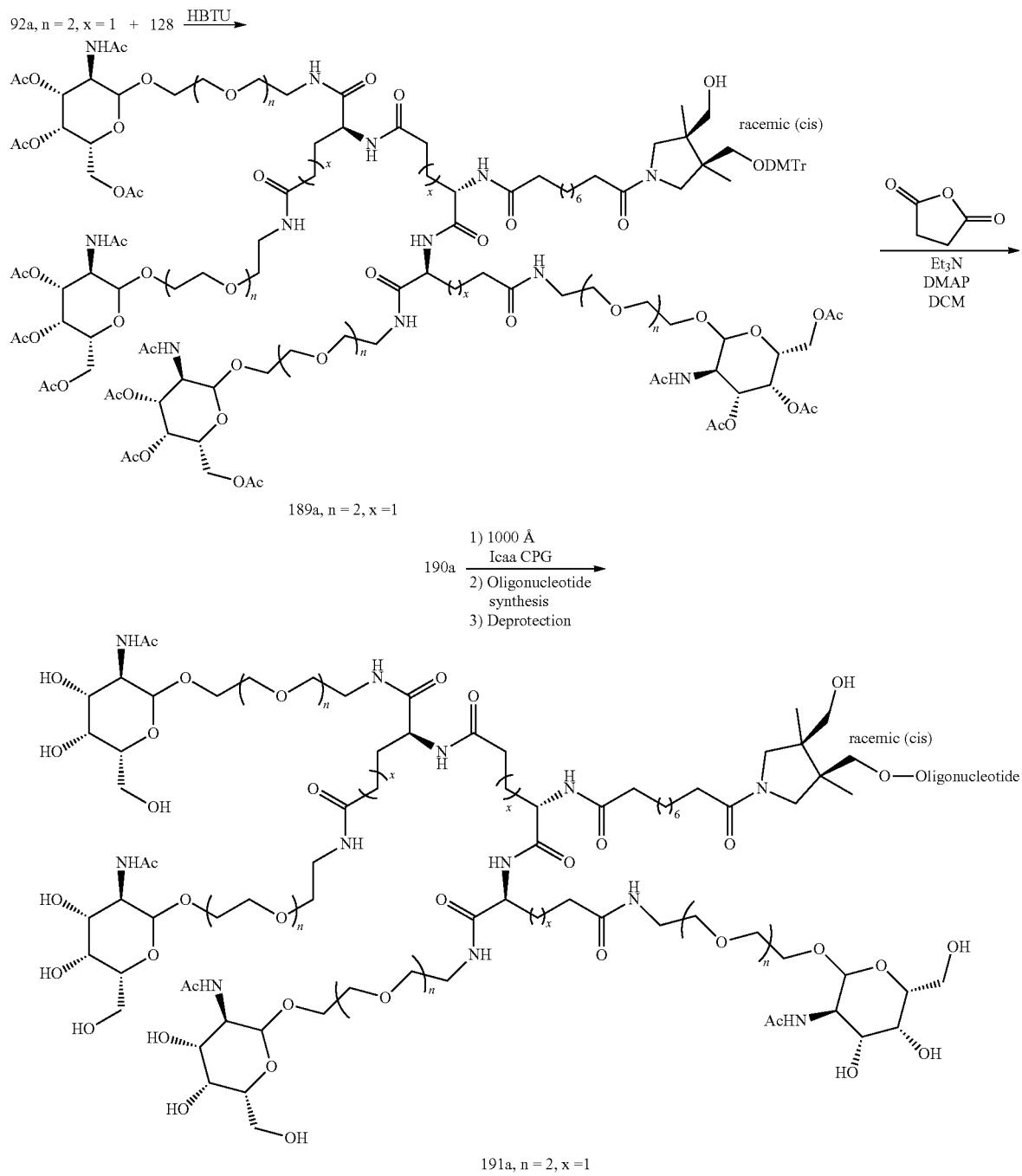

Step 1. Preparation of 2-(2-(2-azidoethoxy)ethoxy)ethan-1-ol 86a

To a solution of 2-(2-(2-chloroethoxy)ethoxy)ethan-1-ol (13 g, 77 mmol) in water (200 mL) was added sodium azide (10 g, 154 mmol). The reaction was heated to 100° C. for 18 hours. The reaction was cooled to room temperature and poured into a 1 L separatory funnel and extracted with dichloromethane (3×200 mL). The combine dichloromethane extracts were dried on magnesium sulfate, filtered and concentrated to dryness to afford 2-(2-(2-azidoethoxy) ethoxy)ethan-1-ol as a colorless oil (11.7 g).

Step 2. Preparation of Compound 87a

Compound 87a was prepared from 86a (4.95 g, 28.3 mmol) and 6a (10 g, 25.7 mmol) using an identical procedure to that used for compound 84. Yield: 10 g, 77%.

Step 3. Preparation of Compound 88a

Compound 88a was prepared from 87a (10 g, 19.8 mmol) using an identical procedure to that used for compound 85. Yield: 7.63 g, 65%.

Step 4. Preparation of Compound 89a

A solution of 88a (2 g, 3.38 mmol) and Z L-glutamic acid (427 mg, 1.52 mmol) in $CH_2Cl_2$ (50 mL) was treated with HBTU (1.41 g, 3.7 mmol) and Hünig's base (1.77 mL, 10.1 mmol). After stirring (18 h) the mixture was concentrated and subjected to chromatography to yield 89a (871 mg, 48%) as a colorless foam. Rf 0.5 (10% $CH_3OH$—$CH_2Cl_2$).

Step 5. Preparation of Compound 90a

A solution of 89a (870 mg, 0.72 mmol) and Pd/C (90 mg, 10%—wet support) in EtOAc (10 mL) was treated with TFA (84 μL, 1.1 mmol) and purged with $H_2$. After stirring vigorously (2 h) the reaction was purged with $N_2$, filtered through Celite and concentrated. The crude material was used without further processing and yielded 90a (850 mg, quantitative) as a colorless foam. Rf 0.25 (10% $CH_3OH$—$CH_2Cl_2$).

Step 6. Preparation of Compound 91a

A solution of 90a (850 mg, 0.72 mmol) and Z-glutamic acid (91 mg, 0.32 mmol) in $CH_2Cl_2$ (10 mL) was treated with HBTU (300 mg, 0.79 mmol) and Hunig's base (502 μL, 2.9 mmol). After stirring (1.5 h) the mixture diluted with $CH_2Cl_2$ and washed with $NaHCO_3$ (Sat. Aq.), dried ($MgSO_4$), filtered and concentrated. The crude material was subjected to chromatography to yield 91a (590 mg, 76%) as a colorless foam. Rf 0.5 (10% $CH_3OH$—$CH_2Cl_2$).

Step 7. Preparation of Compound 92a

A solution of 91a (590 mg, 0.25 mmol) and Pd/C (100 mg, 10%—wet support) in $CH_3OH$ (30 mL) was treated with TFA (29 μL, 0.37 mmol) and purged with $H_2$. After stirring (3 h) the mixture was purged with $N_2$, then filtered through Celite and concentrated. The crude material was used without further processing and yielded 92a (600 mg, quantitative) as a colorless foam. Rf 0.1 (10% $CH_3OH$—$CH_2Cl_2$).

Step 8. Preparation of Conjugate 191a

Conjugate 191a was prepared from compound 128 and compound 92a using an identical procedure to that used for compound 1.

Example 16b. Synthesis of Conjugates 191b

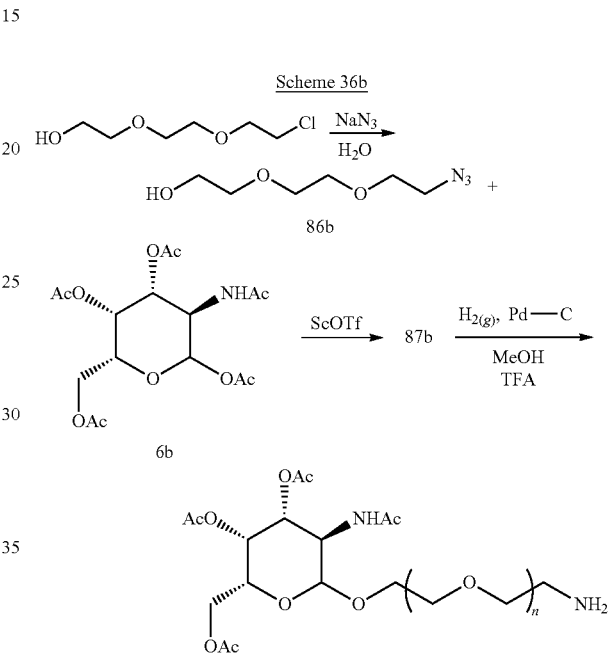

Scheme 36b

Scheme 37b.

-continued
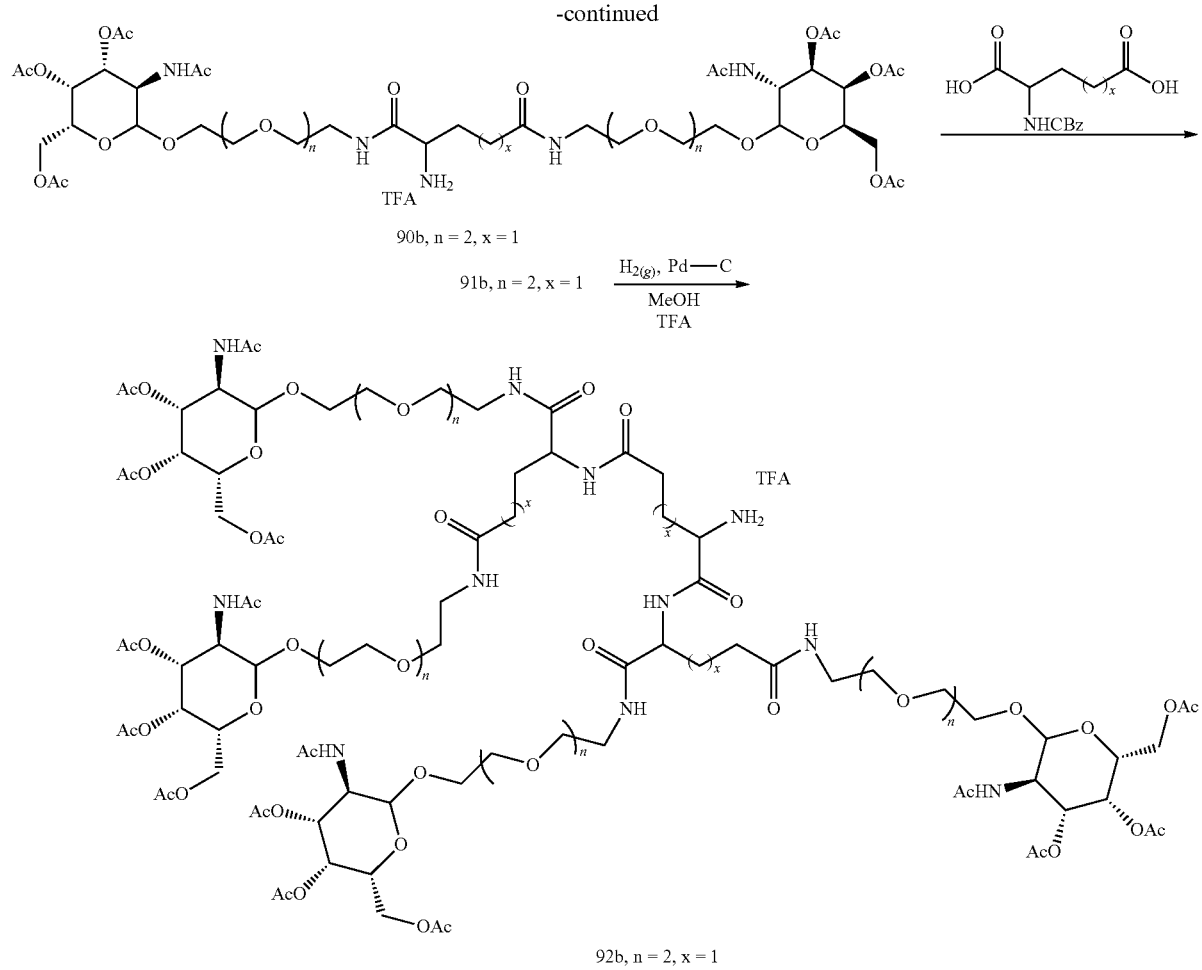
90b, n = 2, x = 1
91b, n = 2, x = 1
92b, n = 2, x = 1
Scheme 38b.
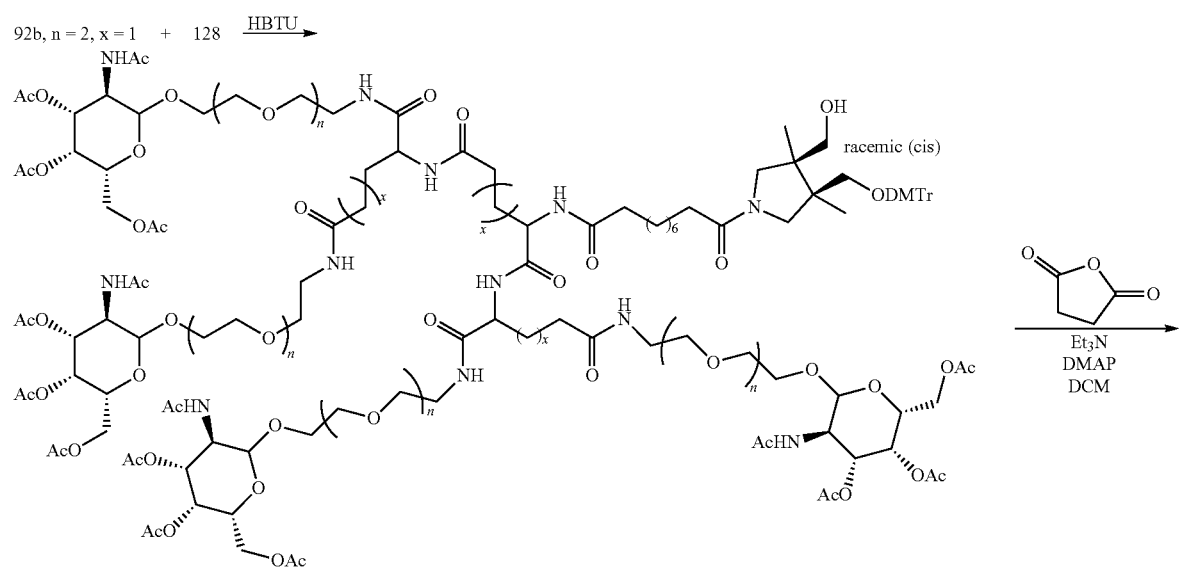
189b, n = 2, x = 1

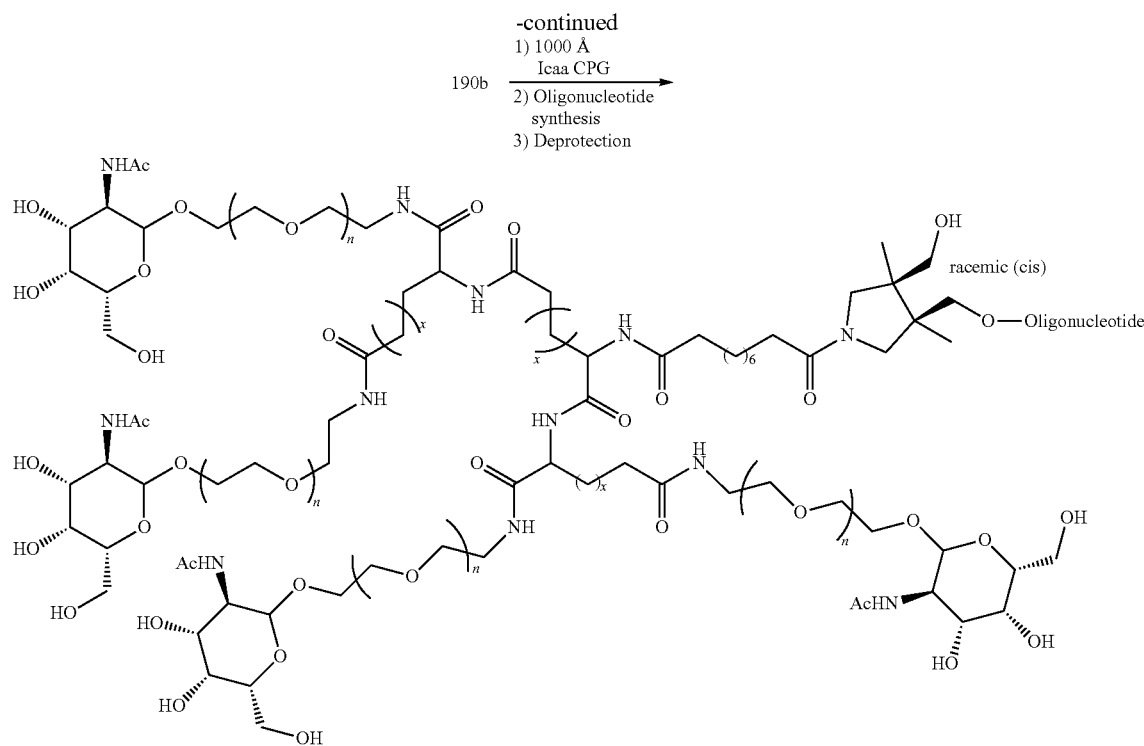

191b, n = 2, x = 1

Step 1. Preparation of 2-(2-(2-azidoethoxy)ethoxy)ethan-1-ol 86b

To a solution of 2-(2-(2-chloroethoxy)ethoxy)ethan-1-ol (13 g, 77 mmol) in water (200 mL) is added sodium azide (10 g, 154 mmol). The reaction was heated to 100° C. for 18 hours. The reaction was cooled to room temperature and poured into a 1 L separatory funnel and extracted with dichloromethane (3×200 mL). The combine dichloromethane extracts were dried on magnesium sulfate, filtered and concentrated to dryness to afford 2-(2-(2-azidoethoxy)ethoxy)ethan-1-ol as a colorless oil (11.7 g).

Step 2. Preparation of Compound 87b

Compound 87a is prepared from 86b (4.95 g, 28.3 mmol) and 6b (10 g, 25.7 mmol) using an identical procedure to that used for compound 84. Yield: 10 g, 77%.

Step 3. Preparation of Compound 88b

Compound 88a is prepared from 87b (10 g, 19.8 mmol) using an identical procedure to that used for compound 85. Yield: 7.63 g, 65%.

Step 4. Preparation of Compound 89b

A solution of 88b (2 g, 3.38 mmol) and racemic Z-glutamic acid (427 mg, 1.52 mmol) in $CH_2Cl_2$ (50 mL) is treated with HBTU (1.41 g, 3.7 mmol) and Hünig's base (1.77 mL, 10.1 mmol). After stirring (18 h) the mixture was concentrated and subjected to chromatography to yield 89b (871 mg, 48%) as a colorless foam. Rf 0.5 (10% $CH_3OH$—$CH_2Cl_2$).

Step 5. Preparation of Compound 90b

A solution of 89b (870 mg, 0.72 mmol) and Pd/C (90 mg, 10%—wet support) in EtOAc (10 mL) is treated with TFA (84 μL, 1.1 mmol) and purged with $H_2$. After stirring vigorously (2 h) the reaction is purged with $N_2$, filtered through Celite and concentrated. The crude material is used without further processing and yielded 90b (850 mg, quantitative) as a colorless foam. Rf 0.25 (10% $CH_3OH$—$CH_2Cl_2$).

Step 6. Preparation of Compound 91b

A solution of 90b (850 mg, 0.72 mmol) and Z-glutamic acid (91 mg, 0.32 mmol) in $CH_2Cl_2$ (10 mL) is treated with HBTU (300 mg, 0.79 mmol) and Hunig's base (502 μL, 2.9 mmol). After stirring (1.5 h) the mixture is diluted with $CH_2Cl_2$ and washed with $NaHCO_3$ (Sat. Aq.), dried ($MgSO_4$), filtered and concentrated. The crude material is subjected to chromatography to yield 91b (590 mg, 76%) as a colorless foam. Rf 0.5 (10% $CH_3OH$—$CH_2Cl_2$).

Step 7. Preparation of Compound 92b

A solution of 91b (590 mg, 0.25 mmol) and Pd/C (100 mg, 10%—wet support) in $CH_3OH$ (30 mL) is treated with TFA (29 μL, 0.37 mmol) and purged with $H_2$. After stirring (3 h) the mixture is purged with $N_2$, then filtered through Celite and concentrated. The crude material is used without further processing and yielded 92b (600 mg, quantitative) as a colorless foam. Rf 0.1 (10% $CH_3OH$—$CH_2Cl_2$).

Step 8. Preparation of Conjugate 191b
Conjugate 191b is prepared from compound 128 and compound 92b using an identical procedure to that used for compound 1.
Example 16c. Synthesis of Conjugates 191c
-continued
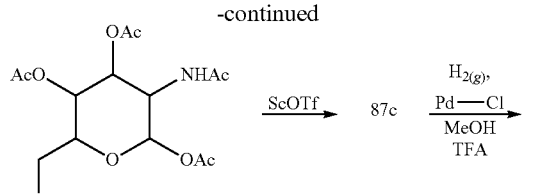
Scheme 36c
Scheme 37c.
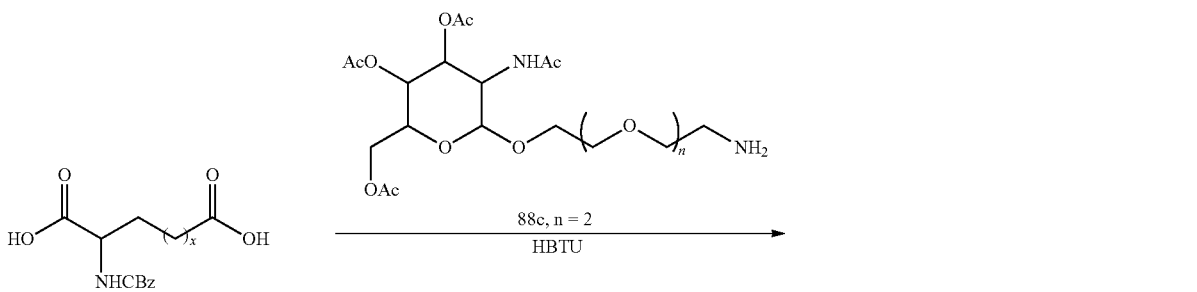
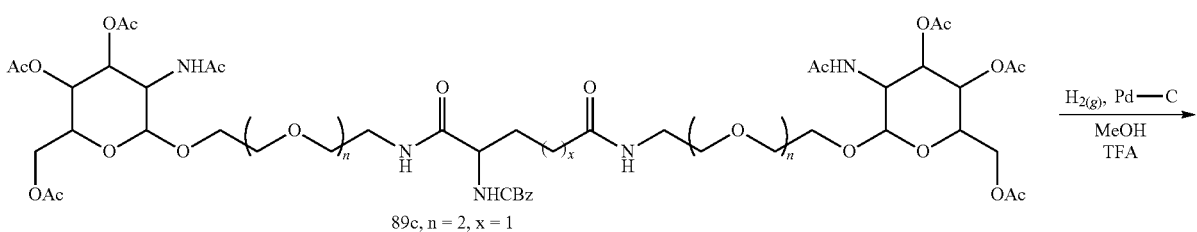
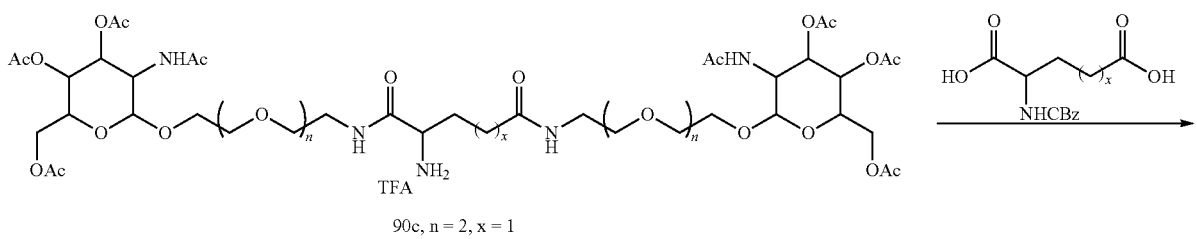
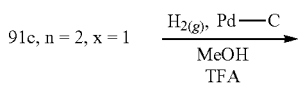

-continued
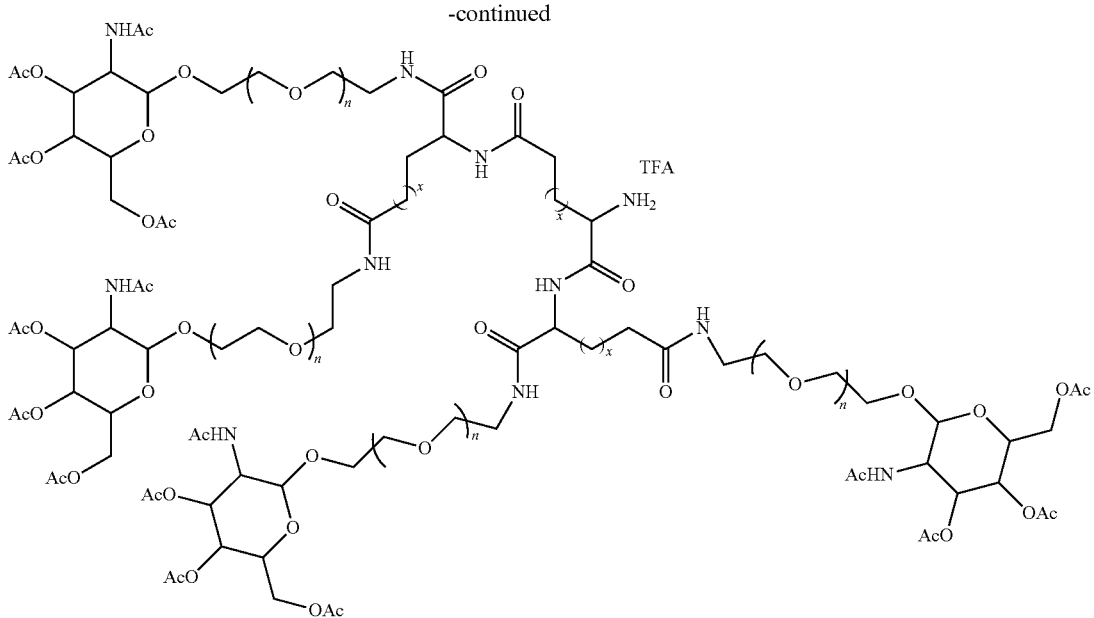
92c, n = 2, x = 1
Scheme 38c.
92c, n = 2, x = 1 + 128 →(HBTU)
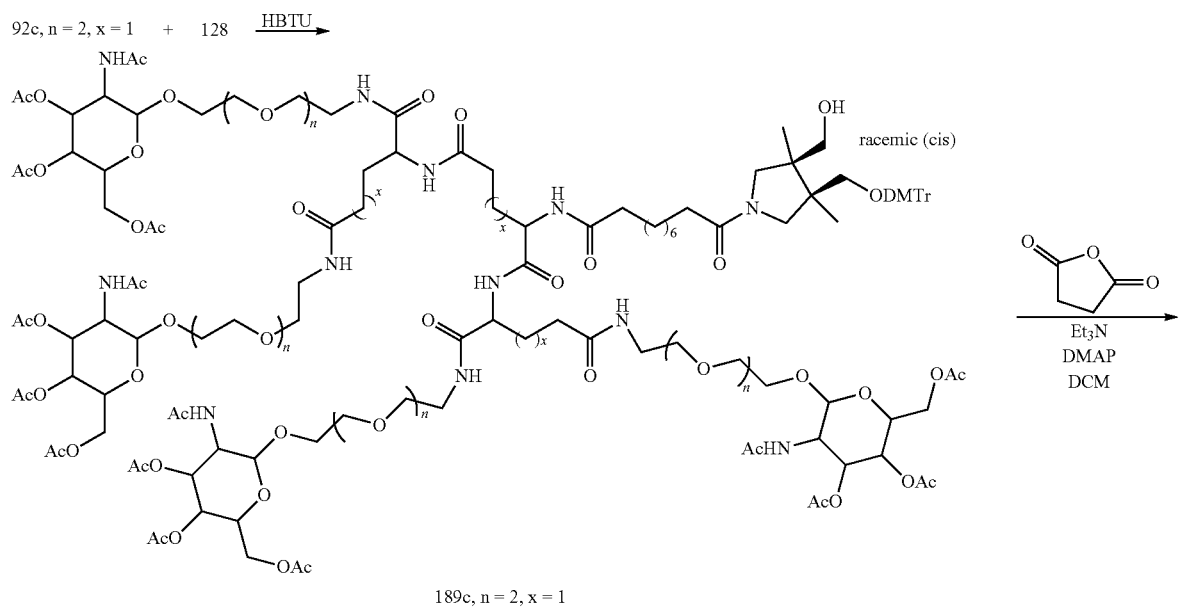
189c, n = 2, x = 1
→ (Et₃N, DMAP, DCM with succinic anhydride)
190c →(1) 1000 Å lcaa CPG; 2) Oligonucleotide synthesis; 3) Deprotection)
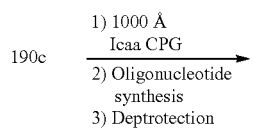

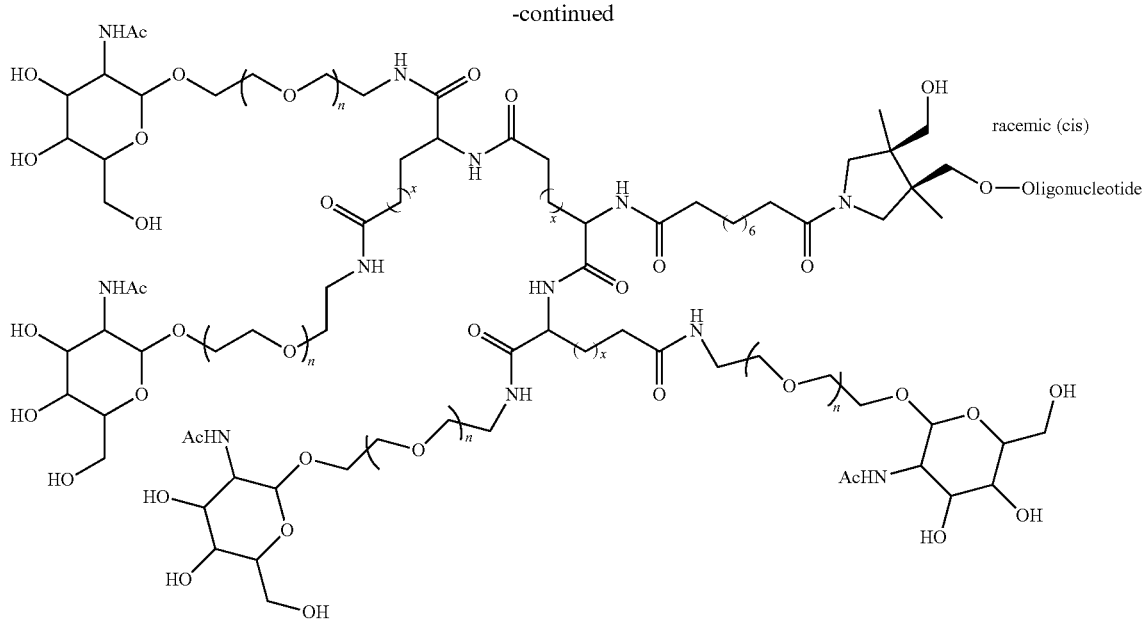

191c, n = 2, x = 1

Step 1. Preparation of 2-(2-(2-azidoethoxy)ethoxy)ethan-1-ol 86c

To a solution of 2-(2-(2-chloroethoxy)ethoxy)ethan-1-ol (13 g, 77 mmol) in water (200 mL) is added sodium azide (10 g, 154 mmol). The reaction was heated to 100° C. for 18 hours. The reaction was cooled to room temperature and poured into a 1 L separatory funnel and extracted with dichloromethane (3×200 mL). The combine dichloromethane extracts were dried on magnesium sulfate, filtered and concentrated to dryness to afford 2-(2-(2-azidoethoxy)ethoxy)ethan-1-ol as a colorless oil (11.7 g).

Step 2. Preparation of Compound 87c

Compound 87c is prepared from 86c (4.95 g, 28.3 mmol) and 6c (10 g, 25.7 mmol) using an identical procedure to that used for compound 84. Yield: 10 g, 77%.

Step 3. Preparation of Compound 88c

Compound 88c is prepared from 87c (10 g, 19.8 mmol) using an identical procedure to that used for compound 85. Yield: 7.63 g, 65%.

Step 4. Preparation of Compound 89c

A solution of 88c (2 g, 3.38 mmol) and racemic Z-glutamic acid (427 mg, 1.52 mmol) in $CH_2Cl_2$ (50 mL) is treated with HBTU (1.41 g, 3.7 mmol) and Hünig's base (1.77 mL, 10.1 mmol). After stirring (18 h) the mixture was concentrated and subjected to chromatography to yield 89c (871 mg, 48%) as a colorless foam. Rf 0.5 (10% $CH_3OH$—$CH_2Cl_2$).

Step 5. Preparation of Compound 90c

A solution of 89c (870 mg, 0.72 mmol) and Pd/C (90 mg, 10%—wet support) in EtOAc (10 mL) is treated with TFA (84 µL, 1.1 mmol) and purged with $H_2$. After stirring vigorously (2 h) the reaction is purged with $N_2$, filtered through Celite and concentrated. The crude material is used without further processing and yielded 90c (850 mg, quantitative) as a colorless foam. Rf 0.25 (10% $CH_3OH$—$CH_2Cl_2$).

Step 6. Preparation of Compound 91c

A solution of 90c (850 mg, 0.72 mmol) and Z-glutamic acid (91 mg, 0.32 mmol) in $CH_2Cl_2$ (10 mL) is treated with HBTU (300 mg, 0.79 mmol) and Hünig's base (502 µL, 2.9 mmol). After stirring (1.5 h) the mixture is diluted with $CH_2Cl_2$ and washed with $NaHCO_3$ (Sat. Aq.), dried ($MgSO_4$), filtered and concentrated. The crude material is subjected to chromatography to yield 91c (590 mg, 76%) as a colorless foam. Rf 0.5 (10% $CH_3OH$—$CH_2Cl_2$).

Step 7. Preparation of Compound 92c

A solution of 91c (590 mg, 0.25 mmol) and Pd/C (100 mg, 10%—wet support) in $CH_3OH$ (30 mL) is treated with TFA (29 µL, 0.37 mmol) and purged with $H_2$. After stirring (3 h) the mixture is purged with $N_2$, then filtered through Celite and concentrated. The crude material is used without further processing and yielded 92c (600 mg, quantitative) as a colorless foam. Rf 0.1 (10% $CH_3OH$—$CH_2Cl_2$).

Step 8. Preparation of Conjugate 191c

Conjugate 191c is prepared from compound 128 and compound 92c using an identical procedure to that used for compound 1.

Example 17. Synthesis of Conjugates 203 and 206
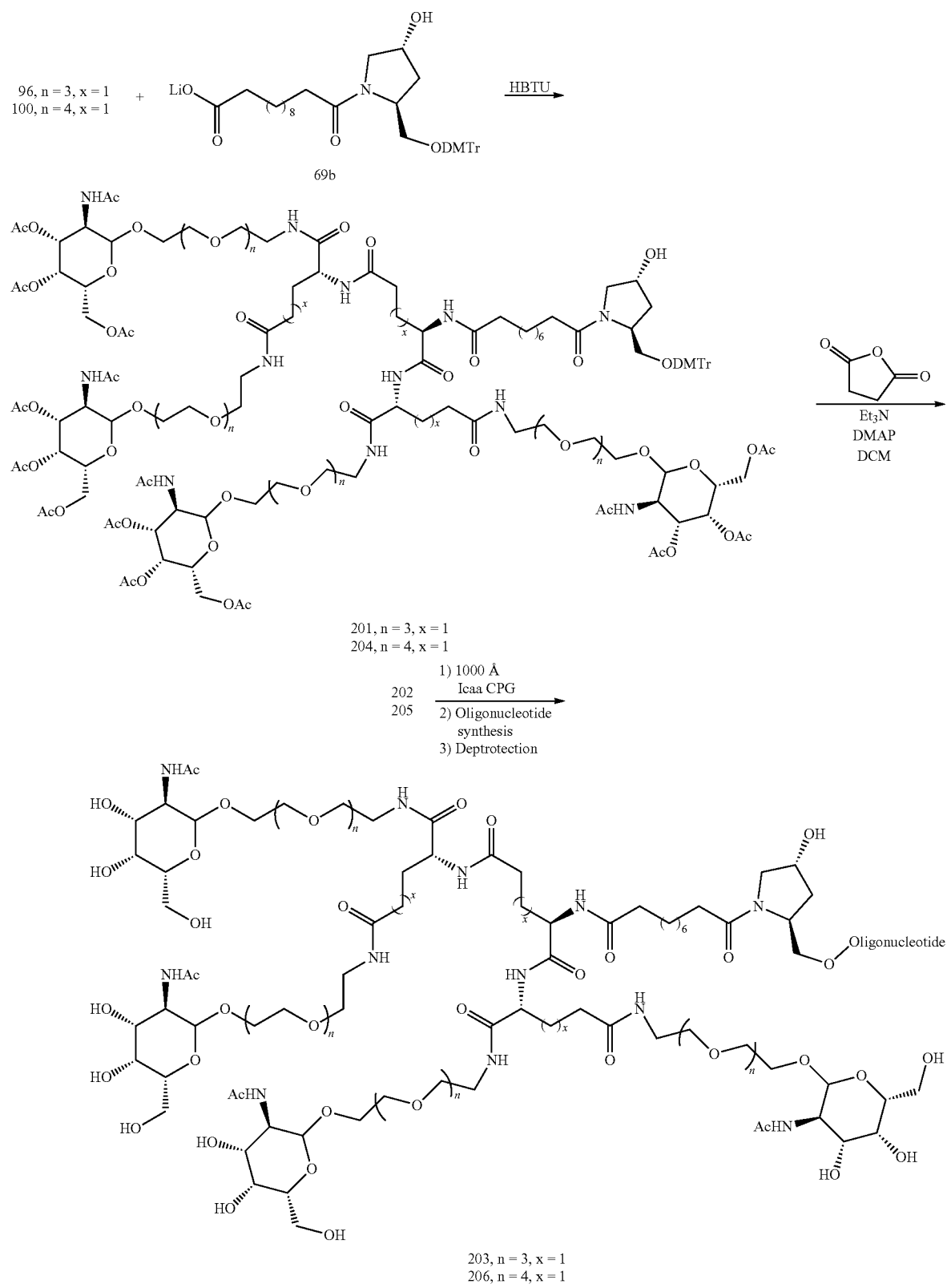
Scheme 39.

243
Step 1. Preparation of Compound 69b
Compound 69b was prepared from (2S,4R)-4-Hydroxy-pyrrolidine-2-carboxylic acid using an identical procedure to that used for compound 69.
244
Step 2. Preparation of Conjugates 203 and 206
Conjugates 203 and 206 were prepared from compound 96 and 100 using an identical procedure to that used for compound 1.
Example 18. Synthesis of Conjugate 209
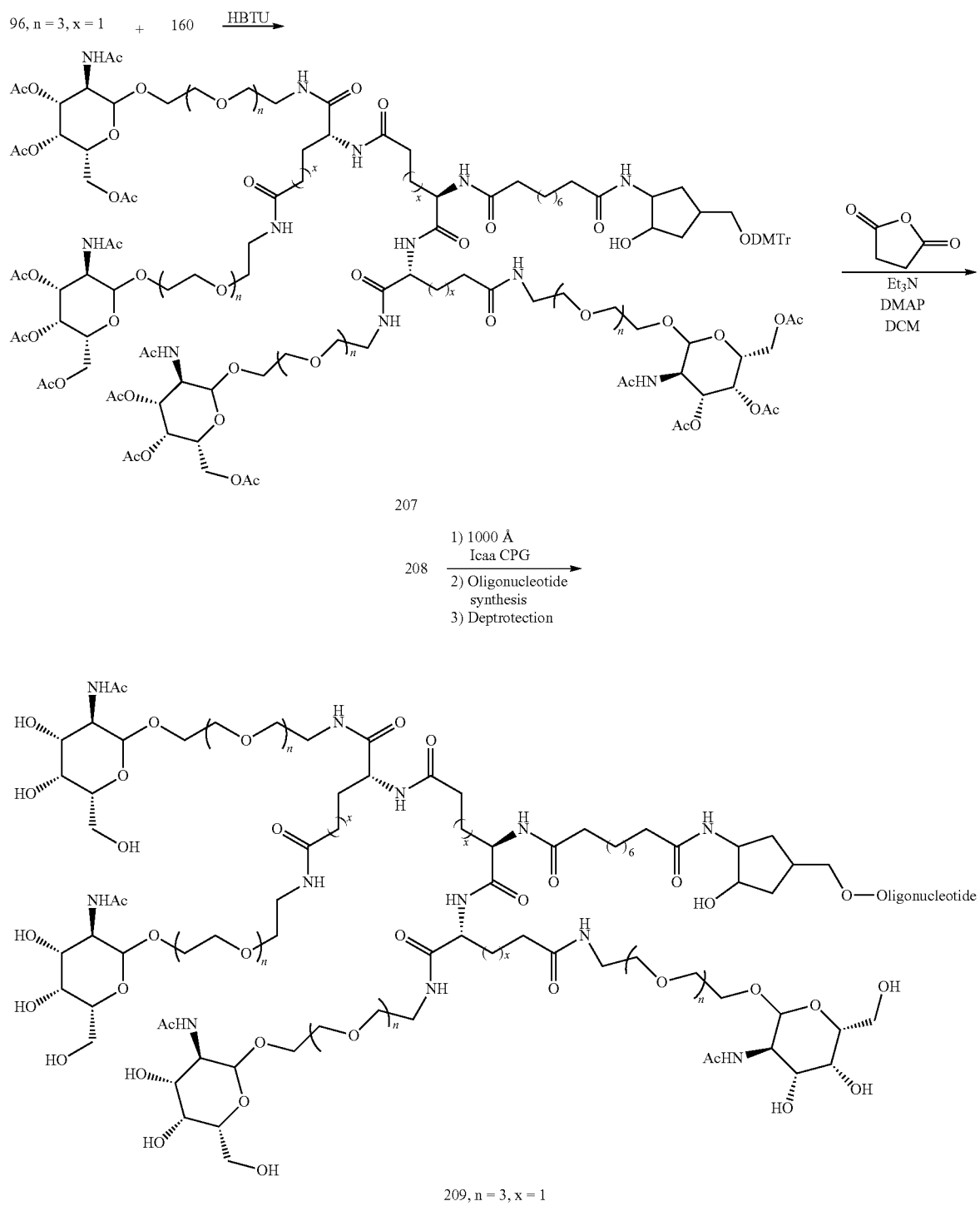

245
Step 1. Preparation of Conjugate 209
Conjugate 209 was prepared from compound 96 and 160 using an identical procedure to that used for compound 1.
Example 18a. Synthesis of Conjugate 209a
Scheme 40a.
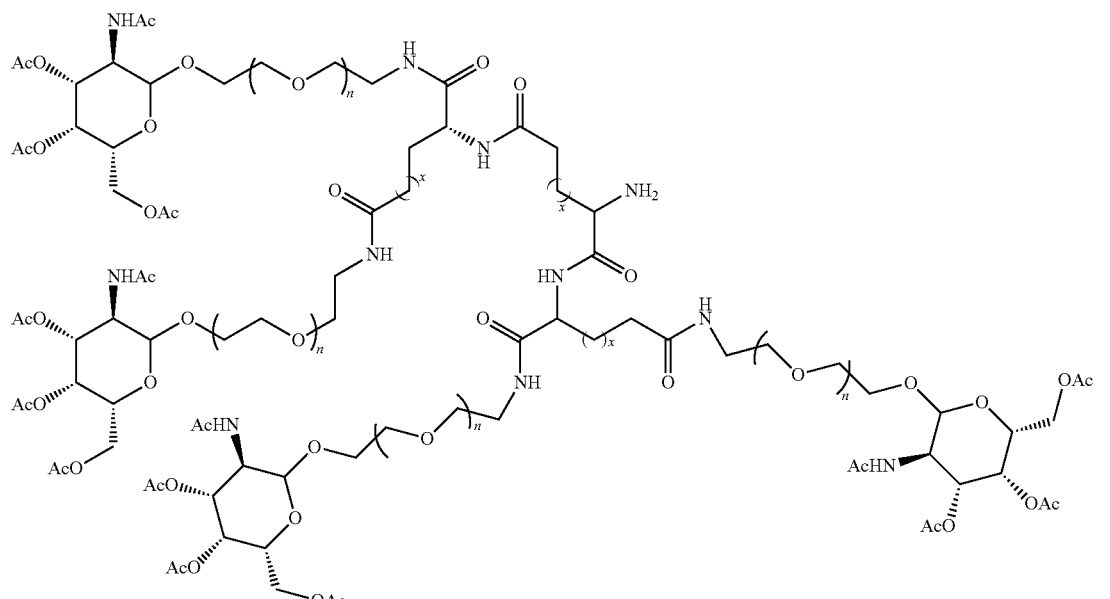
96a, n = 3, x = 1
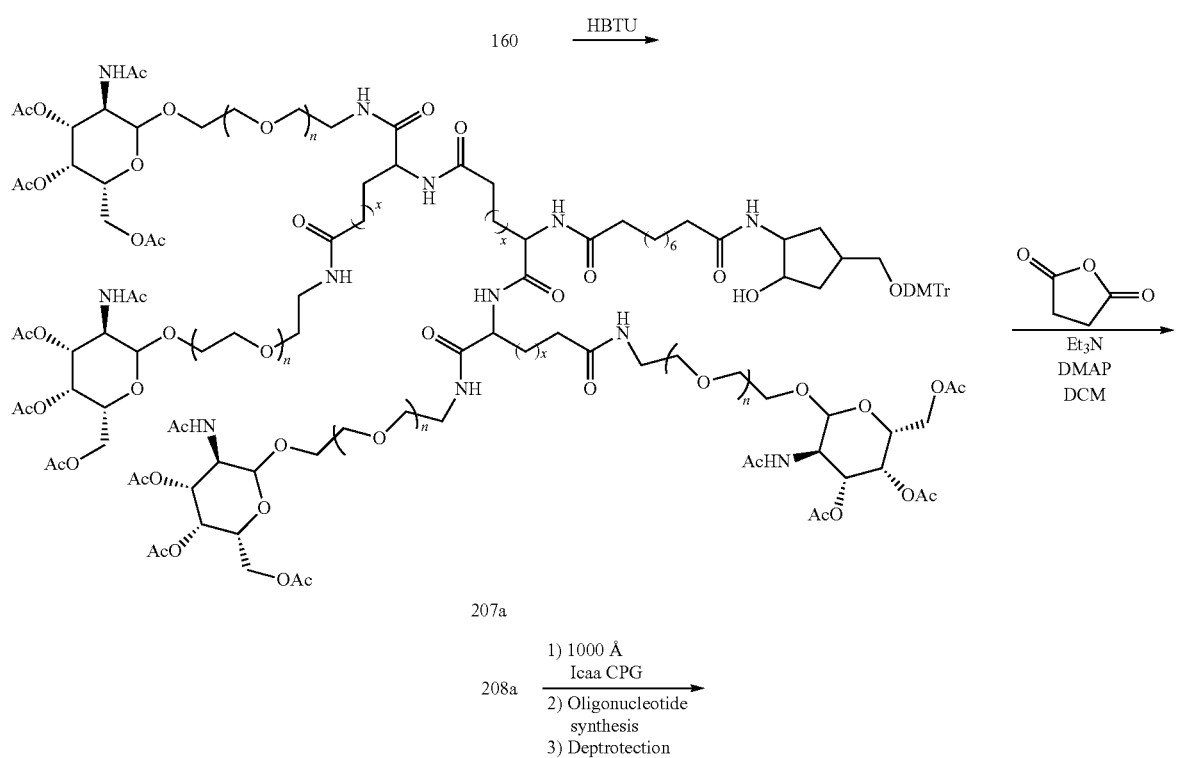
207a
208a  
1) 1000 Å Icaa CPG  
2) Oligonucleotide synthesis  
3) Deptrotection -continued
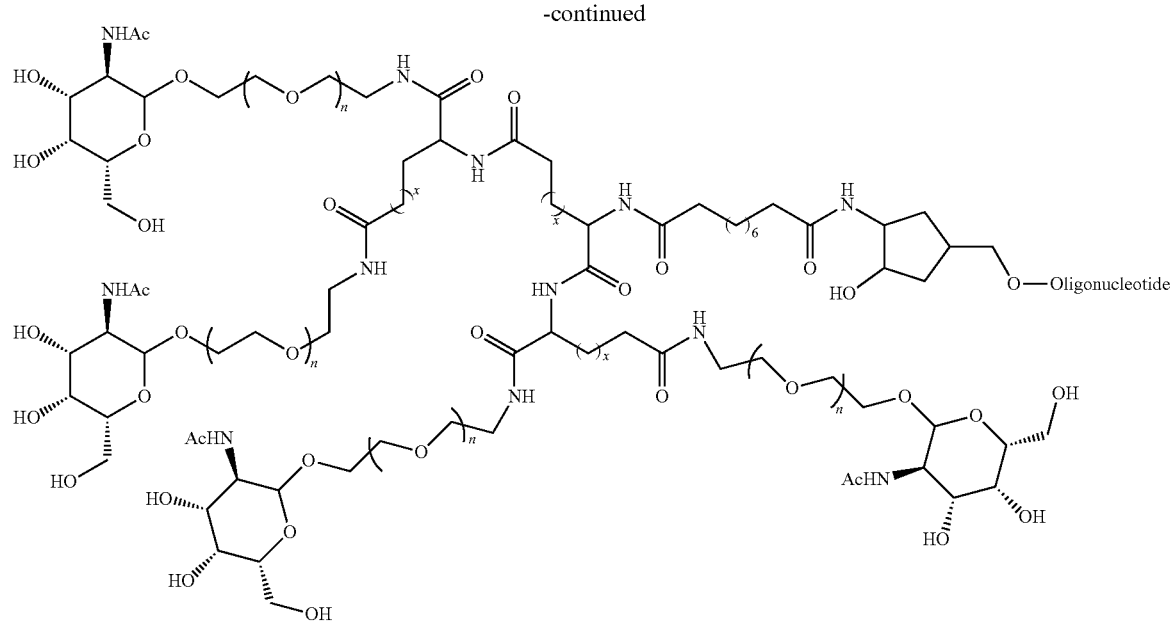
209a, n = 3, x = 1
Step 1. Preparation of Conjugate 209a
Conjugate 209a is prepared from compound 96a and 160 using an identical procedure to that used for compound 1.
Example 19. Synthesis of Conjugates 212 and 215
Scheme 41.
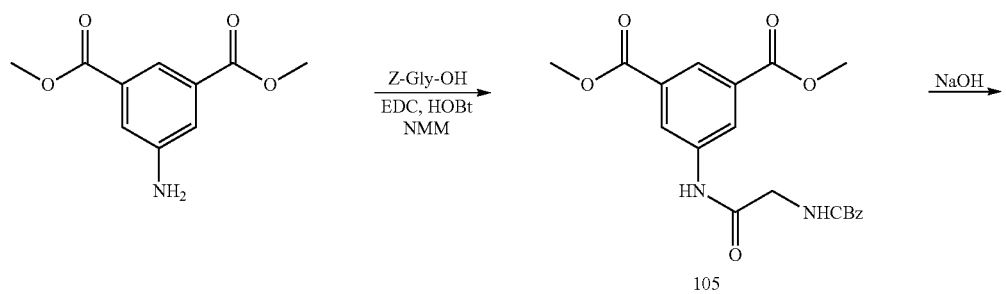
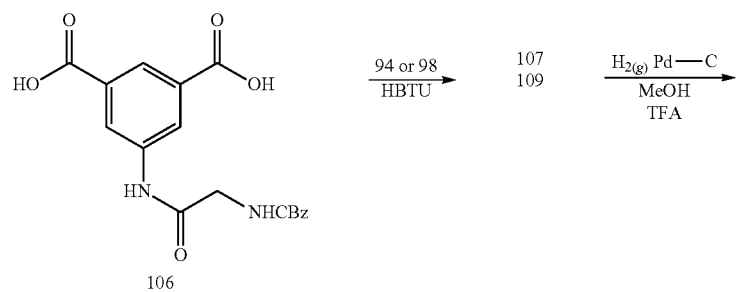

-continued
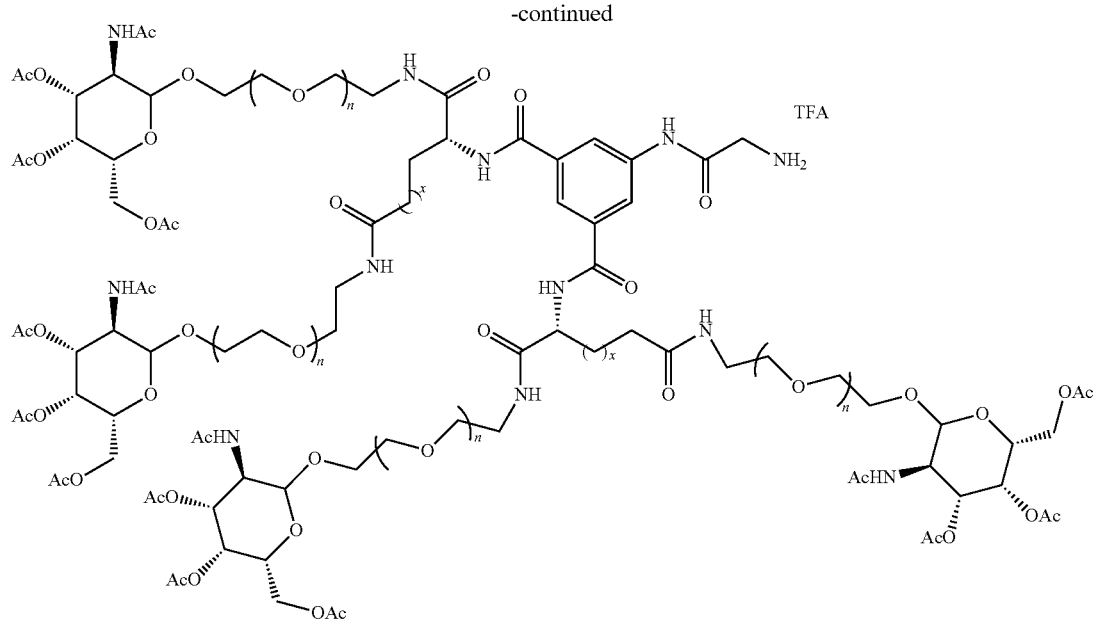
108, n = 3, x = 1
110, n = 4, x = 1
Scheme 42.
108, n = 3, x = 1
110, n = 4, x = 1  + 128  $\xrightarrow{\text{HBTU}}$
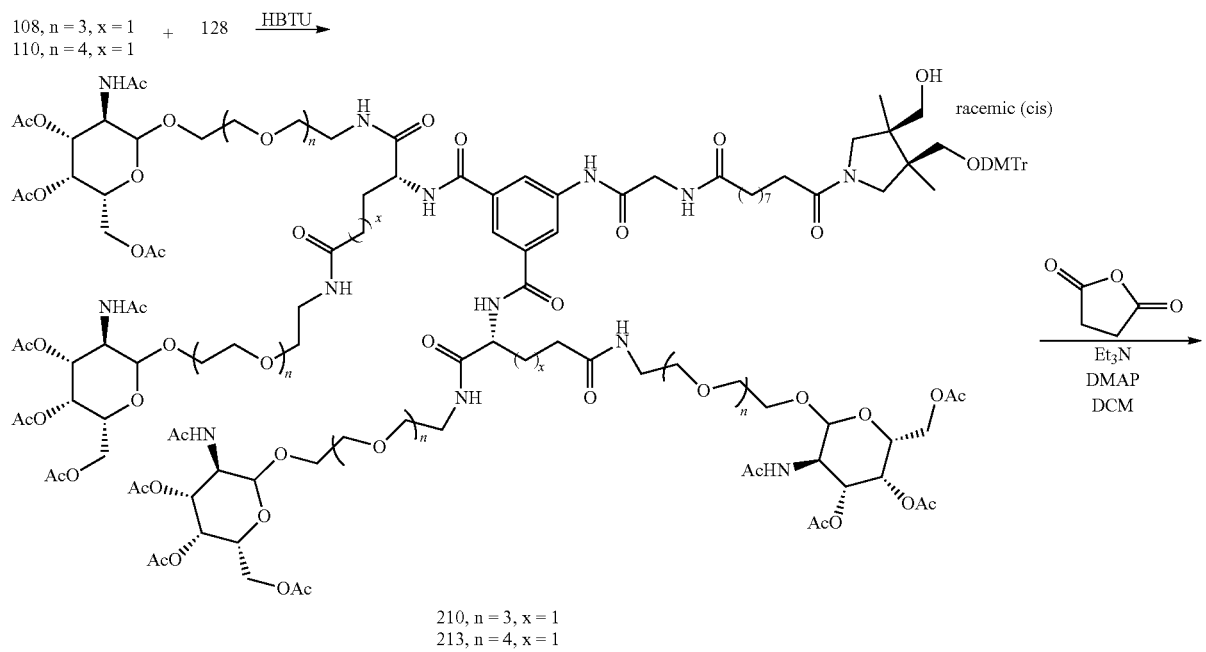
210, n = 3, x = 1
213, n = 4, x = 1
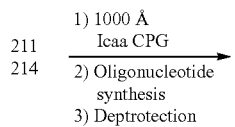
211
214
1) 1000 Å
Icaa CPG
2) Oligonucleotide synthesis
3) Deprotection

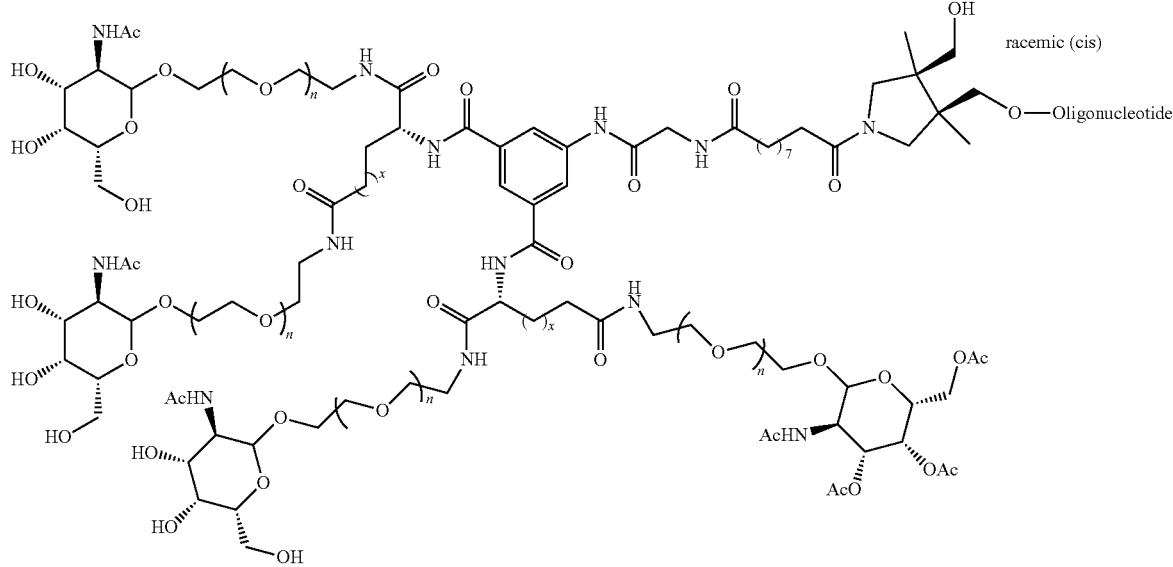

212, n = 3, x = 1
215, n = 4, x = 1

Step 1. Preparation of Dimethyl 5-(2-((2-oxo-2-phenyl-1λ²-ethyl)amino)acetamido)-isophthalate 105

A solution of dimethyl 5-aminoisophthalate (5 g, 24 mmol), Z-Gly-OH (5 g, 24 mmol), EDC (5 g, 26.3 mmol), HOBt (3.6 g, 26.3 mmol), NMM (2.9 mL, 26.3 mmol) in DMF (50 mL) was stirred overnight at room temperature. Upon completion, the reaction mixture was diluted with ethyl acetate (250 mL) and washed with each 1M HCl (2×100 mL), saturated sodium bicarbonate (1×100 mL) and brine (2×100 mL). Dry on magnesium sulfate, filter and concentrate to dryness to afford Dimethyl 5-(2-((2-oxo-2-phenyl-1λ²-ethyl)amino)acetamido)isophthalate as a colorless solid (7.2 g, 79%).

Step 2. Preparation of 5-(2-((2-oxo-2-phenyl-1λ²-ethyl)amino)acetamido)isophthalic acid 106

To a solution of methyl 5-(2-((2-oxo-2-phenyl-1λ²-ethyl)amino)acetamido)isophthalate (7.2 g) in methanol (25 mL) and THF (25 mL) was added 1M NaOH (25 mL). The solution was stirred at room temperature for 2 hours then concentrated to remove THF and MeOH. The aqueous solution remaining was diluted with water (75 mL), cooled on an ice water bath and acidified to pH=1 with 6M HCl. The solid was filtered and washed with water (3×100 mL). The solid was freeze dried to afford 5-(2-((2-oxo-2-phenyl-1λ²-ethyl)amino)acetamido)-isophthalic acid (6.9 g, quantitative).

Step 3. Preparation of Compound 107

Compound 107 was prepared from 5-(2-((2-oxo-2-phenyl-1λ²-ethyl)amino)acetamido)isophthalic acid 106 (200 mg, 0.54 mmol) and 94 (1.7 g, 1.3 mmol) using an identical procedure to that used for compound 95. Yield: 600 mg.

Step 4. Preparation of Compound 108

Compound 108 was prepared from compound 107 (600 mg) using an identical procedure to that used for compound 96. Yield: 650 mg, quantitative.

Step 5. Preparation of Compound 109

Compound 109 was prepared from 5-(2-((2-oxo-2-phenyl-1λ²-ethyl)amino)acetamido)isophthalic acid 106 (180 mg, 0.48 mmol) and 98 (1.5 g, 1.1 mmol) using an identical procedure to that used for compound 99. Yield: 900 mg.

Step 6. Preparation of Compound 110

Compound 110 was prepared from compound 109 (900 mg) using an identical procedure to that used for compound 100. Yield: 920 mg, quantitative.

Step 7. Preparation of Conjugates 212 and 215

Conjugates 212 and 215 were prepared from compound 128 and 108 or 110 using an identical procedure to that used for compound 1.

Example 19a. Synthesis of Conjugates 212a and 215a
Scheme 41a.
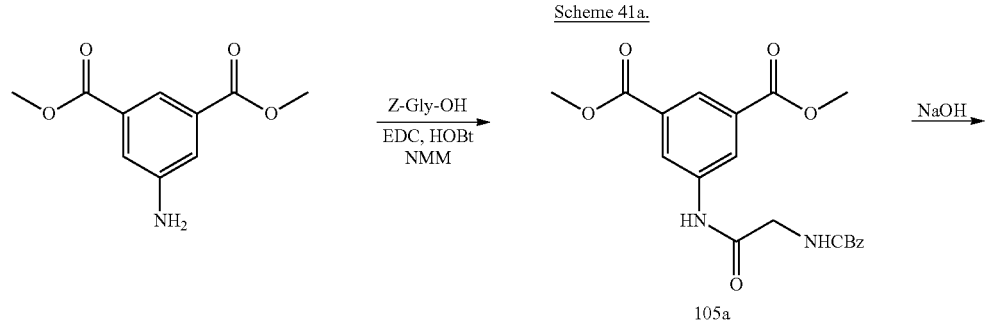
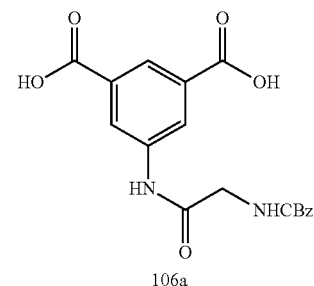
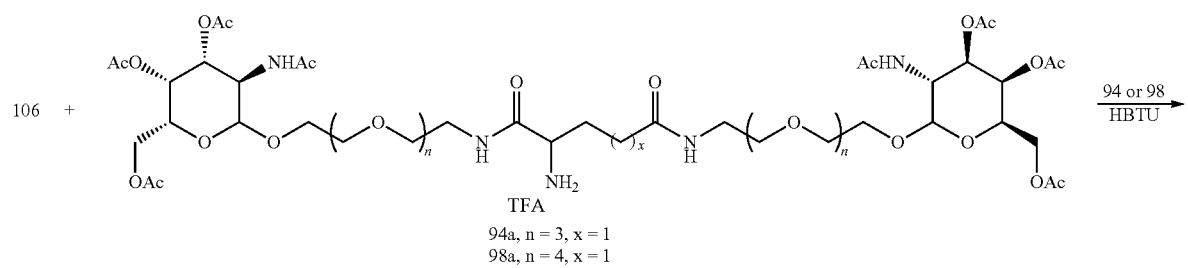
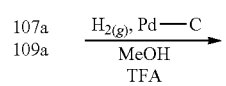

-continued
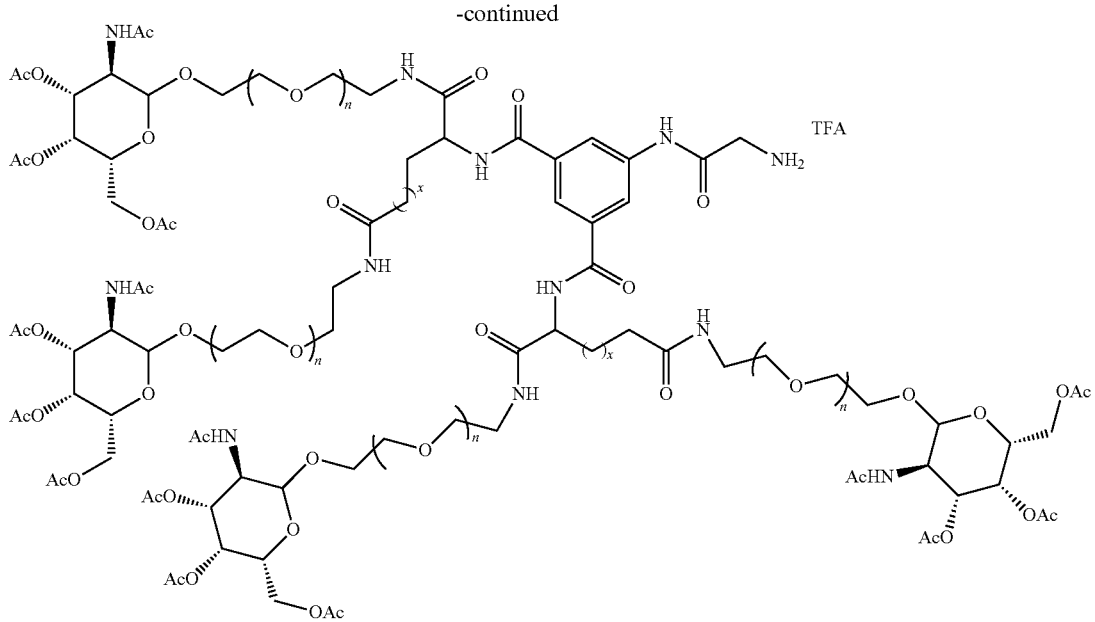
108a, n = 3, x = 1
110a, n = 4, x = 1
Scheme 42a.
108a, n = 3, x = 1
110a, n = 4, x = 1   + 128   $\xrightarrow{\text{HBTU}}$
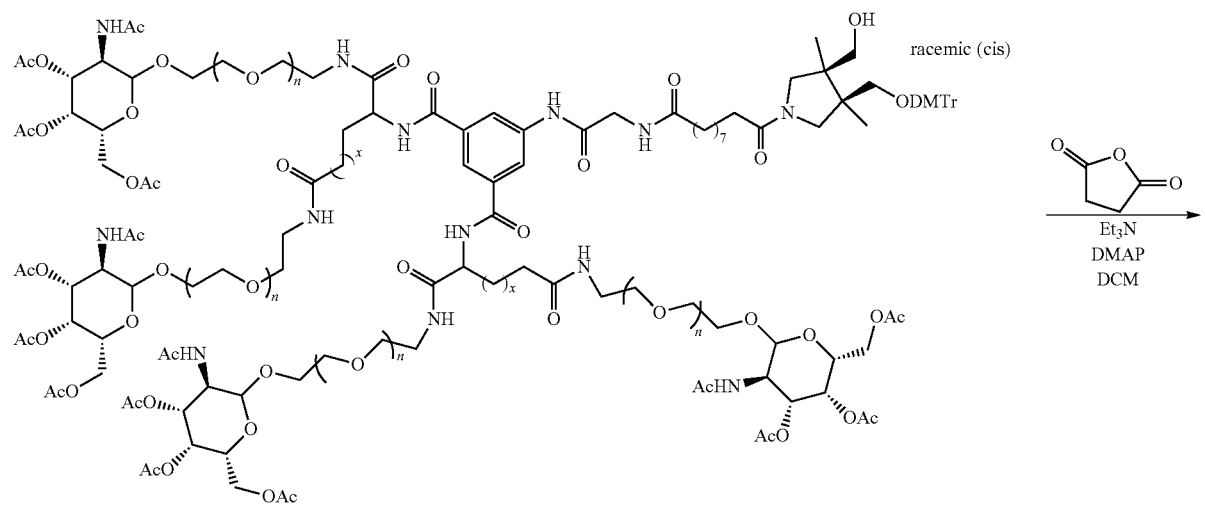
210a, n = 3, x = 1
213a, n = 4, x = 1
211a
214a
$\xrightarrow[\substack{\text{2) Oligonucleotide} \\ \text{synthesis} \\ \text{3) Deptrotection}}]{\text{1) 1000 Å} \\ \text{lcaa CPG}}$ -continued

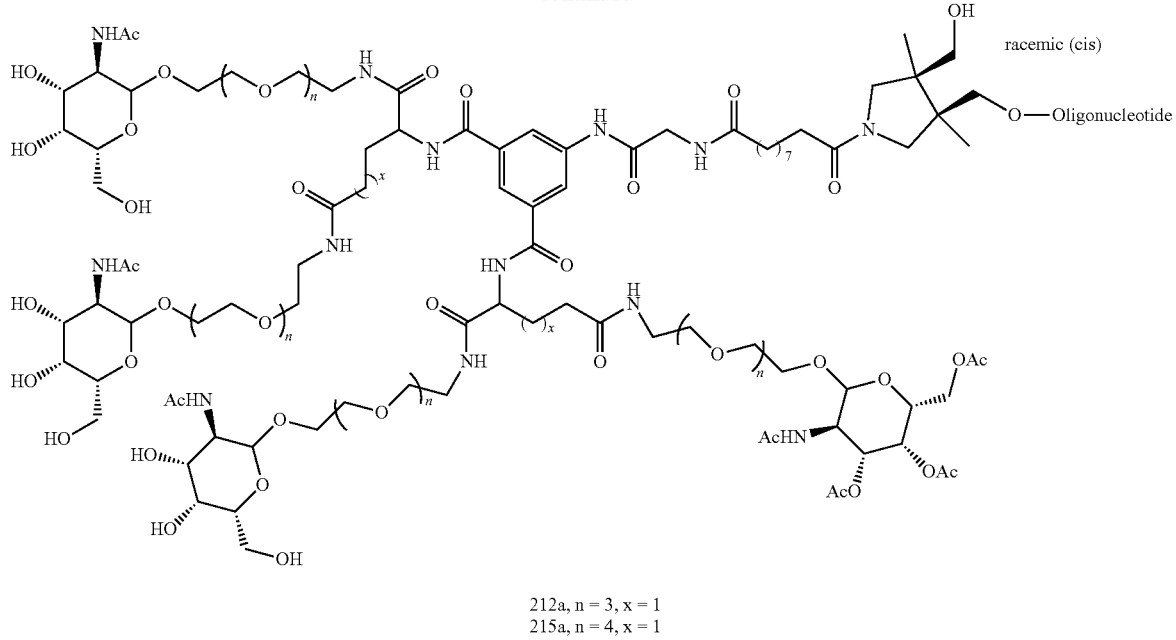

212a, n = 3, x = 1
215a, n = 4, x = 1

Step 1. Preparation of Dimethyl 5-(2-((2-oxo-2-phenyl-1λ²-ethyl)amino)acetamido)-isophthalate 105a A solution of dimethyl 5-aminoisophthalate (5 g, 24 mmol), Z-Gly-OH (5 g, 24 mmol), EDC (5 g, 26.3 mmol), HOBt (3.6 g, 26.3 mmol), NMM (2.9 mL, 26.3 mmol) in DMF (50 mL) is stirred overnight at room temperature. Upon completion, the reaction mixture is diluted with ethyl acetate (250 mL) and washed with each 1M HCl (2×100 mL), saturated sodium bicarbonate (1×100 mL) and brine (2×100 mL). Dry on magnesium sulfate, filter and concentrate to dryness to afford Dimethyl 5-(2-((2-oxo-2-phenyl-1λ²-ethyl)amino)acetamido)isophthalate as a colorless solid (7.2 g, 79%).

Step 2. Preparation of 5-(2-((2-oxo-2-phenyl-1λ²-ethyl)amino)acetamido)isophthalic acid 106a To a solution of methyl 5-(2-((2-oxo-2-phenyl-1λ²-ethyl)amino)acetamido)isophthalate (7.2 g) in methanol (25 mL) and THF (25 mL) is added 1M NaOH (25 mL). The solution is stirred at room temperature for 2 hours then concentrated to remove THF and MeOH. The aqueous solution remaining is diluted with water (75 mL), cooled on an ice water bath and acidified to pH=1 with 6M HCl. The solid is filtered and washed with water (3×100 mL). The solid is freeze dried to afford 5-(2-((2-oxo-2-phenyl-1λ²-ethyl)amino)acetamido)-isophthalic acid (6.9 g, quantitative).

Step 3. Preparation of Compound 107a

Compound 107a is prepared from 5-(2-((2-oxo-2-phenyl-1λ²-ethyl)amino)acetamido)isophthalic acid 106a (200 mg, 0.54 mmol) and 94a (1.7 g, 1.3 mmol) using an identical procedure to that used for compound 95. Yield: 600 mg.

Step 4. Preparation of Compound 108a

Compound 108a is prepared from compound 107a (600 mg) using an identical procedure to that used for compound 96a. Yield: 650 mg, quantitative.

Step 5. Preparation of Compound 109a

Compound 109a is prepared from 5-(2-((2-oxo-2-phenyl-1λ²-ethyl)amino)acetamido)isophthalic acid 106a (180 mg, 0.48 mmol) and 9a8 (1.5 g, 1.1 mmol) using an identical procedure to that used for compound 99. Yield: 900 mg.

Step 6. Preparation of Compound 110a

Compound 110a is prepared from compound 109 (900 mg) using an identical procedure to that used for compound 100. Yield: 920 mg, quantitative.

Step 7. Preparation of Conjugates 212a and 215a

Conjugates 212a and 21a5 are prepared from compound 128 and 108a or 110a using an identical procedure to that used for compound 1.

Example 20. Synthesis of Conjugates 218 and 221
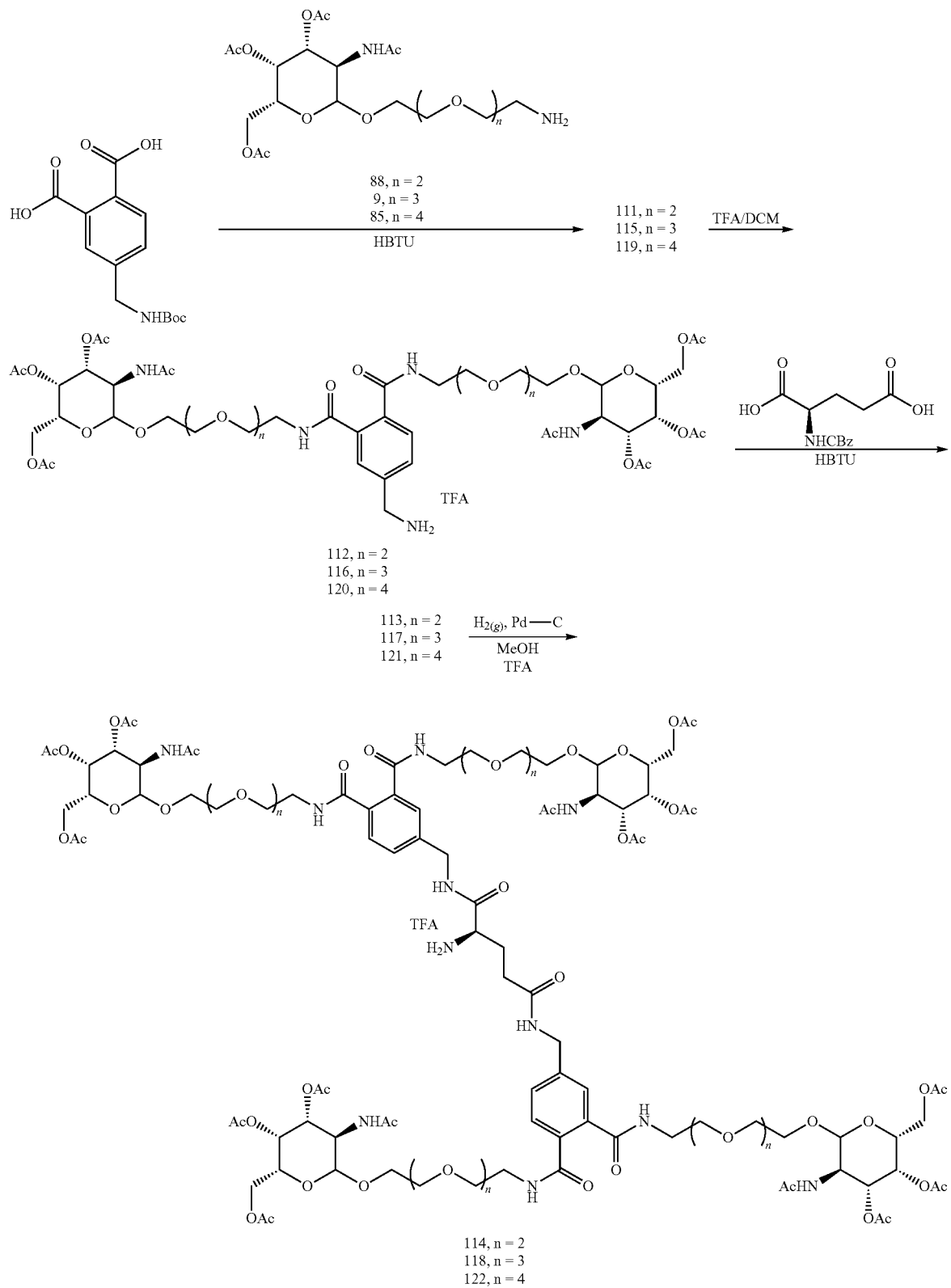
Scheme 43.

Scheme 44.

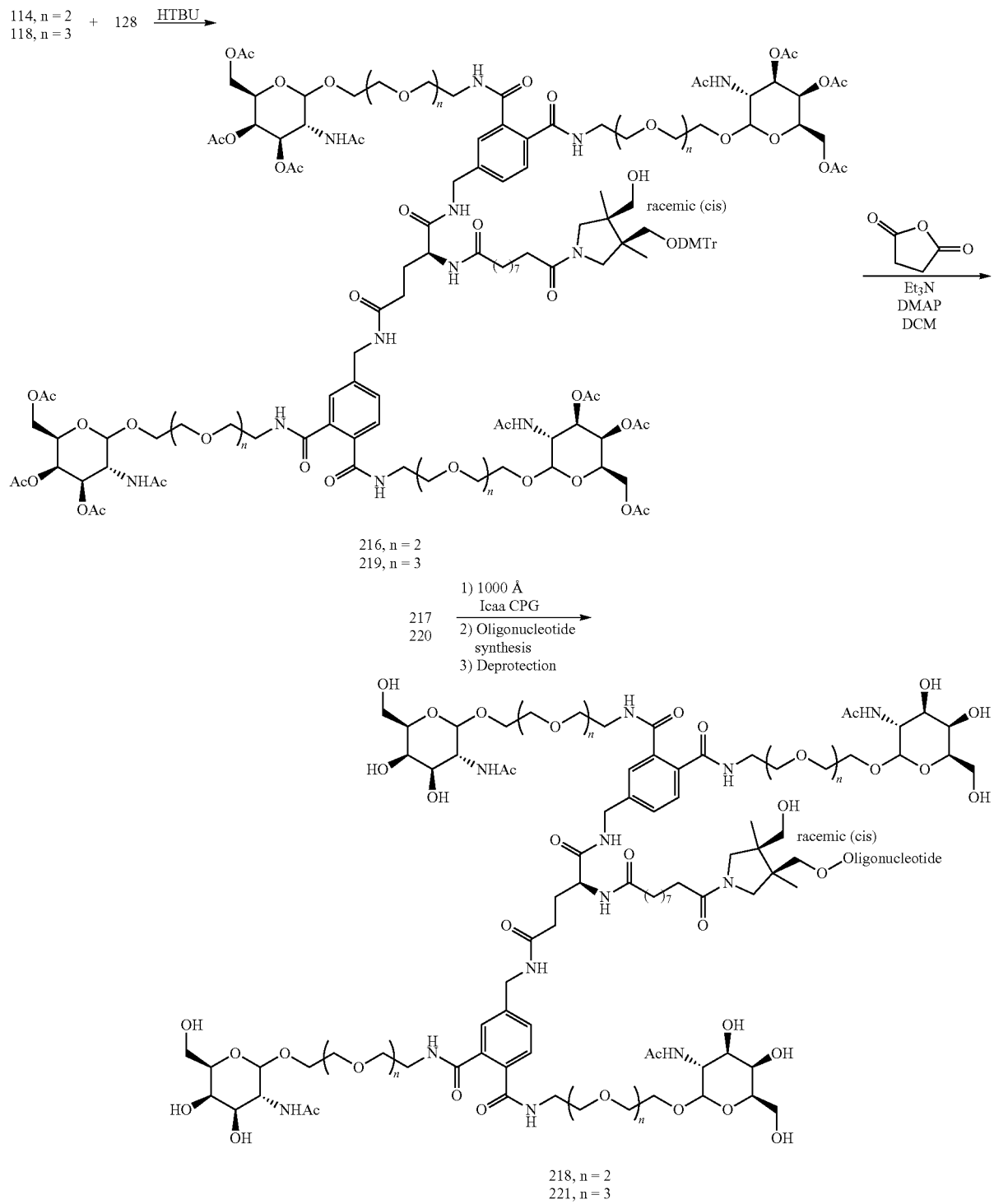

Step 1. Preparation of Compound 111

Compound 111 was prepared from 4-(((tert-butoxycarbonyl)amino)methyl)phthalic acid (1.13 g, 3.84 mmol) and 88 (5 g, 8.44 mmol) using an identical procedure to that used for compound 89. Yield: 2.21 g, 49%.

Step 2. Preparation of Compound 112

A solution of 111 (2.21 g, 1.87 mmol) in $CH_2Cl_2$ (40 mL) was slowly treated with TFA (5 mL). After stirring (2 h) the mixture was concentrated and subjected to chromatography to yield 112 (1.08 g, 47%) as a colorless foam. Rf 0.1 (10% $CH_3OH$—$CH_2Cl_2$).

Step 3. Preparation of Compound 113

Compound 113 was prepared from compound 112 (1.08 g, 0.88 mmol) and (2-oxo-2-phenyl-1λ²-ethyl)-D-glutamic acid (112 mg, 0.39 mmol) using an identical procedure to that used for compound 91. Yield: 600 mg, 62%.

Step 4. Preparation of Compound 114

Compound 114 was prepared from compound 113 using an identical procedure to that used for compound 92.

Step 5. Preparation of Compound 115

Compound 115 was prepared from 4-(((tert-butoxycarbonyl)amino)methyl)phthalic acid (3.94 g, 13.3 mmol) and 9 (18.2 g, 29.4 mmol) using an identical procedure to that used for compound 93. Yield: 9.02 g, 53%.

Step 6. Preparation of Compound 116

Compound 116 was prepared from compound 115 (8 g, 6.3 mmol) using an identical procedure to that used for compound 112. Yield: 3.23 g, 39%.

Step 7. Preparation of Compound 117

Compound 117 was prepared from compound 116 (3.23 g, 2.45 mmol) and (2-oxo-2-phenyl-1λ²-ethyl)-D-glutamic acid (192 mg, 1.1 mmol) using an identical procedure to that used for compound 95. Yield: 2.22 g, 34%.

Step 8. Preparation of Compound 118

Compound 118 was prepared from compound 117 (2.22 g, 0.84 mmol) using an identical procedure to that used for compound 96. Yield: 2.02 g, 91%.

Step 9. Preparation of Conjugates 218 and 221

Conjugates 218 and 221 were prepared from compounds 128 and 114 or 118 using an identical procedure to that used for compound 1.

Example 20a. Synthesis of Conjugates 218a and 221a

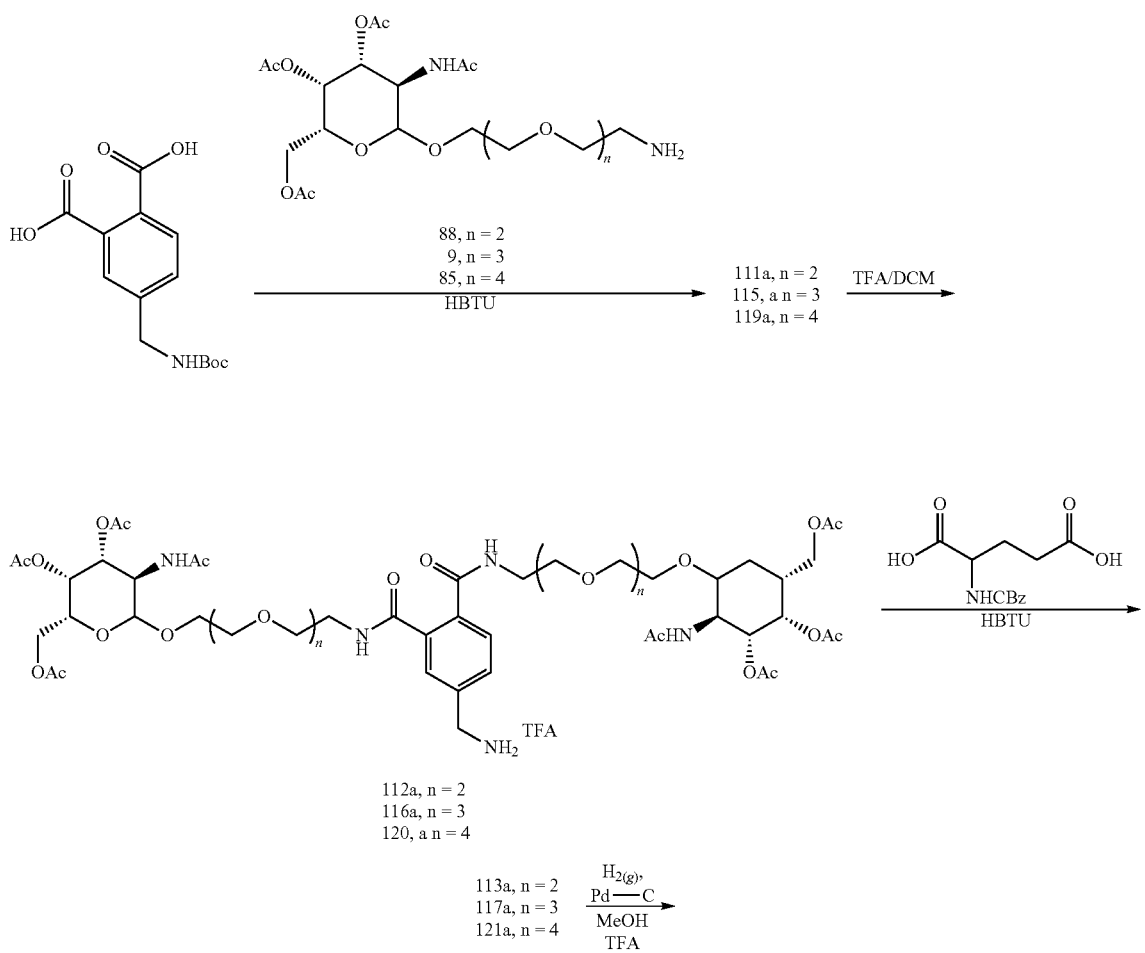

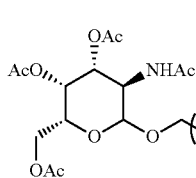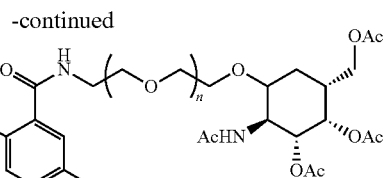
-continued
114a, n = 2
118a, n = 3
122a, n = 4
Scheme 44a.
114a, n = 2
118a, n = 3    + 128  →[HBTU]
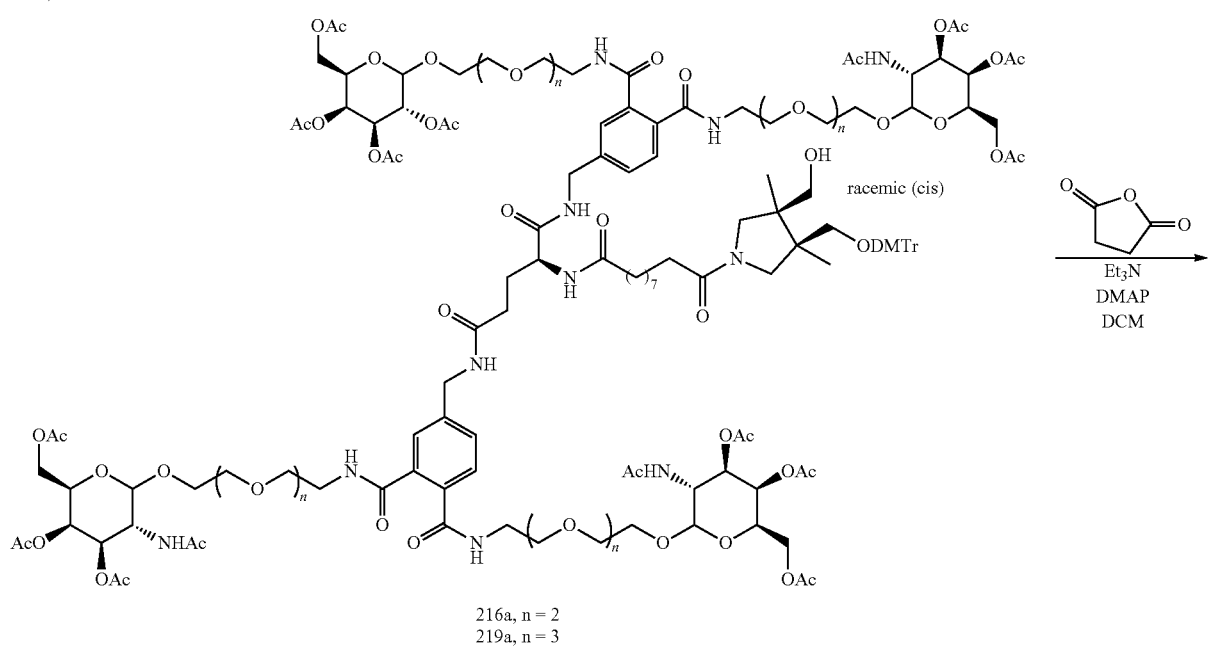
216a, n = 2
219a, n = 3
217a
220a
→ 1) 1000 Å Icaa CPG
2) Oligonucleotide synthesis
3) Deptrotection -continued

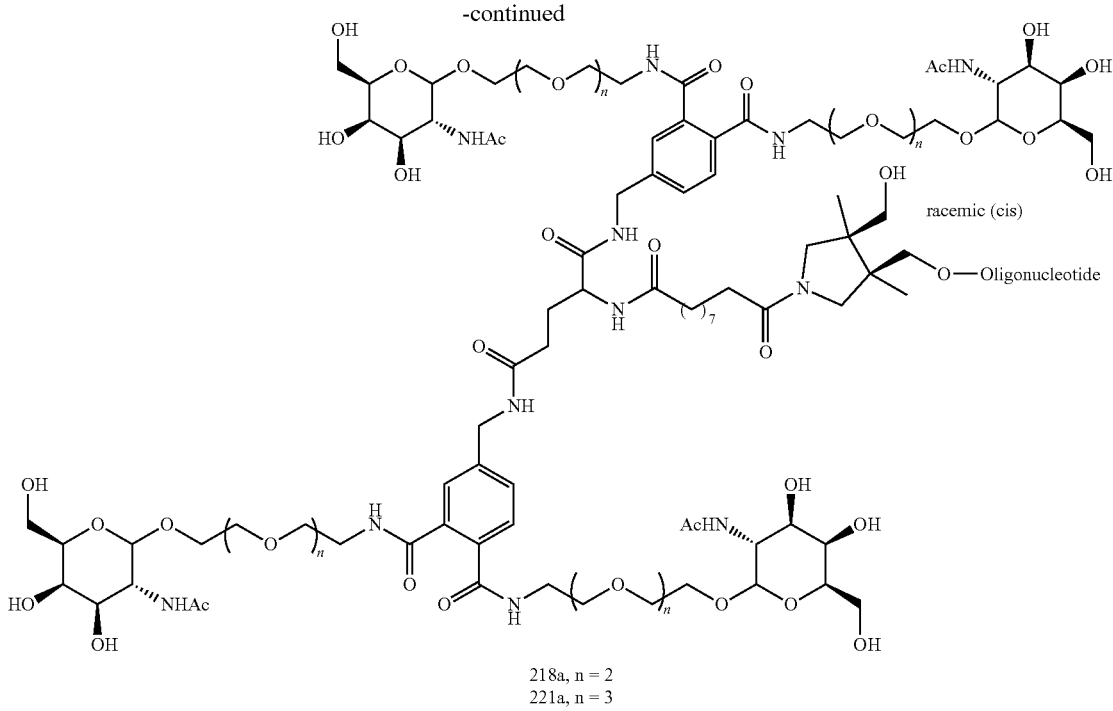

218a, n = 2
221a, n = 3

Step 1. Preparation of Compound 111a

Compound 111a is prepared from 4-(((tert-butoxycarbonyl)amino)methyl)phthalic acid (1.13 g, 3.84 mmol) and 88 (5 g, 8.44 mmol) using an identical procedure to that used for compound 89. Yield: 2.21 g, 49%.

Step 2. Preparation of Compound 112a

A solution of 111a (2.21 g, 1.87 mmol) in $CH_2Cl_2$ (40 mL) is slowly treated with TFA (5 mL). After stirring (2 h) the mixture is concentrated and subjected to chromatography to yield 112a (1.08 g, 47%) as a colorless foam. Rf 0.1 (10% $CH_3OH$—$CH_2Cl_2$).

Step 3. Preparation of Compound 113a

Compound 113a is prepared from compound 112a (1.08 g, 0.88 mmol) and (2-oxo-2-phenyl-1λ²-ethyl)-D-glutamic acid (112 mg, 0.39 mmol) using an identical procedure to that used for compound 91. Yield: 600 mg, 62%.

Step 4. Preparation of Compound 114a

Compound 114a is prepared from compound 113a using an identical procedure to that used for compound 92.

Step 5. Preparation of Compound 115a

Compound 115a is prepared from 4-(((tert-butoxycarbonyl)amino)methyl)phthalic acid (3.94 g, 13.3 mmol) and 9 (18.2 g, 29.4 mmol) using an identical procedure to that used for compound 93. Yield: 9.02 g, 53%.

Step 6. Preparation of Compound 116a

Compound 116a is prepared from compound 115a (8 g, 6.3 mmol) using an identical procedure to that used for compound 11a. Yield: 3.23 g, 39%.

Step 7. Preparation of Compound 117a

Compound 117a is prepared from compound 116a (3.23 g, 2.45 mmol) and (2-oxo-2-phenyl-1λ²-ethyl)glutamic acid (192 mg, 1.1 mmol) using an identical procedure to that used for compound 95. Yield: 2.22 g, 34%.

Step 8. Preparation of Compound 118a

Compound 118a is prepared from compound 117a (2.22 g, 0.84 mmol) using an identical procedure to that used for compound 96. Yield: 2.02 g, 91%.

Step 9. Preparation of Conjugates 21a8 and 221a

Conjugates 218a and 22a1 are prepared from compounds 128 and 114a or 118a using an identical procedure to that used for compound 1.

Example 21. Synthesis of Conjugate 224
Scheme 45.
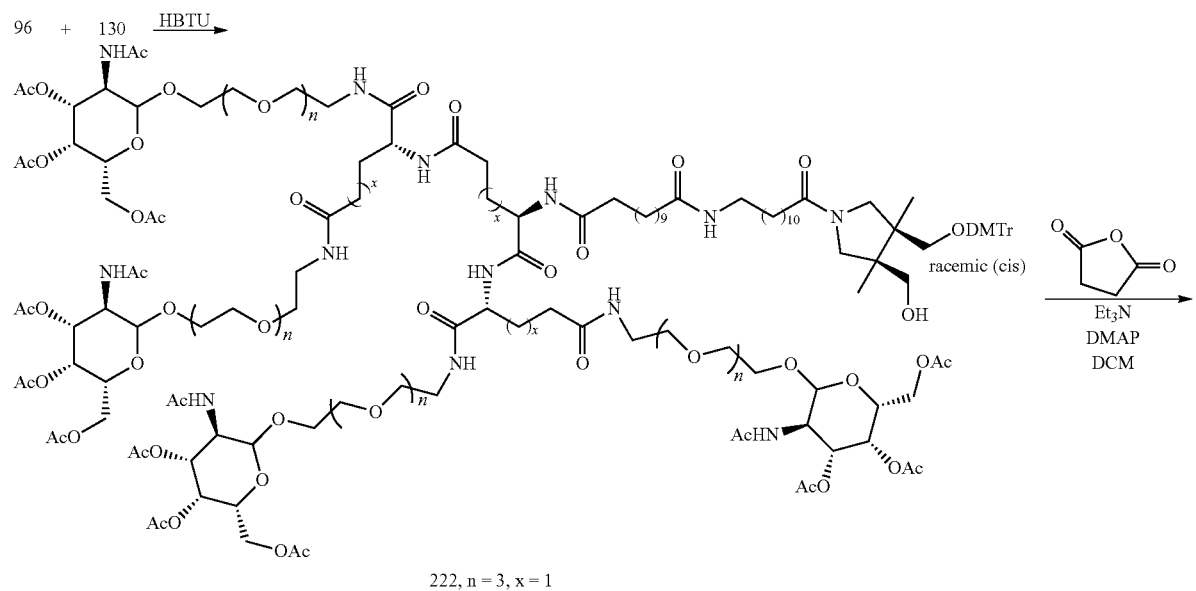
222, n = 3, x = 1
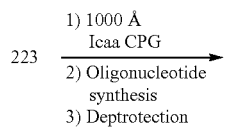
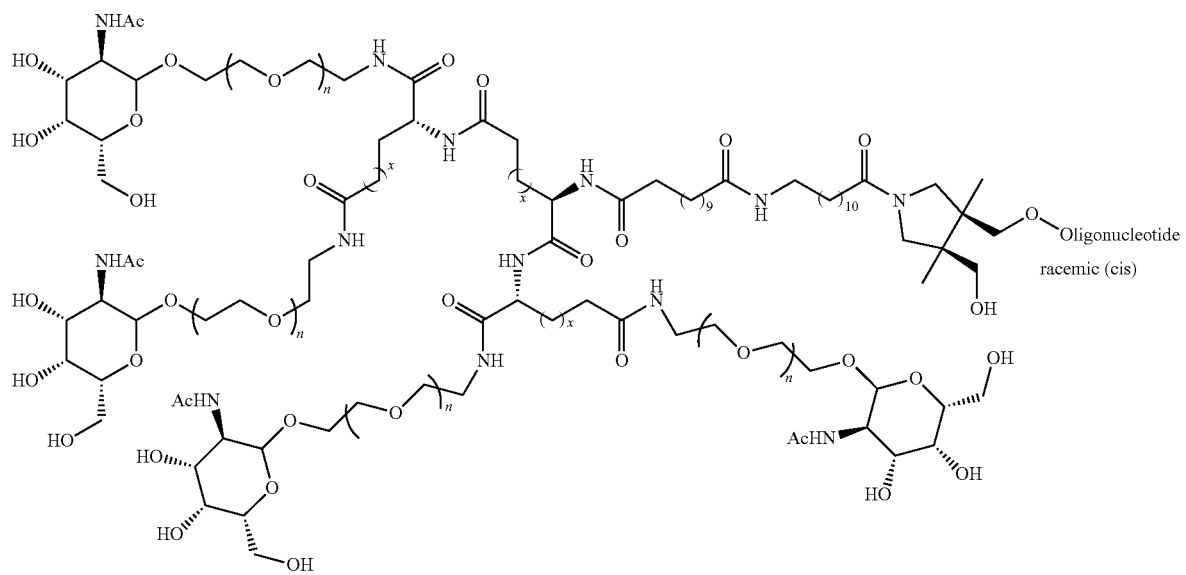
224, n = 3, x = 1

Step 1. Preparation of Compounds 224
Conjugate 224 was prepared from compounds 96 and 130 using an identical procedure to that used for compound 1.
Example 21a. Synthesis of Conjugate 224b
Scheme 45a.
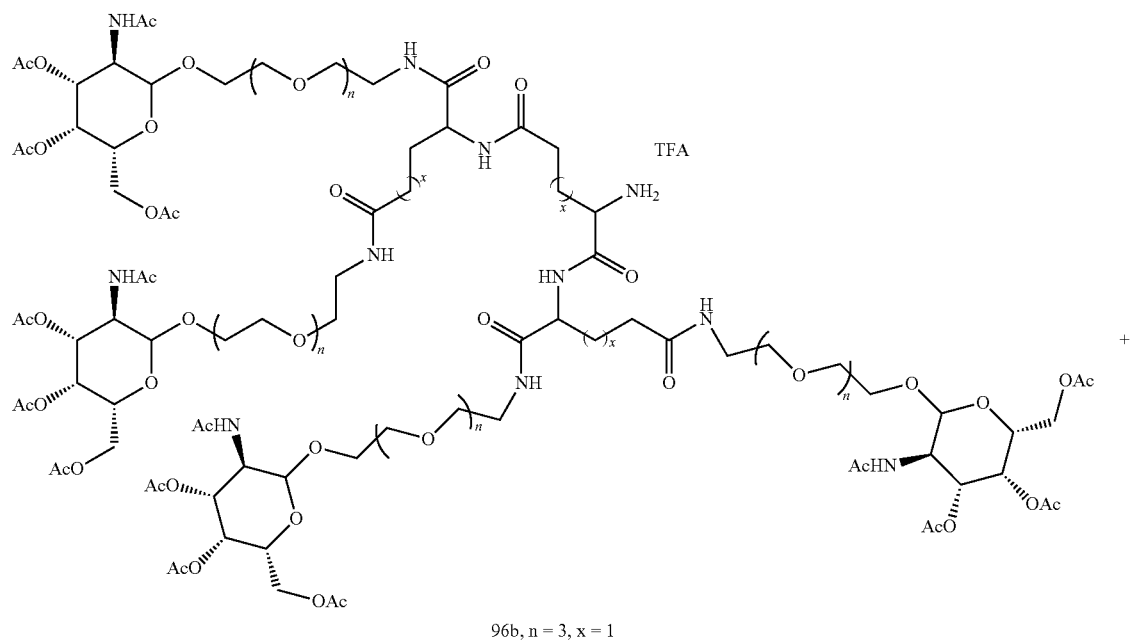
96b, n = 3, x = 1
130 $\xrightarrow{\text{HBTU}}$
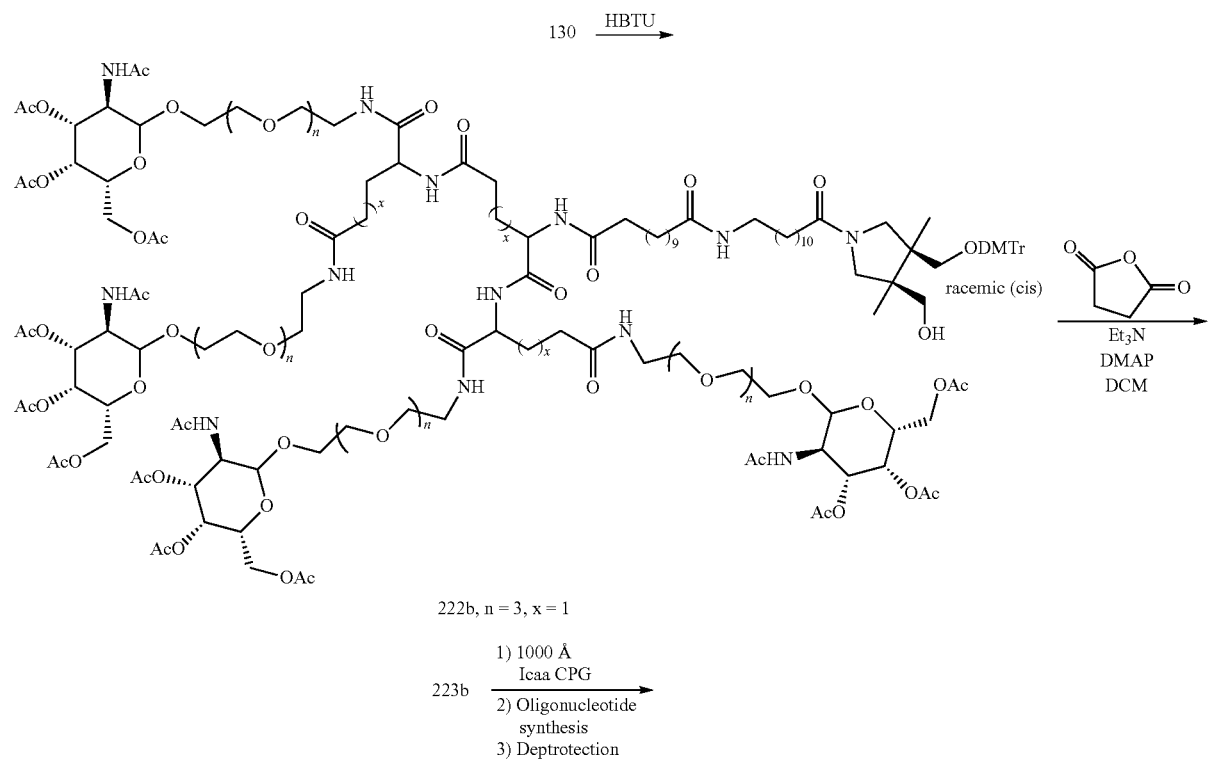
222b, n = 3, x = 1
223b $\xrightarrow[\substack{\text{2) Oligonucleotide} \\ \text{synthesis} \\ \text{3) Deptrotection}}]{\substack{\text{1) 1000 Å} \\ \text{lcaa CPG}}}$

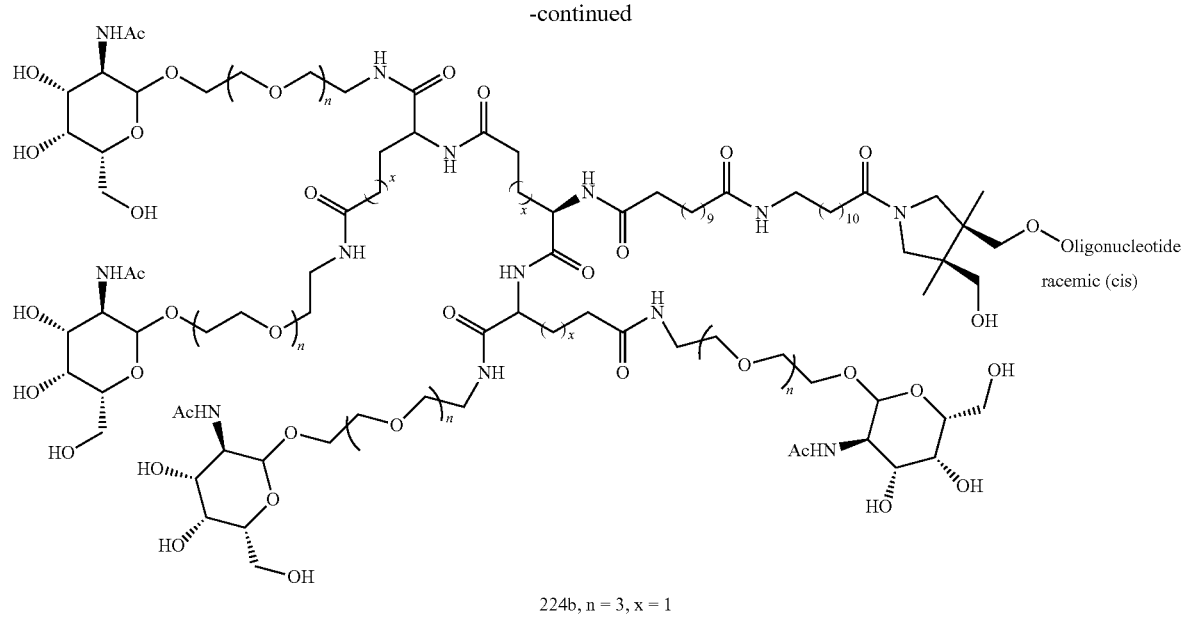
224b, n = 3, x = 1
Step 1. Preparation of Compounds 224b
Conjugate 224b is prepared from compounds 96b and 130 using an identical procedure to that used for compound 1.
Example 22 Synthesis of Conjugate 231
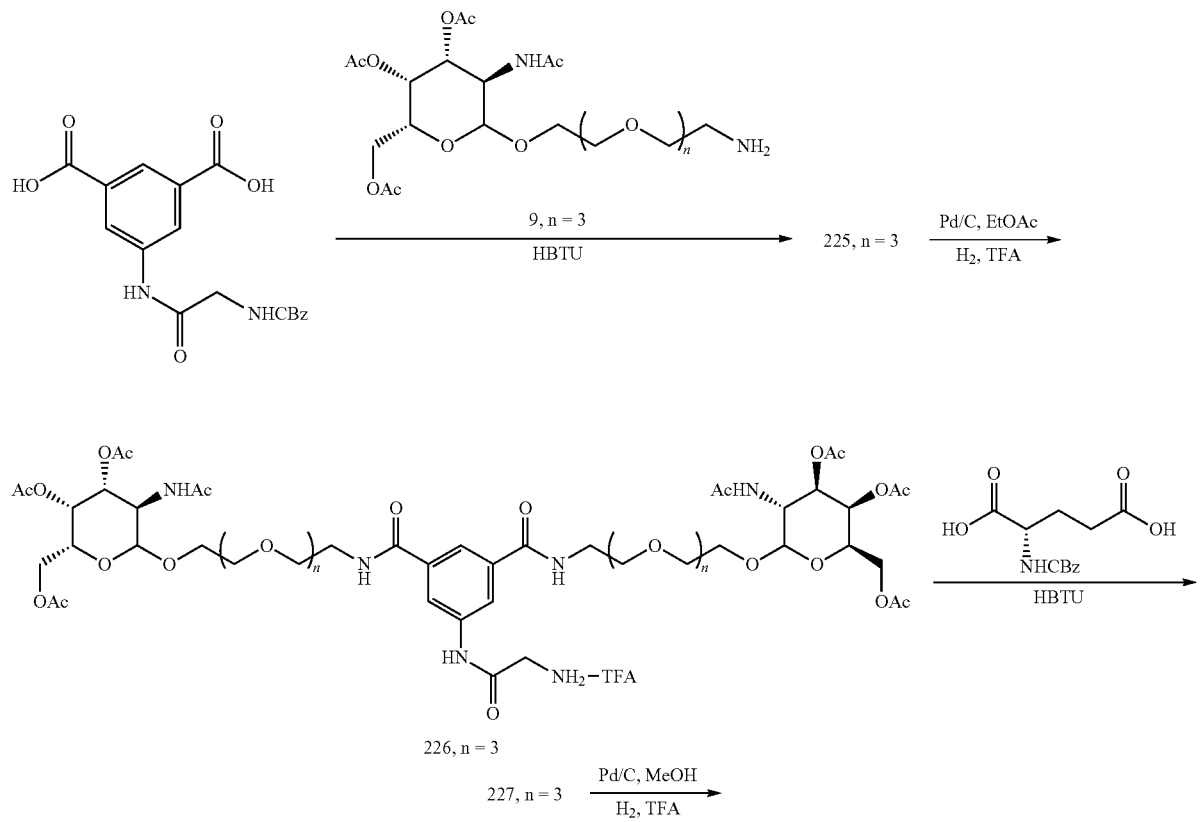
Scheme 46

-continued
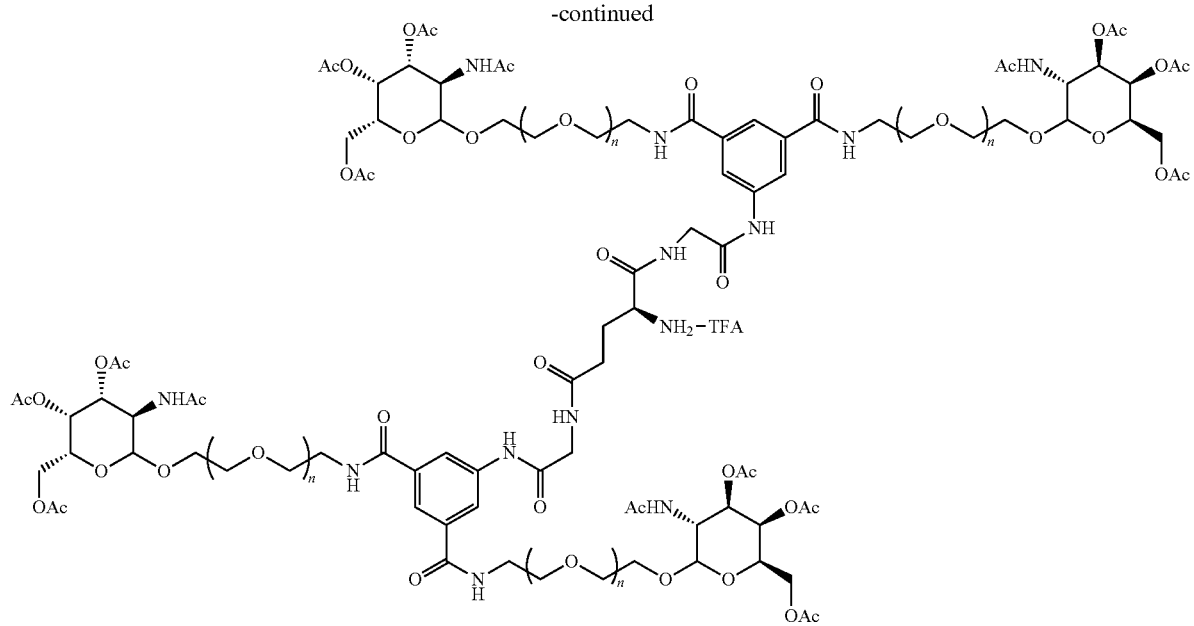
228, n = 3
Scheme 47
228, n = 3 + 128 →[HTBU]
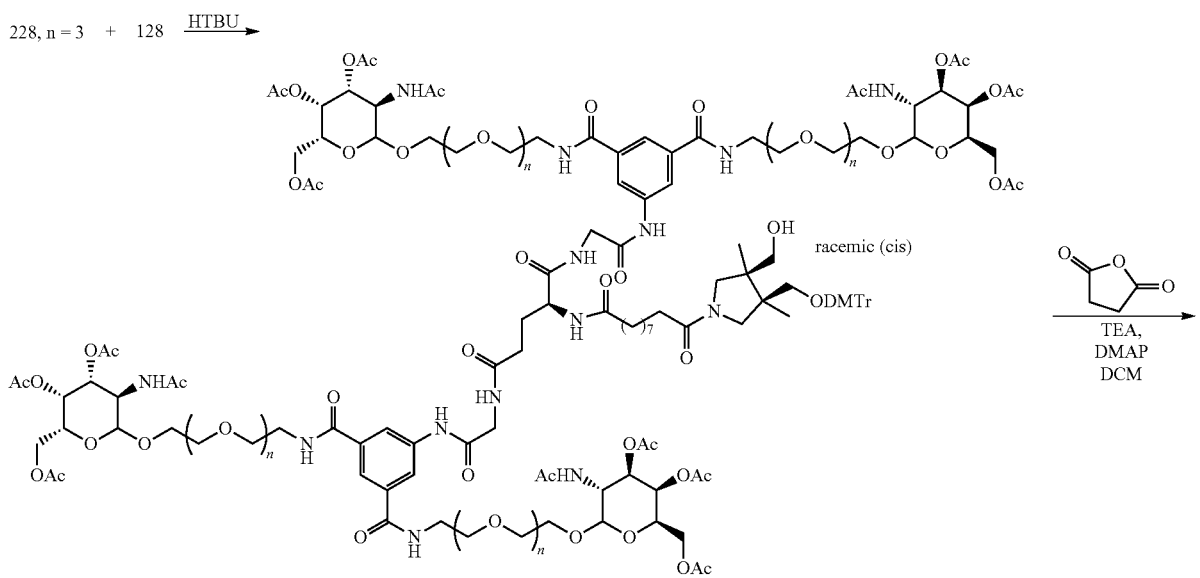
229, n = 3
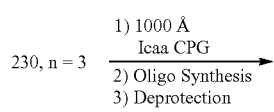
230, n = 3 →[1) 1000 Å Icaa CPG / 2) Oligo Synthesis / 3) Deprotection]

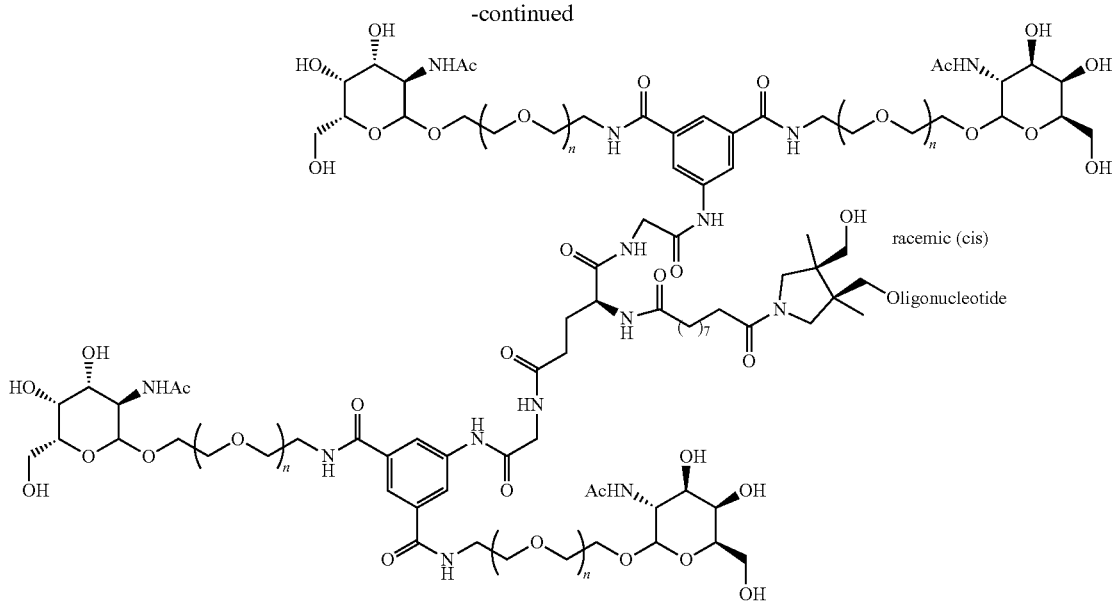

231, n = 3

Step 1 Preparation of Compound 225

Compound 225 was prepared from 5-(2-aminoacetamido) isophthalic acid 106 (560 mg, 1.5 mmol) and 9 (2.24 g, 3.6 mmol) using an identical procedure to that used for 89. Yield 1.6 g, 80%.

Step 2 Preparation of Compound 226

Compound 226 was prepared in the same fashion as 14. Yield 1.22 g, 78%.

Step 3 Preparation of Compound 227

Compound 227 was prepared in the same fashion as 89, from Z-glutamic acid (108 mg, 0.38 mmol) and 226 (1.22 g, 0.92 mmol). Yield 471 mg, 45%.

Step 4 Preparation of Compound 228

Compound 228 was prepared in the same fashion as 14. Yield 460 mg, Quant.

Step 5 Preparation of Compound 229

Compound 229 was prepared from 228 (460 mg, 0.17 mmol) and 128 (125 mg, 0.19 mmol) in the same fashion as 89. Yield 365 mg, 66%.

Step 6 Preparation of Compound 231

Conjugate 231 was prepared using an identical procedure to that used for compound 1.

Example 22a Synthesis of Conjugate 231a

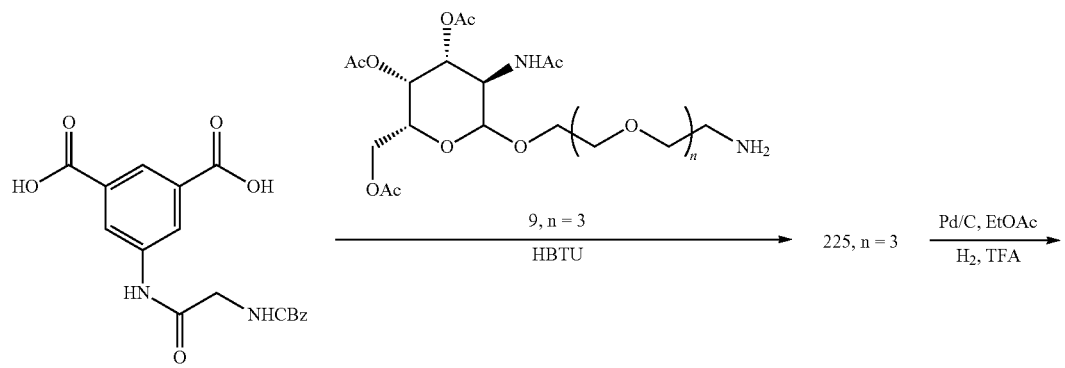

-continued
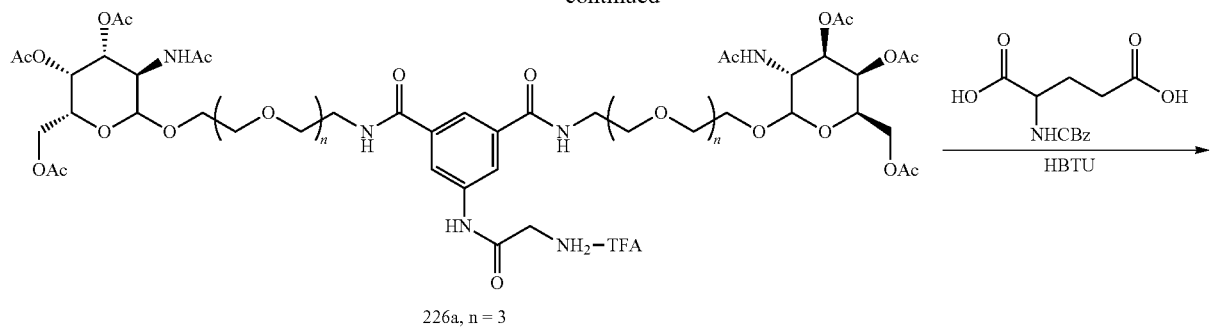
226a, n = 3
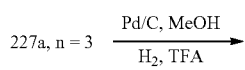
227a, n = 3
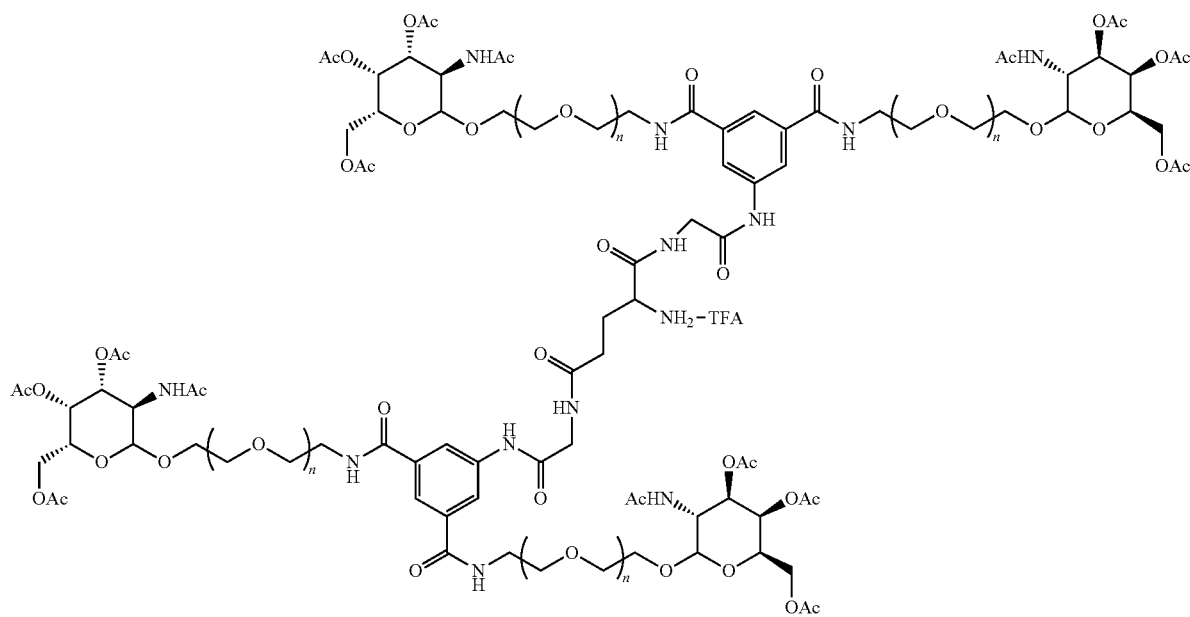
228a, n = 3

Scheme 47a
228a, n = 3   +   128   →(HTBU)
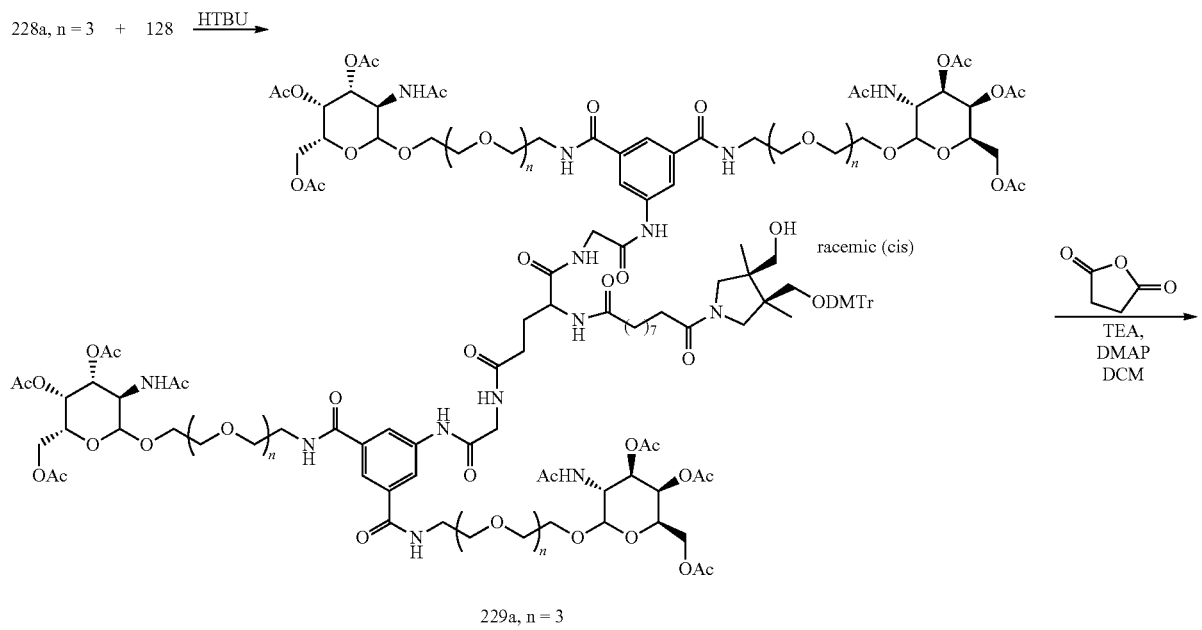
229a, n = 3
→ (succinic anhydride, TEA, DMAP, DCM)
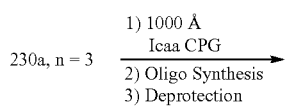
230a, n = 3   →  1) 1000 Å lcaa CPG  2) Oligo Synthesis  3) Deprotection
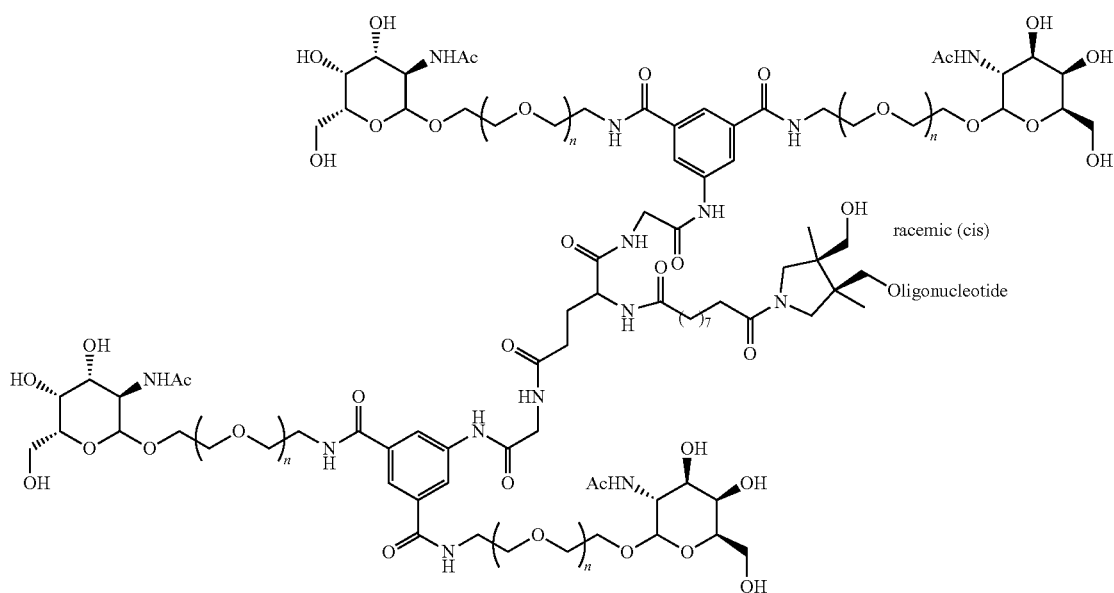
231a, n = 3

Step 1 Preparation of Compound 225a

Compound 225a is prepared from 5-(2-aminoacetamido) isophthalic acid 106 (560 mg, 1.5 mmol) and 9 (2.24 g, 3.6 mmol) using an identical procedure to that used for 89. Yield 1.6 g, 80%.

Step 2 Preparation of Compound 226a

Compound 226a is prepared in the same fashion as 14. Yield 1.22 g, 78%.

Step 3 Preparation of Compound 227a

Compound 227a is prepared in the same fashion as 89, from Z-glutamic acid (108 mg, 0.38 mmol) and 226a (1.22 g, 0.92 mmol). Yield 471 mg, 45%.

Step 4 Preparation of Compound 228a

Compound 228a is prepared in the same fashion as 14. Yield 460 mg, Quant.

Step 5 Preparation of Compound 229a

Compound 229a is prepared from 228a (460 mg, 0.17 mmol) and 128 (125 mg, 0.19 mmol) in the same fashion as 89. Yield 365 mg, 66%.

Step 6 Preparation of Compound 231a

Conjugate 231a is prepared using an identical procedure to that used for compound 1.

Example 22b Synthesis of Conjugate 231b

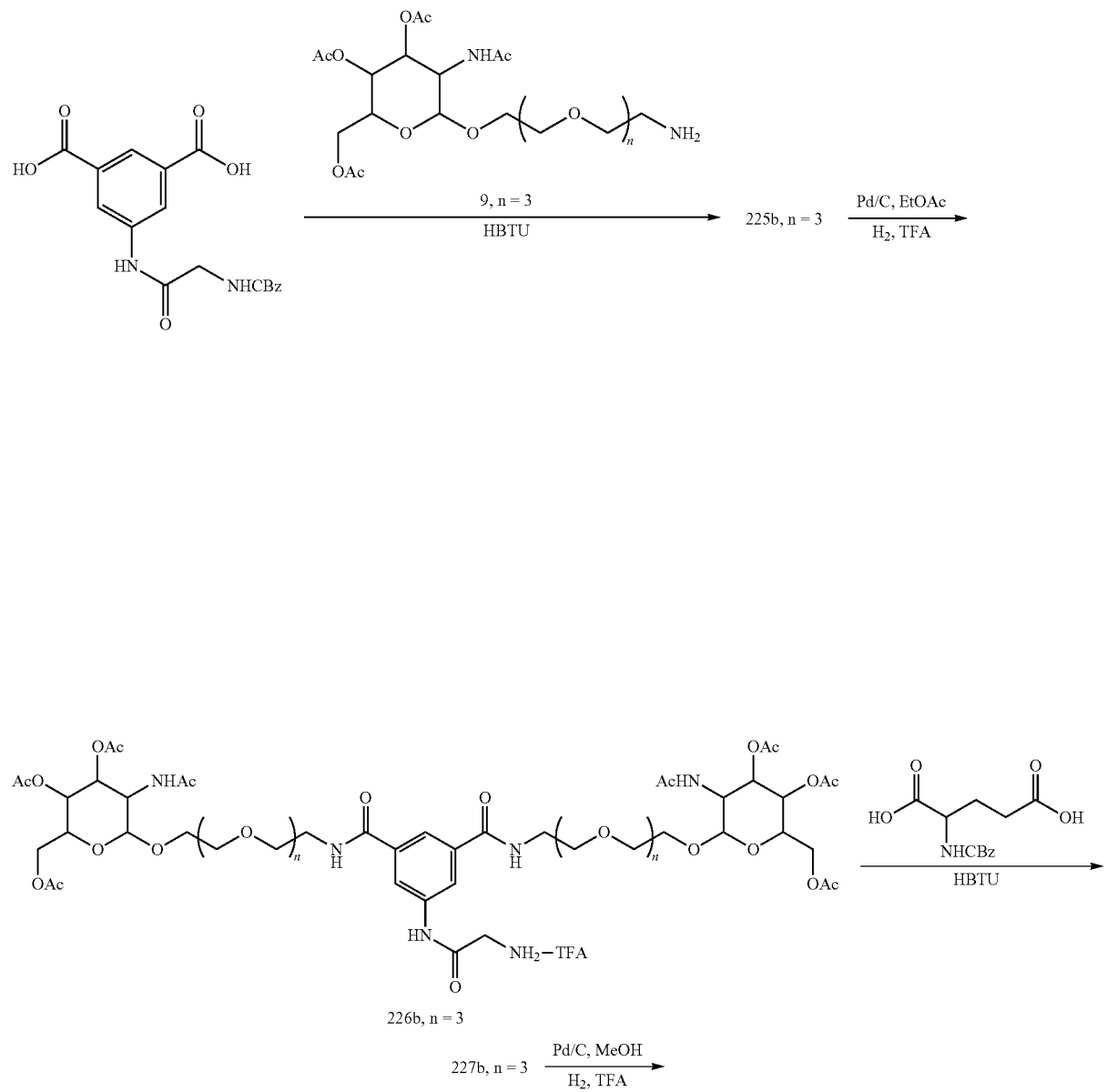

Scheme 46b

-continued
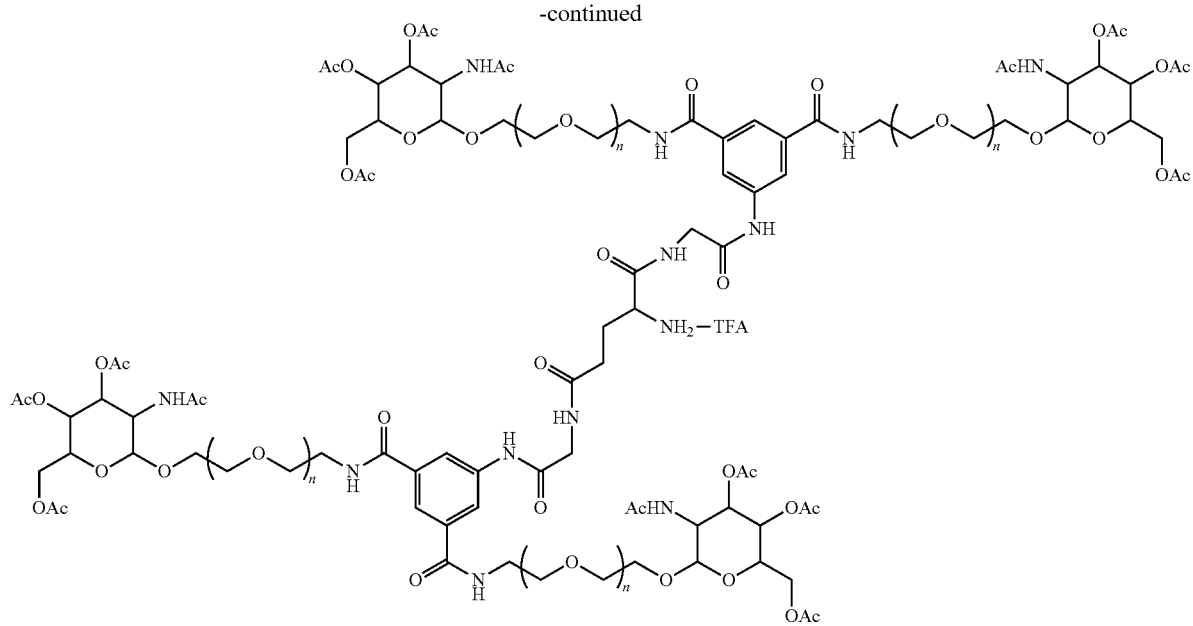
228b, n = 3
Scheme 47b
228a, n = 3 + 128 →[HTBU]
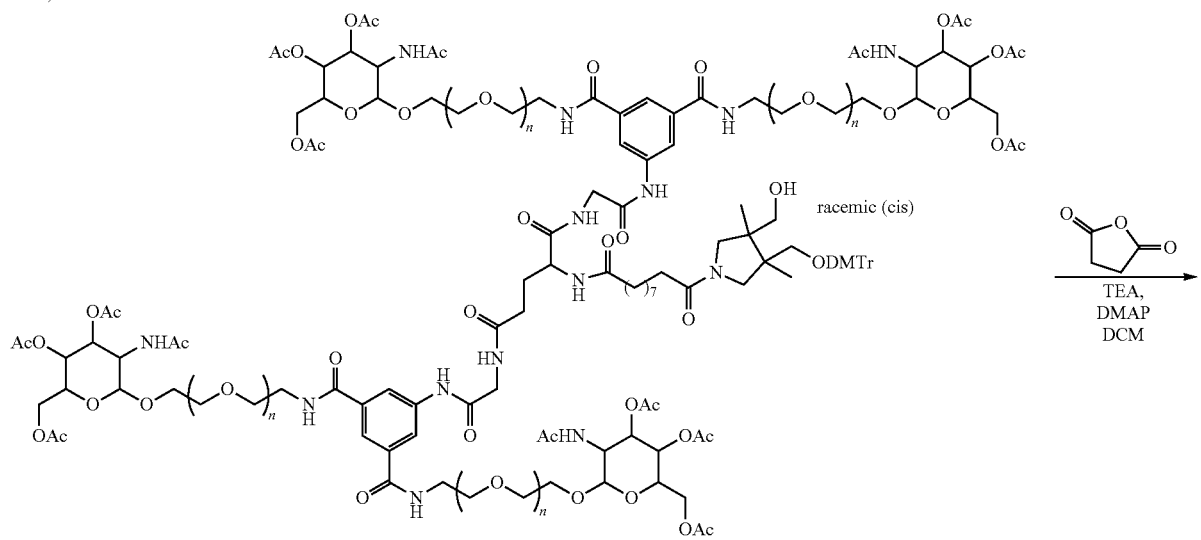
229b, n = 3
→ TEA, DMAP, DCM (succinic anhydride)
230b, n = 3 →[1) 1000 Å lcaa CPG; 2) Oligo Synthesis; 3) Deprotection]

-continued

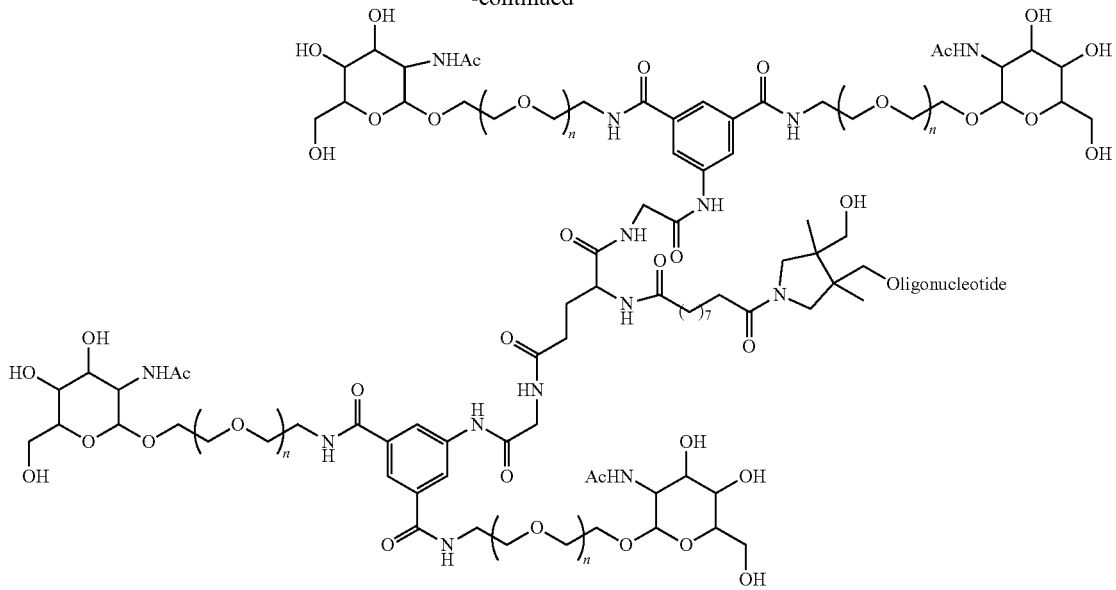

231b, n = 3

Step 1 Preparation of Compound 225b

Compound 225b is prepared from 5-(2-aminoacetamido) isophthalic acid 106 (560 mg, 1.5 mmol) and 9 (2.24 g, 3.6 mmol) using an identical procedure to that used for 89. Yield 1.6 g, 80%.

Step 2 Preparation of Compound 226b

Compound 226b is prepared in the same fashion as 14. Yield 1.22 g, 78%.

Step 3 Preparation of Compound 227b

Compound 227b is prepared in the same fashion as 89, from Z-glutamic acid (108 mg, 0.38 mmol) and 226b (1.22 g, 0.92 mmol). Yield 471 mg, 45%.

Step 4 Preparation of Compound 228b

Compound 228b is prepared in the same fashion as 14. Yield 460 mg, Quant.

Step 5 Preparation of Compound 229b

Compound 229b is prepared from 228b (460 mg, 0.17 mmol) and 128 (125 mg, 0.19 mmol) in the same fashion as 89. Yield 365 mg, 66%.

Step 6 Preparation of Compound 231b

Conjugate 231b is prepared using an identical procedure to that used for compound 1.

Example 23. Synthesis of Conjugate 233

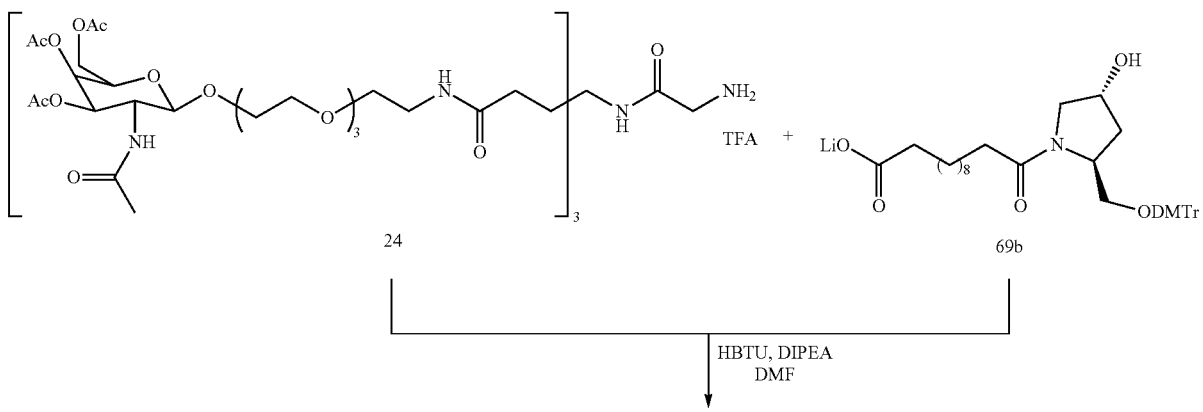

289 290
-continued
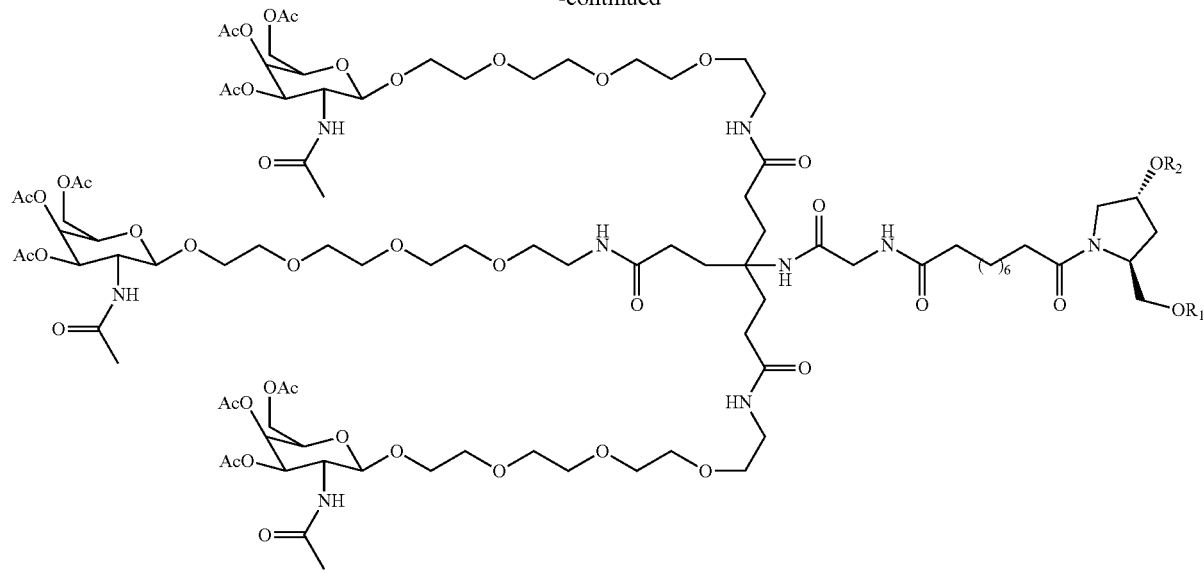
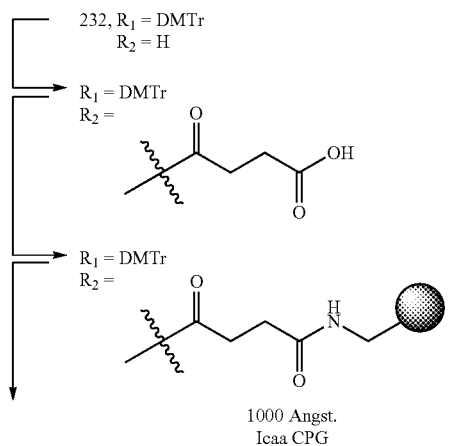
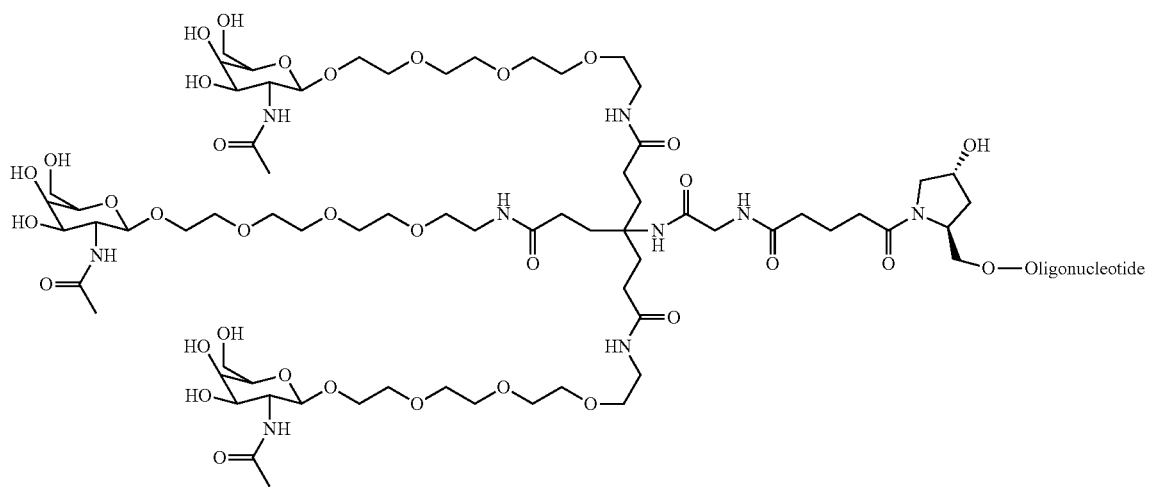
233

Step 1. Preparation of Compound 232
Compound 232 was prepared from compound 24 (650 mg, 0.33 mmol) and compound 69b (175 mg, 0.33 mmol) using an identical procedure to that used for compound 19. Yield: 380 mg, 47%.
Step 2. Preparation of Compound 233
Compound 233 was prepared from compound 232 using identical procedures to that used for compound 1.
Example 24. Synthesis of Conjugate 235
Scheme 49
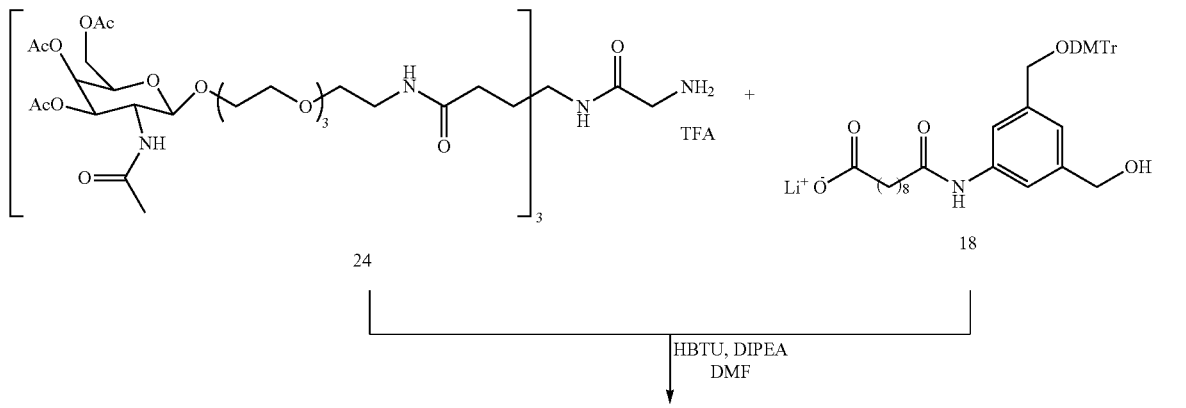
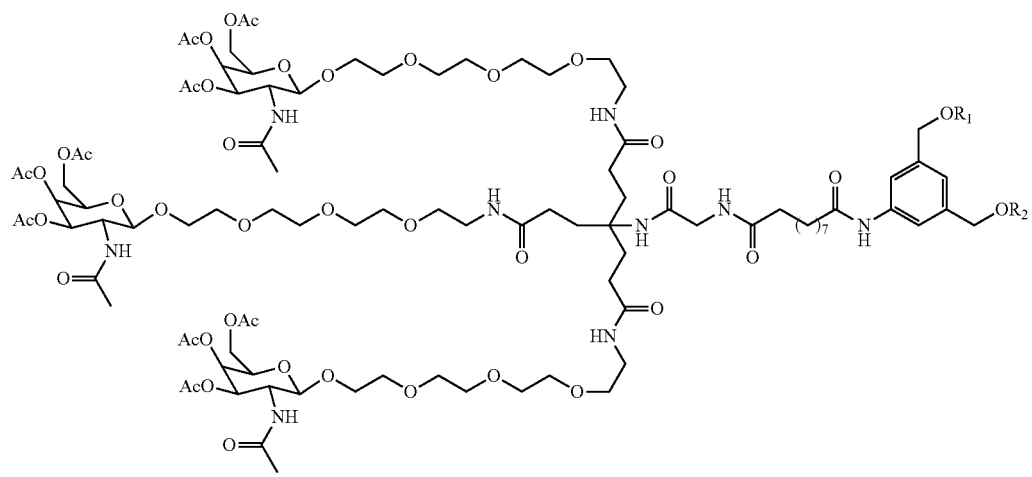

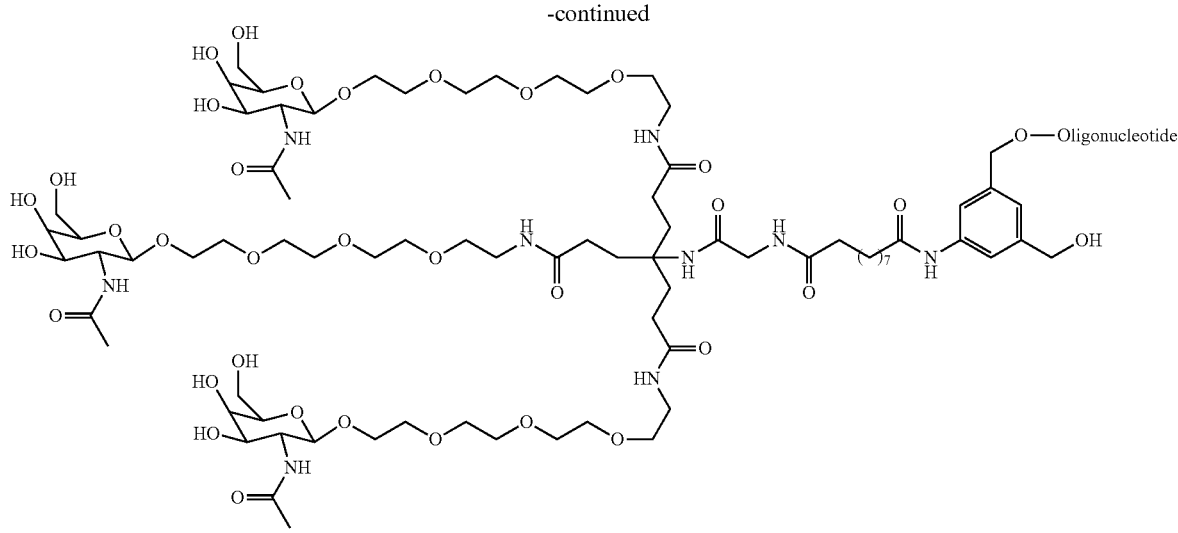

235

Step 1. Preparation of Compound 234

Compound 234 was prepared from compound 24 (1.1 g, 0.55 mmol) and compound 18 (175 mg, 0.33 mmol) using an identical procedure to that used for compound 19. Yield: 685 mg, 51%.

Step 2. Preparation of Compound 235

Compound 235 was prepared from compound 234 using identical procedures to that used for compound 1.

Example 25. In Vivo Testing of HBV siRNA Conjugates

Chronic HBV infection is a worldwide disease with progressing damage to the liver. Current treatments available may reduce the viral DNA but have had little effect on the viral antigens that contribute greatly to the disease progression. Thus, siRNAs to target HBV to reduce the viral antigens were designed.

Chemically modified HBV siRNA described in Table 1 conjugated to GalNAc ligands were tested for in vivo activity in an established mouse model of HBV infection. In the AAV-HBV1.2 C57BL/6 mouse model, stable and persistent HBV expression is achieved after injection of an adeno-associated virus (AAV) vector encoding an overgenomic length sequence of HBV, leading to hepatic expression of HBV RNA and proteins and the secretion of viral and sub-viral particles into the blood.

The AAV-HBV1.2 construct used in these studies was based on details provided in Dion, S., et al., Journal of Virology, 2013, 87(10): 5554-5563. All animal-related procedures were conducted according to written operating procedures, in accordance with Canadian Council on Animal Care (CCAC) Guidelines on Good Animal Practices, and approved by the local Institutional Animal Care and Use Committee (IACUC).

Each animal was inoculated with 1E11 vector genomes (VG) of AAV-HBV1.2 vector. Prior to treatment, all animals were test bled and serum HBsAg levels determined for individual animals to confirm established HBV expression.

siRNA treatment: Groups of mice (typically n=5) were administered a single 3 mg/kg dose of HBV siRNA conjugate once on Day 0 (1 dose per animal) via subcutaneous injection in the scapular region. One group of animals administered vehicle only (saline) served as controls.

Collections: All mice were test bled on Day 0, prior to treatment, and at defined time points after test article administration (for example on study days 7, 14, 21, 28, 35, 42, 49, 56, 63, and 70) to determine maximum reductions in serum HBsAg levels and the duration of pharmacologic activity.

Analysis: HBsAg levels in serum samples were determined using the Biorad EIA GS HBsAg 3.0 kit (BioRad, catalog no. 32591) as per the manufacturer's instructions. Pooled serum from each treatment group was used to determine the group mean HBsAg levels at individual time points. Data was analyzed and expressed as HBsAg levels relative to pre-treatment baseline (% relative to Day 0).

Results: Results from testing each of the chemically modified HBV siRNA described in Table 1 are presented in Table 2. Values represent % HBsAg levels (relative to Day 0 baseline) on Days 7, 14, 21, 28, 42, 49, 56 and 70 post treatment.

TABLE 1

Chemically Modified HBV siRNA duplexes

| siRNA Number | Sense strand SEQ ID NO | Sense strand 5'-3' | Antisense strand SEQ ID NO | Antisense strand 5'-3' |
|---|---|---|---|---|
| 1 | SEQ ID NO: 1 | csgsugugCaCUUcgcuucaccu | SEQ ID NO: 2 | asGsgugAaGCgaagUgCacacgsgsuUU |
| 2 | SEQ ID NO: 3 | usgsCaCUUcgcuucaccu | SEQ ID NO: 4 | asGsgugAaGCgaagUgCacascsgU |

TABLE 1-continued

Chemically Modified HBV siRNA duplexes

| siRNA Number | Sense strand SEQ ID NO | Sense strand 5'-3' | Antisense strand SEQ ID NO | Antisense strand 5'-3' |
|---|---|---|---|---|
| 3 | SEQ ID NO: 5 | usgscaCUUcgcuucaccu | SEQ ID NO: 6 | asGsgugaagcgaagUgCacascsgU |
| 4 | SEQ ID NO: 7 | usgscaCUUCgcuucaccu | SEQ ID NO: 8 | asGsgugAagcgaagUgCacascsgU |
| 5 | SEQ ID NO: 9 | CscsGuGuGcACUucGcuuCacc | SEQ ID NO: 10 | gsGsUgAaGcgAaguGcAcAcGgsusc |
| 6 | SEQ ID NO: 11 | cscsguguGcACUucgcuucacc | SEQ ID NO: 12 | gsGsugaAgCGaaguGcAcacggsusc |
| 7 | SEQ ID NO: 13 | cscsguGuGcAcUucgcuucacc | SEQ ID NO: 14 | gsGsugaAgCGaaguGcAcacggsusc |
| 8 | SEQ ID NO: 15 | cscsguguGcACUucgcuuCacc | SEQ ID NO: 16 | gsGsugaAgCgaaguGcAcacGgsusc |
| 9 | SEQ ID NO: 17 | cscsgugugcACUucgcuucacc | SEQ ID NO: 18 | gsGsugaagcgaaguGcAcacggsusc |
| 10 | SEQ ID NO: 19 | cscsguguGcacuucgcuucacc | SEQ ID NO: 20 | gsgsugaAgCGaagugcacacggsusc |
| 11 | SEQ ID NO: 21 | CscsGuGuGcACUucGcuuCacc | SEQ ID NO: 22 | gsGsUgAaGcgAaguGcAcAcGgsuscUU |
| 12 | SEQ ID NO: 23 | cscsguguGcACUucgcuucacc | SEQ ID NO: 24 | gsGsugaAgCGaaguGcAcacggsuscUU |
| 13 | SEQ ID NO: 25 | cscsguGuGcAcUucgcuucacc | SEQ ID NO: 26 | gsGsugaAgCGaaguGcAcacggsuscUU |
| 14 | SEQ ID NO: 27 | cscsguguGcACUucgcuuCacc | SEQ ID NO: 28 | gsGsugaAgCgaaguGcAcacGgsuscUU |
| 15 | SEQ ID NO: 29 | GsusGcACUucGcuuCacc | SEQ ID NO: 30 | gsGsUgAaGcgAaguGcAcAcsGsgU |
| 16 | SEQ ID NO: 31 | GsusGcACUucGcuuCacc | SEQ ID NO: 32 | gsGsUgAaGcgAaguGcAcAcsGsg |
| 17 | SEQ ID NO: 33 | GsusGcACUucGcuuCacc | SEQ ID NO: 34 | gsGsUgAaGcgAaguGcAcsAscsGsg |
| 18 | SEQ ID NO: 35 | CscsGuGuGcACUucGcuuCaca | SEQ ID NO: 36 | usGsUgAaGcgAaguGcAcAcGgsusc |
| 19 | SEQ ID NO: 37 | CscsGuGuGcACUucGcuuCaca | SEQ ID NO: 38 | usGsUgAaGcgAaguGcAcAcGgsuscUU |
| 20 | SEQ ID NO: 39 | cscsguguGcACUucgcuucaca | SEQ ID NO: 40 | usGsugaAgCGaaguGcAcacggsuscUU |
| 21 | SEQ ID NO: 41 | cscsguGuGcAcUucgcuucaca | SEQ ID NO: 42 | usGsugaAgCGaaguGcAcacggsuscUU |
| 22 | SEQ ID NO: 43 | cscsguguGcACUucgcuuCaca | SEQ ID NO: 44 | usGsugaAgCgaaguGcAcacGgsuscUU |
| 23 | SEQ ID NO: 45 | cscsgugugcACUucgcuucaca | SEQ ID NO: 46 | usGsugaagcgaaguGcAcacggsuscUU |
| 24 | SEQ ID NO: 47 | gsusGcACUucgcuucaca | SEQ ID NO: 48 | usGsugaAgCGaaguGcAcacsgsgU |
| 25 | SEQ ID NO: 49 | gsusgcACUucgcuucaca | SEQ ID NO: 50 | usGsugaagcgaaguGcAcacsgsgU |
| 26 | SEQ ID NO: 51 | gsusGcaCUucgcuucaca | SEQ ID NO: 52 | usGsugaagcgaaguGcAcacsgsgU |
| 27 | SEQ ID NO: 53 | GsusGcACUucGcuuCaca | SEQ ID NO: 54 | usGsUgAaGcgAaguGcAcAcsGsg |
| 28 | SEQ ID NO: 55 | uscsgcuuCaCCUcugcacgucg | SEQ ID NO: 56 | csGsacgUgCAgaggUgAagcgasasgUU |
| 29 | SEQ ID NO: 57 | uscsgcuuCaCCUcugcacguca | SEQ ID NO: 58 | usGsacgUgCAgaggUgAagcgasasgUU |
| 30 | SEQ ID NO: 59 | uscsgcUuCaCcUcugcacguca | SEQ ID NO: 60 | usGsacgUgCAgaggUgAagcgasasgUU |
| 31 | SEQ ID NO: 61 | ususCaCCUcugcacguca | SEQ ID NO: 62 | usGsacgUgCAgaggUgAagcsgsaU |
| 32 | SEQ ID NO: 63 | ususcaCCUcugcacguca | SEQ ID NO: 64 | usGsacgugcagaggUgAagcsgsaU |
| 33 | SEQ ID NO: 65 | ususCaCCUcugcacguca | SEQ ID NO: 66 | usGsacgUgcagaggUgAagcsgsaU |
| 34 | SEQ ID NO: 67 | ususuaCuAgUGCcaUuuguuca | SEQ ID NO: 68 | usGsAaCaAauGgcaCuAgUaAascsu |
| 35 | SEQ ID NO: 69 | ususuaCuAgUGCcaUuuguuca | SEQ ID NO: 70 | usGsAaCaAauGgcaCuAgUaAascsuUU |
| 36 | SEQ ID NO: 71 | ususuacuAgUGCcauuuguuca | SEQ ID NO: 72 | usGsaacAaAUggcaCuAguaaascsuUU |
| 37 | SEQ ID NO: 73 | ususuaCuAgUgCcauuuguuca | SEQ ID NO: 74 | usGsaacAaAUggcaCuAguaaascsuUU |

2'-O-Methyl nucleotides = lower case;
2'-Fluoro nucleotides = UPPER CASE;
Phosphorothioate linker = s;
Unmodified = UPPER CASE

TABLE 2

Serum HBsAg levels in mice after single subcutaneous administration (3 mg/kg) of GalNAc conjugated siRNA from Table 1. HBsAg data expressed as percent of baseline (Day 0) values

| siRNA Number | Ligand Cpd # | Day 7 | Day 14 | Day 21 | Day 28 | Day 42 | Day 49 | Day 56 | Day 70 |
|---|---|---|---|---|---|---|---|---|---|
| Saline | | 95.7 | 118.6 | 101.0 | 111.4 | 115.3 | | 112.2 | 106.5 |
| 1 | 145 | 3.1 | 1.0 | 22.8 | 1.3 | | 3.2 | | 7.3 |
| 2 | 145 | 1.3 | 0.5 | 0.4 | 0.7 | | 3.4 | | 6.5 |
| 5 | 235 | 12.7 | 7.0 | 9.6 | 21.3 | 59.7 | | 74.6 | 98.8 |
| 5 | 233 | 16.6 | 8.2 | 11.0 | 12.6 | 24.4 | | 32.2 | 60.3 |
| 5 | 145 | 4.3 | 1.2 | 1.7 | 2.4 | | 11.9 | | 24.5 |
| 6 | 233 | 20.1 | 10.4 | 10.9 | 13.5 | 30.8 | | 46.0 | 67.5 |
| 7 | 233 | 20.7 | 12.4 | 10.5 | 13.6 | 24.9 | | 46.2 | 77.0 |
| 8 | 233 | 18.1 | 10.5 | 11.5 | 12.1 | 26.0 | | 37.6 | 64.9 |
| 9 | 145 | 10.0 | 2.7 | 2.0 | 3.6 | | 6.8 | | 17.0 |
| 10 | 145 | 16.7 | 16.7 | 16.0 | 16.7 | | 74.4 | | 97.3 |
| 11 | 233 | 20.5 | 14.8 | 16.0 | 23.9 | 65.2 | | 80.2 | |
| 12 | 233 | 18.4 | 11.6 | 12.2 | 14.1 | 23.6 | | 67.1 | 72.6 |
| 12 | 145 | 5.1 | 1.1 | 1.2 | 1.0 | 2.2 | | 4.5 | 8.2 |
| 13 | 233 | 20.7 | 10.1 | 11.6 | 13.2 | 21.1 | | 39.9 | 72.3 |
| 14 | 233 | 16.5 | 8.0 | 11.0 | 11.8 | 28.8 | | 48.0 | 90.0 |
| 15 | 145 | 6.3 | 3.5 | 8.4 | 11.4 | | 89.7 | | 83.1 |
| 16 | 145 | 4.0 | 3.4 | 9.7 | 14.8 | | 85.1 | | 88.9 |
| 17 | 145 | 2.4 | 0.6 | 0.7 | 1.1 | | 6.3 | | 15.1 |
| 18 | 233 | 2.5 | 1.0 | 1.3 | 2.6 | 11.2 | | 24.5 | 55.6 |
| 19 | 233 | 1.9 | 0.8 | 1.5 | 2.6 | 6.5 | | 12.9 | 23.4 |
| 19 | 145 | 1.7 | 0.6 | 0.7 | 1.4 | 3.8 | | 7.3 | 15.0 |
| 19 | 200 | 1.8 | 0.9 | 1.4 | 2.2 | 5.4 | | 10.2 | 27.5 |
| 19 | 197 | 2.0 | 0.8 | 1.4 | 2.1 | 3.1 | | 8.4 | 14.2 |
| 19 | 194 | 2.8 | 1.8 | 2.2 | 4.0 | 10.7 | | 26.0 | 37.3 |
| 20 | 145 | 2.7 | 0.5 | 0.7 | 1.0 | 4.7 | | 9.3 | 11.3 |
| 20 | 215 | 3.4 | 1.5 | 1.7 | 1.7 | 1.9 | | 4.5 | 6.2 |
| 20 | 194 | 1.4 | 0.5 | 0.3 | 0.7 | 1.2 | | 3.0 | 6.0 |
| 20 | 197 | 3.4 | 0.6 | 1.0 | 1.3 | 2.1 | | 4.9 | 8.2 |
| 20 | 212 | 3.2 | 0.8 | 1.0 | 1.9 | 2.4 | | 4.9 | 7.5 |
| 20 | 191 | 3.3 | 1.4 | 1.4 | 2.1 | 1.9 | | 1.2 | 3.4 |
| 21 | 215 | 2.5 | 1.1 | 1.9 | 2.6 | 3.8 | | 7.8 | 9.8 |
| 22 | 233 | 2.5 | 2.0 | 3.1 | 6.1 | 12.2 | | 30.4 | 61.9 |
| 23 | 215 | 1.6 | 0.3 | 0.3 | 0.3 | 0.4 | | 1.0 | 1.7 |
| 24 | 197 | 1.9 | 0.4 | 0.4 | 0.4 | 0.8 | | 1.7 | 3.2 |
| 25 | 197 | 2.1 | 2.2 | 0.9 | 0.5 | 0.9 | | 2.0 | 2.2 |
| 27 | 145 | 0.3 | 0.3 | 1.6 | 7.4 | | 71.1 | | 100.1 |
| 28 | 145 | 11.4 | 6.7 | 7.1 | 9.6 | 20.8 | | 27.1 | 36.7 |
| 29 | 145 | 2.9 | 1.7 | 2.1 | 3.3 | 7.9 | | 21.4 | 18.2 |
| 30 | 145 | 10.0 | 3.8 | 3.5 | 5.9 | 13.7 | | 19.0 | 28.8 |
| 34 | 233 | 13.2 | 7.4 | 8.9 | 16.8 | 55.2 | | 60.5 | |
| 35 | 233 | 11.6 | 8.5 | 14.0 | 19.5 | 58.4 | | 82.0 | |
| 36 | 145 | 11.3 | 8.5 | 11.6 | 12.5 | 36.6 | | 49.7 | 64.7 |
| 37 | 145 | 27.8 | 21.6 | 25.9 | 31.1 | 49.9 | | 43.3 | 64.5 |

Table 2 identifies the compound numbers (column 2) and the corresponding oligonucleotide (column 1) for the HBV siRNA conjugates that were tested.

Example 26 Synthesis of Conjugate 320

Scheme 50 Preparation of activated linker

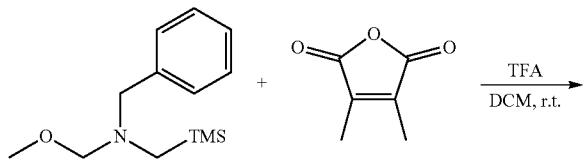

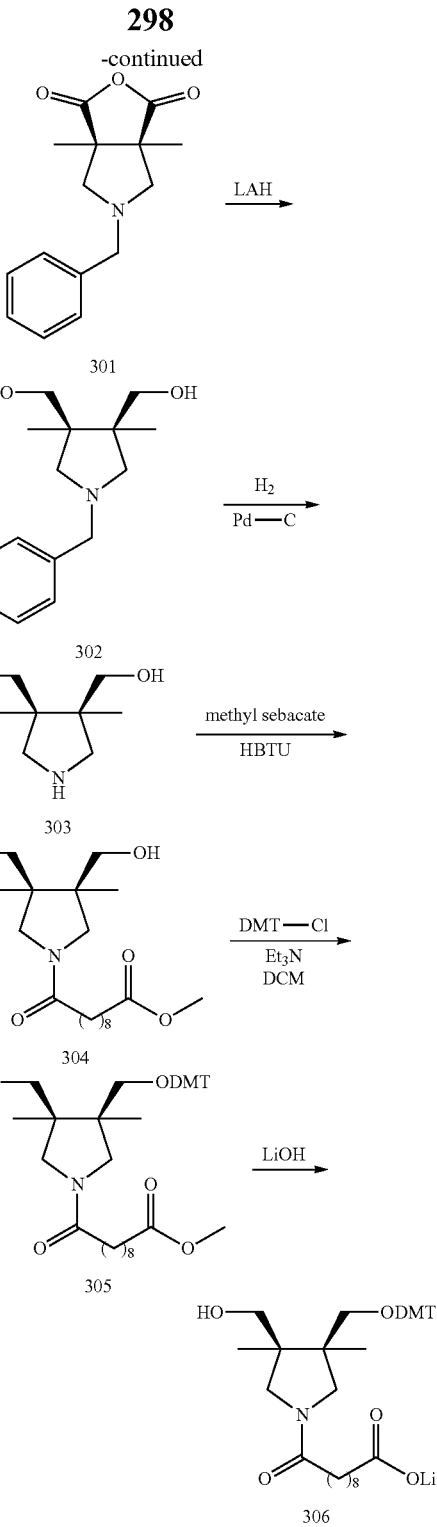

Step 1. Preparation of Racemic (cis) 5-Benzyl-3a,6a-dimethyltetrahydro-1H-furo[3,4-c]pyrrole-1,3(3aH)-dione 301

To a cooled solution (0° C.) of 3,4-dimethylfuran-2,5-dione (3 g, 24 mmol) and N-benzyl-1-methoxy-N-((trimethylsilyl)methyl)methanamine (7 g, 29.8 mmol) in dichloromethane (75 mL) was slowly added trifluoroacetic acid (75 µL). Stir overnight allowing the solution to slowly warm to room temperature as the ice bath melted. The reaction mixture was concentrated to dryness, dissolved in ethyl acetate (100 mL), washed with saturated sodium bicarbonate (2×100 mL), dried on magnesium sulfate, filtered and concentrated to dryness. Purification by column chromatography on silica gel (gradient: 20% ethyl acetate in hexanes to 100% ethyl acetate) afforded (3aR,6aS)-5-Benzyl-3a,6a-dimethyltetrahydro-1H-furo[3,4-c]pyrrole-1,3(3aH)-dione as a yellow oil (3.5 g, 56%).

Step 2. Preparation of Racemic (cis) (1-Benzyl-3,4-dimethylpyrrolidine-3,4-diyl)dimethanol 302

To a cooled (0° C.) solution of (3aR,6aS)-5-Benzyl-3a,6a-dimethyltetrahydro-1H-furo[3,4-c]pyrrole-1,3(3aH)-dione (3.5 g, 13.4 mmol) in anhydrous diethyl ether (50 mL) was added slowly lithium aluminum hydride pellets (1.5 g, 40 mmol) over three portions. The solution was stirred overnight warming to room temperature as the ice water bath melted. Upon completion, the reaction was cooled to 0° C. and very slowly quenched with 1.5 mL of 5M NaOH followed by 1.5 mL of water. Stir for 30 minutes then add magnesium sulfate and filter. The filtrate was concentrated to afford ((3R,4S)-1-Benzyl-3,4-dimethylpyrrolidine-3,4-diyl)dimethanol as a colorless oil (2.7 g).

Step 3. Preparation of Racemic (cis) (3,4-Dimethylpyrrolidine-3,4-diyl)dimethanol 303

To a solution of ((3R,4S)-1-Benzyl-3,4-dimethylpyrrolidine-3,4-diyl)dimethanol (10 g, 40 mmol) in methanol (10 mL) was added 10% palladium on activated charcoal wet (1 g). The solution was stirred vigorously under a hydrogen atmosphere for 16 hours. Upon completion the solution was filtered through Celite, and concentrated to dryness to afford ((3R,4S)-3,4-Dimethylpyrrolidine-3,4-diyl)dimethanol as a colorless solid (5.5 g, 86%).

Step 4. Preparation of Racemic (cis) Methyl 10-(3,4-bis(hydroxymethyl)-3,4-dimethylpyrrolidin-1-yl)-10-oxodecanoate 304

A solution of 3 (1.3 g, 8.2 mmol) and monomethyl sebacate (1.8 g, 8.2 mmol) in $CH_2Cl_2$ (100 mL) was treated with HBTU (3.41 g, 9.02 mmol) and Hunig's base (5.71 mL, 32.8 mmol). After stirring overnight the mixture was washed with $NaHCO_3$ (sat. aq.), water and brine, then dried ($MgSO_4$), filtered and concentrated. The crude material was subjected to chromatography (gradient: 0% $CH_3OH$—$CH_2Cl_2$ to 20%) to yield 4 (1.8 g, 61%).

Step 5. Preparation of Racemic (cis) Methyl 10-(3-((bis(4-methoxyphenyl)(phenyl)-methoxy)methyl)-4-(hydroxymethyl)-3,4-dimethylpyrrolidin-1-yl)-10-oxodecanoate 305

A solution of 304 (1.8 g, 5.0 mmol) and 4,4'-Dimethoxytrityl chloride (1.7 g, 5.0 mmol) in pyridine (180 mL) was stirred overnight. The pyridine was then removed under reduced pressure and the crude material was subjected to chromatography (gradient: 0% $CH_3OH$—$CH_2Cl_2$ to 10%) to yield 5 (1.4 g, 42%) as a yellow oil.

Step 6. Preparation of Racemic (cis) Lithium 10-(3-((bis(4-methoxyphenyl)-(phenyl)methoxy)methyl)-4-(hydroxymethyl)-3,4-dimethylpyrrolidin-1-yl)-10-oxodecanoate 306

To a solution of compound 305 (3.0 g, 4.6 mmol) in THF (50 mL) and water (50 mL) was added lithium hydroxide (121 mg, 5.0 mmol). The solution was stirred for 4 hours at room temperature then concentrated to remove the THF. The remaining aqueous solution was freeze dried overnight to afford a pale pink solid (2.9 g, quantitative). Compound 306 was prepared as a mixture of two cis-diastereomers.

Scheme 51 Synthesis of Peracetylated Galactosamine 307

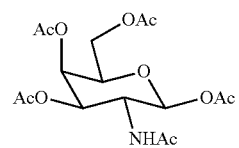 [SMILES: CC(=O)NC1C(OC(C)=O)OC(COC(C)=O)C(OC(C)=O)C1OC(C)=O]

D-Galactosamine hydrochloride (250 g, 1.16 mol) in pyridine (1.5 L) was treated with acetic anhydride (1.25 L, 13.2 mol) over 45 minutes. After stirring overnight the reaction mixture was divided into three 1 L portions. Each 1 L portion was poured into 3 L of ice water and mixed for one hour. After mixing the solids were filtered off, combined, frozen over liquid nitrogen and then lyophilized for five days to yield peracetylated galactosamine 7 (369.4 g, 82%) as a white solid. Rf (0.58, 10% MeOH—$CH_2Cl_2$).

Scheme 52 Synthesis of GalNAc monomer

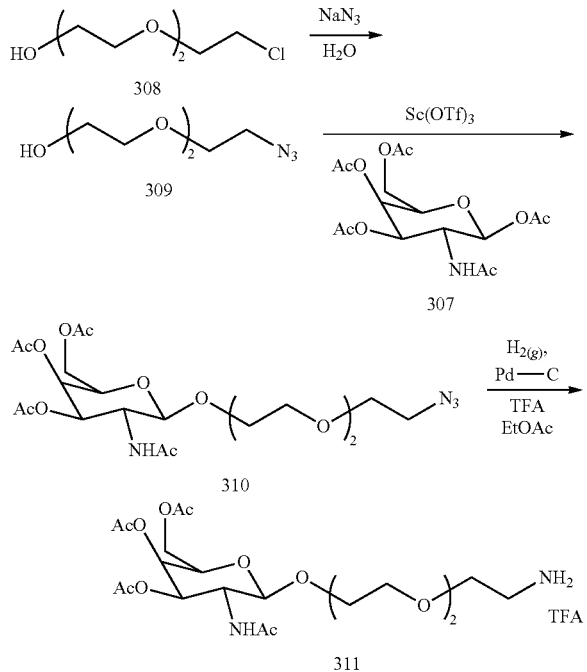

Step 1 Preparation of Compound 309

A solution of 2-[2-(2-chloroethoxy)]ethanol 308 (100 g, 593 mmol) in water (1 L) was treated with $NaN_3$ (77 g, 1.19 mol) and heated (90° C.). After stirring (72 hours) the solution was cooled (RT) and extracted (4×) with CH$_2$Cl$_2$. The combined organics were washed with brine, dried (MgSO$_4$), filtered, concentrated and used without further processing. Compound 9 (88.9 g, 86%) was obtained as a pale yellow oil.

Step 2 Preparation of Compound 310

A solution of 7 (2.76 g, 7.1 mmol) and 309 (1.37 g, 7.8 mmol) in 1,2-dichloroethane (40 mL) was treated with Sc(OTf)$_3$ (174 mg, 0.36 mmol) and heated (85° C.). After stirring (2 hours) the mixture was cooled (RT) and quenched by the addition of TEA (4 mL) and concentrated. The crude material was subjected to chromatography to yield 310 (3.03 g, 85%) as a pale yellow foam.

Step 3 Preparation of Compound 311

A solution of 310 (3.02 g, 5.99 mmol) and Pd/C (300 mg, 10% Pd loading-wet support) in EtOAc (30 mL) was treated with TFA (576 µL, 7.5 mmol). The reaction mixture was purged with hydrogen gas (45 min) then purged with nitrogen gas (10 min), then filtered through celite. The filtrate was concentrated and then subjected to chromatography to yield 311 (2.67 g, 75%) as a brown foam.

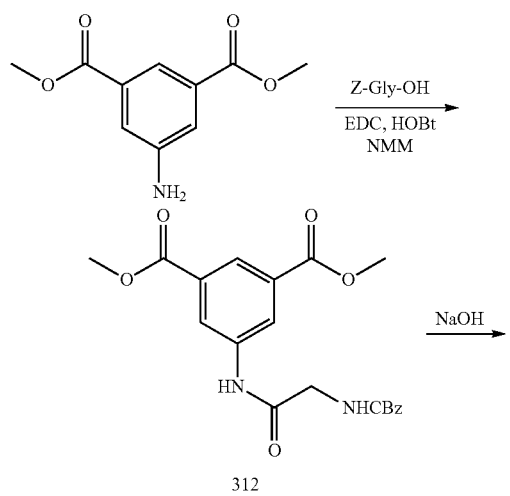

Scheme 53 Synthesis of aromatic core

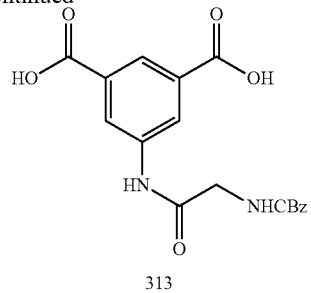

Step 1. Preparation of Dimethyl 5-(2-((2-oxo-2-phenyl-1λ$^2$-ethyl)amino)acetamido)-isophthalate 312

A solution of dimethyl 5-aminoisophthalate (5 g, 24 mmol), Z-Gly-OH (5 g, 24 mmol), EDC (5 g, 26.3 mmol), HOBt (3.6 g, 26.3 mmol), NMM (2.9 mL, 26.3 mmol) in DMF (50 mL) was stirred overnight at room temperature. Upon completion, the reaction mixture was diluted with ethyl acetate (250 mL) and washed with each 1M HCl (2×100 mL), saturated sodium bicarbonate (1×100 mL) and brine (2×100 mL). Dry on magnesium sulfate, filter and concentrate to dryness to afford Dimethyl 5-(2-((2-oxo-2-phenyl-1λ$^2$-ethyl)amino)-acetamido)isophthalate as a colorless solid (7.2 g, 79%).

Step 2. Preparation of 5-(2-((2-oxo-2-phenyl-1λ$^2$-ethyl)amino)acetamido)isophthalic acid 313

To a solution of methyl 5-(2-((2-oxo-2-phenyl-1λ$^2$-ethyl)amino)acetamido)isophthalate (7.2 g) in methanol (25 mL) and THF (25 mL) was added 1M NaOH (25 mL). The solution was stirred at room temperature for 2 hours then concentrated to remove THF and MeOH. The aqueous solution remaining was diluted with water (75 mL), cooled on an ice water bath and acidified to pH=1 with 6M HCl. The solid was filtered and washed with water (3×100 mL). The solid was freeze dried to afford 5-(2-((2-oxo-2-phenyl-1λ$^2$-ethyl)amino)acetamido)-isophthalic acid (6.9 g, quantitative).

Scheme 54: Preparation of tetramer

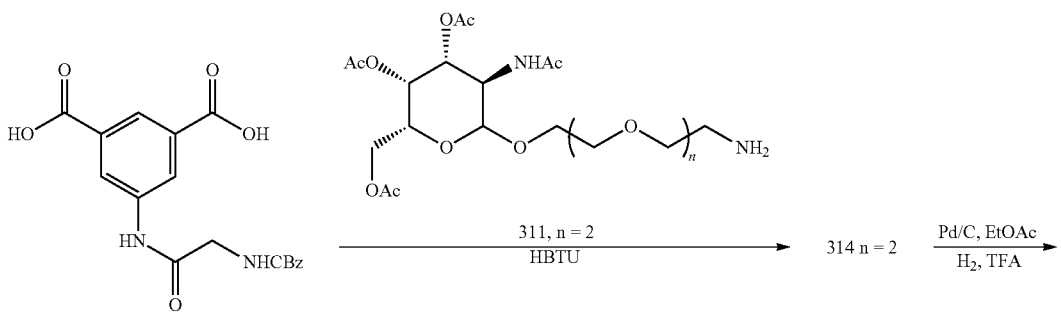

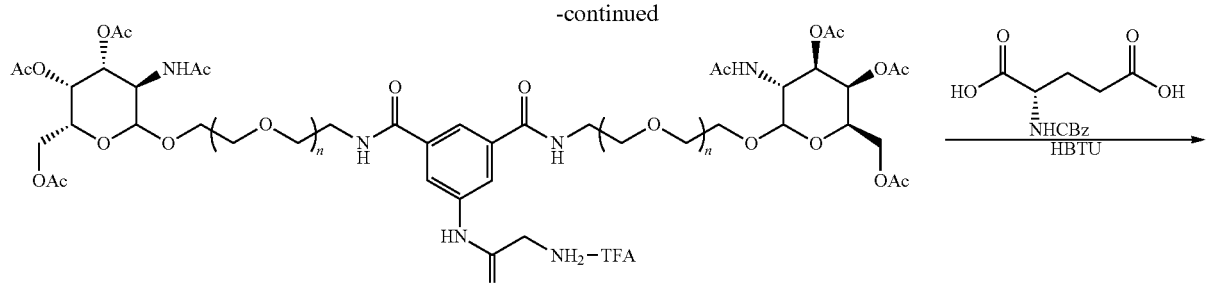

315, n = 2

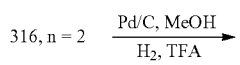

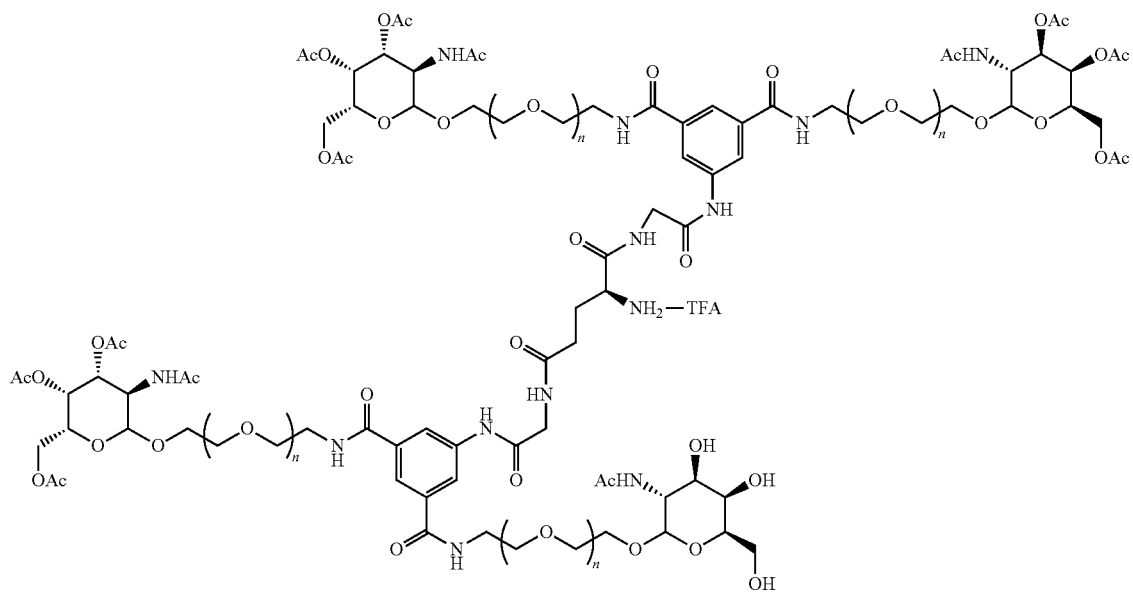

317, n = 2

Step 1 Preparation of Compound 314

A solution of 313 (2.09 g, 5.6 mmol) and 311 (8.34 g, 14.07 mmol) in CH₂Cl₂ (150 mL) was treated with HBTU (6.4 g, 16.9 mmol) and Hunig's base (7.35 mL, 42.2 mmol). After stirring (overnight) the reaction mixture was poured into NaHCO₃ (sat. aq.) then washed with water and brine, dried (MgSO₄), filtered and concentrated. The crude material was subjected to chromatography (gradient 1-12% CH₃OH—CH₂Cl₂) to yield 6 (3.97 g, 55%) as a pale yellow foam.

Step 2 Preparation of Compound 315

Compound 314 (3.92 g, 3.07 mmol), Pd/C (400 mg, 10% loading-wet support) and trifluoroacetic acid (308 µL, 4 mmol) was purged with H₂. After stirring under H₂ (overnight), the mixture was purged with N₂ (15-20 min) then filtered through celite and concentrated. The crude material was subjected to chromatography to yield 7 (3.36 g, 86%) as a white to cream colored foam.

Step 3 Preparation of Compound 316

Compound 316 was prepared in the same fashion as 314, from Z-glutamic acid (306 mg, 1.09 mmol) and 315 (3.3 g, 2.6 mmol). Yield 1.66 g, 60%.

Step 4 Preparation of Compound 317

Compound 317 was prepared in the same fashion as 315. Yield 1.65 g, Quant.

Scheme 55 Preparation of complete conjugate

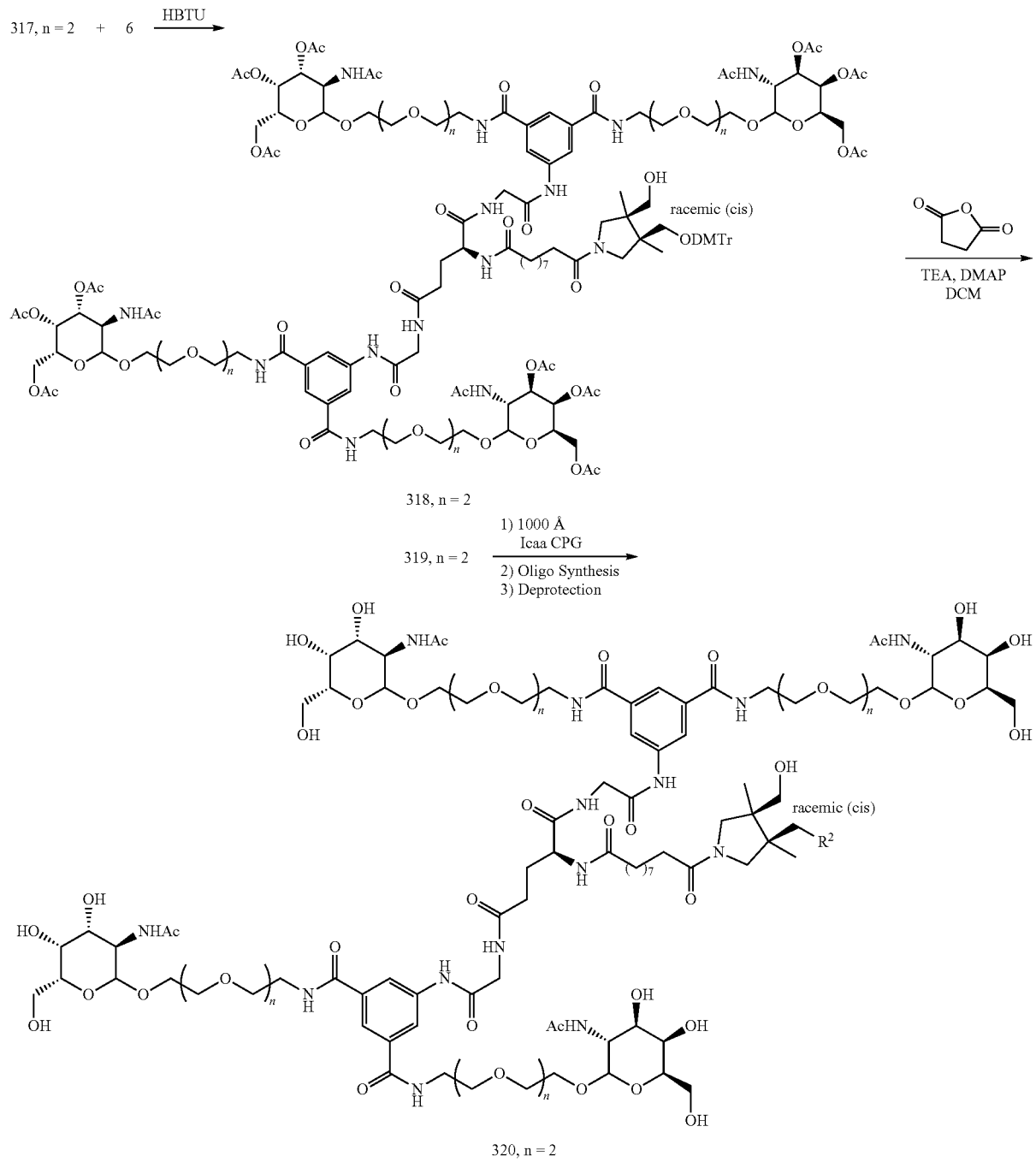

Step 1 Preparation of Compound 318

A solution of 317 (1.91 g, 0.75 mmol) in CH$_2$Cl$_2$ (100 mL) was treated first with Hunig's base (392 µL, 2.25 mmol) then 6 (a mixture of two cis-diastereomers, 509 mg, 0.79 mmol) followed by HBTU (356 mg, 0.94 mmol). After stirring (overnight) the solution was poured into NaHCO$_3$ (sat. aq.) then washed with water and brine, dried (MgSO$_4$), filtered and concentrated. The crude material was subjected to chromatography to yield 318 (1.19 g, 52%) as a white foam.

Step 2 Preparation of Compound 319

A solution of 318 (1.19 g, 0.39 mmol) in 1,2 dichloroethane (100 mL) was treated with TEA (542 µL, 3.9 mmol), DMAP (238 mg, 1.95 mmol) and succinic anhydride (195 mg, 1.95 mmol) and heated (85° C.). After stirring (2.5 hours) the solution was removed from heat and treated with CH$_3$OH (10 mL) and allowed to stir (1 hour). After stirring the mixture was poured into NaHCO$_3$ (sat. aq.) then washed with brine, dried (MgSO₄), filtered and concentrated. The residue obtained was used without further processing. Yield=1.4 g, Quant.

Step 3 Preparation of Conjugate 320

The succinate 319 was loaded onto 1000 Å LCAA (long chain aminoalkyl) CPG (control pore glass) using standard amide coupling chemistry. A solution of diisopropylcarbodiimide (52.6 μmol), N-hydroxy succinimide (0.3 mg, 2.6 μmol) and pyridine (10 μL) in anhydrous acetonitrile (0.3 mL) was added to 319 (20.6 mg, 8 μmol) in anhydrous dichloromethane (0.2 mL). This mixture was added to LCAA CPG (183 mg). The suspension was gently mixed overnight at room temperature. Upon disappearance of 319 (HPLC), the reaction mixture was filtered and the CPG was washed with 1 mL of each dichloromethane, acetonitrile, a solution of 5% acetic anhydride/5% N-methylimidazole/5% pyridine in THF, then THF, acetonitrile and dichloromethane. The CPG was then dried overnight under high vacuum. Loading was determined by standard DMTr assay by UV/Vis (504 nm) to be 19 μmol/g. The resulting GalNAc loaded CPG solid support was employed in automated oligonucleotide synthesis using standard procedures. Nucleotide deprotection followed by removal from the solid support (with concurrent galactosamine acetate deprotection) afforded the GalNAc-oligonucleotide conjugate 320.

Example 27 Synthesis of Conjugate 520

Scheme 56 Preparation of activated linker

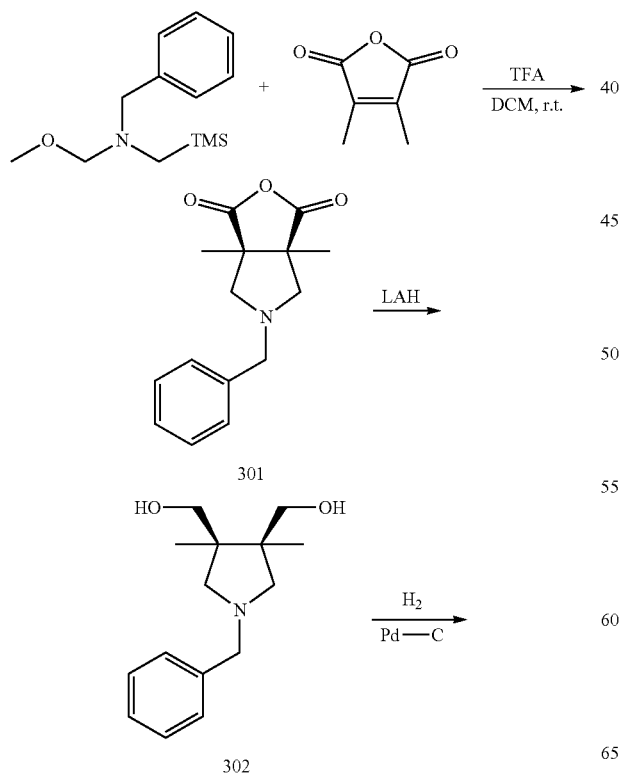

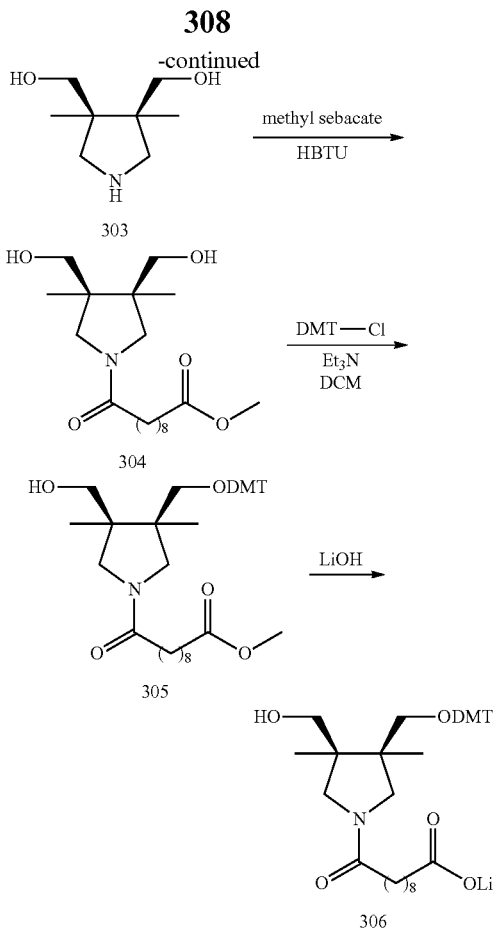

Step 1. Preparation of Racemic (cis) 5-Benzyl-3a,6a-dimethyltetrahydro-1H-furo[3,4-c]pyrrole-1,3(3aH)-dione 301

To a cooled solution (0° C.) of 3,4-dimethylfuran-2,5-dione (3 g, 24 mmol) and N-benzyl-1-methoxy-N-((trimethylsilyl)methyl)methanamine (7 g, 29.8 mmol) in dichloromethane (75 mL) was slowly added trifluoroacetic acid (75 μL). Stir overnight allowing the solution to slowly warm to room temperature as the ice bath melted. The reaction mixture was concentrated to dryness, dissolved in ethyl acetate (100 mL), washed with saturated sodium bicarbonate (2×100 mL), dried on magnesium sulfate, filtered and concentrated to dryness. Purification by column chromatography on silica gel (gradient: 20% ethyl acetate in hexanes to 100% ethyl acetate) afforded (3aR,6aS)-5-Benzyl-3a,6a-dimethyltetrahydro-1H-furo[3,4-c]pyrrole-1,3(3aH)-dione as a yellow oil (3.5 g, 56%).

Step 2. Preparation of Racemic (cis) (1-Benzyl-3,4-dimethylpyrrolidine-3,4-diyl)dimethanol 302

To a cooled (0° C.) solution of (3aR,6aS)-5-Benzyl-3a,6a-dimethyltetrahydro-1H-furo[3,4-c]pyrrole-1,3(3aH)-dione (3.5 g, 13.4 mmol) in anhydrous diethyl ether (50 mL) was added slowly lithium aluminum hydride pellets (1.5 g, 40 mmol) over three portions. The solution was stirred overnight warming to room temperature as the ice water bath melted. Upon completion, the reaction was cooled to 0° C. and very slowly quenched with 1.5 mL of 5M NaOH followed by 1.5 mL of water. Stir for 30 minutes then add magnesium sulfate and filter. The filtrate was concentrated to afford ((3R,4S)-1-Benzyl-3,4-dimethylpyrrolidine-3,4-diyl)dimethanol as a colorless oil (2.7 g).

Step 3. Preparation of Racemic (cis) (3,4-Dimethylpyrrolidine-3,4-diyl)dimethanol 303

To a solution of ((3R,4S)-1-Benzyl-3,4-dimethylpyrrolidine-3,4-diyl)dimethanol (10 g, 40 mmol) in methanol (10 mL) was added 10% palladium on activated charcoal wet (1 g). The solution was stirred vigorously under a hydrogen atmosphere for 16 hours. Upon completion the solution was filtered through Celite, and concentrated to dryness to afford ((3R,4S)-3,4-Dimethylpyrrolidine-3,4-diyl)dimethanol as a colorless solid (5.5 g, 86%).

Step 4. Preparation of Racemic (cis) Methyl 10-(3, 4-bis(hydroxymethyl)-3,4-dimethylpyrrolidin-1-yl)-10-oxodecanoate 304

A solution of 3 (1.3 g, 8.2 mmol) and monomethyl sebacate (1.8 g, 8.2 mmol) in $CH_2Cl_2$ (100 mL) was treated with HBTU (3.41 g, 9.02 mmol) and Hunig's base (5.71 mL, 32.8 mmol). After stirring overnight the mixture was washed with $NaHCO_3$ (sat. aq.), water and brine, then dried ($MgSO_4$), filtered and concentrated. The crude material was subjected to chromatography (gradient: 0% $CH_3OH$—$CH_2Cl_2$ to 20%) to yield 4 (1.8 g, 61%).

Step 5. Preparation of Racemic (cis) Methyl 10-(3-((bis(4-methoxyphenyl)(phenyl)-methoxy)methyl)-4-(hydroxymethyl)-3,4-dimethylpyrrolidin-1-yl)-10-oxodecanoate 305

A solution of 304 (1.8 g, 5.0 mmol) and 4,4'-Dimethoxytrityl chloride (1.7 g, 5.0 mmol) in pyridine (180 mL) was stirred overnight. The pyridine was then removed under reduced pressure and the crude material was subjected to chromatography (gradient: 0% $CH_3OH$—$CH_2Cl_2$ to 10%) to yield 5 (1.4 g, 42%) as a yellow oil.

Step 6. Preparation of Racemic (cis) Lithium 10-(3-((bis(4-methoxyphenyl)-(phenyl)methoxy)methyl)-4-(hydroxymethyl)-3,4-dimethylpyrrolidin-1-yl)-10-oxodecanoate 306

To a solution of compound 305 (3.0 g, 4.6 mmol) in THF (50 mL) and water (50 mL) was added lithium hydroxide (121 mg, 5.0 mmol). The solution was stirred for 4 hours at room temperature then concentrated to remove the THF. The remaining aqueous solution was freeze dried overnight to afford a pale pink solid (2.9 g, quantitative). Compound 306 was prepared as a mixture of two cis-diastereomers.
Scheme 57 Synthesis of Peracetylated Galactosamine 507

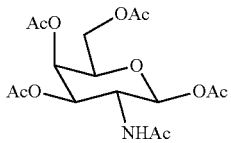

Galactosamine hydrochloride (250 g, 1.16 mol) in pyridine (1.5 L) is treated with acetic anhydride (1.25 L, 13.2 mol) over 45 minutes. After stirring overnight the reaction mixture is divided into three 1 L portions. Each 1 L portion is poured into 3 L of ice water and mixed for one hour. After mixing the solids are filtered off, combined, frozen over liquid nitrogen and then lyophilized for five days to yield peracetylated galactosamine 507 (369.4 g, 82%) as a white solid. Rf (0.58, 10% MeOH—$CH_2Cl_2$).

Scheme 58 Synthesis of GalNAc monomer

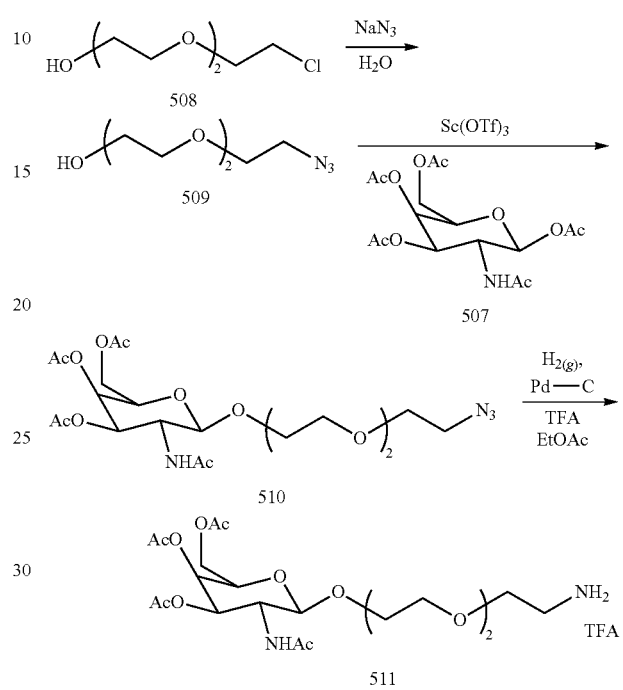

Step 1 Preparation of Compound 509

A solution of 2-[2-(2-chloroethoxy)]ethanol 508 (100 g, 593 mmol) in water (1 L) is treated with $NaN_3$ (77 g, 1.19 mol) and heated (90° C.). After stirring (72 hours) the solution is cooled (RT) and extracted (4×) with $CH_2Cl_2$. The combined organics are washed with brine, dried ($MgSO_4$), filtered, concentrated and used without further processing. Compound 509 (88.9 g, 86%) is obtained as a pale yellow oil.

Step 2 Preparation of Compound 510

A solution of 507 (2.76 g, 7.1 mmol) and 509 (1.37 g, 7.8 mmol) in 1,2-dichloroethane (40 mL) is treated with Sc(OTf)$_3$ (174 mg, 0.36 mmol) and heated (85° C.). After stirring (2 hours) the mixture is cooled (RT) and quenched by the addition of TEA (4 mL) and concentrated. The crude material is subjected to chromatography to yield 510 (3.03 g, 85%) as a pale yellow foam.

Step 3 Preparation of Compound 511

A solution of 510 (3.02 g, 5.99 mmol) and Pd/C (300 mg, 10% Pd loading-wet support) in EtOAc (30 mL) is treated with TFA (576 µL, 7.5 mmol). The reaction mixture is purged with hydrogen gas (45 min) then purged with nitrogen gas (10 min), then filtered through celite. The filtrate is concentrated and then subjected to chromatography to yield 511 (2.67 g, 75%) as a brown foam.

Scheme 59 Synthesis of aromatic core

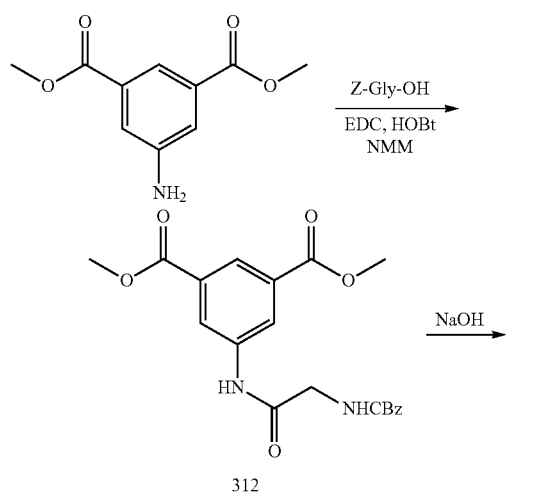

Step 1. Preparation of Dimethyl 5-(2-((2-oxo-2-phenyl-1$\lambda^2$-ethyl)amino)acetamido)-isophthalate 312

A solution of dimethyl 5-aminoisophthalate (5 g, 24 mmol), Z-Gly-OH (5 g, 24 mmol), EDC (5 g, 26.3 mmol), HOBt (3.6 g, 26.3 mmol), NMM (2.9 mL, 26.3 mmol) in DMF (50 mL) was stirred overnight at room temperature. Upon completion, the reaction mixture was diluted with ethyl acetate (250 mL) and washed with each 1M HCl (2×100 mL), saturated sodium bicarbonate (1×100 mL) and brine (2×100 mL). Dry on magnesium sulfate, filter and concentrate to dryness to afford Dimethyl 5-(2-((2-oxo-2-phenyl-1$\lambda^2$-ethyl)amino)-acetamido)isophthalate as a colorless solid (7.2 g, 79%).

Step 2. Preparation of 5-(2-((2-oxo-2-phenyl-1$\lambda^2$-ethyl)amino)acetamido)isophthalic acid 313

To a solution of methyl 5-(2-((2-oxo-2-phenyl-1$\lambda^2$-ethyl)amino)acetamido)isophthalate (7.2 g) in methanol (25 mL) and THF (25 mL) was added 1M NaOH (25 mL). The solution was stirred at room temperature for 2 hours then concentrated to remove THF and MeOH. The aqueous solution remaining was diluted with water (75 mL), cooled on an ice water bath and acidified to pH=1 with 6M HCl. The solid was filtered and washed with water (3×100 mL). The solid was freeze dried to afford 5-(2-((2-oxo-2-phenyl-1$\lambda^2$-ethyl)amino)acetamido)-isophthalic acid (6.9 g, quantitative).

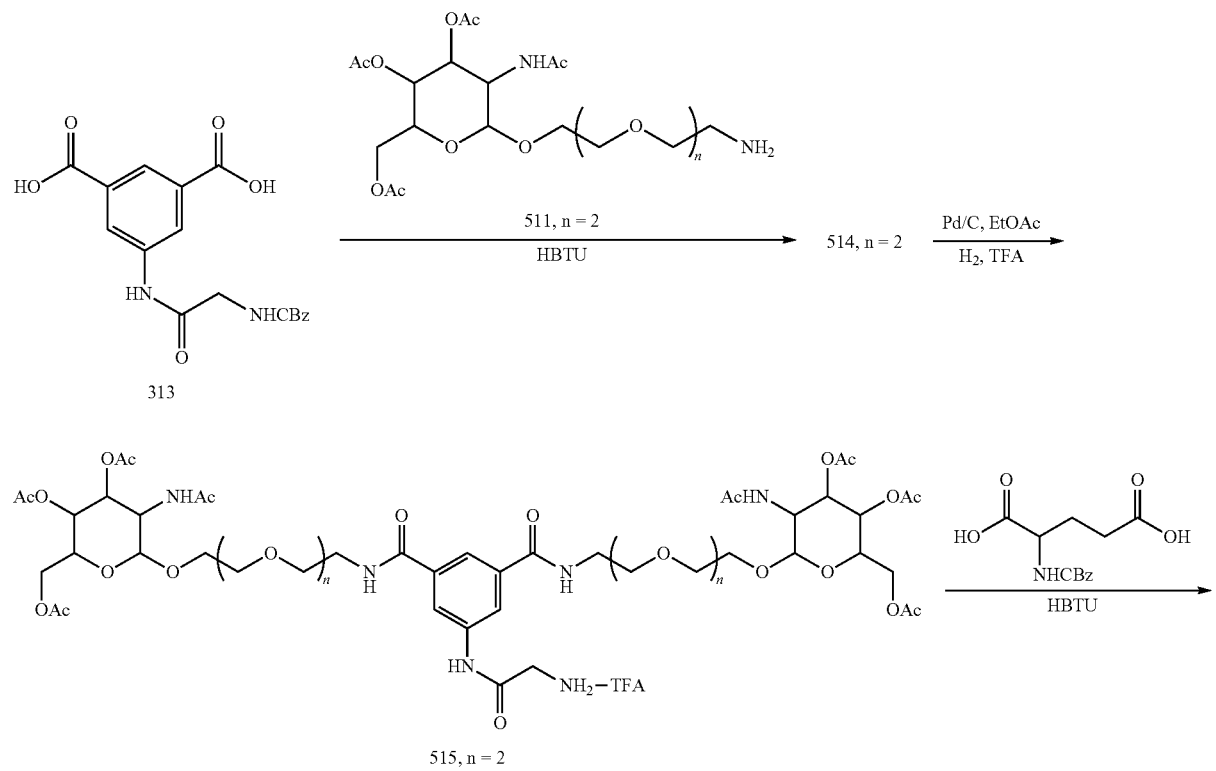

Scheme 60: Preparation of tetramer

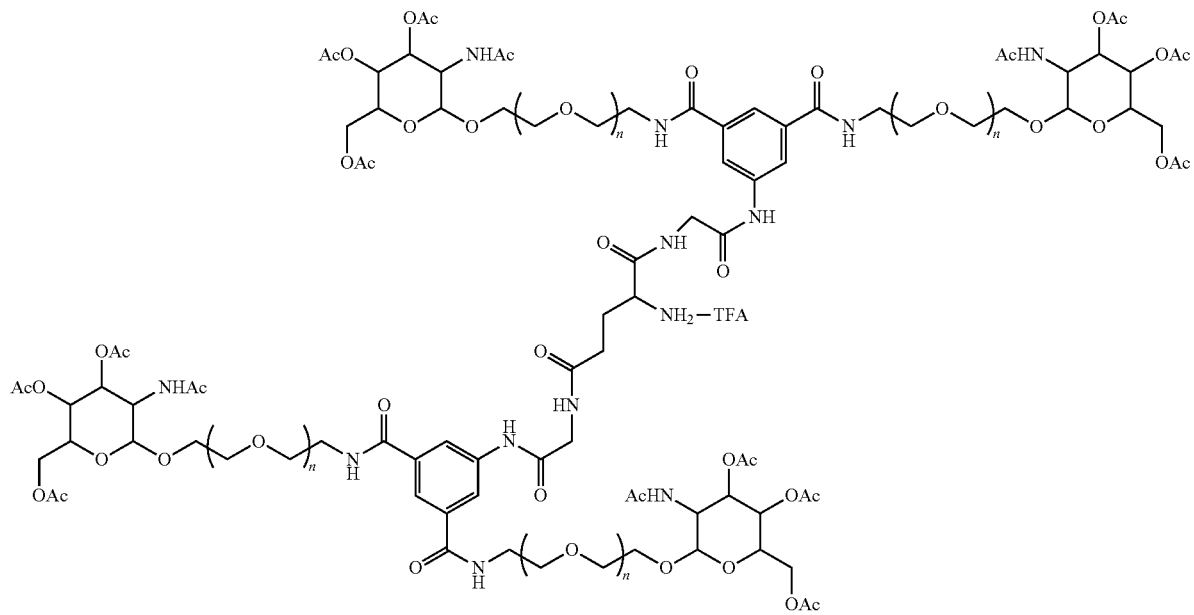

Step 1 Preparation of Compound 514

A solution of 313 (2.09 g, 5.6 mmol) and 511 (8.34 g, 14.07 mmol) in CH$_2$Cl$_2$ (150 mL) is treated with HBTU (6.4 g, 16.9 mmol) and Hunig's base (7.35 mL, 42.2 mmol). After stirring (overnight) the reaction mixture is poured into NaHCO$_3$ (sat. aq.) then washed with water and brine, dried (MgSO$_4$), filtered and concentrated. The crude material is subjected to chromatography (gradient 1-12% CH$_3$OH—CH$_2$Cl$_2$) to yield 6 (3.97 g, 55%) as a pale yellow foam.

Step 2 Preparation of Compound 515

Compound 514 (3.92 g, 3.07 mmol), Pd/C (400 mg, 10% loading-wet support) and trifluoroacetic acid (308 μL, 4 mmol) is purged with H$_2$. After stirring under H$_2$ (overnight), the mixture is purged with N$_2$ (15-20 min) then filtered through celite and concentrated. The crude material is subjected to chromatography to yield 7 (3.36 g, 86%) as a white to cream colored foam.

Step 3 Preparation of Compound 516

Compound 516 is prepared in the same fashion as 514, from Z-glutamic acid (306 mg, 1.09 mmol) and 515 (3.3 g, 2.6 mmol). Yield 1.66 g, 60%.

Step 4 Preparation of Compound 517

Compound 517 is prepared in the same fashion as 515. Yield 1.65 g, Quant.

Scheme 61 Preparation of complete conjugate 517, n = 2 + 306 →(HBTU)

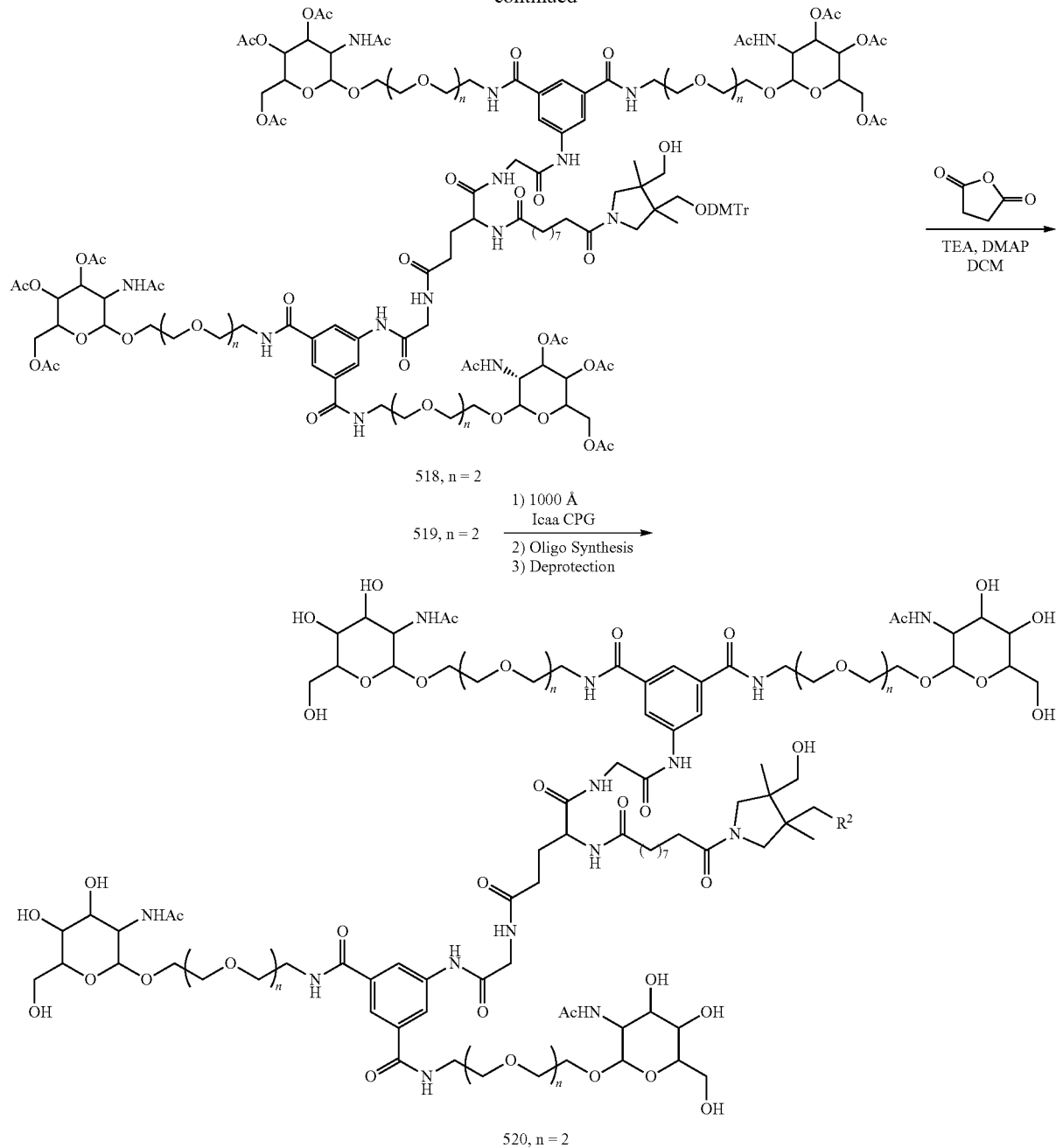

518, n = 2

519, n = 2

520, n = 2

Step 1 Preparation of Compound 518

A solution of 517 (1.91 g, 0.75 mmol) in CH$_2$Cl$_2$ (100 mL) is treated first with Hunig's base (392 μL, 2.25 mmol) then 306 (a mixture of two cis-diastereomers, 509 mg, 0.79 mmol) followed by HBTU (356 mg, 0.94 mmol). After stirring (overnight) the solution was poured into NaHCO$_3$ (sat. aq.) then washed with water and brine, dried (MgSO$_4$), filtered and concentrated. The crude material is subjected to chromatography to yield 518 (1.19 g, 52%) as a white foam.

Step 2 Preparation of Compound 519

A solution of 518 (1.19 g, 0.39 mmol) in 1,2 dichloroethane (100 mL) is treated with TEA (542 μL, 3.9 mmol), DMAP (238 mg, 1.95 mmol) and succinic anhydride (195 mg, 1.95 mmol) and heated (85° C.). After stirring (2.5 hours) the solution is removed from heat and treated with CH$_3$OH (10 mL) and allowed to stir (1 hour). After stirring the mixture is poured into NaHCO$_3$ (sat. aq.) then washed with brine, dried (MgSO$_4$), filtered and concentrated. The residue obtained is used without further processing. Yield=1.4 g, Quant.

Step 3 Preparation of conjugate 520

The succinate 519 is loaded onto 1000 Å LCAA (long chain aminoalkyl) CPG (control pore glass) using standard amide coupling chemistry. A solution of diisopropylcarbodiimide (52.6 µmol), N-hydroxy succinimide (0.3 mg, 2.6 µmol) and pyridine (10 µL) in anhydrous acetonitrile (0.3 mL) is added to 519 (20.6 mg, 8 µmol) in anhydrous dichloromethane (0.2 mL). This mixture is added to LCAA CPG (183 mg). The suspension was gently mixed overnight at room temperature. Upon disappearance of 519 (HPLC), the reaction mixture is filtered and the CPG is washed with 1 mL of each dichloromethane, acetonitrile, a solution of 5% acetic anhydride/5% N-methylimidazole/5% pyridine in THF, then THF, acetonitrile and dichloromethane. The CPG is then dried overnight under high vacuum. Loading was determined by standard DMTr assay by UV/Vis (504 nm) to be 19 µmol/g. The resulting GalNAc loaded CPG solid support is employed in automated oligonucleotide synthesis using standard procedures. Nucleotide deprotection followed by removal from the solid support (with concurrent galactosamine acetate deprotection) affords the GalNAc-oligonucleotide conjugate 520.

Example 28. In Vivo Testing of TTR siRNA Conjugates

Compound 320, wherein $R^2$ comprises the modified TTR siRNA described in Table 3, was tested for in vivo activity in a wild-type mouse model of TTR knock-down. In the present example, Compound 320, wherein $R^2$ comprises the modified TTR siRNA, is demonstrated as a possible treatment for the orphan disease of TTR (Transthyretin) amyloidosis. In those afflicted with this disease, the misfolding and aggregation of the Transthyretin protein is associated with disease progression. By using this siRNA-GalNAc conjugate, the amount of misfolded/aggregated protein in the patient can be reduced, with a potential result of halting the progression of the disease. Accordingly, certain embodiments provide compound 320, wherein the $R^2$ comprises the modified TTR siRNA, and uses thereof to treat transthyretin amyloidosis.

Both the TTR siRNA sequence and animal model were described by Nair et al., *J. Am. Chem. Soc.*, 36(49), 16958-16961 (2014). All animal-related procedures were conducted according to written operating procedures, in accordance with Canadian Council on Animal Care (CCAC) Guidelines on Good Animal Practices, and approved by the local Institutional Animal Care and Use Committee (IACUC).

siRNA treatment: Female $C_{57}BL/6$ mice (n=4) were administered a single 2 mg/kg dose of compound 320 ($R^2$ comprises the modified TTR siRNA) once on Day 0 (1 dose per animal) via subcutaneous injection in the scapular region. One group of animals administered vehicle only (PBS) served as controls.

Collections: All animals were test bled at defined time points after test article administration (days 2, 4, 7, 9, 14 and 21) to determine maximum reductions in plasma TTR levels and the duration of pharmacologic activity.

Analysis: TTR protein levels in plasma samples were determined using the Abnova Prealbumin (Mouse) ELISA kit (Cedar Lane, catalogue number KA2070) as per the manufacturer's instructions. TTR plasma protein values were calculated for the individual plasma samples and the average of each group was determined. From these averages, the TTR protein levels relative to control (% relative to PBS treated animals) were determined.

Results: Results from testing are presented in Table 4. Values represent % TTR protein levels (relative to PBS Control) on Days 2, 4, 7, 9, 14 and 21 post treatment.

TABLE 4

Plasma TTR protein levels in mice after single subcutaneous administration (2 mg/kg) of GalNAc conjugated siRNA from Table 3. TTR protein data expressed as percent of PBS treated mouse values

| siRNA Number | Ligand Cpd # | Day 2 | Day 4 | Day 7 | Day 9 | Day 14 | Day 21 |
|---|---|---|---|---|---|---|---|
| 40 | 320 | 36.6 | 15.7 | 17.2 | 17.7 | 36.9 | 59.2 |

Conclusion: Animals treated with Compound 320, wherein $R^2$ comprises the modified TTR siRNA described in Table 3, exhibited a marked knockdown of target mRNA and protein with maximal knock down of TTR protein occurring between days 4 and 9 post subcutaneous injection.

Example. 29. In Vivo Testing of HBV siRNA Conjugates

Chemically modified HBV siRNA described in Table 1 in Example 25, conjugated to GalNAc ligands, were tested for in vivo activity in an established mouse model of HBV infection. In the AAV-HBV1.2 C57BL/6 mouse model, stable and persistent HBV expression is achieved after injection of an adeno-associated virus (AAV) vector encoding an over-genomic length sequence of HBV, leading to hepatic expression of HBV RNA and proteins and the secretion of viral and sub-viral particles into the blood.

The AAV-HBV1.2 construct used in these studies was based on details provided in Dion et al., *Journal of Virology*, 87(10), 5554-5563 (2013). All animal-related procedures were conducted according to written operating procedures, in accordance with Canadian Council on Animal Care (CCAC) Guidelines on Good Animal Practices, and approved by the local Institutional Animal Care and Use Committee (IACUC).

Each animal was inoculated with 1E11 vector genomes (VG) of AAV-HBV1.2 vector. Prior to treatment, all animals

TABLE 3

Chemically Modified TTR siRNA duplexes

| siRNA Number | Sense strand SEQ ID NO | Sense strand 5'-3' | Antisense strand SEQ ID NO | Antisense strand 5'-3' |
|---|---|---|---|---|
| 40 | SEQ ID NO: 75 | AsasCaGuGuUCUuGcUcUaUaA | SEQ ID NO: 75 | usUsaUaGaGcAagaAcAcUgUususu |

2'-O-Methyl nucleotides = lower case;
2'-Fluoro nucleotides = UPPER CASE;
Phosphorothioate linker = s;
Unmodified = UPPER CASE were test bled and serum HBsAg levels determined for individual animals to confirm established HBV expression.

siRNA treatment: Groups of mice (typically n=5) were administered a single 3 mg/kg dose of HBV siRNA conjugate once on Day 0 (1 dose per animal) via subcutaneous injection in the scapular region. One group of animals administered vehicle only (saline) served as controls.

Collections: All mice were test bled on Day 0, prior to treatment, and at defined time points after test article administration (for example on study days 7, 14, 21, 28, 42, 56, and 70) to determine maximum reductions in serum HBsAg levels and the duration of pharmacologic activity.

Analysis: HBsAg levels in serum samples were determined using the Biorad EIA GS HBsAg 3.0 kit (BioRad, catalog no. 32591) as per the manufacturer's instructions. Pooled serum from each treatment group was used to determine the group mean HBsAg levels at individual timepoints. Data was analysed and expressed as HBsAg levels relative to pre-treatment baseline (0 relative to Day 0).

Results: Results from testing each of the chemically modified HBV siRNA described in Table 1 are presented in Table 5. Values represent 0% HBsAg levels (relative to Day 0 baseline) on Days 7, 14, 21, 28, 42, 56 and 70 post treatment.

TABLE 5

Serum HBsAg levels in mice after single subcutaneous administration (3 mg/kg) of GalNAc conjugated siRNA from Table 1 in Example 25. HBsAg data expressed as percent of baseline (Day 0) values

| siRNA Number | Ligand Cpd # | Day 7 | Day 14 | Day 21 | Day 28 | Day 42 | Day 56 | Day 70 |
|---|---|---|---|---|---|---|---|---|
| 2 | 194 | 7.0 | 4.1 | 4.2 | 5.6 | 10.1 | 17.2 | 29.5 |
| 3 | 194 | 5.8 | 2.4 | 1.8 | 2.3 | 4.6 | 10.6 | 12.9 |
| 3 | 191a | 1.7 | 0.3 | 0.3 | 0.3 | 0.5 | 0.9 | 2.3 |
| 3 | 320 | 3.1 | 0.5 | 0.5 | 0.5 | 0.8 | 1.6 | 3.6 |
| 4 | 194 | 5.5 | 3.1 | 3.2 | 4.4 | 6.0 | 9.5 | 16.2 |
| 20 | 231 | 5.3 | 2.2 | 1.9 | 3.4 | 4.8 | 9.8 | 17.4 |
| 20 | 320 | 2.6 | 1.0 | 1.1 | 1.3 | 3.1 | 6.4 | |
| 25 | 191a | 1.9 | 0.2 | 0.2 | 0.3 | 0.5 | 1.1 | 1.8 |
| 25 | 320 | 1.1 | 0.1 | 0.3 | 0.4 | 1.4 | 2.9 | 3.5 |
| 26 | 194 | 10.4 | 3.2 | 2.7 | 3.0 | 4.0 | 6.3 | 12.3 |
| 31 | 194 | 13.3 | 7.0 | 8.0 | 11.7 | 17.7 | 25.6 | 36.7 |
| 32 | 194 | 13.7 | 5.7 | 8.2 | 11.6 | 16.6 | 25.0 | 46.5 |
| 33 | 194 | 14.4 | 8.0 | 10.8 | 14.4 | 24.3 | 41.8 | 65.2 |

Each of the 13 compounds tested caused serum HBV surface antigen reduction after a single dose of subcutaneously-administered treatment, with maximum effect obtained at Day 14 or 21. The four compounds showing the greatest reductions were compound 191a, wherein the oligonucleotide comprised siRNA 3 or 25, and compound 320, wherein $R^2$ comprised siRNA 3 or 25. These four compounds were notable for a more rapid reduction (>97%) at the first time point (Day 7), greater maximal reduction (>99%), and a more sustained reductive effect (still ≥97% at Day 56, 8 weeks after treatment).

What is claimed is:

1. The compound,

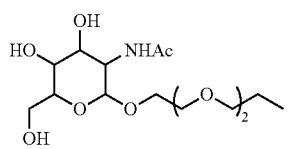

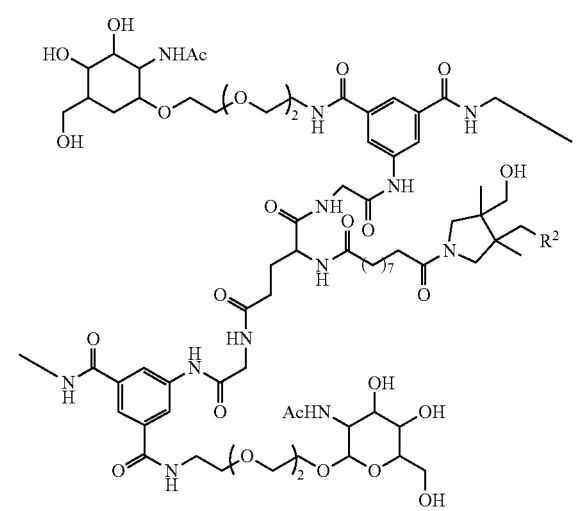

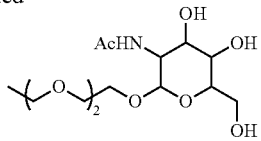

or a salt thereof wherein $R^2$ is a siRNA molecule.

2. The compound of claim 1, or a salt thereof, wherein the siRNA molecule is selected from the group consisting of siRNA 1 (SEQ ID NO:1 and 2), 2 (SEQ ID NO:3 and 4), 3 (SEQ ID NO:5 and 6), 4 (SEQ ID NO:7 and 8), 5 (SEQ ID NO:9 and 10), 6 (SEQ ID NO:11 and 12), 7 (SEQ ID NO:13 and 14), 8 (SEQ ID NO:15 and 16), 9 (SEQ ID NO:17 and 18), 10 (SEQ ID NO: 19 and 20), 11 (SEQ ID NO:21 and 22), 12 (SEQ ID NO:23 and 24), 13 (SEQ ID NO:25 and 26), 14 (SEQ ID NO:27 and 28), 15 (SEQ ID NO:29 and 30), 16 (SEQ ID NO:31 and 32), 17 (SEQ ID NO:33 and 34), 18 (SEQ ID NO:35 and 36), 19 (SEQ ID NO:37 and 38), 20 (SEQ ID NO:39 and 40), 21 (SEQ ID NO:41 and 42), 22 (SEQ ID NO:43 and 44), 23 (SEQ ID NO:45 and 46), 24 (SEQ ID NO:47 and 48), 25 (SEQ ID NO:49 and 50), 26 (SEQ ID NO:51 and 52), 27 (SEQ ID NO:53 and 54), 28 (SEQ ID NO:55 and 56), 29 (SEQ ID NO:57 and 58), 30 (SEQ ID NO:59 and 60), 31 (SEQ ID NO:61 and 62), 32 (SEQ ID NO:63 and 64), 33 (SEQ ID NO:65 and 66), 34 (SEQ ID NO:67 and 68), 35 (SEQ ID NO:69 and 70), 36 (SEQ ID NO:71 and 72) and 37 (SEQ ID NO:73 and 74).

3. A pharmaceutical composition comprising a compound as described in claim 1, or a pharmaceutically acceptable salt thereof, and a pharmaceutically acceptable carrier.

4. A method to deliver a siRNA to the liver of a human comprising administering a compound as described in claim 1, or a pharmaceutically acceptable salt thereof, to the human.

5. A method to treat a hepatitis B viral infection in a human comprising administering an effective amount of a compound as described in claim 1, or a pharmaceutically acceptable salt thereof, to the human.

6. The compound of claim 2, or a salt thereof, wherein the siRNA molecule is siRNA 3.

7. The compound of claim 2, or a salt thereof, wherein the siRNA molecule is siRNA 10.

8. The compound of claim 2, or a salt thereof, wherein the siRNA molecule is siRNA 15.

9. The compound of claim 2, or a salt thereof, wherein the siRNA molecule is siRNA 20.

10. The compound of claim 2, or a salt thereof, wherein the siRNA molecule is siRNA 25.

11. The compound of claim 2, or a salt thereof, wherein the siRNA molecule is siRNA 30.

12. A pharmaceutical composition comprising the compound of claim 2, or a pharmaceutically acceptable salt thereof, and a pharmaceutically acceptable carrier.

13. A pharmaceutical composition comprising the compound of claim 6, or a pharmaceutically acceptable salt thereof, and a pharmaceutically acceptable carrier.

14. A pharmaceutical composition comprising the compound of claim 7, or a pharmaceutically acceptable salt thereof, and a pharmaceutically acceptable carrier.

15. A pharmaceutical composition comprising the compound of claim 8, or a pharmaceutically acceptable salt thereof, and a pharmaceutically acceptable carrier.

16. A pharmaceutical composition comprising the compound of claim 9, or a pharmaceutically acceptable salt thereof, and a pharmaceutically acceptable carrier.

17. A pharmaceutical composition comprising the compound of claim 10, or a pharmaceutically acceptable salt thereof, and a pharmaceutically acceptable carrier.

18. A pharmaceutical composition comprising the compound of claim 11, or a pharmaceutically acceptable salt thereof, and a pharmaceutically acceptable carrier.

* * * * *